(12) United States Patent
Choi et al.

(10) Patent No.: US 9,482,669 B2
(45) Date of Patent: Nov. 1, 2016

(54) CRYSTAL STRUCTURE OF THE NANR AND MANNAC-6P COMPLEX, AND USES THEREOF

(71) Applicants: SNU R&DB FOUNDATION, Seoul (KR); KOREA RESEARCH INSTITUTE OF BIOSCIENCE AND BIOTECHNOLOGY, Daejeon (KR)

(72) Inventors: Sang Ho Choi, Gyeonggi-do (KR); Byoung Sik Kim, Yongin-si (KR); Myung Hee Kim, Daejeon (KR); Jung Won Hwang, Daejeon (KR)

(73) Assignees: SNU R&DB FOUNDATION, Seoul (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 14/310,879

(22) Filed: Jun. 20, 2014

(65) Prior Publication Data
US 2015/0010915 A1    Jan. 8, 2015

(30) Foreign Application Priority Data

Jun. 21, 2013 (KR) .......................... 10-2013-0071369

(51) Int. Cl.
*G01N 33/569* (2006.01)
*C07K 14/28* (2006.01)

(52) U.S. Cl.
CPC ......... *G01N 33/56911* (2013.01); *C07K 14/28* (2013.01); *G01N 2400/00* (2013.01); *G01N 2500/04* (2013.01)

(58) Field of Classification Search
None
See application file for complete search history.

(56) References Cited

U.S. PATENT DOCUMENTS 6,183,121 B1 * 2/2001 Kim et al. ..................... 702/19

FOREIGN PATENT DOCUMENTS

KR    1020100136217    12/2010

OTHER PUBLICATIONS

Böhm et al., "The computer program LUDI: A new method for the de novo design of enzyme inhibitors", Journal of Computer-Aided Molecular Design, 1992, vol. 6, pp. 61-78.*
Morris et al. "Distributed automated docking of flexible ligands to proteins: Parallel applications of AutoDock 2.4*", J. of Computer-Aided Molecular Design. 1996. vol. 10, pp. 293-304.*
Dean, BioEssays, 1994, 16(9):683-687.*
Kim et al., "Cooperative Regulation of the Vibrio vulnificus nan Gene Cluster by NanR Protein, cAMP Receptor Protein, and N-Acetylmannosamine 6-Phosphate," J. Biol. Chem., 286(47):40889-40899, Nov. 25, 2011.
Kim, Byoung Sik et al., "Microbiology: Cooperative Regulation of the Vibrio vulnificus nan Gene Cluster by NanR Protein, cAMP Receptor Protein, and N-Acetylmannosamine 6-Phosphate", The Journal of Biological Chemistry, vol. 286, pp. 40889-40899, Nov. 25, 2011.
NCBI Reference Sequence WP 011081658.3, May 24, 2013.
Office Action issued in Korean Patent Application No. 10-2014-0076763, Nov. 20, 2015.

* cited by examiner

*Primary Examiner* — Suzanne M Noakes
(74) *Attorney, Agent, or Firm* — Joseph R. Baker, Jr; Gavrilovich, Dodd & Lindsey LLP

(57) ABSTRACT

The present invention relates to a three-dimensional structure of a complex explored by crystallization of the complex of NanR which is a key pathogenic regulatory protein of *Vibrio vulnificus* and ManNA6P which is a NanR regulator. Further, the present invention relates to a modified NanR protein, a polynucleotide encoding the protein, a vector including the polynucleotide, and a transformant including the vector. Furthermore, the present invention relates to a method for screening a substance regulating interaction between NanR and the transcriptional control region of nan operon which is a gene cluster regulated by NanR, or a substance regulating interaction between NanR and ManNAc-6P, by designing three-dimensional structure of the complex, and to an antibacterial composition including the screened substance.

6 Claims, 26 Drawing Sheets

FIG. 4f

|  | n | $K_a$ ($10^4$ $M^{-1}$) | $K_d$ (µM) | ΔH (kcal mol$^{-1}$) | TΔS (kcal mol$^{-1}$) | ΔG (kcal mol$^{-1}$) |
|---|---|---|---|---|---|---|
| NanR to DNA | 1.34±0.001 | 71.60±3.36 | 1.40 | 54.90±0.33 | 62.87 | -57.39 |
| NanR/ligand to DNA | 1.13±0.28 | 0.54±0.07 | 185.87 | 157.20±49.24 | 162.11 | -4.91 |

US 9,482,669 B2

CRYSTAL STRUCTURE OF THE NANR AND MANNAC-6P COMPLEX, AND USES THEREOF

CROSS REFERENCE TO RELATED APPLICATIONS

This application claims priority under 35 U.S.C. §119(a) to Korean Patent Application No. 10-2013-0071369, filed on Jun. 21, 2013, the disclosure of which is incorporated herein by reference.

BACKGROUND OF THE INVENTION

1. Field of the Invention

The present invention relates to a three-dimensional structure of crystallization of the complex of NanR which is a key pathogenic regulatory protein of *Vibrio vulnificus* and ManNA6P which is a NanR regulator. Further, the present invention relates to a modified NanR protein, a polynucleotide encoding the protein, a vector including the polynucleotide, and a transformant including the vector. Furthermore, the present invention relates to a method for screening a substance regulating interaction between NanR and the transcriptional control region of nan operon which is a gene cluster regulated by NanR, or a substance regulating interaction between NanR and ManNAc-6P, and an antibacterial composition including the screened substance.

2. Description of the Related Art

When the human body is infected with pathogenic bacteria, the pathogenic bacteria encounter competition with the gut intestinal flora for nutrients in the host (human body). Therefore, these pathogenic bacteria overcome the nutritionally adverse environment by utilizing alternative carbon sources in the gut, and endeavor to survive. The intestinal tract of the human body is protected by a mucus layer containing a glycosylated protein mucin that is composed of 85% carbohydrate. Pathogenic bacteria such as *Vibrio cholera* and *Vibrio vulnificus* (*V. vulnificus*) have most likely evolved elaborate systems for catabolic utilization of N-acetylneuraminic acid (Neu5Ac), which is the most abundant sialic acids constituting mucin, as an alternative energy source.

When the human body is infected with these bacteria, these bacteria overexpress nan genes encoding enzymes essential for Neu5Ac catabolism and membrane transport proteins required for intracellular transport of Neu5Ac in the intestine so as to utilize Neu5Ac as an energy source, and thus they exert their pathogenicity through survival and growth, indicating that Neu5Ac catabolism of pathogenic microorganisms is directly correlated with their pathogenicity.

*V. vulnificus* is a pathogenic bacterium which usually enters the body through traumatic injury or ingestion of undercooked or contaminated sea food, and a life-threatening foodborne enteropathogen which causes septicemia in patients with liver disease or diabetes or in immunocompromised individuals, and the septicemia is associated with a mortality greater than 50% within 48 hours. Before entering the bloodstream, *V. vulnificus* survives and colonizes the small intestine. The present inventors recently demonstrated that NanR protein of *V. vulnificus* is a transcriptional repressor of the nan operon which is a cluster of genes encoding the transporter for intracellular absorption of Neu5Ac and essential catabolic enzymes for Neu5Ac, respectively. They also showed that N-acetylmannosamine 6-phosphate (ManNAc-6P), the catabolic intermediate of Neu5Ac, selectively binds to NanR and induces expression of the nan genes. However, the molecular mechanisms underlying regulation of the nan genes by interaction between NanR protein and ManNAc-6P has not been clarified yet.

On the other hand, recent studies change their approach to development of therapeutic agents from a random approach to exploration of a number of therapeutic candidates to a new approach to development of therapeutic agents with improved target specificity and efficacy by exploration of key target proteins, investigation of three-dimensional structure and function of the target proteins, and designing and development of drug candidates through specific and efficient protein engineering. Therefore, to design and develop selective and specific drug candidates, it is essential that production and crystallization of a large amount of a highly pure, stable protein are conducted and then its three-dimensional structure is investigated. Three-dimensional structure of the NanR protein, in particular, a complex of the NanR protein and ManNAc-6P, for all its importance, has not been revealed yet, because it is difficult to crystallize in stable form.

Accordingly, the present inventors have made many efforts to investigate three-dimensional structure of the NanR protein. As a result, they prepared a crystal of NanR protein and its ligand ManNAc-6P complex, and investigated interaction between the NanR protein and its regulatory ligand at the atomic level with high resolution, thereby completing the present invention.

SUMMARY OF THE INVENTION

An object of the present invention is to provide a method for crystallizing a complex of NanR protein and N-acetylmannosamine 6-phosphate (ManNAc-6P).

Another object of the present invention is to provide a three-dimensional structure of the NanR protein and ManNAc-6P complex, and a crystal of SeMet-NanR protein and ManNAc-6P complex.

Still another object of the present invention is to provide a modified NanR protein, a polynucleotide encoding the protein, an expression vector including the polynucleotide, and a transformant introduced with the expression vector.

Still another object of the present invention is to provide a method for screening a substance regulating interaction between NanR and the transcriptional control region of nan operon which is a gene cluster regulated by NanR, by utilizing three-dimensional structure of the complex of NanR protein and ManNAc-6P.

Still another object of the present invention is to provide a method for screening a substance regulating interaction between NanR and ManNAc-6P, by utilizing three-dimensional structure of the complex of NanR protein and ManNAc-6P.

Still another object of the present invention is to provide an antibacterial composition including the screened substance.

BRIEF DESCRIPTION OF THE DRAWINGS

FIG. 2 shows an overall structure of the NanR/ManNAc-6P complex.

FIG. 3a is an electron density difference map showing the position of ManNAc-6P in the ligand-binding site, in which the residues critical for the interaction with NanR are shown together with ligands; FIG. 3b is the structure of NanR superimposed onto that of GlmS, which has an isomerase domain (upper) and a glutaminase domain (lower), in which the P-loop-binding ligand of each protein is shown; FIG. 3c shows that two NanR monomers form hydrogen bonds with each ligand; and FIG. 3d shows the results of an E. coli dual plasmid system assay, in which cells were cotransformed with a luciferase reporter gene fused to PnanTp and wild-type or mutant NanR, followed by incubation in the presence or absence of Neu5Ac, and the RLU (Relative luminescence unit) was calculated by dividing the luminescence by the $A_{600}$ of each strain and the data represent the mean±SD from at least three experiments.

FIGS. 4a to 4f show that the DNA-binding activity of NanR is regulated by ManNAc-6P. FIG. 4a is surface electrostatic potential showing the distribution of positively charged residues in the DNA binding domain (DBD), in which the positively charged residue is indicated by dark gray circle, and the ligand-binding site is indicated by light gray circle; FIG. 4b shows the position of the positively charged residues in the DBD domain of each NanR molecule; FIG. 4c shows the results of an E. coli dual plasmid system assay, in which cells were cotransformed with a luciferase reporter gene fused to PnanTp and wild-type NanR, mutant NanR, or empty vector (NO), followed by incubation, and the RLU (Relative luminescence unit) was calculated by dividing the luminescence by the $A_{600}$ of each strain, and the data represent the mean±SD from at least three experiments; FIG. 4d shows EMSA analysis of the interaction between the nanTp-nanE intergenic region and wild-type or mutant NanR protein in the absence or presence of ManNAc-6P ligand; FIG. 4e shows the results of in vitro transcription assay, in which the supercoiled pBS0921 plasmid containing PnanE was transcribed in the presence or absence of 100 nM wild-type or mutant NanR protein and 1 mM ManNAc-6P ligand, and the 370-bp PnanE-specific transcript and the vector-derived control transcript (RNA-1) are indicated; and FIG. 4f shows the effect of interaction between NanR and the transcriptional control region of nan operon, which was determined by using isothermal titration calorimetry.

FIG. 7a shows averaged images of apo-NanR, NanR/ManNAc-6P complex, apo-NanR/DNA complex; FIG. 7b shows the result of fitting the atomic models of NanR and DNA to the NanR-DNA complex; and FIG. 7c shows the structure of the NanR/DNA complex, which was modeled based on the electron-microscopic analysis and in vivo and in vitro investigations, in which R57 and R60 residues in α5 and K199 in α11 are found to be required for DNA binding.

FIG. 11a shows that overnight cultures of wild-type, R57A, and H163L NanR mutant V. vulnificus strains were washed with PBS three times and serially diluted, the undiluted samples were streaked (left panel) onto a solid medium, and each serial dilution was spotted onto a medium supplemented with either Neu5Ac (lower left panel) as a sole carbon source or Neu5Ac, D-xylose, and L-proline (lower right panel), followed by incubation at 30° C. for 24 hours; FIG. 11b shows the results of a mouse intestine colonization competition assay using the wild-type and H163L NanR mutant V. vulnificus strain (n=10), in which each mouse was indicated by white circles and median values are indicated by triangles; FIG. 11c shows survival rates for 24 hours after mice were challenged with the wild-type and H163L NanR mutant V. vulnificus strain ($4\times10^8$ CFU) (n=5 per group); and FIG. 11d shows molecular mechanism of Neu5Ac catabolism via the ManNAc-6P-mediated regulation of NanR, in which Neu5Ac is indicated by white circles and CM indicates cell wall.

Figure 1:
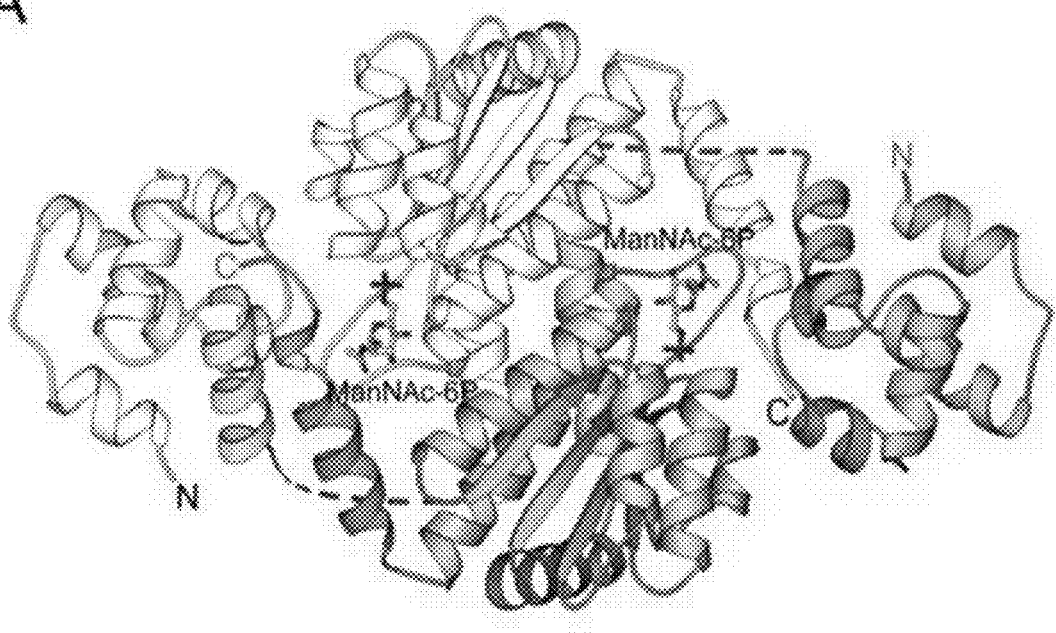
FIG. 1 shows symmetry mates in the dimer of NanR/ManNAc-6P complex (A) and an electron microscopic image of a functional dimeric form of NanR (B).
Figure 1:
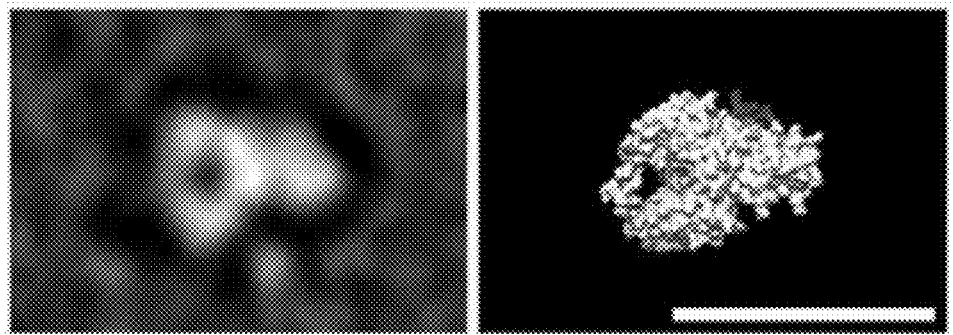

T-COFFEE software was used for sequence comparison and ESPript software was used for visualization. These two softwares are available in ExPASy portal (http://au.>>---<<expasy.org/).

DETAILED DESCRIPTION OF THE PREFERRED EMBODIMENTS

In one aspect to achieve the above objects, the present invention provides a method for crystallizing a complex of NanR protein and N-acetylmannosamine 6-phosphate (ManNAc-6P).

Specifically, the method for crystallizing the complex of NanR protein and ManNAc-6P includes the steps of (a) mixing the NanR protein having an amino acid sequence of SEQ ID NO. 1 with ManNAc-6P; and (b) crystallizing the mixture of step (a), but is not limited thereto.

As used herein, the term "NanR protein" is a transcriptional repressor protein suppressing expression of the genes in nan operon essential for catabolism of Neu5Ac (N-acetylneuraminic acid) which is the most abundant sialic acid in the intestine, and it has an N-terminal DNA binding domain containing a helix-turn-helix(HTH) motif and a C-terminal domain binding to a ligand. In the present invention, the NanR protein includes all of the wild-type NanR protein and modified NanR protein. Further, the NanR protein of the present invention may be a modified NanR protein, in which methionine is substituted with selenomethionine (SeMet). Meanwhile, SeMet, as used herein, refers to an amino acid in which sulfur atom in methionine is replaced by selenium. SeMet shows behavior and chemical characteristics similar to those of methionine. SeMet is used to solve the phase problem for obtaining a three-dimensional crystal structure in X-ray crystallography, when no similar three-dimensional structure has been revealed so far. A crystallization method by substitution of methionine with SeMet for protein structural analysis is also called a SeMet method. Information about the amino acid sequence and nucleotide sequence of the NanR protein can be obtained from the known database such as NCBI GenBank. For example, the NanR protein may have the amino acid sequence of SEQ ID NO. 1. However, as long as a protein has the activity of the protein having the amino acid sequence of SEQ ID NO. 1, the protein having 80% or more homology, specifically 90% or more homology, more specifically 95% or more homology, and much more specifically 99% or more homology thereto may be also included without limitation. It is apparent that a protein having an amino acid sequence in which a part thereof is deleted, altered, substituted, or added is also included in the scope of the present invention.

In one embodiment of the present invention, to solve the phase problem of the crystallized protein, SeMet-NanR was prepared by substitution of SeMet for methionine constituting the protein, and mixed with ManNAc-6P, followed by crystallization. In order to obtain the SeMet-substituted NanR protein, the methionine auxotroph E. coli B834 (DE3) strain (Novagen) was grown in a minimal medium supplemented with 50 mg/ml SeMet. The SeMet-substituted NanR protein was purified and obtained from the culture by addition of 5 mM methionine to all buffers.

Moreover, the NanR protein may be derived from, but is not limited to, V. vulnificus, Escherichia coli, Haemophilus influenzae or V. cholerae.

Meanwhile, the present inventors recently revealed that V. vulnificus NanR protein is a transcriptional repressor of nan operon which is a cluster of genes encoding transporters for intracellular absorption of Neu5Ac and enzymes essential for Neu5Ac catabolism, respectively. In addition, they also demonstrated that the catabolic intermediate of Neu5Ac, ManNAc-6P selectively binds to NanR to induce expression of nan genes (BS Kim et al., THE JOURNAL OF BIOLOGICAL CHEMISTRY, Vol. 286, No. 47, pp. 40889-40899, 2011 Nov. 25). With respect to the objects of the present invention, the NanR protein may be a protein binding to the transcriptional control region of nan operon, and specifically, the NanR protein may be a protein that binds to the nan operon promoter to suppress expression of nan operon, but is not limited thereto. The NanR protein may be also a protein binding to ManNAc-6P, and its binding to ManNAc-6P may cause conformational change, leading to a reduction in binding affinity with the transcriptional control region of nan operon, but is not limited thereto.

As used herein, the term "modified NanR protein" means a protein which is prepared by substituting, inserting, deleting or modifying one or more amino acids in the wild-type NanR protein, and with respect to the objects of the present invention, the modified NanR protein may be a protein which is modified to have increased or reduced binding affinity for the transcriptional control region of nan operon or for the ManNAc-6P ligand, but is not limited thereto.

The modified NanR protein is preferably a protein having modifications of one or more selected from the group consisting of lysine at position 20 (Lys20), lysine at position 21 (Lys21), arginine at position 23 (Arg23), arginine at position 57 (Arg57), arginine at position 60 (Arg60), lysine at position 65 (Lys65), serine at position 138 (Ser138), histidine at position 163 (His163), serine at position 182 (Ser182), serine at position 184 (Ser184), threonine at position 187 (Thr187), glutamic acid at position 229 (Glu229), and lysine at position 240 (Lys240) in the amino acid sequence of SEQ ID NO. 1 of NanR protein, for example, a protein having substituted amino acids, and more preferably, a protein in which Lys20 is substituted with alanine, Lys21 is substituted with alanine, Arg23 is substituted with alanine or leucine, Arg57 is substituted with alanine or leucine, Arg60 is substituted with alanine or leucine, Lys65 is substituted with alanine, Ser138 is substituted with alanine, His163 is substituted with alanine or leucine, Ser182 is substituted with alanine, Ser184 is substituted with alanine, Thr187 is substituted with alanine, Glu229 is substituted with leucine, or Lys240 is substituted with alanine or methionine, but is not limited thereto. In addition to the above modified proteins, it is apparent that a modified NanR protein having 70% or more homology, preferably 80% or more homology, more preferably 95% or more homology, and most preferably 98% or more homology to the amino acid sequence of SEQ ID NO. 1 is also included in the scope of the present invention, as long as its binding ability to the transcriptional control region of nan operon or to the ManNAc-6P is controlled, compared to the wild-type NanR protein. The modified protein of the present invention may be a protein that can undergo crystallization required for 3D structural analysis of the protein.

In one embodiment of the present invention, a modified NanR protein was prepared by substituting Lys20 with alanine, Lys21 with alanine, Arg23 with alanine or leucine, Arg57 with alanine or leucine, Arg60 with alanine or leucine, Lys65 with alanine, Ser138 with alanine, His163 with alanine or leucine, Ser182 with alanine, Ser184 with alanine, Thr187 with alanine, Glu229 with leucine, or Lys240 with alanine or methionine in the NanR protein having the amino acid sequence of SEQ ID NO. 1, and its binding affinity for the transcriptional control region of nan operon or the ManNAc-6P was examined.

As used herein, the term "ManNAc-6P" is, also called acetylmannosamine-6 phosphate, a catabolic intermediate of N-acetylneuraminic acid which constitutes glycoproteins, and synthesized by action of N-acylmannosamine kinase. That is, it is a catabolic intermediate of N-acetylneuraminic acid which is the most common sialic acid found in nature, such as animal cell membranes, glycoproteins and glycolipids, or bacterial cell walls, and ManNAc-6P is present from virus to animals. ManNAc-6P has a chemical formula of $C_8H_{16}NO_9P$. In the present invention, ManNAc-6P binds with the NanR protein, which causes conformational change, leading to a reduction in binding affinity of NanR protein with the transcriptional control region of nan operon, but is not limited thereto. In particular, the ManNAc-6P may binds to the C-terminal ligand of the NanR protein. Eventually, ManNAc-6P functions to reduce the nan gene transcriptional repressor activity of the NanR protein, thereby inducing expression of nan operon genes.

As used herein, the term "complex of NanR protein and ManNAc-6P" means a complex formed by interaction between NanR protein and ManNAc-6P. Preferably, it means a complex formed by interaction between arginine residue at position 71 (Arg71) of a DNA binding domain (DBD) and alanine residue at position 137 (Ala137), Ser138, His163, Ser182, serine residue at position 183 (Ser183), Ser184, Thr187, Glu229, proline residue at position 231 (Pro231), glycine at position 234 (Gly234), and Lys240 of a ligand binding domain (LBD) of NanR protein and ManNAc-6P via a hydrogen bond or a water-mediated hydrogen bond, but is not limited thereto.

Figure 2A:
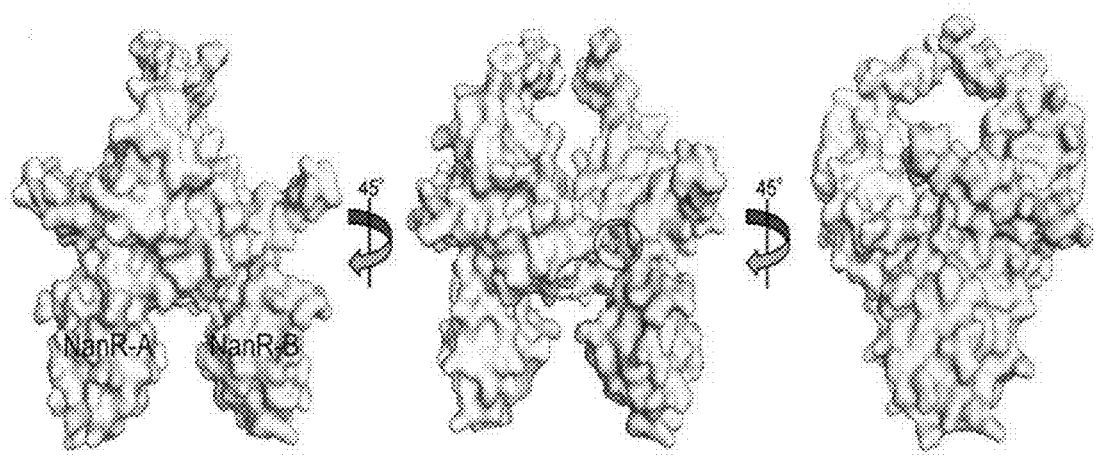
FIG. 2a shows the binding structure of the dimer tilted by 45° and the ligand-binding site is indicated by a circle.
Figure 2B:
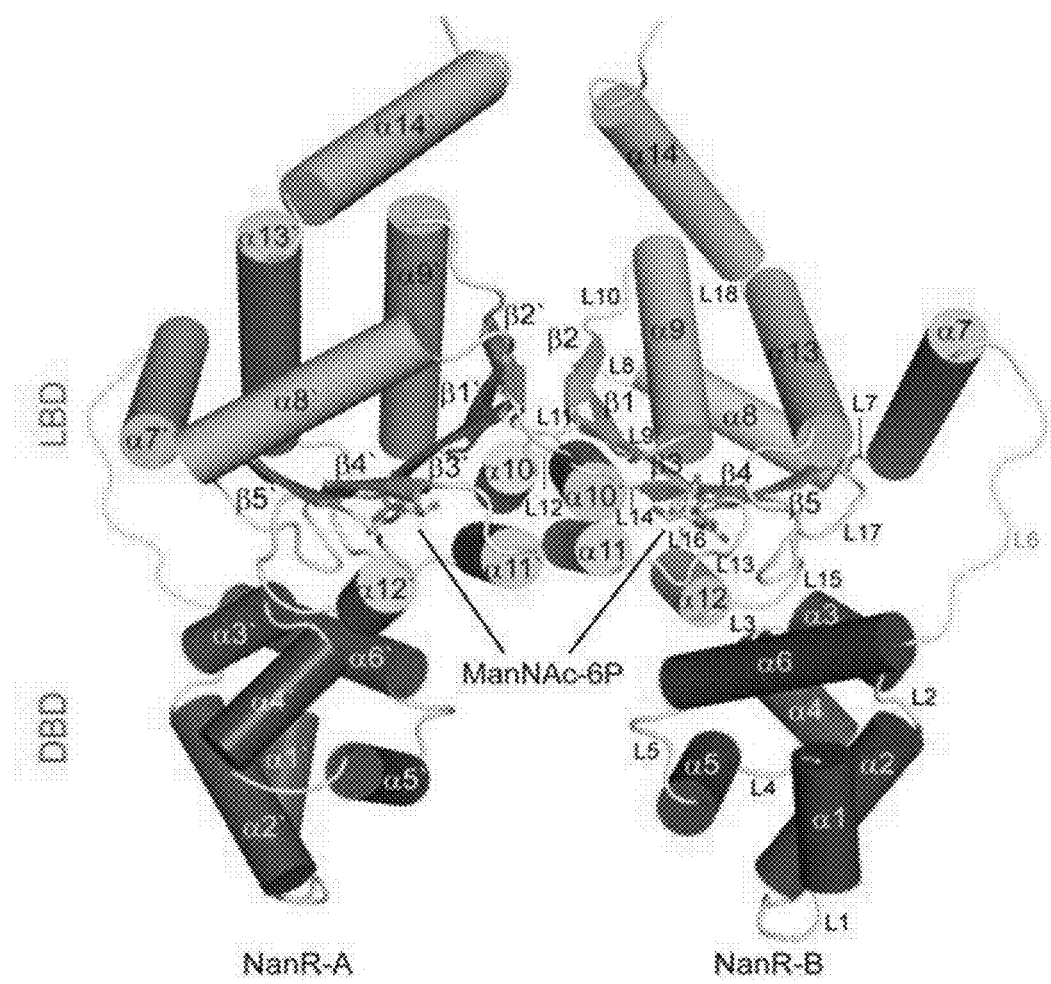
FIG. 2b shows a DBD domain and a LBD domain, the α-helices and β-sheets thereof, and the binding structure of ManNAc-6P.
Figure 3A:
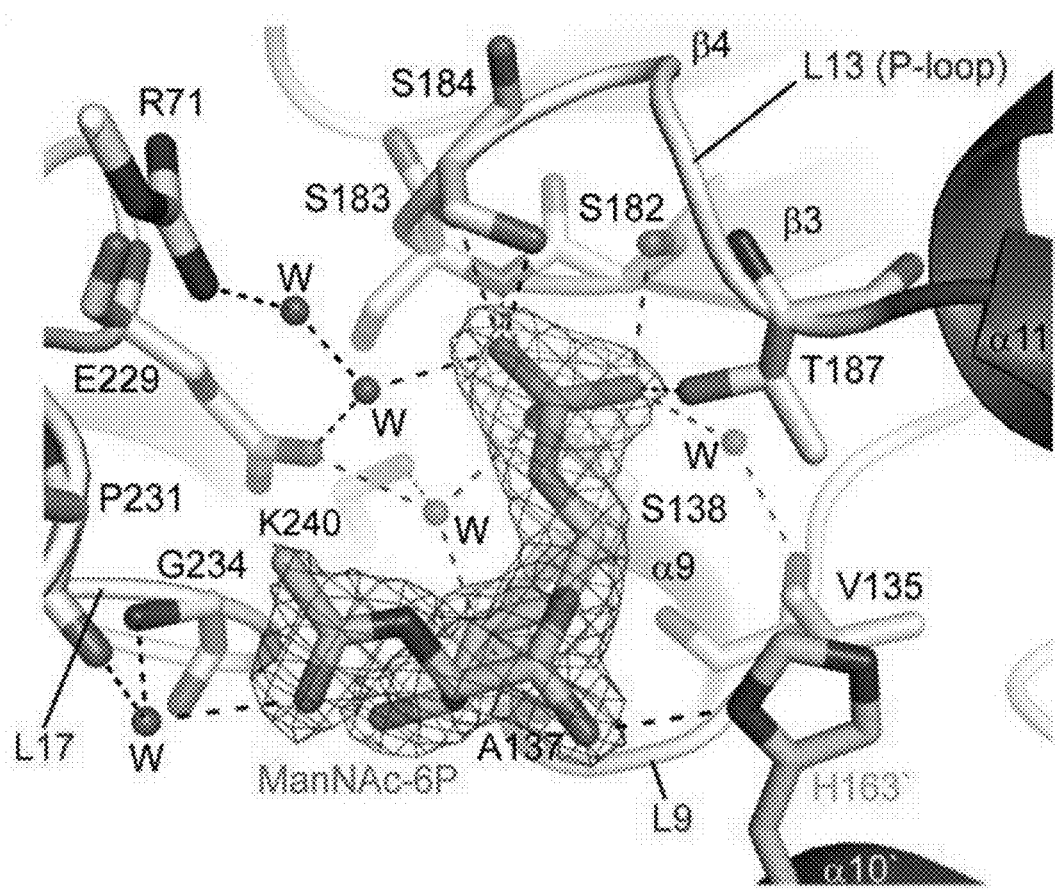
FIGS. 3a to 3d show structural analysis of the interaction between NanR protein and ManNAc-6P.
Figure 3B:
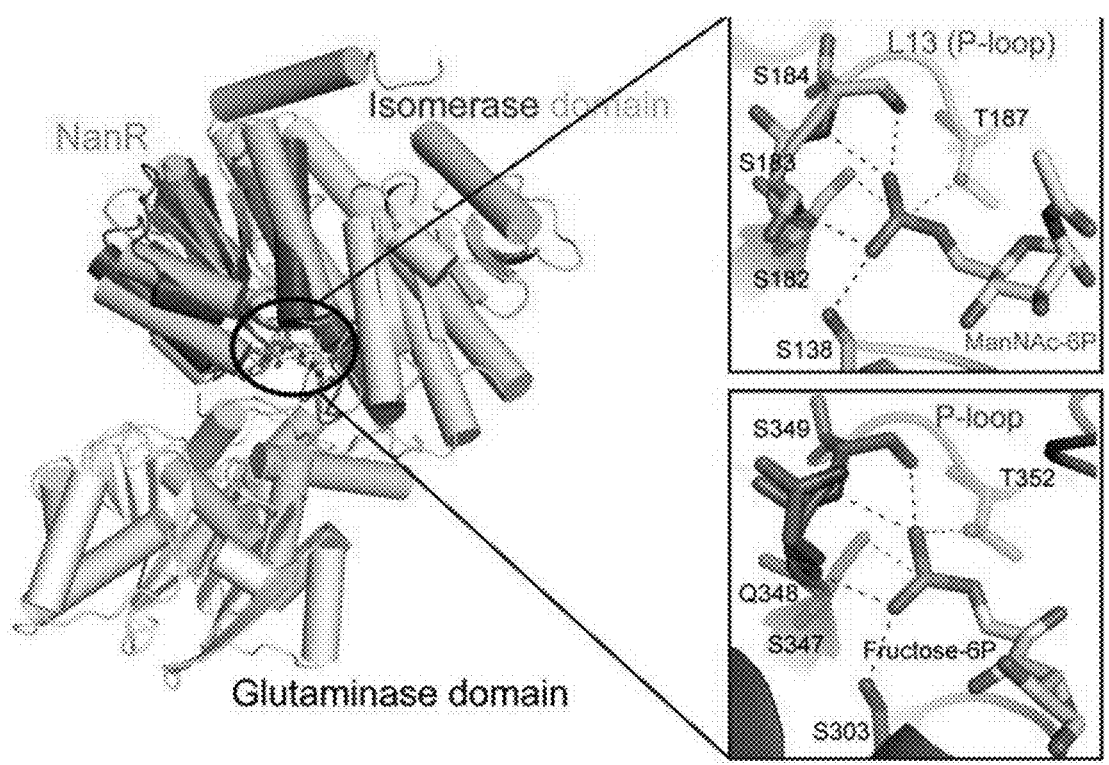
Figure 3C:
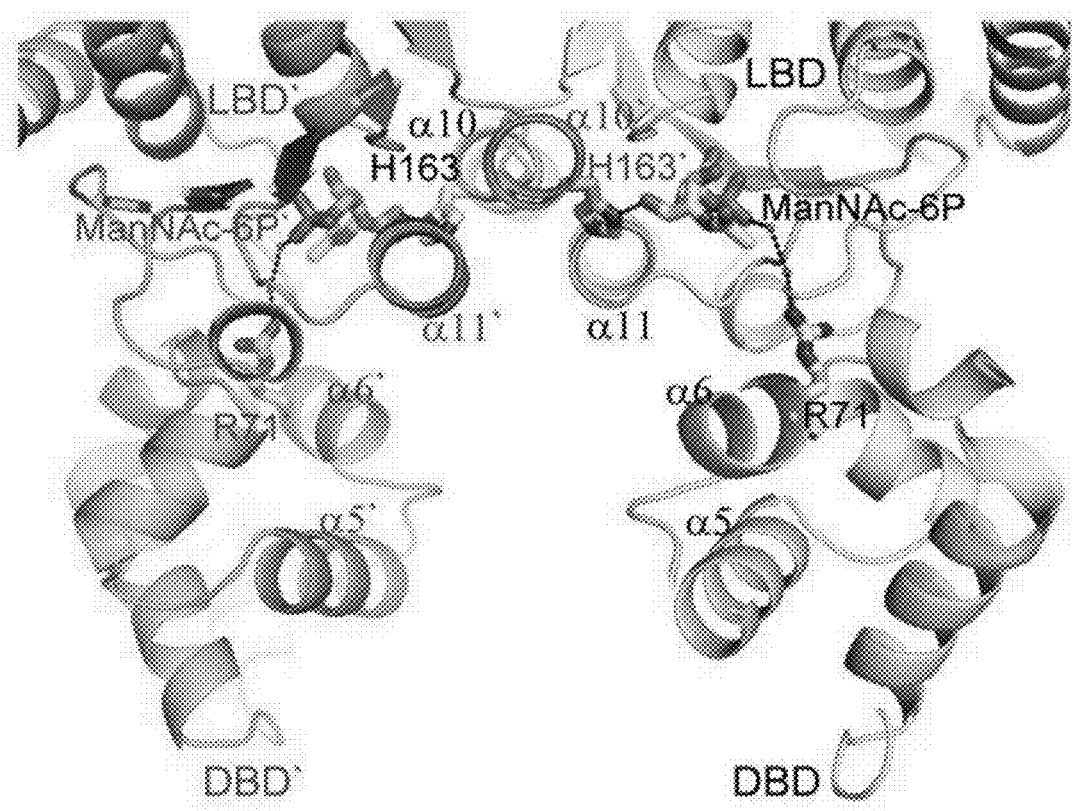

In one specific embodiment of the present invention, the binding structure between NanR protein and ManNAc-6P was examined by analyzing the structure of the crystal prepared in the present invention. In detail, ManNAc-6P binds to L9, L13, and L17 loops of NanR LBD domain (FIG. 3a). L13 crosses over and embraces the phosphate group of ManNAc-6P (FIGS. 3a and 3b); the phosphate oxygen atoms form hydrogen bonds with the side chains of S182, S184, and T187, and with the backbone amide of S183 in the P-loop (FIG. 2b, upper panel). The side chain hydroxyl group of S138 in loop L9 is also hydrogen-bonded to a ManNAc-6P phosphate oxygen atom (FIGS. 3a and 3b). The hydroxyl group at position O4 of the sugar ring forms a hydrogen bond with the A137 backbone amide. A hand-in-hand interaction between the two NanR monomers is formed by hydrogen bonds between the hydroxyl group at position O1 of the sugar ring in each NanR monomer and the nitrogen atom in the imidazole ring of each H163 (FIGS. 3a and 3b). This structure is critical for the conformational change of the NanR dimer and delivery of the signal to the nan operon genes when ligand-binding occurs. Furthermore, the phosphoryl group of the ligand forms a water-mediated hydrogen bond with the side chain amino group of R71 on α6 in the DBD domain (FIGS. 3a and 3c). P231 and G234 form water-mediated hydrogen bonds with the carbonyl oxygen atom of the N-acetyl group (FIG. 3a). In addition, E229 and K240 form water-mediated hydrogen bonds with the sugar and phosphate oxygen atoms of ManNAc-6P (FIG. 3a). These interactions may enable ligand-mediated relocation of the NanR dimer and influence its interaction with the transcriptional control region of nan operon.

In the crystallization method, the mixing step may be carried out by mixing NanR protein and ManNAc-6P in a molar ratio of 1:10 to 1:200, but is not limited thereto. In one embodiment of the present invention, NanR protein and ManNAc-6P were mixed in a molar ratio of 1:100, resulting in successful crystallization.

The NanR protein may be a protein that is separately expressed or obtained by purification of naturally occurring protein. The purification may be a purification method well known in the art. Therefore, the crystallization method may include the step of purifying the NanR protein before the mixing step of (a), and purification of the protein may be carried out by a known purification method such as affinity chromatography.

For example, the protein may be isolated from the medium, in which host cells are grown, by the conventional chromatographic method including immunoaffinity chromatography, receptor affinity chromatography, hydrophobic interaction chromatography, lectin affinity chromatography, size exclusion chromatography, cation or anion exchange chromatography, high performance liquid chromatography (HPLC), reverse phase HPLC or the like. In other purification method, the NanR protein is fused with a specific tag, label, or chelating moiety, and the fusion protein is recognized by a specific binding partner or agent. The purified protein can be cleaved to yield the desired protein, or can be left as an intact fusion protein. A form of the desired polypeptide having additional amino acid residues as a result of the cleavage process of the fusion protein may be produced.

As used herein, "undergoing crystallization" or "having crystallinity" means that in order to prepare a protein in the form suitable for X-ray analysis of three-dimensional structure, a modification is introduced into the protein molecule so as to form solid particles having a uniform shape and size from a uniform liquid or to further stabilize the crystal of the protein. Three-dimensional structure of a protein is very important for the understanding of in vivo actions of the protein and development of therapeutic drugs. That is, understanding of arrangement and three-dimensional structure of atoms constituting a protein as a macromolecule makes it possible to analyze three-dimensional structure of the complex of NanR protein and ManNAc-6P and to provide a platform for development of new drugs for inhibiting interaction between NanR protein and ManNAc-6P. However, it was very difficult to demonstrate three-dimensional structure of a protein or a complex of a protein and a ligand, because a crystal structure of the corresponding complex should be first prepared in order to analyze three-dimensional structure of the complex of NanR protein and ManNAc-6P. In addition, acquisition of a stable crystal depends on the protein and the ligand, and in particular, crystallization conditions vary depending on the protein and the ligand.

In the present invention, the present inventors mixed the NanR protein with ManNAc-6P in a molar ratio of 1:100 in order to obtain the crystal complex of NanR protein and ManNAc-6P.

The crystallization step of (b) may be carried out in a solution containing 1 to 20% PEG 2000 MME, 0.01 to 1 M ammonium sulfate, 0.01 to 2 M sodium formate, 0.5 to 6% low molecular polyglutamic acid (PGA-LM), and 0.01 to 1 M sodium acetate, and in particular, in a solution containing 10 to 20% PEG 2000 MME, 0.05 to 0.2 M ammonium sulfate, 0.1 to 0.5 M sodium formate, 1 to 5% low molecular polyglutamic acid, and 0.1M sodium acetate at pH 5.0 to pH 5.5. In the crystallization step, the mixture was incubated on ice for 1 to 24 hours.

In one embodiment of the present invention, crystallization trials of the purified NanR protein performed using the sitting drop vapor-diffusion method at 21° C. were unsuccessful. However, the crystals were obtained when NanR and ManNAc-6P were mixed in a molar ratio of 1:100 and incubated on ice for 2 hours.

The crystallization of the complex was optimized under the following conditions: 10% PEG 2,000 MME, 0.1 M ammonium sulfate, 0.3 M sodium formate, 3% PGA-LM, and 0.1 M sodium acetate (pH 5.0 to 5.5). Crystals appeared within a day and were grown for a further 5 days for diffraction experiments. The crystals were transferred to a cryoprotectant solution containing 10% PEG 2,000 MME, 0.1 M ammonium sulfate, 0.3 M sodium formate, 3% PGA-LM, 0.1 M sodium acetate (pH 5.5), and 30% glycerol, and then placed immediately in a −173° C. nitrogen gas stream.

The crystallization of step (b) may be carried out by a variety of known crystallization methods, specifically, by a vapor diffusion method. The vapor diffusion method may be a sitting drop vapor diffusion method or a hanging-drop vapor diffusion method, and more specifically, sitting drop vapor diffusion method, but is not limited thereto.

As used herein, the term "sitting drop vapor diffusion method" refers a crystallization method, in which when a microdrop of mother liquor and a much larger reservoir solution exist separately in a closed system, transport of either water or other volatile agent occurs between them, leading to a supersaturated state of protein, and in such a thermodynamically metastable state, proteins are precipitated depending on the precipitant. While the protein precipitation slowly occurs, stable crystals are formed and the precipitant functions to lower the solubility of the concentrated protein solution, and proteins congregate to form crystals in order to reduce an adsorption layer around protein molecules. The reservoir solution contains a mixture of the precipitant, buffer, and detergent at different concentrations. Droplets are usually formed by mixing the protein solution with the reservoir solution of various conditions at a ratio of 1:1, and the droplets thus formed are placed on a microbridge, and sealed. At this time, there is a difference in the concentration between the proteins in the droplets and the reservoir solution, and thus the proteins do not exist as crystals at the beginning. They are equilibrated while sealed, and crystals are formed under the specific conditions by the above described principle. In the sitting drop vapor diffusion method, the type and proper concentration of the salt, the buffer and the surfactant as well as the precipitant in the reservoir solution, pH of the solution, and the experimental temperature vary depending on the type of protein, and in some cases, they become very important factors in crystal formation of proteins.

As used herein, the term "hanging-drop vapor diffusion method" is one of protein crystallization methods, which provides crystals having a size sufficient for protein structural analysis. In the hanging-drop vapor diffusion method, a reagent containing a sample and a pure liquid reagent are placed on the top of the reservoir under vapor equilibration. To achieve equilibrium of the sample having a lower reagent concentration than the reservoir, water contained in the sample eventually ends up in the reservoir. Water contained in the sample is removed until the concentration is approximately the same as that in the liquid reagent, and finally, protein crystals reaching the equilibration can be obtained.

In one embodiment of the present invention, the sitting drop vapor diffusion method was used to obtain complex crystals of NanR protein and ManNAc-6P (Example 8).

In another aspect, the present invention provides a crystal of NanR protein and ManNAc-6P complex or a crystal of SeMet-NanR protein and ManNAc-6P complex.

The NanR protein, ManNAc-6P, complex thereof, and the SeMet-NanR protein are the same as described above.

There are many different methods for analyzing a protein's crystal structure, and two main methods are NMR spectroscopy and X-ray crystallography. NMR Spectroscopy is based on the principle of predicting a distance between particular atoms in a molecule by analyzing signal changes due to chemical factor which can be detected in the NMR spectrum of a molecule. Data of chemical shift obtained by the NMR test is analyzed to obtain a set of the distances between labeled atoms in one protein, and a model or a set of models satisfying information about all distances determined by the experiment is produced. Thus, there is a disadvantage of requiring collection and analysis of a large amount of data. Meanwhile, X-ray crystallography is based on the principle of obtaining the result by analyzing x-ray scattered by electron cloud surrounding an atom of the crystal in an x-ray generator. X-ray diffraction patterns from protein crystals are regular because the individual protein molecules are arranged in a regular lattice. Based on this principle, X-ray crystallography is a method of analyzing a protein structure by producing an electron density of the protein using x-ray scattered and reflected from the protein crystals. However, there is a disadvantage of requiring pure protein samples and protein crystallization. In the present invention, crystallization trials of the NanR protein alone were unsuccessful, but the crystals were obtained when a complex of the NanR protein and its ligand ManNAc-6P was prepared.

In the present invention, to provide a three-dimensional crystal structure of NanR protein and ManNAc-6P, diffraction patterns were obtained using an x-ray image plate, and phase information was obtained by multiple anomalous dispersion (MAD) using Se-Met (selenium-methionine). An electron density map was obtained from the x-ray diffraction patterns and phase information, and atomic coordinates were derived therefrom so as to obtain the three-dimensional structure.

Preferably, the crystal of NanR protein and ManNAc-6P complex of the present invention has a space group of $P3_121$ and a unit-cell dimension of a=109.21±5 Å, b=109.21±5 Å and c=82.47±5 Å, $\alpha=\beta=90°$ and $\gamma=120°$, and specifically, a=109.21 Å, b=109.21 Å and c=82.47 Å, $\alpha=\beta=90°$ and $\gamma=120°$, and has an amino acid sequence of SEQ ID NO. 1, but is not limited thereto (Table 2).

Further, the complex crystal of SeMet-NanR protein and ManNAc-6P of the present invention has a space group of $P3_121$ and a unit-cell dimension of a=109.84±5 Å, b=109.84±5 Å and c=83.38±5 Å, $\alpha=\beta=90°$ and $\gamma=120°$, and specifically, a=109.84 Å, b=109.84 Å and c=83.38 Å, $\alpha=\beta=90°$ and $\gamma=120°$, and the NanR protein has the amino acid sequence of SEQ ID NO. 1, but is not limited thereto (Table 2).

As used herein, the term "space group" means the symmetry of a unit cell of a crystal, and combinations of symmetry elements form symmetry groups. This space is used interchangeably with the space group.

As used herein, the term "unit-cell dimension" is also called lattice parameter, and the unit-cell is the simplest minimum repeating unit constituting the space group, and defined by three crystallographic axes, the lengths of the three vectors (a, b, c) and the inter-axial angles ($\alpha$, $\beta$, $\gamma$).

The phase information can be obtained by multiple isomorphous replacement, multiwavelength anomalous dispersion, molecular replacement or the like. First, multiple isomorphous replacement is a technique of obtaining the phase information by replacing crystals with heavy metals, and collecting and analyzing the data. Second, multiwavelength anomalous dispersion is a technique of obtaining phase information by collecting data using the anomalous dispersion at different wavelengths, in which a specific metal or atom in the crystal is used instead of heavy metals. That is, without the need for data collection of many crystals, data can be easily obtained from one crystal using selenium atom by replacing the amino acid methionine with selenomethionine (Se-Met) using a molecular biological method. However, this method has a disadvantage that data should be obtained from radiation beam. Third, molecular replacement is a method of solving the phase problem from the known similar structure, and it is widely used as the number of known structures is increasing. Data is collected from each structure, and then refinement is conducted to fit our model against the data. This procedure is performed using the known programs (CCP4, Coot, Quanta, CNS, etc.), and standardization of each angle, bond length, etc. is required. In this process, a procedure for fitting the model to the obtained electron density map by computer performance and by eye is repeatedly performed. In the analysis step after refinement of the structure, a lot of information can be derived from the structure with interpretation. In this analysis step, the mechanism of action can be studied, based on the structure. The studies on the correct mechanism of action provide information needed for development of new drugs. Further, the directly related residues can be identified through the structure of the complex of the protein and its regulator, and therefore, important information is provided for the next step for studying the regulator.

In one embodiment of the present invention, diffraction data for the crystal of the present invention were collected at 1.9 Å resolution. Single wavelength anomalous diffraction data for the SeMet-substituted crystals were collected at 2.4 Å resolution. All data were processed with HKL2000 software package. The structure of the NanR/ManNAc-6P complex was determined by analyzing the anomalous signals from Se atoms with the SOLVE program. Density modification and subsequent automated model building were performed using the RESOLVE program. The complex crystal structure was solved at 1.9 Å resolution by molecular replacement with the MOLREP program using the partially refined model of the SeMet crystal. The complex crystal structure was revised using the COOT program and refined using the REFMAC5. The atomic coordinates and structure factor amplitudes of NanR protein/ManNAc-6P obtained by the method have been deposited in the PDB (Protein Data Bank) with accession code of 4IVN. Further, information about this crystal is shown in Table 2.

In still another aspect, the present invention provides a modified NanR protein, a polynucleotide encoding the protein, an expression vector including the polynucleotide, and a transformant introduced with the expression vector.

The modified NanR protein is the same as described above.

The expression vector including the polynucleotide encoding the modified NanR protein provided in the present invention may be, but is not particularly limited to, a vector capable of replicating and/or expressing the polynucleotide in eukaryotic or prokaryotic cells including mammalian cells (e.g., human, monkey, rabbit, rat, hamster, mouse cells, etc.), plant cells, yeast cells, insect cells, or bacteria cells (e.g., *E. coli*, etc.), preferably, a vector which is operably linked to a suitable promoter to express the polynucleotide in the host cells and includes at least one selection marker. More preferably, it may be in the form of a phage, a plasmid, a cosmid, a mini-chromosome, a virus, a retrovirus vector to which the polynucleotide is introduced.

As used herein, the term "transformant" refers to a host cell transformed with the vector, and means a transformant capable of producing a large amount of soluble, or soluble and crystalline NanR protein of the present invention, and also includes a transformant which is introduced with the NanR protein and thus is used to screen candidates for new drug development through NMR, etc, but is not limited thereto. The transformant introduced with the expression vector provided in the present invention may be, but is not particularly limited to, bacterial cells such as *E. coli, Streptomyces, Salmonella typhimurium*, etc.; yeast cells; fungus cells such as *Pichia pastoris*; insect cells such as *Drosophila, Spodoptera* Sf9 cell, etc.; animal cells such as CHO, COS, NSO, 293T, Bowes melanoma cells, etc.; or plants cells, which are transformed by introduction of the expression vector.

As used herein, the term "introduction" refers to delivery of the vector including the polynucleotide encoding the NanR protein into a host cell. This introduction may be performed by various methods known in the art, including calcium phosphate-DNA coprecipitation, DEAE dextran-mediated transfection, polybrene-mediated transfection, electroporation, microinjection, liposome fusion, lipofection and protoplast fusion. Also, term "transfection" means delivery of a desired material into a cell by means of infection using viral particles. In addition, the vector may be introduced into a host cell by gene bombardment. In the present invention, the introduction may be used interchangeably with transformation.

In still another aspect, the present invention provides a method for screening a substance regulating the interaction between NanR and the transcriptional control region of nan operon, which is a cluster of genes regulated by NanR, by utilizing three-dimensional structure of the complex of NanR protein and ManNAc-6P.

Preferably, the method may include the steps of (a) designing a tertiary structure of the complex using the atomic coordinates of the complex of NanR protein and ManNAc-6P, of which protein data bank accession code is 4IVN, that is, the atomic coordinates shown in Table 3; (b) preparing candidates binding to NanR using the tertiary structure thus designed; and (c) examining binding affinity of the candidate for NanR and its regulation of the interaction between NanR and the transcriptional control region of nan operon, but is not limited thereto.

Preferably, the method for screening a substance regulating the interaction between NanR and the transcriptional control region of nan operon may further include the step of determining the candidate as a growth inhibitor for bacteria having nan gene, if the corresponding candidate binding to NanR has the NanR binding affinity similar to or higher than that of ManNAc-6P and maintains or increases interaction between NanR and the transcriptional control region of nan operon, compared to a control group treated without the corresponding candidate. More preferably, the method may further include a method for screening a substance having a higher bacterial growth-inhibiting ability than the candidate screened in step (c) by using the designed tertiary structure.

Preferably, the method for screening a substance regulating interaction between NanR and the transcriptional control region of nan operon may further include the step of determining the candidate as a growth stimulant for bacteria having nan gene, if the corresponding candidate binding to NanR has the NanR binding affinity similar to or higher than that of ManNAc-6P and decreases interaction between NanR and the transcriptional control region of nan operon, compared to a control group treated without the corresponding candidate. More preferably, the method may further include a method for screening a substance having a higher bacterial growth-stimulating ability than the candidate screened in step (c) by using the designed tertiary structure.

In the present invention, the tertiary structure of NanR protein/ManNAc-6P complex was demonstrated, and an electron density difference map showing the interaction of NanR protein and ManNAc-6P in the complex demonstrated that ManNAc-6P mainly binds to L9, L13, and L17 loop structures of the NanR LBD domain. Specifically, it was confirmed that Arg71 of a DNA binding domain (DBD) and Ala137, Ser138, His163, Ser182, Ser183, Ser184, Thr187, Glu229, Pro231, Gly234, or/and Lys240 of a ligand binding domain (LBD) of NanR protein and ManNAc-6P forms a hydrogen bond or a water-mediated hydrogen bond. Based on this information, therefore, a compound or a peptide capable of binding to NanR and regulating its activity can be designed or/and synthesized. The compound is preferably a small molecule compound, but is not limited thereto. In addition, because it is known that the ManNAc-6P binds to NanR to inhibit interaction between NanR and the transcriptional control region of nan operon, the NanR-binding peptides or compounds synthesized by using the NanR structural information may be substances that binds to NanR to inhibit its activity, like ManNAc-6P, but is not limited thereto. The substance may be a substance that maintains or stimulates the inhibitory effect of NanR on transcription of the nan gene through binding competition with ManNAc-6P, if it has the NanR binding affinity similar to or higher than that of ManNAc-6P but does not inhibit the activity.

In the present invention, the bacterial growth may occur in the presence of sialic acid, in particular, N-acetylneuraminic acid (Neu5Ac) as a carbon source.

NanR protein, ManNAc-6P, and the complex thereof are the same as described above. The atomic coordinates for the complex of NanR protein and ManNAc-6P can be obtained from the protein data bank (PDB) accession code or the atomic coordinates shown in Table 3. Atomic coordinates for the complex of NanR protein and ManNAc-6P and the complex of SeMet-NanR protein and ManNAc-6P are shown in Table 3.

Further, the atomic coordinates for the complex of NanR protein and ManNAc-6P and the complex of SeMet-NanR protein and ManNAc-6P can be stored in media for consecutive use in a calculating apparatus such as a computer. Typically, the coordinates can be stored in media (e.g., floppy disks, hard disks, compact disks, magneto-optical media, or electronic media) useful for storing large amounts of data, such as magnetic or optical media. Those skilled in the structural/computational chemistry are used to selecting the computer, storage media, networking and other device or technique.

Based on the three-dimensional structure of the complex of NanR protein and ManNAc-6P or the complex of SeMet-NanR protein and ManNAc-6P demonstrated in the present invention, information about various protein sites including binding sites can be provided by using a computer readable media containing the data of the atomic coordinates and/or three-dimensional structure. Through these procedures, reaction patterns of numerous drug candidates can be predicted without practical experiments, and only the resulting selected substances are subjected to experiments, leading to economic improvement in new drug development.

Further, step (a) of the screening method may include the steps of entering the data of the atomic coordinates for the tertiary structure of the complex into a computer, together with a proper software program; and obtaining a three-dimensional protein structure for visualization and additional computer manipulation, but is not limited thereto.

If all or part of the tertiary structure of the NanR protein/ManNAc-6P complex or the SeMet-NanR protein/ManNAc-6P complex is used, a candidate regulating the binding of NanR protein and ManNAc-6P can be specifically selected or produced. As confirmed by the present inventors, binding of NanR and the transcriptional control region of nan operon is regulated by binding of NanR protein and ManNAc-6P, and thus a candidate regulating the binding of NanR protein and the transcriptional control region of nan operon can be screened by screening the candidate regulating the binding of NanR protein and ManNAc-6P.

The nan operon genes regulated by the transcriptional control region of nan operon are known to be involved in the Neu5Ac catabolism, that is, metabolism for utilizing Neu5Ac as a carbon source, and to play a very important role in proliferation and survival of bacteria in the host intestine in which Neu5Ac is abundant as a carbon source.

Therefore, the candidate which has the NanR binding affinity similar to or higher than that of ManNAc-6P and maintains or increases interaction between NanR and the transcriptional control region of nan operon, compared to a control group treated without the corresponding candidate, is able to prevent a reduction in the function of NanR as the nan operon transcriptional repressor due to binding with ManNAc-6P, and also to maintain or improve the function of NanR as the nan operon transcriptional repressor. Therefore, the candidate inhibits growth of the bacteria having nan operon genes, and shows the effects of reducing proliferation, survival and pathogenicity of the bacteria, and thus it can be determined as a bacterial growth inhibitor or an antibacterial agent.

Meanwhile, the candidate which has the NanR binding affinity similar to or higher than that of ManNAc-6P and decreases interaction between NanR and the transcriptional control region of nan operon, compared to a control group treated without the corresponding candidate, is able to inhibit the function of NanR as the nan operon transcriptional repressor instead of ManNAc-6P and to promote transcription of nan operon. Therefore, the candidate promotes growth of the bacteria having nan operon genes, and shows the effects of increasing proliferation, survival and pathogenicity of the bacteria, and thus it can be determined as a bacterial growth stimulant.

As used herein, the term "candidate" includes DNA, RNA, an antibody, a compound, a peptide or a complex thereof without limitation, as long as it is able to bind with NanR. That is, the candidate may include a substance which is predicted to have a structure capable of binding to the corresponding NanR site based on the analyzed tertiary structure of NanR/ManNAc-6P complex, or which is synthesized, prepared, or modified to have the structure capable of binding thereto, without limitation.

As used herein, the term "nan gene" means a series of genes which are needed for utilizing sialic acid as a carbon source and found in bacteria, and may be a cluster of genes required for catabolism of sialic acid, and in particular, may refer to genes in the form of an operon. Specifically, sialic acid may mean Neu5Ac, and expression of nan genes is up-regulated when sialic acid is supplied. nan genes play an important role in colonization and pathogenic activity of bacteria having nan genes. In the present invention, nan genes may be genes (nanA, nanTL, nanTS, nanTP, nanE or nanK genes, etc.) repressed by NanR protein, but are not limited thereto. For example, *E. coli* requires nanATEK operon for catabolism of Neu5Ac, and NanR is a repressor of this operon. The amino acid sequences and nucleotide sequences of the nan genes can be obtained from the known database such as GenBank at The National Center for Biotechnology Information, and genes represented by amino acid sequences of SEQ ID NOs. 3 to 8 or nucleotide sequences of SEQ ID NOs. 9 to 14 are preferred.

As used herein, the term "bacteria having nan genes" means bacteria that are able to utilize sialic acid as a carbon source because they have nan genes required for utilization of sialic acid as a carbon source. In the present invention, the bacteria may be *V. vulnificus, E. coli, Haemophilus influenza*, or *V. cholerae*, but are not limited thereto, as long as they have nan genes. In particular, the bacteria having nan genes may be those having nan genes, of which transcription is repressed by NanR.

In still another aspect, the present invention provides a method for screening a substance regulating interaction between NanR and ManNAc-6P by using the three-dimensional structure of the complex of NanR protein and ManNAc-6P.

Specifically, the method may be a method for screening a substance regulating interaction between NanR and ManNAc-6P, including the steps of (a) designing a tertiary structure of the complex using the atomic coordinates of the complex of NanR protein and ManNAc-6P, of which protein data bank accession code is 4IVN, that is, the atomic coordinates shown in Table 3; (b) preparing candidates binding to NanR using the tertiary structure thus designed; and (c) examining whether the candidate regulates interaction between NanR protein and ManNAc-6P.

Herein, the terms and designing of the tertiary structure are the same as described above.

In step (c), if the candidate increases interaction between NanR and ManNAc-6P, compared to a control group treated without the corresponding candidate, the candidate is determined as a nan operon expression enhancer or as a bacterial growth stimulant. If the candidate decreases interaction between NanR and ManNAc-6P, compared to a control group treated without the corresponding candidate, the candidate is determined as a nan operon expression suppressor or as a bacterial growth inhibitor. Herein, regulation of the interaction between NanR and the transcriptional control region of nan operon can be also examined.

In still another aspect, the present invention provides an antibacterial composition including the bacterial growth inhibitor as screened above.

The screening method is the same as described above.

As used herein, the term "antibacterial composition" means a composition that functions to inhibit survival and/or growth of microorganisms. In particular, the composition may have an anti-bacterial activity against bacteria having nan genes, and specifically, an anti-bacterial activity against a microorganism selected from the group consisting of *V. vulnificus, E. coli, H. influenza*, and *V. cholera*, but is not limited thereto.

Further, the antibacterial composition of the present invention may be used for the prevention or treatment of various symptoms associated with bacteria having nan genes, in particular, septicemia.

As used herein, the term "septicemia" refers to a systemic inflammatory response caused by severe infection of microorganisms. Septicemia is a condition that is caused by the spread of microorganisms from one organ via the circulating blood, leading to systemic inflammatory response syndrome. However, systemic septicemia can be also caused by inflammatory response and production of inflammatory mediators in a part of the body, even though the microorganisms do not invade the bloodstream. In the present invention, septicemia may be caused by bacteria having nan genes, in particular, *V. vulnificus, E. coli, H. influenza*, and *V. cholera*, but is not limited thereto.

The composition may further include a pharmaceutically acceptable carrier. As used herein, the term "pharmaceutically acceptable carrier" refers to a pharmaceutically acceptable material, composition or vehicle such as a liquid or solid filler, diluent, excipient, solvent or encapsulating material, which is involved in carrying or transporting any composition or component from one organ or a part of the body to another organ or a different region of the body. For administration, the composition of the present invention may include a pharmaceutically acceptable carrier, excipient, or diluent, in addition to the active ingredients described above. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxy benzoate, propylhydroxy benzoate, talc, magnesium stearate, and mineral oil.

According to the conventional methods, the composition of the present invention may be formulated into an oral preparation such as a powder, a granule, a tablet, a capsule, a suspension, an emulsion, a syrup, or an aerosol, an external preparation, suppository, or a sterilized injectable solution. In detail, such preparations may be prepared using diluents or excipients ordinarily employed, such as a filler, an extender, a binder, a wetting agent, a disintegrating agent, and a surfactant. Examples of the solid preparation for oral administration include a tablet, a pill, a powder, a granule, and a capsule, but are not limited thereto. The solid preparation may be prepared by mixing with at least one excipient such as starch, calcium carbonate, sucrose, lactose, or gelatin. Further, in addition to the excipients, lubricants such as magnesium stearate and talc may be used. The liquid formulation for oral administration may include a suspension, a liquid for internal use, an emulsion, a syrup or the like, but is not limited thereto. It may be prepared by adding various excipients such as a wetting agent, a sweetener, a flavor, or a preservative, in addition to general diluents such as water and liquid paraffin. Examples of the formulation for parenteral administration include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, or an injectable ester such as ethyloleate may be used. As a suppository base, witepsol, macrogol, tween 61, cacao butter, lauric butter, glycerogelatin or the like may be used.

Hereinafter, the present invention will be described in more detail with reference to the following Examples. However, these Examples are for illustrative purposes only, and the invention is not intended to be limited by these Examples.

Example 1

Bacterial Strains, Plasmids, and Growth Conditions

The bacterial strains and plasmids used in the present invention are listed in the following Table 1.

TABLE 1

| Strain or plasmid | Relevant characteristics[a] | Reference or source |
|---|---|---|
| Bacterial strains | | |
| *V. vulnificus* | | |
| MO6-24/O | Wild type; Clinical isolate; virulent | Wright AC, 1990 |
| MORR | MO6-24/O with spontaneous Rif[r] mutation, virulent | Laboratory collection |
| MORSR | MO6-24/O with spontaneous Rif[r], Sm[r] mutation, virulent | Laboratory collection |
| BS1209 | MO6-24/O with nanR R57A[b] | This study |
| BS1210 | MO6-24/O with nanR H163L[b] | This study |
| BS1213 | MORSR with nanR H163L[b]; Rif[r], Sm[r] | This study |
| *E. coli* | | |
| DH5α | supE44 ΔlacU169 (φ80 lacZ ΔM15) hsdR17 recA1 endA1 gyrA96 thi-1 relAI | Laboratory collection |
| SM10Δpir | thi thr leu tonA lacY supE recA::RP4-2-Tc::Mu Δ pir, Km[r]; host for π-requiring plasmids; conjugal donor | Miller VL, 1988 |
| BW25113 | lacI[q] rrnB$_{T14}$ ΔlacZ$_{WJ16}$ hsdR514 ΔaraBAD$_{AH33}$ ΔrhaBAD$_{LD78}$ | Datesenko KA, 2000 |
| BSE1201 | BW25113 with ΔnanE | This study |
| BL21 (DE3) | F[−] ompT hsdS (r$_e$[−], m$_B$[−]) gal (DE3) | Laboratory collection |
| Plasmids | | |
| pGEM-T easy | PCR product cloning vector; Ap[r] | Promega |
| pBS1201 | pGEM-T easy with nanR gene orf; Ap[r] | This study |
| pDM4 | Suicide vector; onR6K; Cm[r] | Milton DL, 1996 |
| pBS1206 | pDM4 with nanR R57A[b]; Cm[r] | This study |
| pBS1209 | pDM4 with nanR H163L[b]; Cm[r] | This study |
| pNT-K20A | pGEM-T easy with nanR K20A[b]; Ap[r] | This study |
| pNT-K21A | pGEM-T easy with nanR K21A[b]; Ap[r] | This study |
| pNT-R23A | pGEM-T easy with nanR R23A[b]; Ap[r] | This study |
| pNT-R23L | pGEM-T easy with nanR R23L[b]; Ap[r] | This study |
| pNT-R57A | pGEM-T easy with nanR R57A[b]; Ap[r] | This study |
| pNT-R57L | pGEM-T easy with nanR R57L[b]; Ap[r] | This study |
| pNT-R60A | pGEM-T easy with nanR R60A[b]; Ap[r] | This study |
| pNT-R60L | pGEM-T easy with nanR R60L[b]; Ap[r] | This study |
| pNT-K65A | pGEM-T easy with nanR K65A[b]; Ap[r] | This study |
| pNT-S138A | pGEM-T easy with nanR S138A[b]; Ap[r] | This study |
| pNT-H163A | pGEM-T easy with nanR H163A[b]; Ap[r] | This study |
| pNT-H163L | pGEM-T easy with nanR H163L[b]; Ap[r] | This study |
| pNT-S182A | pGEM-T easy with nanR S182A[b]; Ap[r] | This study |
| pNT-S184A | pGEM-T easy with nanR S184A[b]; Ap[r] | This study |
| pNT-T187A | pGEM-T easy with nanR T187A[b]; Ap[r] | This study |
| pNT-E229L | pGEM-T easy with nanR E229L[b]; Ap[r] | This study |
| pNT-K240A | pGEM-T easy with nanR K240A[b]; Ap[r] | This study |
| pNT-K240M | pGEM-T easy with nanR K240M[b]; Ap[r] | This study |
| pBAD-24BS | pBAD24 with unique XhoI site instead of XbaI site; Ap[r] | Kim Y, 2010 |
| pNB-WT | pBAD-24BS with nanR; Ap[r] | This study |
| pNB-K20A | pBAD-24BS with nanR K20A[b]; Ap[r] | This study |
| pNB-K21A | pBAD-24BS with nanR K21A[b]; Ap[r] | This study |
| pNB-R23A | pBAD-24BS with nanR R23A[b]; Ap[r] | This study |
| pNB-R23L | pBAD-24BS with nanR R23L[b]; Ap[r] | This study |
| pNB-R57A | pBAD-24BS with nanR R57A[b]; Ap[r] | This study |
| pNB-R57L | pBAD-24BS with nanR R57L[b]; Ap[r] | This study |
| pNB-R60A | pBAD-24BS with nanR R60A[b]; Ap[r] | This study |
| pNB-R60L | pBAD-24BS with nanR R60L[b]; Ap[r] | This study |
| pNB-K65A | pBAD-24BS with nanR K65A[b]; Ap[r] | This study |
| pNB-S138A | pBAD-24BS with nanR S138A[b]; Ap[r] | This study |
| pNB-H163A | pBAD-24BS with nanR H163A[b]; Ap[r] | This study |
| pNB-H163L | pBAD-24BS with nanR H163L[b]; Ap[r] | This study |
| pNB-S182A | pBAD-24BS with nanR S182A[b]; Ap[r] | This study |
| pNB-S184A | pBAD-24BS with nanR S184A[b]; Ap[r] | This study |
| pNB-T187A | pBAD-24BS with nanR T187A[b]; Ap[r] | This study |
| pNB-E229L | pBAD-24BS with nanR E229L[b]; Ap[r] | This study |
| pNB-K240A | pBAD-24BS with nanR K240A[b]; Ap[r] | This study |
| pNB-K240M | pBAD-24BS with nanR K240M[b]; Ap[r] | This study |
| pBBR_lux | Broad host range vector containing luxCDABE operon; Cm[r] | Lenz DH, 2004 |
| pBS0915 | pBBR_lux with P$_{nanTp}$; Cm[r] | This study |
| pHis-Parallel1 | Protein expression vector; Ap[r] | Sheffield P, 1999 |
| pBS0820 | pHIS-Parallel1 with nanR; Ap[r] | Kim BS, 2011 |
| pNH-R57A | pHis-Parallel1 with nanR R57A[b]; Ap[r] | This study |
| pNH-R60A | pHis-Parallel1 with nanR R60A[b]; Ap[r] | This study |
| pNH-S138A | pHis-Parallel1 with nanR S138A[b]; Ap[r] | This study |
| pNH-H163L | pHis-Parallel1 with nanR H163L[b]; Ap[r] | This study |
| pNH-S182A | pHis-Parallel1 with nanR S182A[b]; Ap[r] | This study |
| pNH-S184A | pHis-Parallel1 with nanR S184A[b]; Ap[r] | This study |

TABLE 1-continued

| Strain or plasmid | Relevant characteristics[a] | Reference or source |
|---|---|---|
| pNH-E229L | pHis-Parallel1 with nanR E229L[b]; Ap[r] | This study |
| pNH-K240A | pHis-Parallel1 with nanR K240A[b]; Ap[r] | This study |
| pKD46 | $P_{BAD}$-gam-beta-exo oriR101 repA101[ts]; Ap[r] | Datesenko KA, 2000 |
| pKD13 | FRT Km[r] FRT PS1 PS4 oriR6Ky; Ap[r] | Datesenko KA, 2000 |
| pCP20 | c/875 $AP_{aflp\ orip}$SC101[ts]; Ap[r], Cm[r] | Datesenko KA, 2000 |
| pBS0921 | pRLG770 with $P_{nanE}$; Ap[r] | Kim BS, 2011 |

[a]Ap[r] represents ampicillin resistant; Cm[r] represents Chloramphenicol resistant; Km[r] represents kanamycin resistant; Rif[r] represents rifampicin resistant; Sm[r] represents streptomycin resistant.
[b]In the representation of mutant, first letter indicates an original amino acid, number indicates the position of mutation, and the last letter indicates an amino acid substituted due to mutation.

Unless noted otherwise, the *E. coli* and *V. vulnificus* strains were grown at 37° C. in LB (Luria-Bertani) medium and at 30° C. in LB supplemented with 2% NaCl, respectively. Where appropriate, antibiotics were added to medium at the following concentrations: 10 µg/ml chloramphenicol, 100 µg/ml ampicillin, and 100 µg/ml kanamycin for *E. coli*, and 3 µg/ml chloramphenicol, 100 µg/ml rifampicin, and 100 µg/ml streptomycin for *V. vulnificus*. M9 minimal medium was supplemented with the appropriate carbon sources (5 mM Neu5Ac alone, or 5 mM Neu5Ac, 10 mM D-xylose, and 10 mM L-proline). ManNAc-6P was purchased from Carbosynth (Berkshire, UK). All other chemicals were purchased from Sigma (St. Louis, Mo.).

Example 2

Construction of Plasmids and Strains

The nanR gene was amplified by PCR and cloned into the pGEM-T easy vector to form the pBS1201 construct. Site-directed mutations were introduced into this plasmid using the QuickChange™ Site-Directed Mutagenesis Kit (Agilent). The WT or mutant nanR genes were then subcloned into the NcoI and XhoI sites of the pBAD-24BS or pHis-parallell expression vector to construct the pNB- and pNH-plasmids, respectively. The R57A and H163L mutant nanR genes were subcloned into the SphI and SpeI sites of pDM4 to form pBS1208 and 1209, respectively.

To generate the NanR-dependent luciferase promoter-reporter plasmid (pBS0915), the intergenic region between nanE and nanTP was liberated from the pBS0909 plasmid and ligated with BamHI-digested pBBR_lux. To construct the nanR R57A mutant *V. vulnificus* strain (BS1209) by homologous recombination, *E. coli* SM10λ pir,tra (containing pBS1208) (Miller and Mekalanos, J Bacteriol 170(6): pp 2575-2583, 1988) was used as a conjugal donor to MO6-24/O, Similarly, *E. coli* SM10λ pir,tra containing pBS1209 was used as a conjugal donor in conjunction with either MO6-24/O or MORSR to generate the nanR H163L mutants (BS1210 or BS1213, as indicated in Table 1). Conjugation and isolation of the transconjugants were performed as described previously. To construct the nanE deletion mutant *E. coli* strain (BSE1201), the lambda Red-recombineering method was used, as known previously. Briefly, the kanamycin resistant (KmR) cassette from pKD13 was PCR amplified and then electroporated into the BW25113 strain containing pKD46. Insertion of the KmR cassette into nanE was confirmed by PCR, and the cassette was subsequently removed from the chromosome by transforming pCP20 into kanamycin resistant cells. After verifying the deletion of nanE by PCR, the cells were maintained at 37° C. for the plasmid curing.

Example 3

*E. coli* Dual Plasmid System

*E. coli* strains were co-transformed with a luciferase reporter plasmid (pBS0915) and one of the pNB-series of plasmids that express NanR. Cells were cultured overnight and then diluted into the appropriate fresh media (supplemented M9 in FIG. 3; LB in FIG. 4) containing arabinose (0.002%), and incubated at 37° C. until cells grew to early exponential phase. Relative luminescence unit (RLU) was calculated by dividing the luminescence by the $A_{600}$, as described previously. For screening ligand-sensing residues, the BSE1201 strain (ΔaraBAD ΔnanE) was used as the host cell instead of DH5α to ensure that the arabinose was not used as a carbon source and that ManNAc-6P generated from Neu5Ac was accumulated in the cell.

Example 4

In Vitro Transcription Assay and qRT-PCR

In vitro transcription assays with wild-type or mutant NanR proteins were performed according to procedures described previously. RNA extraction, cDNA synthesis, and real time PCR amplification of the cDNA were performed as described previously.

Example 5

In Vitro Growth Defect and Mouse Experiments

MO6-24/O (WT), BS1209 (R57A mutant), and BS1210 (H163L mutant) strains were cultured overnight and then serially diluted in PBS. 10 mL of each dilution were spotted onto M9 minimal media supplemented with 5 mM Neu5Ac only or 5 mM Neu5Ac, 10 mM D-xylose, and 10 mM L-proline. The growth and phenotype of the strains were examined after incubating at 30° C. for 24 hours.

For the mouse intestine colonization competition assay, 10 mice (6 weeks old, female ICR) were provided with drinking water containing rifampicin (50 µg/ml) for 24 hours to eliminate resident bacteria. After a starvation period without food and water, mice were intragastrically injected with the bacterial mixture of MORR (WT; RifR) and BS1213 (H163L mutant; RifR, SmR) (approximately 1×10[6] CFU per strain). At 12 hours after infection, mice were euthanatized and the small intestines were collected and homogenated in 5 ml of PBS. Equal amounts of neat or diluted homogenates were spread onto LBS agar supplemented with 2% NaCl and either rifampicin alone (to count the sum of WT and H163L mutant cells), or rifampicin and streptomycin (to count the H163L mutant cells only). The competitive index was calculated by dividing the recovered mutant/WT ratio by the inoculated mutant/WT ratio. For the mouse survival test, five mice per group were intragastrically infected with 4×10$^8$ CFU of either MO6-24/O (WT) or BS1210 (H163L mutant) strains and monitored for 1 day.

All animal experiments were performed according to the recommended procedures for the care and use of laboratory animals from the Institute of Laboratory Animal Resource at Seoul National University. The protocol was approved by the Committee on the Ethics of Animal Experiments of Seoul National University (Institutional Animal Care and Use Committee approval number: SNU-111130-2).

Example 6

Western Blot, EMSA, and DNaseI Footprinting Assay

Purified His-NanR protein was used to raise a primary polyclonal antibody by immunizing European rabbits (*Oryctolagus curiculus*). First, after one primary injection containing 500 μg of protein, three boosters containing 200 μg of protein was performed at 2-week intervals. Western blotting, EMSA and DNaseI footprinting assays were performed according to typical procedures known in the art.

Example 7

Protein Expression and Purification

Expression and purification of the NanR protein was performed according to typical procedures known in the art. To obtain the selenomethionine (SeMet)-substituted NanR protein, the methionine auxotroph *E. coli* B834 (DE3) strain (Novagen) was grown in minimal medium supplemented with 50 mg/ml SeMet. The SeMet-substituted NanR was purified and obtained from the culture by the addition of 5 mM methionine to all buffers.

Example 8

Crystallization, Diffraction, and Structure Determination

Crystallization trials of the purified NanR protein performed using the sitting drop vapor-diffusion method at 21° C. were unsuccessful. However, the crystals were obtained when NanR and ManNAc-6P were mixed in a 1:100 molar ratio and incubated on ice for 2 hours.

The crystallization of complex was optimized under the following conditions: 10% PEG 2,000 MME, 0.1 M ammonium sulfate, 0.3 M sodium formate, 3% PGA-LM, and 0.1 M sodium acetate (pH 5.0 to 5.5). Crystals appeared within a day and were grown for a further 5 days for diffraction experiments. The complex crystals were transferred to a cryoprotectant solution containing 10% PEG 2,000 MME, 0.1 M ammonium sulfate, 0.3 M sodium formate, 3% PGA-LM, 0.1 M sodium acetate (pH 5.5), and 30% glycerol, and then placed immediately in a −173° C. nitrogen gas stream.

Diffraction data for the complex crystals were collected at 1.9 Å resolution. SeMet-substituted complex crystals were grown under the same crystallization conditions as described above. Single wavelength anomalous diffraction data for the SeMet-substituted crystals were collected at 2.4 Å resolution. All data were processed with HKL2000 package. The structure of the NanR/ManNAc-6P complex was determined by analyzing the anomalous signals from Se atoms with the SOLVE program. Density modification and subsequent automated model building were performed using the RESOLVE program. The complex crystal structure was solved at 1.9 Å resolution by molecular replacement with the MOLREP program using the partially refined model of the SeMet crystal. The complex crystal structure was revised using the COOT program and refined using the REFMAC5. The refinement included the translation-liberation-screw (TLS) procedure. The final refined model resulted in R$_{free}$ and R$_{cryst}$ values of 0.235 and 0.183, respectively. No density was visible for the Met1 to Lys5 and Glu82 to Glu90 regions of NanR-A, and the Met1 to Lys5, Thr81 to Gly91, and Asn278 regions of NanR-B. These residues were not included in the model. The model contained 525 amino acid residues, two ManNAc-6P molecules, and 221 water molecules, and satisfied the quality criteria limits of the PROCHECK program.

The crystallographic data statistics are summarized in the following Table 2.

TABLE 2

| Data collection and refinement statistics for ManNAc-6P/NanR complex | | |
|---|---|---|
| Dataset | SeMet-NanR complexed with ManNAc-6P | NanR complexed with ManNAc-6P |
| Wavelength | 0.97917 | 1.0000 |
| Space group | P3$_1$21 | P3$_1$21 |
| Unit cell (Å) | a = b = 109.84, c = 83.38 | a = b = 109.21, c = 82.47 |
| | α = β = 90°, γ = 120° | α = β = 90°, γ = 120° |
| Resolution, (Å) | 50.0-2.40 (2.49-2.40) | 50.0-1.90 (1.93-1.90) |
| No. of total reflections | 508,845 | 330,826 |
| No. of unique reflections | 23,076 | 45,033 |
| Redundancy | 22.1 (22.47) | 7.3 (7.3) |
| Completeness (%) | 99.9 (100.0) | 99.9 (100.0) |
| R$_{sym}$ (%)$^a$ | 9.4 (31.5) | 4.7 (47.3) |
| I/σ(I) | 50.27 (12.28) | 42.05 (3.15) |
| Refinement | | |
| Resolution (Å) | | 30.0-1.90 |
| Reflections in work/test sets | | 42,737/2,268 |
| R$_{work}$/R$_{free}$ (%)$^{b,c}$ | | 18.3/23.5 |

TABLE 2-continued

Data collection and refinement statistics for ManNAc-6P/NanR complex

| Dataset | SeMet-NanR complexed with ManNAc-6P | NanR complexed with ManNAc-6P |
|---|---|---|
| R.m.s. deviations | | |
| Bond lengths (Å) | | 0.021 |
| Bond angles (°) | | 2.126 |
| Model composition | | 525 residues |
| | | 221 waters |
| | | 2 ManNAc-6P |
| Geometry | | |
| Favored regions (%) | | 98.8 |
| Allowed regions (%) | | 1.2 |
| PDB accession code | | 4IVN |

$^{a}R_{sym} = \Sigma |I_i - <I>|/\Sigma I$ where $I_i$ is the intensity of the i-th observation and $<I>$ is the mean intensity of the reflections.
$^{b}R_{work} = \Sigma ||F_{obs}| - |F_{calc}||/\Sigma |F_{obs}|$ where $F_{calc}$ and $F_{obs}$ are measured and calculated, respectively.
$^{c}R_{free} = \Sigma ||F_{obs}| - |F_{calc}||/\Sigma |F_{obs}|$ where all reflections belong to a test set of randomly selected data.

TABLE 3

```
HEADER   TRANSCRIPTION REGULATOR     23-JAN-13   4IVN

TITLE    THE VIBRIO VULNIFICUS NANR PROTEIN COMPLEXED WITH MANNAC-6P

COMPND   MOL_ID: 1:

COMPND 2 MOLECULE: TRANSCRIPTIONAL REGULATOR:

COMPND 3 CHAIN: A. B:

COMPND 4 SYNONYM: NANR:

COMPND 5 ENGINEERED: YES

SOURCE   MOL_ID: 1:

SOURCE 2 OAGANISM_SCIENTIFIC: VIBRIO VULNIFICUS:

SOURCE 3 ORGANISM_TAXID: 196600:

SOURCE 4 STRAIN: YJ016:

SOURCE 5 EXPRESSION_SYSTEM: ESCHERICHIA COLI:

SOURCE 6 EXPRESSION_SYSTEM_TAXID: 562

KEYWDS   ISOMERASE FOLD. NAN OPERON REGULATOR FOR SIALIC ACID CATABOLISM.

KEYWDS 2 TRANSCRIPTION REGULATOR

EXPDTA   X-RAY DIFFRACTION

AUTHOR   J. HWANG, M. H. KIM

REVDAT 2 20-NOV-13 4INV: JRNL

REVDAT 1 17-JUL-13 4IVN 0

JRNL     AUTH   J. HWANG, B. S. KIM, S. Y. JANG, J. G. LIM, D. J. YOU,
         H. S. JUNG, T. K. OH,

JRNL     AUTH 2 J. O. LEU, S. H. CHOI, M. H. KIM

JRNL     TITL   STRUCTURAL INSIGHTS INTO THE REGULATION OF SIALIC ACID

JRNL     TITL 2 CATABOLISM BY THE VIBRIO VULNIFICUS TRANSCRIPTIONAL

JRNL     TITL 3 REPRESSOR NANR

JRNL     REF    PROC. NATL. ACAD. SCI. USA V. 110 E2829 2013

JRNL     REFN   ISSN 0027-8424
```

TABLE 3-continued

```
JRNL      PMID  23832782
JRNL      DOI   10.1073/PNAS.1302859110
REMARK 2
REMARK 2 RESOLUTION. 1.90 ANGSTROMS.
REMARK 3
REMARK 3 REFINEMENT.
REMARK 3   PROGRAM:     REFMAC 5.6.0117
REMARK 3   AUTHORS:     MURSHUDOV. VAGIN. DODSON
REMARK 3
REMARK 3   REFINEMENT TARGET: MAXIMUM LIKELIHOOD
REMARK 3
REMARK 3 DATA USED IN REFINEMENT.
REMARK 3   RESOLUTION RANGE HIGH (ANGSTROMS): 1.90
REMARK 3   RESOLUTION RANGE LOW  (ANGSTROMS): 30.00
REMARK 3   DATA CUTOFF            (SIGMA(F)): NULL
REMARK 3   COMPLETENESS FOR RANGE        (%): 99.9
REMARK 3   NUMBER OF REFLECTIONS: 42737
REMARK 3
REMARK 3 FIT TO DATA USED IN REFINEMENT.
REMARK 3   CROSS-VALIDATION METHOD: THROUGHOUT
REMARK 3   FREE R VALUE TEST SET SELECTION: RANDOM
REMARK 3   R VALUE (WORKING + TEST SET): 0.183
REMARK 3   R VALUE (WORKING SET): 0.181
REMARK 3   FREE R VALUE: 0.235
REMARK 3   FREE R VALUE TEST SET SIZE (%): 5.000
REMARK 3   FREE R VALUE TEST SET COUNT: 2268
REMARK 3
REMARK 3 FIT IN THE HIGHEST RESOLUTION BIN.
REMARK 3   TOTAL NUMBER OF BINS USED: 20
REMARK 3   BIN RESOLUTION RANGE HIGH (A): 1.90
REMARK 3   BIN RESOLUTION RANGE LOW  (A): 1.95
REMARK 3   REFLECTION IN BIN (WORKING SET): 2947
REMARK 3   BIN COMPLETENESS (WORKING + TEST) (%): 99.97
REMARK 3   BIN R VALUE (WORKING SET): 0.2690
REMARK 3   BIN FREE R VALUE SET COUNT: 162
REMARK 3   BIN FREE R VALUE: 0.3630
REMARK 3
REMARK 3 NUMBER OF NON-HYDROGEN ATOMS USED IN REFINEMENT.
REMARK 3   PROTEIN ATOMS: 4004
REMARK 3   NUCLEIC ACID ATOMS: 0
```

TABLE 3-continued

```
REMARK 3 HETEROGEN ATOMS: 38
REMARK 3 SOLVENT ATOMS: 221
REMARK 3
REMARK 3 B VALUES.
REMARK 3 FROM WILSON PLOT (A**2): NULL
REMARK 3 MEAN B VALUE (OVERALL. A**2): 42.47
REMARK 3 OVERALL ANISOTROPIC B VALUE.
REMARK 3 B11 (A**2): -2.27000
REMARK 3 B22 (A**2): -2.27000
REMARK 3 B33 (A**2): 3.41000
REMARK 3 B12 (A**2): -1.14000
REMARK 3 B13 (A**2): 0.00000
REMARK 3 B23 (A**2): 0.00000
REMARK 3
REMARK 3 ESTIMATED OVERALL COORDINATE ERROR.
REMARK 3 ESU BASED ON R VALUE (A): 0.142
REMARK 3 ESU BASED ON FREE R VALUE (A): 0.144
REMARK 3 ESU BASED ON MAXIMUM LIKELIHOOD (A): 0.106
REMARK 3 ESU FOR B VALUES BASED ON MAXIMUM LIKELIHOOD (A**2): 7.038
REMARK 3
REMARK 3 CORRELATION COEFFICIENTS.
REMARK 3 CORRELATION COEFFICIENT FO-FC: 0.956
REMARK 3 CORRELATION COEFFICIENT FO-FC FREE: 0.941
REMARK 3
REMARK 3 RMS DEVIATIONS FROM IDEAL VALUES COUNT RMS WEIGHT
REMARK 3 BOND LENGTHS REFINED ATOMS (A): 4096 : 0.021 : 0.019
REMARK 3 BOND LENGTHS OTHERS (A): NULL : NULL : NULL
REMARK 3 BOND ANGLES REFINED ATOMS (DEGREES): 5548 : 2.126 : 1.982
REMARK 3 BOND ANGLES OTHERS (DEGREES): NULL : NULL : NULL
REMARK 3 TORSION ANGLES, PERIOD 1 (DEGREES): 521 : 6.387 : 5.000
REMARK 3 TORSION ANGLES, PERIOD 2 (DEGREES): 165 : 35.450 : 23.576
REMARK 3 TORSION ANGLES, PERIOD 3 (DEGREES): 716 : 16.845 : 15.000
REMARK 3 TORSION ANGLES, PERIOD 4 (DEGREES): 32 : 18.969 : 15.000
REMARK 3 CHIRAL-CENTER RESTRAINTS (A**3): 669 : 0.146 : 0.200
REMARK 3 GENERAL PLANES REFINED ATOMS (A): 2984 : 0.010 : 0.021
REMARK 3 GENERAL PLANES OTHERS (A): NULL : NULL : NULL
REMARK 3 NON-BONDED CONTACTS REFINED ATOMS (A): NULL : NULL : NULL
REMARK 3 NON-BONDED CONTACTS OTHERS (A): NULL : NULL : NULL
REMARK 3 NON-BONDED TORSION REFINED ATOMS (A): NULL : NULL : NULL
REMARK 3 NON-BONDED TORSION OTHERS (A): NULL : NULL : NULL
```

TABLE 3-continued

```
REMARK 3 H-BOND (X...Y) REFINED ATOMS (A): NULL : NULL : NULL
REMARK 3 H-BOND (X...Y) OTHERS (A): NULL : NULL : NULL
REMARK 3 POTENTIAL METAL-ION REFINED ATOMS (A): NULL : NULL : NULL
REMARK 3 POTENTIAL METAL-ION OTHERS (A): NULL : NULL : NULL
REMARK 3 SYMMETRY VDW REFINED ATOMS (A): NULL : NULL : NULL
REMARK 3 SYMMETRY VDW OTHERS (A): NULL : NULL : NULL
REMARK 3 SYMMETRY H-BOND REFINED ATOMS (A): NULL : NULL : NULL
REMARK 3 SYMMETRY H-BOND OTHERS (A): NULL : NULL : NULL
REMARK 3 SYMMETRY METAL-ION REFINED ATOMS (A): NULL : NULL : NULL
REMARK 3 SYMMETRY METAL-ION OTHERS (A): NULL : NULL : NULL
REMARK 3
REMARK 3 ISOTROPIC THERMAL FACTOR RESTRAINTS. COUNT RMS WEIGHT
REMARK 3 MAIN-CHAIN BOND REFINED ATOMS (A**2): NULL : NULL : NULL
REMARK 3 MAIN-CHAIN BOND OTHER ATOMS (A**2): NULL : NULL : NULL
REMARK 3 MAIN-CHAIN ANGLE REFINED ATOMS (A**2): NULL : NULL : NULL
REMARK 3 MAIN-CHAIN ANGLE OTHER ATOMS (A**2): NULL : NULL : NULL
REMARK 3 SIDE-CHAIN BOND REFINED ATOMS (A**2): NULL : NULL : NULL
REMARK 3 SIDE-CHAIN BOND OTHER ATOMS (A**2): NULL : NULL : NULL
REMARK 3 SIDE-CHAIN ANGLE REFINED ATOMS (A**2): NULL : NULL : NULL
REMARK 3 SIDE-CHAIN ANGLE OTHER ATOMS (A**2): NULL : NULL : NULL
REMARK 3 LONG RANGE B REFINED ATOMS (A**2): NULL : NULL : NULL
REMARK 3 LONG RANGE B OTHER ATOMS (A**2): NULL : NULL : NULL
REMARK 3
REMARK 3 ANISOTROPIC THERMAL FACTOR RESTRAINTS. COUNT RMS WEIGHT
REMARK 3 RIGID-BOND RESTRAINTS (A**2): NULL : NULL : NULL
REMARK 3 SPHERICITY: FREE ATOMS (A**2): NULL : NULL : NULL
REMARK 3 SPHERICITY: BONDED ATOMS (A**2): NULL : NULL : NULL
REMARK 3
REMARK 3 NCS RESTRAINTS STATISTICS
REMARK 3 NCS TYPE: LOCAL
REMARK 3 NUMBER OF DIFFERENT NCS PAIRS: 1
REMARK 3 GROUP CHAIN1 RANGE CHAIN2 RANGE COUNT RMS WEIGHT
REMARK 3 1 A 6 277 B 6 277 366 0.15 0.05
REMARK 3
REMARK 3 TLS DETAILS
REMARK 3 NUMBER OF TLS GROUPS: 4
REMARK 3
REMARK 3 TLS GROUP: 1
REMARK 3 NUMBER OF COMPONENTS GROUP: 1
REMARK 3 COMPONENTS C SSSEQI TO C SSSEQI
```

TABLE 3-continued

```
REMARK 3 RESIDUE RANGE: A 5 A 81
REMARK 3 ORIGIN FOR THE GROUP (A): 17.7780 -5.8420 8.8420
REMARK 3 T TENSOR
REMARK 3 T11: 0.0449 T22: 0.1497
REMARK 3 T33: 0.1331 T12: 0.0044
REMARK 3 T13: -0.0544 T23: -0.0500
REMARK 3 L TENSOR
REMARK 3 L11: 3.4953 L22: 2.2054
REMARK 3 L33: 2.1117 L12: -0.5910
REMARK 3 L13: 0.7559 L23: 0.5527
REMARK 3 S TENSOR
REMARK 3 S11: 0.2213 S12: 0.2193 S13: -0.1430
REMARK 3 S21: -0.1435 S22: -0.2725 S23: 0.3625
REMARK 3 S31: 0.1735 S32: -0.1381 S33: 0.0512
REMARK 3
REMARK 3 TLS GROUP: 2
REMARK 3 NUMBER OF COMPONENTS GROUP: 1
REMARK 3 COMPONENTS C SSSEQI TO C SSSEQI
REMARK 3 RESIDUE RANGE: A 91 A 278
REMARK 3 ORIGIN FOR THE GROUP (A): 45.2910 8.9760 13.2780
REMARK 3 T TENSOR
REMARK 3 T11: 0.0570 T22: 0.0852
REMARK 3 T33: 0.0778 T12: 0.0414
REMARK 3 T13: 0.0370 T23: 0.0537
REMARK 3 L TENSOR
REMARK 3 L11: 0.5889 L22: 0.6680
REMARK 3 L33: 0.8170 L12: -0.0380
REMARK 3 L13: 0.1453 L23: 0.1381
REMARK 3 S TENSOR
REMARK 3 S11: 0.0958 S12: 0.1783 S13: 0.0946
REMARK 3 S21: -0.1548 S22: -0.0145 S23: -0.0391
REMARK 3 S31: -0.0769 S32: -0.1389 S33: -0.0812
REMARK 3
REMARK 3 TLS GROUP: 3
REMARK 3 NUMBER OF COMPONENTS GROUP: 1
REMARK 3 COMPONENTS C SSSEQI TO C SSSEQI
REMARK 3 RESIDUE RANGE: B 6 B 80
REMARK 3 ORIGIN FOR THE GROUP (A): 82.6480 3.2410 8.3210
REMARK 3 T TENSOR
REMARK 3 T11: 0.0362 T22: 0.1890
```

TABLE 3-continued

```
REMARK 3 T33: 0.2221 T12: 0.0038
REMARK 3 T13: 0.0694 T23: -0.0873
REMARK 3 L TENSOR
REMARK 3 L11: 1.7284 L22: 1.3274
REMARK 3 L33: 2.4459 L12: 0.2465
REMARK 3 L13: -1.0201 L23: 0.0720
REMARK 3 S TENSOR
REMARK 3 S11: 0.0630 S12: 0.0848 S13: -0.0810
REMARK 3 S21: -0.1023 S22: 0.0872 S23: -0.1534
REMARK 3 S31: -0.0463 S32: 0.4472 S33: -0.1502
REMARK 3
REMARK 3 TLS GROUP: 4
REMARK 3 NUMBER OF COMPONENTS GROUP: 1
REMARK 3 COMPONENTS C SSSEQI TO C SSSEQI
REMARK 3 RESIDUE RANGE: B 92 B 277
REMARK 3 ORIGIN FOR THE GROUP (A): 55.3100 -10.8280 14.5630
REMARK 3 T TENSOR
REMARK 3 T11: 0.0555 T22: 0.0233
REMARK 3 T33: 0.1270 T12: 0.0218
REMARK 3 T13: -0.0027 T23: -0.0342
REMARK 3 L TENSOR
REMARK 3 L11: 0.9177 L22: 0.6147
REMARK 3 L33: 0.8648 L12: -0.0846
REMARK 3 L13: -0.0381 L23: 0.0605
REMARK 3 S TENSOR
REMARK 3 S11: 0.1126 S12: 0.1400 S13: -0.1727
REMARK 3 S21: -0.1213 S22: -0.0199 S23: -0.1418
REMARK 3 S31: 0.1198 S32: 0.0177 S33: -0.0927
REMARK 3
REMARK 3 BULK SOLVENT MODELLING
REMARK 3 METHOD USED: MASK
REMARK 3 PARAMETERS FOR MASK CALCULATION
REMARK 3 VDW PROBE RADIUS: 1.20
REMARK 3 ION PROBE RADIUS: 0.80
REMARK 3 SHRINKAGE RADIUS: 0.80
REMARK 3
REMARK 3 OTHER REFINEMENT REMARKS: NULL
REMARK 4
REMARK 4 4IVN COMPLIES WITH FORMAT V. 3.30. 13-JUL-11
REMARK 100
```

TABLE 3-continued

```
REMARK 100 THIS ENTRY HAS BEEN PROCESSED BY PDBJ ON 28-JAN-13.
REMARK 100 THE RCSB ID CODE IS RCSB077266.
REMARK 200
REMARK 200 EXPERIMENTAL DETAILS
REMARK 200 EXPERIMENT TYPE: X-RAY DIFFRACTION
REMARK 200 DATE OF DATA COLLECTION: 08-JUN-12
REMARK 200 TEMPERATURE (KELVIN): 100.15
REMARK 200 PH: 5.0
REMARK 200 NUMBER OF CRYSTALS USED: 1
REMARK 200
REMARK 200 SYNCHROTRON (Y/N): Y
REMARK 200 RADIATION SOURCE: PHOTON FACTORY
REMARK 200 BEAMLINE: BL -17A
REMARK 200 X-RAY GENERATOR MODEL: NULL
REMARK 200 MONOCHROMATIC OR LAUE (M/L): M
REMARK 200 WAVELENGTH OR RANGE (A): 1.0000
REMARK 200 MONOCHROMATOR: NULL
REMARK 200 OPTICS: NULL
REMARK 200
REMARK 200 DETECTOR TYPE: CCD
REMARK 200 DETECTOR MANUFACTURER: NULL
REMARK 200 INTENSITY-INTEGRATION SOFTWARE: NULL
REMARK 200 DATA SCALING SOFTWARE: NULL
REMARK 200
REMARK 200 NUMBER OF UNIQUE REFLECTIONS: 45033
REMARK 200 RESOLUTION RANGE HIGH (A): 1.900
REMARK 200 RESOLUTION RANGE LOW (A): 50.000
REMARK 200 REJECTION CRITERIA (SIGMA00): 2.000
REMARK 200
REMARK 200 OVERALL.
REMARK 200 COMPLETENESS FOR RANGE (%): 99.9
REMARK 200 DATA REDUNDANCY: NULL
REMARK 200 R MERGE (1): NULL
REMARK 200 R SYM (1): NULL
REMARK 200 <I/SIGMA(1)> FOR THE DATA SET: NULL
REMARK 200
REMARK 200 IN THE HIGHEST RESOLUTION SHELL
REMARK 200 HIGHEST RESOLUTION SHELL. RANGE HIGH (A): 1.90
REMARK 200 HIGHEST RESOLUTION SHELL. RANGE LOW (A): 1.93
REMARK 200 COMPLETENESS FOR SHELL (%): 100.0
```

TABLE 3-continued

```
REMARK 200 DATA REDUNDANCY IN SHELL: NULL
REMARK 200 R MERGE FOR SHELL (1): NULL
REMARK 200 R SYM FOR SHELL (1): NULL
REMARK 200 <I/SIGMA(1)> FOR SHELL: NULL
REMARK 200
REMARK 200 DIFFRACTION PROTOCOL: SINGLE WAVELENGTH
REMARK 200 METHOD USED TO DETERMINE THE STRUCTURE: MOLECULAR REPLACEMENT
REMARK 200 SOFTWARE USED: NULL
REMARK 200 STARTING MODEL: NULL
REMARK 200
REMARK 200 REMARK: NULL
REMARK 280
REMARK 280 CRYSTAL
REMARK 280 SOLVENT CONTENT. VS (%): 47.42
REMARK 280 MATTHEWS COEFFICIET. VM (ANGSTROMS**3/DA): 2.34
REMARK 280
REMARK 280 CRYSTALLIZATION CONDITIONS: 10% PEG 2000 MME. 0.1M AMMONIUM
REMARK 280 SULFATE. 0.3M SODIUM FORMATE. 3% PGA-LM. 0.1M SODIUM ACETATE. PH
REMARK 280 5.0. VAPOR DIFFUSION. SITTING DROP. TEMPERATURE 294.15K
REMARK 290
REMARK 290 CRYSTALLOGRAPHIC SYMMETRY
REMARK 290 SYMMETRY OPERATORS FOR SPACE GROUP: P 31 2 1
REMARK 290
REMARK 290 SYMOP SYMMETRY
REMARK 290 NNNMMM OPERATOR
REMARK 200 1555 X, Y, Z
REMARK 290 2555 -Y, X-Y, Z + 1/3
REMARK 290 3555 -X + Y, -X, Z + 2/3
REMARK 200 4555 Y, X, -Z
REMARK 290 5555 X-Y, -Y, -Z + 2/3
REMARK 290 6555 -X, -X + Y, -Z + 1/3
REMARK 290
REMARK 290 WHERE NMN -> OPERATOR NUMBER
REMARK 290 MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290 SMTRY1 1 1.000000 0.000000 0.000000 0.00000
```

TABLE 3-continued

```
REMARK 290 SMTRY2 1 0.000000 1.000000 0.000000 0.00000
REMARK 290 SMTRY3 1 0.000000 0.000000 1.000000 0.00000
REMARK 290 SMTRY1 2 -0.500000 -0.866025 0.000000 0.00000
REMARK 290 SMTRY2 2 0.866025 -0.500000 0.000000 0.00000
REMARK 290 SMTRY3 2 0.000000 0.000000 1.000000 27.49067
REMARK 290 SMTRY1 3 -0.500000 0.866025 0.000000 0.00000
REMARK 290 SMTRY2 3 -0.866025 -0.500000 0.000000 0.00000
REMARK 290 SMTRY3 3 0.000000 0.000000 1.000000 54.98133
REMARK 290 SMTRY1 4 -0.500000 0.866025 0.000000 0.00000
REMARK 290 SMTRY2 4 0.866025 0.500000 0.000000 0.00000
REMARK 290 SMTRY3 4 0.000000 0.000000 -1.000000 0.00000
REMARK 290 SMTRY1 5 1.000000 0.000000 0.000000 0.00000
REMARK 290 SMTRY2 5 0.000000 -1.000000 0.000000 0.00000
REMARK 290 SMTRY3 5 0.000000 0.000000 -1.000000 54.98133
REMARK 290 SMTRY1 6 -0.500000 -0.866025 0.000000 0.00000
REMARK 290 SMTRY2 6 -0.866025 0.500000 0.000000 0.00000
REMARK 290 SMTRY3 6 0.000000 0.000000 -1.000000 27.49067
REMARK 290
REMARK 290 REMARK: NULL
REMARK 300
REMARK 300 BIOMOLECULE: 1
REMARK 300 SEE REMARK 350 FOR THE AUTHOR PROVIDED AND/OR PROGRAM
REMARK 300 GENERATED ASSEMBLY INFORMATION FOR THE STRUCTURE IN
REMARK 300 THIS ENTRY. THE REMARK MAY ALSO PROVIDE INFORMATION ON
REMARK 300 BURIED SURFACE AREA.
REMARK 350
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN RE GENERATED BY APPLYING BIOMT TRANSFORMATIONS
REMARK 350 GIVEN BELOW. BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 AUTHOR DETERMINED BIOLOGICAL UNIT: DIMERIC
REMARK 350 SOFTWARE DETERMINED QUATERNARY STRUCTURE: DIMERIC
REMARK 350 SOFTWARE USED: PISA
REMARK 350 TOTAL BURIED SURFACE AREA: 4850 ANGSTROM**2
REMARK 350 SURFACE AREA OF THE COMPLEX: 21940 ANGSTROM**2
REMARK 350 CHANGE IN SOLVENT FREE ENERGY: -45.0 KCAL/MOL
REMARK 350 APPLY THE FOLLOWING TO CHAINS: A. B
```

TABLE 3-continued

```
REMARK 350 BIOMT1 1 1.000000 0.000000 0.000000 0.00000
REMARK 350 BIOMT2 1 0.000000 1.000000 0.000000 0.00000
REMARK 350 BIOMT3 1 0.000000 0.000000 1.000000 0.00000
REMARK 465
REMARK 465 MISSING: RESIDUES
REMARK 465 THE FOLLOWING RESIDUES WERE NOT LOCATED IN THE
REMARK 465 EXPERIMENT. (M = MODEL NUMBER; RES = RESIDUE NAME; C=  CHAIN
REMARK 465 IDENTIFIER, SSSEQ = SEQUENCE NUMBER, I = INSERTION CODE.)
REMARK 465
REMARK 465 M RES C SSSEQI
REMARK 465 MET A 1
REMARK 465 GLY A 2
REMARK 465 SER A 3
REMARK 465 PRO A 4
REMARK 465 LYS A 5
REMARK 465 GLU A 82
REMARK 465 SER A 83
REMARK 465 ARG A 84
REMARK 465 GLN A 85
REMARK 465 GLN A 86
REMARK 465 ASN A 87
REMARK 465 HIS A 88
REMARK 465 ILE A 89
REMARK 465 GLU A 90
REMARK 465 MET B 1
REMARK 465 GLY B 2
REMARK 465 SER B 3
REMARK 465 PRO B 4
REMARK 465 LYS B 5
REMARK 465 THR B 81
REMARK 465 GLU B 82
REMARK 465 SER B 83
REMARK 465 ARG B 84
REMARK 465 GLN B 85
REMARK 465 GLN B 86
REMARK 465 ASN B 87
REMARK 465 HIS B 88
REMARK 465 ILE B 89
REMARK 465 GLU B 90
REMARK 465 GLY B 91
```

TABLE 3-continued

```
REMARK 465 ASN B 278
REMARK 500
REMARK 500 GEOMETRY AND STEREOCHEMISTRY
REMARK 500 SUBTOPIC: CLOSE CONTACTS IN SAME ASYMMETRIC UNIT
REMARK 500
REMARK 500 THE FOLLOWING ATOMS ARE IN CLOSE CONTACT.
REMARK 500
REMARK 500 ATM1 RES C SSEQI ATM2 RES C SSEQI DISTANCE
REMARK 500 O HOH A 1189 O HOH A 1200 2.18
REMARK 500 O HOH B 1186 O HOH B 1205 2.19
REMARK 500
REMARK 500 REMARK: NULL
REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M = MODEL NUMBER: RES = RESIDUE NAME: C = CHAIN
REMARK 500 IDENTIFIER; SSEQ = SEQUENCE NUMBER: I = INSERTION CODE)
REMARK 500
REMARK 500 STANDARD TABLE:
REMARK 500 FORMAT: (10X, I3, 1X.2(A3, 1X, A1, I4, A1, 1X, A4, 3X), 1X, F6.3)
REMARK 500
REMARK 500 EXPECTED VALUES PROTEIN: ENGH AND HUBER. 1999
REMARK 500 EXPECTED VALUES NUCLEIC ACID: CLOWNEY ET AL 1996
REMARK 500
REMARK 500 M RES CSSEQI ATM1 RES CSSEQI ATM2 DEVIATION
REMARK 500 HIS A 34 CG HIS A 34 CD2 0.064
REMARK 500 GLU A 160 C GLU A 160 O 0.118
REMARK 500 HIS A 192 CG HIS A 192 CD2 0.055
REMARK 500 THR B 220 CB THR B 220 CG2 -0.202
REMARK 500
REMARK 500 REMARK: NULL
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
```

TABLE 3-continued

```
REMARK 500 THAN 6*RMSD (M = MODEL NUMBER: RES = RESIDUE NAME: C = CHAIN
REMARK 500 IDENTIEIER; SSEQ = SEQUENCE NUMBER: I = INSERTION CODE).
REMARK 500
REMARK 500 STANDARD TABLE:
REMARK 500 FORMAT: (10X, I3, 1X, A3, 1X, A1, I4, A1.3
            (1X, A4, 2X), I2X, F5.1)
REMARK 500
REMARK 500 EXPECTED VALUES PROTEIN: ENGH AND HUBER. 1999
REMARK 500 EXPECTED VALUES NUCLEIC ACID: CLOWNEY ET AL 1996
REMARK 500
REMARK 500 M RES CSSEQI ATM1 ATM2 ATM3
REMARK 500 ASP A 161 CB - CG - OD1 ANGL. DEV. = 6.7 DEGREES
REMARK 500 ARG A 171 NE - CZ - NH1 ANGL. DEV. = 4.1 DEGREES
REMARK 500 ARG A 171 NE - CZ - NH2 ANGL. DEV. = -3.1 DEGREES
REMARK 500 ARG A 227 NE - CZ - NH1 ANGL. DEV. = 3.5 DEGREES
REMARK 500 ASP A 248 CB - CG - OD2 ANGL. DEV. = -5.8 DEGREES
REMARK 500 ARG S 227 NE - CZ - NH2 ANGL. DEV. = -4.0 DEGREES
REMARK 500
REMARK 500 REMARK: NULL
REMARK 500
REMARK 500 GEOMETRY AND STEREOCHEMISTRY
REMARK 500 SUBTOPIC: TORSION ANGLES
REMARK 500
REMARK 500 TORSION ANGLES OUTSIDE THE EXPECTED RAMACHANDRAN REGIONS:
REMARK 500 (M = MODEL NUMBER; RES = RESIDUE NAME: C = CHAIN IDENTIFIER:
REMARK 500 SSEQ = SEQUENCE NUMBER: I = INSERTION CODE).
REMARK 500
REMARK 500 STANDARD TABLE:
REMARK 500 FORMAT: (10X, I3, 1X, A3, 1X, A1, I4, A1, 4X, F7.2, 3X, F7.2)
REMARK 500
REMARK 500 EXPECTED VALUES: G J KLEYWEGT AND T A JONES 1996). PHI/PSI-
REMARK 500 CHOLOGY. RAMACHANDRAN REVISITED. STRUCTURE 4. 1395-1400
REMARK 500
REMARK 500 M RES CSSEQI PSI PHI
REMARK 500 ARG A 227 81.53 63.17
REMARK 500 PRO A 259 -19.64 -49.20
REMARK 500 THR B 50 -143.74 -116.57
REMARK 500 ASP B 201 31.72 70.03
REMARK 500 ARG B 227 76.48 65.91
REMARK 500
```

TABLE 3-continued

```
REMARK 500 REMARK: NULL
REMARK 500
REMARK 500 GEOMETRY AND STEREOCHEMISTRY
REMARK 500 SUBTOPIC: NON-CIS. NON-TRANS
REMARK 500
REMARK 500 THE FOLLOWING PEPTIDE BONDS DEVIATE SIGNIFICANTLY FROM BOTH
REMARK 500 CIS AND TRANS CONFORMATION. CIS BONDS, IF ANY, ARE LISTED
REMARK 500 ON CISPEP RECORDS. TRANS IS DEFINED AS 180 +/- 30 AND
REMARK 500 CIS IS DEFINED AS 0 +/- 30 DEGREES.
REMARK 500 MODEL OMEGA
REMARK 500 ALA A 277 ASN A 276 -135.53
REMARK 500
REMARK 500 REMARK: NULL
REMARK 500
REMARK 500 GEOMETRY AND STEREOCHEMISTRY
REMARK 500 SUBTOPIC: CHIRAL CENTERS
REMARK 500
REMARK 500 UNEXPECTED CONFIGURATION OF THE FOLLOWING CHIRAL
REMARK 500 CENTER(S) USING IMPROPER CA--C--CB--N CHIRALITY
REMARK 500 FOR AMINO ACIDS AND C1'--O4'--N1(N9)--C2' FOR
REMARK 500 NUCLEIC ACIDS OR EQUIVALENT ANGLE
REMARK 500 M = MODEL NUMBER: RES = RESIDUE NAME: C = CHAIN
REMARK 500 IDENTIFIER: SSEQ = SEQUENCE NUMBER: I = INSERTION CODE
REMARK 500
REMARK 500 STANDARD TABLE:
REMARK 500 FORMAT: (10X, I3, 1X, A3, 1X, A1, I4, A1, 6X, F5.1,
       6X, A1, 10X, A1, 3X, A16)
REMARK 500
REMARK 500 M RES CSSEQI IMPROPER EXPECTED FOUND DETAILS
REMARK 500 VAL B 25 24.5 L L OUTSIDE RANGE
REMARK 500 SER B 216 24.9 L L OUTSIDE RANGE
REMARK 500
REMARK 500 REMARK: NULL
REMARK 800
REMARK 800 SITE
REMARK 800 SITE_IDENTIFIER: AC1
REMARK 800 EVIDENCE_CODE: SOFTWARE
REMARK 800 SITE_DESCRIPTION: BINDING SITE FOR RESIDUE BMX A 1000
REMARK 800
REMARK 800 SITE_IDENTIFIER: AC2
```

TABLE 3-continued

```
REMARK 800 EVIDENCE_CODE: SOFTWARE
REMARK 800 SITE_DESCRIPTION: BINDING SITE FOR RESIDUE BMX B 1000
DBREF  4IVN A 1 278 UNP Q7MD38 Q7MD38_VIBVY 1 278
DBREF  4IVN B 1 278 UNP Q7MD38 Q7MD38_VIBVY 1 278
SEQRES 1  A 278 MET GLY SER PRO LYS ASN LEU LEU VAL ARG LEU ARG SER
SEQRES 2  A 278 ASN MET GLU PRO PHE SER LYS LYS LEU ARG VAL VAL ALA
SEQRES 3  A 278 ASP TYR ILE LEU GLU ASN ALA HIS ASP VAL GLN PHE GLN
SEQRES 4  A 278 THR ILE THR ASP LEU ALA ARG ASN THR GLN THR SER GLU
SEQRES 5  A 278 ALA THR VAL VAL ARG LEU CYS ARG ASP MET GLY TYR LYS
SEQRES 6  A 278 GLY TYR SER ASP PHE ARG MET ALA LEU ALA VAL ASP LEU
SEQRES 7  A 278 SER GLN THR GLU SER ARG GLN GLN ASN HIS ILE GLU GLY
SEQRES 8  A 278 ASP ILE CYS ASP VAL SER ALA GLN SER ALA VAL ASP SER
SEQRES 9  A 278 LEU GLN ASP THR ALA LYS LEU ILE ASP ARG LYS SER LEU
SEQRES 10 A 278 ALA ARG ILE VAL GLU ARG VAL HIS GLN ALA GLU PHE ILE
SEQRES 11 A 278 GLY CYS ILE GLY VAL GLY ALA SER SER ILE VAL GLY ARG
SEQRES 12 A 278 TYR LEU ALA TYR ARG LEU ILE ARG ILE GLY LYS LYS ALA
SEQRES 13 A 278 ILE MET PHE GLU ASP THR HIS LEU ALA ALA MET SER ALA
SEQRES 14 A 278 SER ARG SER SER GLN GLY ASP LEU TRP PHE ALA VAL SER
SEQRES 15 A 278 SER SER GLY SER THR LYS GLU VAL ILE HIS ALA ALA GLY
SEQRES 16 A 278 LEU ALA TYR LYS ARG ASP ILE PRO VAL VAL SER LEU THR
SEQRES 17 A 278 ASN ILE ASN HIS SER PRO LEU SER SER LEU SEE THR GLU
SEQRES 18 A 278 MET LEU VAL ALA ALA ARG PRO GLU GLY PRO LEU THR GLY
SEQRES 19 A 278 GLY ALA PHE ALA SER LYS VAL GLY ALA LEU LEU LEU VAL
SEQRES 20 A 278 ASP VAL LEU VAL ASN SER LEU LEU GLU SER TYR PRO GLU
SEQRES 21 A 278 TYR LYS ASP SER VAL GLN GLU THR ALA GLU VAL VAL ILE
SEQRES 22 A 278 PRO LEU MET ALA ASN
SEQRES 1  B 278 MET GLY SER PRO LYS ASN LEU LEU VAL ARG LEU ARG SER
SEQRES 2  B 278 ASN MET GLU PRO PHE SER LYS LYS LEU ARG VAL VAL ALA
SEQRES 3  B 278 ASP TYR ILE LEU GLU ASN ALA HIS ASP VAL GLN PHE GLN
SEQRES 4  B 278 THR ILE THR ASP LEU ALA ARG ASN THR GLN THR SER GLU
SEQRES 5  B 278 ALA THR VAL VAL ARG LEU CYS ARG ASP MET GLY TYR LYS
SEQRES 6  B 278 GLY TYR SER ASP PHE ARG MET ALA LEU ALA VAL ASP LEU
SEQRES 7  B 278 SER GLN THR GLU SER ARG GLN GLN ASN HIS ILE GLU GLY
SEQRES 8  B 278 ASP ILE CYS ASP VAL SER ALA GLN SER ALA VAL ASP SER
SEQRES 9  B 278 LEU GLN ASP THR ALA LYS LEU ILE ASP ARG LYS SER LEU
SEQRES 10 B 278 ALA ARG ILE VAL GLU ARG VAL HIS GLN ALA GLU PHE ILE
SEQRES 11 B 278 GLY CYS ILE GLY VAL GLY ALA SER SER ILE VAL GLY ARG
SEQRES 12 B 278 TYR LEU ALA TYR ARG LEU ILE ARG ILE GLY LYS LYS ALA
SEQRES 13 B 278 ILE MET PHE GLU ASP THR HIS LEU ALA ALA MET SER ALA
SEQRES 14 B 278 SER ARG SER SER GLN GLY ASP LEU TRP PHE ALA VAL SER
```

TABLE 3-continued

```
SEQRES  15 B  278  SER SER GLY SER THR LYS GLU VAL ILE HIS ALA ALA GLY
SEQRES  16 B  278  LEU ALA TYR LYS ARG ASP ILE PRO VAL VAL SER LEU THR
SEQRES  17 B  278  ASN ILE ASN HIS SER PRO LEU SER SER LEU SER THR GLU
SEQRES  18 B  278  MET LEU VAL ALA ALA ARG PRO GLU GLY PRO LEU THR GLY
SEQRES  19 B  278  GLY ALA PHE ALA SER LYS VAL GLY ALA LEU LEU LEU VAL
SEQRES  20 B  278  ASP VAL LEU VAL ASN SER LEU LEU GLU SER TYR PRO GLU
SEQRES  21 B  278  TYR LYS ASP SER VAL GLN GLU THR ALA GLU VAL VAL ILE
SEQRES  22 B  278  PRO LEU MET ALA ASN
HET       BMX  A1000     19
HET       BMX  B1000     19
HETNAM    BMX  2-(ACETYLAMINO)-2-DEOXY-5-O-PHOSPHONO-ALPHA-D-
HETNAM  2 BMX  MANNOPYRANOSE
FORMUL  3 BMX  2(C8 H16 N O9 P)
FORMUL  5 HOH  *221(H2 O)
HELIX    1  1 ASN A    6  ASN A   14  1                                   9
HELIX    2  2 SER A   19  GLN A   37  1                                  19
HELIX    3  3 THR A   40  GLN A   49  1                                  10
HELIX    4  4 SER A   51  MET A   62  1                                  12
HELIX    5  5 GLY A   66  SER A   79  1                                  14
HELIX    6  6 ASP A   92  ILE A  112  1                                  21
HELIX    7  7 ASP A  113  ALA A  127  1                                  15
HELIX    8  8 GLY A  136  ILE A  152  1                                  17
HELIX    9  9 ASP A  161  ARG A  171  1                                  11
HELIX   10 10 THR A  187  ARG A  200  1                                  14
HELIX   11 11 LEU A  215  SER A  219  5                                   5
HELIX   12 12 ALA A  236  TYR A  258  1                                  23
HELIX   13 13 GLU A  260  VAL A  271  1                                  12
HELIX   14 14 VAL A  272  MET A  276  5                                   5
HELIX   15 15 LEU B    7  ASN B   14  1                                   8
HELIX   16 16 SER B   19  GLN B   37  1                                  19
HELIX   17 17 THR B   40  GLN B   49  1                                  10
HELIX   18 18 SER B   51  MET B   62  1                                  12
HELIX   19 19 GLY B   66  GLN B   80  1                                  15
HELIX   20 20 ILE B   93  ILE B  112  1                                  20
HELIX   21 21 ASP B  113  ALA B  127  1                                  15
HELIX   22 22 GLY B  136  ILE B  152  1                                  17
HELIX   23 23 ASP B  161  ARG B  171  1                                  11
HELIX   24 24 THR B  187  ARG B  200  1                                  14
HELIX   25 25 SER B  213  SER B  219  5                                   7
HELIX   26 26 ALA B  236  TYR B  258  1                                  23
```

TABLE 3-continued

```
HELIX   27 27 GLU B 260  VAL B 271 1                                  12
HELIX   28 28 VAL B 272  MET B 276 5                                   5
SHEET    1 A 5 ALA A 156  PHE A 159  0
SHEET    2 A 5 PHE A 129  ILE A 133  1  N  CYS A 132   O  ILE A 157
SHEET    3 A 5 ASP A 176  VAL A 181  1  O  VAL A 181   N  ILE A 133
SHEET    4 A 5 VAL A 204  THR A 208  1  O  VAL A 205   N  TRP A 178
SHEET    5 A 5 GLU A 221  VAL A 224  1  O  LEU A 223   N  SER A 206
SHEET    1 B 5 LYS B 155  PHE B 169  0
SHEET    2 B 5 PHE B 129  ILE B 133  1  N  CYS B 132   O  PHE B 150
SHEET    3 B 5 ASP B 176  VAL B 181  1  O  VAL B 181   N  ILE B 133
SHEET    4 B 5 VAL B 204  THR B 208  1  O  VAL B 205   N  TRP B 178
SHEET    5 B 5 GLU B 221  VAL B 224  1  O  LEU B 223   N  SER B 206
SITE     1 AC1 19 VAL A 135  ALA A 137  SER A 138  HIS A 163
SITE     2 AC1 19 MET A 167  SER A 182  SER A 183  SER A 184
SITE     3 AC1 19 THR A 187  GLY A 230  HOH A1102  HOH A1103
SITE     4 AC1 19 HOH A1105  HOH A1108  HOH A1109  TYR B 147
SITE     5 AC1 19 ARG B 151  VAL B 272  MET B 276
SITE     1 AC2 19 TYR A 147  ARG A 151  VAL A 272  VAL B 135
SITE     2 AC2 19 ALA B 137  SER B 138  HIS B 163  MET B 167
SITE     3 AC2 19 SER B 182  SER B 183  SER B 184  THR B 187
SITE     4 AC2 19 GLY B 230  GLY B 234  HOH B1102  HOH B1104
SITE     5 AC2 19 HOH B1113  HOH B1116  HOH B1119
CRYST1  109.205  109.205  82.472  90.00  90.00  120.00 P 31 2 1    12
ORIGX1    1.000000  0.000000  0.000000        0.00000
ORIGX2    0.000000  1.000000  0.000000        0.00000
ORIGX3    0.000000  0.000000  1.000000        0.00000
SCALE1    0.009157  0.005287  0.000000        0.00000
SCALE2    0.000000  0.010574  0.000000        0.00000
SCALE3    0.000000  0.000000  0.012125        0.00000
ATOM      1  N   ASN A   6      18.407 -18.282   7.841  1.00 65.46           N
ANISOU    1  N   ASN A   6       8081   7427   9362    -71  -1349  -1116     N
ATOM      2  CA  ASN A   6      17.833 -18.480   9 220  1.00 78.17           C
ANISOU    2  CA  ASN A   6       9687   8914  11100   -298  -1254   -922     C
ATOM      3  C   ASN A   6      17.340 -17.238   9.992  1.00 70.53           C
ANISOU    3  C   ASN A   6       8645   8122  10032   -404  -1084   -781     C
ATOM      4  O   ASN A   6      16.118 -17.096  10.194  1.00 66.38           O
ANISOU    4  O   ASN A   6       8016   7595   9612   -550  -1052   -786     O
ATOM      5  CB  ASN A   6      18.736 -19.329  10.109  1.00 88.32           C
ANISOU    5  CB  ASN A   6      11096  10027  12435   -313  -1258   -782     C
ATOM      6  CG  ASN A   6      17.953 -20.005  11.207  1.00 95.86           C
```

TABLE 3-continued

| | | |
|---|---|---|
| ANISOU 6 CG ASN A 6 | 12184 10920 13697 -546 -1219 -623 | C |
| ATOM 7 OD1 ASN A 6 | 17.873 -21.226 11.251 1.00 107.17 | O |
| ANISOU 7 OD1 ASN A 6 | 13547 11970 15202 -597 -1328 -633 | O |
| ATOM 8 ND2 ASN A 6 | 17.322 -19.210 12.071 1.00 97.16 | N |
| ANISOU 8 ND2 ASN A 6 | 12156 11085 13676 -693 -1062 -481 | N |
| ATOM 9 N LEU A 7 | 18.256 -16.363 10.444 1.00 58.71 | N |
| ANISOU 9 N LEU A 7 | 7186 5771 8352 -334 -981 -670 | N |
| ATOM 10 CA LEU A 7 | 17.874 -14.959 10.576 1.00 53.24 | C |
| ANISOU 10 CA LEU A 7 | 6409 6277 7542 -347 -868 -634 | C |
| ATOM 11 C LEU A 7 | 17.247 -14.501 9.231 1.00 52.37 | C |
| ANISOU 11 C LEU A 7 | 6217 6266 7416 -252 -947 -805 | C |
| ATOM 12 O LEU A 7 | 16.236 -13.769 9.229 1.00 51.26 | O |
| ANISOU 12 O LEU A 7 | 5972 6208 7298 -314 -908 -823 | O |
| ATOM 13 CB LEU A 7 | 19.043 -14.019 10.921 1.00 50.90 | C |
| ANISOU 13 CB LEU A 7 | 6155 6120 7063 -254 -782 -540 | C |
| ATOM 14 CG LEU A 7 | 18.713 -12 520 10 859 1.00 49.25 | C |
| ANISOU 14 CG LEU A 7 | 5865 6091 6757 -243 -693 -528 | C |
| ATOM 15 CD1 LEU A 7 | 19.803 -11.693 11.514 1.00 47.98 | C |
| ANISOU 15 CD1 LEU A 7 | 5741 6023 6467 -204 -605 -420 | C |
| ATOM 16 CD2 LEU A 7 | 18.585 -12.057 9.419 1.00 55.09 | C |
| ANISOU 16 CD2 LEU A 7 | 6565 6925 7442 -106 -766 -653 | C |
| ATOM 17 N LEU A 8 | 17.826 -14.909 8.095 1.00 48.71 | N |
| ANISOU 17 N LEU A 8 | 5796 5808 6902 -89 -1061 -936 | N |
| ATOM 18 CA LEU A 8 | 17.236 -14.480 6.813 1.00 52.64 | C |
| ANISOU 18 CA LEU A 8 | 6227 6424 7349 14 -1145 -1090 | C |
| ATOM 19 C LEU A 8 | 15.872 -15.125 6.516 1.00 54.82 | C |
| ANISOU 19 C LEU A 8 | 6418 6600 7813 -84 -1252 -1224 | C |
| ATOM 20 O LEU A 8 | 14.938 -14.452 5.025 1.00 53.15 | O |
| ANISOU 20 O LEU A 8 | 6104 6493 7596 -80 -1276 -1290 | O |
| ATOM 21 CB LEU A 8 | 18.198 -14.636 5.632 1.00 56.78 | C |
| ANISOU 21 CB LEU A 8 | 6811 7036 7725 226 -1224 -1200 | C |
| ATOM 22 CG LEU A 8 | 19.337 -13.604 5.585 1.00 59.35 | C |
| ANISOU 22 CG LEU A 8 | 7168 7535 7847 331 -1112 -1082 | C |
| ATOM 23 CD1 LEU A 8 | 20.359 -14.019 4.548 1.00 61.43 | C |
| ANISOU 23 CD1 LEU A 8 | 7482 7879 7980 527 -1172 -1189 | C |
| ATOM 24 CD2 LEU A 8 | 18.807 -12.203 5.309 1.00 61.52 | C |
| ANISOU 24 CD2 LEU A 8 | 7375 7970 8028 336 -1051 -1023 | C |
| ATOM 25 N VAL A 9 | 15.746 -15.410 6.841 1.00 55.47 | N |
| ANISOU 25 N VAL A 9 | 6532 6467 8078 -175 -1322 -1259 | N |
| ATOM 26 CA VAL A 9 | 14.429 - 17.074 6.760 1.00 58.23 | C |

TABLE 3-continued

| ANISOU | 26 | CA | VAL | A | 9 | 6780 6689 8654 -317 -1409 -1365 | C |
|---|---|---|---|---|---|---|---|
| ATOM | 27 | C | VAL | A | 9 | 13.437 -16.415 7.731 1.00 57.99 | C |
| ANISOU | 27 | C | VAL | A | 9 | 6635 6706 8693 -504 -1271 -1237 | C |
| ATOM | 28 | O | VAL | A | 9 | 12.280 16.188 7.358 1.00 57.55 | O |
| ANISOU | 28 | O | VAL | A | 9 | 6441 5695 8730 -557 -1316 -1342 | O |
| ATOM | 29 | CB | VAL | A | 9 | 14.474 -18.614 7.032 1.00 57.89 | C |
| ANISOU | 29 | CB | VAL | A | 9 | 6796 6362 8839 -410 -1507 -1399 | C |
| ATOM | 30 | CG1 | VAL | A | 9 | 13.036 -19.236 6.987 1.00 59.10 | C |
| ANISOU | 30 | CG1 | VAL | A | 9 | 5817 6379 9260 -593 -1588 -1499 | C |
| ATOM | 31 | CG2 | VAL | A | 9 | 15.470 -19.286 6.080 1.00 54.95 | C |
| ANISOU | 31 | CG2 | VAL | A | 9 | 6529 5945 8405 -202 -1649 -1558 | C |
| ATOM | 32 | N | ARG | A | 10 | 13.879 -16.101 8.950 1.00 60.02 | N |
| ANISOU | 32 | N | ARG | A | 10 | 6938 5969 8896 -592 -1109 -1030 | N |
| ATOM | 33 | CA | ARG | A | 10 | 12.962 -15.536 9.943 1.00 59.43 | C |
| ANISOU | 33 | CA | ARG | A | 10 | 6753 6954 8872 -762 -966 -924 | C |
| ATOM | 34 | C | ARG | A | 10 | 12.503 -14.194 9.486 1.00 63.36 | C |
| ANISOU | 34 | C | ARG | A | 10 | 7151 7660 9262 -673 -937 -984 | C |
| ATOM | 35 | O | ARG | A | 10 | 11.310 -13.887 9.640 1.00 63.30 | O |
| ANISOU | 35 | O | ARG | A | 10 | 6991 7700 9361 -772 -910 -1026 | O |
| ATOM | 36 | CB | ARG | A | 10 | 13.483 -15.574 11.378 1.00 60.57 | C |
| ANISOU | 36 | CB | ARG | A | 10 | 6973 7073 8969 -872 -810 -704 | C |
| ATOM | 37 | CG | ARG | A | 10 | 13.546 -17.002 11.931 1.00 65.64 | C |
| ANISOU | 37 | CG | ARG | A | 10 | 7688 7478 9776 -1007 -843 -620 | C |
| ATOM | 38 | CD | ARG | A | 10 | 13.686 -17.062 13.447 1.00 73.54 | C |
| ANISOU | 38 | CD | ARG | A | 10 | 8733 8471 10736 -1155 -681 -384 | C |
| ATOM | 39 | NE | ARC | A | 10 | 14.758 -16.175 13.887 1.00 83.65 | N |
| ANISOU | 39 | NE | ARG | A | 10 | 10100 9901 11784 -1032 -604 -301 | N |
| ATOM | 40 | CZ | ARG | A | 10 | 14.600 -14.871 14.134 1.00 85.86 | C |
| ANISOU | 40 | CZ | ARG | A | 10 | 10308 10389 11926 -998 -497 -305 | C |
| ATOM | 41 | NH1 | ARG | A | 10 | 13.408 -14.290 14.008 1.00 89.12 | N |
| ANISOU | 41 | NH1 | ARG | A | 10 | 10562 10898 12401 -1065 -449 -383 | N |
| ATOM | 42 | NH2 | ARG | A | 10 | 15.640 -14.143 14.496 1.00 80.60 | N |
| ANISOU | 42 | HH2 | ARG | A | 10 | 9719 9828 11079 -893 -449 -243 | N |
| ATOM | 43 | N | LEU | A | 11 | 13.396 -13.442 8.823 1.00 61.15 | N |
| ANISOU | 43 | N | LEU | A | 11 | 6945 7497 8793 -484 -958 -996 | N |
| ATOM | 44 | CA | LEU | A | 11 | 13.060 -12.083 8.336 1.00 57.08 | C |
| ANISOU | 44 | CA | LEU | A | 11 | 6356 7160 8172 -383 -941 -1026 | C |
| ATOM | 45 | C | LEU | A | 11 | 11.935 -12.184 7.310 1.00 62.42 | C |
| ANISOU | 45 | C | LEU | A | 11 | 6914 7862 8941 -350 -1083 -1203 | C |
| ATOM | 46 | O | LEU | A | 11 | 10.889 -11.519 7.422 1.00 64.23 | O |

TABLE 3-continued

| | | | | |
|---|---|---|---|---|
| ANISOU | 46 | O LEU A 11 | 7004 8166 9235 -392 -1064 -1235 | O |
| ATOM | 47 | CB LEU A 11 | 14.281 -11.356 7.750 1.00 51.02 | C |
| ANISOU | 47 | CB LEU A 11 | 5694 6496 7197 -202 -938 -983 | C |
| ATOM | 48 | CG LEU A 11 | 14.332 -9.827 7.472 1.00 48.59 | C |
| ANISOU | 48 | CG LEU A 11 | 5355 6343 6764 -103 -890 -936 | C |
| ATOM | 49 | CD1 LEU A 11 | 13.734 -8.925 8.551 1.00 47.87 | C |
| ANISOU | 49 | CD1 LEU A 11 | 5180 6286 6723 -204 -766 -554 | C |
| ATOM | 50 | CD2 LEU A 11 | 15.773 -9.397 7.195 1.00 47.01 | C |
| ANISOU | 50 | CD2 LEU A 11 | 5268 6201 6391 18 -854 -849 | C |
| ATOM | 51 | N ARG A 12 | 12.177 -13.000 6.304 1.00 62.22 | N |
| ANISOU | 51 | N ARG A 12 | 6940 7784 8916 -260 -1236 -1333 | N |
| ATOM | 52 | CA ARG A 12 | 11.161 -13.339 5.313 1.00 65.79 | C |
| ANISOU | 52 | CA ARG A 12 | 7414 8371 9592 -229 -1406 -1532 | C |
| ATOM | 53 | C ARG A 12 | 9.747 -13.675 5.870 1.00 67.06 | C |
| ANISOU | 53 | C ARG A 12 | 7271 8334 9875 -427 -1403 -1582 | C |
| ATOM | 54 | O ARG A 12 | 8.751 -13.026 5.515 1.00 61.31 | O |
| ANISOU | 54 | O ARG A 12 | 6398 7712 9184 -407 -1448 -1664 | O |
| ATOM | 55 | CB ARG A 12 | 11.668 -14.512 4.477 1.00 58.50 | C |
| ANISOU | 55 | CB ARG A 12 | 7719 8488 9821 -148 -1562 -1678 | C |
| ATOM | 56 | CG ARC A 12 | 12.419 14.097 3.240 1.00 75.79 | C |
| ANISOU | 56 | CG ARG A 12 | 8726 9567 10502 94 -1645 -1751 | C |
| ATOM | 57 | CD ARG A 12 | 11.467 -13.429 2.259 1.00 83.06 | C |
| ANISOU | 57 | CD ARG A 12 | 9543 10643 11373 192 -1765 -1875 | C |
| ATOM | 58 | NE ARG A 12 | 10.071 -13.817 2.471 1.00 86.82 | N |
| ANISOU | 58 | NE ARG A 12 | 9855 11037 12095 45 -1841 -1987 | N |
| ATOM | 59 | CZ ARG A 12 | 9.063 -13.495 1.655 1.00 94.85 | C |
| ANISOU | 59 | CZ ARG A 12 | 10751 12158 13130 111 -1987 -2137 | C |
| ATOM | 60 | NH1 ARG A 12 | 9.288 -12.784 0.554 1.00 95.02 | N |
| ANISOU | 60 | NH1 ARG A 12 | 10819 12358 12918 329 -2075 -2177 | N |
| ATOM | 61 | NH2 ARG A 12 | 7.824 -13.893 1.931 1.00 93.22 | N |
| ANISOU | 61 | NH2 ARG A 12 | 10371 11873 13174 -42 -2046 -2241 | N |
| ATOM | 62 | N SER A 13 | 9.670 -14.704 6.712 1.00 67.77 | N |
| ANISOU | 62 | N SER A 13 | 7366 8244 10138 -613 -1355 -1528 | N |
| ATOM | 63 | CA SER A 13 | 8.381 -15.232 7.120 1.00 76.61 | C |
| ANISOU | 63 | CA SER A 13 | 8312 9283 11514 -816 -1359 -1580 | C |
| ATOM | 64 | C SER A 13 | 7.775 -14.367 8.210 1.00 76.77 | C |
| ANISOU | 64 | C SER A 13 | 8216 9413 11542 -935 -1164 -1448 | C |
| ATOM | 65 | O SER A 13 | 6.606 -14.025 8.129 1.00 79.19 | O |
| ANISOU | 65 | O SER A 13 | 8326 9795 11967 -990 -1176 -1538 | O |
| ATOM | 66 | CB SER A 13 | 8.434 -16.730 7.498 1.00 78.82 | C |

TABLE 3-continued

| | | | |
|---|---|---|---|
| ANISOU | 66 CB SER A 13 | 8635 9307 12006 -982 -1399 -1569 | C |
| ATOM | 67 CG SER A 13 | 9.521 -17.045 8.351 1.00 73.03 | O |
| ANISOU | 67 CG SER A 13 | 8072 8485 11192 -1009 -1285 -1375 | O |
| ATOM | 68 N ASN A 14 | 8.568 -13.947 9.191 1.00 76.90 | N |
| ANISOU | 68 N ASN A 14 | 8338 9458 11421 -952 -992 -1257 | N |
| ATOM | 69 CA ASN A 14 | 7.991 -13.183 10.305 1.00 84.08 | C |
| ANISOU | 69 CA ASN A 14 | 9136 10480 12330 -1063 -802 -1153 | C |
| ATOM | 70 C ASN A 14 | 7.750 -11.709 9.956 1.00 83.18 | C |
| ANISOU | 70 C ASN A 14 | 8950 10557 12097 -907 -792 -1207 | C |
| ATOM | 71 O ASDN A 14 | 7.525 -10.880 10.861 1.00 86.57 | O |
| ANISOU | 71 O ASN A 14 | 9318 11092 12482 -945 -637 -1134 | O |
| ATOM | 72 CB ASN A 14 | 8.801 -13.297 11.628 1.00 85.20 | C |
| ANISOU | 72 CB ASN A 14 | 9408 10595 12376 -1154 -624 -938 | C |
| ATOM | 73 CG ASN A 14 | 9.451 -14.662 11.830 1.00 91.38 | C |
| ANISOU | 73 CG ASN A 14 | 10325 11168 13226 -1237 -666 -856 | C |
| ATOM | 74 OD1 ASN A 14 | 9.088 -15.673 11.203 1.00 91.91 | O |
| ANISOU | 74 OD1 ASN A 14 | 10369 11081 13471 -1287 -803 -955 | O |
| ATOM | 75 ND2 ASN A 14 | 10.448 -14.689 12.714 1.00 97.54 | N |
| ANISOU | 75 ND2 ASN A 14 | 11268 11947 13885 -1242 -664 -681 | N |
| ATOM | 76 N MET A 15 | 7.772 -11.377 8.666 1.00 74.06 | N |
| ANISOU | 76 N MET A 15 | 7805 9447 10889 -728 -961 -1336 | N |
| ATOM | 77 CA MET A 15 | 7.565 -9.982 8.288 1.00 77.63 | C |
| ANISOU | 77 CA MET A 15 | 8204 10052 11238 -574 -968 -1362 | C |
| ATOM | 78 C MET A 15 | 6.144 -9.578 7.896 1.00 78.15 | C |
| ANISOU | 78 C MET A 15 | 8047 10200 11445 -568 -1045 -1509 | C |
| ATOM | 79 O MET A 15 | 5.857 -8.381 7.712 1.00 79.92 | O |
| ANISOU | 79 O MET A 15 | 8214 10538 11613 -444 -1049 -1523 | O |
| ATOM | 80 CB MET A 15 | 8.625 -9.488 7.287 1.00 80.06 | C |
| ANISOU | 80 CB MET A 15 | 8676 10402 11342 -360 -1060 -1346 | C |
| ATOM | 81 CG MET A 15 | 8.410 -9.785 5.813 1.00 86.13 | C |
| ANISOU | 81 CG MET A 15 | 9445 11196 12086 -220 -1273 -1497 | C |
| ATOM | 82 SD MET A 15 | 9.633 -8.823 4.869 1.00 92.69 | S |
| ANISOU | 82 SD MET A 15 | 10448 12136 12634 22 -1806 -1413 | S |
| ATOM | 83 CE MET A 15 | 8.742 -7.282 4.601 1.00 82.39 | C |
| ANISOU | 83 CE MET A 15 | 9022 10958 11324 128 -1333 -1413 | C |
| ATOM | 84 N GLU A 16 | 5.258 -10.571 7.781 1.00 81.86 | N |
| ANISOU | 84 N GLU A 16 | 8364 10602 12117 -703 -1115 -1620 | N |
| ATOM | 85 CA GLU A 16 | 3.818 -10.315 7.647 1.00 77.99 | C |
| ANISOU | 85 CA GLU A 16 | 7637 10190 11804 -742 -1165 -1761 | C |
| ATOM | 86 C GLU A 16 | 3.317 -9.343 8.732 1.00 77.39 | C |

TABLE 3-continued

| | | | | |
|---|---|---|---|---|
| ANISOU | 86 | C GLU A 16 | 7433 10229 11742 -791 -971 -1696 | C |
| ATOM | 87 | O GLU A 16 | 2.746 -8.286 8.401 1.00 69.65 | O |
| ANISOU | 87 | O GLU A 16 | 6342 9367 10756 -654 -1019 -1773 | O |
| ATOM | 88 | CB GLU A 16 | 3.022 -11.633 7.657 1.00 85.67 | C |
| ANISOU | 88 | CB GLU A 16 | 8475 11048 13029 -942 -1224 -1859 | C |
| ATOM | 89 | CG GLU A 16 | 3.185 -12.455 6.390 1.00 92.96 | C |
| ANISOU | 89 | CG GLU A 16 | 9463 11881 13975 -858 -1469 -2012 | C |
| ATOM | 90 | CD GLU A 16 | 2.443 -11.857 5.197 1.00 105.10 | C |
| ANISOU | 90 | CD GLU A 16 | 10880 13548 15504 -676 -1680 -2205 | C |
| ATOM | 91 | OE1 GLU A 16 | 2.076 -12.639 4.279 1.00 107.96 | O |
| ANISOU | 91 | OE1 GLU A 16 | 11197 13856 15965 -659 -1892 -2389 | O |
| ATOM | 92 | OE2 GLU A 16 | 2.215 -10.614 5.172 1.00 98.81 | O |
| AISOU | 92 | OE2 GLU A 16 | 10034 12901 14609 -543 -1650 -2179 | O |
| ATOM | 93 | N PRO A 17 | 3.566 -9.674 10.029 1.00 79.96 | N |
| ANISOU | 93 | N PRO A 17 | 7784 10526 12073 -968 -759 -1556 | N |
| ATOM | 94 | CA PRO A 17 | 3.139 -8.757 11.101 1.00 82.09 | C |
| ANISOU | 94 | CA PRO A 17 | 7936 10928 12326 -1000 -568 -1515 | C |
| ATOM | 95 | C PRO A 17 | 3.819 -7.368 11.136 1.00 83.55 | C |
| ANISOU | 95 | C RRO A 17 | 8230 11192 12325 -803 -542 -1474 | C |
| ATOM | 96 | O PRO A 17 | 3.335 -6.502 11.868 1.00 86.28 | O |
| ANISOU | 96 | O PRO A 17 | 8455 11648 12678 -793 -422 -1495 | O |
| ATOM | 97 | CB PRO A 17 | 3.469 -9.533 12.395 1.00 83.52 | C |
| ANISOU | 97 | CB PRO A 17 | 8173 11063 12499 -1217 -364 -1353 | C |
| ATOM | 98 | CG PRO A 17 | 4.501 -10.541 12.014 1.00 83.68 | C |
| ANISOU | 98 | CG PRO A 17 | 8415 10909 12470 -1233 -451 -1269 | C |
| ATOM | 99 | CD PRO A 17 | 4.198 -10.900 10.582 1.00 80.28 | C |
| ANISOU | 99 | CD PRO A 17 | 7954 10417 12131 -1136 -693 -1433 | C |
| ATOM | 100 | N PHE A 18 | 4.907 -7.148 10.383 1.00 78.01 | N |
| ANISOU | 100 | N PHE A 18 | 7737 10434 11469 -652 -546 -1422 | N |
| ATOM | 101 | CA PHE A 18 | 5.588 -5.834 10.389 1.00 71.25 | C |
| ANISOU | 101 | CA PHE A 18 | 6981 9628 10464 -485 -625 -1366 | C |
| ATOM | 102 | C PHE A 18 | 4.782 -4.762 9.667 1.00 69.19 | C |
| ANISOU | 102 | C PHE A 18 | 6590 9442 10257 -319 -741 -1479 | C |
| ATOM | 103 | O PHE A 18 | 4.179 -5.039 8.606 1.00 61.10 | O |
| ANISOU | 103 | O PHE A 18 | 5495 8423 9299 -253 -917 -1583 | O |
| ATOM | 104 | CB PHE A 18 | 6.973 -5.893 9.715 1.00 73.47 | C |
| ANISOU | 104 | CB PHE A 18 | 7501 9841 10575 -376 -697 -1268 | C |
| ATOM | 105 | CG PHE A 18 | 7.977 -6.778 10.413 1.00 63.72 | C |
| ANISOU | 105 | CG PHE A 18 | 8950 11060 11801 -495 -598 -1147 | C |
| ATOM | 106 | CD1 PHE A 18 | 7.769 -7.243 11.725 1.00 89.89 | C |

TABLE 3-continued

| | | | |
|---|---|---|---|
| ANISOU | 106 CD1 PHE A 18 | 9687 11840 12627 -674 -434 -1088 | C |
| ATOM | 107 CD2 PHE A 18 | 9.172 -7.125 9.765 1.00 84.61 | C |
| ANISOU | 107 CD2 PHE A 18 | 9249 1111 11787 -413 -669 -1084 | C |
| ATOM | 108 CE1 PHE A 18 | 8.711 -8.052 12.360 1.00 90.93 | C |
| ANISOU | 108 CE1 PHE A 18 | 9969 11894 12687 -765 -363 -961 | C |
| ATOM | 109 CE2 PHE A 18 | 10.119 -7.936 10.397 1.00 86.75 | C |
| ANISOU | 109 CE2 PHE A 18 | 9653 11305 12003 -499 -597 -980 | C |
| ATOM | 110 CZ PHE A 18 | 9.891 -8.390 11.701 1.00 94.92 | C |
| ANISOU | 110 CZ PHE A 18 | 10655 12323 13089 -672 -453 -912 | C |
| ATOM | 111 N SER A 19 | 4.844 -3.544 10.227 1.00 62.85 | N |
| ANISOU | 111 N SER A 19 | 5771 8688 9420 -240 -660 -1460 | N |
| ATOM | 112 CA SER A 19 | 4.353 -2.300 9.614 1.00 66.57 | C |
| ANISOU | 112 CA SER A 19 | 6171 9198 9926 -48 -770 -1527 | C |
| ATOM | 113 C SER A 19 | 5.045 -1.954 8.290 1.00 68.58 | C |
| ANISOU | 113 C SER A 19 | 6589 9408 10061 126 -944 -1461 | C |
| ATOM | 114 O SER A 19 | 6.112 -2.481 8.003 1.00 63.85 | O |
| ANISOU | 114 O SER A 19 | 6171 8758 9330 108 -942 -1358 | O |
| ATOM | 115 CB SER A 19 | 4.565 -1.120 10.575 1.00 66.24 | C |
| ANISOU | 115 CB SER A 19 | 6126 9175 9865 -5 -642 -1506 | C |
| ATOM | 116 OG SER A 19 | 5.957 -0.769 10.649 1.00 62.18 | O |
| ANISOU | 116 OG SER A 19 | 5836 8589 9199 29 -608 -1361 | O |
| ATOM | 117 N LYS A 20 | 4.447 -1.053 7.503 1.00 69.33 | N |
| ANISOU | 117 N LYS A 20 | 6616 9531 10195 300 -1089 -1513 | N |
| ATOM | 118 CA LYS A 20 | 5.043 -0.594 6.238 1.00 68.35 | C |
| ANISOU | 118 CA LYS A 20 | 6645 9388 9937 476 -1246 -1425 | C |
| ATOM | 119 C LYS A 20 | 6.471 -0.065 6.440 1.00 66.56 | C |
| ANISOU | 119 C LYS A 20 | 6643 9108 9576 492 -1152 -1244 | C |
| ATOM | 120 O LYS A 20 | 7.372 -0.387 5.658 1.00 67.62 | O |
| ANISOU | 120 O LYS A 20 | 6925 9223 9544 534 -1200 -1146 | O |
| ATOM | 121 CB LYS A 20 | 4.195 0.478 5 509 1.00 68.61 | C |
| ANISOU | 121 CB LYS A 20 | 6582 9450 10036 672 -1410 -1474 | C |
| ATOM | 122 CG LY3 A 20 | 4.834 0.882 4.174 1.00 69.04 | C |
| ANISOU | 122 CG LYS A 20 | 6810 9502 9919 845 -1564 -1347 | C |
| ATOM | 123 CD LYS A 20 | 3.876 1.370 3.103 1.00 72.11 | C |
| ANISOU | 123 CD LYS A 20 | 7111 9949 10337 1035 -1791 -1412 | C |
| ATOM | 124 CE LYS A 20 | 4.145 2.828 2.768 1.00 74.09 | C |
| ANISOU | 124 CE LYS A 20 | 7450 10140 10560 1208 -1846 -1263 | C |
| ATOM | 125 NZ LYS A 20 | 3.385 3.265 1.568 1.00 77.24 | N |
| ANISOU | 125 NZ LYS A 20 | 7812 10599 10938 1417 -2090 -1280 | N |
| ATOM | 126 N LYS A 21 | 6.665 0.764 7.462 1.00 62.17 | N |

TABLE 3-continued

| | | |
|---|---|---|
| ANISOU 126 N LYS A 21 | 6062 8502 9057 466 -1024 -127 | N |
| ATOM 127 CA LYS A 21 | 7.940 1.408 7.636 1.00 59.46 | C |
| ANISOU 127 CA LYS A 21 | 5891 8090 8610 486 -957 -1064 | C |
| ATOM 128 C LYS A 21 | 9.017 0.317 7.890 1.00 54.84 | C |
| ANISOU 128 C LYS A 21 | 5437 7500 7901 358 -864 -989 | C |
| ATOM 129 O LYS A 21 | 10.090 0.292 7.235 1.00 55.38 | O |
| ANISOU 129 O LYS A 21 | 5658 7549 7833 404 -887 -865 | O |
| ATOM 130 CB LYS A 21 | 7.864 2.446 8.763 1.00 65.36 | C |
| ANISOU 130 CB LYS A 21 | 6582 8797 9455 479 -852 -1094 | C |
| ATOM 131 CG LYS A 21 | 8.880 3.589 8.643 1.00 73.84 | C |
| ANISOU 131 CG LYS A 21 | 7795 9771 10491 558 -854 -956 | C |
| ATOM 132 CD LYS A 21 | 8.363 4.894 9.278 1.00 79.58 | C |
| ANISOU 132 CD LYS A 21 | 8430 10434 11371 635 -850 -1034 | C |
| ATOM 133 CE LLS A 21 | 9.460 5.752 9.945 1.00 84.28 | C |
| ANISOU 133 CE LYS A 21 | 9132 10925 11965 613 -772 -957 | C |
| ATOM 134 NZ LYS A 21 | 10.730 6.111 9.226 1.00 80.19 | N |
| ANISOU 134 NZ LYS A 21 | 8790 10320 11357 634 -802 -753 | N |
| ATOM 135 N LEU A 22 | 8.725 -0.583 8.825 1.00 52.25 | N |
| ANISOU 135 N LEU A 22 | 5041 7193 7619 204 -760 -1057 | N |
| ATOM 136 CA LEU A 22 | 9.595 -1.736 9.117 1.00 54.36 | C |
| ANISOU 136 CA LEU A 22 | 5419 7439 7797 87 -692 -996 | C |
| ATOM 137 C LEU A 22 | 9.814 -2.643 7.867 1.00 53.25 | C |
| ANISOU 137 C LEU A 22 | 5349 7300 7565 135 -823 -998 | C |
| ATOM 138 O LEU A 22 | 10.910 -3.151 7.663 1.00 47.30 | O |
| ANISOU 138 O LEU A 22 | 4734 6522 6716 130 -807 -917 | O |
| ATOM 139 CB LEU A 22 | 9.077 -2.535 10.331 1.00 53.78 | C |
| ANISOU 139 CB LEU A 22 | 5253 7383 7799 -89 -565 -1051 | C |
| ATOM 140 CG LEU A 22 | 9.539 -2.308 11.786 1.00 55.43 | C |
| ANISOU 140 CG LEU A 22 | 5484 7602 7974 -188 -393 -1005 | C |
| ATOM 141 CD1 LEU A 22 | 10.333 -1.048 12.060 1.00 56.18 | C |
| ANISOU 141 CD1 LEU A 22 | 5655 7678 8014 -100 -364 -953 | C |
| ATOM 142 CD2 LEU A 22 | 8.337 -2.323 12.714 1.00 57.32 | C |
| ANISOU 142 CD2 LEU A 22 | 5538 7918 8322 -280 -294 -1108 | C |
| ATOM 143 N ARG A 23 | 8.778 -2.790 7.031 1.00 49.75 | N |
| ANISOU 143 N ARG A 23 | 4800 6895 7206 198 -961 -1107 | N |
| ATOM 144 CA ARG A 23 | 8.808 -3.622 5.795 1.00 56.34 | C |
| ANISOU 144 CA ARG A 23 | 5682 7751 7974 264 -1112 -1156 | C |
| ATOM 145 C ARG A 23 | 9.814 -3.086 4.812 1.00 52.25 | C |
| ANISOU 145 C ARG A 23 | 5320 7263 7270 415 -1167 -1042 | C |
| ATOM 146 O ARG A 23 | 10.472 -3.867 4.114 1.00 47.78 | O |

TABLE 3-continued

| | | | |
|---|---|---|---|
| ANISOU | 146 O ARG A 23 | 4854 5714 6586 447 -1216 -1041 | O |
| ATOM | 147 CB ARG A 23 | 7.446 -3.694 5.064 1.00 61.34 | C |
| ANISOU | 147 CB ARG A 23 | 6156 8439 8713 324 -1274 -1310 | C |
| ATOM | 148 CG ARG A 23 | 6.450 -4.698 5.637 1.00 74.43 | C |
| ANISOU | 148 CG ARG A 23 | 7649 10075 10556 159 -1259 -1448 | C |
| ATOM | 149 CD ARG A 23 | 5.251 -4.971 4.711 1.00 80.04 | C |
| ANISOU | 149 CD ARG A 23 | 8205 10840 11366 221 -1455 -1621 | C |
| ATOM | 150 NE ARG A 23 | 4.820 -6.369 4.853 1.00 90.41 | N |
| ANISOU | 150 NE ARG A 23 | 9441 12098 12812 59 -1477 -1734 | N |
| ATOM | 151 CZ ARG A 23 | 5.184 -7.381 4.052 1.00 93.29 | C |
| ANISOU | 151 CZ ARG A 23 | 9694 12424 13129 73 -1600 -1799 | C |
| ATOM | 152 NH1 ARG A 23 | 5.966 -7.186 2.990 1.00 94.85 | N |
| ANISOU | 152 NH1 ARG A 23 | 10250 12670 13118 252 -1706 -1771 | N |
| ATOM | 153 NH2 ARG A 23 | 4.751 -8.608 4.310 1.00 93.58 | N |
| ANISOU | 153 NH2 ARG A 23 | 9852 12373 13332 -93 -1615 -1897 | N |
| ATOM | 154 N VAL A 24 | 9.920 -1.754 4.754 1.00 49.46 | N |
| ANISOU | 154 N VAL A 24 | 4981 6914 6897 509 -1156 -947 | N |
| ATOM | 155 CA VAL A 24 | 10.883 -1.125 3.856 1.00 46.37 | C |
| ANISOU | 155 CA VAL A 24 | 4731 6552 6336 636 -1187 -800 | C |
| ATOM | 156 C VAL A 24 | 12.280 -1.575 4.276 1.00 44.04 | C |
| ANISOU | 156 C VAL A 24 | 4559 6230 5943 560 -1059 -704 | C |
| ATOM | 157 O VAL A 24 | 13.116 -1.952 3.453 1.00 43.78 | O |
| ANISOU | 157 O VAL A 24 | 4681 6252 5753 624 -1083 -649 | O |
| ATOM | 158 CB VAL A 24 | 10.756 0.404 3.933 1.00 47.32 | C |
| ANISOU | 158 CB VAL A 24 | 4840 6634 6504 718 -1185 -700 | C |
| ATOM | 159 CG1 VAL A 24 | 11.994 1.073 3.364 1.00 47.00 | C |
| ANISOU | 159 CG1 VAL A 24 | 4950 6592 6316 785 -1152 501 | C |
| ATOM | 160 CG2 VAL A 24 | 9.483 0 858 3.161 1.00 47.49 | C |
| ANISOU | 160 CG2 VAL A 24 | 4760 6699 6585 851 -1357 -777 | C |
| ATOM | 161 N VAL A 25 | 12.524 -1.558 5.582 1.00 40.88 | N |
| ANISOU | 161 N VAL A 25 | 4139 5762 5632 430 -925 -695 | N |
| ATOM | 162 CA VAL A 25 | 13.859 -1.929 6.062 1.00 41.30 | C |
| ANISOU | 162 CA VAL A 25 | 4299 5790 5603 365 -817 -605 | C |
| ATOM | 163 C VAL A 25 | 14.041 -3.435 5.925 1.00 40.07 | C |
| ANISOU | 163 C VAL A 25 | 4174 5638 5414 316 -840 -681 | C |
| ATOM | 164 O VAL A 25 | 15.135 -3.887 5.550 1.00 44.59 | O |
| ANISOU | 164 O VAL A 25 | 4846 6228 5868 347 -825 -627 | O |
| ATOM | 165 CB VAL A 25 | 14.073 -1.539 7.547 1.00 40.89 | C |
| ANISOU | 165 CB VAL A 25 | 4222 5679 5637 248 -683 -586 | C |
| ATOM | 166 CG1 VAL A 25 | 15.488 -1.915 7.990 1.00 41.37 | C |

TABLE 3-continued

| | | | |
|---|---|---|---|
| ANISOU | 166 CG1 VAL A 25 | 4387 5722 5609 197 -596 -498 | C |
| ATOM | 167 CG2 VAL A 25 | 13.847 -0.036 7.779 1.00 39.72 | C |
| ANISOU | 167 CG2 VAL A 25 | 4035 5499 5558 298 -670 -547 | C |
| ATOM | 168 N ALA A 26 | 12.981 -4.222 6.224 1.00 42.21 | N |
| ANISOU | 168 N ALA A 26 | 4351 5884 5804 237 -878 -808 | N |
| ATOM | 169 CA ALA A 26 | 13.115 -5.671 6.096 1.00 42.62 | C |
| ANISOU | 169 CA ALA A 26 | 4434 5899 5862 183 -916 -682 | C |
| ATOM | 170 C ALA A 26 | 13.446 -5.975 4.625 1.00 43.94 | C |
| ANISOU | 170 C ALA A 26 | 4667 6135 5895 383 -1046 -924 | C |
| ATOM | 171 O ALA A 26 | 14.376 -6.734 4.326 1.00 46.92 | O |
| ANISOU | 171 O ALA A 26 | 5187 6507 6188 361 -1048 -922 | O |
| ATOM | 172 CB ALA A 26 | 11.855 -6 400 6.606 1.00 42.36 | C |
| ANISOU | 172 CB ALA A 26 | 4272 5818 6006 57 -937 -1000 | C |
| ATOM | 173 N ASP A 27 | 12.777 -5.290 3.708 1.00 45.90 | N |
| ANISOU | 173 N ASP A 27 | 4870 6463 6106 450 -1150 -954 | N |
| ATOM | 174 CA ASP A 27 | 12.956 -5.554 2.245 1.00 45.22 | C |
| ANISOU | 174 CA ASP A 27 | 4842 6481 5859 610 -1286 -1005 | C |
| ATOM | 175 C ASP A 27 | 14.348 -5.193 1.713 1.00 45.46 | C |
| ANISOU | 175 C ASP A 27 | 5002 6588 5684 706 -1222 -867 | C |
| ATOM | 176 O ASP A 27 | 14.937 -5.952 0.892 1.00 45.61 | O |
| ANISOU | 176 O ASP A 27 | 5089 6677 5565 792 -1274 -926 | O |
| ATOM | 177 CB ASP A 27 | 11.916 -4.827 1.397 1.00 46.21 | C |
| ANISOU | 177 CB ASP A 27 | 4895 6690 5972 727 -1424 -1048 | C |
| ATOM | 178 CG ASP A 27 | 10.606 -5.573 1.306 1.00 53.18 | C |
| ANISOU | 178 CG ASP A 27 | 5644 7552 7010 684 -1555 -1250 | C |
| ATOM | 179 OD1 ASP A 27 | 10.608 -6.809 1.454 1.00 53.71 | O |
| ANISOU | 179 OD1 ASP A 27 | 5706 7556 7146 599 -1579 -1368 | O |
| ATOM | 180 OD2 ASP A 27 | 9.555 -4.936 1.067 1.00 55.13 | O |
| ANISOU | 180 OD2 ASP A 27 | 5783 7837 7327 735 -1646 -1295 | O |
| ATOM | 181 N TYR A 28 | 14.832 -4.028 2 134 1.00 45.13 | N |
| ANISOU | 181 N TYR A 28 | 4981 6538 5629 697 -1116 -697 | N |
| ATOM | 182 CA TYR A 28 | 16.185 -3.595 1.787 1.00 40.73 | C |
| ANISOU | 182 CA TYR A 28 | 4520 6042 4912 753 -1028 -544 | C |
| ATOM | 183 C TYR A 28 | 17.212 -4.619 2.283 1.00 43.93 | C |
| ANISOU | 183 C TYR A 28 | 49746415 5302 691 -952 -572 | C |
| ATOM | 184 O TYR A 28 | 18.131 -4.972 1.554 1.00 41.57 | O |
| ANISOU | 184 O TYR A 28 | 4738 6209 4846 778 -943 -556 | O |
| ATOM | 185 CB TYR A 28 | 16.510 -2.185 2.304 1.00 42.18 | C |
| ANISOU | 185 CB TR A 28 | 4704 6182 5141 723 -932 -369 | C |
| ATOM | 186 CG TYR A 28 | 17.901 -1.705 1.956 1.00 41.46 | C |

TABLE 3-continued

| | | | | | |
|---|---|---|---|---|---|
| ANISOU | 186 | CG TYR A 28 | 4690 6149 4915 756 -835 -201 | | C |
| ATOM | 187 | CD1 TYR A 28 | 18.126 -0.862 0.860 1.00 44.75 | | C |
| ANISOU | 187 | CD1 TYR A 28 | 5149 6664 5190 870 -856 -57 | | C |
| ATOM | 188 | CD2 TYR A 28 | 19.025 -2.070 2.747 1.00 42.22 | | C |
| ANISOU | 188 | CD2 TYR A 28 | 4807 6207 5027 669 -719 -171 | | C |
| ATOM | 189 | CE1 TYR A 28 | 19.433 -0.433 0.529 1.00 43.85 | | C |
| ANISOU | 189 | CE1 TYR A 28 | 5087 6615 4959 881 -747 113 | | C |
| ATOM | 190 | CE2 TYR A 28 | 20.311 -1.626 2.424 1.00 40.08 | | C |
| ANISOU | 190 | CE2 TYR A 28 | 4578 6001 4651 691 -626 -25 | | C |
| ATOM | 191 | CZ TYR A 28 | 20.503 -0.810 1.317 1.00 45.12 | | C |
| ANISOU | 191 | CZ TYR A 28 | 5246 6741 5158 768 -632 118 | | C |
| ATOM | 192 | OH TYR A 28 | 21.734 -0.408 1.001 1.00 44.38 | | O |
| ANISOU | 192 | OH TYR A 28 | 5174 6721 4968 792 -522 272 | | O |
| ATOM | 193 | N ILE A 29 | 17.061 -5.118 3.507 1.00 40.87 | | N |
| ANISOU | 193 | N ILE A 29 | 4555 5904 5068 552 -699 -614 | | N |
| ATOM | 194 | CA ILE A 29 | 18.019 -6.066 4.010 1.00 40.97 | | C |
| ANISOU | 194 | CA ILE A 29 | 4621 5872 5075 505 -845 -625 | | C |
| ATOM | 195 | C ILE A 29 | 17.970 -7.390 3.241 1.00 46.14 | | C |
| ANISOU | 195 | C ILE A 29 | 5302 6538 5691 572 -954 -779 | | C |
| ATOM | 196 | O ILE A 29 | 19.026 -7.976 2.940 1.00 46 44 | | O |
| ANISOU | 196 | O ILE A 29 | 5401 6610 5635 635 -938 -788 | | O |
| ATOM | 197 | CB ILE A 29 | 17.803 -6.330 5.522 1.00 40.88 | | C |
| ANISOU | 197 | CB ILE A 29 | 4580 5733 5220 343 -771 -617 | | C |
| ATOM | 198 | CG1 ILE A 29 | 18.006 -5.025 6.311 1.00 38.67 | | C |
| ANISOU | 198 | CG1 ILE A 29 | 4278 5448 4966 293 -668 -496 | | C |
| ATOM | 199 | CG2 ILE A 29 | 18.855 -7.307 6.003 1.00 41.88 | | C |
| ANISOU | 199 | CG2 ILE A 29 | 4773 5809 5332 315 -735 -610 | | C |
| ATOM | 200 | CD1 ILE A 29 | 17.535 -5.036 7.772 1.00 37.47 | | C |
| ANISOU | 200 | CD1 ILE A 29 | 4081 5214 4940 150 -596 -501 | | C |
| ATOM | 201 | N LEU A 30 | 16.760 -7.892 2.983 1.00 44.25 | | N |
| ANISOU | 201 | N LEL A 30 | 5006 6262 5544 555 -1069 -918 | | N |
| ATOM | 202 | CA LEU A 30 | 16.557 -9.177 2.297 1.00 49.28 | | C |
| ANISOU | 202 | CA LEU A 30 | 5658 6879 6189 605 -1199 -1100 | | C |
| ATOM | 203 | C LEU A 30 | 17.185 -9.121 0.900 1.00 53.86 | | C |
| ANISOU | 203 | C LEU A 30 | 6295 7630 6538 800 -1259 -1139 | | C |
| ATOM | 204 | O LEU A 30 | 17.626 -10.162 0.366 1.00 55.53 | | O |
| ANISOU | 204 | O LEU A 30 | 6549 7847 6701 877 -1329 -1276 | | O |
| ATOM | 205 | CB LEU A 30 | 15.049 -9.545 2.174 1.00 51.05 | | C |
| ANISOU | 205 | CB LEU A 30 | 5783 7049 6566 549 -1325 -1247 | | C |
| ATOM | 206 | CG LEU A 30 | 14.354 -10.172 3.395 1.00 50.90 | | C |

TABLE 3-continued

| | | | | | | | | | |
|---|---|---|---|---|---|---|---|---|---|
| ANISOU | 206 | CG | LEU | A | 30 | 5697 6857 6784 349 -1289 -1265 | | | C |
| ATOM | 207 | CD1 | LEU | A | 30 | 12.800 -10.168 3.263 1.00 49.75 | | | C |
| ANISOU | 207 | CD1 | LEU | A | 30 | 5411 6699 6792 290 -1387 -1385 | | | C |
| ATOM | 208 | CD2 | LEU | A | 30 | 14.898 -11.571 3.648 1.00 54.15 | | | C |
| ANISOU | 208 | CD2 | LEU | A | 30 | 6174 7131 7271 302 -1317 -1331 | | | C |
| ATOM | 209 | N | GLU | A | 31 | 17.196 -7.920 0.307 1 00 47.67 | | | N |
| ANISOU | 209 | N | GLU | A | 31 | 5513 6986 5614 884 -1233 -1021 | | | N |
| ATOM | 210 | CA | GLU | A | 31 | 17.746 -7.730 -1.026 1.00 50.66 | | | C |
| ANISOU | 210 | CA | GLU | A | 31 | 5945 7563 5741 1066 -1269 -1019 | | | C |
| ATOM | 211 | C | GLU | A | 31 | 19.198 -7.394 -1.062 1.00 49.82 | | | C |
| ANISOU | 211 | C | GLU | A | 31 | 5894 7542 5493 1105 -1124 -873 | | | C |
| ATOM | 212 | O | GLU | A | 31 | 19.803 -7.561 -2.103 1.00 49.63 | | | O |
| ANISOU | 212 | O | GLU | A | 31 | 5911 7690 5256 1251 -1134 -900 | | | O |
| ATOM | 213 | CB | GLU | A | 31 | 16.955 -6.718 -1.861 1.00 52.72 | | | C |
| ANISOU | 213 | CB | GLU | A | 31 | 6187 7946 5900 1158 -1344 -962 | | | C |
| ATOM | 214 | CG | GLU | A | 31 | 15.556 -7.226 -2.157 1.00 59.04 | | | C |
| ANISOU | 214 | CG | GLU | A | 31 | 6916 8712 6804 1165 -152 -1160 | | | C |
| ATOM | 215 | CD | GLU | A | 31 | 14.509 -6.134 -2.312 1.00 65.19 | | | C |
| ANISOU | 215 | CD | GLU | A | 31 | 7634 9917 7618 1186 -1590 -1090 | | | C |
| ATOM | 216 | OE1 | GLU | A | 31 | 14.791 -5.085 -2.925 1.00 70.75 | | | O |
| ANISOU | 216 | OE1 | GLU | A | 31 | 8385 10340 8158 1288 -1566 -922 | | | O |
| ATOM | 217 | OE2 | GLU | A | 31 | 13.379 -6.355 -1.841 1.00 70.00 | | | O |
| ANISOU | 217 | OE2 | GLU | A | 31 | 8141 10026 8430 1102 -1668 -1205 | | | O |
| ATOM | 218 | N | ASN | A | 32 | 19.764 -6.927 0.049 1.00 46.51 | | | N |
| ANISOU | 218 | N | ASN | A | 32 | 5467 7021 5183 981 -989 -731 | | | N |
| ATOM | 219 | CA | ASN | A | 32 | 21.134 -6.345 0.023 1.00 49.80 | | | C |
| ANISOU | 219 | CA | ASN | A | 32 | 5910 7527 5483 1005 -845 -567 | | | C |
| ATOM | 220 | C | ASN | A | 32 | 22.045 -6.938 1.058 1.00 42.49 | | | C |
| ANISOU | 220 | C | ASN | A | 32 | 4987 6498 4660 920 -765 -568 | | | C |
| ATOM | 221 | O | ASN | A | 32 | 23.011 -6 305 1.513 1.00 46.19 | | | O |
| ANISOU | 221 | O | ASN | A | 32 | 5447 6982 5121 878 -643 -424 | | | O |
| ATOM | 222 | CB | ASN | A | 32 | 21.062 -4.825 0.214 1.00 47.53 | | | C |
| ANISOU | 222 | CB | ASS | A | 32 | 5606 7242 5211 956 -768 -357 | | | C |
| ATOM | 223 | CG | ASN | A | 32 | 20.366 -4.155 -0.923 1.00 53.03 | | | C |
| ANISOU | 223 | CG | ASS | A | 32 | 6315 8059 5775 1066 -847 -313 | | | C |
| ATOM | 224 | OD1 | ASN | A | 32 | 20.923 -4.046 -1.993 1.00 55.18 | | | O |
| ANISOU | 224 | OD1 | ASN | A | 32 | 6624 8511 5830 1189 -831 -259 | | | O |
| ATOM | 225 | ND2 | ASN | A | 32 | 19.123 -3.729 -0.710 1.00 49.55 | | | N |
| ANISOU | 225 | ND2 | ASN | A | 32 | 5838 7535 5454 1037 -935 -340 | | | N |
| ATOM | 226 | N | ALA | A | 33 | 21.648 -8.116 1.508 1.00 46.62 | | | N |

TABLE 3-continued

| | | | |
|---|---|---|---|
| ANISOU | 226 N ALA A 33 | 5516 6895 5303 882 -845 -723 | N |
| ATOM | 227 CA ALA A 33 | 22.095 -8.660 2.783 1.00 45.21 | C |
| ANISOU | 227 CA ALA A 33 | 5343 6563 5271 769 -797 -709 | C |
| ATOM | 228 C ALA A 33 | 23.591 -8.808 2.847 1.00 44.97 | C |
| ANISOU | 228 C ALA A 33 | 5328 6597 5163 823 -713 -658 | C |
| ATOM | 229 O ALA A 33 | 24.204 -8.507 3.886 1.00 37.52 | O |
| ANISOU | 229 O ALA A 33 | 4375 5590 4292 733 -631 -555 | O |
| ATOM | 230 CB ALA A 33 | 21.417 -9.987 3.104 1.00 48.63 | C |
| ANISOU | 220 CB ALA A 33 | 5790 6843 5846 725 -906 -869 | C |
| ATOM | 231 N HIS A 34 | 24.202 -9.252 1.757 1.00 39.90 | N |
| ANISOU | 231 N HIS A 34 | 4697 6095 4367 977 -734 -740 | N |
| ATOM | 232 CA HIS A 34 | 25.656 -9.313 1.717 1.00 46.43 | C |
| ANISOU | 232 CA HIS A 34 | 5509 7019 5112 1043 -642 -695 | C |
| ATOM | 233 C HIS A 34 | 26.279 -7.971 2.053 1.00 44.81 | C |
| ANISOU | 233 C HIS A 34 | 5261 6881 4863 971 -503 -484 | C |
| ATOM | 234 O HIS A 34 | 27.232 -7.690 2.868 1.00 42.38 | O |
| ANISOU | 234 O HIS A 34 | 4924 6540 4638 918 -431 -417 | O |
| ATOM | 235 O3 HIS A 34 | 26.211 -9.857 0.375 1.00 56.07 | C |
| ANISOU | 235 CB HIS A 34 | 6733 8434 6138 1237 -663 -820 | C |
| ATOM | 236 CG HIS A 34 | 27.131 -9.710 0.254 1.00 62.18 | C |
| ANISOU | 236 CG HIS A 34 | 7457 9355 6815 1305 -538 -755 | C |
| ATOM | 237 ND1 HIS A 34 | 28.581 -10.721 0.522 1.00 61.86 | N |
| ANISOU | 237 ND1 HIS A 34 | 7407 9279 6819 1376 -557 -873 | N |
| ATOM | 238 CD2 HIS A 34 | 28.536 -8.583 -0.050 1.00 59.79 | C |
| ANISOU | 238 CD2 HIS A 34 | 7096 9224 6396 1297 -387 -569 | C |
| ATOM | 239 CE1 HIS A 34 | 29.860 -10.276 0.366 1.00 60.77 | C |
| ANISOU | 239 CE1 HIS A 34 | 7194 9308 6589 1421 -424 -784 | C |
| ATOM | 240 NE2 HIS A 34 | 29.817 -8.977 0.000 1.00 59.58 | N |
| ANISOU | 240 NE2 HiS A 34 | 7013 9284 6342 1363 -316 -595 | N |
| ATOM | 241 N ASP A 35 | 25.791 -6.898 1.434 1.00 41.75 | N |
| ANISOU | 241 N ASP A 35 | 4866 6581 4415 971 -475 -377 | N |
| ATOM | 242 CA ASP A 35 | 26.406 -5.582 1.711 1.00 42.64 | C |
| ANISOU | 242 CA ASP A 35 | 4938 6730 4535 895 -351 -170 | C |
| ATOM | 243 C ASP A 35 | 26.040 -4.957 3.097 1.00 41 15 | C |
| ANISOU | 243 C ASP A 35 | 4735 6356 4543 731 -336 -101 | C |
| ATOM | 244 O ASP A 35 | 26.806 -4.170 3.654 1.00 40.03 | O |
| ANISOU | 244 O ASP A 35 | 4553 6203 4454 657 -247 19 | O |
| ATOM | 245 CB ASP A 35 | 26.116 -4.560 0.608 1.00 48.67 | C |
| ANISOU | 245 CB ASP A 35 | 5706 7.631 5155 950 -324 -42 | C |
| ATOM | 246 CG ASP A 35 | 26.934 -3.281 0.782 1.00 46.96 | C |

TABLE 3-continued

| | | | |
|---|---|---|---|
| ANISOU | 246 CG ASP A 35 | 5443 7441 4959 872 -191 179 | C |
| ATOM | 247 OD1 ASP A 35 | 28.191 -3.349 0.785 1.00 54.68 | O |
| ANISOU | 247 OD1 ASP A 35 | 6367 8509 5899 876 -90 225 | O |
| ATOM | 248 OD2 ASP A 35 | 26 329 -2.198 0.987 1.00 53.32 | O |
| ANISOU | 248 OD2 ASP A 35 | 6254 8158 5848 799 -194 301 | O |
| ATOM | 249 N VAL A 36 | 24.881 -5.325 3.636 1 00 36.93 | N |
| ANISOU | 249 N VAL A 36 | 4478 5944 4368 677 -421 -190 | N |
| ATOM | 250 CA VAL A 36 | 24.430 -4.797 4.890 1.00 36.66 | C |
| ANISOU | 250 CA VAL A 36 | 4176 5517 4237 541 -403 -150 | C |
| ATOM | 251 C VAL A 36 | 25.471 -5.159 5.997 1.00 36.13 | C |
| ANISOU | 251 C VAL A 36 | 4100 5397 4230 478 -353 -138 | C |
| ATOM | 252 O VAL A 36 | 25.593 -4.416 6.985 1.00 33.19 | O |
| ANISOU | 252 O VAL A 36 | 3703 4961 3945 379 -307 -73 | O |
| ATOM | 253 CB VAL A 36 | 22.972 -5.227 5.254 1.00 36.96 | C |
| ANISOU | 253 CB VAL A 36 | 4220 5450 4372 491 -489 -254 | C |
| ATOM | 254 CG1 VAL A 36 | 22.598 -4.849 6.718 1.00 35.56 | C |
| ANISOU | 254 CG1 VAL A 36 | 4021 5154 4337 352 -450 -230 | C |
| ATOM | 255 CG2 VAL A 36 | 21.957 -4.592 4.312 1.00 36.36 | C |
| ANISOU | 255 CG2 VAL A 36 | 4132 5425 4258 549 -546 -252 | C |
| ATOM | 256 N GLN A 37 | 26.159 -6.295 5.855 1.00 39.85 | N |
| ANISOU | 256 N GLN A 37 | 4590 5891 4661 546 -378 -215 | N |
| ATOM | 257 CA GLN A 37 | 27.245 -6.717 6.817 1.00 38.48 | C |
| ANISOU | 257 CA GLN A 37 | 4407 5681 4534 517 -351 -204 | C |
| ATOM | 258 C GLN A 37 | 28.230 -5.587 7.067 1.00 39.95 | C |
| ANISOU | 258 C GLN A 37 | 4526 5931 4721 476 -257 -84 | C |
| ATOM | 259 O GLN A 37 | 28 810 -5.437 8.167 1.00 39.29 | O |
| ANISOU | 259 O GLN A 37 | 4422 5798 4709 405 -241 -57 | O |
| ATOM | 260 CB GLN A 37 | 26.084 -7.862 6.223 1.00 42.25 | C |
| ANISOU | 260 CB GLN A 37 | 4892 6216 4945 646 -384 -295 | C |
| ATOM | 261 CG GLN A 37 | 27.349 -9.086 5.777 1.00 44.83 | C |
| ANISOU | 261 CG GLN A 37 | 5278 6477 5280 710 -492 -439 | C |
| ATOM | 262 CD GLN A 37 | 28.303 -10.155 5.243 1.00 45.53 | C |
| ANISOU | 262 CD GLN A 37 | 5369 6614 5317 856 -529 -549 | C |
| ATOM | 263 OE1 GLN A 37 | 28.620 -10.202 4051 1.00 46.35 | O |
| ANISOU | 263 OE1 GLN A 37 | 5450 6872 5290 986 -517 -610 | O |
| ATOM | 264 NE2 GLN A 37 | 28.698 -11.052 6.114 1.00 40.50 | N |
| ANISOU | 264 NE2 GLN A 37 | 4762 5847 4779 846 -582 -580 | N |
| ATOM | 265 N PHE A 38 | 23.423 -4.785 6.036 1.00 41.57 | N |
| ANISOU | 265 N PHE A 38 | 4697 6250 4846 518 -201 -8 | N |
| ATOM | 266 CA PHE A 38 | 29.455 -3.741 6.090 1.00 42.37 | C |

TABLE 3-continued

| | | |
|---|---|---|
| ANISOU | 266 CA PHE A 38 | 4721 6414 4963 474 -106 118 C |
| ATOM | 267 C PHE A 38 | 28.870 -2.356 6.332 1.00 41.2 C |
| ANISOU | 267 C PHE A 38 | 4573 6200 4908 376 -82 222 C |
| ATOM | 268 O PHE A 38 | 29.623 -1.398 6.256 1.00 38.70 O |
| ANISOU | 268 O PHE A 38 | 4164 5903 4617 328 -9 387 O |
| ATOM | 269 CB PHE A 38 | 30.362 -3.768 4.839 1.00 40.21 C |
| ANISOU | 269 CB PHE A 38 | 4398 6329 4550 577 -33 163 C |
| ATOM | 270 CG PHE A 38 | 30.824 -5.150 4.467 1.00 43.62 C |
| ANISOU | 270 CG PHE A 38 | 4840 6836 4899 706 -71 23 C |
| ATOM | 271 CD1 PHE A 38 | 31.780 -5.818 5.229 1.00 40.97 C |
| ANISOU | 271 CD1 PHE A 38 | 4464 6479 4624 716 -81 -36 C |
| ATOM | 272 CD2 PHE A 38 | 30.318 -5.786 3.324 1.00 43.50 C |
| ANISOU | 272 CD2 PHE A 38 | 4872 6913 4744 834 -111 -63 C |
| ATOM | 273 CE1 PHE A 38 | 32.200 -7.117 4 897 1.00 38.72 C |
| ANISOU | 273 CE1 PHE A 38 | 4190 6237 4286 852 -132 -176 C |
| ATOM | 274 CE2 PHE A 38 | 30.725 -7.069 2.988 1.00 47.43 C |
| ANISOU | 274 CE2 PHE A 38 | 5378 7459 5184 964 -161 -221 C |
| ATOM | 275 CZ PHE A 38 | 31.661 -7.746 3.792 1.00 48.72 C |
| ANISOU | 275 CZ PHE A 38 | 5505 7574 5433 974 -171 -276 C |
| ATOM | 276 N GLN A 39 | 27.559 -2.259 6.686 1.00 34.59 N |
| ANISOU | 276 N GLN A 39 | 3777 5249 4117 342 -144 176 N |
| ATOM | 277 CA GLN A 39 | 26.935 -0.950 6.883 1.00 32.55 C |
| ANISOU | 277 CA GLN A 39 | 3506 4912 3951 274 -135 252 C |
| ATOM | 278 C GLN A 39 | 26.790 -0.709 8.3638 1.00 34.18 C |
| ANISOU | 278 C GLN A 39 | 3699 5001 4285 172 -146 197 C |
| ATOM | 279 O GLN A 39 | 26.562 -1.657 9.105 1.00 35.04 O |
| ANISOU | 279 O GLN A 39 | 3837 5085 4393 158 -179 102 O |
| ATOM | 280 CB GLN A 39 | 25.511 -0.912 6.259 1.00 34.84 C |
| ANISOU | 280 CB GLN A 39 | 3837 5183 4217 323 -202 220 C |
| ATOM | 281 CG GLN A 39 | 25.550 -0.947 4.724 1.00 39.65 C |
| ANISOU | 281 CG GLN A 39 | 4466 5926 4673 438 -204 282 C |
| ATOM | 282 CD GLN A 39 | 24.177 -0.751 4.066 1.00 41.60 C |
| ANISOU | 282 CD GLN A 39 | 4745 6164 4898 496 -291 257 C |
| ATOM | 283 OE1 GLN A 39 | 23.262 -0.174 4.657 1.00 41.02 O |
| ANISOU | 283 OE1 GLN A 39 | 4658 5977 4949 446 -328 237 O |
| ATOM | 284 NE2 GLN A 39 | 24.054 -1.211 2.830 1.00 40.35 N |
| ANISOU | 284 NE2 GLN A 39 | 4617 6140 4576 614 -327 247 N |
| ATOM | 285 N THR A 40 | 26.870 0.553 8.738 1.00 34.94 N |
| ANISOU | 285 N THR A 40 | 3758 5029 4487 105 -122 259 N |
| ATOM | 286 CA THR A 40 | 26.604 1.015 10.080 1.00 36.19 C |

TABLE 3-continued

| | | |
|---|---|---|
| ANISOU 286 CA THR A 40 | 3902 5090 4760 21 -136 190 | C |
| ATOM 287 C THR A 40 | 25.117 1.259 10.255 1.00 34.18 | C |
| ANISOU 287 C THR A 40 | 3667 4770 4549 25 -176 125 | C |
| ATOM 288 O THR A 40 | 24.356 1.251 9.276 1.00 36.16 | O |
| ANISOU 288 O THR A 40 | 3937 5039 4764 89 -203 151 | O |
| ATOM 289 CB THR A 40 | 27.368 2.319 10.391 1.00 34.41 | C |
| ANISOU 289 CB THR A 40 | 3616 4802 4656 -47 -108 257 | C |
| ATOM 290 OG1 THR A 40 | 26.833 3.405 9.604 1.00 33.29 | O |
| ANISOU 290 OG1 THR A 40 | 3473 4596 4578 -34 -109 352 | O |
| ATOM 291 CG2 THR A 40 | 28.854 2.104 10.115 1.00 30.81 | C |
| ANISOU 291 CG2 THR A 40 | 3109 4429 4168 -55 -60 324 | C |
| ATOM 292 N ILE A 41 | 24.674 1.471 11.496 1.00 34.84 | N |
| ANISOU 292 N ILE A 41 | 3738 4797 4702 -36 -182 32 | N |
| ATOM 293 CA ILE A 41 | 23.228 1.755 11.667 1.00 36.82 | C |
| ANISOU 293 CA ILE A 41 | 3981 5004 5006 -28 -208 -42 | C |
| ATOM 294 C ILE A 41 | 22.906 3.010 10.863 1.00 38.44 | C |
| ANISOU 294 C ILE A 41 | 4166 5143 5298 12 -231 30 | C |
| ATOM 295 O ILE A 41 | 21.795 3.108 10.261 1.00 37.24 | O |
| ANISOU 295 O ILE A 41 | 4011 4983 5156 70 -273 15 | O |
| ATOM 296 CB ILE A 41 | 22.834 1.861 18.147 1.00 36.95 | C |
| ANISOU 296 CB ILE A 41 | 3975 4999 5064 -92 -193 -158 | C |
| ATOM 297 CG1 ILE A 41 | 21.323 1.995 13.276 1.00 40.02 | C |
| ANISOU 297 CG1 ILE A 41 | 4332 5374 5499 -79 -205 -245 | C |
| ATOM 298 CG2 ILE A 41 | 23.722 2.883 13.871 1.00 32.61 | C |
| ANISOU 298 CG2 ILE A 41 | 3422 4425 4619 -136 -186 -166 | C |
| ATOM 299 CD1 ILE A 41 | 20.904 1.832 14.723 1.00 43.04 | C |
| ANISOU 299 CD2 ILE A 42 | 4692 5786 5874 -140 -166 -358 | C |
| ATOM 300 N THR A 42 | 23.895 3.932 10.800 1.00 35.28 | N |
| ANISOU 300 N THR A 42 | 3747 4691 4965 -17 -211 118 | N |
| ATOM 301 CA THR A 42 | 23.732 5.285 10.150 1.00 36.89 | C |
| ANISOU 301 CA THR A 42 | 3938 4790 5287 3 -234 218 | C |
| ATOM 302 C THR A 42 | 23.549 5.083 8.644 1.00 35.03 | C |
| ANISOU 302 C THR A 42 | 3741 4623 4946 87 -245 353 | C |
| ATOM 303 C THR A 42 | 22.665 5.674 8.031 1.00 35.95 | O |
| ANISOU 303 O THR A 42 | 3869 4690 5101 150 -298 393 | O |
| ATOM 304 CB THR A 42 | 24.914 6.266 10.454 1.00 36.99 | C |
| ANISOU 304 CB THR A 42 | 3915 4717 5423 -74 -208 291 | C |
| ATOM 305 OG1 THR A 42 | 25.331 6.131 11.821 1.00 39.80 | O |
| ANISOU 305 OG1 THR A 42 | 4240 5066 5816 -141 -204 152 | O |
| ATOM 306 CG2 THR A 42 | 24.571 7.726 10.194 1.00 39.76 | C |

TABLE 3-continued

| | | | |
|---|---|---|---|
| ANISOU | 306 CG2 THR A 42 | 4253 4899 5955 -72 -249 359 | C |
| ATOM | 307 N ASP A 43 | 24.282 4.146 8.071 1.00 35.09 | N |
| ANISOU | 307 N ASP A 43 | 3769 4758 4804 105 -206 400 | N |
| ATOM | 308 CA ASP A 43 | 24.066 3.794 6.623 1.00 36.36 | C |
| ANISOU | 308 CA ASP A 43 | 3971 5026 4818 204 -220 494 | C |
| ATOM | 309 C ASP A 43 | 22.738 3.134 6.354 1.00 38.06 | C |
| ANISOU | 309 C ASP A 43 | 4208 5272 4981 277 -298 383 | C |
| ATOM | 310 O ASP A 43 | 22.029 6026 5.404 1.00 43.89 | O |
| ANISOU | 310 O ASP A 43 | 4967 6026 5683 361 -356 442 | O |
| ATOM | 311 CB ASP A 43 | 25.092 2.741 6.153 1.00 37.67 | C |
| ANISOU | 311 CB ASP A 43 | 4144 5342 4827 227 -166 510 | C |
| ATOM | 312 CG ASP 43 | 26.494 3.314 5.995 1.00 39.98 | C |
| ANISOU | 312 CG ASP A 43 | 4394 5659 5137 173 -79 650 | C |
| ATOM | 313 OD1 ASP A 43 | 26.657 4.441 5.462 1.00 41.53 | O |
| ANISOU | 313 OD1 ASP A 43 | 4582 5807 5391 155 -56 812 | O |
| ATOM | 314 OD2 ASP A 43 | 27.441 2.581 6.364 1.00 43.89 | O |
| ANISOU | 314 OD2 ASP A 43 | 4860 6226 5592 152 -37 602 | O |
| ATOM | 315 N LEU A 44 | 22.403 2.117 7.143 1.00 39.04 | N |
| ANISOU | 315 N LEU A 44 | 4325 5409 5100 246 -306 230 | N |
| ATOM | 316 CA LEU A 44 | 21.123 1.373 6.901 1.00 40.82 | C |
| ANISOU | 316 CA LEU A 44 | 4550 5660 5298 295 -379 114 | C |
| ATOM | 317 C LEU A 44 | 19.921 2.327 6.955 1.00 43.83 | C |
| ANISOU | 317 C LEU A 44 | 4893 5963 5796 320 -436 91 | C |
| ATOM | 318 O LEU A 44 | 18.985 2.230 6.132 1.00 44.18 | O |
| ANISOU | 318 O LEU A 44 | 4933 6044 5809 403 -518 68 | O |
| ATOM | 319 CB LEU A 44 | 20.937 0.301 7.954 1.00 39.47 | C |
| ANISOU | 319 CB LEU A 44 | 4370 5480 5145 224 -364 -18 | C |
| ATOM | 320 CG LEU A 44 | 19.737 -0.605 7.708 1.00 45.48 | C |
| ANISOU | 320 CG LEU A 44 | 5118 6262 5901 246 -431 -133 | C |
| ATOM | 321 CD1 LEU A 44 | 19.705 -1.107 6.280 1.00 41.22 | C |
| ANISOU | 321 CD1 LEU A 44 | 4612 5809 5239 354 -499 -121 | C |
| ATOM | 322 CD2 LEU A 44 | 19.730 -1.750 8.694 1.00 39.47 | C |
| ANISOU | 322 CD2 LEU A 44 | 4360 5482 5154 161 -405 -218 | C |
| ATOM | 323 N ALA A 45 | 19.973 3.258 7.911 1.00 43.67 | N |
| ANISOU | 323 N ALA A 45 | 4839 5840 5913 260 -406 81 | N |
| ATOM | 324 CA ALA A 45 | 18.980 4.303 8.043 1.00 45.17 | C |
| ANISOU | 324 CA ALA A 45 | 4986 5938 6240 296 -459 50 | C |
| ATOM | 325 C ALA A 45 | 18.911 5.2056 6.820 1.00 45.80 | C |
| ANISOU | 325 C ALA A 45 | 5097 5987 6317 390 -520 205 | C |
| ATOM | 326 O ALA A 45 | 17.806 5.427 6.252 1.00 45.33 | O |

TABLE 3-continued

| | | | | |
|---|---|---|---|---|
| ANISOU | 326 | O ALA A 45 | 5018 5927 6280 482 -611 180 | O |
| ATOM | 327 | CB ALA A 45 | 19.176 5.107 9.324 1.00 41.04 | C |
| ANISOU | 327 | CB ALA A 45 | 4423 5311 5858 224 -418 -15 | C |
| ATOM | 328 | N ARG A 46 | 20.058 5.720 5.396 1.00 44.63 | N |
| ANISOU | 328 | N ARG A 46 | 4992 5822 6144 369 -473 373 | N |
| ATOM | 329 | CA ARG A 46 | 20.108 6.535 5.185 1.00 48.79 | C |
| ANISOU | 329 | CA ARG A 46 | 5562 6333 6642 448 -515 569 | C |
| ATOM | 330 | C ARG A 46 | 19.662 5.802 3.935 1.00 48.49 | C |
| ANISOU | 330 | C ARG A 46 | 5565 6453 6407 560 -572 599 | C |
| ATOM | 331 | O ARG A 46 | 18.871 6.321 3.147 1.00 48.11 | O |
| ANISOU | 331 | O ARG A 46 | 5534 6396 6351 664 -668 662 | O |
| ATOM | 332 | CB ARG A 46 | 21.551 6.995 4.907 1.00 53.91 | C |
| ANISOU | 332 | CB ARG A 46 | 6237 6976 7272 382 -425 758 | C |
| ATOM | 333 | CG ARG A 46 | 22.129 8.004 5.863 1.00 55.16 | C |
| ANISOU | 333 | CG ARG A 46 | 6359 6959 7642 278 -391 771 | C |
| ATOM | 334 | CD ARG A 46 | 23.608 8.211 5.499 1.00 61.83 | C |
| ANISOU | 334 | CD ARG A 46 | 7204 7834 8453 199 -294 950 | C |
| ATOM | 335 | NE ARG A 46 | 23.822 9.304 4.526 1.00 61.58 | N |
| ANISOU | 335 | NE ARG A 46 | 7206 7726 8465 214 -297 1205 | N |
| ATOM | 336 | CZ ARG A 46 | 24.080 9.167 3.223 1.00 64.41 | C |
| ANISOU | 336 | CZ ARG A 46 | 7613 8224 8636 275 -266 1403 | C |
| ATOM | 337 | NH1 ARG A 46 | 24.183 7.978 2.618 1.00 66.99 | N |
| ANISOU | 337 | NH1 ARG A 46 | 7959 8781 8715 343 -235 1358 | N |
| ATOM | 338 | NH2 ARG A 46 | 24.260 10.249 2.514 1.00 62.68 | N |
| ANISOU | 338 | NH2 ARG A 46 | 7425 7911 8478 271 -266 1651 | N |
| ATOM | 339 | N ASN A 47 | 20.227 4.621 3.701 1.00 45.22 | N |
| ANISOU | 339 | N ASN A 47 | 5168 6183 5830 551 -525 555 | N |
| ATOM | 340 | CA ASN A 47 | 19.899 3.892 2.485 1.00 46.66 | C |
| ANISOU | 340 | CA ASN A 47 | 5390 6525 5813 665 -586 557 | C |
| ATOM | 341 | C ASN A 47 | 18.414 3.501 2.381 1.00 49.08 | C |
| ANISOU | 341 | C ASN A 47 | 5663 6638 6149 736 -714 395 | C |
| ATOM | 342 | O ASN A 47 | 17.917 3.236 1.238 1.00 52.38 | O |
| ANISOU | 342 | O ASN A 47 | 6108 7367 6428 853 -806 402 | O |
| ATOM | 343 | CB ASN A 47 | 20.741 2.642 2.406 1.00 47.08 | C |
| ANISOU | 343 | CB ASN A 47 | 5457 6707 5723 648 -522 490 | C |
| ATOM | 344 | CG ASN A 47 | 22.208 2.962 2.328 1.00 48.03 | C |
| ANISOU | 344 | CG ASN A 47 | 5588 6862 5798 597 -400 644 | C |
| ATOM | 345 | OD1 ASN A 47 | 22.587 4.050 1.864 1.00 43.26 | O |
| ANISOU | 345 | OD1 ASN A 47 | 4998 6231 5207 596 -367 842 | O |
| ATOM | 346 | ND2 ASN A 47 | 23.038 2.046 2.797 1.00 43.71 | N |

TABLE 3-continued

| | | | |
|---|---|---|---|
| ANISOU | 346 ND2 ASN A 47 | 5026 6365 5215 550 -334 562 | N |
| ATOM | 347 N THR A 48 | 17.737 3.415 3.524 1.00 43.99 | N |
| ANISOU | 347 N THR A 48 | 4949 6093 5672 664 -717 242 | N |
| ATOM | 348 CA THR 4 48 | 16.336 3.068 3.509 1.00 46.99 | C |
| ANISOU | 348 CA THR A 48 | 5265 6482 6108 712 -824 85 | C |
| ATOM | 349 C THR A 48 | 15.430 4.301 3.680 1.00 45.39 | C |
| ANISOU | 349 C THR A 48 | 5010 6168 6068 763 -892 98 | C |
| ATOM | 350 O THR A 48 | 14.196 4.171 3.614 1.00 45.99 | O |
| ANISOU | 350 O THR A 48 | 5009 6257 6209 816 -990 -30 | O |
| ATOM | 351 CB THR A 48 | 15.995 2.098 4.647 1.00 42.76 | C |
| ANISOU | 351 CB THR A 48 | 4666 5929 5653 602 -778 -98 | C |
| ATOM | 352 OG1 THR A 48 | 16.378 2.703 5.885 1.00 39.24 | O |
| ANISOU | 352 OG1 THR A 48 | 4196 5381 5332 504 -683 -95 | O |
| ATOM | 353 CG2 THR A 48 | 16.642 0.692 4.409 1.00 42.62 | C |
| ANISOU | 353 CG2 THR A 48 | 4694 6000 5500 574 -751 -145 | C |
| ATOM | 354 N GLN A 49 | 16.041 5.465 3.900 1.00 48.72 | N |
| ANISOU | 354 N GLN A 49 | 5462 6475 6573 746 -849 241 | N |
| ATOM | 355 CA GLN A 49 | 15.319 6.701 4.257 1.00 53.62 | C |
| ANISOU | 355 CA GLN A 49 | 6036 6947 7390 790 -910 238 | C |
| ATOM | 356 C GLN A 49 | 14.355 6.500 5.450 1.00 52.27 | C |
| ANISOU | 356 C GLN A 49 | 5746 6742 7372 746 -902 2 | C |
| ATOM | 357 O GLN A 49 | 13.170 6.870 5.384 1.00 54.02 | O |
| ANISOU | 357 O GLN A 49 | 5886 6940 7698 833 -999 -91 | O |
| ATOM | 358 CB GLN A 49 | 14.513 7.213 3.057 1.00 58.34 | C |
| ANISOU | 358 CB GLN A 49 | 6652 7563 7953 951 -1059 325 | C |
| ATOM | 359 CG GLN A 49 | 15.296 7.882 1.925 1.00 70.89 | C |
| ANISOU | 359 CG GLN A 49 | 8356 9155 9423 1011 -1072 603 | C |
| ATOM | 360 CD GLN A 49 | 14.441 7.949 0.661 1.00 80.36 | C |
| ANISOU | 360 CD GLN A 49 | 9582 10448 10504 1183 -1231 663 | C |
| ATOM | 361 OE1 GLN A 49 | 14.248 6.939 -0.021 1.00 89.83 | O |
| ANISOU | 361 OE1 GLN A 49 | 10790 11829 11511 1232 -1272 594 | O |
| ATOM | 362 NE2 GLN A 49 | 13.894 9.127 0.360 1.00 88.39 | N |
| ANISOU | 362 NE2 GLN A 49 | 10609 11334 11642 1285 -1340 775 | N |
| ATOM | 363 N THR A 50 | 14.845 5.915 6.539 1.00 45.32 | N |
| ANISOU | 363 N THR A 50 | 4846 5874 6499 617 -787 -91 | N |
| ATOM | 364 CA THR A 50 | 14.050 5.708 7.748 1.00 43.84 | C |
| ANISOU | 364 CA THH A 50 | 4552 5683 6424 561 -748 -291 | C |
| ATOM | 365 C THR A 50 | 14.929 6.228 8.880 1.00 46.84 | C |
| ANISOU | 365 C THR A 50 | 4949 5981 6568 467 -648 -295 | C |
| ATOM | 366 O THR A 50 | 16.120 6.465 8.686 1.00 57.26 | O |

TABLE 3-continued

| | | | | | | | | | | |
|---|---|---|---|---|---|---|---|---|---|---|
| ANISOU | 366 | O | THR | A | 50 | 6351 7264 8143 431 -611 -158 | | | | O |
| ATOM | 367 | CB | THR | A | 50 | 13.621 | 4.201 | 7.914 | 1.00 45.44 | C |
| ANISOU | 367 | CB | THR | A | 50 | 4715 6012 6537 495 -720 -406 | | | | C |
| ATOM | 368 | OG1 | THR | A | 50 | 14.766 | 3.357 | 8.167 | 1.00 46.98 | O |
| ANISOU | 368 | OG1 | THR | A | 50 | 4991 6245 6614 399 -632 -353 | | | | O |
| ATOM | 369 | OG2 | THR | A | 50 | 12.967 | 3.662 | 6.650 | 1.00 44.81 | C |
| ANISOU | 369 | OG2 | THR | A | 50 | 4631 6012 6382 589 -839 -404 | | | | C |
| ATOM | 370 | N | SER | A | 51 | 14.405 | 6.386 | 10.072 | 1.00 51.12 | N |
| ANISOU | 370 | N | SER | A | 51 | 5406 6512 7505 426 -601 -459 | | | | N |
| ATOM | 371 | CA | SER | A | 51 | 15.267 | 6.781 | 11.187 | 1.00 51.23 | C |
| ANISOU | 371 | CA | SER | A | 51 | 5438 6474 7552 342 -518 -488 | | | | C |
| ATOM | 372 | C | SER | A | 51 | 16.129 | 5.590 | 11.683 | 1.00 51.03 | C |
| ANISOU | 372 | C | SER | A | 51 | 5465 6549 7376 228 -426 -470 | | | | C |
| ATOM | 373 | O | SER | A | 51 | 15.882 | 4.428 | 11.359 | 1.00 44.63 | O |
| ANISOU | 373 | O | SER | A | 51 | 4661 5835 6462 20 -417 -469 | | | | O |
| ATOM | 374 | CB | SER | A | 51 | 14.402 | 7.258 | 12.303 | 1.00 50.13 | C |
| ANISOU | 374 | CB | SER | A | 51 | 5192 6328 7527 350 -493 -686 | | | | C |
| ATOM | 375 | OG | SER | A | 51 | 13.577 | 6.178 | 12.627 | 1.00 53.50 | O |
| ANISOU | 375 | OG | SER | A | 51 | 5550 6895 7884 309 -446 -785 | | | | O |
| ATOM | 376 | N | GLU | A | 52 | 17.125 | 5.880 | 12.503 | 1.00 46.44 | N |
| ANISOU | 376 | N | GLU | A | 52 | 4914 5934 6796 159 -371 -468 | | | | N |
| ATOM | 377 | CA | GLU | A | 52 | 17.815 | 4.813 | 13.172 | 1.00 45.04 | C |
| ANISOU | 377 | CA | GLU | A | 52 | 4774 5849 6491 67 -298 -473 | | | | C |
| ATOM | 378 | C | GLU | A | 52 | 16.890 | 4.136 | 14.165 | 1.00 42.54 | C |
| ANISOU | 378 | C | GLU | A | 52 | 4394 -5625 6143 21 -241 -614 | | | | C |
| ATOM | 379 | O | GLU | A | 52 | 17.047 | 2.958 | 14.454 | 1.00 44.75 | O |
| ANISOU | 379 | O | GLU | A | 52 | 4704 5986 6314 -45 -196 -599 | | | | O |
| ATOM | 380 | CB | GLU | A | 52 | 19.041 | 5.341 | 13.892 | 1.00 45.10 | C |
| ANISOU | 380 | CB | GLU | A | 52 | 4812 5809 6514 12 -270 -458 | | | | C |
| ATOM | 381 | CG | GLU | A | 52 | 19.994 | 6.056 | 12.973 | 1.00 50.45 | C |
| ANISOU | 381 | CG | GLU | A | 52 | 5531 6395 7242 32 -305 -304 | | | | C |
| ATOM | 382 | CD | GLU | A | 52 | 21.295 | 6.439 | 13.673 | 1.00 54.72 | C |
| ANISOU | 382 | CD | GLU | A | 52 | 6063 6900 7810 -40 -281 -294 | | | | C |
| ATOM | 383 | OE1 | GLU | A | 52 | 21.502 | 6.036 | 14.845 | 1.00 53.04 | O |
| ANISOU | 383 | OE1 | GLU | A | 52 | 5660 6750 7544 -92 -247 -406 | | | | O |
| ATOM | 384 | OE2 | GLU | A | 52 | 22.117 | 7.123 | 13.023 | 1.00 58.16 | O |
| ANISOU | 384 | OE2 | GLU | A | 52 | 6532 7253 8315 -47 -298 -166 | | | | O |
| ATOM | 385 | N | ALA | A | 53 | 15.938 | 4.670 | 14.696 | 1.00 41.68 | N |
| ANISOU | 385 | N | ALA | A | 53 | 4197 5506 6135 57 -240 -747 | | | | N |
| ATOM | 386 | CA | ALA | A | 53 | 14.939 | 4.219 | 15.609 | 1.00 50.52 | C |

TABLE 3-continued

| | | |
|---|---|---|
| ANISOU 386 CA ALA A 53 | 5232 6745 7219 8 -163 -876 | C |
| ATOM 387 C ALA A 53 | 14.134 3.084 14.92 1.00 46.94 | C |
| ANISOU 387 C ALA A 53 | 4748 6354 6733 -12 -172 -848 | C |
| ATOM 388 O ALA A 53 | 13.753 2.079 15.550 1.00 44.7 | O |
| ANISOU 388 O ALA A 53 | 4445 6170 6392 -102 -98 -875 | O |
| ATOM 389 CB ALA A 53 | 13.972 5.248 16.168 1.00 46.28 | C |
| ANISOU 389 CB ALA A 53 | 4831 6456 7057 73 -160 -1044 | C |
| ATOM 390 N THR A 54 | 13.810 3.310 13.655 1.00 48.56 | N |
| ANISOU 390 N THR A 54 | 4950 6506 6994 74 -272 -798 | N |
| ATOM 391 CA THR A 54 | 13.043 2.333 2.333 12.873 1.00 47.18 | C |
| ANISOU 391 CA THR A 54 | 4740 5381 6804 72 -315 -797 | C |
| ATOM 392 C THR A 54 | 13.898 1.055 12.699 1.00 45.63 | C |
| ANISOU 392 C THR A 54 | 4648 6207 6463 -5 -294 -702 | C |
| ATOM 393 O THR A 54 | 13.425 -0.059 12.933 1.00 42.99 | O |
| ANISOU 393 O THR A 54 | 4285 5919 6129 -84 -265 -732 | O |
| ATOM 394 CB THR A 54 | 12.605 2.892 11.510 1.00 48.29 | C |
| ANISOU 394 CB THR A 54 | 4869 6476 7002 202 -446 -764 | C |
| ATOM 395 OG1 THR A 54 | 11.84 4.084 11.686 1.00 54.69 | O |
| ANISOU 395 OG1 THR A 54 | 5587 7245 7949 289 -481 -849 | O |
| ATOM 396 CG2 THR A 54 | 11.723 1.859 10.770 1.00 46.86 | C |
| ANISOU 396 CG2 THR A 54 | 4632 6360 6812 201 -508 -805 | C |
| ATOM 397 N VAL A 55 | 15.173 1.246 12.362 1.00 39.75 | N |
| ANISOU 397 N VAL A 55 | 4015 5420 5670 16 -306 -591 | N |
| ATOM 398 CA VAL A 55 | 16.080 0.124 12.117 1.00 41.43 | C |
| ANISOU 398 CA VAL A 55 | 4321 5648 5772 -26 -299 -512 | C |
| ATOM 399 C VAL A 55 | 16.210 -0.671 13.413 1.00 40.01 | C |
| ANISOU 399 C VAL A 55 | 4148 5502 5552 -141 -210 -538 | C |
| ATOM 400 O VAL A 55 | 16.116 -1.899 13.394 1.00 40.78 | O |
| ANISOU 400 O VAL A 55 | 4270 5610 5614 -195 -209 -527 | O |
| ATOM 401 CB VAL A 55 | 17.463 0.661 11.647 1.00 41.50 | C |
| ANISOU 401 CB VAL A 55 | 4416 5624 5728 17 -309 -396 | C |
| ATOM 402 CG1 VAL A 55 | 18.478 -0.453 11.456 1.00 39.61 | C |
| ANISOU 402 CG1 VAL A 55 | 4258 5411 5380 -7 -299 -334 | C |
| ATOM 403 CG2 VAL A 55 | 17.319 1.451 10.351 1.00 46.94 | C |
| ANISOU 403 CG2 VAL A 55 | 5109 6289 6438 126 -387 -333 | C |
| ATOM 404 N VAL A 56 | 16.399 0.052 14.536 1.00 39.35 | N |
| ANISOU 404 N VAL A 56 | 4045 5431 5474 -172 -145 -575 | N |
| ATOM 405 CA VAL A 56 | 16.532 -0.586 15.837 1.00 41.03 | C |
| ANISOU 405 CA VAL A 56 | 4271 5701 5616 -270 -59 -588 | C |
| ATOM 406 C VAL A 56 | 15.267 -1.388 16.164 1.00 42.41 | C |

TABLE 3-continued

| | | | | |
|---|---|---|---|---|
| ANISOU | 406 | C VAL A 56 | 4367 5931 5817 -343 -11 -639 | C |
| ATOM | 407 | O VAL A 56 | 15.356 -2.550 16.606 1.00 41.25 | O |
| ANISOU | 407 | O VAL A 56 | 4262 5798 5612 -432 26 -584 | O |
| ATOM | 408 | CB VAL A 56 | 16.808 0.438 16.980 1.00 43.27 | C |
| ANISOU | 408 | CB VAL A 56 | 4534 6015 5891 -272 -7 -657 | C |
| ATOM | 409 | CG1 VAL A 56 | 16.804 -0.264 18.304 1.00 41.87 | C |
| ANISOU | 409 | CG1 VAL A 56 | 4372 5933 5605 -364 82 -665 | C |
| ATOM | 410 | CG2 VAL A 56 | 18.160 1.157 16.822 1.00 42.91 | C |
| ANISOU | 410 | CG2 VAL A 56 | 4556 5908 5841 -232 -51 -606 | C |
| ATOM | 411 | N ARG A 57 | 14.090 -0.782 15.930 1.00 42.94 | N |
| ANISOU | 411 | N ARG A 57 | 4312 6018 5985 -307 -17 -738 | N |
| ATOM | 412 | CA ARG A 57 | 12.850 -1.458 16.227 1.00 45.14 | C |
| ANISOU | 412 | CA ARG A 57 | 4480 6360 6312 -385 36 -796 | C |
| ATOM | 413 | C ARG A 57 | 12.727 -2.734 15.419 1.00 39.67 | C |
| ANISOU | 413 | C ARG A 57 | 3818 5618 5636 -431 -24 -739 | C |
| ATOM | 414 | O ARG A 57 | 12.346 -3.773 15.964 1.00 43.90 | O |
| ANISOU | 414 | O ARG A 57 | 4337 6173 6170 -552 37 -713 | O |
| ATOM | 415 | CB ARG A 57 | 11.619 -0.530 16.057 1.00 49.08 | C |
| ANISOU | 415 | CB ARG A 57 | 4819 6895 6933 -319 25 -932 | C |
| ATOM | 416 | CG ARG A 57 | 10.384 -1.007 16.812 1.00 58.34 | C |
| ANISOU | 416 | CG ARG A 57 | 5840 8179 8149 -416 131 -1012 | C |
| ATOM | 417 | CD ARG A 57 | 9.190 -0.060 16.633 1.00 72.05 | C |
| ANISOU | 417 | CD ARG A 57 | 7396 9960 10018 -328 113 -1167 | C |
| ATOM | 418 | NE ARG A 57 | 9 578 1.119 15.853 1.00 81.97 | N |
| ANISOU | 418 | NE ARG A 57 | 8696 11120 11327 -159 -8 -1182 | N |
| ATOM | 419 | CZ ARG A 57 | 8.858 1.664 14.872 1.00 83.53 | C |
| ANISOU | 419 | CZ ARG A 57 | 8813 11279 11645 -55 -126 -1239 | C |
| ATOM | 420 | NH1 ARG A 57 | 7.666 1.156 14.555 1.00 86.02 | N |
| ANISOU | 420 | NH1 ARG A 57 | 8976 11656 12052 -77 -144 -1317 | N |
| ATOM | 421 | NH2 ARG A 57 | 9.337 2.727 14.215 1.00 78.00 | N |
| ANISOU | 421 | NH2 ARG A 57 | 8180 10475 10980 79 -230 -1210 | N |
| ATOM | 422 | N LEU A 58 | 13.078 -2.703 14.136 1.00 43.67 | N |
| ANISOU | 422 | N LEU A 58 | 4377 6060 6156 -337 -144 -716 | N |
| ATOM | 423 | CA LEU A 58 | 13.112 -3.945 13-354 1.00 41.71 | C |
| ANISOU | 423 | C ALEU A 58 | 4172 5763 5912 -363 -216 -689 | C |
| ATOM | 424 | C LEU A 58 | 14.026 -4.997 14.055 1.00 43.03 | C |
| ANISOU | 424 | C LEU A 58 | 4454 5894 6000 -452 -167 -592 | C |
| ATOM | 425 | O LEU A 58 | 13.612 -6.138 14.353 1.00 42.00 | O |
| ANISOU | 425 | O LEU A 58 | 4316 5731 5910 -560 -149 -577 | O |
| ATOM | 426 | CB LEU A 58 | 13.571 -3.645 11.906 1.00 42.99 | C |

TABLE 3-continued

| | | | | |
|---|---|---|---|---|
| ANISOU | 426 | CB  LEU A  58 | 4391  5895  6047   -224  -342  -677 | C |
| ATOM   | 427 | CG  LEU A  58 | 13.785  -4.648  10.989  1.00  44.91 | C |
| ANISOU | 427 | CG  LEU A  58 | 4694  6098  6272   -214  -434  -677 | C |
| ATOM   | 428 | CD1 LEU A  58 | 12.470  -5.550  10.766  1.00  46.33 | C |
| ANISOU | 428 | CD1 LEU A  58 | 4758  6273   -275  -482  -779 | C |
| ATOM   | 429 | CD2 LEU A  58 | 14.343  -4.503   9.631  1.00  41.98 | C |
| ANISOU | 429 | CD2 LEU A  58 | 4365  5741  5825    -67  -636  -560 | C |
| ATOM   | 430 | N   CYS A  59 | 15.296  -4.609  14.310  1.00  39.52 | N |
| ANISOU | 430 | N   CYS A  59 | 4115  5445  5456   -406  -153  -521 | N |
| ATOM   | 431 | CA  CYS A  59 | 16.221  -5.451  15.016  1.00  38.24 | C |
| ANISOU | 431 | CA  CYS A  59 | 4057  5257  5216   -464  -122  -433 | C |
| ATOM   | 432 | C   CYS A  59 | 15.604  -6.042  16.279  1.00  37.83 | C |
| ANISOU | 432 | C   CYS A  59 | 3976  5237  5161   -601   -22  -407 | C |
| ATOM   | 433 | O   CYS A  59 | 15.639  -7.274  16.453  1.00  39.95 | O |
| ANISOU | 433 | O   CYS A  59 | 4297  5442  5440   -679   -29  -341 | O |
| ATOM   | 434 | CB  CYS A  59 | 17.573  -4.691  15.307  1.00  31.78 | C |
| ANISOU | 434 | CB  CYS A  59 | 3312  4456  4306   -400  -114  -384 | C |
| ATOM   | 435 | SG  CYS A  59 | 18.316  -4.365  13.676  1.00  38.09 | S |
| ANISOU | 435 | SG  CYS A  59 | 4148  5223  5100   -263  -215  -372 | S |
| ATOM   | 436 | N   ARG A  60 | 15.044  -5.218  17.162  1.00  37.75 | N |
| ANISOU | 436 | N   ARG A  60 | 3886  5323  5135   -631    72  -454 | N |
| ATOM   | 437 | CA  ARG A  60 | 14.535  -5.794  18.402  1.00  43.59 | C |
| ANISOU | 437 | CA  ARG A  60 | 4602  6127  5832   -762   188  -410 | C |
| ATOM   | 438 | C   ARG A  60 | 13.264  -6.636  18.197  1.00  47.77 | C |
| ANISOU | 438 | C   ARG A  60 | 5029  6639  6482   -872   213  -423 | C |
| ATOM   | 439 | O   ARG A  60 | 13.094  -7.656  18.860  1.00  47.28 | O |
| ANISOU | 439 | O   ARG A  60 | 4994  6562  6408  -1000   273  -323 | O |
| ATOM   | 440 | CB  ARG A  60 | 14.314  -4.721  19.450  1.00  44.11 | C |
| ANISOU | 440 | CB  ARG A  60 | 4606  6329  5826   -755   290  -478 | C |
| ATOM   | 441 | CG  ARG A  60 | 15.598  -4.019  19.790  1.00  47.38 | C |
| ANISOU | 441 | CG  ARG A  60 | 5117  6748  6136   -674   258  -467 | C |
| ATOM   | 442 | CD  ARG A  60 | 15.399  -3.025  20.914  1.00  58.02 | C |
| ANISOU | 442 | CD  ARG A  60 | 6409  8228  7409   -865   346  -561 | C |
| ATOM   | 443 | NE  ARG A  60 | 16.709  -2.419  21.194  1.00  63.91 | N |
| ANISOU | 443 | NE  ARG A  60 | 7244  8959  8078   -597   292  -558 | N |
| ATOM   | 444 | CZ  ARG A  60 | 16.925  -1.183  21.657  1.00  60.67 | C |
| ANISOU | 444 | CZ  ARG A  60 | 6799  8593  7661   -533   293  -676 | C |
| ATOM   | 445 | NH1 ARG A  60 | 15.915  -0.368  21.897  1.00  58.59 | N |
| ANISOU | 445 | NH1 ARG A  60 | 6416  8392  7454   -509   346  -816 | N |
| ATOM   | 446 | NH2 ARG A  60 | 18.177  -0.762  21.877  1.00  52.18 | N |

TABLE 3-continued

| | | | | | | | | |
|---|---|---|---|---|---|---|---|---|
| ANISOU | 446 | NH2 | ARG A | 60 | 5799 7492 6536 | -491 | 231 | -868 N |
| ATOM | 447 | N | ASP A | 61 | 12.434 -6.257 17 221 | 1.00 | 49.01 | N |
| ANISOU | 447 | N | ASP A | 61 | 5073 6785 6764 | -821 | 150 | -534 N |
| ATOM | 448 | CA | ASP A | 61 | 11.227 -7.018 16.923 | 1.00 | 52.46 | C |
| ANISOU | 448 | CA | A3P A | 61 | 5388 7202 7342 | -922 | 151 | -571 C |
| ATOM | 449 | C | ASP A | 61 | 11.627 -8.407 16.526 | 1.00 | 57.44 | C |
| ANISOU | 449 | C | ASP A | 61 | 6120 7690 8014 | -986 | 76 | -486 C |
| ATOM | 450 | O | ASP A | 61 | 10.846 -9.374 16.690 | 1.00 | 59.21 | O |
| ANISOU | 450 | O | ASP A | 61 | 6279 7868 8350 | -1129 | 102 | -462 O |
| ATOM | 451 | CB | ASP A | 61 | 10.402 -6.383 15.797 | 1.00 | 54.41 | C |
| ANISOU | 451 | CB | ASP A | 61 | 5507 7456 7709 | -825 | 53 | -714 C |
| ATOM | 452 | CG | ASP A | 61 | 9.570 -5.217 16.275 | 1.00 | 56.33 | C |
| ANISOU | 452 | CG | ASP A | 61 | 5598 7828 7978 | -790 | 131 | -819 C |
| ATOM | 453 | OD1 | ADP A | 61 | 9.607 -4.900 17.478 | 1.00 | 52.76 | O |
| ANISOU | 453 | OD1 | ASP A | 61 | 5132 7472 7442 | -841 | 270 | -800 O |
| ATOM | 454 | OD2 | ASP A | 61 | 8.883 -4.610 15.438 | 1.00 | 59.70 | O |
| ANISOU | 454 | OD2 | ASP A | 61 | 5918 8263 8503 | -695 | 45 | -930 O |
| ATOM | 455 | N | MET A | 62 | 12.839 -8.526 16.006 | 1.00 | 52.50 | N |
| ANISOU | 455 | N | MET A | 62 | 5644 6989 7314 | -884 | -16 | -445 N |
| ATOM | 456 | CA | MET A | 62 | 13.270 -9.815 15.480 | 1.00 | 51.82 | C |
| ANISOU | 456 | CA | MET A | 62 | 5655 6755 7280 | -907 | -113 | -399 C |
| ATOM | 457 | C | MET A | 62 | 13.980 -10.571 16.548 | 1.00 | 52.66 | C |
| ANISOU | 457 | C | MET A | 62 | 5881 6816 7313 | -991 | -51 | -245 C |
| ATOM | 458 | O | MET A | 62 | 14.495 -11.643 16.271 | 1.00 | 47.02 | O |
| ANISOU | 458 | O | MET A | 62 | 5265 5961 6640 | -999 | -132 | -194 O |
| ATOM | 459 | CB | MET A | 62 | 14.179 -9.663 14.297 | 1.00 | 56.89 | C |
| ANISOU | 459 | CB | MET A | 62 | 6382 7354 7880 | -743 | -243 | -446 C |
| ATOM | 460 | CG | MET A | 62 | 13.602 -8.747 13.241 | 1.00 | 59.05 | C |
| ANISOU | 460 | CG | MET A | 62 | 6560 7693 8184 | -635 | -309 | -570 C |
| ATOM | 461 | SD | MET A | 62 | 13.988 -9.733 11.830 | 1.00 | 77.50 | S |
| ANISOU | 461 | SD | MET A | 62 | 8968 9927 10552 | -547 | -478 | -634 S |
| ATOM | 462 | CE | MET A | 62 | 12.669 -10.948 12.042 | 1.00 | 50.44 | C |
| ANISOU | 462 | CE | MET A | 62 | 5438 6399 7327 | -724 | -498 | -585 C |
| ATOM | 463 | N | GLY A | 63 | 13.983 -10.022 17.769 | 1.00 | 47.98 | N |
| ANISOU | 463 | N | GLY A | 63 | 5278 6343 6609 | -1042 | 83 | -181 N |
| ATOM | 464 | CA | GLY A | 63 | 14.541 -10.726 18.910 | 1.00 | 49.98 | C |
| ANISOU | 464 | CA | GLY A | 63 | 5643 6581 6768 | -1127 | 146 | -17 C |
| ATOM | 465 | C | GLY A | 63 | 16.030 -10 462 19.127 | 1.00 | 50.07 | C |
| ANISOU | 465 | C | GLY A | 63 | 5795 6596 6633 | -1008 | 97 | 33 C |
| ATOM | 466 | O | GLY A | 63 | 16.677 -11.199 19.842 | 1.00 | 46.14 | O |

TABLE 3-continued

| | | |
|---|---|---|
| ANISOU 466 O GLY A 63 | 5412 6053 6066 -1042 97 168 | O |
| ATOM 467 N TYR A 64 | 16.583 -9.428 18.506 1.00 47.27 | N |
| ANISOU 467 N TYR A 64 | 5428 6290 6242 -870 49 -66 | N |
| ATOM 468 CA TYR A 64 | 18.002 -9.087 18.731 1.00 46.70 | C |
| ANISOU 468 CA TYR A 64 | 5458 6235 6049 -769 8 -29 | C |
| ATOM 469 C TYR A 64 | 18.071 -7.933 19.686 1.00 45.48 | C |
| ANISOU 469 C TYR A 64 | 5267 6231 5784 -763 96 -59 | C |
| ATOM 470 O TYR A 64 | 17.051 -7.297 19.907 1.00 42.82 | O |
| ANISOU 470 O TYR A 64 | 4820 5976 5472 -804 175 -133 | O |
| ATOM 471 CB TYR A 64 | 18.703 -8.717 17.422 1.00 44.76 | C |
| ANISOU 471 CB TYR A 64 | 5221 5945 5839 -630 -96 -103 | C |
| ATOM 472 CG TYR A 64 | 18.781 -9.207 16.546 1.00 41.30 | C |
| ANISOU 472 CG TYR A 64 | 4832 5374 5487 -613 -193 -98 | C |
| ATOM 473 CD1 TYR A 64 | 19.788 -10.857 16.706 1.00 41.22 | C |
| ANISOU 473 CD1 TYR A 64 | 4934 5275 5451 -582 -255 -21 | C |
| ATOM 474 CD2 TYR A 64 | 17.786 -10.138 15.607 1.00 45.04 | C |
| ANISOU 474 CD2 TYR A 64 | 5232 5804 6079 -626 -234 -186 | C |
| ATOM 475 CE1 TYR A 64 | 19.826 -12.000 15.927 1.00 45.63 | C |
| ANISOU 475 CE1 TYR A 64 | 5538 5693 6108 -557 -355 -41 | C |
| ATOM 476 CE2 TYR A 64 | 17.608 -11.285 14.820 1.00 48.41 | C |
| ANISOU 476 CE2 TYR A 64 | 5700 6099 6595 -611 -338 -212 | C |
| ATOM 477 CZ TYR A 64 | 18.820 -12.205 14.997 1.00 44.62 | C |
| ANISOU 477 CZ TYR A 64 | 5337 5521 6096 -577 -394 -143 | C |
| ATOM 478 OH TYR A 64 | 18.806 -13.287 14.162 1.00 51.69 | O |
| ANISOU 478 OH TYR A 64 | 6267 6276 7096 -545 -509 -202 | O |
| ATOM 479 N LYS A 65 | 19.253 -7.662 20.236 1.00 43.57 | N |
| ANISOU 479 N LYS A 65 | 5103 6024 5427 -705 72 -21 | N |
| ATOM 480 CA LYS A 65 | 19.410 -6.561 21.182 1.00 47.04 | C |
| ANISOU 480 CA LYS A 65 | 5512 6600 5761 -692 134 -76 | C |
| ATOM 481 C LYS A 65 | 19.407 -5.217 20.490 1.00 45.63 | C |
| ANISOU 481 C LYS A 65 | 5250 6434 5852 -609 113 -207 | C |
| ATOM 482 O LYS A 65 | 19.111 -4.185 21.137 1.00 46.32 | O |
| ANISOU 482 O LYS A 65 | 5276 6615 5707 -603 167 -299 | O |
| ATOM 483 CB LYS A 65 | 20.662 -6.699 22.033 1.00 48.73 | C |
| ANISOU 483 CB LYS A 65 | 5825 6853 5837 -659 96 -9 | C |
| ATOM 484 CG LYS A 65 | 20.467 -7.697 23.156 1.00 62.37 | C |
| ANISOU 484 CG LYS A 65 | 7629 8620 7448 -748 147 128 | C |
| ATOM 485 CD LYS A 65 | 21.581 -8.712 23.185 1.00 64.02 | C |
| ANISOU 485 CD LYS A 65 | 7965 8735 7626 -708 44 254 | C |
| ATOM 486 CE LYS A 65 | 21.072 -9.958 23.895 1.00 72.21 | C |

TABLE 3-continued

| | | | |
|---|---|---|---|
| ANISOU | 486 CE LYS A 65 | 9081 9736 8620 -817 85 425 | C |
| ATOM | 487 NZ LYS A 65 | 21.402 -11.183 23.112 1.00 69.91 | N |
| ANISOU | 487 NZ LYS A 65 | 6862 9241 8458 -802 -17 508 | N |
| ATOM | 488 N GLY A 66 | 19.718 -5.211 19.186 1.00 40.53 | N |
| ANISOU | 488 N GLY A 66 | 4604 5695 5100 -540 32 -217 | N |
| ATOM | 489 CA GLY A 66 | 19.985 -3.947 18.496 1.00 35.60 | C |
| ANISOU | 489 CA GLY A 66 | 3928 50666 4532 -456 1 -294 | C |
| ATOM | 490 C GLY A 66 | 20.631 -4.208 17.139 1.00 37.45 | C |
| ANISOU | 490 C GLY A 66 | 4192 5224 4812 -380 -81 -259 | C |
| ATOM | 491 O GLY A 66 | 20.724 -5.361 16.711 1.00 35.04 | O |
| ANISOU | 491 O GLY A 66 | 3937 4868 4507 -383 -119 -212 | O |
| ATOM | 492 N TYR A 67 | 21.082 -3.145 16.462 1.00 32.81 | N |
| ANISOU | 492 N TYR A 67 | 3573 4629 4263 -311 -107 -282 | N |
| ATOM | 493 CA TYR A 67 | 21.595 -3.286 15.099 1.00 31.31 | C |
| ANISOU | 493 CA TYR A 67 | 3401 4403 4092 -233 -165 -246 | C |
| ATOM | 494 C TYR A 67 | 22.866 -4.135 15.076 1.00 32.53 | C |
| ANISOU | 494 C TYR A 67 | 3622 4554 4183 -206 -196 -186 | C |
| ATOM | 495 O TYR A 67 | 23.028 -5.041 14.230 1.00 29.85 | O |
| ANISOU | 495 O TYR A 67 | 3317 4189 3835 -159 -240 -172 | O |
| ATOM | 496 CB TYR A 67 | 21.865 -1.912 14.489 1.00 31.93 | C |
| ANISOU | 496 CB TYR A 67 | 3435 4476 4220 -180 -171 -247 | C |
| ATOM | 497 CG TYR A 67 | 22.476 -2.041 13.154 1.00 34.71 | C |
| ANISOU | 497 CG TYR A 67 | 3807 4828 4554 -103 -209 -189 | C |
| ATOM | 498 CD1 TYR A 67 | 21.714 -2.557 12.093 1.00 34.38 | C |
| ANISOU | 498 CD1 TYR A 67 | 3767 4787 4510 -56 -250 -204 | C |
| ATOM | 499 CD2 TYR A 67 | 23.859 -1.790 12.944 1.00 33.24 | C |
| ANISOU | 499 CD2 TYR A 67 | 3630 4661 4340 -76 -206 -126 | C |
| ATOM | 500 CE1 TYR A 67 | 22.271 -2.751 10.831 1.00 36.50 | C |
| ANISOU | 500 CE1 TYR A 67 | 4058 5088 4724 30 -284 -162 | C |
| ATOM | 501 CE2 TYR A 67 | 24.420 -1.962 11.665 1.00 33.19 | C |
| ANISOU | 501 CE2 TYR A 67 | 3631 4688 4291 1 -221 -71 | C |
| ATOM | 502 CZ TYR A 67 | 23.602 -2.415 10.605 1.00 31.81 | C |
| ANISOU | 502 CZ TYR A 67 | 3471 4527 4090 59 -258 -90 | C |
| ATOM | 503 OH TYR A 67 | 24.083 -2.694 9.382 1.00 33.21 | O |
| ANISOU | 503 OH TYR A 67 | 3662 4767 4188 150 -275 -54 | O |
| ATOM | 504 N SER A 68 | 23.816 -3.812 15.961 1.00 33.40 | N |
| ANISOU | 504 N SER A 68 | 3744 4693 4255 -220 -186 -168 | N |
| ATOM | 505 CA SER A 68 | 25.107 -4.557 15.900 1.00 31.87 | C |
| ANISOU | 505 CA SER A 68 | 3594 4502 4013 -174 -228 -119 | C |
| ATOM | 506 C SER A 68 | 24.901 -6.076 16.126 1.00 30.50 | C |

TABLE 3-continued

| | | | | | | | |
|---|---|---|---|---|---|---|---|
| ANISOU | 506 | C SER A 68 | 3495 4283 3811 | -184 | -260 | -89 | C |
| ATOM | 507 | O SER A 68 | 25.576 -6.864 15.531 | 1.00 | 29.83 | | O |
| ANISOU | 507 | O SER A 68 | 3441 4171 3721 | -117 | -310 | -74 | O |
| ATOM | 508 | CB SER A 68 | 25.086 -3.991 16.913 | 1.00 | 34.59 | | C |
| ANISOU | 508 | CB SER A 68 | 3925 4890 4326 | -190 | -230 | -119 | C |
| ATOM | 509 | OG SER A 68 | 28.574 -2.710 16.439 | 1.00 | 38.20 | | O |
| ANISOU | 509 | OG SER A 68 | 4311 5358 4847 | -175 | -218 | -134 | O |
| ATOM | 510 | N ADP A 69 | 24.069 -6.455 17.107 | 1.00 | 32.20 | | N |
| ANISOU | 510 | N ASP A 69 | 3737 4490 4008 | -269 | -229 | -77 | N |
| ATOM | 511 | CA ASP A 69 | 23.701 -7.883 17.382 | 1.00 | 32.55 | | C |
| ANISOU | 511 | CA ASP A 69 | 3854 4460 4053 | -308 | -254 | -23 | C |
| ATOM | 512 | C ASP A 69 | 23.075 -8.574 16.143 | 1.00 | 32.67 | | C |
| ANISOU | 512 | C ASP A 69 | 3864 4395 4155 | -282 | -296 | -61 | C |
| ATOM | 513 | O ASP A 69 | 23.470 -9.655 15.688 | 1.00 | 36.11 | | O |
| ANISOU | 513 | O ASP A 69 | 4355 4749 4618 | -236 | -366 | -50 | O |
| ATOM | 514 | CB ASP A 69 | 22.656 -7.866 18.490 | 1.00 | 32.49 | | C |
| ANISOU | 514 | CB ASP A 69 | 3841 4484 4018 | -423 | -179 | 0 | C |
| ATOM | 515 | CG ASP A 69 | 22.352 -9.265 18.990 | 1.00 | 38.30 | | C |
| ANISOU | 515 | CG ASP A 69 | 4656 5140 4756 | -490 | -192 | 96 | C |
| ATOM | 516 | OD1 ASP A 69 | 23.237 -10.180 18.949 | 1.00 | 37.71 | | O |
| ANISOU | 516 | OD1 ASP A 65 | 4654 4989 4575 | -436 | -272 | 157 | O |
| ATOM | 517 | OD2 ASP A 69 | 21.201 -9.473 19.428 | 1.00 | 35.88 | | O |
| ANISOU | 517 | OD2 ASP A 69 | 4323 4840 4470 | -598 | -122 | 114 | O |
| ATOM | 518 | N PHE A 70 | 22.047 -7.934 15.620 | 1.00 | 31.66 | | N |
| AMISOU | 518 | N PHE A 70 | 3664 4289 4076 | -305 | -264 | -122 | N |
| ATOM | 519 | CA PHE A 70 | 21.459 -8.300 14.296 | 1.00 | 33.63 | | C |
| ANISOU | 519 | CA PHE A 70 | 3890 4495 4392 | -259 | -320 | -187 | C |
| ATOM | 520 | C PHE A 70 | 22.500 -8.447 13.188 | 1.00 | 31.74 | | C |
| ANISOU | 520 | C PHE A 70 | 3675 4264 4119 | -129 | -382 | -207 | C |
| ATOM | 521 | O PHE A 70 | 22.519 -9.468 12.465 | 1.00 | 37.08 | | O |
| ANISOU | 521 | O PHE A 70 | 4387 4879 4824 | -79 | -455 | -249 | O |
| ATOM | 522 | CB PHE A 70 | 20.416 -7.252 13.916 | 1.00 | 35.08 | | C |
| ANISOU | 522 | CB PHE A 70 | 3983 4732 4615 | -271 | -287 | -247 | C |
| ATOM | 523 | CG PHE A 70 | 19.808 -7.481 12.561 | 1.00 | 36.66 | | C |
| ANISOU | 523 | CG PHE A 70 | 4154 4915 4862 | -210 | -358 | -319 | C |
| ATOM | 524 | CD1 PHE A 70 | 20.460 -7.053 11.431 | 1.00 | 38.73 | | C |
| ANISOU | 524 | CD1 PHE A 70 | 4424 5222 5071 | -90 | -399 | -329 | C |
| ATOM | 525 | CD2 PHE A 70 | 18.549 -8.107 12.447 | 1.00 | 42.13 | | C |
| ANISOU | 525 | CD2 PHE A 70 | 4801 5561 5647 | -277 | -383 | -376 | C |
| ATOM | 526 | CE1 PHE A 70 | 19.903 -7.287 10.161 | 1.00 | 36.96 | | C |

TABLE 3-continued

| | | | |
|---|---|---|---|
| ANISOU | 526 CE1 PHE A 70 | 4181 5007 4855 -17 -476 -402 | C |
| ATOM | 527 CE2 PHE A 70 | 17.976 -8.340 11.201 1.00 46.07 | C |
| ANISOU | 527 CE2 PHE A 70 | 5268 6053 6184 -213 -472 -465 | C |
| ATOM | 528 CZ PHE A 70 | 18.659 -7.900 10.055 1.00 43.17 | C |
| ANISOU | 528 CZ PHE A 70 | 4925 5744 5733 -73 -522 -480 | C |
| ATOM | 529 N ARG A 71 | 23.383 -7.424 13.024 1.00 33.14 | N |
| ANISOU | 529 N ARG A 71 | 3827 4523 4243 -72 -352 -185 | N |
| ATOM | 530 CA ARG A 71 | 24.316 -7.446 11.903 1.00 30.96 | C |
| ANISOU | 530 CA ARG A 71 | 3550 4291 3922 46 -383 -196 | C |
| ATOM | 531 C ARG A 71 | 25.306 -8.640 12.082 1.00 30.94 | C |
| ANISOU | 531 C ARG A 71 | 3605 4248 3904 100 -435 -192 | C |
| ATOM | 532 O ARG A 71 | 25.664 -9.306 11.142 1.00 31.69 | O |
| ANISOU | 532 O ARG A 71 | 3714 4344 3984 199 -485 -245 | O |
| ATOM | 533 CB ARG A 71 | 25.076 -6.138 11.831 1.00 31.36 | C |
| ANISOU | 533 CB ARG A 71 | 3550 4422 3942 65 -330 -149 | C |
| ATOM | 534 CG ARG A 71 | 25.762 -5.929 10.464 1.00 37.50 | C |
| ANISOU | 534 CG ARG A 71 | 4305 5280 4664 175 -332 -143 | C |
| ATOM | 535 CD ARG A 71 | 26.529 -4.605 10.537 1.00 39.36 | C |
| ANISOU | 535 CD ARG A 71 | 4482 5571 4902 158 -270 -69 | C |
| ATOM | 536 NE ARG A 71 | 27.790 -4.838 11.252 1.00 33.84 | N |
| ANISOU | 536 NE ARG A 71 | 3769 4889 4198 155 -263 -51 | N |
| ATOM | 537 CZ ARG A 71 | 28.960 -4.212 11.034 1.00 40.34 | C |
| ANISOU | 537 CZ ARG A 71 | 4527 5782 5018 174 -223 -2 | C |
| ATOM | 538 NH1 ARG A 71 | 29.062 -3.248 10.125 1.00 40.55 | N |
| ANISOU | 538 NH1 ARG A 71 | 4506 5860 5041 184 -173 60 | N |
| ATOM | 539 NH2 ARG A 71 | 30.049 -4.524 11.779 1.00 38.05 | N |
| ANISOU | 539 NH2 ARG A 71 | 4214 5511 4737 175 -238 -6 | N |
| ATOM | 540 N MET A 72 | 25.740 -8.883 13.321 1.00 30.52 | N |
| ANISOU | 540 N MET A 72 | 3585 4163 3846 46 -429 -137 | N |
| ATOM | 541 CA MET A 72 | 26.597 -10.058 13.611 1.00 31.07 | C |
| ANISOU | 541 CA MET A 72 | 3716 4171 3919 103 -496 -122 | C |
| ATOM | 542 C MET A 72 | 25.877 -11.384 13.207 1.00 37.86 | C |
| ANISOU | 542 C MET A 72 | 4636 4897 4852 106 -570 -166 | C |
| ATOM | 543 O MET A 72 | 26.468 -12.243 12.501 1.00 35.91 | O |
| ANISOU | 543 O MET A 72 | 4414 4608 4623 219 -644 -226 | O |
| ATOM | 544 CB MET A 72 | 26.866 -10.086 15.136 1.00 30.13 | C |
| ANISOU | 544 CB MET A 72 | 3635 4039 3773 29 -487 -39 | C |
| ATOM | 545 CB MET A 72 | 27.719 -11.262 15.653 1.00 54.11 | C |
| ANISOU | 545 CB MET A 72 | 4213 4467 4279 97 -572 5 | C |
| ATOM | 546 SD MET A 72 | 29.522 -11.016 15.312 1.00 37.82 | S |

TABLE 3-continued

| | | | |
|---|---|---|---|
| ANISOU | 546 SD MET A 72 | 4622 5036 4713 234 -608 -26 | S |
| ATOM | 547 CE MET A 72 | 29 591 -12.134 13.917 1.00 36.99 | C |
| ANISOU | 547 CE MET A 72 | 4533 4857 4664 365 -675 -121 | C |
| ATOM | 548 N ALA A 73 | 24.621 -11.570 13.671 1.00 34.56 | N |
| ANISOU | 548 N ALA A 73 | 4231 4410 4490 -17 -551 -146 | N |
| ATOM | 549 CA ALA A 73 | 23.880 -22.799 13.245 1.00 37.46 | C |
| ANISOU | 549 CA ALA A 73 | 4638 4632 4962 -36 -627 -194 | C |
| ATOM | 550 C ALA A 73 | 23.775 -12.849 11.743 1.00 38.12 | C |
| ANISOU | 550 C ALA A 73 | 4687 4745 5053 75 -682 -329 | C |
| ATOM | 551 O ALA A 73 | 23.839 -13.947 11.110 1.00 40.11 | O |
| ANISOU | 551 O ALA A 73 | 4978 4891 5370 143 -783 -415 | O |
| ATOM | 552 CB ALA A 73 | 22.483 -12.825 13.835 1.00 39.86 -161 | C |
| ANISOU | 552 CB ALA A 73 | 4921 4888 5335 -197 -580 -161 | C |
| ATOM | 553 N LEU A 74 | 23.552 -11.684 11.154 1.00 37.81 | N |
| ANISOU | 553 N LEU A 74 | 4577 4841 4947 97 -627 -354 | N |
| ATOM | 554 CA LEU A 74 | 23.447 -11.660 9 707 1 00 36.77 | C |
| ANISOU | 554 CA LEU A 74 | 4419 4770 4782 211 -677 -466 | C |
| ATOM | 555 C LEU A 74 | 24.701 -12.260 9.058 1.00 38.94 | C |
| ANISOU | 555 C LEU A 74 | 4722 5073 5001 366 -725 -520 | C |
| ATOM | 556 O LEU A 74 | 24.606 -13.148 8.151 1.00 35.78 | O |
| ANISOU | 556 O LEU A 74 | 4341 4633 4619 460 -818 -650 | O |
| ATOM | 557 CB LEU A 74 | 23.183 -10.232 9.208 1.00 36.57 | C |
| ANISOU | 557 CB LEU A 74 | 4326 4888 4682 223 -611 -444 | C |
| ATOM | 558 CG LEU A 74 | 23.199 -10.096 7.682 1.00 36.01 | C |
| ANISOU | 558 CG LEU A 74 | 4236 4919 4527 357 -655 -529 | C |
| ATOM | 559 CD1 LEU A 74 | 22.052 -10.938 7.032 1.00 40.19 | C |
| ANISOU | 559 CD1 LEU A 74 | 4767 5378 5126 361 -764 -664 | C |
| ATOM | 560 CD2 LEU A 74 | 23.028 -8.655 7.261 1.00 34.53 | C |
| ANISOU | 560 CD2 LEU A 74 | 3997 4853 4269 367 -591 -463 | C |
| ATOM | 561 N ALA A 75 | 25.884 -11.789 9.504 1.00 36.22 | N |
| ANISOU | 561 N ALA A 75 | 4366 4804 4593 400 -567 -443 | N |
| ATOM | 562 CA ALA A 75 | 27.147 -12.187 8.845 1.00 39.53 | C |
| ANISOU | 562 CA ALA A 75 | 4776 5294 4951 557 -690 -498 | C |
| ATOM | 563 C ALA A 75 | 27.362 -13.696 9.059 1.00 42.03 | C |
| ANISOU | 563 C ALA A 75 | 5163 5447 5360 610 -803 -567 | C |
| ATOM | 564 O ALA A 75 | 27.808 -14.408 8.170 1.00 41.98 | O |
| ANISOU | 564 O ALA A 75 | 5160 5451 5340 755 -868 -695 | O |
| ATOM | 565 CB ALA A 75 | 28.359 -11.332 9.364 1.00 35.99 | C |
| ANISOU | 565 CB ALA A 75 | 4274 4958 4443 564 -608 -401 | C |
| ATOM | 566 N VAL A 76 | 27.018 -14.132 10.251 1.00 43.81 | N |

TABLE 3-continued

| | | |
|---|---|---|
| ANISOU 566 N VAL A 76 | 5448 5518 5679 496 -827 -482 | N |
| ATOM 567 CA VAL A 76 | 27.175 -15.596 10.573 1.00 43.37 | C |
| ANISOU 567 CA VAL A 76 | 5473 5268 5736 528 -941 -509 | C |
| ATOM 568 C VAL A 76 | 26.211 -16.402 9.705 1.00 46.98 | C |
| ANISOU 568 C VAL A 76 | 5952 5610 6290 5.36 -1031 -647 | C |
| ATOM 569 O VAL A 76 | 26.621 -17.443 9.162 1.00 52.07 | O |
| ANISOU 569 O VAL A 76 | 6632 6155 6998 661 -1142 -770 | O |
| ATOM 570 CB VAL A 76 | 26.923 -15.875 12.058 1.00 40.62 | C |
| ANISOU 570 CB VAL A 76 | 5191 4793 5446 386 -935 -349 | C |
| ATOM 571 CG1 VAL A 76 | 26.894 -17.391 12.355 1.00 43.16 | C |
| ANISOU 571 CG1 VAL A 76 | 5613 4870 5916 399 -1063 -348 | C |
| ATOM 572 CG2 VAL A 76 | 28.011 -15.209 12.889 1.00 44.04 | C |
| ANISOU 572 CG2 VAL A 76 | 5605 5341 5786 408 -883 -248 | C |
| ATOM 573 N ASP A 77 | 24.978 -15.881 9.507 1.00 44.58 | N |
| ANISOU 573 N ASP A 77 | 5612 5330 5997 421 -994 -652 | N |
| ATOM 574 CA ASP A 77 | 23.928 -16.580 8.751 1.00 48.86 | C |
| ANISOU 574 CA ASP A 77 | 6154 5765 6644 405 -1089 -791 | C |
| ATOM 575 C ASP A 77 | 24.370 -16.673 7.266 1.00 54.24 | C |
| ANISOU 575 C ASP A 77 | 6809 6565 7233 604 -1151 -982 | C |
| ATOM 576 O ASP A 77 | 24.283 -17.762 6.631 1.00 56.34 | O |
| ANISOU 576 O ASP A 77 | 7107 6710 7568 688 -1283 -1149 | O |
| ATOM 577 CB ASP A 77 | 22.572 -15.870 8.919 1.00 52.98 | C |
| ANISOU 577 CB ASP A 77 | 6617 6322 7192 249 -1030 -753 | C |
| ATOM 578 CG ASP A 77 | 21.363 -16.768 8.624 1.00 66.58 | C |
| ANISOU 578 CG ASP A 77 | 6331 7877 9088 164 -1132 -857 | C |
| ATOM 579 OD1 ASP A 77 | 21.413 -18.010 8.900 1.00 73.09 | O |
| ANISOU 579 OD1 ASP A 77 | 9220 8484 10067 139 -1226 -876 | O |
| ATOM 580 OD2 ASP A 77 | 20.334 -16.206 8.125 1.00 59.17 | O |
| ANISOU 580 OD2 ASP A 77 | 7315 7018 8150 119 -1126 -918 | O |
| ATOM 581 N LEU A 78 | 24.908 -15 581 6.725 1 00 47.73 | N |
| ANISOU 581 N LEU A 78 | 5931 5975 6231 684 -1060 -961 | N |
| ATOM 582 CA LEU A 78 | 25.437 -15.582 5.350 1.00 52.40 | C |
| ANISOU 582 CA LEU A 78 | 6494 6728 6686 877 -1088 -1112 | C |
| ATOM 583 C LEU A 78 | 26.602 -16.552 5.173 1.00 53.92 | C |
| ANISOU 583 C LEU A 78 | 6714 6883 6890 1037 -1150 -1212 | C |
| ATOM 584 O LEU A 78 | 26.777 -17.148 4.117 1.00 60.12 | O |
| ANISOU 584 O LEU A 78 | 7497 7714 7630 1197 -1229 -1405 | O |
| ATOM 585 CB LEU A 78 | 25.857 -14.167 4.954 1.00 48.67 | C |
| ANISOU 585 CB LEU A 78 | 5958 6503 6031 905 -955 -1012 | C |
| ATOM 586 CG LEU A 78 | 24.695 -13.198 4.630 1.00 49.90 | C |

TABLE 3-continued

| | | | |
|---|---|---|---|
| ANISOU | 586 CG LEU A 78 | 6081 6729 6150 821 -926 -971 | C |
| ATOM | 587 CD1 LEU A 78 | 25.210 -11.803 4.357 1.00 49.89 | C |
| ANISOU | 587 CD1 LEU A 78 | 6030 6927 6000 838 -799 -840 | C |
| ATOM | 588 CD2 LEU A 78 | 23.885 -13.683 3.444 1.00 52.17 | C |
| ANISOU | 588 CD2 LEU A 78 | 6370 7044 6409 908 -1042 -1154 | C |
| ATOM | 589 N SER A 79 | 27.428 -16.635 6.208 1.00 57.86 | N |
| ANISOU | 589 N SER A 79 | 7230 7319 7435 1008 -1113 -1087 | N |
| ATOM | 590 CA SER A 79 | 28.665 -17.407 6.239 1.00 61.23 | C |
| ANISOU | 590 CA SER A 79 | 7667 7719 7880 1163 -1163 -1152 | C |
| ATOM | 591 C SER A 79 | 28.609 -18.838 5.708 1.00 72.71 | C |
| ANISOU | 591 C SER A 79 | 9175 8997 9456 1289 -1328 -1358 | C |
| ATOM | 592 O SER A 79 | 29.630 -16.379 5.231 1.00 73.62 | O |
| ANISOU | 592 O SER A 79 | 9270 9160 9543 1484 -1370 -1468 | O |
| ATOM | 593 CB SER A 79 | 29.121 -17.511 7.676 1.00 59.22 | C |
| ANISOU | 593 CB SER A 79 | 7450 7339 7712 1070 -1152 -978 | C |
| ATOM | 594 OG SER A 79 | 30.421 -17.003 7.752 1.00 62.93 | O |
| ANISOU | 594 OG SER A 79 | 7850 7977 8082 1166 -1081 -939 | O |
| ATOM | 595 N GLN A 80 | 27.448 -19.470 5.834 1.00 74.00 | N |
| ANISOU | 595 N GLN A 80 | 9397 8947 9773 1177 -1425 -1396 | N |
| ATOM | 596 CA GLN A 80 | 27.291 -20.837 5.353 1.00 92.13 | C |
| ANISOU | 596 CA GLN A 80 | 11747 11033 12227 1275 -1601 -1602 | C |
| ATOM | 597 C GLN A 80 | 27.085 -20.893 3.831 1.00 98.84 | C |
| ANISOU | 597 C GLN A 80 | 12552 12040 12963 1436 -1655 -1863 | C |
| ATOM | 598 O GLN A 80 | 26.665 -21.926 3.306 1.00103.30 | O |
| ANISOU | 598 O GLN A 80 | 13153 12436 13662 1499 -1815 -2073 | O |
| ATOM | 599 CB GLN A 80 | 26.148 -21.539 6.083 1.00 96.22 | C |
| ANISOU | 599 CB GLN A 80 | 12332 11247 12980 1077 -1686 -1537 | C |
| ATOM | 600 CG GLN A 80 | 25.854 -20.957 7.457 1.00 99.68 | C |
| ANISOU | 600 CG GLN A 80 | 12788 11647 13437 862 -1572 -1251 | C |
| ATOM | 601 CD GLN A 80 | 24.365 -20.796 7.711 1.00 96 67 | C |
| ANISOU | 601 CD GLN A 80 | 12393 11184 13153 643 -1556 -1195 | C |
| ATOM | 602 OE1 GLN A 80 | 23.954 -20.405 8.799 1.00105.29 | O |
| ANISOU | 602 OE1 GLN A 80 | 13494 12247 14265 463 -1463 -987 | O |
| ATOM | 603 NE2 GLN A 80 | 23.553 -21.083 6.705 1.00 93.40 | N |
| ANISOU | 603 NE2 GLN A 80 | 11944 10751 12791 664 -1646 -1394 | N |
| ATOM | 604 N THR A 81 | 27.375 -19.786 3.136 1.00 98.15 | N |
| ANISOU | 604 N THR A 81 | 12391 12273 12630 1501 -1527 -1846 | N |
| ATOM | 605 CA THR A 81 | 27.430 -19.760 1.661 1.00 99.77 | C |
| ANISOU | 605 CA THR A 81 | 12555 12696 12656 1690 -1556 -2072 | C |
| ATOM | 606 C THR A 81 | 28.474 -18.762 1.150 1.00 96.99 | C |

TABLE 3-continued

| | | |
|---|---|---|
| ANISOU 606 C THR A 81 | 12124 12686 12042 1805 -1390 -2003 | C |
| ATOM 607 O THR A 81 | 28.192 -17.932 0.280 1.00 88.18 | O |
| ANISOU 607 O THR A 81 | 10968 11813 10722 1836 -1320 -2002 | O |
| ATOM 608 CB THR A 81 | 26.060 -19.433 1.021 1.00 101.17 | C |
| ANISOU 608 CB THR A 81 | 12727 12909 12805 1611 -1606 -2137 | C |
| ATOM 609 OG1 THR A 81 | 25.428 -18.377 1.762 1.00 96.54 | O |
| ANISOU 609 OG1 THR A 81 | 12122 12340 12220 1404 -1492 -1891 | O |
| ATOM 610 CG2 THR A 81 | 25.149 -20.682 0.964 1.00 96.71 | C |
| ANISOU 610 CG2 THR A 81 | 12211 12051 12484 1575 -1810 -2832 | C |
| ATOM 611 N GLY A 91 | 47.291 -17.018 -6.584 1.00 6976 | N |
| ANISOU 611 N GLY A 91 | 9436 9270 7801 526 -543 -1048 | N |
| ATOM 612 CA GLY A 91 | 46.882 -18.155 -5.748 1.00 71 02 | C |
| ANISOU 612 CA GLY A 91 | 9610 9325 8050 466 -637 -1088 | C |
| ATOM 613 C GLY A 91 | 47.505 -18.348 -4.355 1.00 71.89 | C |
| ANISOU 613 C GLY A 91 | 9695 9331 8289 445 -626 -1059 | C |
| ATOM 614 O GLY A 91 | 46.772 -18.620 -3.387 1.00 68.11 | O |
| ANISOU 614 O GLY A 91 | 9202 8797 7878 373 -686 -1021 | O |
| ATOM 615 N ASP A 92 | 48.837 -18.235 -4.241 1.00 65.60 | N |
| ANISOU 615 N ASP A 92 | 8891 8509 7524 505 -552 -1079 | N |
| ATOM 616 CA ASP A 92 | 49.583 -18.449 -2.975 1.00 63.49 | C |
| ANISOU 616 CA ASP A 92 | 8603 8145 7376 496 -542 -1061 | C |
| ATOM 617 C ASP A 92 | 49.182 -17.457 -1.815 1.00 63.40 | C |
| ANISOU 617 C ASP A 92 | 8533 8135 7422 446 -518 -941 | C |
| ATOM 618 O ASP A 92 | 48.943 -16.273 -2.030 1.00 55.84 | O |
| ANISOU 618 O ASP A 92 | 7540 7258 6420 452 -459 -868 | O |
| ATOM 619 CB ASP A 92 | 51.073 -18.510 -3.343 1.00 64.67 | C |
| ANISOU 619 CB ASP A 92 | 8752 8289 7530 579 -468 -1119 | C |
| ATOM 620 CG ASP A 92 | 52.023 -18.042 -2.268 1.00 68.95 | C |
| ANISOU 620 CG ASP A 92 | 9246 8785 8166 590 -412 -1071 | C |
| ATOM 621 OD1 ASP A 92 | 52.810 -18.869 -1.766 1.00 72.78 | O |
| ANISOU 621 OD1 ASP A 92 | 9744 9184 8726 613 -434 -1127 | O |
| ATOM 622 OD2 ASP A 92 | 52.108 -16.834 -2.007 1.00 57.33 | O |
| ANISOU 622 OD2 ASP A 92 | 7725 7365 6691 587 -341 -984 | O |
| ATOM 623 N ILE A 93 | 49.048 -17.968 -0.601 1.00 59.05 | N |
| ANISOU 623 N ILE A 93 | 7979 7499 6966 395 -557 -922 | N |
| ATOM 624 CA ILE A 93 | 48.528 -17.150 0.500 1.00 59.91 | C |
| ANISOU 624 CA ILE A 93 | 8038 7602 7122 343 -555 -818 | C |
| ATOM 625 C ILE A 93 | 49.311 -15.862 0.686 1.00 55.48 | C |
| ANISOU 625 C ILE A 93 | 7427 7085 6566 384 -451 -755 | C |
| ATOM 626 O ILE A 93 | 48 728 -14.847 0.967 1.00 56 94 | O |

TABLE 3-continued

| | | | | |
|---|---|---|---|---|
| ANISOU | 626 | O ILE A 93 | 7575 7321 6740 361 -423 -672 | O |
| ATOM | 627 | CB ILE A 93 | 48.361 -17.954 1.807 1.00 63.95 | C |
| ANISOU | 627 | CB ILE A 93 | 8559 8007 7732 284 -621 -809 | C |
| ATOM | 628 | CG1 ILE A 93 | 47.427 -17.224 2.783 1.00 69.15 | C |
| ANISOU | 628 | CG1 ILE A 93 | 9173 8684 8417 217 -624 -708 | C |
| ATOM | 629 | CG2 ILE A 93 | 49.715 -18.244 2.448 1.00 70.74 | C |
| ANISOU | 629 | CG2 ILE A 93 | 9420 8791 8667 327 -593 -834 | C |
| ATOM | 630 | CD1 ILE A 93 | 46.038 -17.000 2.215 1.00 76.48 | C |
| ANISOU | 630 | CD1 ILE A 93 | 10093 9687 9279 173 -660 -686 | C |
| ATOM | 631 | N CYS A 94 | 50.620 -15.870 0.466 1.00 55.79 | N |
| ANISOU | 631 | N CYS A 94 | 7465 7112 6620 447 -393 -796 | N |
| ATOM | 632 | CA CYS A 94 | 51.360 -14.631 0.482 1.00 53.36 | C |
| ANISOU | 632 | CA CYS A 94 | 7112 6854 6310 483 -292 -740 | C |
| ATOM | 633 | C CYS A 94 | 50.890 -13.659 -0.550 1.00 55.68 | C |
| ANISOU | 633 | C CYS A 94 | 7398 7253 6504 500 -242 -702 | C |
| ATOM | 634 | O CYS A 94 | 50.787 -12.464 -0.266 1.00 48.81 | O |
| ANISOU | 634 | O CYS A 94 | 6489 6421 5634 493 -187 -617 | O |
| ATOM | 635 | CB CYS A 94 | 52.842 -14 848 0.208 1.00 55.56 | C |
| ANISOU | 635 | CB CYS A 94 | 7385 7114 6610 550 -235 -801 | C |
| ATOM | 636 | SG CYS A 94 | 53.702 -15.632 1.584 1.00 68.24 | S |
| ANISOU | 636 | SG CYS A 94 | 8963 8600 9346 547 -271 -826 | S |
| ATOM | 637 | N ASP A 95 | 50.692 -14.153 -1.770 1.00 53.56 | N |
| ANISOU | 637 | N ASP A 95 | 7171 7029 6150 527 -260 -766 | N |
| ATOM | 638 | CA ASP A 95 | 50.453 -13.276 -2.899 1.00 52.88 | C |
| ANISOU | 638 | CA ASP A 95 | 7086 7047 5958 557 -207 -737 | C |
| ATOM | 639 | C ASP A 95 | 49.063 -12.689 -2.806 1.00 48.80 | C |
| ANISOU | 639 | C ASP A 95 | 6559 6574 5409 510 -247 -663 | C |
| ATOM | 640 | O ASP A 95 | 48.838 -11.533 -3.151 1.00 47.88 | O |
| ANISOU | 640 | O ASP A 95 | 6423 6527 5244 522 -193 -591 | O |
| ATOM | 641 | CB ASP A 95 | 50 664 -14.016 -4.233 1.00 59.07 | C |
| ANISOU | 641 | CB ASP A 95 | 7921 7870 6552 603 -217 -833 | C |
| ATOM | 642 | CG ASP A 95 | 52.150 -14.410 -4.466 1.00 63.52 | C |
| ANISOU | 642 | CG ASP A 95 | 8486 8411 7238 665 -156 -905 | C |
| ATOM | 643 | OD1 ASP A 95 | 52.407 -15.613 -4.688 1.00 65.12 | O |
| ANISOU | 643 | OD1 ASP A 95 | 8726 8566 7450 683 -207 -1004 | O |
| ATOM | 644 | OD2 ASP A 95 | 53.052 -13.540 -4.370 1.00 62.19 | O |
| ANISOU | 644 | OD2 ASP A 95 | 8278 8266 7085 693 -61 -864 | O |
| ATOM | 645 | N VAL A 96 | 48.109 -13.481 -2.353 1.00 45.40 | N |
| ANISOU | 645 | N VAL A 96 | 6140 6104 5006 455 -342 -680 | N |
| ATOM | 646 | CA VAL A 96 | 46.755 -12.953 -2.148 1.00 44.62 | C |

TABLE 3-continued

| | | | |
|---|---|---|---|
| ANISOU | 646 CA VAL A 96 | 6020 6047 4888 407 -382 -611 | C |
| ATOM | 647 C VAL A 95 | 46.694 -11.948 -0.985 1.00 42.69 | C |
| ANISOU | 647 C VAL A 95 | 5721 5786 4712 383 -341 -515 | C |
| ATOM | 648 O VAL A 96 | 46.031 -10.888 -1.088 1.00 42.06 | O |
| ANISOU | 648 O VAL A 96 | 5615 5769 4598 381 -318 -440 | O |
| ATOM | 649 CB VAL A 96 | 45.721 -14.072 -1.928 1.00 48.61 | C |
| ANISOU | 649 CB VAL A 96 | 6544 6516 5409 346 -493 -653 | C |
| ATOM | 650 CG1 VAL A 96 | 44.317 -13.457 -1 969 1.00 48.28 | C |
| ANISOU | 650 CG1 VAL A 96 | 6472 6541 5330 307 -529 -589 | C |
| ATOM | 651 CG2 VAL A 96 | 45.870 -15.189 -3.004 1.00 46.43 | C |
| ANISOU | 651 OG2 VAL A 96 | 6327 6239 5075 370 -540 -763 | C |
| ATOM | 652 N SER A 97 | 47.407 -12.211 0.106 1.00 40.76 | N |
| ANISOU | 652 N SER A 97 | 5463 5461 4563 369 -331 -515 | N |
| ATOM | 653 CA SER A 97 | 47.282 -11.318 1.248 1.00 41.24 | C |
| ANISOU | 653 CA SER A 97 | 5477 5506 4686 342 -300 -430 | C |
| ATOM | 654 C SER A 97 | 47.895 -9.985 0.850 1.00 40.75 | C |
| ANISOU | 654 C SER A 97 | 5393 5497 4594 390 -202 -377 | C |
| ATOM | 655 O SER A 97 | 47.331 -8.914 1.128 1.00 40.30 | O |
| ANISOU | 655 O SER A 97 | 5305 5475 4532 381 -176 -296 | O |
| ATOM | 656 CB SER A 97 | 47.994 -11.887 2.486 1.00 42.57 | C |
| ANISOU | 656 CB SER A 97 | 5640 5578 4957 321 -311 -444 | C |
| ATOM | 657 OG SER A 97 | 47.477 -13.186 2.822 1.00 45.48 | O |
| ANISOU | 657 OG SER A 97 | 6039 5889 5354 275 -402 -493 | O |
| ATOM | 658 N ALA A 98 | 49.040 -10.045 0.147 1.00 42.05 | N |
| ANISOU | 658 N ALA A 98 | 5573 5668 4735 443 -146 -421 | N |
| ATOM | 659 CA ALA A 98 | 49.715 -8.825 -0.367 1.00 41.79 | C |
| ANISOU | 659 CA ALA A 98 | 5524 5688 4667 486 -46 -374 | C |
| ATOM | 660 C ALA A 98 | 48.846 -8.097 -1.402 1.00 45.61 | C |
| ANISOU | 660 C ALA A 98 | 6021 6261 5049 500 -39 -330 | C |
| ATOM | 661 O ALA A 98 | 48.696 -6.833 -1.349 1.00 41.70 | O |
| ANISOU | 661 O ALA A 98 | 5503 5798 4543 507 15 -247 | O |
| ATOM | 662 CB ALA A 98 | 51.050 -9.185 -1.026 1.00 44.11 | C |
| ANISOU | 662 CB ALA A 98 | 5831 5979 4949 536 10 -439 | C |
| ATOM | 663 N GLN A 99 | 48.231 -8.864 -2.309 1.00 45.74 | N |
| ANISOU | 663 N GLN A 99 | 6075 6314 4992 505 -97 -385 | N |
| ATOM | 664 CA GLN A 99 | 47.375 -8.205 -3.304 1.00 43.56 | C |
| ANISOU | 664 CA GLN A 99 | 5813 6126 4613 521 -100 -345 | C |
| ATOM | 665 C GLN A 99 | 46.189 -7.447 -2.698 1.00 41.45 | C |
| ANISOU | 665 C GLN A 99 | 5512 5875 4362 488 -131 -262 | C |
| ATOM | 666 O GLN A 99 | 45.925 -6.312 -3.139 1.00 35.07 | O |

TABLE 3-continued

| | | |
|---|---|---|
| ANISOU 666 O GLN A 99 | 4699 5123 3504 513 -89 -192 | O |
| ATOM 667 CB GLN A 99 | 46.939 -9.127 -4.443 1.00 47.48 | C |
| ANISOU 667 CB GLN A 99 | 6356 6666 5019 534 -159 -421 | C |
| ATOM 668 CG GLN A 99 | 46.252 -8.392 -5.635 1.00 46.15 | C |
| ANISOU 668 CG GLN A 99 | 6207 6598 4728 565 -153 -382 | C |
| ATOM 669 CD GLN A 99 | 47.218 -7.514 -6.431 1.00 49.52 | C |
| ANISOU 669 CD GLN A 99 | 6649 7072 5094 620 -47 -352 | C |
| ATOM 670 OE1 GLN A 99 | 48.256 -7.978 -6.909 1.00 47.86 | O |
| ANISOU 670 OE1 GLN A 99 | 6461 6858 4866 650 -2 -414 | O |
| ATOM 671 NE2 GLN A 99 | 45.880 -6.228 -6.584 1.00 49.20 | N |
| ANISOU 671 NE2 GLN A 99 | 6597 7076 5020 633 -4 -255 | N |
| ATOM 672 N SER A 100 | 45.508 -8.008 -1.677 1.00 39.71 | N |
| ANISOU 672 N SER A 100 | 5269 5606 4213 433 -199 -267 | N |
| ATOM 673 CA SER A 100 | 44.415 -7.300 -1.069 1.00 42.09 | C |
| ANISOU 673 CA SER A 100 | 5533 5928 4532 404 -222 -194 | C |
| ATOM 674 C SER A 100 | 44.900 -5.956 -0.549 1.00 39.63 | C |
| ANISOU 674 C SER A 100 | 5192 5610 4255 425 -139 -113 | C |
| ATOM 675 O SER A 100 | 44.193 -4.956 -0.654 1.00 38.14 | O |
| ANISOU 675 O SER A 100 | 4986 5467 4038 436 -128 -44 | O |
| ATOM 676 CB SER A 100 | 43.846 -8.060 0.125 1.00 47.00 | O |
| ANISOU 676 CB SER A 100 | 6131 6491 5236 340 -268 -207 | C |
| ATOM 677 OG SER A 100 | 43.222 -9.208 -0.338 2.00 51.97 | O |
| ANISOU 677 OG SER A 100 | 6784 7126 5835 312 -371 -272 | O |
| ATOM 678 N ALA A 101 | 46.030 -5.994 0.178 1.00 41.18 | N |
| ANISOU 678 N ALA A 101 | 5381 5741 4525 423 -90 -124 | N |
| ATOM 679 CA ALA A 101 | 46.554 -4.803 0.817 1.00 37.26 | C |
| ANISOU 679 CA ALA A 101 | 4856 5227 4076 434 -16 -56 | C |
| ATOM 680 C ALA A 101 | 46.937 -3.793 -9.259 1.00 40.05 | C |
| ANISOU 680 C ALA A 101 | 5226 5636 4355 484 57 -15 | C |
| ATOM 681 O ALA A 101 | 46.683 -2 594 -0.089 1.00 41.58 | O |
| ANISOU 681 O ALA A 101 | 5404 5845 4551 494 95 61 | O |
| ATOM 682 CB ALA A 101 | 47.735 -5.169 1.739 1.00 42.54 | C |
| ANISOU 682 CB ALA A 101 | 5512 5818 4835 422 13 -86 | C |
| ATOM 683 N VAL A 102 | 47.497 -4.260 -1.390 1.00 36.65 | N |
| ANISOU 683 N VAL A 102 | 4831 5236 3855 516 74 -65 | N |
| ATOM 684 CA VAL A 102 | 47.756 -3.349 -2.530 1.00 39.26 | C |
| ANISOU 684 CA VAL A 102 | 5186 5633 4099 561 140 -24 | C |
| ATOM 685 C VAL A 102 | 46.522 -2.651 -2.999 1.00 40.19 | C |
| ANISOU 685 C VAL A 102 | 5310 5811 4151 571 108 38 | C |
| ATOM 686 O VAL A 102 | 46.535 -1.411 -3.156 1.00 37.37 | O |

TABLE 3-continued

| | | | |
|---|---|---|---|
| ANISOU | 686 O VAL A 102 | 4952 5472 3776 592 164 117 | O |
| ATOM | 687 CB VAL A 102 | 48.460 -4.031 -3.718 1.00 39.32 | C |
| ANISOU | 687 CB VAL A 102 | 5233 5677 4029 595 162 -93 | C |
| ATOM | 688 CG1 VAL A 102 | 48 489 -3.120 -4.946 1.00 37.65 | C |
| ANISOU | 688 CG1 VAL A 102 | 5053 5542 3710 636 219 -42 | C |
| ATOM | 689 CG2 VAL A 102 | 49.899 -4.350 -3.290 1.00 37.59 | C |
| ANISOU | 689 CG2 VAL A 102 | 4999 5404 3879 598 221 -137 | C |
| ATOM | 690 N ASP A 103 | 45.440 -3.421 -3.189 1.00 44.61 | N |
| ANISOU | 690 N ASP A 103 | 5874 6397 4677 554 16 3 | N |
| ATOM | 691 CA ASP A 103 | 44.176 -2.892 -3.785 1.00 44.64 | C |
| ANISOU | 691 CA ASP A 103 | 5882 6472 4608 568 -29 51 | C |
| ATOM | 692 C ASP A 103 | 43.638 -1.882 -2.770 1.00 39.39 | C |
| ANISOU | 692 C A3P A 103 | 5173 5783 4010 555 -19 131 | C |
| ATOM | 693 O ASP A 103 | 43.208 -0.820 -3.130 1.00 39.33 | O |
| ANISOU | 693 O ASP A 103 | 5167 5813 3963 586 1 202 | O |
| ATOM | 694 CB ASP A 103 | 43.094 -3.991 -3.950 1.00 44.25 | C |
| ANISOU | 694 CB ASP A 103 | 5832 6447 4534 539 -138 -8 | C |
| ATOM | 695 CG ASP A 103 | 43.476 -5.065 -4.952 1.00 48.96 | C |
| ANISOU | 695 CG ASP A 103 | 6475 7065 5061 551 -152 -97 | C |
| ATOM | 696 OD1 ASP A 103 | 44.344 -4.819 -5.777 1.00 44.27 | O |
| ANISOU | 696 OD1 ASP A 103 | 5916 6495 4409 593 -98 -103 | O |
| ATOM | 697 OD2 ASP A 103 | 42.936 -6.175 -4.853 1.00 53.52 | O |
| ANISOU | 697 OD2 ASP A 103 | 7056 7632 5649 516 -243 -162 | O |
| ATOM | 698 N SER A 104 | 43.666 -2.244 -1.497 1.00 40.29 | N |
| ANISOU | 698 N SER A 104 | 5250 5833 4224 512 -36 117 | N |
| ATOM | 699 CA SER A 104 | 43.239 -1.291 -0.478 1.00 40.35 | C |
| ANISOU | 699 CA SER A 104 | 5218 5818 4297 501 -20 185 | C |
| ATOM | 700 C SER A 104 | 43.967 0.042 -0.405 1.00 38.02 | C |
| ANISOU | 700 C SER A 104 | 4924 5503 4017 533 70 254 | C |
| ATOM | 701 O SER A 104 | 43.343 1.080 -0.118 1.00 41.45 | O |
| ANISOU | 701 O SER A 104 | 5342 5948 4461 547 78 322 | O |
| ATOM | 702 CB SER A 104 | 43.245 -1.955 0.885 1.00 39.14 | C |
| ANISOU | 702 CB SER A 104 | 5030 5599 4242 448 -49 156 | C |
| ATOM | 703 OG SER A 104 | 42.144 -2.608 0.848 1.00 52.58 | O |
| ANISOU | 703 OG SER A 104 | 6722 7331 5926 417 -137 123 | O |
| ATOM | 704 N LEU A 105 | 45.285 -0.002 -0.530 1.00 37.01 | N |
| ANISOU | 704 N LEU A 105 | 4814 5343 3906 539 137 233 | N |
| ATOM | 705 CA LEU A 105 | 46.099 1.215 -0.571 1.00 34.88 | C |
| ANISOU | 705 CA LEU A 105 | 4549 5054 3548 562 228 294 | C |
| ATOM | 706 C LEU A 105 | 45.706 2.032 -1.756 1.00 38.10 | C |

TABLE 3-continued

| | | | | | | | | |
|---|---|---|---|---|---|---|---|---|
| ANISOU | 706 | C | LEU A | 105 | 4992 5526 3960 | 606 247 351 | | C |
| ATOM | 707 | O | LEU A | 105 | 45.492 3.224 -1.659 | 1.00 | 37.80 | O |
| ANISOU | 707 | O | LEU A | 105 | 4953 5483 3926 | 625 281 427 | | O |
| ATOM | 708 | CB | LEU A | 105 | 47.582 0.854 -0.619 | 1.00 | 37.21 | C |
| ANISOU | 708 | CB | LEU A | 105 | 4852 5315 3972 | 559 291 250 | | C |
| ATOM | 709 | CG | LEU A | 105 | 48.135 0.349 0.735 | 1.00 | 34.89 | C |
| ANISOU | 709 | CG | LEU A | 105 | 4521 4945 3789 | 520 283 213 | | C |
| ATOM | 710 | CD1 | LEU A | 105 | 49.463 -0.347 0.461 | 1.00 | 35.96 | C |
| ANISOU | 710 | CD1 | LEU A | 105 | 4664 5062 3938 | 525 322 149 | | C |
| ATOM | 711 | CD2 | LEU A | 105 | 48.370 1.559 1.635 | 1.00 | 34.19 | C |
| ANISOU | 711 | CD2 | LEU A | 105 | 4406 4813 3771 | 513 333 278 | | C |
| ATOM | 712 | N | GLN A | 106 | 45.574 1.400 -2.905 | 1.00 | 39.15 | N |
| ANISOU | 712 | N | GLN A | 106 | 5160 5717 3998 | 626 223 314 | | N |
| ATOM | 713 | CA | GLN A | 106 | 45.282 2.194 -4.087 | 1.00 | 41.21 | C |
| ANISOU | 713 | CA | GLN A | 106 | 5461 6041 4156 | 671 244 372 | | C |
| ATOM | 714 | C | GLN A | 106 | 43.872 2.765 -4.007 | 1.00 | 40.26 | C |
| ANISOU | 714 | C | GLN A | 106 | 5327 5953 4017 | 686 182 426 | | C |
| ATOM | 715 | O | GLN A | 106 | 43.668 3.946 -4.292 | 1.00 | 42.89 | O |
| ANISOU | 715 | O | GLN A | 106 | 5675 6297 4324 | 719 215 508 | | O |
| ATOM | 716 | CB | GLN A | 106 | 45.491 1.365 -5.333 | 1.00 | 40.37 | C |
| ANISOU | 716 | CC | GLN A | 106 | 5398 5995 3947 | 690 232 314 | | C |
| ATOM | 717 | CG | GLN A | 106 | 46.943 0.896 -5.474 | 1.00 | 44.75 | C |
| ANISOU | 717 | CG | GLN A | 106 | 5962 6524 4518 | 685 304 262 | | C |
| ATOM | 718 | CD | GLN A | 106 | 47.120 -0.049 -6.647 | 1.00 | 50.84 | C |
| ANISOU | 718 | CD | GLN A | 106 | 6774 7352 5189 | 705 287 190 | | C |
| ATOM | 719 | OE1 | GLN A | 106 | 46.214 -0.837 -7.027 | 1.00 | 50.30 | O |
| ANISOU | 719 | OE1 | GLN A | 106 | 6718 7323 5072 | 705 199 144 | | O |
| ATOM | 720 | NE2 | GLN A | 106 | 48.278 0.037 -7.244 | 1.00 | 49.57 | N |
| ANISOU | 720 | NE2 | GLN A | 106 | 6634 7202 4997 | 723 372 177 | | N |
| ATOM | 721 | N | ASP A | 107 | 42.913 1.952 -3.592 | 1.00 | 41.68 | N |
| ANISOU | 721 | N | ASP A | 107 | 5477 6145 4214 | 661 94 382 | | N |
| ATOM | 722 | CA | ASP A | 107 | 41.573 2.488 -3.335 | 1.00 | 43.13 | C |
| ANISOU | 722 | CA | ASP A | 107 | 5631 6358 4397 | 672 36 430 | | C |
| ATOM | 723 | C | ASP A | 107 | 41.530 3.630 -2.351 | 1.00 | 41.97 | C |
| ANISOU | 723 | C | ASP A | 107 | 5456 6162 4330 | 676 76 498 | | C |
| ATOM | 724 | O | ASP A | 107 | 40.854 4.610 -2.620 | 1.00 | 40.76 | O |
| ANISOU | 724 | O | ASP A | 107 | 5304 6035 4147 | 715 72 566 | | O |
| ATOM | 725 | CB | ASP A | 107 | 40.617 1.386 -2.900 | 1.00 | 43.00 | C |
| ANISOU | 725 | CB | ASP A | 107 | 5578 6359 4402 | 632 -59 369 | | C |
| ATOM | 726 | CG | ASP A | 107 | 40.334 0.416 -4.019 | 1.00 | 49.56 | C |

TABLE 3-continued

| | | | | |
|---|---|---|---|---|
| ANISOU | 726 CG ASP A 107 | 6440 7250 5140 | 637 -117 309 | C |
| ATOM | 727 OD1 ASP A 107 | 40.647 0.738 -5.186 | 1.00 49.58 | O |
| ANISOU | 727 OD1 ASP A 107 | 6492 7299 5049 | 680 -90 325 | O |
| ATOM | 728 OD2 ASP A 107 | 39.803 -0.659 -3.734 | 1.00 57.05 | O |
| ANISOU | 728 OD2 ASP A 107 | 7368 8202 6108 | 595 -188 246 | O |
| ATOM | 729 N THR A 108 | 42.223 3.508 -1.208 | 1.00 37.74 | N |
| ANISOU | 729 N THR A 108 | 4893 5554 3894 | 638 111 479 | N |
| ATOM | 730 CA THR A 108 | 42.300 4.594 -0.220 | 1.00 39.10 | C |
| ANISOU | 730 CA THR A 108 | 5040 5672 4143 | 639 154 535 | C |
| ATOM | 731 C THR A 108 | 42.898 5.892 -0.800 | 1.00 40.49 | C |
| ANISOU | 731 C THR A 108 | 5254 5836 4293 | 680 231 610 | C |
| ATOM | 732 O THR A 108 | 42.332 6.997 -0.630 | 1.00 36.81 | O |
| ANISOU | 732 O THR A 108 | 4786 5365 3837 | 711 238 678 | O |
| ATOM | 733 CB THR A 108 | 43.079 4.134 1.056 | 1.00 34.93 | C |
| ANISOU | 733 CB THR A 108 | 4483 5070 3720 | 590 176 493 | C |
| ATOM | 734 OG1 THR A 108 | 42.357 3.058 1.676 | 1.00 31.89 | O |
| ANISOU | 734 OG1 THR A 108 | 4064 4693 3361 | 550 102 440 | O |
| ATOM | 735 CG2 THR A 108 | 43.210 5.248 2.081 | 1.00 33.69 | C |
| ANISOU | 735 CG2 THR A 108 | 4303 4857 3640 | 591 220 545 | C |
| ATOM | 736 N ALA A 109 | 44.027 5.750 -1.494 | 1.00 43.13 | N |
| ANISOU | 736 N ALA A 109 | 5626 6167 4595 | 681 291 597 | N |
| ATOM | 737 CA ALA A 109 | 44.610 6.863 -2.260 | 1.00 45.45 | C |
| ANISOU | 737 CA ALA A 109 | 5964 6460 4846 | 714 366 668 | C |
| ATOM | 738 C ALA A 109 | 43.629 7.552 -3.176 | 1.00 42.88 | C |
| ANISOU | 738 C ALA A 109 | 5669 6191 4431 | 766 335 732 | C |
| ATOM | 739 O ALA A 109 | 43.636 8.762 -3.177 | 1.00 44.81 | O |
| ANISOU | 739 O ALA A 109 | 5932 6409 4684 | 791 75 810 | O |
| ATOM | 740 CD ALA A 109 | 45.895 6.480 -3.037 | 1.00 43.35 | C |
| ANISOU | 740 CB ALA A 109 | 5730 6200 4540 | 708 432 639 | C |
| ATOM | 741 N LYS A 110 | 42.787 6.841 -3.936 | 1.00 45.79 | N |
| ANISOU | 741 N LYS A 110 | 6047 6635 4718 | 783 262 703 | N |
| ATOM | 742 CA LYS A 110 | 41.913 7.560 -4.846 | 1.00 49.53 | C |
| ANISOU | 742 CA LYS A 110 | 6562 7164 5102 | 837 232 769 | C |
| ATOM | 743 C LYS A 110 | 40.838 8.304 -4.113 | 1.00 54.16 | C |
| ANISOU | 743 C LYS A 110 | 7107 7738 5740 | 858 190 815 | C |
| ATOM | 744 O LYS A 110 | 40.475 9.390 -4.528 | 1.00 54.04 | O |
| ISOU | 744 O LYS A 110 | 7113 7728 5691 | 906 200 894 | O |
| ATOM | 745 CB LYS A 110 | 41.226 6.672 -5.882 | 1.00 56.99 | C |
| ANISOU | 745 CB LYS A 110 | 7514 8198 5941 | 853 158 727 | C |
| ATOM | 746 CG LYS A 110 | 42.094 5.687 -6.627 | 1.00 62.40 | C |

TABLE 3-continued

| | | | |
|---|---|---|---|
| ANISOU | 746 CG LYS A 110 | 8232 8909 6589 836 180 659 | C |
| ATOM | 747 CD LYS A 110 | 41.236 4.494 -7.045 1.00 65.75 | C |
| ANISOU | 747 DD LYS A 110 | 8646 9397 6939 829 81 585 | C |
| ATOM | 748 CE LYS A 110 | 41.801 3.777 -8.272 1.00 71.49 | C |
| ANISOU | 748 CE LYS A 110 | 9427 10177 7558 839 92 535 | C |
| ATOM | 749 NZ LYS A 110 | 40.734 2.917 -8.877 1.00 75.32 | N |
| ANISOU | 749 NZ LYS A 110 | 9912 10736 7972 845 -15 483 | N |
| ATOM | 750 N LEU A 111 | 40.319 7.694 -3.038 1.00 51.15 | N |
| ANISOU | 750 N LEU A 111 | 6658 7341 5436 822 142 765 | N |
| ATOM | 751 CA LEU A 111 | 39.269 8.241 -2.167 1.00 55.41 | C |
| ANISOU | 751 CA LEU A 111 | 7147 7872 6033 835 101 792 | C |
| ATOM | 752 C LEU A 111 | 39.677 9.415 -1.294 1.00 51.59 | C |
| ANISOU | 752 C LEU A 111 | 8659 7309 5632 843 164 846 | C |
| ATOM | 753 O DEC A 111 | 38.819 10.081 -0.794 1.00 44.12 | O |
| ANISOU | 753 O LEU A 111 | 5684 6361 4717 871 138 879 | O |
| ATOM | 754 CB LEU A 111 | 38.835 7.174 -1.130 1.00 57.68 | C |
| ANISOU | 754 CB LEU A 111 | 7371 8156 6387 780 49 718 | C |
| ATOM | 755 CG LEU A 111 | 38.105 5.876 -1.476 1.00 58.03 | C |
| ANISOU | 755 CG LEU A 111 | 7394 8266 6390 754 -35 650 | C |
| ATOM | 756 CD1 LEU A 111 | 37.794 5.159 -0.146 1.00 59.49 | C |
| ANISOU | 756 CD1 LEU A 111 | 7517 8421 6665 695 -64 600 | C |
| ATOM | 757 CD2 LEU A 111 | 36.856 6.120 -2.321 1.00 51.51 | C |
| ANISOU | 757 CD2 LEU A 111 | 6562 7524 5484 802 -106 678 | C |
| ATOM | 758 N LEU A 112 | 40.966 9.624 -1.026 1.00 50.08 | N |
| ANISOU | 758 N LEU A 112 | 6491 7053 5484 816 245 846 | N |
| ATOM | 759 CA ILE A 112 | 41.358 10.657 -0.047 1.00 49.44 | C |
| ANISOU | 759 CA ILE A 112 | 6400 6891 5493 813 299 885 | C |
| ATOM | 760 C ILE A 112 | 40.824 12.030 -0.462 1.00 43.48 | C |
| ANISOU | 760 C ILE A 112 | 5676 6130 4714 876 308 975 | C |
| ATOM | 761 O ILE A 112 | 40.923 12.417 -1.567 1.00 47.34 | O |
| ANISOU | 761 O ILE A 112 | 6217 6646 5124 909 322 1022 | O |
| ATOM | 762 CB ILE A 112 | 42.889 10.668 0.277 1.00 50.17 | C |
| ANISOU | 762 CB ILE A 112 | 6508 6917 5638 771 382 869 | C |
| ATOM | 763 CG1 ILE A 112 | 43.150 9.751 1.475 1.00 58.24 | C |
| ANISOU | 763 CG1 ILE A 112 | 7478 7908 6741 716 365 794 | C |
| ATOM | 764 CG2 ILE A 112 | 43.390 12.074 0.587 1.00 50.43 | C |
| ANISOU | 764 CG2 ILE A 112 | 6564 6878 5721 785 450 938 | C |
| ATOM | 765 CD1 ILE A 112 | 44.498 9.062 1.403 1.00 61.79 | C |
| ANISOU | 765 CD1 ILE A 112 | 7937 8333 7206 675 413 746 | C |
| ATOM | 766 N ASP A 113 | 40.144 12.691 0.455 1.00 51.65 | N |

TABLE 3-continued

| | | | | | | | | |
|---|---|---|---|---|---|---|---|---|
| ANISOU | 766 | N | ASP A 113 | 6676 7134 5813 | 893 | 290 | 994 | N |
| ATOM | 767 | CA | ASP A 113 | 39.577 14.016 0.198 | 1.00 | 49.25 | | C |
| ANISOU | 767 | CA | ASP A 113 | 6399 6815 5500 | 958 | 293 | 1075 | C |
| ATOM | 768 | C | ASP A 113 | 40.673 15.004 0.560 | 1.00 | 44 50 | | C |
| ANISOU | 768 | C | ASP A 113 | 5834 6117 4958 | 946 | 380 | 1116 | C |
| ATOM | 769 | O | ASP A 113 | 41.006 15.156 1.735 | 1.00 | 39.14 | | O |
| ANISOU | 769 | O | ASP A 113 | 5123 5377 4372 | 914 | 403 | 1089 | O |
| ATOM | 770 | CB | ASP A 113 | 38.355 14.176 1.111 | 1.00 | 49.83 | | C |
| ANISOU | 770 | CB | ASP A 113 | 6410 6902 5623 | 982 | 235 | 1063 | C |
| ATOM | 771 | CG | ASP A 113 | 37.907 15.621 1.249 | 1.00 | 54.99 | | C |
| ANISOU | 771 | CG | ASP A 113 | 7082 7510 6301 | 1047 | 246 | 1135 | C |
| ATOM | 772 | OD1 | ASP A 113 | 38.359 16.496 0.517 | 1.00 | 52.05 | | O |
| ANISOU | 772 | OD1 | ASP A 113 | 6775 7104 5897 | 1078 | 286 | 1204 | O |
| ATOM | 773 | OD2 | ASP A 113 | 37.116 15.854 2.141 | 1.00 | 64.78 | | O |
| ANISOU | 773 | OD2 | ASP A 113 | 8270 8748 7595 | 1064 | 217 | 1121 | O |
| ATOM | 774 | N | ARG A 114 | 41.257 15.629 -0.452 | 1.00 | 43.00 | | N |
| ANISOU | 774 | N | ARG A 114 | 5711 5915 4713 | 965 | 427 | 1178 | N |
| ATOM | 775 | CA | ARG A 114 | 42.451 16.424 -0.259 | 1.00 | 41.80 | | C |
| ANISOU | 775 | CA | ARG A 114 | 5595 5677 4611 | 939 | 516 | 1213 | C |
| ATOM | 776 | C | ARG A 114 | 42.135 17.756 0.441 | 1.00 | 40.22 | | C |
| ANISOU | 776 | C | ARG A 114 | 5402 5397 4481 | 972 | 528 | 1267 | C |
| ATOM | 777 | O | ARG A 114 | 43.035 18.309 1.113 | 1.00 | 39.62 | | O |
| ANISOU | 777 | O | ARG A 114 | 5332 5237 4485 | 936 | 590 | 1270 | O |
| ATOM | 778 | CB | ARG A 114 | 43.142 16.698 -1.601 | 1.00 | 45.18 | | C |
| ANISOU | 778 | CB | ARG A 114 | 6094 6121 4952 | 946 | 567 | 1269 | C |
| ATOM | 779 | CG | ARG A 114 | 44.149 15.608 -1.996 | 1.00 | 52.76 | | C |
| ANISOU | 779 | CG | ARG A 114 | 7049 7115 5881 | 893 | 602 | 1210 | C |
| ATOM | 780 | CD | ARG A 114 | 43.492 14.436 -2.723 | 1.00 | 57.95 | | C |
| ANISOU | 780 | CD | ARG A 114 | 7697 7874 6448 | 906 | 533 | 1162 | C |
| ATOM | 781 | NE | ARG A 114 | 44.417 13.401 -3.266 | 1.00 | 62.98 | | N |
| ANISOU | 781 | NE | ARG A 114 | 8339 8548 7043 | 866 | 565 | 1104 | N |
| ATOM | 782 | CZ | ARG A 114 | 45.624 13.695 -3.819 | 1.00 | 68.55 | | C |
| ANISOU | 782 | CZ | ARG A 114 | 9080 9236 7728 | 843 | 651 | 1123 | C |
| ATOM | 783 | NH1 | ARG A 114 | 46.152 14.813 -3.925 | 1.00 | 61.99 | | N |
| ANISOU | 783 | NH1 | ARG A 114 | 8288 8347 6917 | 846 | 720 | 1202 | N |
| ATOM | 784 | NH2 | ARG A 114 | 46.340 12.577 -4.265 | 1.00 | 70.30 | | N |
| ANISOU | 784 | NH2 | ARG A 114 | 9298 9499 7914 | 815 | 670 | 1059 | N |
| ATOM | 785 | N | LYS A 115 | 40.885 18.245 0.260 | 1.00 | 37.39 | | N |
| ANISOU | 785 | N | LYS A 115 | 5043 5067 4095 | 1040 | 468 | 1304 | N |
| ATOM | 786 | CA | LYS A 115 | 40.401 19.454 0.943 | 1.00 | 42.96 | | C |

TABLE 3-continued

| | | | | | | | | | | |
|---|---|---|---|---|---|---|---|---|---|---|
| ANISOU | 786 | CA | LYS | A | 115 | 5752 5703 4867 1084 468 1346 | | | | C |
| ATOM | 787 | C | LYS | A | 115 | 40.316 | 19.195 | 2.463 | 1.00 40.86 | C |
| ANISOU | 787 | C | LYS | A | 115 | 5418 5405 4703 1050 461 1275 | | | | C |
| ATOM | 788 | O | LYS | A | 115 | 40.783 | 20.027 | 3.203 | 1.00 41.96 | O |
| ANISOU | 788 | O | LYS | A | 115 | 5567 5455 4919 1042 504 1288 | | | | O |
| ATOM | 789 | CB | LYS | A | 115 | 39.016 | 19.973 | 0.427 | 1.00 44.68 | C |
| ANISOU | 789 | CB | LYS | A | 115 | 5976 5967 5034 1174 398 1395 | | | | C |
| ATOM | 790 | CG | LYS | A | 115 | 38.962 | 20.370 | -1.059 | 1.00 47.51 | C |
| ANISOU | 790 | CG | LYS | A | 115 | 6410 6357 5286 1220 395 1476 | | | | C |
| ATOM | 791 | CD | LYS | A | 115 | 40.009 | 21.448 | -1.375 | 1.00 51.11 | C |
| ANISOU | 791 | CD | LYS | A | 115 | 6945 6717 5756 1210 480 1551 | | | | C |
| ATOM | 792 | CE | LYS | A | 115 | 39.534 | 22.485 | -2.408 | 1.00 56.20 | C |
| ANISOU | 792 | CE | LYS | A | 115 | 7541 7227 6206 1287 466 1657 | | | | C |
| ATOM | 793 | NZ | LYS | A | 115 | 40.532 | 23.619 | -2.533 | 1.00 55.31 | N |
| ANISOU | 793 | NZ | LYS | A | 115 | 7632 7131 6254 1269 551 1733 | | | | N |
| ATOM | 794 | N | SER | A | 116 | 39.751 | 18.058 | 2.923 | 1.00 41.32 | N |
| ANISOU | 794 | N | SER | A | 116 | 5409 5531 4760 1028 408 1203 | | | | N |
| ATOM | 795 | CA | SER | A | 116 | 39.790 | 17.750 | 4.353 | 1.00 36.71 | C |
| ANISOU | 795 | CA | SER | A | 116 | 4767 4918 4265 988 408 1138 | | | | C |
| ATOM | 796 | C | SER | A | 116 | 41.183 | 17.604 | 4.888 | 1.00 34.71 | C |
| ANISOU | 796 | C | SER | A | 116 | 4523 4597 4068 919 473 1109 | | | | C |
| ATOM | 797 | O | SER | A | 116 | 41.445 | 18.019 | 5.993 | 1.00 35.48 | O |
| ANISOU | 797 | O | SER | A | 116 | 4603 4632 4247 900 495 1089 | | | | O |
| ATOM | 798 | CB | SER | A | 116 | 39.047 | 16.438 | 4.787 | 1.00 39.22 | C |
| ANISOU | 798 | CB | SER | A | 116 | 5014 5316 4571 961 345 1065 | | | | C |
| ATOM | 799 | OG | SER | A | 116 | 37.662 | 16.419 | 4.387 | 1.00 46.80 | O |
| ANISOU | 799 | OG | SER | A | 116 | 5946 6352 5483 1018 276 1079 | | | | O |
| ATOM | 800 | N | LEU | A | 117 | 42.001 | 16.813 | 4.174 | 1.00 35.22 | N |
| ANISOU | 800 | N | LEU | A | 117 | 4605 4688 4088 878 495 1093 | | | | N |
| ATOM | 801 | CA | LEU | A | 117 | 43.366 | 16.518 | 4.545 | 1.00 36.86 | C |
| ANISOU | 801 | CA | LEU | A | 117 | 4816 4847 4344 814 553 1060 | | | | C |
| ATOM | 802 | C | LEU | A | 117 | 44.132 | 17.844 | 4.835 | 1.00 37.24 | C |
| ANISOU | 802 | C | LEU | A | 117 | 4900 4795 4453 812 070 1139 | | | | O |
| ATOM | 803 | O | LEU | A | 117 | 44.809 | 17.938 | 5.903 | 1.00 33.93 | O |
| ANISOU | 803 | O | LEU | A | 117 | 4458 4316 4118 769 647 1072 | | | | O |
| ATOM | 804 | CB | LEU | A | 117 | 44.052 | 15.738 | 3.404 | 1.00 34.97 | C |
| ANISOU | 804 | CB | LEU | A | 117 | 4602 4655 4030 792 572 1053 | | | | C |
| ATOM | 805 | CG | LEU | A | 117 | 45.527 | 15.382 | 3.666 | 1.00 40.44 | C |
| ANISOU | 805 | CG | LEU | A | 117 | 5291 5306 4767 730 634 1017 | | | | C |
| ATOM | 806 | CD1 | LEU | A | 117 | 45.736 | 14.542 | 4.939 | 1.00 35.91 | C |

TABLE 3-continued

| | | | | | | | | | |
|---|---|---|---|---|---|---|---|---|---|
| ANISOU | 806 | CD1 | LEU A | 117 | 4660 | 4717 | 4266 | 683 | 611 | 937 | C |
| ATOM | 807 | CD2 | LEU A | 117 | 46.166 | 14.709 | 2.447 | 1.00 | 40.38 | C |
| ANISOU | 807 | CD2 | LEU A | 117 | 5312 | 5351 | 4681 | 719 | 659 | 1012 | C |
| ATOM | 808 | N | ALA A | 118 | 44.054 | 18.821 | 3.906 | 1.00 | 36.70 | N |
| ANISOU | 808 | N | ALA A | 118 | 4892 | 4710 | 4343 | 854 | 644 | 1190 | N |
| ATOM | 809 | CA | ALA A | 118 | 44.775 | 20.131 | 4.118 | 1.00 | 34.99 | C |
| ANISOU | 809 | CA | ALA A | 118 | 4717 | 4390 | 4186 | 848 | 708 | 1243 | C |
| ATOM | 810 | C | ALA A | 118 | 44.305 | 20.827 | 5.396 | 1.00 | 35.57 | C |
| ANISOU | 810 | C | ALA A | 118 | 4766 | 4400 | 4348 | 864 | 691 | 1227 | C |
| ATOM | 811 | O | ALA A | 118 | 45.126 | 21.302 | 6.198 | 1.00 | 32.87 | O |
| ANISOU | 811 | O | ALA A | 118 | 4423 | 3979 | 4087 | 824 | 734 | 1211 | O |
| ATOM | 812 | CB | ALA A | 118 | 44.666 | 21.052 | 2.890 | 1.00 | 40.99 | C |
| ANISOU | 812 | CB | ALA A | 118 | 5552 | 5141 | 4862 | 894 | 781 | 1340 | C |
| ATOM | 313 | N | ARG A | 119 | 42.983 | 20.823 | 5.624 | 1.00 | 33.64 | N |
| ANISOU | 813 | N | ARG A | 119 | 4497 | 4198 | 4086 | 922 | 627 | 1222 | N |
| ATOM | 814 | CA | ARG A | 119 | 42.520 | 21.347 | 6.848 | 1.00 | 36.08 | C |
| ANISOU | 814 | CA | ARG A | 119 | 4776 | 4459 | 4472 | 937 | 612 | 1196 | C |
| ATOM | 815 | C | ARG A | 119 | 43.021 | 20.605 | 8.089 | 1.00 | 33.17 | C |
| ANISOU | 815 | C | ARG A | 119 | 4353 | 4083 | 4168 | 873 | 615 | 1112 | C |
| ATOM | 816 | O | ARG A | 119 | 43.318 | 21.240 | 9.096 | 1.00 | 31.95 | O |
| ANISOU | 816 | O | ARG A | 119 | 4194 | 3855 | 4089 | 861 | 636 | 1094 | O |
| ATOM | 817 | CB | ARG A | 119 | 41.008 | 21.381 | 6.861 | 1.00 | 40.56 | C |
| ANISOU | 817 | CB | ARG A | 119 | 5315 | 5087 | 5008 | 1009 | 544 | 1201 | C |
| ATOM | 818 | CG | ARG A | 119 | 40.519 | 22.605 | 6.155 | 1.00 | 39.12 | C |
| ANISOU | 818 | CG | ARG A | 119 | 5189 | 4868 | 4805 | 1085 | 543 | 1284 | C |
| ATOM | 819 | CD | ARG A | 119 | 39.086 | 22.837 | 6.590 | 1.00 | 43.00 | C |
| ANISOU | 819 | CD | ARG A | 119 | 5639 | 5398 | 5301 | 1158 | 481 | 1274 | C |
| ATOM | 820 | NE | ARG A | 119 | 38.262 | 21.597 | 6.498 | 1.00 | 39.39 | N |
| ANISOU | 820 | NE | ARG A | 119 | 5116 | 5059 | 4792 | 1153 | 421 | 1227 | N |
| ATOM | 821 | CZ | ARG A | 119 | 37.707 | 21.134 | 5.399 | 1.00 | 36.71 | C |
| ANISOU | 821 | CZ | ARG A | 119 | 4781 | 4801 | 4366 | 1182 | 380 | 1252 | C |
| ATOM | 822 | NH1 | ARG A | 119 | 37.885 | 21.765 | 4.210 | 1.00 | 38.98 | N |
| ANISOU | 822 | NH1 | ARG A | 119 | 5140 | 5074 | 4597 | 1220 | 391 | 1330 | N |
| ATOM | 823 | NH2 | ARG A | 119 | 36.974 | 20.036 | 5.473 | 1.00 | 36.03 | N |
| ANISOU | 823 | NH2 | ARG A | 119 | 4630 | 4811 | 4247 | 1169 | 325 | 1201 | N |
| ATOM | 824 | N | ILE A | 120 | 43.058 | 19.268 | 8.021 | 1.00 | 32.10 | N |
| ANISOU | 824 | N | ILE A | 120 | 4178 | 4021 | 3997 | 836 | 589 | 1061 | N |
| ATOM | 825 | CA | ILE A | 120 | 43.491 | 18.464 | 9.175 | 1.00 | 32.96 | C |
| ANISOU | 825 | CA | ILE A | 120 | 4238 | 4125 | 4159 | 777 | 585 | 985 | C |
| ATOM | 826 | C | ILE A | 120 | 44.995 | 18.764 | 9.502 | 1.00 | 33.48 | C |

TABLE 3-continued

| ANISOU | 826 | C   | ILE A 120 | 4323 4112 4285 721 649 975      | C |
|--------|-----|-----|-----------|---------------------------------|---|
| ATOM   | 827 | O   | ILE A 120 | 45.400 18.895 10.657 1.00 31.27 | O |
| ANISOU | 827 | O   | 1E A 120  | 4022 3784 4077 690 658 934      | O |
| ATOM   | 828 | CB  | ILE A 120 | 43.242 16.950 8.905 1.00 32.22  | C |
| ANISOU | 828 | CB  | ILE A 120 | 4108 4120 4013 750 542 937      | C |
| ATOM   | 829 | CG1 | ILE A 120 | 41.711 16.714 8.754 1.00 85.60  | C |
| ANISOU | 829 | CG1 | ILE A 120 | 4507 4625 4395 799 476 941      | C |
| ATOM   | 830 | CG2 | ILE A 120 | 43.872 16.110 10.017 1.00 34.50 | C |
| ANISOU | 830 | CG2 | ILE A 120 | 4358 4394 4355 687 541 866      | C |
| ATOM   | 831 | CD1 | ILE A 120 | 41.307 15.314 8.268 1.00 29.54  | C |
| ANISOU | 831 | CD1 | ILE A 120 | 3712 3946 3567 778 427 904      | C |
| ATOM   | 832 | N   | VAL A 121 | 45.810 18.866 8.472 1 00 32.18  | N |
| ANISOU | 832 | N   | VAL A 121 | 4197 3940 4090 707 692 1012     | N |
| ATOM   | 833 | CA  | VAL A 121 | 47.216 19.275 8.636 1.00 31.34  | C |
| ANISOU | 833 | CA  | VAL A 121 | 4106 3763 4040 655 757 1011     | C |
| ATOM   | 834 | C   | VAL A 121 | 47.378 20.538 9.410 1.00 30.32  | C |
| ANISOU | 834 | C   | VAL A 121 | 3994 3538 3987 659 783 1030     | C |
| ATOM   | 835 | O   | VAL A 121 | 43.197 20.605 10.356 1.00 31.39 | O |
| ANISOU | 835 | O   | VAL A 121 | 4109 3621 4197 611 803 987      | O |
| ATOM   | 836 | CB  | VAL A 121 | 47.855 19.555 7.290 1.00 33.75  | C |
| ANISOU | 836 | CB  | VAL A 121 | 4459 4071 4293 653 807 1070     | C |
| ATOM   | 837 | CG1 | VAL A 121 | 49.246 20.239 7.517 1.00 30.53  | C |
| ANISOU | 837 | CG1 | VAL A 121 | 4065 3581 3955 600 881 1079     | C |
| ATOM   | 838 | CG2 | VAL A 121 | 47.976 18.227 6.482 1.00 36.71  | C |
| ANISOU | 838 | CG2 | VAL A 121 | 4818 4537 4593 641 792 1040     | C |
| ATOM   | 839 | N   | GLU A 122 | 46.557 21.550 9.081 1.00 32.23  | N |
| ANISOU | 839 | N   | GLU A 122 | 4274 3756 4215 719 775 1090     | N |
| ATOM   | 840 | CA  | GLU A 122 | 46.653 22.817 9.771 1.00 34.78  | C |
| ANISOU | 840 | CA  | GLU A 122 | 4622 3981 4612 730 797 1108     | C |
| ATOM   | 841 | C   | GLU A 122 | 46.246 22.699 11.230 1.00 33.87 | C |
| ANISOU | 841 | C   | GLU A 122 | 4460 3853 4555 728 763 1039     | C |
| ATOM   | 842 | O   | GLU A 122 | 46.911 23.237 12.098 1.00 31.48 | O |
| ANISOU | 842 | O   | GLU A 122 | 4159 3475 4328 695 788 1014     | O |
| ATOM   | 843 | CB  | GLU A 122 | 45.742 23.831 9.037 1.00 44.09  | C |
| ANISOU | 843 | CB  | GLU A 122 | 5853 5143 5756 806 786 1186     | C |
| ATOM   | 844 | CG  | GLU A 122 | 46.165 25.275 9.084 1.00 49.83  | C |
| ANISOU | 844 | CG  | GLU A 122 | 6638 5755 6540 813 830 1239     | C |
| ATOM   | 845 | CD  | GLU A 122 | 47.662 25.462 9.009 1.00 58.44  | C |
| ANISOU | 845 | CD  | GLU A 122 | 7744 6785 7674 733 897 1242     | C |
| ATOM   | 846 | OE1 | GLU A 122 | 48.343 24.809 8.145 1.00 47.68  | O |

TABLE 3-continued

| | | |
|---|---|---|
| ANISOU 846 OE1 GLU A 122 | 6383 5471 6263 696 927 1255 | O |
| ATOM 847 OE2 GLU A 122 | 48.150 26.282 9.859 1.00 67.06 | O |
| ANISOU 847 OE2 GLU A 122 | 8846 7781 8853 709 920 1227 | O |
| ATOM 848 N ARG A 123 | 45.167 21.971 11.503 1.00 35.91 | N |
| ANISOU 848 N ARG A 123 | 4678 4189 4776 759 707 1008 | N |
| ATOM 849 CA ARG A 123 | 44.795 21.667 12.922 1.00 35.90 | C |
| ANISOU 849 CA ARG A 123 | 4628 4191 4820 749 677 939 | C |
| ATOM 850 C ARG A 123 | 45.938 21.018 13.729 1.00 34.25 | C |
| ANISOU 850 C ARG A 123 | 4393 3962 4659 672 694 878 | C |
| ATOM 851 O ARG A 123 | 46.230 21.434 14.843 1.00 37.66 | O |
| ANISOU 851 O ARG A 123 | 4816 4339 5153 654 701 841 | O |
| ATOM 852 CB ARG A 123 | 43.550 20.813 12.917 1.00 34.52 | C |
| ANISOU 852 CB ARG A 123 | 4410 4115 4590 781 620 920 | C |
| ATOM 853 CG ARG A 123 | 42.365 21.652 12.351 1.00 37.48 | C |
| ANISOU 853 CG ARG A 123 | 4804 4503 4935 867 598 974 | C |
| ATOM 854 CD ARG A 123 | 41.006 21.129 12.762 1.00 45.89 | C |
| ANISOU 854 CD ARG A 123 | 5814 5652 5972 904 542 945 | C |
| ATOM 855 NE ARG A 123 | 39.856 21.799 12.105 1.00 46.24 | N |
| ANISOU 855 NE ARG A 123 | 5867 5722 5981 990 514 995 | N |
| ATOM 856 CZ ARG A 123 | 39.122 22.764 12.660 1.00 53.34 | C |
| ANISOU 856 CZ ARG A 123 | 6763 6589 6914 1053 507 1000 | C |
| ATOM 857 NH1 ARG A 123 | 39.437 23.260 13.868 1.00 41.17 | N |
| ANISOU 857 NH1 ARG A 123 | 5217 4984 5443 1038 530 959 | N |
| ATOM 858 NH2 ARG A 123 | 38.047 23.228 12.002 1.00 53.51 | N |
| ANISOU 858 NH2 ARG A 123 | 6786 6647 6900 1134 473 1043 | N |
| ATOM 859 N VAL A 124 | 46.565 19.998 13.166 1.00 32.56 | N |
| ANISOU 859 N VAL A 124 | 4167 3793 4412 631 698 866 | N |
| ATOM 860 CA VAL A 124 | 47.708 19.369 13.800 1.00 32.16 | C |
| ANISOU 860 CA VAL A 124 | 4092 3724 4405 564 712 812 | C |
| ATOM 861 O VAL A 124 | 46.859 20.353 14.048 1.00 33.36 | C |
| ANISOU 861 O VAL A 124 | 4268 3781 4627 531 766 821 | C |
| ATOM 862 O VAL A 124 | 49.429 20.433 15.159 1.00 37.71 | O |
| ANISOU 862 O VAL A 124 | 4799 4288 5241 495 766 772 | O |
| ATOM 863 CB VAL A 124 | 48.180 18.162 13.011 1.00 32.66 | C |
| ANISOU 863 CB VAL A 124 | 4142 3849 4420 536 709 799 | C |
| ATOM 864 CG1 VAL A 124 | 49.434 17.545 13.702 1.00 32.71 | C |
| ANISOU 864 CG1 VAL A 124 | 4120 3830 4477 472 722 742 | C |
| ATOM 865 CG2 VAL A 124 | 47.027 17 127 12.969 1.00 29.93 | C |
| ANISOU 865 CG2 VAL A 124 | 3768 3590 4015 558 649 779 | C |
| ATOM 866 N HIS A 125 | 49.110 21.163 13.064 1.00 34.73 | N |

TABLE 3-continued

| | | |
|---|---|---|
| ANISOU 866 N HIS A 125 | 4485 3921 4789 545 807 885 | N |
| ATOM 867 CA HIS A 125 | 50.181 22.136 13.169 1.00 36.69 | C |
| ANISOU 867 CA HIS A 125 | 4758 4078 5103 508 661 901 | C |
| ATOM 868 C HIS A 125 | 49.905 23.062 14.321 1.00 35.30 | C |
| ANISOU 868 C HIS A 125 | 4589 3829 4994 520 851 881 | C |
| ATOM 869 O HIS A 125 | 50.807 23.304 15.133 1.00 36.67 | O |
| ANISOU 869 O HIS A 125 | 4749 3946 5237 471 867 841 | O |
| ATOM 870 CB HIS A 125 | 50.321 22.923 11.881 1.00 33.31 | C |
| ANISOU 870 CB HIS A 125 | 4385 3627 4644 526 906 985 | C |
| ATOM 871 CG HIS A 125 | 51.330 24.030 12.001 1.00 38.67 | C |
| ANISOU 871 CG HIS A 125 | 5093 4204 5395 485 933 1009 | C |
| ATOM 872 ND1 HIS A 125 | 52.611 23.794 12.261 1.00 39.87 | N |
| ANISOU 872 ND1 HIS A 125 | 5218 4334 5565 415 998 975 | N |
| ATOM 873 CD2 HIS A 125 | 51.179 25.429 12.004 1.00 45.43 | C |
| ANISOU 873 CD2 HIS A 125 | 6003 4968 6290 505 985 1060 | C |
| ATOM 874 CE1 HIS A 125 | 53.281 24.971 12.370 1.00 40.49 | C |
| ANISOU 874 CE1 HIS A 125 | 5328 4315 5740 385 1043 1004 | C |
| ATOM 875 NE2 HIS A 125 | 52.418 25.961 12.180 1.00 41.10 | N |
| ANISOU 875 NE2 HIS A 125 | 5459 4346 5810 439 1036 1058 | N |
| ATOM 876 N GLN A 126 | 48.656 23.527 14.438 1.00 32.05 | N |
| ANISOU 876 N GLN A 126 | 4191 3424 4561 587 819 900 | N |
| ATOM 877 CA GLN A 126 | 48.274 24.457 15.521 1.00 38.06 | C |
| ANISOU 877 CA GLN A 126 | 4961 4118 5381 610 809 877 | C |
| ATOM 878 C GLN A 126 | 48.218 23.779 16.908 1.00 39.80 | C |
| ANISOU 878 C GLN A 126 | 5131 4363 5627 586 775 792 | C |
| ATOM 879 O GLN A 126 | 48.347 24.450 17.949 1.00 37.09 | O |
| ANISOU 879 O GLN A 126 | 4792 3957 5342 581 775 756 | O |
| ATOM 880 CB GLN A 126 | 46.901 25.130 15.264 1.00 35.18 | C |
| ANISOU 880 CB GLN A 126 | 4621 3760 4986 697 784 917 | C |
| ATOM 881 CG GLN A 126 | 46.800 25.972 13.963 1.00 49.72 | C |
| ANISOU 881 CG GLN A 126 | 6523 5567 6601 734 811 1008 | C |
| ATOM 882 CD GLN A 126 | 47.814 27.137 13.894 1.00 54.30 | C |
| ANISOU 882 CD GLN A 126 | 7156 6027 7447 700 864 1041 | C |
| ATOM 883 OE1 GLN A 126 | 48.211 27.690 14.920 1.00 58.09 | O |
| ANISOU 883 OE1 GLN A 126 | 7635 6434 8001 677 870 997 | O |
| ATOM 884 NE2 GLN A 126 | 48.238 27.501 12.674 1.00 60.30 | N |
| ANISOU 884 NE2 GLN A 126 | 7964 6769 8180 694 902 1117 | N |
| ATOM 885 N ALA A 127 | 48.030 22.456 16.930 1.00 37.37 | N |
| ANISOU 885 N ALA A 127 | 4781 4144 5274 569 745 761 | N |
| ATOM 886 CA ALA A 127 | 47.625 21.836 18.169 1.00 35.09 | C |

TABLE 3-continued

| | | |
|---|---|---|
| ANISOU 886 CA ALA A 127 | 4451 3890 4993 561 706 696 | C |
| ATOM 887 C ALA A 127 | 48.787 21.844 19.165 1.00 37.25 | C |
| ANISOU 887 C ALA A 127 | 4700 4096 5318 500 717 642 | C |
| ATOM 888 O ALA A 127 | 49.941 21.603 18.802 1.00 40.24 | O |
| ANISOU 888 O ALA A 127 | 5091 4468 5731 450 742 641 | O |
| ATOM 889 CB ALA A 127 | 47.113 20.441 17.905 1.00 37.55 | C |
| ANISOU 889 CB ALA A 127 | 4725 4301 5241 556 669 682 | C |
| ATOM 890 N GLU A 128 | 48.506 22.146 20.420 1.00 33.40 | N |
| ANISOU 890 N GLU A 128 | 4217 3600 4875 504 698 594 | N |
| ATOM 891 CA GLU A 128 | 49.531 22.004 21.444 1.00 36.86 | C |
| ANISOU 891 CA GLU A 128 | 4640 4000 5365 448 697 536 | C |
| ATOM 892 C GLU A 128 | 49.523 20.579 22.041 1.00 35.36 | C |
| ANISOU 892 C GLU A 128 | 4408 3684 5144 417 657 491 | C |
| ATOM 893 O GLU A 128 | 50.546 20.049 22.531 1.00 32.86 | O |
| ANISOU 893 O GLU A 128 | 4074 3556 4856 365 650 451 | O |
| ATOM 894 CB GLU A 128 | 49.284 23.046 22.531 1.00 43.74 | C |
| ANISOU 894 CB GLU A 128 | 5529 4809 6282 467 695 504 | C |
| ATOM 895 CG GLU A 128 | 49.786 24.436 22.054 1.00 53.11 | C |
| ANISOU 895 CG GLU A 128 | 6763 5895 7523 472 737 540 | C |
| ATOM 896 CD GLU A 128 | 49.519 25.539 23.078 1.00 61.91 | C |
| ANISOU 896 CD GLU A 128 | 7901 6938 8685 496 734 505 | C |
| ATOM 897 OE1 GLU A 128 | 48.515 25.448 23.804 1.00 62.23 | O |
| ANISOU 897 OE1 GLU A 128 | 7928 7018 8699 539 707 475 | O |
| ATOM 898 OE2 GLU A 128 | 50.299 26.518 23.162 1.00 73.05 | O |
| ANISOU 898 OE2 GLU A 128 | 9343 8252 10160 472 760 505 | O |
| ATOM 899 N PHE A 129 | 48.361 19.919 21.952 1.00 31.26 | N |
| ANISOU 899 N PHE A 129 | 3872 3441 4566 449 628 497 | N |
| ATOM 900 CA PHE A 129 | 48.305 18.561 22.588 1.00 35.38 | C |
| ANISOU 900 CA PHE A 129 | 4359 4027 5058 416 588 457 | C |
| ATOM 901 C PHE A 129 | 47.368 17.746 21.742 1.00 37.44 | C |
| ANISOU 901 C PHE A 129 | 4605 4367 5252 439 569 487 | C |
| ATOM 902 O PHE A 129 | 46.319 18.272 21.274 1.00 35.24 | O |
| ANISOU 902 O PHE A 129 | 4333 4111 4947 492 571 521 | O |
| ATOM 903 CB PHE A 129 | 47.783 18.636 24.046 1.00 33.63 | C |
| ANISOU 903 CB PHE A 129 | 4125 3812 4842 418 564 409 | C |
| ATOM 904 CG PHE A 129 | 47.468 17.243 24.657 1.00 34.07 | C |
| ANISOU 904 CG PHE A 129 | 4150 3938 4856 388 523 380 | C |
| ATOM 905 CD1 PHE A 129 | 48.457 16.521 25.281 1.00 36.32 | C |
| ANISOU 905 CD1 PHE A 129 | 4428 4211 5161 337 504 342 | C |
| ATOM 906 CD2 PHE A 129 | 46.178 16.677 24.528 1.00 41.60 | C |

TABLE 3-continued

| | | | | | | | | | | |
|---|---|---|---|---|---|---|---|---|---|---|
| ANISOU | 906 | CD2 | PHE | A | 129 | 5083 4969 5754 412 501 394 | | | | C |
| ATOM | 907 | CE1 | PHE | A | 129 | 48.153 | 15.263 | 25.870 | 1.00 39.68 | C |
| ANISOU | 907 | CE1 | PHE | A | 129 | 4834 4694 5550 309 463 320 | | | | C |
| ATOM | 908 | CE2 | PHE | A | 129 | 45.902 | 15.433 | 25.073 | 1.00 37.79 | C |
| ANISOU | 908 | CE2 | PHE | A | 129 | 4578 4544 5238 378 465 371 | | | | C |
| ATOM | 909 | CZ | PHE | A | 129 | 46.887 | 14.744 | 25.746 | 1.00 32.27 | C |
| ANISOU | 909 | CZ | PHE | A | 129 | 3879 3825 4557 328 447 337 | | | | C |
| ATOM | 910 | N | ILE | A | 130 | 47.762 | 16.501 | 21.479 | 1.00 31.98 | N |
| ANISOU | 910 | N | ILE | A | 130 | 3897 3717 4538 403 548 474 | | | | N |
| ATOM | 911 | CA | ILE | A | 130 | 46.958 | 15.667 | 20.616 | 1.00 31.17 | C |
| ANISOU | 911 | CA | IEL | A | 130 | 3783 3686 4374 418 526 498 | | | | C |
| ATOM | 912 | C | ILE | A | 130 | 46.658 | 14.374 | 21.358 | 1.00 30.70 | C |
| ANISOU | 912 | C | ILE | A | 130 | 3695 3677 4290 384 481 461 | | | | C |
| ATOM | 913 | O | ILE | A | 130 | 47.603 | 13.585 | 21.758 | 1.00 28.44 | O |
| ANISOU | 913 | O | ILE | A | 130 | 3405 3377 4023 339 468 428 | | | | O |
| ATOM | 914 | CB | ILE | A | 130 | 47.696 | 15.372 | 19.271 | 1.00 33.45 | C |
| ANISOU | 914 | C8 | ILE | A | 130 | 4086 3976 4649 410 546 526 | | | | C |
| ATOM | 915 | CG1 | ILE | A | 130 | 47.938 | 16.704 | 18.504 | 1.00 30.29 | C |
| ANISOU | 915 | CG1 | ILE | A | 130 | 3719 3524 4267 441 594 573 | | | | C |
| ATOM | 916 | CG2 | ILE | A | 130 | 46.860 | 14.412 | 18.365 | 1.00 31.42 | C |
| ANISOU | 916 | CG2 | ILE | A | 130 | 3819 3797 4323 424 517 543 | | | | C |
| ATOM | 917 | CD1 | ILL | A | 130 | 48.794 | 16.547 | 17.255 | 1.00 32.50 | C |
| ANISOU | 917 | CD1 | ILE | A | 130 | 4015 3800 4534 429 625 601 | | | | C |
| ATOM | 918 | N | GLY | A | 131 | 45.373 | 14.125 | 21.519 | 1.00 27.60 | N |
| ANISOU | 918 | N | GLY | A | 131 | 3284 3344 3857 405 457 467 | | | | N |
| ATOM | 919 | CA | GLY | A | 131 | 44.900 | 12.910 | 22.209 | 1.00 27.55 | C |
| ANISOU | 919 | CA | GLY | A | 131 | 3253 3390 3824 370 416 439 | | | | C |
| ATOM | 920 | C | GLY | A | 131 | 44.410 | 11.939 | 21.146 | 1.00 29.39 | C |
| ANISOU | 920 | C | GLY | A | 131 | 3477 3681 4008 367 390 457 | | | | C |
| ATOM | 921 | O | GLY | A | 131 | 43.668 | 12.341 | 20.210 | 1.00 28.36 | O |
| ANISOU | 921 | O | GLY | A | 131 | 3346 3582 3848 409 396 492 | | | | O |
| ATOM | 922 | N | CYS | A | 132 | 44.734 | 10.645 | 21.272 | 1.00 26.18 | N |
| ANISOU | 922 | N | CYS | A | 132 | 3066 3291 3589 322 358 434 | | | | N |
| ATOM | 923 | CA | CYS | A | 132 | 44.253 | 9.689 | 20.251 | 1.00 29.13 | C |
| ANISOU | 923 | CA | CYS | A | 132 | 3434 3717 3916 318 330 445 | | | | C |
| ATOM | 924 | C | CYS | A | 132 | 43.496 | 8.547 | 20.939 | 1.00 28.79 | C |
| ANISOU | 924 | C | CYS | A | 132 | 3369 3721 3848 278 285 426 | | | | C |
| ATOM | 925 | O | CYS | A | 132 | 43.882 | 8.187 | 22.045 | 1.00 26.72 | O |
| ANISOU | 925 | O | CYS | A | 132 | 3108 3436 3607 243 274 400 | | | | O |
| ATOM | 926 | CB | CYS | A | 132 | 45.420 | 9.062 | 19.488 | 1.00 29.60 | C |

TABLE 3-continued

| | | | | | | | | | |
|---|---|---|---|---|---|---|---|---|---|
| ANISOU | 926 | CB | CYS A 132 | 3514 | 3750 | 3982 | 300 | 332 | 434 C |
| ATOM | 927 | SG | CYS A 132 | 46.470 | 10.328 | 18.719 | 1.00 | 30.93 | S |
| ANISOU | 927 | SG | CYS A 132 | 3707 | 3862 | 4182 | 332 | 392 | 458 S |
| ATOM | 928 | N | ILE A 133 | 42.435 | 8.042 | 25.306 | 1.00 | 24.86 | N |
| ANISOU | 928 | N | ILE A 133 | 2852 | 3286 | 3306 | 282 | 258 | 440 N |
| ATOM | 929 | CA | ILE A 133 | 41.550 | 7.081 | 20.979 | 1.00 | 30.37 | C |
| ANISOU | 929 | CA | ILE A 133 | 3525 | 4033 | 3982 | 241 | 220 | 427 C |
| ATOM | 930 | C | ILE A 133 | 41.246 | 5.958 | 20.000 | 1.00 | 29.47 | C |
| ANISOU | 930 | C | ILE A 133 | 3411 | 3955 | 3832 | 220 | 180 | 426 C |
| ATOM | 931 | O | ILE A 133 | 40.842 | 6.213 | 18.866 | 1.00 | 30.82 | O |
| ANISOU | 931 | O | ILE A 133 | 3579 | 4156 | 3974 | 255 | 180 | 445 O |
| ATOM | 932 | CB | ILE A 133 | 40.203 | 7.712 | 21.503 | 1.00 | 33.09 | C |
| ANISOU | 932 | CB | ILE A 133 | 3829 | 4431 | 4311 | 263 | 226 | 441 C |
| ATOM | 933 | CG1 | ILE A 133 | 40.376 | 8.957 | 22.358 | 1.00 | 32.51 | C |
| ANISOU | 933 | CG1 | ILE A 133 | 3758 | 4324 | 4270 | 295 | 266 | 439 C |
| ATOM | 934 | CG2 | ILE A 133 | 39.403 | 6.680 | 22.288 | 1.00 | 32.09 | C |
| ANISOU | 934 | CG2 | ILE A 133 | 3675 | 4354 | 4164 | 208 | 192 | 428 C |
| ATOM | 935 | CD1 | ILE A 133 | 39.039 | 9.717 | 22.376 | 1.00 | 42.57 | C |
| ANISOU | 935 | CD1 | ILE A 133 | 4992 | 5655 | 5526 | 341 | 275 | 456 C |
| ATOM | 936 | N | GLY A 134 | 41.410 | 4.689 | 20.459 | 1.00 | 27.55 | N |
| ANISOU | 936 | N | GLY A 134 | 3174 | 3707 | 3587 | 163 | 143 | 403 N |
| ATOM | 937 | CA | GLY A 134 | 41.019 | 3.566 | 19.654 | 1.00 | 29.95 | C |
| ANISOU | 937 | CA | GLY A 134 | 3479 | 4043 | 3859 | 138 | 100 | 396 C |
| ATOM | 938 | C | GLY A 134 | 41.244 | 2.272 | 20.403 | 1.00 | 31.31 | C |
| ANISOU | 938 | C | GLY A 134 | 3664 | 4193 | 4038 | 74 | 61 | 372 C |
| ATOM | 939 | O | GLY A 134 | 42.119 | 2.213 | 21.312 | 1.00 | 30.51 | O |
| ANISOU | 939 | O | GLY A 134 | 3582 | 4040 | 3970 | 57 | 67 | 359 O |
| ATOM | 940 | N | VAL A 135 | 40.405 | 1.276 | 20.085 | 1.00 | 29.72 | N |
| ANISOU | 940 | N | VAL A 135 | 3452 | 4033 | 3809 | 36 | 17 | 369 N |
| ATOM | 941 | CA | VAL A 135 | 40.516 | -0.046 | 20.722 | 1.00 | 26.74 | C |
| ANISOU | 941 | CA | VAL A 135 | 3091 | 3632 | 3436 | -29 | -20 | 351 C |
| ATOM | 942 | C | VAL A 135 | 40.655 | -1.205 | 19.812 | 1.00 | 26.12 | C |
| ANISOU | 942 | C | VAL A 135 | 3037 | 3544 | 3343 | -51 | -71 | 330 C |
| ATOM | 943 | O | VAL A 135 | 40.426 | -1.110 | 18.573 | 1.00 | 26.71 | O |
| ANISOU | 943 | O | VAL A 135 | 3108 | 3648 | 3391 | -20 | -75 | 328 O |
| ATOM | 944 | CB | VAL A 135 | 39.316 | -0.324 | 21.695 | 1.00 | 31.15 | C |
| ANISOU | 944 | CB | VAL A 135 | 3615 | 4239 | 3981 | -79 | -40 | 366 C |
| ATOM | 945 | CG1 | VAL A 135 | 39.198 | 0.773 | 22.808 | 1.00 | 30.31 | C |
| ANISOU | 945 | CG1 | VAL A 135 | 3488 | 4140 | 3887 | -59 | 5 | 380 C |
| ATOM | 946 | CG2 | VAL A 135 | 38.021 | -0.445 | 20.904 | 1.00 | 31.98 | C |

TABLE 3-continued

| | | | |
|---|---|---|---|
| ANISOU | 946 CG2 VAL A 135 | 3679 4420 4051 -82 -59 376 | C |
| ATOM | 947 N GLY A 136 | 41.086 -2.357 20.349 1.00 26.13 | N |
| ANISOU | 947 N GLY A 136 | 3069 3500 3359 -101 -109 312 | N |
| ATOM | 948 CA GLY A 136 | 41.239 -3.561 19.501 1.00 28.01 | C |
| ANISOU | 948 CA GLY A 136 | 3336 3719 3587 -122 -157 284 | C |
| ATOM | 949 C GLY A 136 | 42.232 -3.238 18.389 1.00 28.42 | C |
| ANISOU | 949 C GLY A 136 | 3409 3749 3540 -64 -136 264 | C |
| ATOM | 950 O GLY A 136 | 43.312 -2.695 18.661 1.00 30.81 | O |
| ANISOU | 950 O GLY A 136 | 3724 4009 3972 -32 -102 260 | O |
| ATOM | 951 N ALA A 137 | 41.917 -3.588 17.143 1.00 27.12 | N |
| ANISOU | 951 N ALA A 137 | 3249 3614 3442 -50 -156 250 | N |
| ATOM | 952 CA ALA A 137 | 42.858 -3.364 16.052 1.00 28.11 | C |
| ANISOU | 952 CA ALA A 137 | 3397 3724 3561 2 -133 230 | C |
| ATOM | 953 C ALA A 137 | 43.092 -1.885 15.789 1.00 27.59 | C |
| ANISOU | 953 C ALA A 137 | 3313 3678 3493 59 -70 259 | C |
| ATOM | 954 O ALA A 137 | 44.141 -1.505 15.229 1.00 28.79 | O |
| ANISOU | 954 O ALA A 137 | 3482 3803 3653 98 -35 249 | O |
| ATOM | 955 CB ALA A 137 | 42.398 -3.994 14.764 1.00 24.83 | C |
| ANISOU | 955 CB ALA A 137 | 2892 3343 3100 6 -157 208 | C |
| ATOM | 956 N SER A 138 | 42.115 -1.060 16.126 1.00 25.42 | N |
| ANISOU | 956 N SER A 138 | 3003 3449 3207 64 -55 294 | N |
| ATOM | 957 CA SER A 138 | 42.319 0.416 15.951 1.00 25.59 | C |
| ANISOU | 957 CA SER A 138 | 3025 3491 3245 119 4 325 | C |
| ATOM | 958 C SER A 138 | 43.365 0 954 16.905 1 00 27.30 | C |
| ANISOU | 958 C SER A 138 | 3237 3636 3500 123 41 324 | C |
| ATOM | 959 O SER A 138 | 43.903 2.033 16.653 1.00 28.54 | O |
| ANISOU | 959 O 3ER A 138 | 3395 3779 3668 164 90 341 | O |
| ATOM | 960 CB SER A 138 | 40.979 1.196 16.114 1.00 23.36 | C |
| ANISOU | 960 CB SER A 138 | 2691 3261 2932 131 9 360 | C |
| ATOM | 961 OG SER A 138 | 40.287 1.095 14.815 1.00 27.41 | O |
| ANISOU | 961 OG SER A 138 | 3196 3827 3391 154 -13 365 | O |
| ATOM | 962 N SER A 139 | 43.594 0.265 18.039 1.00 28.06 | N |
| ANISOU | 962 N SER A 139 | 3338 3697 3625 78 16 308 | N |
| ATOM | 963 CA SER A 139 | 44.801 0.623 18.900 1.00 27.74 | C |
| ANISOU | 963 CA SER A 139 | 3310 3595 3634 81 42 298 | C |
| ATOM | 964 C SER A 139 | 46.105 0.724 18.043 1.00 30.32 | C |
| ANISOU | 964 C SER A 139 | 2657 3887 3976 115 68 278 | C |
| ATOM | 965 O SER A 139 | 46.939 1.606 18.260 1.00 26.07 | O |
| ANISOU | 965 O SER A 139 | 3116 3319 3470 138 111 282 | O |
| ATOM | 966 CB SER A 139 | 45.052 -0.470 19.955 1.00 31.68 | C |

TABLE 3-continued

| | | | |
|---|---|---|---|
| ANISOU | 966 CB SER A 139 | 3825 4058 4154 31 -2 277 | C |
| ATOM | 967 OG SER A 139 | 46.224 -0.214 20.710 1.00 35.53 | O |
| ANISOU | 967 OG SER A 139 | 4323 4490 4685 36 13 264 | O |
| ATOM | 968 N ILE A 140 | 46.267 -0.189 17.103 1.00 28.39 | N |
| ANISOU | 968 N ILE A 140 | 3430 3648 3710 115 43 254 | N |
| ATOM | 969 CA ILE A 140 | 47.532 -0.290 16.273 1.00 32.68 | C |
| ANISOU | 969 CA ILE A 140 | 3990 4163 4264 145 67 227 | C |
| ATOM | 970 C ILE A 140 | 47.662 0.974 15.448 1.00 30.47 | C |
| ANISOU | 970 C ILE A 140 | 3703 3907 3969 189 127 257 | C |
| ATOM | 971 O ILE A 140 | 48.760 1.564 15.357 1.00 26.83 | O |
| ANISOU | 971 O ILE A 140 | 3242 3415 3539 208 173 253 | O |
| ATOM | 972 CB ILE A 140 | 47.468 -1.551 15.329 1.00 30.71 | C |
| ANISOU | 972 CB ILE A 140 | 3764 3924 3982 140 24 192 | C |
| ATOM | 973 CG1 ILE A 140 | 47.781 -2.853 16.111 1.00 30.06 | C |
| ANISOU | 973 CG1 ILE A 140 | 3699 3793 3928 102 -32 157 | C |
| ATOM | 974 CG2 ILE A 140 | 48.426 -1.466 14.130 1.00 36.56 | C |
| ANISOU | 974 CG2 ILE A 140 | 4517 4665 4711 181 60 170 | C |
| ATOM | 975 CD1 ILE A 140 | 46.904 -3.159 17.312 1.00 31.87 | C |
| ANISOU | 975 CD1 ILE A 140 | 3923 4021 4165 52 -70 177 | C |
| ATOM | 976 N VAL A 141 | 46.531 1.414 14.876 1.00 28.15 | N |
| ANISOU | 976 N VAL A 141 | 3401 3665 3629 202 127 288 | N |
| ATOM | 977 CA VAL A 141 | 46.531 2.644 14.054 1.00 27.28 | C |
| ANISOU | 977 CA VAL A 141 | 3291 3577 3499 247 180 324 | C |
| ATOM | 978 C VAL A 141 | 46.780 3.927 14.864 1.00 26.91 | C |
| ANISOU | 978 C VAL A 141 | 3231 3499 3494 258 225 353 | C |
| ATOM | 979 O VAL A 141 | 47.613 4.759 14.418 1.00 26.46 | O |
| ANISOU | 979 O VAL A 141 | 3182 3420 3452 282 278 367 | O |
| ATOM | 980 CB VAL A 141 | 45.226 2.772 13.169 1.00 28.79 | C |
| ANISOU | 980 CB VAL A 141 | 3477 3834 3626 266 160 351 | C |
| ATOM | 981 CG1 VAL A 141 | 45.233 4.083 12.344 1.00 30.12 | C |
| ANISOU | 981 CG1 VAL A 141 | 3653 4020 3773 316 213 396 | C |
| ATOM | 982 CG2 VAL A 141 | 45.152 1.518 12.292 1.00 27.71 | C |
| ANISOU | 982 CG2 VAL A 141 | 3359 3722 3446 255 117 314 | C |
| ATOM | 983 N GLY A 142 | 46.088 4.053 16.010 1.00 27.16 | N |
| ANISOU | 983 N GLY A 142 | 3244 3531 3545 237 206 360 | N |
| ATOM | 984 CA GLY A 142 | 46.241 5.176 16.920 1.00 27.43 | C |
| ANISOU | 984 CA GLY A 142 | 3268 3534 3619 245 240 378 | C |
| ATOM | 985 C GLY A 142 | 47.685 5.234 17.497 1.00 31.29 | C |
| ANISOU | 985 C GLY A 142 | 3763 3961 4163 232 262 352 | C |
| ATOM | 986 O GLY A 142 | 48.285 6.285 17.578 1.00 27.91 | O |

TABLE 3-continued

| | | |
|---|---|---|
| ANISOU 986 O GLY A 142 | 3336 3502 3767 248 307 365 | O |
| ATOM 987 N ARG A 143 | 43.279 4.079 17.832 1.00 26.29 | N |
| ANISOU 987 N ARG A 143 | 3136 3308 3545 202 226 314 | N |
| ATOM 988 CA ARG A 143 | 49.683 4.041 18.237 1.00 27.35 | C |
| ANISOU 988 CA ARG A 143 | 3271 3369 3730 195 241 286 | C |
| ATOM 989 C ARG A 143 | 50.594 4.496 17.127 1.00 25.76 | C |
| ANISOU 989 C ARG A 143 | 3073 3182 3533 222 290 288 | C |
| ATOM 990 O ARG A 143 | 51.586 5.148 17.393 1.00 30.35 | O |
| ANISOU 990 O ARG A 143 | 3646 3726 4160 223 326 283 | O |
| ATOM 991 CB ARG A 143 | 50.086 2.594 18.629 1.00 29.70 | C |
| ANISOU 991 CB ARG A 143 | 3577 3669 4037 167 187 245 | C |
| ATOM 992 CG ARG A 143 | 49.574 2.098 20.004 1.00 33.21 | C |
| ANISOU 992 CG ARG A 143 | 4023 4105 4492 130 141 241 | C |
| ATOM 993 CD ARG A 143 | 49.904 3.023 21.222 1.00 43.54 | C |
| ANISOU 993 CD ARG A 143 | 5321 5385 5839 125 160 246 | C |
| ATOM 994 NE ARG A 143 | 49.194 2.663 22.511 1.00 46.52 | N |
| ANISOU 994 NE ARG A 143 | 5700 5766 6208 91 123 249 | N |
| ATOM 995 CZ ARG A 143 | 49.402 3.206 23.728 1.00 42.15 | C |
| ANISOU 995 CZ ARG A 143 | 5144 5192 5680 81 126 246 | C |
| ATOM 996 NH1 ARG A 143 | 50.266 4.220 23.885 1.00 39.65 | N |
| ANISOU 996 NH1 ARG A 143 | 4820 4843 5404 100 164 239 | N |
| ATOM 997 NH2 ARG A 143 | 48.744 2.716 24.815 1.00 52.62 | N |
| ANISOU 997 NH2 ARG A 143 | 6476 6528 6988 48 92 249 | N |
| ATOM 998 N TYR A 144 | 50.335 4.084 15.907 1.00 25.18 | N |
| ANISOU 998 N TYR A 144 | 3012 3145 3412 239 291 291 | N |
| ATOM 999 CA TYR A 144 | 51.226 4.573 14.831 1.00 26.37 | C |
| ANISOU 999 CA TYR A 144 | 3166 3294 3559 264 346 296 | C |
| ATOM 1000 C TYR A 144 | 51.129 6.082 14.688 1.00 28.45 | C |
| ANISOU 1000 C TYR A 144 | 3430 3551 3830 282 402 344 | C |
| ATOM 1001 O TYR A 144 | 52.116 6.752 14.455 1.00 26.48 | O |
| ANISOU 1001 O TYR A 144 | 3177 3274 3612 286 453 349 | O |
| ATOM 1002 CB TYR A 144 | 50.929 3.882 13.489 1.00 24.48 | C |
| ANISOU 1002 CB TYR A 144 | 2944 3101 3256 282 338 290 | C |
| ATOM 1003 CG TYR A 144 | 51.985 4.190 12.423 1.00 26.69 | C |
| ANISOU 1003 CG TYR A 144 | 3229 3384 3529 304 396 287 | C |
| ATOM 1004 CD1 TYR A 144 | 53.398 3.902 12.643 1.00 27.05 | C |
| ANISOU 1004 CD1 TYR A 144 | 3257 3393 3626 296 418 248 | C |
| ATOM 1005 CD2 TYR A 144 | 51.568 4.676 11.162 1.00 30.26 | C |
| ANISOU 1005 CD2 TYR A 144 | 3700 3879 3919 332 428 322 | C |
| ATOM 1006 CE1 TYR A 144 | 54.339 4.159 11.633 1.00 31.03 | C |

TABLE 3-continued

| | | | | | | | | | |
|---|---|---|---|---|---|---|---|---|---|
| ANISOU | 1006 | CE1 | TYR | A | 144 | 3760 3909 4122 | 313 478 244 | | C |
| ATOM | 1007 | CE2 | TYR | A | 144 | 52.531 4.908 10.176 | 1.00 | 31.11 | C |
| ANISOU | 1007 | CE2 | TYR | A | 144 | 3813 3994 4012 | 348 486 322 | | C |
| ATOM | 1008 | CZ | TYR | A | 144 | 53.890 4.646 10.432 | 1.00 | 29.62 | C |
| ANISOU | 1008 | CZ | TYR | A | 144 | 3604 3773 3877 | 337 512 282 | | C |
| ATOM | 1009 | OH | TYR | A | 144 | 54.769 4.941 9.426 | 1.00 | 30.64 | O |
| ANISOU | 1009 | OH | TYR | A | 144 | 3734 3919 3989 | 352 577 285 | | O |
| ATOM | 1010 | N | LEU | A | 145 | 49.918 6.614 14.796 | 1.00 | 28.11 | N |
| ANISOU | 1010 | N | LEU | A | 145 | 3390 3531 3759 | 294 391 379 | | N |
| ATOM | 1011 | CA | LEU | A | 145 | 49.761 8.086 14.758 | 1.00 | 24.42 | C |
| ANISOU | 1011 | CA | LEU | A | 145 | 2927 3047 3304 | 316 438 425 | | C |
| ATOM | 1012 | C | LEU | A | 145 | 50.525 8.820 15.892 | 1.00 | 25.57 | C |
| ANISOU | 1012 | C | LEU | A | 145 | 3061 3132 3522 | 298 461 416 | | C |
| ATOM | 1013 | O | LEU | A | 145 | 51.256 9.816 15.606 | 1.00 | 27.08 | O |
| ANISOU | 1013 | O | LEU | A | 145 | 3258 3290 3742 | 304 515 436 | | O |
| ATOM | 1014 | CB | LEU | A | 145 | 48.239 8.399 14.858 | 1.00 | 23.01 | C |
| ANISOU | 1014 | CB | LEU | A | 145 | 2747 2907 3088 | 336 411 456 | | C |
| ATOM | 1015 | CG | LEU | A | 145 | 47.852 9.914 14.837 | 1.00 | 23.44 | C |
| ANISOU | 1015 | CG | LEU | A | 145 | 2809 2944 3152 | 369 450 505 | | C |
| ATOM | 1016 | CD1 | LEU | A | 145 | 48.449 10 627 13.574 | 1.00 | 27.23 | C |
| ANISOU | 1016 | CD1 | LEU | A | 145 | 3316 3417 3614 | 394 503 542 | | C |
| ATOM | 1017 | CD2 | LEU | A | 145 | 46.301 9.907 14.788 | 1.00 | 26.07 | C |
| ANISOU | 1017 | CD2 | LEU | A | 145 | 3133 3332 3441 | 393 412 525 | | C |
| ATOM | 1018 | N | ALA | A | 146 | 50.355 8.396 17.138 | 1.00 | 23 37 | N |
| ANISOU | 1018 | N | ALA | A | 146 | 2769 2841 3270 | 274 422 387 | | N |
| ATOM | 1019 | CA | ALA | A | 146 | 51.005 9.050 18.186 | 1.00 | 26.88 | C |
| ANISOU | 1019 | CA | ALA | A | 146 | 3205 3235 3775 | 258 436 374 | | C |
| ATOM | 1020 | C | ALA | A | 146 | 52.534 8.925 17.980 | 1.00 | 26.33 | C |
| ANISOU | 1020 | C | ALA | A | 146 | 3126 3129 3748 | 243 463 348 | | C |
| ATOM | 1021 | O | ALA | A | 146 | 53.266 9.837 18.285 | 1.00 | 25.80 | O |
| ANISOU | 1021 | O | ALA | A | 146 | 3054 3020 3730 | 236 499 350 | | O |
| ATOM | 1022 | CB | ALA | A | 146 | 50.626 8.392 19.513 | 1.00 | 28.25 | C |
| ANISOU | 1022 | CB | ALA | A | 146 | 3368 3407 3957 | 233 385 345 | | C |
| ATOM | 1023 | N | TYR | A | 147 | 53.012 7.751 17.602 | 1.00 | 26.57 | N |
| ANISOU | 1023 | N | TYR | A | 147 | 3151 3176 3767 | 235 439 317 | | N |
| ATOM | 1024 | CA | TYR | A | 147 | 54.415 7.610 17.237 | 1.00 | 28.09 | C |
| ANISOU | 1024 | CA | TYR | A | 147 | 3329 3347 3997 | 228 468 291 | | C |
| ATOM | 1025 | C | TYR | A | 147 | 54.860 8.581 16.192 | 1.00 | 26.55 | C |
| ANISOU | 1025 | C | TYR | A | 147 | 3139 3151 3799 | 242 538 325 | | C |
| ATOM | 1026 | O | TYR | A | 147 | 55.881 9.262 16.394 | 1.00 | 25.72 | O |

TABLE 3-continued

| | | | | | | | | | | |
|---|---|---|---|---|---|---|---|---|---|---|
| ANISOU | 1026 | O | TYR | A | 147 | 3016 | 3008 | 3749 | 227 | 578 | 319 | O |
| ATOM | 1027 | CB | TYR | A | 147 | 54.765 | 6.129 | 16.804 | 1.00 | 25.81 | C |
| ANISOU | 1027 | CB | TYR | A | 147 | 3038 | 3080 | 3688 | 228 | 432 | 250 | C |
| ATOM | 1028 | CG | TYR | A | 147 | 56.123 | 6.043 | 16.124 | 1.00 | 25.23 | C |
| ANISOU | 1028 | CG | TYR | A | 147 | 2946 | 3000 | 3642 | 232 | 474 | 226 | C |
| ATOM | 1029 | CD1 | TYR | A | 147 | 57.293 | 5.875 | 16.865 | 1.00 | 26.74 | C |
| ANISOU | 1029 | CD1 | TYR | A | 147 | 3107 | 3155 | 3899 | 216 | 468 | 186 | C |
| ATOM | 1030 | CD2 | TYR | A | 147 | 56.218 | 6.213 | 14.708 | 1.00 | 24.58 | C |
| ANISOU | 1030 | CD2 | TYR | A | 147 | 2873 | 2951 | 3516 | 253 | 523 | 246 | C |
| ATOM | 1031 | CE1 | TYR | A | 147 | 58.573 | 5.801 | 16.251 | 1.00 | 29.25 | C |
| ANISOU | 1031 | CE1 | TYR | A | 147 | 3396 | 3471 | 4245 | 220 | 509 | 160 | C |
| ATOM | 1032 | CE2 | TYR | A | 147 | 57.491 | 6.158 | 14.099 | 1.00 | 27.09 | C |
| ANISOU | 1032 | CE2 | TYR | A | 147 | 3167 | 3268 | 3857 | 255 | 569 | 222 | C |
| ATOM | 1033 | CZ | TYR | A | 147 | 58.633 | 5.942 | 14.872 | 1.00 | 28.64 | C |
| ANISOU | 1033 | CZ | TYR | A | 147 | 3327 | 3431 | 4125 | 239 | 562 | 178 | C |
| ATOM | 1034 | OH | TYR | A | 147 | 59.841 | 5.930 | 14.301 | 1.00 | 28.36 | O |
| ANISOU | 1034 | OH | TYR | A | 147 | 3260 | 3400 | 4115 | 240 | 609 | 155 | O |
| ATOM | 1035 | N | ARG | A | 148 | 54.141 | 8.693 | 15.058 | 1.00 | 26.47 | N |
| ANISOU | 1035 | N | ARG | A | 148 | 3404 | 3434 | 3979 | 267 | 555 | 361 | N |
| ATOM | 1036 | CA | ARG | A | 148 | 54.594 | 9.540 | 14.004 | 1.00 | 27.83 | C |
| ANISOU | 1036 | CA | ARG | A | 148 | 3334 | 3354 | 3888 | 279 | 622 | 398 | C |
| ATOM | 1037 | C | ARG | A | 148 | 54.553 | 11.069 | 14.468 | 1.00 | 30.14 | C |
| ANISOU | 1037 | C | ARG | A | 148 | 3633 | 3598 | 4222 | 275 | 660 | 439 | C |
| ATOM | 1038 | O | ARG | A | 148 | 55.422 | 11.897 | 14.080 | 1.00 | 28.79 | O |
| ANISOU | 1038 | O | ARG | A | 148 | 3460 | 3396 | 4081 | 264 | 720 | 458 | O |
| ATOM | 1039 | CB | ARG | A | 148 | 53.705 | 9.376 | 12.728 | 1.00 | 28.21 | C |
| ANISOU | 1039 | CB | ARG | A | 148 | 3411 | 3457 | 3850 | 311 | 624 | 433 | C |
| ATOM | 1040 | CG | ARG | A | 148 | 53.920 | 8.031 | 12.000 | 1.00 | 28.77 | C |
| ANISOU | 1040 | CG | ARG | A | 148 | 3481 | 3572 | 3878 | 316 | 601 | 393 | C |
| ATOM | 1041 | CD | ARG | A | 148 | 55.376 | 7.936 | 11.483 | 1.00 | 32.31 | C |
| ANISOU | 1041 | CD | ARG | A | 148 | 3912 | 4013 | 4353 | 308 | 654 | 369 | C |
| ATOM | 1042 | NE | ARG | A | 148 | 55.589 | 8.942 | 10.449 | 1.00 | 29.77 | N |
| ANISOU | 1042 | NE | ARG | A | 148 | 3608 | 3700 | 4003 | 319 | 726 | 421 | N |
| ATOM | 1043 | CZ | ARG | A | 148 | 55.132 | 8.929 | 9.195 | 1.00 | 33.71 | C |
| ANISOU | 1043 | CZ | ARG | A | 148 | 4138 | 4248 | 4422 | 346 | 744 | 452 | C |
| ATOM | 1044 | NH1 | ARG | A | 148 | 54.449 | 7.897 | 8.696 | 1.00 | 29.18 | N |
| ANISOU | 1044 | NH1 | ARG | A | 148 | 3578 | 3723 | 3787 | 365 | 695 | 428 | N |
| ATOM | 1045 | NH2 | ARG | A | 148 | 55.368 | 9.994 | 8.428 | 1.00 | 32.89 | N |
| ANISOU | 1045 | NH2 | ARG | A | 148 | 4054 | 4142 | 4300 | 351 | 811 | 508 | N |
| ATOM | 1046 | N | LEU | A | 149 | 53.551 | 11.397 | 15.275 | 1.00 | 29.85 | N |

TABLE 3-continued

| | | | | | | | | | |
|---|---|---|---|---|---|---|---|---|---|
| ANISOU | 1046 | N | LEU A | 149 | 3604 3553 4185 | 283 | 626 | 449 | N |
| ATOM | 1047 | CA | LEU A | 149 | 53.488 12.756 15.962 | 1.00 | 30.95 | | C |
| ANISOU | 1047 | CA | LEU A | 149 | 3751 3638 4371 | 281 | 651 | 473 | C |
| ATOM | 1048 | C | LEU A | 149 | 54.676 13.048 16.850 | 1.00 | 31.79 | | C |
| ANISOU | 1048 | C | LEU A | 149 | 3633 3689 4555 | 245 | 664 | 437 | C |
| ATOM | 1049 | O | LEU A | 149 | 55.199 14.163 16.790 | 1.00 | 30.43 | | O |
| ANISOU | 1049 | O | LEU A | 149 | 3667 3470 4424 | 235 | 711 | 460 | O |
| ATOM | 1050 | CB | LEU A | 149 | 52.187 13.005 16.746 | 1.00 | 27.12 | | C |
| ANISOU | 1050 | CB | LEU A | 149 | 3273 3160 3872 | 301 | 611 | 482 | C |
| ATOM | 1051 | CG | LEU A | 149 | 51.002 12.987 15.708 | 1.00 | 34.00 | | C |
| ANISOU | 1051 | CG | LEU A | 149 | 4166 4085 4669 | 342 | 605 | 526 | C |
| ATOM | 1052 | CD1 | LEU A | 149 | 49.597 12.944 16.307 | 1.00 | 27.23 | | C |
| ANISOU | 1052 | CD1 | LEU A | 149 | 3304 3257 3786 | 363 | 561 | 530 | C |
| ATOM | 1053 | CD2 | LEU A | 149 | 51.061 14.089 14.645 | 1.00 | 32.27 | | C |
| ANISOU | 1053 | CD2 | LEU A | 149 | 3977 3850 4435 | 367 | 658 | 585 | C |
| ATOM | 1054 | N | ILE A | 150 | 55.060 12.091 17.686 | 1.00 | 26.86 | | N |
| ANISOU | 1054 | N | ILE A | 150 | 3184 3059 3952 | 224 | 619 | 384 | N |
| ATOM | 1055 | CA | ILE A | 150 | 56.178 12.259 18.577 | 1.00 | 28.24 | | C |
| ANISOU | 1055 | CA | ILE A | 150 | 3333 3193 4199 | 192 | 620 | 345 | C |
| ATOM | 1056 | C | ILE A | 150 | 57.480 12.411 17.783 | 1.00 | 30.56 | | C |
| ANISOU | 1056 | C | ILE A | 150 | 3606 3482 4524 | 175 | 674 | 342 | C |
| ATOM | 1057 | O | ILE A | 150 | 58.322 13.220 18.242 | 1.00 | 31.73 | | O |
| ANISOU | 1057 | O | ILE A | 150 | 3738 3582 4737 | 148 | 701 | 333 | O |
| ATOM | 1058 | CB | ILE A | 150 | 56.231 11.058 19.593 | 1.00 | 29.51 | | C |
| ANISOU | 1058 | CB | ILE A | 150 | 3476 3371 4365 | 179 | 552 | 292 | C |
| ATOM | 1059 | CG1 | ILE A | 150 | 55.136 11.266 20.614 | 1.00 | 31.04 | | C |
| ANISOU | 1059 | CG1 | ILE A | 150 | 3686 3563 4544 | 184 | 515 | 296 | C |
| ATOM | 1060 | CG2 | ILE A | 150 | 57.644 10.918 20.292 | 1.00 | 27.11 | | C |
| ANISOU | 1060 | CG2 | ILE A | 150 | 3138 3032 4131 | 149 | 546 | 244 | C |
| ATOM | 1061 | CD1 | ILE A | 150 | 54.870 9.976 21.413 | 1.00 | 36.52 | | C |
| ANISOU | 1061 | CD1 | ILE A | 150 | 4375 4281 5220 | 173 | 448 | 261 | C |
| ATOM | 1062 | N | ARG A | 151 | 57.587 11.759 16.601 | 1.00 | 27.66 | | N |
| ANISOU | 1062 | N | ARG A | 151 | 3240 3159 4110 | 190 | 692 | 351 | N |
| ATOM | 1063 | CA | ARG A | 151 | 58.771 11.931 15.725 | 1.00 | 29.69 | | C |
| ANISOU | 1063 | CA | ARG A | 151 | 3476 3417 4388 | 176 | 754 | 351 | C |
| ATOM | 1064 | C | ARG A | 151 | 58.931 13 394 15.284 | 1.00 | 32.49 | | C |
| ANISOU | 1064 | C | ARG A | 151 | 3848 3735 4762 | 165 | 821 | 405 | C |
| ATOM | 1065 | O | ARG A | 151 | 60.070 13.921 15.230 | 1.00 | 30.84 | | O |
| ANISOU | 1065 | O | ARG A | 151 | 3611 3497 4609 | 133 | 869 | 399 | O |
| ATOM | 1066 | CB | ARG A | 151 | 58.697 11.034 14.476 | 1.00 | 27.99 | | C |

TABLE 3-continued

| | | | | | | | | | | | |
|---|---|---|---|---|---|---|---|---|---|---|---|
| ANISOU | 1066 | CB | ARG | A | 151 | 3268 | 3262 | 4106 | 200 | 764 | 353 C |
| ATOM | 1067 | CG | ARG | A | 151 | 58.977 | 9.498 | 14.747 | 1.00 | 26.90 | C |
| ANISOU | 1067 | CG | ARG | A | 151 | 3107 | 3150 | 3963 | 206 | 708 | 290 C |
| ATOM | 1068 | CD | ARG | A | 151 | 60.199 | 9.170 | 15.586 | 1.00 | 28.80 | C |
| ANISOU | 1068 | CD | ARG | A | 151 | 3301 | 3363 | 4280 | 182 | 694 | 234 C |
| ATOM | 1069 | NE | ARG | A | 151 | 61.452 | 9.701 | 14.978 | 1.00 | 29.72 | N |
| ANISOU | 1069 | NE | ARG | A | 151 | 3381 | 3475 | 4435 | 165 | 766 | 232 N |
| ATOM | 1070 | CZ | ARG | A | 151 | 62.049 | 9.233 | 13.878 | 1.00 | 31.50 | C |
| ANISOU | 1070 | CZ | ARG | A | 151 | 3592 | 3741 | 4635 | 177 | 808 | 222 C |
| ATOM | 1071 | NH1 | ARG | A | 151 | 61.646 | 8.109 | 13.288 | 1.00 | 30.51 | N |
| ANISOU | 1071 | NH1 | ARG | A | 151 | 3483 | 3658 | 4450 | 209 | 778 | 201 N |
| ATOM | 1072 | NH2 | ARG | A | 151 | 63.114 | 9.874 | 13.358 | 1.00 | 30.42 | N |
| ANISOU | 1072 | NH2 | ARG | A | 151 | 3421 | 3501 | 4535 | 155 | 880 | 228 N |
| ATOM | 1073 | N | ILE | A | 152 | 57.806 | 14.055 | 14.985 | 1.00 | 25.74 | N |
| ANISOU | 1073 | N | ILE | A | 152 | 3543 | 3385 | 4370 | 191 | 824 | 458 N |
| ATOM | 1074 | CA | ILE | A | 152 | 57.813 | 15.514 | 14.689 | 1.00 | 29.46 | C |
| ANISOU | 1074 | CA | ILE | A | 152 | 3535 | 3302 | 4355 | 185 | 879 | 514 C |
| ATOM | 1075 | C | ILE | A | 152 | 57.734 | 16.461 | 15.867 | 1.00 | 32.97 | C |
| ANISOU | 1075 | C | ILE | A | 152 | 3983 | 3670 | 4855 | 170 | 356 | 507 C |
| ATOM | 1076 | O | ILE | A | 152 | 57.645 | 17.690 | 15.631 | 1.00 | 32.84 | O |
| ANISOU | 1076 | O | ILE | A | 152 | 3996 | 3812 | 4868 | 168 | 905 | 553 O |
| ATOM | 1077 | CB | ILE | A | 152 | 56.820 | 15.869 | 13.585 | 1.00 | 25.30 | C |
| ANISOU | 1077 | CB | ILE | A | 152 | 3563 | 3310 | 4280 | 225 | 898 | 580 C |
| ATOM | 1078 | CG1 | ILE | A | 152 | 55.345 | 15.711 | 14.068 | 1.0 | 29.59 | C |
| ANISOU | 1078 | CG1 | ILE | A | 152 | 3634 | 3379 | 4267 | 265 | 838 | 588 C |
| ATOM | 1079 | CG2 | ILE | A | 152 | 57.228 | 15.018 | 12.388 | 1.00 | 29.07 | C |
| ANISOU | 1079 | CG2 | ILE | A | 152 | 3542 | 3458 | 4238 | 231 | 922 | 580 C |
| ATOM | 1080 | CD1 | ILE | A | 152 | 54.410 | 18.018 | 12.959 | 1.00 | 34.45 | C |
| ANISOU | 1080 | CD1 | ILE | A | 152 | 4283 | 4001 | 4835 | 307 | 856 | 558 C |
| ATOM | 1081 | N | GLY | A | 153 | 57.844 | 15.924 | 17.368 | 1.00 | 27.89 | N |
| ANISOU | 1081 | N | GLY | A | 153 | 3313 | 3027 | 4255 | 157 | 813 | 450 N |
| ATOM | 1082 | CA | GLY | A | 153 | 53.008 | 18.754 | 13.265 | 1.00 | 29.31 | C |
| ANISOU | 1082 | CA | GLY | A | 153 | 3491 | 3145 | 4500 | 136 | 801 | 429 C |
| ATOM | 1083 | C | GLY | A | 153 | 56.652 | 17.240 | 18.815 | 1.00 | 33.85 | C |
| ANISOU | 1383 | C | GLY | A | 153 | 4103 | 3712 | 5050 | 172 | 771 | 447 C |
| ATOM | 1084 | O | GLY | A | 153 | 56.620 | 13.142 | 19.644 | 1.00 | 82.87 | O |
| ANISOU | 1084 | O | GLY | A | 153 | 3988 | 3532 | 4971 | 184 | 769 | 433 O |
| ATOM | 1085 | N | LYS | A | 154 | 55.527 | 16.613 | 18.431 | 1.00 | 30.12 | N |
| ANISOU | 1085 | N | LYS | A | 154 | 3644 | 3255 | 4005 | 211 | 742 | 466 N |
| ATOM | 1086 | CA | LYS | A | 154 | 54.222 | 17.034 | 18.063 | 1.00 | 30.49 | C |

TABLE 3-continued

| | | | | | | | | | | |
|---|---|---|---|---|---|---|---|---|---|---|
| ANISOU | 1086 | CA | LYS | A | 154 | 3714 | 3342 | 4527 | 246 | 714 | 479 | C |
| ATOM | 1087 | C | LYS | A | 154 | 54.011 | 16.287 | 20.271 | 1.30 | 31.69 | C |
| ANISOU | 1087 | C | LYS | A | 154 | 3844 | 3512 | 4686 | 235 | 650 | 423 | C |
| ATOM | 1088 | O | LYS | A | 154 | 54.481 | 15.074 | 20.403 | 1.00 | 33.10 | O |
| ANISOU | 1088 | O | LYS | A | 154 | 4001 | 3727 | 4861 | 215 | 627 | 387 | O |
| ATOM | 1089 | CB | LYS | A | 154 | 53.065 | 10.663 | 18.034 | 1.00 | 30.87 | C |
| ANISOU | 1089 | CB | LYS | A | 154 | 3781 | 3452 | 4498 | 290 | 705 | 521 | C |
| ATOM | 1090 | CG | LYS | A | 154 | 53.520 | 17.302 | 16.353 | 1.00 | 35.36 | C |
| ANISOU | 1090 | CG | LYS | A | 154 | 4444 | 4075 | 5101 | 312 | 755 | 585 | C |
| ATOM | 1091 | CD | LYS | A | 154 | 53.106 | 18-883 | 16.775 | 1.00 | 41.82 | C |
| ANISOU | 1091 | CD | LYS | A | 154 | 5230 | 4758 | 5903 | 318 | 793 | 621 | C |
| ATOM | 1092 | CE | LYS | A | 154 | 51.795 | 19.507 | 17.157 | 1.00 | 43.41 | C |
| ANISOU | 1092 | CE | LYS | A | 154 | 5453 | 4954 | 6067 | 367 | 703 | 840 | C |
| ATOM | 1093 | NZ | LYS | A | 154 | 51.853 | 20.982 | 10.756 | 1.00 | 35.02 | N |
| ANISOU | 1093 | NZ | LYS | A | 154 | 4510 | 3693 | 5130 | 353 | 313 | 303 | N |
| ATOM | 1094 | N | LYS | A | 155 | 50.230 | 16.806 | 21.181 | 1.00 | 30.54 | N |
| ANISOU | 1094 | N | LYS | A | 15S | 3710 | 3348 | 4545 | 252 | 637 | 415 | N |
| ATOM | 1095 | CA | LYS | A | 155 | 52.812 | 15.953 | 22.323 | 1.00 | 31.50 | C |
| ANISOU | 1095 | CA | LYS | A | 155 | 3814 | 3503 | 4652 | 244 | 582 | 370 | C |
| ATOM | 1096 | C | LYS | A | 155 | 51.616 | 15.134 | 21 871 | 1.00 | 31.55 | C |
| ANISOU | 1096 | C | LYS | A | 155 | 3820 | 3531 | 4533 | 271 | 555 | 391 | C |
| ATOM | 1097 | O | LYS | A | 155 | 50.602 | 15.731 | 21.453 | 1.00 | 31.95 | O |
| ANISOU | 1097 | O | LYS | A | 155 | 3887 | 3843 | 4809 | 310 | 567 | 423 | O |
| ATOM | 1098 | CB | LYS | A | 155 | 52.397 | 10.356 | 23.524 | 1.00 | 35.26 | C |
| ANISOU | 1098 | CB | LYS | A | 155 | 4301 | 3942 | 5154 | 252 | 574 | 349 | C |
| ATOM | 1099 | CG | LYS | A | 155 | 53.570 | 17.740 | 24.005 | 1.00 | 37.40 | C |
| ANISOU | 1099 | CG | LYS | A | 155 | 4574 | 4137 | 5500 | 221 | 596 | 324 | C |
| ATOM | 1100 | CD | LYS | A | 155 | 54.645 | 15.744 | 24.570 | 1.00 | 42.21 | C |
| ANISOU | 1100 | CD | LYS | A | 155 | 5152 | 4756 | 6130 | 177 | 534 | 276 | C |
| ATOM | 1101 | CE | LYS | A | 155 | 55.082 | 17.406 | 25.450 | 1.00 | 45.01 | C |
| ANISOU | 1101 | CE | LYS | A | 155 | 5499 | 5348 | 5550 | 142 | 564 | 233 | C |
| ATOM | 1102 | NZ | LYS | A | 155 | 56.283 | 18.597 | 24.753 | 1.00 | 41.30 | N |
| ANISOU | 1102 | NZ | LYS | A | 155 | 5103 | 4585 | 6203 | 133 | 620 | 280 | N |
| ATOM | 1103 | N | ALA | A | 156 | 51.720 | 13.812 | 21.593 | 1 | 00 | 33.12 | N |
| ANISOU | 1103 | N | ALA | A | 156 | 3622 | 3442 | 4379 | 252 | 520 | 369 | N |
| ATOM | 1104 | CA | ALA | A | 156 | 50.553 | 12.052 | 21.503 | 1.00 | 32.81 | C |
| ANISOU | 1104 | CA | ALA | A | 156 | 3961 | 3850 | 4857 | 250 | 490 | 334 | C |
| ATOM | 1105 | C | ALA | A | 156 | 50.455 | 11 856 | 22.512 | 1.00 | 36.84 | C |
| ANISOU | 1105 | C | ALA | A | 156 | 4458 | 4333 | 5158 | 241 | 439 | 345 | C |
| ATOM | 1106 | O | ALA | A | 156 | 51.504 | 11.229 | 22.920 | 1.00 | 33.79 | O |

TABLE 3-continued

| | | | | | | | | | |
|---|---|---|---|---|---|---|---|---|---|
| ANISOU | 1106 | O | ALA | A | 156 | 4333 3073 4800 210 421 311 | | | O |
| ATOM | 1107 | CB | ALA | A | 156 | 54.775 | 12.384 | 23.110 1.00 28.91 | C |
| ANISOU | 1107 | CB | ALA | A | 156 | 3470 3886 4129 276 501 405 | | | C |
| ATOM | 1108 | N | ILE | A | 157 | 49.266 | 11.516 | 22.937 1.00 38.97 | N |
| ANISOU | 1108 | N | ILE | A | 157 | 4724 4595 5388 251 413 351 | | | N |
| ATOM | 1109 | CA | ILE | A | 157 | 49.018 | 14.433 | 23.757 1.00 35.83 | C |
| ANISOU | 1109 | CA | ILE | A | 157 | 4441 4450 5393 220 364 325 | | | C |
| ATOM | 1110 | C | ILE | A | 157 | 47.532 | 9.503 | 23.083 1.00 40.11 | C |
| ANISOU | 1110 | C | ILE | A | 157 | 4654 4931 5456 224 340 344 | | | C |
| ATOM | 1111 | O | ILE | A | 157 | 46.904 | 10.038 | 22.335 1.00 37.03 | O |
| ANISOU | 1111 | O | ILE | A | 157 | 4457 4576 5335 254 351 372 | | | O |
| ATOM | 1112 | CB | ILE | A | 157 | 48.507 | 10.831 | 25.134 1.00 37.13 | O |
| ANISOU | 1112 | CB | ILE | A | 157 | 4430 4491 5133 215 354 308 | | | C |
| ATOM | 1113 | CG1 | ILE | A | 157 | 48.232 | 9.572 | 25.973 1.00 44.39 | C |
| ANISOU | 1113 | CG1 | ILE | A | 157 | 5390 5442 2030 173 305 288 | | | C |
| ATOM | 1114 | CG2 | ILE | A | 157 | 47.212 | 11.550 | 24.953 1.00 45.95 | C |
| ANISOU | 1114 | CG2 | ILE | A | 157 | 5591 5342 6226 252 372 334 | | | C |
| ATOM | 1115 | CD1 | ILE | A | 157 | 47.955 | 9.045 | 27.372 1.00 43.40 | C |
| ANISOU | 1115 | CD1 | ILE | A | 157 | 5271 5314 5905 169 298 238 | | | C |
| ATOM | 1116 | N | MET | A | 158 | 48.303 | 8.284 | 22.974 1.00 36.56 | N |
| ANISOU | 1116 | N | MET | A | 158 | 4405 4493 4995 196 304 327 | | | N |
| ATOM | 1117 | CA | MET | A | 158 | 47.317 | 7.285 | 22.577 1.00 35.12 | C |
| ANISOU | 1117 | CA | MET | A | 158 | 4217 4365 4752 186 270 336 | | | C |
| ATOM | 1118 | C | MET | A | 158 | 46.388 | 5.612 | 23.840 1.00 37.48 | C |
| ANISOU | 1118 | C | MET | A | 158 | 4510 4684 5046 151 232 323 | | | C |
| ATOM | 1119 | O | MET | A | 158 | 47.405 | 6.107 | 24.701 1.00 36.58 | O |
| ANISOU | 1119 | O | MET | A | 158 | 4406 4538 4953 122 209 298 | | | O |
| ATOM | 1120 | CB | MET | A | 158 | 47.982 | 5.317 | 21.614 1.00 36.83 | C |
| ANISOU | 1120 | CB | MET | A | 158 | 4443 4579 4972 178 254 325 | | | C |
| ATOM | 1121 | CG | MET | A | 158 | 47.167 | 5.126 | 21.141 1.00 29.56 | C |
| ANISOU | 1121 | CG | MET | A | 158 | 3522 3703 4005 162 212 325 | | | C |
| ATOM | 1122 | SD | MET | A | 158 | 45.632 | 5.631 | 20.442 1.00 34.46 | S |
| ANISOU | 1122 | SD | MET | A | 158 | 4127 4396 4578 190 219 356 | | | S |
| ATOM | 1123 | CE | MET | A | 158 | 44.739 | 4.056 | 29.461 1.00 34.30 | C |
| ANISOU | 1123 | CE | MET | A | 158 | 4102 4414 4518 145 157 352 | | | C |
| ATOM | 1124 | N | PHE | A | 159 | 45.363 | 6.600 | 23.953 1.00 29.65 | N |
| ANISOU | 1124 | N | PHE | A | 159 | 3539 3784 4055 153 224 341 | | | N |
| ATOM | 1125 | CA | PHE | A | 159 | 44.585 | 5.863 | 25.358 1.00 35.28 | C |
| ANISOU | 1125 | CA | PHE | A | 159 | 4208 4488 4710 112 192 334 | | | C |
| ATOM | 1126 | C | PHE | A | 159 | 44.052 | 4.531 | 24.476 1.00 35.95 | C |

TABLE 3-continued

| | | | | | | | | | | | |
|---|---|---|---|---|---|---|---|---|---|---|---|
| ANISOU | 1126 | C | PHE | A | 159 | | 4418 | 4740 | 4387 | 81 151 340 | C |
| ATOM | 1127 | O | PHE | A | 159 | | 43.182 | 4.653 | 23.552 | 1.00 44.07 | O |
| ANISOU | 1127 | O | PHE | A | 159 | | 5299 | 5536 | 5755 | 100 154 359 | C |
| ATOM | 1128 | CB | PHE | A | 159 | | 43.541 | 6.723 | 25.597 | 1.00 32.15 | C |
| ANISOU | 1128 | CB | PHE | A | 159 | | 3824 | 4174 | 4332 | 132 216 343 | C |
| ATOM | 1129 | CG | PHE | A | 159 | | 43.885 | 8.064 | 26.185 | 1.00 27.80 | C |
| ANISOU | 1129 | CG | PHE | A | 159 | | 3239 | 3550 | 3774 | 166 254 339 | C |
| ATOM | 1130 | CD1 | PHE | A | 159 | | 44.005 | 9.104 | 25.377 | 1.00 30.52 | C |
| ANISOU | 1130 | CD1 | PHE | A | 159 | | 3584 | 3874 | 4137 | 215 291 354 | C |
| ATOM | 1131 | CD2 | PHE | A | 159 | | 44.050 | 8.209 | 27.570 | 1.00 34.76 | C |
| ANISOU | 1131 | CD2 | PHE | A | 159 | | 4126 | 4413 | 4653 | 146 253 317 | C |
| ATOM | 1132 | CE1 | PHE | A | 159 | | 44.276 | 10.457 | 25 934 | 1.00 32.09 | C |
| ANISOU | 1132 | CE1 | PHE | A | 159 | | 3790 | 4034 | 4368 | 245 324 345 | C |
| ATOM | 1133 | CE2 | PHE | A | 159 | | 44.381 | 9.442 | 28.104 | 1.00 33.45 | C |
| ANISOU | 1133 | CE2 | PHE | A | 159 | | 3665 | 4217 | 4526 | 176 285 303 | C |
| ATOM | 1134 | CZ | PHE | A | 159 | | 44.465 | 10.554 | 27.290 | 1.00 36.63 | C |
| ANISOU | 1134 | CZ | PHE | A | 159 | | 4359 | 4505 | 4952 | 225 320 317 | C |
| ATOM | 1135 | N | GLU | A | 160 | | 44.320 | 3.373 | 24.698 | 1.00 47.87 | N |
| ANISOU | 1135 | N | GLU | A | 160 | | 5816 | 6138 | 6266 | 34 110 326 | N |
| ATOM | 1136 | CA | GLU | A | 160 | | 48.175 | 2.339 | 24.855 | 1.00 43.24 | C |
| ANISOU | 1136 | CA | GLU | A | 160 | | 5217 | 5572 | 5639 | -5 74 338 | C |
| ATOM | 1137 | C | GLU | A | 160 | | 42.372 | 2.121 | 25.151 | 1.00 51.40 | C |
| ANISOU | 1137 | C | GLU | A | 160 | | 6239 | 6637 | 6652 | -46 66 346 | C |
| ATOM | 1138 | O | GLU | A | 160 | | 41.263 | 1.315 | 26.125 | 1.00 42.89 | O |
| ANISOU | 1138 | O | GLU | A | 160 | | 5144 | 5609 | 5542 | -88 40 659 | O |
| ATOM | 1139 | CB | GLU | A | 160 | | 43.592 | 0.941 | 24.284 | 1.00 47.84 | C |
| ANISOU | 1139 | CB | GLU | A | 160 | | 5526 | 5122 | 6219 | -37 25 225 | C |
| ATOM | 1140 | CG | GLU | A | 160 | | 44.437 | 1.075 | 23.047 | 1.00 41.36 | C |
| ANISOU | 1140 | CG | GLU | A | 160 | | 5318 | 5285 | 5113 | 2 37 312 | C |
| ATOM | 1141 | CD | GLU | A | 160 | | 45.857 | 1.410 | 23.356 | 0.50 40.71 | C |
| ANISOU | 1141 | CD | GLU | A | 160 | | 4953 | 5141 | 5373 | 20 53 292 | C |
| ATOM | 1142 | OE1 | GLU | A | 160 | | 46.200 | 1.513 | 24.566 | 1.00 43.83 | O |
| ANISOU | 1142 | OE1 | GLU | A | 160 | | 5355 | 5512 | 5788 | 2 48 287 | O |
| ATOM | 1143 | OE2 | GLU | A | 160 | | 46.336 | 1.539 | 22.411 | 1.00 38.00 | O |
| ANISOU | 1143 | OE2 | GLU | A | 160 | | 4615 | 4773 | 5343 | 40 58 282 | O |
| ATOM | 1144 | N | ASP | A | 161 | | 42.879 | 2.756 | 27.262 | 1.00 36.99 | N |
| ANISOU | 1144 | N | ASP | A | 161 | | 4423 | 4786 | 4845 | -41 85 337 | N |
| ATOM | 1145 | CA | ASP | A | 161 | | 41.975 | 2.858 | 28.440 | 1.00 30.48 | C |
| ANISOU | 1145 | CA | ASP | A | 161 | | 3582 | 4006 | 3993 | -88 93 345 | C |
| ATOM | 1146 | C | ASP | A | 161 | | 40.900 | 3.942 | 28.171 | 1.00 29.48 | C |

TABLE 3-continued

| | | | | | | | | | |
|---|---|---|---|---|---|---|---|---|---|
| ANISOU | 1146 | CA | SP A | 161 | 3411 | 3938 | 3852 | -26 134 357 | C |
| ATOM | 1147 | O | ASP A | 161 | 41.221 | 5.144 | 28.240 | 1.00 28.77 | O |
| ANISOU | 1147 | O | ASP A | 161 | 3318 | 3829 | 3783 | 24 170 349 | O |
| ATOM | 1148 | CB | ASP A | 161 | 42.696 | 3.087 | 29.769 | 1.00 28.81 | C |
| ANISOU | 1148 | CB | ASP A | 161 | 3396 | 3759 | -79 | 95 329 | C |
| ATOM | 1149 | CG | ASP A | 161 | 41.722 | 2.969 | 30.962 | 1.00 29.50 | C |
| ANISOU | 1149 | CG | ASP A | 161 | 3470 | 3901 | 3839 | -115 101 339 | C |
| ATOM | 1150 | OD1 | ASP A | 161 | 42.057 | 2.584 | 32.173 | 1.00 30.23 | O |
| ANISOU | 1150 | OD1 | ASP A | 161 | 3590 | 3978 | 3917 | -151 85 335 | O |
| ATOM | 1151 | OD2 | ASP A | 161 | 40 504 | 3.255 | 30.684 | 1.00 31 66 | O |
| ANISOU | 1151 | OD2 | ASP A | 161 | 3700 | 4240 | 4088 | -108 123 353 | O |
| ATOM | 1152 | N | THR A | 162 | 39.695 | 3.538 | 27.876 | 1.00 29 79 | N |
| ANISOU | 1152 | N | THR A | 162 | 3415 | 4043 | 3860 | -44 126 373 | N |
| ATOM | 1153 | CA | THR A | 162 | 38.622 | 4.475 | 27.394 | 1.00 30.80 | C |
| ANISOU | 1153 | CA | THR A | 162 | 3494 | 4232 | 3976 | 3 157 384 | C |
| ATOM | 1154 | C | THR A | 162 | 38.028 | 5.248 | 28.556 | 1.00 33.29 | C |
| ANISOU | 1154 | C | THR A | 162 | 3785 | 4582 | 4282 | 15 192 379 | C |
| ATOM | 1155 | O | THR A | 162 | 37.404 | 6.280 | 28.339 | 1.00 31.23 | O |
| ANISOU | 1155 | O | THR A | 162 | 3492 | 4353 | 4022 | 70 223 381 | O |
| ATOM | 1156 | CB | THR A | 162 | 37.551 | 3.755 | 26.588 | 1.00 33.20 | C |
| ANISOU | 1156 | CB | THR A | 162 | 3763 | 4599 | 4254 | -19 131 400 | C |
| ATOM | 1157 | OG1 | THR A | 162 | 37.219 | 2.576 | 27.292 | 1.00 34.72 | O |
| ANISOU | 1157 | OG1 | THR A | 162 | 3957 | 4809 | 4426 | -96 103 403 | O |
| ATOM | 1158 | CG2 | THR A | 162 | 38.119 | 3.279 | 25.205 | 1.00 30.39 | C |
| ANISOU | 1158 | CG2 | THR A | 162 | 3431 | 4211 | 3905 | -9 104 400 | C |
| ATOM | 1159 | N | HIS A | 163 | 38.271 | 4.780 | 29.711 | 1.00 30.54 | N |
| ANISOU | 1159 | N | HIS A | 163 | 3456 | 4225 | 3922 | -32 186 370 | N |
| ATOM | 1160 | CA | HIS A | 163 | 37.975 | 5.534 | 31.010 | 1.00 27.07 | C |
| ANISOU | 1160 | CA | HIS A | 163 | 3006 | 3808 | 3470 | -20 221 357 | C |
| ATOM | 1161 | C | HIS A | 163 | 38.869 | 6.703 | 31.137 | 1.00 29.09 | C |
| ANISOU | 1161 | C | HIS A | 163 | 3287 | 4004 | 3761 | 36 246 336 | C |
| ATOM | 1162 | O | HIS A | 163 | 38.382 | 7.842 | 31.299 | 1.00 28.18 | O |
| ANISOU | 1162 | O | HIS A | 163 | 3149 | 3909 | 3649 | 89 284 326 | O |
| ATOM | 1163 | CB | HIS A | 163 | 38.074 | 4.610 | 32.212 | 1.00 30.05 | C |
| ANISOU | 1163 | CB | HIS A | 163 | 3407 | 4190 | 3819 | -90 203 358 | C |
| ATOM | 1164 | CG | HIS A | 163 | 36.906 | 3.665 | 32.281 | -149 1.00 31.76 | C |
| ANISOU | 1164 | CG | HIS A | 163 | 3589 | 4481 | 3999 | -149 192 381 | C |
| ATOM | 1165 | ND1 | HIS A | 163 | 36.022 | 3.671 | 33.312 | 1.00 30.75 | N |
| ANISOU | 1165 | ND1 | HIS A | 163 | 3432 | 4421 | 3832 | -177 217 384 | N |
| ATOM | 1166 | CD2 | HIS A | 163 | 36.483 | 2.678 | 31.377 | 1.00 29.90 | C |

TABLE 3-continued

| | | | | | | | | | | |
|---|---|---|---|---|---|---|---|---|---|---|
| ANISOU | 1166 | CD2 | HIS | A | 163 | 3339 | 4261 | 3759 | -187 | 157 | 400 | C |
| ATOM | 1167 | CE1 | HIS | A | 163 | 35.081 | 2.686 | 33.110 | 1.00 | 29.33 | C |
| ANISOU | 1167 | CE1 | HIS | A | 163 | 3220 | 4298 | 3627 | -238 | 200 | 408 | C |
| ATOM | 1168 | NE2 | HIS | A | 163 | 35.352 | 2.103 | 31.892 | 1.00 | 30.65 | N |
| ANISOU | 1168 | NE2 | HIS | A | 163 | 3396 | 4431 | 3818 | -242 | 161 | 416 | N |
| ATOM | 1169 | N | LEU | A | 164 | 40.184 | 6.417 | 30.952 | 1.00 | 28.37 | N |
| ANISOU | 1169 | N | LEU | A | 164 | 3243 | 3837 | 3701 | 28 | 225 | 327 | N |
| ATOM | 1170 | CA | LEU | A | 164 | 41.153 | 7.566 | 31.008 | 1.00 | 32.27 | C |
| ANISOU | 1170 | CA | LEU | A | 164 | 3759 | 4267 | 4235 | 74 | 247 | 306 | C |
| ATOM | 1171 | C | LEU | A | 164 | 40.902 | 8.537 | 2.848 | 1.00 | 29.85 | C |
| ANISOU | 1171 | C | LEU | A | 164 | 3436 | 3959 | 3952 | 136 | 274 | 318 | C |
| ATOM | 1172 | O | LEU | A | 164 | 40.979 | 9.789 | 30.036 | 1.00 | 25.42 | O |
| ANISOU | 1172 | O | LEU | A | 164 | 2875 | 3374 | 3411 | 186 | 308 | 306 | O |
| ATOM | 1173 | CB | LEU | A | 164 | 42.577 | 7.044 | 30.949 | 1.00 | 31.08 | C |
| ANISOU | 1173 | CB | LEU | A | 164 | 3650 | 4044 | 4114 | 51 | 218 | 295 | C |
| ATOM | 1174 | CG | LEU | A | 164 | 43.134 | 6.444 | 32.261 | 1.00 | 40.89 | C |
| ANISOU | 1174 | CG | LEU | A | 164 | 4922 | 5268 | 5345 | 6 | 192 | 278 | C |
| ATOM | 1175 | CD1 | LEU | A | 164 | 44.021 | 5.082 | 32.070 | 1.00 | 40.50 | C |
| ANISOU | 1175 | CD1 | LEU | A | 164 | 4906 | 5145 | 5337 | -2 | 163 | 263 | C |
| ATOM | 1176 | CD2 | LEU | A | 164 | 43.022 | 7.431 | 33.413 | 1.00 | 40.21 | C |
| ANISOU | 1176 | CD2 | LEU | A | 164 | 4838 | 5188 | 5253 | 25 | 221 | 254 | C |
| ATOM | 1177 | N | ALA | A | 165 | 40.628 | 7.560 | 28.652 | 1.00 | 27.50 | N |
| ANISOU | 1177 | N | ALA | A | 165 | 3138 | 3691 | 3653 | 134 | 257 | 340 | N |
| ATOM | 1178 | CA | ALA | A | 165 | 40.430 | 6.812 | 27.465 | 1.00 | 29.72 | C |
| ANISOU | 1178 | CA | ALA | A | 165 | 3396 | 3957 | 3940 | 193 | 278 | 358 | C |
| ATOM | 1179 | C | ALA | A | 165 | 39.182 | 9.717 | 27.739 | 1.00 | 29.80 | C |
| ANISOU | 1179 | C | ALA | A | 165 | 3366 | 4023 | 3035 | 239 | 306 | 352 | C |
| ATOM | 1180 | O | ALA | A | 165 | 39.102 | 10.942 | 27.441 | 1.00 | 27.67 | O |
| ANISOU | 1180 | O | ALA | A | 165 | 3098 | 3727 | 3687 | 333 | 335 | 354 | O |
| ATOM | 1181 | CB | ALA | A | 165 | 40.138 | 7.925 | 26.245 | 1.00 | 27.53 | C |
| ANISOU | 1181 | CB | ALA | A | 165 | 3110 | 3708 | 3544 | 183 | 249 | 379 | C |
| ATOM | 1182 | N | ALA | A | 166 | 38.115 | 9.115 | 28.282 | 1.00 | 29.86 | N |
| ANISOU | 1182 | N | ALA | A | 166 | 3335 | 4104 | 3935 | 209 | 296 | 363 | N |
| ATOM | 1183 | CA | ALA | A | 166 | 36.538 | 9.958 | 28.698 | 1.00 | 29.65 | C |
| ANISOU | 1183 | CA | ALA | A | 166 | 3252 | 4140 | 3565 | 254 | 326 | 360 | C |
| ATOM | 1184 | C | ALA | A | 166 | 37.299 | 11.060 | 29.686 | 1.00 | 27.62 | C |
| ANISOU | 1184 | C | ALA | A | 166 | 3324 | 3842 | 3626 | 289 | 363 | 331 | C |
| ATOM | 1185 | O | ALA | A | 166 | 36.531 | 12.217 | 29.530 | 1.00 | 28.30 | O |
| ANISOU | 1185 | O | ALA | A | 166 | 3095 | 3930 | 3727 | 357 | 348 | 328 | O |
| ATOM | 1186 | CB | ALA | A | 166 | 35.755 | 9.150 | 29.257 | 1.0 | 25.24 | C |

TABLE 3-continued

| | | | | | | | | | | |
|---|---|---|---|---|---|---|---|---|---|---|
| ANISOU | 1186 | CB | ALA | A | 166 | 2655 | 3671 | 3265 | 209 | 318 | 362 | C |
| ATOM | 1187 | N | MET | A | 167 | 38.055 | 10.723 | 30.747 | 1.00 | 33.10 | N |
| ANISOU | 1187 | N | MET | A | 167 | 3383 | 4135 | 3954 | 244 | 356 | 309 | N |
| ATOM | 1188 | CA | MET | A | 167 | 38.437 | 11.733 | 31.712 | 1.00 | 28.03 | C |
| ANISOU | 1188 | CA | MET | A | 167 | 3130 | 3825 | 3597 | 274 | 384 | 276 | C |
| ATOM | 1189 | C | MET | A | 167 | 39.268 | 12.861 | 21.112 | 100 | 28.40 | C |
| ANISOU | 1189 | C | MET | A | 167 | 3208 | 3789 | 3795 | 326 | 400 | 272 | C |
| ATOM | 1190 | O | MET | A | 167 | 38.036 | 14.362 | 31.347 | 1.00 | 32.41 | O |
| ANISOU | 1190 | O | MET | A | 167 | 3711 | 4284 | 4318 | 385 | 430 | 255 | O |
| ATOM | 1191 | CB | MET | A | 167 | 39.103 | 11.107 | 32.969 | 1.00 | 28.43 | C |
| ANISOU | 1191 | CB | MET | A | 167 | 3211 | 3860 | 3731 | 215 | 370 | 252 | C |
| ATOM | 1192 | CG | MET | A | 167 | 38.145 | 10.379 | 33.517 | 1.00 | 48.40 | C |
| ANISOU | 1192 | CG | MET | A | 167 | 3176 | 3942 | 3571 | 161 | 352 | 263 | C |
| ATOM | 1193 | SD | MET | A | 167 | 30.140 | 9.503 | 35.007 | 1.00 | 31.56 | S |
| ANISOU | 1193 | SD | MET | A | 167 | 3529 | 4307 | 4056 | 103 | 341 | 243 | S |
| ATOM | 1194 | CE | MET | A | 167 | 37.838 | 8.657 | 35.917 | 1.00 | 32.72 | C |
| ANISOU | 1194 | CE | MET | A | 167 | 3740 | 4559 | 4132 | 50 | 349 | 253 | C |
| ATOM | 1195 | N | SER | A | 168 | 40.256 | 12.529 | 30.271 | 1.00 | 26.98 | N |
| ANISOU | 1195 | N | SER | A | 168 | 3056 | 3553 | 3541 | 339 | 382 | 287 | N |
| ATOM | 1196 | CA | SER | A | 168 | 41.233 | 13.603 | 29.570 | 1.60 | 29.45 | C |
| ANISOU | 1196 | CA | SER | A | 168 | 3398 | 3789 | 4034 | 353 | 401 | 291 | C |
| ATOM | 1197 | C | SER | A | 168 | 40.222 | 14.452 | 28.580 | 1.30 | 28.04 | C |
| ANISOU | 1197 | C | SER | A | 168 | 3201 | 3626 | 38241 | 420 | 421 | 317 | C |
| ATOM | 1198 | O | SER | A | 168 | 40.320 | 15.685 | 28.660 | 1.00 | 29.18 | O |
| ANISOU | 1198 | O | SER | A | 168 | 3360 | 3723 | 4303 | 471 | 443 | 311 | O |
| ATOM | 1199 | CB | SER | A | 168 | 42.240 | 13.044 | 28.741 | 1.00 | 29.97 | C |
| ANISOU | 1199 | CB | SER | A | 168 | 349 | 3804 | 4094 | 322 | 384 | 304 | C |
| ATOM | 1200 | OG | SER | A | 168 | 43.272 | 12.925 | 29.663 | 1.00 | 48.80 | O |
| ANISOU | 1200 | OG | SER | A | 168 | 5900 | 6141 | 5499 | 287 | 375 | 272 | O |
| ATOM | 1201 | N | ALA | A | 169 | 39.388 | 13.817 | 27.954 | 1.00 | 28.22 | N |
| ANISOU | 1201 | N | ALA | A | 169 | 3191 | 3712 | 3813 | 421 | 405 | 345 | N |
| ATOM | 1202 | CA | ALA | A | 169 | 38.537 | 14.569 | 26.595 | 1.00 | 29.82 | C |
| ANISOU | 1202 | CA | ALA | A | 169 | 3373 | 3938 | 4018 | 489 | 416 | 375 | C |
| ATOM | 1203 | CA | ALA | A | 169 | 37.607 | 15.491 | 27.659 | 1.00 | 32.72 | C |
| ANISOU | 1203 | CA | ALA | A | 169 | 3715 | 4333 | 4385 | 542 | 440 | 355 | C |
| ATOM | 1204 | O | ALA | A | 169 | 37.311 | 16.603 | 27.205 | 1.00 | 31.83 | O |
| ANISOU | 1204 | O | ALA | A | 169 | 3607 | 4195 | 4293 | 612 | 457 | 367 | O |
| ATOM | 1205 | CB | ALA | A | 169 | 37.705 | 13.615 | 26.011 | 1.00 | 30.28 | C |
| ANISOU | 1205 | CB | ALA | A | 169 | 3395 | 4073 | 4037 | 475 | 387 | 403 | C |
| ATOM | 1206 | N | SER | A | 170 | 37.151 | 15.054 | 28.842 | 1.00 | 28.98 | N |

TABLE 3-continued

| | | | | |
|---|---|---|---|---|
| ANISOU | 1206 | N   SER A 170 | 3215 3909 3886   511  441  325 | N |
| ATOM   | 1207 | CA  SER A 170 | 36.099  15.838  29.498  1.00  34.32 | C |
| ANISOU | 1207 | CA  SER A 170 | 3856 4630 4555   565  466  304 | C |
| ATOM   | 1208 | C   SER A 170 | 36.670  17.168  30.044  1.00  31.85 | C |
| ANISOU | 1208 | C   SER A 170 | 3584 4235 4283   614  495  274 | C |
| ATOM   | 1209 | O   SER A 170 | 35.907  18.059  30.306  1.00  31.66 | O |
| ANISOU | 1209 | O   SER A 170 | 3540 4227 4264   679  516  259 | O |
| ATOM   | 1210 | CB  SER A 170 | 35.387  15.098  30.658  1.00  31.43 | C |
| ANISOU | 1210 | CB  SER A 170 | 3449 4347 4145   521  469  279 | C |
| ATOM   | 1211 | OG  SER A 170 | 36.323  15.072  31.677  1.00  30.11 | O |
| ANISOU | 1211 | OG  SER A 170 | 3325 4129 3985   483  474  248 | O |
| ATOM   | 1212 | N   ARG A 171 | 37.991  17.288  30.132  1.00  32.38 | N |
| ANISOU | 1212 | N   ARG A 171 | 3705 4214 4383   583  493  266 | N |
| ATOM   | 1213 | CA  ARG A 171 | 38.603  18.496  30.673  1.00  32.42 | C |
| ANISOU | 1213 | CA  ARG A 171 | 3751 4137 4431   618  515  235 | C |
| ATOM   | 1214 | C   ARG A 171 | 39.411  19.189  29.569  1.00  34.25 | C |
| ANISOU | 1214 | C   ARG A 171 | 4024 4280 4711   640  520  266 | C |
| ATOM   | 1215 | O   ARG A 171 | 40.203  20.099  29.789  1.00  34.65 | O |
| ANISOU | 1215 | O   ARG A 171 | 4116 4242 4806   652  535  248 | O |
| ATOM   | 1216 | CB  ARG A 171 | 39.494  18.175  31.881  1.00  33.97 | C |
| ANISOU | 1216 | CB  ARG A 171 | 3974 4305 4628   560  510  191 | C |
| ATOM   | 1217 | CG  ARG A 171 | 38.746  17.520  33.085  1.00  38.76 | C |
| ANISOU | 1217 | CG  ARG A 171 | 4549 4998 5180   533  510  162 | C |
| ATOM   | 1218 | CD  ARG A 171 | 38.162  18.596  34.069  1.00  45.95 | C |
| ANISOU | 1218 | CD  ARG A 171 | 5455 5914 6089   590  541  113 | C |
| ATOM   | 1219 | NE  ARG A 171 | 37 255  19.510  33.465  1.00  55.37 | N |
| ANISOU | 1219 | NE  ARG A 171 | 6625 7116 7297   672  561  124 | N |
| ATOM   | 1220 | CZ  ARG A 171 | 36.987  20.776  33.832  1.00  63.43 | C |
| ANISOU | 1220 | CZ  ARG A 171 | 7657 8099 8343   744  586   90 | C |
| ATOM   | 1221 | NH1 ARG A 171 | 37.601  21.417  34.823  1.00  63.82 | N |
| ANISOU | 1221 | NH1 ARG A 171 | 7747 8092 8409   745  597   37 | N |
| ATOM   | 1222 | NH2 ARG A 171 | 36.081  21.421  33.140  1.00  65.34 | N |
| ANISOU | 1222 | NH2 ARG A 171 | 7872 8359 8595   820  597  109 | N |
| ATOM   | 1223 | N   SER A 172 | 39.221  18.735  28.369  1.00  31.33 | N |
| ANISOU | 1223 | N   SER A 172 | 3643 3934 4328   642  507  314 | N |
| ATOM   | 1224 | CA  SER A 172 | 39.953  19.218  27.240  1.00  31.69 | C |
| ANISOU | 1224 | CA  SER A 172 | 3725 3909 4405   656  513  351 | C |
| ATOM   | 1225 | C   SER A 172 | 39.697  20.738  26.972  1.00  35.30 | C |
| ANISOU | 1225 | C   SER A 172 | 4208 4306 4900   735  537  360 | C |
| ATOM   | 1226 | O   SER A 172 | 38.559  21.235  27.208  1.00  33.82 | O |

TABLE 3-continued

| | | | | | | | | | | |
|---|---|---|---|---|---|---|---|---|---|---|
| ANISOU | 1226 | O | SER | A | 172 | 3992 4159 4700 797 542 353 | | | | O |
| ATOM | 1227 | CB | SER | A | 172 | 39.455 | 18.464 | 26.052 | 1.00 32.63 | C |
| ANISOU | 1227 | CB | SER | A | 172 | 3821 4088 4489 655 493 396 | | | | C |
| ATOM | 1228 | OG | SER | A | 172 | 40.415 | 18.526 | 25.004 | 1.00 36.27 | O |
| ANISOU | 1228 | OG | SER | A | 172 | 4320 4492 4970 643 497 430 | | | | O |
| ATOM | 1229 | N | SER | A | 173 | 40.738 | 21.446 | 26.529 | 1.00 33.86 | N |
| ANISOU | 1229 | N | SER | A | 173 | 4076 4026 4765 732 553 375 | | | | N |
| ATOM | 1230 | CA | SER | A | 173 | 40.688 | 22.937 | 26.506 | 1.00 36.21 | C |
| ANISOU | 1230 | CA | SER | A | 173 | 4409 4242 5106 796 576 377 | | | | C |
| ATOM | 1231 | C | SER | A | 173 | 41.407 | 23.425 | 25.263 | 1.00 37.70 | C |
| ANISOU | 1231 | C | SER | A | 173 | 4642 4361 5323 799 583 432 | | | | C |
| ATOM | 1232 | O | SER | A | 173 | 42.032 | 22.641 | 24.543 | 1.00 34.38 | O |
| ANISOU | 1232 | O | SER | A | 173 | 4221 3953 4887 750 583 459 | | | | O |
| ATOM | 1233 | CB | SER | A | 173 | 41.382 | 23 525 | 27.734 | 1.00 39.74 | C |
| ANISOU | 1233 | CB | SER | A | 173 | 4882 4321 5595 775 588 317 | | | | C |
| ATOM | 1234 | OG | SER | A | 173 | 42.704 | 23.277 | 27.585 | 1.00 36.10 | O |
| ANISOU | 1234 | OG | SER | A | 173 | 4461 4112 5177 706 590 314 | | | | O |
| ATOM | 1235 | N | GLN | A | 174 | 41.225 | 24.719 | 24.973 | 1.00 37.88 | N |
| ANISOU | 1235 | N | GLN | A | 174 | 4700 4311 5381 352 605 451 | | | | N |
| ATOM | 1236 | CA | GLN | A | 174 | 41.853 | 25.330 | 23.306 | 1.00 38.15 | C |
| ANISOU | 1236 | CA | GLN | A | 174 | 4735 4270 5442 869 623 511 | | | | C |
| ATOM | 1237 | C | GLN | A | 174 | 43.295 | 24.935 | 23.613 | 1.00 32.75 | C |
| ANISOU | 1237 | C | GLN | A | 174 | 4121 3540 4782 766 636 513 | | | | C |
| ATOM | 1238 | O | GLN | A | 174 | 44.071 | 25.049 | 24.541 | 1.00 39.85 | O |
| ANISOU | 1238 | O | GLN | A | 174 | 5001 4371 5592 741 541 454 | | | | O |
| ATOM | 1239 | CB | GLN | A | 174 | 41.788 | 23.930 | 23.953 | 1.00 40.04 | C |
| ANISOU | 1239 | CB | GLN | A | 174 | 5112 4443 5774 930 642 514 | | | | C |
| ATOM | 1240 | CG | GLN | A | 174 | 40.491 | 27.497 | 23.424 | 1.00 53.58 | C |
| ANISOU | 1240 | CG | GLN | A | 174 | 6795 5150 7442 1023 631 543 | | | | C |
| ATOM | 1241 | CD | GLN | A | 174 | 40.235 | 27.331 | 22.022 | 1.00 51.34 | C |
| ANISOU | 1241 | CD | GLN | A | 174 | 6494 5913 7398 1037 620 620 | | | | C |
| ATOM | 1242 | OE1 | GLN | A | 174 | 39.128 | 26.545 | 21.719 | 1.00 57.40 | O |
| ANISOU | 1242 | OE1 | GLN | A | 174 | 7218 6774 7818 1082 595 632 | | | | O |
| ATOM | 1243 | NE2 | GLN | A | 174 | 41.286 | 26.950 | 21.191 | 1.00 49.80 | N |
| ANISOU | 1243 | NE2 | GLN | A | 174 | 6277 5504 5851 988 538 554 | | | | N |
| ATOM | 1244 | N | GLY | A | 175 | 43.623 | 24.535 | 22.400 | 1.00 33.94 | N |
| ANISOU | 1244 | N | GLY | A | 175 | 4280 3705 4905 770 640 568 | | | | N |
| ATOM | 1245 | CA | GLY | A | 175 | 44.548 | 24.1142 | 22.031 | 1.00 33.72 | C |
| ANISOU | 1245 | CA | GLY | A | 175 | 4290 3672 4925 697 656 573 | | | | C |
| ATOM | 1246 | C | GLY | A | 175 | 45.007 | 22.594 | 21.957 | 1.00 33 10 | C |

TABLE 3-continued

| ANISOU | 1246 | C | GLY | A | 175 | 4142 | 3661 | 4772 | 630 | 631 | 559 | | C |
|---|---|---|---|---|---|---|---|---|---|---|---|---|---|
| ATOM | 1247 | O | GLY | A | 175 | 45.972 | 22.021 | 21.445 | 1.00 | 35.80 | | | O |
| ANISOU | 1247 | O | GLY | A | 175 | 4486 | 3939 | 5116 | 598 | 640 | 558 | | O |
| ATOM | 1248 | N | ASP | A | 176 | 43.995 | 21.908 | 22.493 | 1.00 | 31.91 | | | N |
| ANISOU | 1248 | N | ASP | A | 176 | 3950 | 3593 | 4580 | 567 | 501 | 584 | | N |
| ATOM | 1249 | CA | ASP | A | 176 | 44.000 | 20.391 | 22.341 | 1.00 | 31.95 | | | C |
| ANISOU | 1249 | CA | ASP | A | 176 | 3919 | 3652 | 4539 | 621 | 574 | 525 | | C |
| ATOM | 1250 | C | ASP | A | 176 | 43.399 | 20.025 | 25.956 | 1.00 | 33.53 | | | C |
| ANISOU | 1250 | C | ASP | A | 176 | 3736 | 3557 | 4308 | 550 | 565 | 579 | | C |
| ATOM | 1251 | O | ASP | A | 176 | 42.579 | 20.767 | 20.498 | 1.00 | 29.53 | | | O |
| ANISOU | 1251 | O | ASP | A | 176 | 3618 | 3433 | 4169 | 713 | 567 | 615 | | O |
| ATOM | 1252 | CB | ASP | A | 176 | 43.123 | 19.701 | 23.420 | 1.00 | 32.11 | | | C |
| ANISOU | 1252 | CB | ASP | A | 176 | 3307 | 3773 | 4531 | 617 | 545 | 481 | | C |
| ATOM | 1253 | CG | ASP | A | 176 | 43.529 | 19.940 | 24.801 | 1.00 | 33.22 | | | C |
| ANISOU | 1253 | CG | ASP | A | 176 | 4053 | 3887 | 4720 | 589 | 549 | 423 | | C |
| ATOM | 1254 | OD1 | ASP | A | 176 | 44.835 | 20.205 | 24.885 | 1.00 | 34.73 | | | O |
| ANISOU | 1254 | OD1 | ASP | A | 176 | 4280 | 3791 | 4945 | 555 | 585 | 416 | | O |
| ATOM | 1255 | OD2 | ASP | A | 176 | 42.873 | 19.722 | 25.811 | 1.50 | 33.56 | | | O |
| ANISOU | 1255 | OD2 | ASP | A | 176 | 4057 | 3964 | 4730 | 595 | 535 | 390 | | O |
| ATOM | 1256 | N | LEU | A | 177 | 43.579 | 13.819 | 20.454 | 1.00 | 31.244 | | | N |
| ANISOU | 1256 | N | LEU | A | 177 | 3839 | 3697 | 4262 | 608 | 547 | 580 | | N |
| ATOM | 1257 | CA | LEU | A | 177 | 43.038 | 18.256 | 19.263 | 1.00 | 30.24 | | | C |
| ANISOU | 1257 | CA | LEU | A | 177 | 3675 | 3537 | 4176 | 629 | 529 | 619 | | C |
| ATOM | 1258 | C | LEU | A | 177 | 42.925 | 13.724 | 19.538 | 1.00 | 29.01 | | | C |
| ANISOU | 1258 | C | LEU | A | 177 | 3463 | 3552 | 3989 | 579 | 490 | 585 | | C |
| ATOM | 1259 | O | LEU | A | 177 | 43.842 | 16.138 | 20.109 | 1.00 | 29.60 | | | O |
| ANISOU | 1259 | O | LEU | A | 177 | 3555 | 5604 | 4085 | 523 | 492 | 653 | | O |
| ATOM | 1260 | CB | LEU | A | 177 | 43.984 | 18.392 | 18.052 | 1.00 | 29.50 | | | C |
| ANISOU | 1260 | CB | LEU | A | 177 | 3813 | 3503 | 4082 | 613 | 556 | 853 | | C |
| ATOM | 1261 | CG | LEU | A | 177 | 43.752 | 17.697 | 16.733 | 1.00 | 33.30 | | | C |
| ANISOU | 1261 | CG | LEU | A | 177 | 4399 | 4354 | 4500 | 622 | 540 | 690 | | C |
| ATOM | 1262 | CD1 | LEU | A | 177 | 42.512 | 13.214 | 15.104 | 1.00 | 35.45 | | | C |
| ANISOU | 1262 | CD1 | LEU | A | 177 | 4374 | 4351 | 4735 | 694 | 525 | 734 | | C |
| ATOM | 1263 | CD2 | LEU | A | 177 | 44.857 | 17.804 | 15.730 | 1.00 | 37.01 | | | C |
| ANISOU | 1263 | CD2 | LEU | A | 177 | 4503 | 4484 | 4970 | 506 | 678 | 723 | | C |
| ATOM | 1264 | N | TRP | A | 178 | 41.306 | 16.135 | 19.142 | 1.00 | 25.45 | | | N |
| ANISOU | 1264 | N | TRP | A | 178 | 3129 | 3310 | 3615 | 597 | 460 | 595 | | N |
| ATOM | 1265 | CA | TRP | A | 178 | 41.591 | 14.544 | 19.343 | 1.00 | 26.50 | | | C |
| ANISOU | 1265 | CA | TRP | A | 178 | 3115 | 3391 | 3800 | 546 | 422 | 551 | | C |
| ATOM | 1266 | C | TRP | A | 178 | 41.455 | 13.905 | 13.352 | 1.30 | 29.07 | | | C |

TABLE 3-continued

| | | | | | | | | | |
|---|---|---|---|---|---|---|---|---|---|
| ANISOU | 1266 | C | TRP | A | 178 | 3432 3750 3865 545 402 590 | | | C |
| ATOM | 1267 | O | TRP | A | 178 | 40.793 | 14.785 | 17.147 1.00 33.38 | O |
| ANISOU | 1267 | O | TRP | A | 178 | 4019 4360 4419 595 399 623 | | | O |
| ATOM | 1268 | CB | TRP | A | 178 | 40.327 | 14.387 | 20.111 1.00 35.77 | C |
| ANISOU | 1268 | CB | TRP | A | 178 | 3092 3478 3503 555 357 553 | | | C |
| ATOM | 1269 | CG | TRP | A | 178 | 40.540 | 14.375 | 21.497 1.00 29.00 | C |
| ANISOU | 1269 | CG | TRP | A | 178 | 3772 3722 3925 545 414 516 | | | C |
| ATOM | 1270 | CD1 | TRP | A | 178 | 43.393 | 16.154 | 21.995 1.00 31.35 | C |
| ANISOU | 1270 | CD1 | TRP | A | 178 | 3341 3977 4256 593 443 515 | | | C |
| ATOM | 1271 | CD2 | TRP | A | 178 | 41.021 | 14.097 | 22.554 1.00 27.71 | C |
| ANISOU | 1271 | CD2 | TRP | A | 178 | 3202 3554 3771 485 404 475 | | | C |
| ATOM | 1272 | NE1 | TAP | A | 178 | 40.755 | 16.232 | 23.214 1.00 32.60 | N |
| ANISOU | 1272 | NE1 | TRP | A | 178 | 3833 4109 4441 5814 455 473 | | | N |
| ATOM | 1273 | CE2 | TRP | A | 178 | 41.143 | 14.999 | 27.723 1.00 30.22 | C |
| ANISOU | 1273 | CE2 | TRP | A | 178 | 3525 2331 4125 495 427 450 | | | C |
| ATOM | 1274 | CE3 | TRP | A | 178 | 41.303 | 12.718 | 22.717 1.80 29.02 | C |
| ANISOU | 1274 | CE3 | TRP | A | 178 | 7360 7747 7918 424 373 453 | | | C |
| ATOM | 1275 | CZ2 | TRP | A | 178 | 41.545 | 14.535 | 24.092 1.00 29.73 | C |
| ANISOU | 1275 | CZ2 | TRP | A | 178 | 3462 3761 4073 4.52 420 409 | | | C |
| ATOM | 1276 | CZ3 | TRP | A | 178 | 41.729 | 12.269 | 23.977 1.00 27.33 | C |
| ANISOU | 1276 | CZ3 | TRP | A | 178 | 3153 3525 3728 313 356 421 | | | C |
| ATOM | 1277 | CH2 | TRP | A | 178 | 41.819 | 13.162 | 25 595 1.30 29.10 | C |
| ANISOU | 1277 | CH2 | TRP | A | 178 | 3375 3710 3971 392 339 393 | | | C |
| ATOM | 1278 | N | PHE | A | 179 | 42.055 | 12.709 | 17.972 1.00 23.31 | N |
| ANISOU | 1278 | N | PHE | A | 179 | 3835 3654 3163 492 383 555 | | | N |
| ATOM | 1279 | CA | PHE | A | 179 | 41.732 | 11.798 | 16.380 1.00 27.50 | C |
| ANISOU | 1279 | CA | PHE | A | 179 | 3230 3614 3604 436 355 514 | | | C |
| ATOM | 1280 | C | PHE | A | 179 | 41.012 | 10.572 | 17.408 1.00 31.54 | C |
| ANISOU | 1280 | C | PHE | A | 179 | 3742 4224 4130 445 307 544 | | | C |
| ATOM | 1281 | O | PHE | A | 179 | 41.451 | 9.958 | 18.419 1.00 29.54 | O |
| ANISOU | 1281 | O | PHE | A | 179 | 3453 3953 3377 397 298 611 | | | O |
| ATOM | 1282 | CB | PHE | A | 179 | 43.103 | 11.316 | 18.357 1.00 20.14 | C |
| ANISOU | 1282 | CB | PHE | A | 179 | 3594 3910 3948 455 370 554 | | | C |
| ATOM | 1283 | CG | PHE | A | 179 | 43.723 | 12.295 | 15.390 1.00 28.88 | C |
| ANISOU | 1283 | CG | PHE | A | 179 | 3471 3714 3738 440 415 503 | | | C |
| ATOM | 1284 | CD1 | PHE | A | 179 | 44.549 | 13.293 | 15.872 1.00 20.44 | C |
| ANISOU | 1284 | CD1 | PHE | A | 179 | 3433 3595 3797 492 459 609 | | | C |
| ATOM | 1285 | CD2 | PHE | A | 179 | 43.460 | 12.241 | 14.029 1.00 29.14 | C |
| ANISOU | 1285 | CD2 | PHE | A | 179 | 3520 3734 3755 519 412 635 | | | C |
| ATOM | 1286 | CE1 | PHE | A | 179 | 45.156 | 14.202 | 15.020 1.00 23.30 | C |

TABLE 3-continued

| | | | | | | | | | | | |
|---|---|---|---|---|---|---|---|---|---|---|---|
| ANISOU | 1286 | CE1 | PHE | A | 179 | | 3451 | 3528 | 3775 | 515 503 648 | C |
| ATOM | 1287 | CE2 | PHE | A | 179 | 44.057 | 13.174 | 13.175 | 1.00 | 28.55 | C |
| ANISOU | 1287 | CE2 | PHE | A | 179 | | 9563 | 3673 | 3590 | 541 457 678 | C |
| ATOM | 1288 | CZ | PHE | A | 179 | 44.335 | 14.176 | 13.574 | 1.55 | 29.33 | C |
| ANISOU | 1288 | CZ | PHE | A | 179 | | 3500 | 3597 | 3346 | 545 503 688 | C |
| ATOM | 1289 | N | ALA | A | 180 | 39.909 | 10.243 | 15.771 | 1.00 | 29.60 | N |
| ANISOU | 1289 | N | ALA | A | 180 | | 3460 | 4335 | 3326 | 452 274 558 | N |
| ATOM | 1290 | CA | ALA | A | 180 | 39.069 | 9.039 | 17.178 | 1.00 | 28.617 | C |
| ANISOU | 1290 | CA | ALA | A | 180 | | 3278 | 3953 | 3561 | 419 226 534 | C |
| ATOM | 1291 | C | ALA | A | 180 | 39.349 | 8.097 | 15.075 | 1.00 | 29.85 | C |
| ANISOU | 1291 | C | ALA | A | 180 | | 3445 | 4121 | 3773 | 398 1 99 528 | C |
| ATOM | 1292 | O | ALA | A | 180 | 33.935 | 8.355 | 14.942 | 1.00 | 29.17 | O |
| ANISOU | 1292 | O | ALA | A | 180 | | 3366 | 4066 | 3650 | 438 192 553 | O |
| ATOM | 1293 | CB | ALA | A | 180 | 37.535 | 9.531 | 17.207 | 1.00 | 24.90 | C |
| ANISOU | 1293 | CB | ALA | A | 180 | | 2752 | 3549 | 3151 | 459 210 550 | C |
| ATOM | 1294 | N | VAL | A | 181 | 40.025 | 5.939 | 15.400 | 1.00 | 233.63 | N |
| ANISOU | 1294 | N | VAL | A | 181 | | 3305 | 3943 | 3629 | 342 182 494 | N |
| ATOM | 1295 | CA | VAL | A | 181 | 46.398 | 5.943 | 15.429 | 1.00 | 27.68 | C |
| ANISOU | 1295 | CA | VAL | A | 181 | | 3205 | 3836 | 3478 | 321 153 476 | C |
| ATOM | 1296 | C | VAL | A | 181 | 39.442 | 4.748 | 19.591 | 1.00 | 23.93 | C |
| ANISOU | 1296 | C | VAL | A | 181 | | 3336 | 4045 | 3512 | 275 97 458 | C |
| ATOM | 1297 | O | VAL | A | 181 | 39.484 | 4.052 | 15.611 | 1.30 | 26.59 | O |
| ANISOU | 1297 | O | VAL | A | 181 | | 3343 | 3747 | 3351 | 223 80 438 | O |
| ATOM | 1298 | CB | VAL | A | 181 | 41.334 | 5.440 | 15.589 | 1.00 | 30.79 | C |
| ANISOU | 1298 | CB | VAL | A | 181 | | 3604 | 4163 | 3802 | 293 168 478 | C |
| ATOM | 1299 | CG1 | VAL | A | 181 | 42.207 | 4.457 | 14.425 | 1.00 | 26.28 | C |
| ANISOU | 1299 | CG1 | VAL | A | 181 | | 3087 | 3504 | 3294 | 285 144 431 | C |
| ATOM | 1300 | CG2 | VAL | A | 181 | 42.755 | 6.695 | 15.551 | 1.50 | 33.57 | C |
| ANISOU | 1300 | CG2 | VAL | A | 181 | | 4005 | 4450 | 4289 | 328 228 470 | C |
| ATOM | 1301 | N | SER | A | 182 | 38.520 | 4.500 | 14.593 | 1.00 | 27.13 | N |
| ANISOU | 1301 | N | SER | A | 182 | | 3095 | 3877 | 3337 | 289 55 455 | N |
| ATOM | 1302 | CA | SER | A | 182 | 37.554 | 3.436 | 14.668 | 1.90 | 23.14 | C |
| ANISOU | 1302 | CA | SER | A | 182 | | 3189 | 4062 | 3442 | 244 9 448 | C |
| ATOM | 1303 | C | SER | A | 182 | 37.151 | 3.171 | 13.210 | 1.00 | 28.95 | C |
| ANISOU | 1303 | C | SER | A | 182 | | 3298 | 4212 | 3483 | 267 -25 449 | C |
| ATOM | 1304 | O | SER | A | 182 | 35.639 | 4.087 | 12.549 | 1.05 | 28.83 | O |
| ANISOU | 1304 | O | SER | A | 182 | | 3274 | 4231 | 3448 | 325 -15 481 | O |
| ATOM | 1305 | CB | SER | A | 182 | 35.355 | 4.040 | 15.423 | 1.00 | 29.12 | C |
| ANISOU | 1305 | CB | SER | A | 182 | | 3255 | 4238 | 3572 | 251 9 467 | C |
| ATOM | 1306 | OG | SER | A | 182 | 35.273 | 3.111 | 15.454 | 1.00 | 26.35 | O |

TABLE 3-continued

| | | | | | | | | | |
|---|---|---|---|---|---|---|---|---|---|
| ANISOU | 1306 | OG | SER | A | 182 | 3076 4163 3415 | 204 | -41 | 453 O |
| ATOM | 1307 | N | SER | A | 183 | 37.263 1.932 12.750 | 1.30 | 25.98 | N |
| ANISOU | 1307 | N | SER | A | 183 | 2539 3839 3093 | 224 | -58 | 416 N |
| ATOM | 1308 | CA | SER | A | 183 | 36.850 1.603 11.355 | 1.65 | 29.34 | C |
| ANISOU | 1308 | CA | SER | A | 183 | 3374 4315 3453 | 244 | -105 | 410 C |
| ATOM | 1309 | C | SER | A | 183 | 35.349 1.777 11.254 | 1.00 | 32.69 | C |
| ANISOU | 1309 | C | SER | A | 183 | 3704 4340 3885 | 249 | -143 | 425 C |
| ATOM | 1310 | O | SER | A | 183 | 34.852 2.254 10.243 | 1.00 | 32.24 | O |
| ANISOU | 1310 | O | SER | A | 183 | 3573 4815 3757 | 208 | -155 | 444 O |
| ATOM | 1311 | CB | SER | A | 183 | 37.157 0.127 11.053 | 1.00 | 29.54 | C |
| ANISOU | 1311 | CB | SER | A | 183 | 3425 4324 3474 | 189 | -151 | 361 C |
| ATOM | 1312 | OG | SER | A | 183 | 38.518 0.000 10.626 | 1.00 | 31.35 | O |
| ANISOU | 1312 | OG | SER | A | 183 | 3703 4495 3707 | 205 | -122 | 344 O |
| ATOM | 1313 | N | SER | A | 184 | 34.529 1.340 12.310 | 1.30 | 31.44 | N |
| ANISOU | 1313 | N | SER | A | 184 | 3536 4581 3730 | 198 | -161 | 418 N |
| ATOM | 1314 | CA | SER | A | 184 | 33.159 1.369 12.265 | 1.00 | 30.85 | C |
| ANISOU | 1314 | CA | SER | A | 184 | 3395 4690 3638 | 191 | -198 | 426 C |
| ATOM | 1315 | C | SER | A | 184 | 32.557 2.896 12.675 | 1.00 | 32.25 | C |
| ANISOU | 1315 | C | SER | A | 184 | 3525 4901 3827 | 255 | -164 | 454 C |
| ATOM | 1316 | O | SER | A | 184 | 31.344 2.392 12.468 | 1.00 | 32.73 | O |
| ANISOU | 1316 | O | SER | A | 184 | 3524 5047 3874 | 263 | -194 | 472 O |
| ATOM | 1317 | CB | SER | A | 184 | 32.620 0.281 13.181 | 1.30 | 32.50 | C |
| ANISOU | 1317 | CB | SER | A | 184 | 3506 4347 3805 | 139 | -230 | 402 C |
| ATOM | 1318 | OG | SER | A | 184 | 32.854 0.655 14.564 | 1.00 | 31.97 | O |
| ANISOU | 1318 | OG | SER | A | 184 | 3491 4809 3847 | 86 | -185 | 414 O |
| ATOM | 1319 | N | GLY | A | 185 | 33.320 9.541 19.384 | 1.00 | 34.61 | N |
| ANISOU | 1319 | N | GLY | A | 185 | 3349 5140 4160 | 2781 | -105 | 480 N |
| ATOM | 1320 | CA | GLY | A | 185 | 32.736 4.657 14.143 | 1.00 | 29.59 | C |
| ANISOU | 1320 | CA | GLY | A | 185 | 3170 4523 3548 | 320 | -71 | 505 C |
| ATOM | 1321 | C | GLY | A | 185 | 31.551 4.246 14.987 | 1.00 | 32.76 | C |
| ANISOU | 1321 | C | GLY | A | 185 | 3493 4990 3959 | 275 | -93 | 495 C |
| ATOM | 1322 | O | GLY | A | 185 | 30.661 5.075 15.211 | 1.09 | 33.43 | O |
| ANISOU | 1322 | O | GLY | A | 185 | 3535 5133 4053 | 322 | -83 | 512 O |
| ATOM | 1323 | N | SER | A | 186 | 31.524 2.993 15.479 | 1.00 | 36.20 | N |
| ANISOU | 1323 | N | SER | A | 186 | 3929 5424 4401 | 168 | -120 | 458 N |
| ATOM | 1324 | CA | SER | A | 186 | 30.354 2.494 16.225 | 1.00 | 32.53 | C |
| ANISOU | 1324 | CA | SER | A | 186 | 3392 5027 3942 | 184 | -140 | 459 C |
| ATOM | 1325 | C | SER | A | 186 | 30.751 1.851 17.540 | 1.00 | 34.48 | C |
| ANISOU | 1325 | C | SER | A | 186 | 3652 5231 4219 | 59 | -121 | 448 C |
| ATOM | 1326 | O | SER | A | 186 | 29.935 1.207 18.162 | 1.06 | 34.41 | O |

TABLE 3-continued

| | | | | | | | | | |
|---|---|---|---|---|---|---|---|---|---|
| ANISOU | 1326 | O | SER | A | 186 | 3593 5259 4211 -5 -133 432 | | | O |
| ATOM | 1327 | CB | SER | A | 186 | 29.494 | 1.530 | 15.372 1.00 32.76 | C |
| ANISOU | 1327 | CB | SER | A | 186 | 3387 5121 3938 92 -207 445 | | | C |
| ATOM | 1328 | OG | SER | A | 186 | 29.137 | 2.086 | 14.036 1.00 32.91 | O |
| ANISOU | 1328 | OG | SER | A | 186 | 3401 5184 3920 135 -293 456 | | | O |
| ATOM | 1329 | N | THR | A | 187 | 32.305 | 2.023 | 17.958 1.00 29.66 | N |
| ANISOU | 1329 | N | THR | A | 187 | 3104 4534 13630 55 -88 446 | | | N |
| ATOM | 1330 | CA | THR | A | 187 | 32.472 | 1.423 | 19.230 1.00 32.19 | C |
| ANISOU | 1330 | CA | THA | A | 187 | 3444 4810 5976 0 -74 435 | | | C |
| ATOM | 1331 | C | THR | A | 187 | 32.107 | 2.299 | 20.421 1.00 32.59 | C |
| ANISOU | 1331 | C | THR | A | 187 | 3459 4331 4044 18 -27 447 | | | C |
| ATOM | 1332 | O | THR | A | 187 | 32.475 | 3.440 | 20.509 1.00 33.52 | O |
| ANISOU | 1332 | O | THR | A | 187 | 3208 4598 3795 85 13 456 | | | O |
| ATOM | 1333 | CB | THR | A | 187 | 33.994 | 1.188 | 19.191 1.00 35.12 | C |
| ANISOU | 1333 | CB | THR | A | 187 | 3894 5034 41365 -1 -65 425 | | | C |
| ATOM | 1334 | OG1 | THR | A | 187 | 34.255 | 0.259 | 18.115 1.00 41.03 | O |
| ANISOU | 1334 | OG1 | THR | A | 187 | 4573 5320 5095 -20 -110 406 | | | O |
| ATOM | 1335 | OG2 | THR | A | 187 | 34.443 | 0.515 | 23.498 1.00 34.33 | C |
| ANISOU | 1335 | OG2 | THR | A | 187 | 3515 4940 4289 -67 -50 417 | | | C |
| ATOM | 1336 | N | LYS | A | 188 | 31.364 | 1.749 | 21.363 1.00 33.54 | N |
| ANISOU | 1336 | N | LYS | A | 188 | 3537 5043 4162 -45 -30 445 | | | N |
| ATOM | 1337 | CA | LYS | A | 188 | 30.557 | 2.571 | 22.304 1.00 33.53 | C |
| ANISOU | 1337 | CA | LYS | A | 188 | 3492 5100 4175 -24 12 453 | | | C |
| ATOM | 1338 | C | LYS | A | 188 | 31.673 | 3.519 | 23.152 1.00 35.82 | C |
| ANISOU | 1338 | C | LYS | A | 188 | 3814 5313 4479 20 64 451 | | | C |
| ATOM | 1339 | O | LYS | A | 188 | 31.227 | 4.744 | 23.246 1.00 30.97 | O |
| ANISOU | 1339 | O | LYS | A | 188 | 3174 4721 3871 94 99 455 | | | O |
| ATOM | 1340 | CB | LYS | A | 188 | 29.854 | 1.528 | 23.180 1.00 34.71 | C |
| ANISOU | 1340 | CB | LYS | A | 188 | 3590 5292 4396 -115 2 451 | | | C |
| ATOM | 1341 | CG | LYS | A | 188 | 28.645 | 2.207 | 23.358 1.00 48.11 | C |
| ANISOU | 1341 | CG | LYS | A | 188 | 5201 7082 5995 -104 33 455 | | | C |
| ATOM | 1342 | CD | LYS | A | 188 | 29.051 | 2.493 | 25.263 1.00 45.16 | C |
| ANISOU | 1342 | CD | LYS | A | 188 | 5229 7062 5039 -118 80 453 | | | C |
| ATOM | 1343 | CE | LYS | A | 188 | 27.950 | 2.161 | 25.263 1.00 48.58 | C |
| ANISOU | 1343 | CE | LYS | A | 188 | 5211 7201 6346 -177 100 456 | | | C |
| ATOM | 1344 | NZ | LYS | A | 188 | 28.389 | 2.901 | 27.512 1.00 47.47 | N |
| ANISOU | 1344 | NZ | LYS | A | 188 | 5092 7037 5907 -152 155 450 | | | N |
| ATOM | 1345 | N | GLU | A | 189 | 82.502 | 2.961 | 23.798 1.00 28.14 | N |
| ANISOU | 1345 | N | GLU | A | 189 | 2905 4278 3524 -25 55 443 | | | N |
| ATOM | 1346 | CA | GLU | A | 189 | 83.419 | 3.772 | 24.685 1.00 84.41 | C |

TABLE 3-continued

| | | | | |
|---|---|---|---|---|
| ANISOU | 1346 CA GLU A 189 | 3726 5014 4334 5 107 433 | | C |
| ATOM | 1347 C GLU A 189 | 34.341 4.713 23.872 1.00 30.66 | | C |
| ANISOU | 1347 C GLU A 189 | 3319 4503 3905 82 123 439 | | C |
| ATOM | 1348 O GLU A 189 | 34.595 5.835 24.299 1.00 29.73 | | O |
| ANISOU | 1348 O GLU A 189 | 3135 4331 3781 135 163 437 | | O |
| ATOM | 1349 CB GLU A 189 | 34.165 2.921 25.770 1.00 29.82 | | C |
| ANISOU | 1349 CB GLU A 189 | 3191 4261 3757 -65 101 430 | | C |
| ATOM | 1350 CG GLU A 189 | 33.132 2.312 26.709 1.00 31.20 | | C |
| ANISOU | 1350 CG GLU A 189 | 3222 4524 3909 -132 101 435 | | C |
| ATOM | 1351 CD GLU A 189 | 33.679 1.700 27.995 1.00 34.59 | | C |
| ANISOU | 1351 CD GLU A 189 | 3792 5015 4334 -194 103 434 | | C |
| ATOM | 1352 OE1 GLU A 189 | 32.921 1.139 28.803 1.00 33.24 | | O |
| ANISOU | 1352 OE1 GLU A 189 | 3594 4896 4140 -257 106 444 | | O |
| ATOM | 1353 OE2 GLU A 189 | 34.884 1.761 23.245 1.00 38.15 | | O |
| ANISOU | 1353 OE2 GLU A 189 | 4303 5383 4804 -184 102 425 | | O |
| ATOM | 1354 N VAL A 190 | 34.644 4.327 22.543 1.00 29.85 | | N |
| ANISOU | 1354 N VAL A 190 | 3211 4359 3770 90 04 443 | | N |
| ATOM | 1355 CA VAL A 190 | 35.447 5.246 21.813 1.00 28.36 | | C |
| ANISOU | 1355 CA VAL A 190 | 3135 4198 3672 159 115 450 | | C |
| ATOM | 1356 C VAL A 190 | 34.501 5.457 21.472 1.00 33.83 | | C |
| ANISOU | 1356 C VAL A 190 | 3711 4359 4282 234 137 457 | | C |
| ATOM | 1357 O VAL A 190 | 35.103 7.508 21.605 1.00 33.48 | | O |
| ANISOU | 1357 O VAL A 190 | 3639 4771 4262 289 174 479 | | O |
| ATOM | 1358 CB VAL A 190 | 35.938 4.550 20.534 1.30 28.08 | | C |
| ANISOU | 1358 CB VAL A 190 | 3055 4053 3546 153 82 449 | | C |
| ATOM | 1359 CG1 VAL A 190 | 35.568 5.533 49.564 1.39 27.77 | | C |
| ANISOU | 1359 CG1 VAL A 190 | 3045 3994 3511 224 137 464 | | C |
| ATOM | 1360 CG2 VAL A 190 | 37.019 3.540 20.978 1.50 27.25 | | C |
| ANISOU | 1360 CG2 VAL A 190 | 2987 3898 3457 95 56 428 | | C |
| ATOM | 1361 N ILE A 191 | 33.382 6.261 20.944 1.00 32.29 | | N |
| ANISOU | 1361 N ILE A 191 | 3462 4745 4551 239 111 475 | | N |
| ATOM | 1362 CA ILE A 191 | 32.412 7.370 20.618 1.00 31.82 | | C |
| ANISOU | 1362 CA ILE A 191 | 3354 4740 3995 316 124 492 | | C |
| ATOM | 1363 C ILE A 191 | 32.173 8.268 21.788 1.00 34.76 | | C |
| ANISOU | 1363 C ILE A 191 | 3705 5112 4339 345 167 485 | | C |
| ATOM | 1364 O ILE A 191 | 32.057 9.477 21.531 1.00 36.34 | | O |
| ANISOU | 1364 O ILE A 191 | 3905 5301 4603 423 193 495 | | O |
| ATOM | 1365 CB ILE A 191 | 30.999 3.781 20.340 1.00 34.40 | | C |
| ANISOU | 1365 CB ILE A 191 | 3606 5170 4293 295 86 493 | | C |
| ATOM | 1366 CG1 ILE A 191 | 30.971 6.064 19.009 1.00 40.95 | | C |

TABLE 3-continued

| | | | | | | | | | | |
|---|---|---|---|---|---|---|---|---|---|---|
| ANISOU | 1366 | CG1 | ILE | A | 191 | 4448 | 6016 | 5095 | 283 | 37 | 438 | C |
| ATOM | 1367 | CG2 | ILE | A | 191 | 29.879 | 7.841 | 20.373 | 1.00 | 44.85 | C |
| ANISOU | 1367 | CG2 | ILE | A | 191 | 4866 | 6561 | 5618 | 369 | 100 | 502 | C |
| ATOM | 1368 | CD1 | ILE | A | 191 | 23.541 | 5.453 | 18.906 | 1.00 | 40.26 | C |
| ANISOU | 1368 | CD1 | ILE | A | 191 | 4279 | 6033 | 4986 | 251 | -2 | 493 | C |
| ATOM | 1369 | N | HIS | A | 192 | 32.055 | 7.551 | 22.088 | 1.00 | 30.94 | N |
| ANISOU | 1369 | N | HIS | A | 192 | 3206 | 4643 | 3907 | 281 | 175 | 457 | N |
| ATOM | 1370 | CA | HIS | A | 192 | 31.707 | 8.417 | 24.165 | 1.00 | 31.50 | C |
| ANISOU | 1370 | CA | HIS | A | 192 | 3239 | 4766 | 4027 | 303 | 216 | 454 | C |
| ATOM | 1371 | C | HIS | A | 192 | 32.835 | 9.394 | 24.511 | 1.00 | 31.70 | C |
| ANISOU | 1371 | C | HIS | A | 192 | 3337 | 4560 | 4046 | 346 | 252 | 448 | C |
| ATOM | 1372 | O | HIS | A | 192 | 32.508 | 10.595 | 24.771 | 1.00 | 27.87 | O |
| ANISOU | 1372 | O | HIS | A | 192 | 2843 | 4170 | 3578 | 416 | 284 | 445 | O |
| ATOM | 1373 | CB | HIS | A | 192 | 31.399 | 7.465 | 25.317 | 1.00 | 30.59 | C |
| ANISOU | 1373 | CB | HIS | A | 192 | 3114 | 4649 | 3860 | 218 | 215 | 440 | C |
| ATOM | 1174 | CG | HIS | A | 192 | 31.146 | 8.190 | 26.507 | 1.00 | 30.95 | C |
| ANISOU | 1374 | CG | HIS | A | 192 | 3143 | 4703 | 3910 | 237 | 262 | 422 | C |
| ATOM | 1375 | ND1 | HIS | A | 192 | 30.014 | 8.974 | 25.816 | 1.00 | 29.94 | N |
| ANISOU | 1375 | ND1 | HIS | A | 192 | 2945 | 4655 | 3777 | 232 | 285 | 417 | N |
| ATOM | 1376 | CD2 | HIS | A | 192 | 31.914 | 3.273 | 27.85 | 1.00 | 29.67 | C |
| ANISOU | 1376 | CD2 | HIS | A | 192 | 3021 | 4497 | 3755 | 212 | 263 | 405 | C |
| ATOM | 1377 | CE1 | HIS | A | 192 | 30.085 | 9.526 | 28.028 | 1.00 | 23.35 | C |
| ANISOU | 1377 | CE1 | HIS | A | 192 | 2745 | 4448 | 3078 | 303 | 327 | 395 | C |
| ATOM | 1378 | NE2 | HIS | A | 192 | 31.254 | 9.933 | 28.621 | 1 00 | 33.25 | N |
| ANISOU | 1378 | NE2 | HIS | A | 192 | 3056 | 4614 | 3825 | 253 | 327 | 388 | N |
| ATOM | 1379 | N | ALA | A | 193 | 34.571 | 8.909 | 24.482 | 1.00 | 29.31 | N |
| ANISOU | 1379 | N | ALA | A | 193 | 3096 | 4234 | 3757 | 307 | 245 | 444 | N |
| ATOM | 1380 | CA | ALA | A | 193 | 36.181 | 9.700 | 24.752 | 1.00 | 33.59 | C |
| ANISOU | 1380 | CA | ALA | A | 193 | 3312 | 4350 | 3052 | 338 | 274 | 437 | C |
| ATOM | 1381 | C | ALA | A | 193 | 35.299 | 10 815 | 23.626 | 1.00 | 26.36 | C |
| ANISOU | 1381 | C | ALA | A | 193 | 2353 | 3358 | 3491 | 417 | 285 | 480 | C |
| ATOM | 1382 | O | ALA | A | 193 | 35.453 | 12.041 | 23.934 | 1.00 | 30.25 | O |
| ANISOU | 1382 | O | ALA | A | 193 | 3297 | 4251 | 3549 | 474 | 319 | 458 | O |
| ATOM | 1383 | CB | ALA | A | 193 | 35.496 | 8.923 | 24.940 | 3.00 | 24.05 | C |
| ANISOU | 1383 | CB | ALA | A | 193 | 2538 | 3454 | 3137 | 277 | 250 | 425 | C |
| ATOM | 1384 | N | ALA | A | 194 | 35.156 | 10.433 | 22.351 | 1.00 | 30.88 | N |
| ANISOU | 1384 | N | ALA | A | 194 | 2364 | 4388 | 3982 | 424 | 258 | 482 | N |
| ATOM | 1385 | CA | ALA | A | 194 | 35.313 | 13.460 | 21.304 | 1.00 | 39.34 | C |
| ANISOU | 1385 | CA | ALA | A | 194 | 3310 | 4289 | 3919 | 490 | 270 | 510 | C |
| ATOM | 1386 | C | ALA | A | 194 | 34.243 | 12.539 | 21.476 | 1.00 | 34.26 | C |

TABLE 3-continued

| | | | | |
|---|---|---|---|---|
| ANISOU | 1386 | C ALA A 194 | 3775 4825 4413 571 234 518 | C |
| ATOM | 1387 | O ALA A 194 | 34.490 13.754 21.329 1.00 34.92 | O |
| ANISOU | 1387 | O ALA A 194 | 3885 4857 4521 637 332 532 | O |
| ATOM | 1388 | CB ALA A 194 | 35.236 10.865 19.872 1.09 31.58 | C |
| ANISOU | 1388 | CB ALA A 194 | 3482 4473 4043 448 235 533 | C |
| ATOM | 1389 | N GLY A 195 | 33.033 12.031 21.792 1.00 31.93 | N |
| ANISOU | 1389 | N GLY A 195 | 3413 4620 4100 561 268 510 | N |
| ATOM | 1390 | CA GLY A 195 | 31.833 12.939 22.059 1.00 32.14 | C |
| ANISOU | 1390 | CA GLY A 195 | 3381 4704 4125 628 275 509 | C |
| ATOM | 1391 | C GLY A 195 | 32.027 13.933 23.162 1.00 35.94 | C |
| ANISOU | 1391 | C GLY A 195 | 3520 4388 4337 653 320 467 | C |
| ATOM | 1392 | O GLY A 195 | 31.552 15.057 23.377 1.00 36.40 | O |
| ANISOU | 1392 | O GLY A 195 | 3922 5195 4714 748 335 493 | O |
| ATOM | 1393 | N LEU A 196 | 32.774 13.559 24.199 1.00 33.73 | N |
| ANISOU | 1393 | N LEU A 196 | 3620 4823 4372 605 338 461 | N |
| ATOM | 1394 | CA LEU A 196 | 33.072 14.562 25.256 1.00 32.59 | C |
| ANISOU | 1394 | CA LEU A 196 | 3532 4655 4295 637 373 434 | C |
| ATOM | 1395 | C LEU A 196 | 33.913 15.732 24.321 1.00 31.63 | C |
| ANISOU | 1395 | C LEU A 199 | 3450 4404 4201 697 399 446 | C |
| ATOM | 1396 | O LEU A 196 | 33.599 16.941 25.256 1.00 32.02 | O |
| ANISOU | 1396 | O LEU A 196 | 3482 4436 4247 703 425 434 | O |
| ATOM | 1397 | CB LEU A 196 | 33.791 13.853 25.328 1.00 30.61 | C |
| ANISOU | 1397 | CB LEU A 196 | 3250 4353 4005 559 383 404 | C |
| ATOM | 1398 | CG LEU A 196 | 32.776 12.922 27.172 1.00 34.22 | C |
| ANISOU | 1398 | CG LEU A 196 | 3059 4316 4426 507 379 350 | C |
| ATOM | 1399 | CD1 LEU A 196 | 33.621 11.839 27.992 1.00 30.65 | C |
| ANISOU | 1399 | CD1 LEU A 196 | 3242 4437 3966 414 371 376 | C |
| ATOM | 1400 | CD2 LEU A 196 | 31.776 13.740 28.034 1.00 36.84 | C |
| ANISOU | 1400 | CD2 LEU A 196 | 3940 5302 4755 559 412 365 | C |
| ATOM | 1401 | N ALA A 197 | 34.935 15.551 23.994 1.00 31.49 | N |
| ANISOU | 1401 | N ALA A 197 | 3468 4330 4155 573 390 469 | N |
| ATOM | 1402 | CA ALA A 157 | 35.745 16.613 23.425 1.00 32.73 | C |
| ANISOU | 1402 | CA ALA A 197 | 3682 4396 4357 719 410 490 | C |
| ATOM | 1403 | C ALA A 197 | 34.395 17.415 22.429 1.50 38.15 | C |
| ANISOU | 1403 | C ALA A 197 | 4355 5103 5035 334 434 527 | C |
| ATOM | 1404 | O ALA A 197 | 34.857 13.650 22.471 1.00 33.58 | O |
| ANISOU | 1404 | O ALA A 197 | 3338 4510 4525 372 425 533 | O |
| ATOM | 1405 | CB ALA A 197 | 35.954 16.031 22.792 1.00 31.28 | C |
| ANISOU | 1405 | CB ALA A 197 | 3546 4152 4177 659 404 536 | C |
| ATOM | 1406 | N TYR A 198 | 34.218 16.703 21 534 1.00 36.44 | N |

TABLE 3-continued

| | | | | | | | | | | |
|---|---|---|---|---|---|---|---|---|---|---|
| ANISOU | 1406 | N | TYR A | 198 | 4106 | 4955 | 4778 | 802 | 360 | 551 N |
| ATOM | 1407 | CA | TYR A | 198 | 33.351 | 17.353 | 20.595 | 1.00 | 43.04 | C |
| ANISOU | 1407 | CA | TYR A | 198 | 4572 | 5473 | 5246 | 882 | 354 | 586 C |
| ATOM | 1408 | C | TYR A | 198 | 32.332 | 18.207 | 21.276 | 1.00 | 40.17 | C |
| ANISOU | 1408 | C | TYR A | 198 | 4522 | 5486 | 5254 | 955 | 367 | 559 C |
| ATOM | 1409 | O | TYR A | 198 | 32.193 | 19.440 | 20.822 | 1.00 | 44.53 | O |
| ANISOU | 1409 | O | TYR A | 198 | 5095 | 5997 | 5325 | 1039 | 374 | 594 O |
| ATOM | 1410 | CB | TYR A | 198 | 32.557 | 16.334 | 19.785 | 1.00 | 43.37 | C |
| ANISOU | 1410 | CB | TYR A | 198 | 4922 | 5962 | 5593 | 861 | 309 | 600 C |
| ATOM | 1411 | CG | TYR A | 198 | 31.045 | 16.964 | 18.515 | 1.00 | 50.57 | C |
| ANISOU | 1141 | CG | TYR A | 198 | 5527 | 6904 | 6465 | 945 | 285 | 642 C |
| ATOM | 1412 | CD1 | TYR A | 198 | 32.518 | 17.199 | 17.339 | 1.00 | 52.24 | C |
| ANISOU | 1412 | CD1 | TYR A | 198 | 6090 | 7067 | 5531 | 952 | 280 | 687 C |
| ATOM | 1413 | CD2 | TYR A | 198 | 30.482 | 17.203 | 18.718 | 1.00 | 50.02 | C |
| ANISOU | 1413 | CD2 | TYR A | 198 | 5686 | 5913 | 6436 | 1036 | 256 | 539 C |
| ATOM | 1414 | CE1 | TYR A | 198 | 31.858 | 17.760 | 16.303 | 1.00 | 53.65 | C |
| ANISOU | 1414 | CE1 | TYR A | 198 | 6282 | 7275 | 5838 | 1038 | 254 | 733 C |
| ATOM | 1415 | CE2 | TYR A | 198 | 29.780 | 17.357 | 17.635 | 1.00 | 55.84 | C |
| ANISOU | 1415 | CE2 | TYR A | 198 | 5782 | 7044 | 6430 | 1337 | 236 | 670 C |
| ATOM | 1416 | CZ | TYR A | 198 | 30.477 | 18.071 | 10.427 | 1.00 | 56.52 | C |
| ANISOU | 1416 | CZ | TYR A | 198 | 6795 | 7941 | 7413 | 1102 | 220 | 726 C |
| ATOM | 1417 | OH | TYR A | 198 | 29.850 | 18.594 | 15.320 | 1.00 | 63.59 | O |
| ANISOU | 1417 | OH | TYR A | 198 | 7468 | 8535 | 8057 | 1181 | 194 | 770 O |
| ATOM | 1418 | N | LYS A | 199 | 31.318 | 17.374 | 22.435 | 1.00 | 42.42 | N |
| ANISOU | 1418 | N | LYS A | 199 | 4754 | 5829 | 5536 | 927 | 374 | 527 N |
| ATOM | 1419 | CA | LYS A | 199 | 30.840 | 18.723 | 23.113 | 1.00 | 46.20 | C |
| ANISOU | 1419 | CA | LYS A | 199 | 4813 | 5057 | 5555 | 939 | 390 | 503 C |
| ATOM | 1420 | C | LYS A | 199 | 21.426 | 19.943 | 20.823 | 1.00 | 46.02 | C |
| ANISOU | 1420 | C | LYS A | 199 | 5215 | 6220 | 6352 | 1044 | 429 | 462 C |
| ATOM | 1421 | O | LYS A | 199 | 30.737 | 20.029 | 24.112 | 1.00 | 39.55 | O |
| ANISOU | 1421 | O | LYS A | 199 | 4389 | 5413 | 5263 | 1128 | 442 | 469 O |
| ATOM | 1422 | CB | LYS A | 199 | 20.914 | 17.912 | 24.030 | 1.00 | 46.72 | C |
| ANISOU | 1422 | CB | LYS A | 199 | 5171 | 6513 | 5009 | 958 | 389 | 466 C |
| ATOM | 1423 | CG | LYS A | 199 | 29.302 | 17.001 | 23.224 | 1.00 | 48.71 | C |
| ANISOU | 1423 | CG | LYS A | 199 | 5350 | 6357 | 6251 | 940 | 1347 | 457 C |
| ATOM | 1424 | CD | LYS A | 199 | 28.429 | 15.852 | 24.056 | 1.00 | 59.06 | C |
| ANISOU | 1424 | CD | LYS A | 199 | 6720 | 8386 | 7682 | 358 | 345 | 458 C |
| ATOM | 1425 | CE | LYS A | 199 | 27.888 | 14.737 | 23.157 | 1.00 | 61.96 | C |
| ANISOU | 1425 | CE | LYS A | 199 | 1931 | 8715 | 7901 | 811 | 297 | 479 C |
| ATOM | 1426 | NZ | LYS A | 199 | 26.594 | 14.101 | 23.536 | 1.00 | 57.90 | N |

TABLE 3-continued

| | | | | | | | | | | |
|---|---|---|---|---|---|---|---|---|---|---|
| ANISOU | 1426 | NZ | LYS | A | 199 | 6314 3323 7304 | 787 | 259 | 460 | N |
| ATOM | 1427 | N | ARG | A | 200 | 32.721 19.032 24.020 | 1.00 | 40.56 | | N |
| ANISOU | 1427 | N | ARG | A | 200 | 4592 5441 5384 | 593 | 445 | 473 | N |
| ATOM | 1428 | CA | ARG | A | 200 | 33.361 21.087 24.606 | 1.00 | 39.35 | | C |
| ANISOU | 1428 | CA | ARG | A | 200 | 4491 5135 5275 | 1028 | 478 | 469 | C |
| ATOM | 1429 | C | ARG | A | 200 | 34.005 21.968 23.532 | 1.00 | 39.25 | | C |
| ANISOU | 1429 | C | ARG | A | 200 | 4545 5078 5291 | 1070 | 480 | 507 | C |
| ATOM | 1430 | O | ARG | A | 200 | 34.880 22.752 23.689 | 1.00 | 37.91 | | O |
| ANISOU | 1430 | O | ARG | A | 200 | 4433 4807 5164 | 1072 | 505 | 497 | O |
| ATOM | 1431 | CB | ARG | A | 200 | 34.455 20.509 25.531 | 1.00 | 37.57 | | C |
| ANISOU | 1431 | CB | ARG | A | 200 | 4295 4015 5062 | 544 | 494 | 424 111 | C |
| ATOM | 1432 | CG | ARG | A | 200 | 33.390 20.115 26.825 | 1.00 | 33.23 | | C |
| ANISOU | 1432 | CG | ARG | A | 200 | 4464 5232 5257 | 915 | 592 | 373 | C |
| ATOM | 1433 | CD | ARG | A | 200 | 34.974 19.404 27 556 | 1.00 | 43.31 | | C |
| ANISOU | 1433 | CD | ARG | A | 200 | 5007 5530 5770 | 625 | 505 | 349 | C |
| ATOM | 1434 | NE | ARG | A | 200 | 36.028 20.334 27.995 | 1.00 | 45.27 | | N |
| ANISOU | 1434 | NE | ARG | A | 200 | 5319 5817 6065 | 834 | 527 | 328 | N |
| ATOM | 1435 | CZ | ARG | A | 200 | 35.914 21.139 29.050 | 1.00 | 41.30 | | C |
| ANISOU | 1435 | CZ | ARG | A | 200 | 4823 5290 5560 | 366 | 550 | 281 | C |
| ATOM | 1436 | NH1 | ARG | A | 200 | 34.798 21.161 29.783 | 1.00 | 46.48 | | N |
| ANISOU | 1436 | NH1 | ARG | A | 200 | 5426 6327 6209 | 808 | 560 | 250 | N |
| ATOM | 1437 | NH2 | ARG | A | 200 | 36.932 21.900 29.384 | 1.00 | 41.85 | | N |
| ANISOU | 1437 | NH2 | ARG | A | 200 | 4950 5255 5694 | 364 | 554 | 261 | N |
| ATOM | 1438 | N | ASP | A | 201 | 33.581 21.826 22.286 | 1.00 | 36.25 | | N |
| ANISOU | 1438 | N | ASP | A | 201 | 4153 4731 4884 | 1100 | 454 | 558 | N |
| ATOM | 1439 | CA | ASP | A | 201 | 34.106 22.599 21.142 | 1.00 | 37.99 | | C |
| ANISOU | 1439 | CA | ASP | A | 201 | 4443 4872 5119 | 1140 | 455 | 615 | C |
| ATOM | 1440 | C | ASP | A | 201 | 35.616 22.445 20.890 | 1.00 | 41.36 | | C |
| ANISOU | 1440 | C | ASP | A | 201 | 4999 5276 5628 | 1069 | 476 | 628 | C |
| ATOM | 1441 | O | ASP | A | 201 | 36.254 23.377 20.410 | 1.00 | 35.40 | | O |
| ANISOU | 1441 | O | ASP | A | 201 | 4244 4365 4841 | 1095 | 495 | 660 | O |
| ATOM | 1442 | CB | ASP | A | 201 | 33.719 24.079 21.264 | 1.00 | 43.95 | | C |
| ANISOU | 1442 | CB | ASP | A | 201 | 5223 5562 5913 | 1239 | 469 | 621 | C |
| ATOM | 1443 | CG | ASP | A | 201 | 32.249 24.217 21.525 | 1.00 | 46 19 | | C |
| ANISOU | 1443 | CG | ASP | A | 201 | 5434 5936 6181 | 1313 | 450 | 503 | C |
| ATOM | 1444 | OD1 | ASP | A | 201 | 31.479 23.656 20.725 | 1.00 | 48.93 | | O |
| ANISOU | 1444 | OD1 | ASP | A | 201 | 5737 6371 6485 | 1328 | 415 | 631 | O |
| ATOM | 1445 | OD2 | ASP | A | 201 | 31.849 24.772 22.567 | 1.00 | 50.88 | | O |
| ANISOU | 1445 | OD2 | ASP | A | 201 | 6007 6525 6800 | 1349 | 469 | 554 | O |
| ATOM | 1446 | N | ILE | A | 202 | 36.157 21.255 21.194 | 1.00 | 34.53 | | N |

TABLE 3-continued

| | | | | | | | | |
|---|---|---|---|---|---|---|---|---|
| ANISOU | 1446 | N   | ILE A 202 | 4055 4082 4681 | 981 | 470 | 604 | N |
| ATOM   | 1447 | CA  | ILE A 202 | 37.569 20.956 20.807 | 1.00 | 35.66 | | C |
| ANISOU | 1447 | CA  | ILE A 202 | 4250 4459 4841 | 914 | 486 | 513 | C |
| ATOM   | 1448 | C   | ILE A 202 | 37.532 20.153 19.628 | 1.00 | 33.46 | | C |
| ANISOU | 1448 | C   | ILE A 202 | 3969 4230 4515 | 899 | 463 | 654 | C |
| ATOM   | 1449 | O   | ILE A 202 | 36.662 19.310 19.530 | 1.00 | 37.38 | | O |
| ANISOU | 1449 | O   | ILE A 202 | 4413 4819 4969 | 892 | 431 | 647 | O |
| ATOM   | 1450 | CB  | ILE A 202 | 38.170 20.126 22.056 | 1.00 | 31.89 | | C |
| ANISOU | 1450 | CB  | ILE A 202 | 3756 3987 4372 | 6134 | 490 | 558 | C |
| ATOM   | 1451 | CG1 | ILE A 202 | 38.051 20.941 23.367 | 1.00 | 34.15 | | C |
| ANISOU | 1451 | CG1 | ILE A 202 | 4043 4236 4596 | 857 | 510 | 511 | C |
| ATOM   | 1452 | CG2 | ILE A 202 | 39.623 19.658 21.718 | 1.00 | 28.60 | | C |
| ANISOU | 1452 | CG2 | ILE A 202 | 3379 3514 3970 | 765 | 500 | 563 | C |
| ATOM   | 1453 | CD1 | ILE A 202 | 38.546 22.395 20.321 | 1.00 | 36.33 | | C |
| ANISOU | 1453 | CD1 | ILE A 202 | 4375 4404 5026 | 905 | 538 | 521 | C |
| ATOM   | 1454 | N   | PRO A 203 | 38.376 20.462 18.607 | 1.00 | 36.85 | | N |
| ANISOU | 1454 | N   | PRO A 203 | 4462 4603 4946 | 895 | 478 | 697 | N |
| ATOM   | 1455 | CA  | PRO A 203 | 38.280 19.689 17.383 | 1.00 | 32.80 | | C |
| ANISOU | 1455 | CA  | PRO A 203 | 3938 4146 4379 | 885 | 455 | 732 | C |
| ATOM   | 1456 | C   | PRO A 203 | 36.545 18.172 17.522 | 1.00 | 34.34 | | C |
| ANISOU | 1456 | C   | PRO A 203 | 4132 4399 4546 | 307 | 433 | 698 | C |
| ATOM   | 1457 | O   | PRO A 203 | 39.423 17 718 18.312 | 1.00 | 29.30 | | O |
| ANISOU | 1457 | O   | PRO A 203 | 3468 3728 3936 | 745 | 447 | 560 | O |
| ATOM   | 1458 | CB  | PRO A 203 | 39.364 20.312 16.437 | 1.00 | 36.68 | | C |
| ANISOU | 1458 | CB  | PRO A 203 | 4498 4557 4881 | 884 | 487 | 779 | C |
| ATOM   | 1459 | CG  | PRO A 203 | 40.360 20.893 17.426 | 1.00 | 41.83 | | C |
| ANISOU | 1459 | CG  | PRO A 203 | 5175 5117 5600 | 851 | 525 | 749 | C |
| ATOM   | 1460 | CD  | PRO A 203 | 39.492 21.430 18.561 | 1.00 | 41.64 | | C |
| ANISOU | 1460 | CD  | PRO A 203 | 5121 5098 5602 | 891 | 518 | 713 | C |
| ATOM   | 1461 | N   | VAL A 204 | 37.775 17.401 16.759 | 1.00 | 28.37 | | N |
| ANISOU | 1461 | N   | VAL A 204 | 3316 3727 3735 | 813 | 395 | 712 | N |
| ATOM   | 1462 | CA  | VAL A 204 | 37.597 15.935 16.776 | 1 00 | 28.92 | | C |
| ANISOU | 1462 | CA  | VAL A 204 | 3361 3852 3776 | 744 | 368 | 682 | C |
| ATOM   | 1463 | C   | VAL A 204 | 38.044 15.529 5.359 | 1.00 | 29.16 | | C |
| ANISOU | 1463 | C   | VAL A 204 | 3414 3907 3758 | 748 | 353 | 715 | C |
| ATOM   | 1464 | O   | VAL A 204 | 37.164 15.886 14.568 | 1.00 | 29.73 | | O |
| ANISOU | 1464 | O   | VAL A 204 | 3478 4023 3701 | 805 | 321 | 749 | O |
| ATOM   | 1465 | CB  | VAL A 204 | 36.302 15.267 17.354 | 1.00 | 30.57 | | C |
| ANISOU | 1465 | CB  | VAL A 204 | 3501 4150 3964 | 737 | 331 | 354 | C |
| ATOM   | 1466 | CG1 | VAL A 204 | 36.580 13.712 17.293 | 1.00 | 29.25 | | C |

TABLE 3-continued

| | | | | | | | | | | | |
|---|---|---|---|---|---|---|---|---|---|---|---|
| ANISOU | 1466 | CG1 | VAL | A | 204 | 3313 | 4035 | 3765 | 864 | 297 | 629 | C |
| ATOM | 1467 | CG2 | VAL | A | 204 | 33.425 | 15.701 | 18.850 | 1.00 | 23.94 | C |
| ANISOU | 1467 | CG2 | VAL | A | 204 | 3271 | 3927 | 3798 | 737 | 351 | 613 | C |
| ATOM | 1468 | N | VAL | A | 205 | 39.055 | 14.745 | 15.035 | 1.00 | 28.03 | N |
| ANISOU | 1468 | N | VAL | A | 205 | 3295 | 3746 | 3609 | 693 | 359 | 703 | N |
| ATOM | 1469 | CA | VAL | A | 205 | 39.282 | 14.245 | 13.635 | 1.00 | 27.42 | C |
| ANISOU | 1469 | CA | VAL | A | 205 | 3242 | 8698 | 3477 | 695 | 345 | 728 | C |
| ATOM | 1470 | C | VAL | A | 205 | 39.057 | 12.709 | 13.704 | 1.00 | 31.77 | C |
| ANISOU | 1470 | C | VAL | A | 205 | 3762 | 4309 | 4001 | 637 | 303 | 688 | C |
| ATOM | 1471 | O | VAL | A | 205 | 39.705 | 12.045 | 14.504 | 1.00 | 33.42 | O |
| ANISOU | 1471 | O | VAL | A | 205 | 3933 | 4492 | 4239 | 581 | 333 | 647 | O |
| ATOM | 1472 | CB | VAL | A | 205 | 40.714 | 14.506 | 13.145 | 1.00 | 27.28 | C |
| ANISOU | 1472 | CB | VAL | A | 205 | 3273 | 3605 | 3470 | 675 | 353 | 741 | C |
| ATOM | 1473 | CG1 | VAL | A | 205 | 41.000 | 13.875 | 11.755 | 1.00 | 28.33 | C |
| ANISOU | 1473 | CG1 | VAL | A | 205 | 3437 | 3780 | 3547 | 672 | 364 | 758 | C |
| ATOM | 1474 | CG2 | VAL | A | 205 | 40.949 | 16.046 | 13.028 | 1.00 | 31.16 | C |
| ANISOU | 1474 | CG2 | VAL | A | 205 | 3308 | 4033 | 3998 | 725 | 436 | 788 | C |
| ATOM | 1475 | N | SER | A | 206 | 38.190 | 12.157 | 12.873 | 1.00 | 32.33 | N |
| ANISOU | 1475 | N | SER | A | 206 | 3814 | 4455 | 4015 | 551 | 259 | 394 | N |
| ATOM | 1476 | CA | SER | A | 206 | 37.973 | 10.713 | 12.900 | 1.00 | 34.46 | C |
| ANISOU | 1476 | CA | SER | A | 206 | 4059 | 4774 | 4261 | 594 | 213 | 654 | C |
| ATOM | 1477 | C | SER | A | 206 | 38.725 | 10.053 | 11.775 | 1.00 | 35.82 | C |
| ANISOU | 1477 | C | SER | A | 206 | 4271 | 4945 | 4394 | 579 | 213 | 552 | C |
| ATOM | 1478 | O | SER | A | 206 | 38.715 | 10.571 | 10.647 | 1.00 | 25.54 | O |
| ANISOU | 1478 | O | SER | A | 206 | 3517 | 4175 | 3570 | 5624 | 219 | 589 | O |
| ATOM | 1479 | CB | SER | A | 206 | 36.493 | 10.413 | 12.710 | 1.00 | 34.89 | C |
| ANISOU | 1479 | CB | SER | A | 206 | 4060 | 4916 | 4279 | 611 | 164 | 855 | C |
| ATOM | 1480 | OG | SER | A | 206 | 35.931 | 10.754 | 13.542 | 1.00 | 42.02 | O |
| ANISOU | 1480 | OG | SER | A | 206 | 4921 | 5822 | 5221 | 309 | 172 | 843 | O |
| ATOM | 1481 | N | LEU | A | 207 | 39.333 | 8.520 | 12.096 | 1.00 | 31.44 | N |
| ANISOU | 1481 | N | LEU | A | 207 | 3717 | 4378 | 3849 | 518 | 201 | 308 | N |
| ATOM | 1482 | CA | LEU | A | 207 | 39.970 | 8.105 | 11.003 | 1.00 | 32.95 | C |
| ANISOU | 1482 | CA | LEU | A | 207 | 3945 | 4583 | 4033 | 502 | 192 | 594 | C |
| ATOM | 1483 | C | LEU | A | 207 | 39.255 | 5.789 | 10.972 | 1.00 | 33.08 | C |
| ANISOU | 1483 | C | LEU | A | 207 | 3931 | 4550 | 3937 | 462 | 130 | 553 | C |
| ATOM | 1484 | O | LEU | A | 207 | 39.400 | 5.985 | 11.882 | 1.00 | 31.37 | O |
| ANISOU | 1484 | O | LEU | A | 207 | 3700 | 4417 | 3804 | 409 | 114 | 522 | O |
| ATOM | 1485 | CB | LEU | A | 207 | 41.395 | 7.824 | 11.423 | 1.00 | 33.46 | C |
| ANISOU | 1485 | CB | LEU | A | 207 | 4032 | 4576 | 4106 | 467 | 228 | 568 | C |
| ATOM | 1486 | CG | LEU | A | 207 | 42.367 | 8.951 | 11.583 | 1.00 | 36.75 | C |

TABLE 3-continued

| | | | | | | | | | |
|---|---|---|---|---|---|---|---|---|---|
| ANISOU | 1486 | CG | LEU | A | 207 | 4475 4525 4563 | 489 | 293 | 595 C |
| ATOM | 1487 | CD1 | LEU | A | 207 | 43.802 8.449 11.673 | 1.00 | 37.87 | C |
| ANISOU | 1487 | CD1 | LEU | A | 207 | 4538 5018 4734 | 452 | 320 | 562 C |
| ATOM | 1488 | CD2 | LEU | A | 207 | 42.284 9.979 10.389 | 1.00 | 36.79 | C |
| ANISOU | 1488 | CD2 | LEU | A | 207 | 4511 4941 4525 | 545 | 320 | 850 C |
| ATOM | 1489 | N | THR | A | 208 | 38.455 6.544 9.900 | 1.00 | 33.55 | N |
| ANISOU | 1489 | N | THR | A | 208 | 4000 4783 3997 | 485 | 90 | 567 N |
| ATOM | 1490 | CA | THR | A | 208 | 37.541 5.357 9.909 | 1.00 | 32.07 | C |
| ANISOU | 1490 | CA | THR | A | 208 | 3755 4647 3774 | 443 | 24 | 532 C |
| ATOM | 1491 | C | THR | A | 208 | 37.534 4.725 8.545 | 1.00 | 32.35 | C |
| ANISOU | 1491 | C | THR | A | 208 | 3831 4716 3744 | 451 | -6 | 519 C |
| ATOM | 1492 | O | THR | A | 208 | 38.458 5.135 7.712 | 1.00 | 31.69 | O |
| ANISOU | 1492 | O | THR | A | 208 | 3794 452 3635 | 484 | 29 | 535 O |
| ATOM | 1493 | CB | THR | A | 208 | 36.049 5.831 9.980 | 1.00 | 39.50 | C |
| ANISOU | 1493 | CB | THR | A | 208 | 4652 5653 4700 | 472 | -10 | 556 C |
| ATOM | 1494 | OG1 | THR | A | 208 | 35.754 6.512 8.729 | 1.00 | 33.53 | O |
| ANISOU | 1494 | OG1 | THR | A | 208 | 4543 5571 4520 | 537 | -15 | 592 O |
| ATOM | 1495 | CG2 | THR | A | 208 | 35.899 6.330 11.034 | 1.00 | 36.41 | C |
| ANISOU | 1495 | CG2 | THR | A | 208 | 4490 5403 4011 | 491 | 27 | 577 C |
| ATOM | 1496 | N | ASN | A | 209 | 36.808 3.712 8.324 | 1.00 | 29.02 | N |
| ANISOU | 1496 | N | ASN | A | 209 | 3423 4386 3332 | 417 | -70 | 486 N |
| ATOM | 1497 | CA | ASN | A | 209 | 36.599 3.100 7.005 | 1.00 | 23.54 | C |
| ANISOU | 1497 | CA | ASN | A | 209 | 3350 4333 3154 | 425 | -109 | 471 C |
| ATOM | 1498 | C | ASN | A | 209 | 35.245 3.122 6.568 | 1.00 | 32.35 | C |
| ANISOU | 1498 | C | ASN | A | 209 | 3850 4902 3669 | 441 | -169 | 481 C |
| ATOM | 1499 | O | ASN | A | 209 | 34.533 2.307 5.753 | 1.00 | 33.31 | O |
| ANISOU | 1499 | O | ASN | A | 209 | 3912 5067 3678 | 425 | -224 | 452 O |
| ATOM | 1500 | CB | ASN | 0 | 209 | 37.149 1.582 7.087 | 1.00 | 25.05 | C |
| ANISOU | 1500 | CB | ASN | A | 209 | 3413 4359 2223 | 359 | -143 | 407 C |
| ATOM | 1501 | CG | ASN | A | 209 | 38.628 1.420 7.407 | 1.00 | 32.49 | C |
| ANISOU | 1501 | CG | ASN | A | 209 | 3909 4723 3709 | 343 | -92 | 389 C |
| ATOM | 1502 | OD1 | ASN | A | 209 | 39.411 0.963 6.561 | 1.00 | 32.52 | O |
| ANISOU | 1502 | OD1 | ASN | A | 209 | 3968 4733 3693 | 355 | -86 | 363 O |
| ATOM | 1503 | ND2 | ASN | A | 209 | 35.997 1.374 3.627 | 1.00 | 25.74 | N |
| ANISOU | 1503 | ND2 | ASN | A | 209 | 3039 3822 2920 | 226 | -52 | 395 N |
| ATOM | 1504 | N | ILE | A | 210 | 34.483 4.107 7.046 | 1.00 | 31.45 | N |
| ANISOU | 1504 | N | ILE | A | 210 | 3631 4408 3511 | 475 | -150 | 521 N |
| ATOM | 1505 | CA | ILE | A | 210 | 32.126 4.238 6.586 | 1.00 | 37.91 | C |
| ANISOU | 1505 | CA | ILE | A | 210 | 4430 5712 4292 | 501 | -214 | 533 C |
| ATOM | 1506 | C | ILE | A | 210 | 32.725 5.739 60.601 | 1 00 | 34.78 | C |

TABLE 3-continued

| | | | | | | | | | |
|---|---|---|---|---|---|---|---|---|---|
| ANISOU | 1506 | C | ILE | A | 210 | 3990 5325 3930 581 -135 592 | | | C |
| ATOM | 1507 | O | ILE | A | 210 | 33.123 5.475 7.480 1.00 37.23 | | | O |
| ANISOU | 1507 | O | ILE | A | 210 | 4297 5578 4260 592 -132 511 | | | O |
| ATOM | 1508 | CB | ILE | A | 210 | 32.179 3.303 7.402 1.00 38.91 | | | C |
| ANISOU | 1508 | CB | ILE | A | 210 | 4460 5877 4448 432 -293 497 | | | C |
| ATOM | 1509 | CG1 | ILE | A | 210 | 30.869 3.133 6.575 1.00 42.64 | | | C |
| ANISOU | 1509 | CG1 | ILE | A | 210 | 4882 6446 4873 445 -333 495 | | | C |
| ATOM | 1510 | CG2 | ILE | A | 210 | 31.992 3.775 8.733 1.00 36.54 | | | C |
| ANISOU | 1510 | CG2 | ILE | A | 210 | 4117 5353 4212 419 -227 509 | | | C |
| ATOM | 1511 | CD1 | ILE | A | 210 | 30.729 1.731 6.144 1.00 42.06 | | | C |
| ANISOU | 1511 | CD1 | ILE | A | 210 | 481.5 6395 4760 381 -395 442 | | | C |
| ATOM | 1512 | N | ASN | A | 211 | 32.335 6.171 5.567 1.00 37.89 | | | N |
| ANISOU | 1512 | N | ASN | A | 211 | 4381 5780 4235 639 -221 619 | | | N |
| ATOM | 1513 | CA | ASN | A | 211 | 31.559 7.555 5.504 1.00 41.85 | | | C |
| ANISOU | 1513 | CA | ASN | A | 211 | 4373 6291 4734 722 -203 676 | | | C |
| ATOM | 1514 | C | ASN | A | 211 | 30.559 7.999 6.535 1.00 40.65 | | | C |
| ANISOU | 1514 | C | ASN | A | 211 | 4645 6169 4640 732 -239 650 | | | C |
| ATOM | 1515 | O | ASN | A | 211 | 30.654 9.131 7.002 1.00 43.30 | | | O |
| ANISOU | 1515 | O | ASN | A | 211 | 5046 6527 5070 783 -166 716 | | | O |
| ATOM | 1516 | CB | ASN | A | 211 | 31.073 7.872 4.079 1.00 41.05 | | | C |
| ANISOU | 1516 | CB | ASN | A | 211 | 4792 6251 4553 785 -247 706 | | | C |
| ATOM | 1517 | CG | ASN | A | 211 | 32.217 7.817 3.114 1.00 45.85 | | | C |
| ANISOU | 1517 | CG | ASN | A | 211 | 5484 6821 5111 792 -216 717 | | | C |
| ATOM | 1518 | OD1 | ASN | A | 211 | 33.112 5.648 3.173 1.00 48.31 | | | O |
| ANISOU | 1518 | OD1 | ASN | A | 211 | 5849 7065 5441 819 -149 754 | | | O |
| ATOM | 1519 | ND2 | ASN | A | 211 | 32.293 6.751 2.349 1.00 52.29 | | | N |
| ANISOU | 1519 | ND2 | ASN | A | 211 | 6321 7673 5573 757 -257 670 | | | N |
| ATOM | 1520 | N | HIS | A | 212 | 29.590 7.139 6.879 1.00 35.59 | | | N |
| ANISOU | 1520 | N | HIS | A | 212 | 4313 5972 4380 684 -252 643 | | | N |
| ATOM | 1521 | CA | HIS | A | 212 | 2.575 7.558 7.450 1.00 35.54 | | | C |
| ANISOU | 1521 | CA | HIS | A | 212 | 3853 5637 4051 694 -285 645 | | | C |
| ATOM | 1522 | C | HIS | A | 212 | 28.474 6.634 9.018 1.00 34.41 | | | C |
| ANISOU | 1522 | C | HIS | A | 212 | 3854 5479 3942 504 -280 802 | | | C |
| ATOM | 1523 | O | HIS | A | 212 | 28.433 5.403 8.847 1.00 32.84 | | | O |
| ANISOU | 1523 | O | HIS | A | 212 | 3451 5298 3723 530 -300 554 | | | O |
| ATOM | 1524 | CB | HIS | A | 212 | 27.225 7.842 7.193 1.00 40.20 | | | C |
| ANISOU | 1524 | CB | HIS | A | 212 | 4365 6313 4591 735 -333 651 | | | C |
| ATOM | 1525 | CG | HIS | A | 212 | 27.250 8.464 5.917 1.00 42.65 | | | C |
| ANISOU | 1525 | CG | HIS | A | 212 | 4749 5665 4867 826 -350 697 | | | C |
| ATOM | 1526 | ND1 | HIS | A | 212 | 27.092 9.812 8.925 1.00 43.91 | | | N |

TABLE 3-continued

```
ANISOU 1526  ND1 HIS A 212     4890 6782 5032   913 -324  747       N
ATOM   1527  CD2 HIS A 212    27.407   8.068   4.590  1.00 45.33    C
ANISOU 1527  CD2 HIS A 212     5110 7007 5106   838 -352  700       C
ATOM   1528  CE1 HIS A 212    27.185  13.261   4.662  1.00 45.23    C
ANISOU 1528  CE1 HIS A 212     5111 5961 5115   981 -347  788       C
ATOM   1529  NE2 HIS A 212    27.345   9.204   3.849  1.00 45.75    N
ANISOU 1529  NE2 HIS A 212     5196 7051 5120  9333 -389  756       N
ATOM   1530  N   SER A 213    28.353   7.160  10.215  1.00 34.32    N
ANISOU 1530  N   SER A 213     3510 5447 3985   505 -217  606       N
ATOM   1531  CA  SER A 213    28.493   6.306  11.352  1.00 34.29    C
ANISOU 1531  CA  SER A 213     3583 5424 4020   517 -204  570       C
ATOM   1532  C   SER A 213    28.102   7.227  12.492  1.00 35.78    C
ANISOU 1532  C   SER A 213     3728 5613 4255   549 -350  582       C
ATOM   1533  O   SER A 213    28.087   9.439  12.303  1.00 35.36    O
ANISOU 1533  O   SER A 213     3688 5547 4208   635 -135  814       O
ATOM   1534  CB  SER A 213    22.976   5.835  11.457  1.00 32.35    C
ANISOU 1534  CB  SER A 213     3612 5272 3976   473 -170  553       C
ATOM   1535  OG  SER A 213    30.749   6.853  12.157  1.00 32.85    O
ANISOU 1535  OG  SER A 213     3513 5072 3690   510   -1.00 573     O
ATOM   1536  N   PRO A 214    27.817   5.667  13.890  1.00 35.60    N
ANISOU 1536  N   PRO A 214     3812 5753 4417   481 -147  556       N
ATOM   1537  CA  PRO A 214    27.584   7.482  14.903  1.00 37.15    C
ANISOU 1537  CA  PRO A 214     3823 5791 4503   505  -97  559       C
ATOM   1538  C   PRO A 214    23.712   6.511  15.156  1.00 35.29    C
ANISOU 1538  C   PRO A 214     3660 5457 4293   557  -39  578       C
ATOM   1539  O   PRO A 214    28.499   9.962  15.658  1.00 33.57    O
ANISOU 1539  O   PRO A 214     3427 5227 4100   623   -2  591       O
ATOM   1540  CB  PRO A 214    27.816   6.421  16.033  1.00 35.98    C
ANISOU 1540  CB  PRO A 214     3651 5640 4372   402  -90  529       C
ATOM   1541  CG  PRO A 214    27.058   5.168  15.353  1.00 38.66    C
ANISOU 1541  CG  PRO A 214     3966 8039 4585   335 -154  512       C
ATOM   1542  CD  PRO A 214    27.498   5.228  13.905  1.00 36.72    C
ANISOU 1542  CD  PRO A 214     8774 5775 4401   378 -136  523       C
ATOM   1543  N   LEU A 215    29.535   8.033  14.873  1.00 35.02    N
ANISOU 1543  N   LEU A 215     3702 5347 4257   523  -28  575       N
ATOM   1544  CA  LEU A 215    31.102   3.940  15.053  1.00 33.68    C
ANISOU 1544  CA  LEU A 215     3600 5083 4114   558   25  590       C
ATOM   1545  C   LEU A 215    31.110  13.139  14.116  1.00 30.35    C
ANISOU 1545  C   LEU A 215     3843 5281 4311   653   34  531       C
ATOM   1546  O   LEU A 215    31.572  11.250  14.453  1.00 37.01    O
```

TABLE 3-continued

| | | | |
|---|---|---|---|
| ANISOU | 1546 O   LEU A 215 | 4050 5431 4552   703   79 643 | O |
| ATOM   | 1547 CB  LEU A 215 | 32.417  8.082 15.317 1.00 31.71 | C |
| ANISOU | 1547 CB  LEU A 215 | 3415 4784 3889   493   33 572 | C |
| ATOM   | 1548 CG  LEU A 215 | 33.776  8.780 15.309 1.00 32.72 | C |
| ANISOU | 1548 CG  LEU A 215 | 3611 4794 4032   510   83 580 | C |
| ATOM   | 1549 CD1 LEU A 215 | 33.784  9.359 18.715 1.00 34.91 | C |
| ANISOU | 1549 CD1 LEU A 215 | 3869 5043 4354   506  126 570 | C |
| ATOM   | 1550 CD2 LEU A 215 | 34.978  7.768 15.217 1.00 26.46 | C |
| ANISOU | 1550 CD2 LEU A 215 | 2869 3948 3243   446   85 557 | C |
| ATOM   | 1551 N   SER A 216 | 30.589  9.991 12.894 1.00 39.82 | N |
| ANISOU | 1551 N   SER A 216 | 4400 5901 4320   682  -11 648 | N |
| ATOM   | 1552 CA  SER A 216 | 30.650 11.180 12.008 1.00 43.87 | C |
| ANISOU | 1552 CA  SER A 216 | 4951 6394 5325   775   -2 694 | C |
| ATOM   | 1553 C   SER A 216 | 29.895 12.392 12.508 1.00 42.67 | C |
| ANISOU | 1553 C   SER A 216 | 4761 6251 5200   853   14 713 | C |
| ATOM   | 1554 O   SER A 216 | 30.320 13.507 12.276 1.00 44.91 | O |
| ANISOU | 1554 O   SER A 216 | 5092 5475 5496   917   45 748 | O |
| ATOM   | 1555 CB  SER A 216 | 30.242 10.855 10.536 1.00 43.78 | C |
| ANISOU | 1555 CB  SER A 216 | 4889 6370 5184   799  -53 713 | C |
| ATOM   | 1556 OG  SER A 216 | 29.189 10.119 10.521 1.00 43.21 | O |
| ANISOU | 1556 OG  SER A 216 | 4805 6455 5155   775 -109 689 | O |
| ATOM   | 1557 N   SER A 217 | 28.857 12.224 13.302 1.00 40.28 | N |
| ANISOU | 1557 N   SER A 217 | 4377 6014 4915   846    0 689 | N |
| ATOM   | 1558 CA  SER A 217 | 28.188 13.389 13.762 1.00 40.42 | C |
| ANISOU | 1558 CA  SER A 217 | 4260 5088 4959   927   17 702 | C |
| ATOM   | 1559 C   SER A 217 | 28.912 13.938 15.015 1.00 44.89 | C |
| ANISOU | 1559 C   SER A 217 | 4953 5524 5580   915   81 585 | C |
| ATOM   | 1560 O   SER A 217 | 28.448 14.868 15.625 1.00 44.04 | O |
| ANISOU | 1560 O   SER A 217 | 4820 5412 5502   975  193 685 | O |
| ATOM   | 1561 CB  SER A 217 | 25.700 13.046 14.064 1.00 48.70 | C |
| ANISOU | 1561 CB  SER A 217 | 5299 7203 6002   921  -22 680 | C |
| ATOM   | 1562 OG  SER A 217 | 26.629 12.440 15.852 1.00 54.10 | O |
| ANISOU | 1562 OG  SER A 217 | 5941 7899 5714   857    4 539 | O |
| ATOM   | 1563 N   LEU A 218 | 30.072 13.989 15.397 1.00 35.24 | N |
| ANISOU | 1563 N   LEU A 218 | 2792 5247 4284   842  108 670 | N |
| ATOM   | 1564 CA  LEU A 218 | 30.830 13.989 15.505 1.00 27.25 | C |
| ANISOU | 1564 CA  LEU A 218 | 4081 5422 4683   837  164 655 | C |
| ATOM   | 1565 C   LEU A 218 | 32.225 14.287 16.041 1.00 38.53 | C |
| ANISOU | 1565 C   LEU A 218 | 4381 5486 4850   833  192 575 | C |
| ATOM   | 1566 O   LEU A 218 | 33.132 14.157 16.860 1.00 43.95 | O |

TABLE 3-continued

| | | | | | | | |
|---|---|---|---|---|---|---|---|
| ANISOU | 1566 | O LEU A 218 | 5334 5099 5567 | 783 | 225 | 552 | O |
| ATOM | 1567 | CB LEU A 218 | 80.965 12.978 17.693 | 1.00 | 28.15 | | C |
| ANISOU | 1567 | CB LEU A 218 | 4154 5537 4803 | 744 | 172 | 610 | C |
| ATOM | 1568 | CG LEU A 218 | 29.584 12.271 18.255 | 1.00 | 41.48 | | C |
| ANISOU | 1568 | CG LEU A 218 | 4486 6063 5213 | 719 | 143 | 587 | C |
| ATOM | 1569 | CD1 LEU A 218 | 30.055 11.076 13.959 | 1.00 | 40.64 | | C |
| ANISOU | 1569 | CD1 LEU A 218 | 4377 5950 5104 | 612 | 144 | 557 | C |
| ATOM | 1570 | CD2 LEU A 218 | 29.012 13.403 19.177 | 1.00 | 42.90 | | C |
| ANISOU | 1570 | CD2 LEU A 218 | 4623 6257 5421 | 761 | 180 | 575 | C |
| ATOM | 1571 | N SER A 219 | 32.380 14.638 14.755 | 1.00 | 27.47 | | N |
| ANISOU | 1571 | N SER A 219 | 4223 5830 4582 | 872 | 179 | 715 | N |
| ATOM | 1572 | CA SER A 219 | 32.718 14.172 14.117 | 1.00 | 37.09 | | C |
| ANISOU | 1572 | CA SER A 219 | 4257 5231 4635 | 850 | 207 | 738 | C |
| ATOM | 1573 | C SER A 219 | 33.810 15.124 13.465 | 1.00 | 38.91 | | C |
| ANISOU | 1573 | C SER A 219 | 4533 5383 4869 | 942 | 225 | 789 | C |
| ATOM | 1574 | O SER A 219 | 22.351 16.524 12.755 | 1.00 | 28.48 | | O |
| ANISOU | 1574 | O SER A 219 | 4459 5380 4783 | 1009 | 193 | 819 | O |
| ATOM | 1575 | CB SER A 219 | 38.921 12.708 13.023 | 1.00 | 36.22 | | C |
| ANISOU | 1575 | CB SER A 219 | 4160 5131 4470 | 821 | 173 | 741 | C |
| ATOM | 1576 | OG SER A 219 | 33.950 12.422 13.534 | 1.00 | 37.53 | | O |
| ANISOU | 1576 | OG SER A 219 | 4296 5323 4537 | 740 | 154 | 695 | O |
| ATOM | 1577 | N THR A 220 | 34.882 16.865 13.788 | 1.00 | 38.05 | | N |
| ANISOU | 1577 | N THR A 220 | 4481 5175 4800 | 940 | 277 | 800 | N |
| ATOM | 1578 | CA THR A 220 | 35.127 16.157 13.081 | 1.00 | 38.09 | | C |
| ANISOU | 1578 | CA THR A 220 | 4543 5117 4817 | 1009 | 300 | 855 | C |
| ATOM | 1579 | C THR A 220 | 35.552 17.862 11.645 | 1.00 | 39.19 | | C |
| ANISOU | 1579 | C THR A 220 | 4728 5268 4594 | 1008 | 290 | 897 | C |
| ATOM | 1580 | O THR A 220 | 35.225 18.607 10.744 | 1.00 | 35.37 | | O |
| ANISOU | 1580 | O THR A 220 | 4275 4731 4382 | 1073 | 232 | 550 | O |
| ATOM | 1581 | CB THR A 220 | 30.168 19.027 13.344 | 1.00 | 34.27 | | C |
| ANISOU | 1581 | CB THR A 220 | 4135 4521 4394 | 995 | 357 | 851 | C |
| ATOM | 1582 | OG1 THR A 220 | 35.323 18.065 15.240 | 1.00 | 37.58 | | O |
| ANISOU | 1582 | OG1 THR A 220 | 4480 4941 4856 | 987 | 353 | 801 | O |
| ATOM | 1583 | CG2 THR A 220 | 35.225 20.498 13.393 | 1.00 | 35.05 | | C |
| ANISOU | 1583 | CG2 THR A 220 | 4642 4930 4896 | 1073 | 379 | 906 | C |
| ATOM | 1584 | N GLU A 221 | 36.390 16.836 11.404 | 1.00 | 34.30 | | N |
| ANISOU | 1584 | N GLU A 221 | 4197 4723 4335 | 934 | 297 | 872 | N |
| ATOM | 1585 | CA GLU A 221 | 36.854 15.395 10.164 | 1.00 | 31.37 | | C |
| ANISOU | 1585 | CA GLU A 221 | 3853 4963 3883 | 825 | 291 | 889 | C |
| ATOM | 1586 | C GLU A 221 | 35.583 14.654 19.115 | 1.00 | 35.52 | | C |

TABLE 3-continued

| | | | | | |
|---|---|---|---|---|---|
| ANISOU | 1586 | C   | GLU A 221 | 4233 4837 4325  857  258  849 | C |
| ATOM   | 1587 | O   | GLU A 221 | 95.937 14.217 11.175 1.00 33.00 | O |
| ANISOU | 1587 | O   | GLU A 221 | 3927 4553 4042  505  256  800 | O |
| ATOM   | 1588 | CB  | GLU A 221 | 38.316 16.349  9.940 1.00 31.94 | C |
| ANISOU | 1588 | CB  | GLU A 221 | 3327 4382 3325  899  553  319 | C |
| ATOM   | 1589 | CG  | GLU A 221 | 38.522 18.350 10.198 1.00 36.88 | C |
| ANISOU | 1589 | CG  | GLU A 221 | 4554 4813 4501  943  357  901 | C |
| ATOM   | 1590 | CD  | GLU A 221 | 38.135 19.358  9.121     45.37 | C |
| ANISOU | 1590 | CD  | GLU A 221 | 5840 6014 5753 1322  391 1036 | C |
| ATOM   | 1591 | OE1 | GLU A 221 | 37.583 18.901  8.071 1.00 41.04 | O |
| ANISOU | 1591 | OE1 | GLU A 221 | 5156 5414 5015 1046  352 1058 | O |
| ATOM   | 1592 | OE2 | GLU A 221 | 38.351 20.632  9.327 1.00 47.32 | O |
| ANISOU | 1592 | OE2 | GLU A 221 | 5076 6127 6003 1060  425 1073 | O |
| ATOM   | 1593 | N   | MET A 222 | 36.941 34.252  8.920 1.00 32.33 | N |
| ANISOU | 1593 | N   | MET A 222 | 3901 4523 3555  555  235  551 | N |
| ATOM   | 1594 | CA  | MET A 222 | 37.053 12.787  8.858 1.00 40.53 | C |
| ANISOU | 1594 | CA  | MET A 222 | 4838 5554 4840  790  203  810 | C |
| ATOM   | 1595 | C   | MET A 222 | 38.004 12.428  7.724 1.00 40.55 | C |
| ANISOU | 1595 | C   | MET A 222 | 4975 5607 4524  777  222  820 | C |
| ATOM   | 1596 | O   | MET A 222 | 37.985 13.079  6.705 1.00 41.53 | O |
| ANISOU | 1596 | O   | MET A 222 | 5975 5573 4839  826  230  870 | O |
| ATOM   | 1597 | CB  | MET A 222 | 55.108 12.167  8.430 1.00 44.61 | C |
| ANISOU | 1597 | CB  | MET A 222 | 5385 6223 5335  805  133  800 | C |
| ATOM   | 1598 | CG  | MET A 222 | 34.771 11.743  9.544 1.00 54.18 | C |
| ANISOU | 1598 | CG  | MET A 222 | 5524 7480 5582  780  132  763 | C |
| ATOM   | 1599 | SD  | MET A 222 | 33.983 15.126  9.175 1.00 54.33 | S |
| ANISOU | 1599 | SD  | MET A 222 | 6560 7655 6617  724   23  716 | S |
| ATOM   | 1600 | CE  | MET A 222 | 33.384  9.717 10.821 1.00 49.94 | C |
| ANISOU | 1600 | CE  | MET A 222 | 5368 7048 6058  673   25  575 | C |
| ATOM   | 1601 | N   | LEU A 223 | 35.793 11.353 7687  1.00 37.07 | N |
| ANISOU | 1601 | N   | LEU A 223 | 4514 5231 4466  715  227  773 | N |
| ATOM   | 1602 | CA  | LEU A 223 | 59.557 39.432  6.731 1.00 43.48 | C |
| ANISOU | 1602 | CA  | LEU A 223 | 5013 5600 4757  704  235  771 | C |
| ATOM   | 1603 | C   | LEU A 223 | 39.032  9.402  6.735 1.00 38.74 | C |
| ANISOU | 1603 | C   | LEU A 223 | 4761 5439 4520  663  174  715 | C |
| ATOM   | 1604 | O   | LEU A 223 | 38.871  5.525  7.743 1.00 34.30 | O |
| ANISOU | 1604 | O   | LEU A 223 | 4151 4865 4004  620  158  678 | O |
| ATOM   | 1605 | CB  | LEU A 223 | 41.038 10.885  6.934 1.30 42.92 | C |
| ANISOU | 1605 | CB  | LEU A 223 | 5955 5837 5115  670  239  769 | C |
| ATOM   | 1606 | CG  | LEU A 223 | 41.712 12.255  6.8929 1.00 45.92 | C |

TABLE 3-continued

| | | | | | | | | | |
|---|---|---|---|---|---|---|---|---|---|
| ANISOU | 1606 | CG | LEU A 223 | 5774 6152 5321 703 364 835 | | | | | C |
| ATOM | 1607 | CD1 | LEU A 223 | 43.221 | 12.124 | 6.847 | 1.00 | 38.40 | C |
| ANISOU | 1607 | CD1 | LEU A 223 | 4846 5146 4000 660 423 799 | | | | | C |
| ATOM | 1608 | CD2 | LEU A 223 | 41.239 | 13.039 | 5.599 | 1.00 | 47.31 | C |
| ANISOU | 1608 | CD2 | LEU A 223 | 5939 6358 5629 762 365 882 | | | | | C |
| ATOM | 1609 | N | VAL A 224 | 38.692 | 8.913 | 5.520 | 1.00 | 35.69 | N |
| ANISOU | 1609 | N | VAL A 224 | 4391 5112 4056 678 139 715 | | | | | N |
| ATOM | 1610 | CA | VAL A 224 | 38.053 | 7.619 | 5.337 | 1.00 | 33.42 | C |
| ANISOU | 1610 | CA | VAL A 224 | 4077 4885 3737 647 72 664 | | | | | C |
| ATOM | 1611 | C | VAL A 224 | 38.975 | 6.699 | 4.534 | 1.00 | 34.94 | C |
| ANISOU | 1611 | C | VAL A 224 | 4310 5077 3839 617 75 523 | | | | | C |
| ATOM | 1612 | O | VAL A 224 | 39.263 | 6.987 | 3.417 | 1.00 | 34.78 | O |
| ANISOU | 1612 | O | VAL A 224 | 4333 5075 3806 652 93 652 | | | | | O |
| ATOM | 1613 | CB | VAL A 224 | 35.672 | 7.326 | 4.355 | 1.00 | 33.13 | C |
| ANISOU | 1613 | CB | VAL A 224 | 4649 5554 4275 688 12 589 | | | | | C |
| ATOM | 1614 | CG1 | VAL A 224 | 36.035 | 6.473 | 4.247 | 1.00 | 34.99 | C |
| ANISOU | 1614 | CG1 | VAL A 224 | 4227 5231 3836 648 -62 635 | | | | | C |
| ATOM | 1615 | CG2 | VAL A 224 | 35.783 | 8.655 | 5.593 | 1.00 | 32.84 | C |
| ANISOU | 1615 | CG2 | VAL A 224 | 7923 4895 3656 713 3 715 | | | | | C |
| ATOM | 1616 | N | ALA A 225 | 34.314 | 5.572 | 5.595 | 1.00 | 33.01 | N |
| ANISOU | 1616 | N | ALA A 225 | 4353 4813 3575 559 60 559 | | | | | N |
| ATOM | 1617 | CA | ALA A 225 | 45.116 | 4.545 | 4.365 | 1.00 | 35.35 | C |
| ANISOU | 1617 | CA | ALA A 225 | 4385 5111 3939 537 57 521 | | | | | C |
| ATOM | 1618 | C | ALA A 225 | 39.341 | 3.552 | 3.555 | 1.00 | 37.67 | C |
| ANISOU | 1618 | C | ALA A 225 | 4668 5474 4170 523 -20 486 | | | | | C |
| ATOM | 1619 | O | ALA A 225 | 37.993 | 3.399 | 4.170 | 1.00 | 39.05 | O |
| ANISOU | 1619 | O | ALA A 225 | 4795 5684 4351 511 -75 435 | | | | | O |
| ATOM | 1620 | CB | ALA A 225 | 40.985 | 3.791 | 5.454 | 1.00 | 32.85 | C |
| ANISOU | 1620 | CB | ALA A 225 | 4064 4772 3701 480 71 473 | | | | | C |
| ATOM | 1621 | N | ALA A 226 | 34.581 | 2.870 | 2.619 | 1.00 | 35.81 | N |
| ANISOU | 1621 | N | ALA A 226 | 4473 5261 3873 529 -33 453 | | | | | N |
| ATOM | 1622 | CA | ALA A 226 | 78.600 | 1.574 | 1.945 | 1.00 | 39.341 | C |
| ANISOU | 1622 | CA | ALA A 226 | 4917 5767 4263 514 -109 210 | | | | | C |
| ATOM | 1623 | C | ALA A 226 | 33.612 | 0.632 | 2.716 | 1.00 | 33.54 | C |
| ANISOU | 1623 | C | ALA A 226 | 4155 5310 3575 446 -157 350 | | | | | C |
| ATOM | 1624 | O | ALA A 226 | 79.210 | 0.466 | 3.841 | 1.00 | 76.40 | O |
| ANISOU | 1624 | O | ALA A 226 | 4508 5758 4015 412 -129 338 | | | | | O |
| ATOM | 1625 | CB | ALA A 226 | 39.422 | 1.528 | 0.581 | 1.00 | 38.22 | C |
| ANISOU | 1625 | CB | ALA A 226 | 4872 5452 4073 543 -101 787 | | | | | C |
| ATOM | 1626 | N | ARG A 227 | 37.720 | -0.235 | 2.317 | 1.00 | 33.51 | N |

TABLE 3-continued

| | | | | | | | | | |
|---|---|---|---|---|---|---|---|---|---|
| ANISOU | 1626 | N | ARG A | 227 | 4140 | 5053 | 3576 | 423 -233 313 | N |
| ATOM | 1627 | CA | ARG A | 227 | 37.369 | -1.523 | 3.010 | 1.00 34.30 | C |
| ANISOU | 1627 | CA | ARG A | 227 | 4217 | 5109 | 3678 | 251 -293 256 | C |
| ATOM | 1628 | C | ARG A | 227 | 35.742 | -1.367 | 4.381 | 1.00 33.88 | C |
| ANISOU | 1628 | C | ARG A | 227 | 4107 | 5355 | 9597 | 311 -295 277 | C |
| ATOM | 1629 | O | ARG A | 227 | 37.409 | -1.646 | 5.374 | 1.00 33.47 | O |
| ANISOU | 1629 | O | ARG A | 227 | 4057 | 4551 | 3710 | 277 -268 265 | O |
| ATOM | 1630 | CB | ARG A | 227 | 38.560 | -2.417 | 3.227 | 1.00 37.30 | C |
| ANISOU | 1630 | CB | ARG A | 227 | 4750 | 5510 | 4132 | 322 -270 203 | C |
| ATOM | 1631 | CG | ARG A | 227 | 39.453 | -2.457 | 2.011 | 1.00 44.09 | C |
| ANISOU | 1631 | CG | ARG A | 227 | 5552 | 3314 | 4885 | 365 -243 182 | C |
| ATOM | 1632 | CD | ARG A | 227 | 39.299 | -3.775 | 1.245 | 1.00 58.42 | C |
| ANISOU | 1632 | CD | ARG A | 227 | 7396 | 8147 | 6655 | 342 -308 108 | C |
| ATOM | 1633 | NE | ARG A | 227 | 38.505 | -3.532 | 0.041 | 1.00 53.27 | N |
| ANISOU | 1633 | NE | ARG A | 227 | 5751 | 7580 | 6539 | 377 -345 117 | N |
| ATOM | 1634 | CZ | ARG A | 227 | 38.889 | -2.621 | -1.040 | 1.00 59.64 | C |
| ANISOU | 1634 | CZ | ARG A | 227 | 7545 | 8326 | 6540 | 439 -336 142 | C |
| ATOM | 1635 | NH1 | ARG A | 227 | 40.372 | -2.244 | -1.159 | 1.00 52.61 | N |
| ANISOU | 1635 | NH1 | ARG A | 227 | 5704 | 7501 | 5753 | 472 -222 163 | N |
| ATOM | 1636 | NH2 | ARG A | 227 | 33.044 | -2.694 | -2.040 | 1.00 61.05 | N |
| ANISOU | 1636 | NH2 | ARG A | 227 | 7779 | 8683 | 6735 | 466 -353 149 | N |
| ATOM | 1637 | N | PRO A | 228 | 35.410 | -1.099 | 4.419 | 1.00 35.30 | N |
| ANISOU | 1637 | N | PRO A | 228 | 4234 | 5315 | 3863 | 311 -339 299 | N |
| ATOM | 1638 | CA | PRO A | 228 | 34.640 | -1.078 | 5.655 | 1.00 34.16 | C |
| ANISOU | 1638 | CA | PRO A | 228 | 4028 | 5172 | 3779 | 268 -350 312 | C |
| ATOM | 1639 | C | PRO A | 228 | 34.776 | -2.426 | 6.330 | 1.00 34.46 | C |
| ANISOU | 1639 | C | PRO A | 228 | 4068 | 5168 | 3857 | 185 -384 261 | C |
| ATOM | 1640 | O | PRO A | 228 | 34.767 | -3.470 | 5.675 | 1.00 34.02 | O |
| ANISOU | 1640 | O | PRO A | 228 | 4038 | 5116 | 3772 | 156 -434 212 | O |
| ATOM | 1641 | CB | PRO A | 228 | 33.204 | -0.977 | 5.149 | 1.00 36.75 | C |
| ANISOU | 1641 | CB | PRO A | 228 | 4304 | 5594 | 4066 | 277 -411 322 | C |
| ATOM | 1642 | CG | PRO A | 228 | 33.251 | -0.381 | 3.808 | 1.00 34.24 | C |
| ANISOU | 1642 | CG | PRO A | 228 | 4019 | 5319 | 3672 | 348 -413 340 | C |
| ATOM | 1643 | CD | PRO A | 228 | 34.598 | -0.714 | 3.237 | 1.00 34.61 | C |
| ANISOU | 1643 | CD | PRO A | 228 | 4141 | 5311 | 3698 | 358 -377 315 | C |
| ATOM | 1644 | N | GLU A | 229 | 34.846 | -2.455 | 7.652 | 1.00 31.28 | N |
| ANISOU | 1644 | N | GLU A | 229 | 3641 | 4723 | 3520 | 145 -362 271 | N |
| ATOM | 1645 | CA | GLU A | 229 | 34.897 | -3.779 | 8.326 | 1.00 29.28 | C |
| ANISOU | 1645 | CA | GLU A | 229 | 3394 | 4428 | 3304 | 62 -399 229 | C |
| ATOM | 1646 | C | GLU A | 229 | 33.505 | -4.339 | 8.517 | 1.00 30.23 | C |

TABLE 3-continued

| | | | | |
|---|---|---|---|---|
| ANISOU | 1646 | C   | GLU A 229 | 3457 4608 3422    5 -461 222       C |
| ATOM   | 1647 | O   | GLU A 229 | 32.571  -3.569   8.609  1.00 35.50 O |
| ANISOU | 1647 | O   | GLU A 229 | 4066 5341 4081   27 -460 255       O |
| ATOM   | 1648 | CB  | GLU A 229 | 35.556  -3.591   9.734  1.00 30.45 C |
| ANISOU | 1648 | CB  | GLU A 229 | 3542 4507 3520   39 -351 246       C |
| ATOM   | 1649 | CG  | GLU A 229 | 37.015  -3.264   9.509  1.00 30.55 C |
| ANISOU | 1649 | CG  | GLU A 229 | 3611 4457 3541   84 -299 241       C |
| ATOM   | 1650 | CD  | GLU A 229 | 37.834  -3.356  10.735  1.00 33.82 C |
| ANISOU | 1650 | CD  | GLU A 229 | 4036 4797 4017   58 -266 242       C |
| ATOM   | 1651 | OE1 | GLU A 229 | 37.289  -3.191  11.856  1.00 35.26 O |
| ANISOU | 1651 | OE1 | GLU A 229 | 4181 4983 4234  234 -262 264       O |
| ATOM   | 1652 | OE2 | GLU A 229 | 39.050  -3.531  10.600  1.00 33.05 O |
| ANISOU | 1652 | OE2 | GLU A 229 | 3983 4642 3934   75 -241 222       O |
| ATOM   | 1653 | N   | GLY A 230 | 33.358  -5.660   8.624  1.00 28.87 N |
| ANISOU | 1653 | N   | GLY A 230 | 3298 4412 3261  -70 -515 178       N |
| ATOM   | 1654 | CA  | GLY A 230 | 32.047  -6.313   8.917  1.00 31.12 C |
| ANISOU | 1654 | CA  | GLY A 230 | 3524 4748 3551 -143 -574 170       C |
| ATOM   | 1655 | C   | GLY A 230 | 32.266  -7.090  10.214  1.00 34.23 C |
| ANISOU | 1655 | C   | GLY A 230 | 2925 5076 4005 -223 -570 167       C |
| ATOM   | 1656 | O   | GLY A 230 | 33.407  -7.113  10.727  1.00 36.84 O |
| ANISOU | 1656 | O   | GLY A 230 | 4305 5326 4365 -212 -531 166       O |
| ATOM   | 1657 | N   | PRO A 231 | 31.216  -7.768  10.716  1.00 33.86 N |
| ANISOU | 1657 | N   | PRO A 231 | 3833 5063 3978 -305 -613 163       N |
| ATOM   | 1658 | CA  | PRO A 231 | 31.263  -8.417  11.993  1.00 34.91 C |
| ANISOU | 1658 | CA  | PRO A 231 | 3965 5142 4159 -384 -608 172       C |
| ATOM   | 1659 | C   | PRO A 231 | 32.373  -9.455  12.062  1.00 35.15 C |
| ANISOU | 1659 | C   | PRO A 231 | 4080 5066 4210 -412 -625 136       C |
| ATOM   | 1660 | O   | PRO A 231 | 32.851  -9.742  13.161  1.00 29.72 O |
| ANISOU | 1660 | O   | PRO A 231 | 3414 4316 3564 -448 -604 151       O |
| ATOM   | 1661 | CB  | PRO A 231 | 29.869  -9.107  12.082  1.00 34.13 C |
| ANISOU | 1661 | CB  | PRO A 231 | 3802 5105 4060 -471 -665 165       C |
| ATOM   | 1662 | CG  | PRO A 231 | 28.957  -8.128  11.803  1.00 36.11 C |
| ANISOU | 1662 | CG  | PRO A 231 | 3984 5466 4270 -410 -668 179       C |
| ATOM   | 1663 | CD  | PRO A 231 | 29.879  -7.927  10.087  1.00 37.15 C |
| ANISOU | 1663 | CD  | PRO A 231 | 4184 5571 4362 -330 -670 154       C |
| ATOM   | 1664 | N   | LEU A 232 | 32.713 -10.073  10.934  1.00 33.04 N |
| ANISOU | 1664 | N   | LEU A 232 | 3860 4781 3914 -397 -667  88       N |
| ATOM   | 1665 | CA  | LEU A 232 | 33.667 -11.165  10.939  1 00 35.50 C |
| ANISOU | 1665 | CA  | LEU A 232 | 4249 4993 4247 -423 -692  47       C |
| ATOM   | 1666 | C   | LEU A 232 | 35.025 -10.741  10.308  1.00 36.14 C |

TABLE 3-continued

| | | | | | | | | | | |
|---|---|---|---|---|---|---|---|---|---|---|
| ANISOU | 1666 | C | LEU | A | 232 | 4386 | 5032 | 4313 | -333 | -652 28 C |
| ATOM | 1667 | O | LEU | A | 232 | 35.934 | -11.587 | 10.206 | 1.00 | 34.68 O |
| ANISOU | 1667 | O | LEU | A | 232 | 4265 | 4766 | 4144 | -337 | -669 -13 O |
| ATOM | 1668 | CB | LEU | A | 232 | 33.128 | -12 341 | 10.122 | 1.00 | 36.97 C |
| ANISOU | 1668 | CB | LEU | A | 232 | 4455 | 5179 | 4414 | -477 | -774 -7 C |
| ATOM | 1669 | CG | LEU | A | 232 | 31.975 | -13.121 | 10.744 | 1.00 | 40.58 C |
| ANISOU | 1669 | CG | LEU | A | 232 | 4870 | 5651 | 4896 | -587 | -823 0 C |
| ATOM | 1670 | CD1 | LEU | A | 232 | 31.421 | -14.171 | 9.766 | 1.00 | 38.22 C |
| ANISOU | 1670 | CD1 | LEU | A | 232 | 4589 | 5358 | 4574 | -634 | -906 -59 C |
| ATOM | 1671 | CD2 | LEU | A | 232 | 32.517 | -13.761 | 12.019 | 1.00 | 38.34 C |
| ANISOU | 1671 | CD2 | LEU | A | 232 | 4624 | 5274 | 4668 | -645 | -812 17 C |
| ATOM | 1672 | N | THR | A | 233 | 35.131 | -9.486 | 9.839 | 1.00 | 30.76 N |
| ANISOU | 1672 | N | THR | A | 233 | 3682 | 4406 | 3601 | -254 | -602 56 N |
| ATOM | 1673 | CA | THR | A | 233 | 36.424 | -8.979 | 9.342 | 1.00 | 34.57 C |
| ANISOU | 1673 | CA | THR | A | 233 | 4210 | 4852 | 4072 | -175 | -552 47 C |
| ATOM | 1674 | C | THR | A | 233 | 37.028 | -7.809 | 10.138 | 1.00 | 33.17 C |
| ANISOU | 1674 | C | THR | A | 233 | 4017 | 4661 | 3924 | -131 | -476 96 C |
| ATOM | 1675 | O | THR | A | 233 | 37.707 | -6.950 | 9.615 | 1.00 | 34.74 O |
| ANISOU | 1675 | O | THR | A | 233 | 4228 | 4866 | 4104 | -61 | -427 108 O |
| ATOM | 1676 | CB | THR | A | 233 | 36.223 | -8.649 | 7.821 | 1.00 | 37.93 C |
| ANISOU | 1676 | CB | THR | A | 233 | 4643 | 5343 | 4427 | -117 | -564 28 C |
| ATOM | 1677 | OG1 | THR | A | 233 | 35.202 | -7.675 | 7.736 | 1.00 | 37.25 O |
| ANISOU | 1677 | OB1 | THR | A | 233 | 4495 | 5343 | 4316 | -98 | -556 74 O |
| ATOM | 1678 | CG2 | THR | A | 233 | 35.715 | -9.893 | 7.021 | 1.00 | 40.75 C |
| ANISOU | 1678 | CG2 | THR | A | 233 | 5023 | 5707 | 4755 | -162 | -646 -32 C |
| ATOM | 1679 | N | GLY | A | 234 | 36.865 | -7.763 | 11.472 | 1.00 | 29.36 N |
| ANISOU | 1679 | N | GLY | A | 234 | 3511 | 4154 | 3489 | -175 | -462 126 N |
| ATOM | 1680 | CA | GLY | A | 234 | 37.455 | -6.636 | 12.131 | 1.00 | 32.28 C |
| ANISOU | 1680 | CA | GLY | A | 234 | 3870 | 4511 | 3883 | -130 | -393 165 C |
| ATOM | 1681 | C | GLY | A | 234 | 38.955 | -6.871 | 12.092 | 1.00 | 31.45 C |
| ANISOU | 1681 | C | GLY | A | 234 | 3821 | 4328 | 3801 | -101 | -369 138 C |
| ATOM | 1682 | O | GLY | A | 234 | 39.401 | -8.018 | 12.102 | 1.00 | 29.10 O |
| ANISOU | 1682 | O | GLY | A | 234 | 3565 | 3974 | 3519 | -133 | -408 98 O |
| ATOM | 1683 | N | GLY | A | 235 | 39.721 | -5.803 | 12.038 | 1.00 | 31.17 N |
| ANISOU | 1683 | N | GLY | A | 235 | 3787 | 4287 | 3770 | -39 | -307 159 N |
| ATOM | 1684 | CA | GLY | A | 235 | 41.177 | -5.998 | 12.087 | 1.00 | 34.52 C |
| ANISOU | 1684 | CA | GLY | A | 235 | 4254 | 4640 | 4222 | -14 | -281 134 C |
| ATOM | 1685 | C | GLY | A | 235 | 41.869 | -6.459 | 10.827 | 1.00 | 35.18 C |
| ANISOU | 1685 | C | GLY | A | 235 | 4377 | 4716 | 4273 | 22 | -287 89 C |
| ATOM | 1686 | O | GLY | A | 235 | 43.098 | -6.501 | 10.860 | 1.00 | 32.01 O |

TABLE 3-continued

| | | | | |
|---|---|---|---|---|
| ANISOU | 1686 O GLY A 235 | 4001 4264 3897 50 -258 68 | | O |
| ATOM | 1687 N ALA A 236 | 41.115 -6.776 9.729 1.00 29.12 | | N |
| ANISOU | 1687 N ALA A 236 | 3612 4003 3450 25 -324 71 | | N |
| ATOM | 1688 CA ALA A 236 | 41.665 -7.259 8.493 1.00 33.61 | | C |
| ANISOU | 1688 CA ALA A 236 | 4220 4573 3976 59 -333 23 | | C |
| ATOM | 1689 C ALA A 236 | 42.781 -6.321 6.037 1.00 32.76 | | C |
| ANISOU | 1689 C ALA A 236 | 4124 4463 3862 126 -258 35 | | C |
| ATOM | 1690 O ALA A 236 | 42.672 -5.072 8.100 1.00 34.03 | | O |
| ANISOU | 1690 O ALA A 236 | 4258 4654 4016 158 -207 87 | | O |
| ATOM | 1691 CB ALA A 236 | 40.580 -7.328 7.352 1.00 33.65 | | C |
| ANISOU | 1691 CB ALA A 236 | 4219 4657 3910 63 -374 15 | | C |
| ATOM | 1692 N PHE A 237 | 43.844 -6.905 7.510 1.00 29.62 | | N |
| ANISOU | 1692 N PHE A 237 | 3764 4029 3463 150 -250 -15 | | N |
| ATOM | 1693 CA PHE A 237 | 44-978 4029 3463 150 -250 -15 | | C |
| ANISOU | 1693 CA PHE A 237 | 3842 4098 3538 205 -173 -4 | | C |
| ATOM | 1694 C PHE A 237 | 44.599 -5.101 6.007 1.00 32.94 | | C |
| ANISOU | 1694 C PHE A 237 | 4186 4520 3809 251 -140 28 | | C |
| ATOM | 1695 O PHE A 237 | 45.025 -3.984 4.965 1.00 34.81 | | O |
| ANISOU | 1695 O PHE A 237 | 4413 4767 4048 285 -75 71 | | O |
| ATOM | 1696 CB PHE A 237 | 46.166 -6.952 6.851 1.00 33.29 | | C |
| ANISOU | 1686 CB PHE A 237 | 4268 4439 3942 222 -173 -70 | | C |
| ATOM | 1697 CG PHE A 237 | 47.398 -6.237 6.393 1.00 31.86 | | C |
| ANISOU | 1697 CG PHE A 237 | 4087 4253 3760 275 -95 -68 | | C |
| ATOM | 1698 CD1 PHE A 237 | 47.953 -5.167 7.116 1.00 31.99 | | C |
| ANISOU | 1698 CD1 PHE A 237 | 4075 4257 3823 284 -34 -21 | | C |
| ATOM | 1699 CD2 PHE A 237 | 48.016 -5.628 5.175 1.00 31.38 | | C |
| ANISOU | 1699 CD2 PHE A 237 | 4055 4219 3849 315 -78 -118 | | C |
| ATOM | 1700 CE1 PHE A 237 | 49.135 -4.549 8.698 1.00 32.26 | | C |
| ANISOU | 1700 CE1 PHE A 237 | 4107 4290 3861 325 39 -21 | | C |
| ATOM | 1701 CE2 PHE A 237 | 49.196 -5.998 4.775 1.00 31.52 | | C |
| ANISOU | 1701 CE2 PHE A 237 | 4082 4252 3681 369 0 -117 | | C |
| ATOM | 1702 CZ PHE A 237 | 49.737 -4.974 5.434 1.00 35.02 | | C |
| ANISOU | 1702 CZ PHE A 237 | 4481 4663 4161 361 58 -68 | | C |
| ATOM | 1703 N ALA A 238 | 43.733 -5.532 5.172 1.00 32.19 | | N |
| ANISOU | 1703 N ALA A 238 | 4103 4477 3651 249 -188 10 | | N |
| ATOM | 1704 CA ALA A 238 | 43.354 -4.858 4.048 1.00 40.10 | | C |
| ANISOU | 1704 CA ALA A 238 | 5107 5551 4579 295 -163 44 | | C |
| ATOM | 1705 C ALA A 238 | 42.563 -3.397 4.575 1.00 40.82 | | C |
| ANISOU | 1705 C ALA A 238 | 5157 5672 4681 301 -141 121 | | C |
| ATOM | 1706 O ALA A 238 | 42.590 -2.305 4.001 1.00 36.66 | | O |

TABLE 3-continued

| | | | | | | | | |
|---|---|---|---|---|---|---|---|---|
| ANISOU | 1706 | O ALA A 238 | 4634 | 5177 | 4119 | 347 | -91 | 167 O |
| ATOM | 1707 | CB ALA A 238 | 42.609 | -5.428 | 2.937 | 1.00 | 41.88 | C |
| ANISOU | 1707 | CB ALA A 238 | 5329 | 5803 | 4703 | 294 | -226 | 2 C |
| ATOM | 1708 | N SER A 239 | 41.853 | -3.522 | 5.594 | 1.00 | 35.52 | N |
| ANISOU | 1708 | N SER A 239 | 4451 | 4985 | 4050 | 256 | -172 | 136 N |
| ATOM | 1709 | CA SER A 233 | 41.206 | -2.357 | 6.314 | 1.00 | 34.89 | C |
| ANISOU | 1709 | CA SER A 239 | 4331 | 4927 | 3999 | 265 | -147 | 201 C |
| ATOM | 1710 | C SER A 239 | 42.202 | -1.473 | 7.092 | 1.00 | 32.55 | C |
| ANISOU | 1710 | C SER A 239 | 4045 | 4583 | 3773 | 282 | -75 | 231 C |
| ATOM | 1711 | O SER A 239 | 42.158 | -0.232 | 6.989 | 1.00 | 31.59 | O |
| ANISOU | 1711 | O SER A 239 | 3901 | 4970 | 3631 | 321 | -28 | 284 O |
| ATOM | 1712 | CB SER A 239 | 40.110 | -2.795 | 7.252 | 1.00 | 33.93 | C |
| ANISOU | 1712 | CB SER A 239 | 4170 | 4814 | 3909 | 211 | -200 | 204 C |
| ATOM | 1713 | OG SER A 239 | 39.135 | -3.426 | 6.455 | 1.00 | 31.01 | O |
| ANISOU | 1713 | OG SER A 239 | 3796 | 4502 | 3488 | 198 | -264 | 182 O |
| ATOM | 1714 | N LYS A 240 | 43.123 | -2.092 | 7.800 | 1.00 | 30.82 | N |
| ANISOU | 1714 | N LYS A 240 | 3823 | 4292 | 3595 | 256 | -68 | 198 N |
| ATOM | 1715 | CA LYS A 240 | 44.061 | -1.340 | 8.597 | 1.00 | 31.64 | C |
| ANISOU | 1715 | CA LYS A 240 | 3920 | 4345 | 3755 | 256 | -9 | 220 C |
| ATOM | 1716 | C LYS A 240 | 45.132 | -0.667 | 7.729 | 1.00 | 31.46 | C |
| ANISOU | 1716 | C LYS A 240 | 3923 | 4320 | 3713 | 313 | 57 | 227 C |
| ATOM | 1717 | O LYS A 240 | 45.846 | 0.386 | 8.072 | 1.00 | 30.20 | O |
| ANISOU | 1717 | O LYS A 240 | 3753 | 4139 | 3584 | 331 | 114 | 264 O |
| ATOM | 1718 | CB LYS A 240 | 44.760 | -2.259 | 9.611 | 1.00 | 28.42 | C |
| ANISOU | 1718 | CB LYS A 240 | 3518 | 3871 | 2411 | 225 | -28 | 180 C |
| ATOM | 1719 | CG LYS A 240 | 43.830 | -2.930 | 10.661 | 1.00 | 32.44 | C |
| ANISOU | 1719 | CG LYS A 240 | 4008 | 4373 | 3946 | 168 | -86 | 178 C |
| ATOM | 1720 | CD LYS A 240 | 43.003 | -1.915 | 11.529 | 1.00 | 29.16 | C |
| ANISOU | 1720 | CD LYS A 240 | 3553 | 3580 | 3545 | 163 | -69 | 231 C |
| ATOM | 1721 | CE LYS A 240 | 41.557 | -1.303 | 11.071 | 1.00 | 35.50 | C |
| ANISOU | 1721 | CE LYS A 240 | 4330 | 4856 | 4304 | 160 | -103 | 252 C |
| ATOM | 1722 | NZ LYS A 240 | 40.721 | -0.389 | 12.083 | 1.00 | 29.77 | N |
| ANISOU | 1722 | NZ LYS A 240 | 3561 | 4150 | 3602 | 151 | -90 | 794 N |
| ATOM | 1723 | N VAL A 241 | 45.463 | -1.273 | 6.592 | 1.00 | 37.05 | N |
| ANISOU | 1723 | N VAL A 241 | 4651 | 5050 | 4360 | 331 | 51 | 191 N |
| ATOM | 1724 | CA VAL A 241 | 46.545 | -0.720 | 5.799 | 1.00 | 33.73 | C |
| ANISOU | 1724 | CA VAL A 241 | 4637 | 5009 | 4309 | 371 | 119 | 195 C |
| ATOM | 1725 | C VAL A 241 | 46.115 | 7.624 | 5.252 | 1.00 | 35.06 | C |
| ANISOU | 1725 | C VAL A 241 | 4425 | 4835 | 4055 | 406 | 161 | 264 C |
| ATOM | 1726 | O VAL A 241 | 46.909 | 1.558 | 5.197 | 1.00 | 35.63 | O |

TABLE 3-continued

| | | | | | | | | | | |
|---|---|---|---|---|---|---|---|---|---|---|
| ANISOU | 1726 | O | VAL A | 241 | 4500 4890 4146 | 425 | 230 | 297 | | O |
| ATOM | 1727 | CB | VAL A | 241 | 47.059 -1.717 4.730 | 1.00 | 37.45 | | | C |
| ANISOU | 1727 | CB | VAL A | 241 | 4761 5338 4351 | 385 | 108 | 304 | | C |
| ATOM | 1728 | CG1 | VAL A | 241 | 46.159 -1.724 3.532 | 1.00 | 73.85 | | | C |
| ANISOU | 1728 | CG1 | VAL A | 241 | 4326 4775 3371 | 408 | 80 | 142 | | C |
| ATOM | 1729 | CG2 | VAL A | 241 | 48.492 -1.302 4.318 | 1.00 | 37.55 | | | C |
| ANISOU | 1729 | CG2 | VAL A | 241 | 4795 7125 4385 | 414 | 187 | 123 | | C |
| ATOM | 1730 | N | GLY A | 242 | 44.857 0.783 4.890 | 1.00 | 32.25 | | | N |
| ANISOU | 1730 | N | GLY A | 242 | 4065 4575 3657 | 414 | 119 | 290 | | N |
| ATOM | 1731 | CA | GLY A | 242 | 44.480 2.114 4.418 | 1.00 | 32.41 | | | C |
| ANISOU | 1731 | CA | GLY A | 242 | 4085 4535 3540 | 454 | 156 | 350 | | C |
| ATOM | 1732 | C | GLY A | 242 | 44.390 3.155 5.516 | 1.00 | 35.41 | | | C |
| ANISOU | 1732 | C | GLY A | 242 | 4443 4926 4086 | 451 | 187 | 406 | | C |
| ATOM | 1733 | O | GLY A | 242 | 44.645 4.340 8.258 | 1.00 | 36.59 | | | O |
| ANISOU | 1733 | O | GLY A | 242 | 4501 5069 4232 | 483 | 241 | 457 | | O |
| ATOM | 1734 | N | ALA A | 243 | 43.991 2.713 6.720 | 1.00 | 23.72 | | | N |
| ANISOU | 1734 | N | ALA A | 243 | 3562 4054 3297 | 412 | 150 | 387 | | N |
| ATOM | 1735 | CA | ALA A | 243 | 43.941 3.625 7.947 | 1.00 | 32.55 | | | C |
| ANISOU | 1735 | CA | ALA A | 243 | 4059 4537 3888 | 406 | 177 | 421 | | C |
| ATOM | 1736 | C | ALA A | 243 | 45.379 4.108 8.247 | 1.00 | 32.57 | | | C |
| ANISOU | 1736 | C | ALA A | 243 | 4074 4479 3902 | 406 | 244 | 420 | | C |
| ATOM | 1737 | O | ALA A | 243 | 45.631 5.325 8.433 | 1.00 | 28.59 | | | O |
| ANISOU | 1737 | O | ALA A | 243 | 3527 3906 3417 | 427 | 294 | 455 | | O |
| ATOM | 1738 | CB | ALA A | 243 | 43.298 2.942 3.142 | 1.00 | 20.96 | | | C |
| ANISOU | 1738 | CB | ALA A | 243 | 3280 3782 3183 | 361 | 127 | 395 | | C |
| ATOM | 1739 | N | LEU A | 244 | 46.346 3.390 8.136 | 1.00 | 31.93 | | | N |
| ANISOU | 1739 | N | LEU A | 244 | 3927 4297 3794 | 388 | 245 | 370 | | N |
| ATOM | 1740 | CA | LEU A | 244 | 47.747 3.891 8.310 | 1.00 | 31.90 | | | C |
| ANISOU | 1740 | CA | LEU A | 244 | 3955 4282 3875 | 389 | 303 | 355 | | C |
| ATOM | 1741 | C | LEU A | 244 | 43.274 4.524 7.225 | 1.00 | 32.18 | | | C |
| ANISOU | 1741 | C | LEU A | 244 | 4022 4332 3672 | 424 | 374 | 403 | | C |
| ATOM | 1742 | O | LEU A | 244 | 49.725 5.437 7.551 | 1.00 | 32.69 | | | O |
| ANISOU | 1742 | O | LEU A | 244 | 4082 4351 3981 | 425 | 431 | 429 | | O |
| ATOM | 1743 | CB | LEU A | 244 | 48.561 2.362 8.443 | 1.00 | 70.38 | | | C |
| ANISOU | 1743 | CB | LEU A | 244 | 3334 4123 3766 | 367 | 290 | 296 | | C |
| ATOM | 1744 | CG | LEU A | 244 | 48.337 1.492 9.053 | 1.00 | 30.57 | | | C |
| ANISOU | 1744 | CG | LEU A | 244 | 3781 4055 3778 | 327 | 233 | 264 | | C |
| ATOM | 1745 | CD1 | LEU A | 244 | 49.054 0.055 9.419 | 1.00 | 32.12 | | | C |
| ANISOU | 1745 | CD1 | LEU A | 244 | 3092 4236 9976 | 316 | 199 | 196 | | C |
| ATOM | 1746 | CD2 | LEU A | 244 | 43.804 2.126 11.015 | 1.00 | 28.32 | | | C |

TABLE 3-continued

| | | | | | | | | | | |
|---|---|---|---|---|---|---|---|---|---|---|
| ANISOU | 1746 | CD2 | LEO | A | 244 | 3448 3593 3543 | 308 | 252 | 279 | C |
| ATOM | 1747 | N | LEU | A | 245 | 47.940 4.272 5.942 | 1.00 | 31.23 | | N |
| ANISOU | 1747 | N | LEU | A | 245 | 3929 4258 3570 | 450 | 357 | 406 | N |
| ATOM | 1748 | CA | LEU | A | 245 | 48.239 5.214 4.455 | 1.00 | 35.78 | | C |
| ANISOU | 1748 | CA | LEU | A | 245 | 4522 4356 4195 | 434 | 427 | 456 | C |
| ATOM | 1749 | C | LEU | A | 245 | 47.709 6.860 5.157 | 1.00 | 34.98 | | C |
| ANISOU | 1749 | C | LEU | A | 245 | 4432 4750 4110 | 503 | 452 | 531 | C |
| ATOM | 1750 | O | LEU | A | 245 | 48.435 7.629 4.989 | 1.00 | 33.78 | | O |
| ANISOU | 1750 | O | LEU | A | 245 | 4292 4568 3975 | 511 | 510 | 570 | O |
| ATOM | 1751 | CB | LEU | A | 245 | 47.522 4.725 7.581 | 1.00 | 31.35 | | C |
| ANISOU | 1751 | CB | LEU | A | 245 | 4001 4378 8535 | 511 | 397 | 451 | C |
| ATOM | 1752 | CG | LEU | A | 245 | 47.756 5.667 2.372 | 1.00 | 39.57 | | C |
| ANISOU | 1752 | CG | LEU | A | 245 | 5079 5450 4505 | 549 | 451 | 509 | C |
| ATOM | 1753 | CD1 | LEU | A | 245 | 49.205 5.782 1.958 | 1.00 | 47.82 | | C |
| ANISOU | 1753 | CD1 | LEU | A | 245 | 5243 5539 4572 | 545 | 531 | 499 | C |
| ATOM | 1754 | CD2 | LEU | A | 245 | 46.925 5.164 1.157 | 1.00 | 34.43 | | C |
| ANISOU | 1754 | CD2 | LEU | A | 245 | 4455 4675 3749 | 577 | 405 | 504 | C |
| ATOM | 1755 | N | LEU | A | 246 | 46.456 6.783 5.602 | 1.00 | 36.38 | | N |
| ANISOU | 1755 | N | LEU | A | 246 | 4554 4544 4284 | 510 | 400 | 548 | N |
| ATOM | 1756 | CA | LEU | A | 246 | 45.960 8.103 6.099 | 1.00 | 40.90 | | C |
| ANISOU | 1756 | CA | LEU | A | 246 | 5161 5492 4686 | 530 | 419 | 608 | C |
| ATOM | 1757 | C | LEU | A | 246 | 46.681 8.747 7.115 | 1.00 | 38.74 | | C |
| ANISOU | 1757 | C | LEU | A | 246 | 4875 5144 4699 | 507 | 459 | 610 | C |
| ATOM | 1758 | O | LEU | A | 246 | 47.125 9.975 7.013 | 1.00 | 56.75 | | O |
| ANISOU | 1758 | O | LEU | A | 246 | 4640 4860 4403 | 527 | 515 | 563 | O |
| ATOM | 1759 | CB | LEU | A | 246 | 44.571 8.011 5.751 | 1.00 | 40.07 | | C |
| ANISOU | 1759 | CB | LEU | A | 246 | 5925 5413 4797 | 553 | 365 | 610 | C |
| ATOM | 1760 | CG | LEU | A | 246 | 6370 7.332 6.032 | 1.00 | 50.72 | | C |
| ANISOU | 1760 | CG | LEU | A | 246 | 5370 5358 5063 | 543 | 289 | 603 | C |
| ATOM | 1761 | CD1 | LEU | A | 246 | 42.171 7.371 7.013 | 1.00 | 56.72 | | C |
| ANISOU | 1761 | CD1 | LEU | A | 246 | 7086 7014 6851 | 542 | 239 | 553 | C |
| ATOM | 1762 | CD2 | LEU | A | 246 | 43.085 7 965 4.700 | 1.00 | 47.40 | | C |
| ANISOU | 1762 | CD2 | LEU | A | 246 | 5985 6452 5551 | 595 | 295 | 652 | C |
| ATOM | 1763 | N | VAL | A | 247 | 47.331 7.373 8.118 | 1.00 | 33.57 | | N |
| ANISOU | 1763 | N | VAL | A | 247 | 4194 4460 4102 | 463 | 449 | 555 | N |
| ATOM | 1764 | CA | VAL | A | 247 | 48.305 8.451 9.110 | 1.00 | 34.16 | | C |
| ANISOU 7 | 1764 | CA | VAL | A | 247 | 4254 4455 4259 | 443 | 490 | 549 | C |
| ATOM | 1765 | C | VAL | A | 247 | 49.583 8.950 6.400 | 1.00 | 34.23 | | C |
| ANISOU | 1765 | C | VAL | A | 247 | 4281 4453 4273 | 444 | 551 | 562 | C |
| ATOM | 1766 | O | VAL | A | 247 | 50.143 10.097 8.659 | 1.00 | 51.52 | | O |

TABLE 3-continued

| | | | | |
|---|---|---|---|---|
| ANISOU | 1766 O VAL A 247 | 3941 4060 3974 442 615 597 | | O |
| ATOM | 1767 CB VAL A 247 | 48.694 7.405 10.218 | 1.00 30.44 | C |
| ANISOU | 1767 CB VAL A 247 | 3755 3969 3641 402 454 487 | | C |
| ATOM | 1768 CG1 VAL A 247 | 49.348 7.986 11.039 | 1.00 30.37 | C |
| ANISOU | 1768 CG1 VAL A 247 | 3734 3896 3909 380 456 477 | | C |
| ATOM | 1769 CG2 VAL A 247 | 47.533 7.184 11.209 | 1.00 23.55 | C |
| ANISOU | 1769 CG2 VAL A 247 | 3496 3742 3514 390 395 430 | | C |
| ATOM | 1770 N ASP A 248 | 50.076 8.121 7.476 | 1.00 32.34 | N |
| ANISOU | 1770 N ASP A 248 | 4052 4249 3985 445 556 533 | | N |
| ATOM | 1771 CA ASP A 248 | 51.334 8.493 5.809 | 1.00 31.81 | C |
| ANISOU | 1771 CA ASP A 248 | 3935 4159 3924 443 640 540 | | C |
| ATOM | 1772 C ASP A 248 | 51.224 9.764 5.992 | 1.00 35.32 | C |
| ANISOU | 1772 C ASP A 248 | 4473 4616 4333 468 695 616 | | C |
| ATOM | 1773 O ASP A 248 | 52.107 10.838 6.108 | 1.00 31.84 | O |
| ANISOU | 1773 O ASP A 248 | 4032 4130 3937 453 759 643 | | O |
| ATOM | 1774 CB ASP A 248 | 51.814 7.333 5.919 | 1.00 35.37 | C |
| ANISOU | 1774 CB ASP A 248 | 4451 4664 4323 443 630 490 | | C |
| ATOM | 1775 CG ASP A 248 | 53.201 7.544 5.397 | 1.00 37.81 | C |
| ANISOU | 1775 CG ASP A 248 | 4757 4964 4643 439 713 484 | | C |
| ATOM | 1776 OD1 ASP A 248 | 54.190 7.875 5.145 | 1.00 34.80 | O |
| ANISOU | 1776 OD1 ASP A 248 | 4345 4532 4344 412 749 471 | | O |
| ATOM | 1777 OD2 ASP A 248 | 53.205 7.248 4.255 | 1.00 32.43 | O |
| ANISOU | 1777 OD2 ASP A 248 | 4999 4332 3592 459 733 453 | | O |
| ATOM | 1778 N VAL A 249 | 55.165 9.344 5.160 | 1.00 35.34 | N |
| ANISOU | 1778 N VAL A 249 | 4314 4475 4064 503 667 652 | | N |
| ATOM | 1779 CA VAL A 249 | 49.830 11.026 4.359 | 1.00 37.23 | C |
| ANISOU | 1779 CA VAL A 249 | 4786 4916 4454 534 706 731 | | C |
| ATOM | 1780 C VAL A 249 | 49.638 12.262 5.225 | 1.00 38.13 | C |
| ANISOU | 1780 C VAL A 249 | 4895 4963 4631 536 719 777 | | C |
| ATOM | 1781 O VAL A 249 | 50.165 13.546 4.941 | 1.00 41.42 | O |
| ANISOU | 1781 O VAL A 249 | 5537 5340 5062 537 751 351 | | O |
| ATOM | 1782 CB VAL A 249 | 48.653 10.756 3.406 | 1.00 39.70 | C |
| ANISOU | 1782 CB VAL A 249 | 5122 5297 4665 575 655 753 | | C |
| ATCOM | 1783 CG1 VAL A 249 | 48.385 12.001 2.632 | 1.00 44.42 | C |
| ANISOU | 1783 CG1 VAL A 249 | 5765 5895 5219 512 890 840 | | C |
| ATOM | 1784 CG2 VAL A 249 | 44.995 9 589 2.446 | 1.00 35.63 | C |
| ANISOU | 1784 CG2 VAL A 249 | 4749 4976 4210 576 646 705 | | C |
| ATOM | 1785 N LEU A 250 | 48.994 12.092 6.372 | 1.00 38.89 | N |
| ANISOU | 1785 N LEU A 250 | 4959 5040 4776 529 669 750 | | N |
| ATOM | 1786 CA LEU A 250 | 48.843 13.227 7.246 | 1.00 33.59 | C |

TABLE 3-continued

| | | | | |
|---|---|---|---|---|
| ANISOU | 1786 CA LEU A 250 | 4287 4307 4170 532 683 781 | | C |
| ATOM | 1787 C LEU A 250 | 50.197 13.773 7.623 1.00 32.20 | | C |
| ANISOU | 1787 C LEU A 250 | 4107 4065 4063 495 749 779 | | C |
| ATOM | 1788 O LEU A 250 | 50.416 14.949 7.514 1.00 30.97 | | O |
| ANISOU | 1788 O LEU A 250 | 3975 3852 3929 501 794 831 | | O |
| ATOM | 1789 CB LEU A 250 | 47.973 12.854 8.495 1.00 34.85 | | C |
| ANISOU | 1789 CB LEU A 250 | 4409 4465 4358 527 521 744 | | C |
| ATOM | 1790 CG LEU A 250 | 47.818 13.919 9.554 1.00 40.16 | | C |
| ANISOU | 1790 CG LEU A 250 | 5074 5074 5110 530 532 751 | | C |
| ATOM | 1791 CD1 LEU A 200 | 47.274 15.286 9.045 1.00 37.55 | | C |
| ANISOU | 1791 CD1 LEU A 250 | 4783 4723 4754 577 555 836 | | C |
| ATOM | 1792 CD2 LEU A 250 | 46.977 13.415 10.771 1.00 34.54 | | C |
| ANISOU | 1792 CD2 LEU A 250 | 4375 4425 4475 523 574 719 | | C |
| ATOM | 1793 N VAL A 251 | 51.093 12.933 8.162 1.00 31.64 | | N |
| ANISOU | 1793 N VAL A 251 | 4302 3965 4034 455 750 716 | | N |
| ATOM | 1794 CA VAL A 251 | 52.354 18.417 8.732 1.00 34.03 | | C |
| ANISOU | 1794 CA VAL A 251 | 4288 4225 4415 416 801 703 | | C |
| ATOM | 1795 C VAL A 251 | 53.289 13.808 7.616 1.00 36.76 | | C |
| ANISOU | 1795 C VAL A 251 | 4654 4575 4737 409 875 735 | | C |
| ATOM | 1796 O VAL A 251 | 53.937 14.310 7.722 1.00 36.49 | | O |
| ANISOU | 1796 O VAL A 251 | 4525 4487 4750 385 901 769 | | O |
| ATOM | 1797 CB VAL A 251 | 52.985 12.385 9.724 1.00 34.00 | | C |
| ANISOU | 1797 CB VAL A 251 | 4277 4251 4505 381 770 525 | | C |
| ATOM | 1798 CG1 VAL A 251 | 54.302 12.935 10.330 1.00 32.24 | | C |
| ANISOU | 1798 CG1 VAL A 251 | 3992 3929 4328 342 818 509 | | C |
| ATOM | 1799 CG2 VAL A 251 | 51.911 12.140 10.792 1.00 31.69 | | C |
| ANISOU | 1799 CG2 VAL A 251 | 3934 3913 4183 388 702 605 | | C |
| ATOM | 1800 N ASN A 252 | 53.255 13.036 6.539 1.00 34.58 | | N |
| ANISOU | 1800 N ASN A 252 | 4443 4415 4433 426 878 733 | | N |
| ATOM | 1801 CA ASN A 252 | 54.052 13.562 5.372 1.00 40.62 | | C |
| ANISOU | 1801 CA ANN A 252 | 5182 5140 5110 422 955 774 | | C |
| ATOM | 1802 C ASN A 252 | 53.639 14.342 4.800 1.00 37.40 | | C |
| ANISOU | 1802 C ASN A 252 | 4826 4737 4677 442 922 367 | | C |
| ATOM | 1803 O ASN A 252 | 54.513 15.692 4.338 1.00 35.95 | | O |
| ANISOU | 1803 O ASN A 252 | 4733 4623 4632 419 1053 908 | | O |
| ATOM | 1804 CB ADN A 252 | 54.097 12.515 4.258 1.00 37.67 | | C |
| ANISOU | 1804 CB ASN A 252 | 4617 4646 4649 439 951 745 | | C |
| ATOM | 1805 CG ASN A 252 | 54.325 11.234 4.725 1.00 35.45 | | C |
| ANISOU | 1805 CG ANN A 252 | 4515 4604 4428 417 331 657 | | C |
| ATOM | 1806 OD1 ASN A 252 | 55.485 11.230 5.773 1.00 34.15 | | O |

TABLE 3-continued

| | | | | | | | | |
|---|---|---|---|---|---|---|---|---|
| ANISOU | 1806 | OD1 ASN A 252 | 4287 | 4356 | 4328 | 386 | 931 | 521 | O |
| ATOM | 1807 | ND2 ASN A 252 | 54.649 | 10.105 | 3.937 | 1.00 | 36.34 | N |
| ANISOU | 1807 | ND2 ASN A 252 | 4608 | 4752 | 4445 | 437 | 905 | 518 | N |
| ATOM | 1808 | N SER A 253 | 52.333 | 15.236 | 4.756 | 1.00 | 41.31 | N |
| ANISOU | 1808 | N SER A 253 | 5348 | 5214 | 5133 | 485 | 941 | 203 | N |
| ATOM | 1809 | CA SER A 253 | 51.872 | 16.595 | 4.404 | 1.00 | 41.99 | C |
| ANISOU | 1809 | CA SER A 253 | 5484 | 5262 | 5209 | 511 | 966 | 990 | C |
| ATOM | 1810 | C SER A 253 | 52.376 | 17.605 | 5.352 | 1.00 | 41.20 | C |
| ANISOU | 1810 | C SER A 253 | 5376 | 5070 | 5208 | 462 | 997 | 1003 | C |
| ATOM | 1811 | O SER A 253 | 52.865 | 18.671 | 4.907 | 1.00 | 41.39 | O |
| ANISOU | 1811 | O SER A 253 | 5437 | 5347 | 5242 | 473 | 1059 | 1066 | O |
| ATOM | 1812 | CB SER A 253 | 50.373 | 16.727 | 4.310 | 1.00 | 38.43 | C |
| ANISOU | 1812 | CB SER A 253 | 5053 | 4840 | 4709 | 558 | 899 | 1018 | C |
| ATOM | 1813 | OG SER A 253 | 49.953 | 15.683 | 3.525 | 1.00 | 38.78 | O |
| ANISOU | 1813 | OG SER A 253 | 5596 | 4969 | 4568 | 587 | 863 | 994 | O |
| ATOM | 1814 | N LEU A 254 | 52.290 | 17.304 | 6.545 | 1.00 | 39.93 | N |
| ANISOU | 1814 | N LEU A 254 | 5173 | 4851 | 5119 | 465 | 956 | 943 | N |
| ATOM | 1815 | CA LEU A 254 | 52.337 | 18.213 | 7656 | 1.00 | 39.22 | C |
| ANISOU | 1815 | CA LEU A 254 | 5072 | 4702 | 5327 | 434 | 981 | 942 | C |
| ATOM | 1816 | C LEU A 254 | 54.325 | 18.525 | 7.353 | 1.00 | 43.12 | C |
| ANISOU | 1816 | C LEU A 254 | 5179 | 4783 | 5281 | 353 | 3051 | 947 | C |
| ATOM | 1817 | O LEU A 254 | 54.752 | 19.704 | 7.391 | 1.00 | 138.20 | O |
| ANISOU | 1817 | O LEU A 254 | 4961 | 4459 | 5054 | 350 | 1130 | 995 | O |
| ATOM | 1818 | CB LEU A 254 | 52.708 | 17.547 | 9.373 | 1.00 | 35.19 | C |
| ANISOU | 1818 | CB LEU A 254 | 4533 | 4178 | 4583 | 418 | 928 | 868 | C |
| ATOM | 1819 | CG LEU A 254 | 51.411 | 17.875 | 9.827 | 1.00 | 38.60 | C |
| ANISOU | 1819 | CG LEU A 254 | 4947 | 4505 | 5115 | 457 | 858 | 857 | C |
| ATOM | 1820 | CD1 LEU A 254 | 51.203 | 16.744 | 10.841 | 1.00 | 43.41 | C |
| ANISOU | 1820 | CD1 LEU A 254 | 5507 | 5244 | 5742 | 442 | 810 | 790 | C |
| ATOM | 1821 | CD2 LEU A 254 | 51.327 | 10.312 | 13.391 | 1.00 | 37.51 | C |
| ANISOU | 1821 | CD2 LEU A 254 | 4834 | 4383 | 5037 | 464 | 890 | 904 | C |
| ATOM | 1822 | N LEU A 255 | 55.105 | 17.473 | 1.095 | 1.00 | 36.01 | N |
| ANISOU | 1822 | N LEU A 255 | 4622 | 4312 | 4747 | 355 | 1073 | 595 | N |
| ATOM | 1823 | CA LEU A 255 | 56.519 | 37.524 | 6.839 | 1.00 | 35.55 | C |
| ANISOU | 1823 | CA LEU A 255 | 4544 | 4238 | 4729 | 335 | 1146 | 889 | C |
| ATOM | 1824 | C LEU A 255 | 55.725 | 15.442 | 5.558 | 1.00 | 43.18 | C |
| ANISOU | 1824 | C LEU A 255 | 5183 | 4827 | 5253 | 357 | 1218 | 974 | C |
| ATOM | 1825 | O LEU A 255 | 57.534 | 19.249 | 5.452 | 1.00 | 36.45 | O |
| ANISOU | 1825 | O LEU A 255 | 4773 | 4370 | 4896 | 253 | 1267 | 1005 | O |
| ATOM | 1826 | CB LEU A 255 | 57.178 | 16.240 | 6.724 | 1.00 | 35.65 | C |

TABLE 3-continued

| | | | | | | | | | | |
|---|---|---|---|---|---|---|---|---|---|---|
| ANISOU | 1826 | CB | LEU | A | 255 | 4634 | 4439 | 4855 | 203 | 1337 | 814 C |
| ATOM | 1827 | CG | LEU | A | 255 | 57.507 | 15.577 | 5.131 | 1.00 | 35.79 C |
| ANISOU | 1827 | CG | LEU | A | 255 | 4469 | 4300 | 4829 | 269 | 1089 | 736 C |
| ATOM | 1828 | CD1 | LEU | A | 255 | 57.667 | 14.174 | 8.091 | 1.00 | 37.35 C |
| ANISOU | 1828 | CD1 | LEU | A | 255 | 4633 | 4558 | 5000 | 278 | 1049 | 664 C |
| ATOM | 1829 | CD2 | LEU | A | 255 | 58.808 | 16.329 | 8.675 | 1.00 | 37.17 C |
| ANISOU | 1829 | CD2 | LEU | A | 255 | 4608 | 4415 | 5090 | 213 | 1142 | 723 C |
| ATOM | 1830 | N | GLU | A | 256 | 55.833 | 18.295 | 4.619 | 1.00 | 40.57 N |
| ANISOU | 1830 | N | GLU | A | 256 | 5275 | 4929 | 5203 | 356 | 1198 | 1015 N |
| ATOM | 1831 | CA | GLU | A | 256 | 55.949 | 19.378 | 3.387 | 1.00 | 42.99 C |
| ANISOU | 1831 | CA | GLU | A | 256 | 5633 | 5241 | 5453 | 351 | 1254 | 1104 C |
| ATOM | 1832 | C | GLU | A | 256 | 55.550 | 20.532 | 3.531 | 1.00 | 44.07 C |
| ANISOU | 1832 | C | GLU | A | 256 | 5824 | 5290 | 5529 | 347 | 1275 | 1380 C |
| ATOM | 1833 | O | GLU | A | 256 | 56.178 | 21.415 | 3.094 | 1.00 | 43.97 O |
| ANISOU | 1833 | O | GLU | A | 256 | 5345 | 5239 | 5623 | 335 | 1347 | 1243 O |
| ATOM | 1834 | CB | GLU | A | 256 | 55.108 | 18.490 | 2.322 | 1.00 | 45.61 C |
| ANISOU | 1834 | CB | GLU | A | 256 | 6006 | 5657 | 5565 | 414 | 1234 | 1123 C |
| ATOM | 1835 | CG | GLU | A | 256 | 55.153 | 19.281 | 1.044 | 1.00 | 53.52 C |
| ANISOU | 1835 | CG | GLU | A | 256 | 7088 | 6532 | 5602 | 425 | 1294 | 1218 C |
| ATOM | 1836 | CD | GLU | A | 256 | 55.319 | 18.349 | -0.097 | 1.00 | 72.50 C |
| ANISOU | 1836 | CD | GLU | A | 256 | 9485 | 9173 | 8588 | 433 | 1310 | 1202 C |
| ATOM | 1837 | OE1 | GLU | A | 256 | 56.392 | 17.703 | -0.162 | 1.00 | 82.05 O |
| ANISOU | 1837 | OE1 | GLU | A | 256 | 10655 | 10409 | 10115 | 400 | 1355 | 1148 O |
| ATOM | 1838 | OE2 | GLU | A | 256 | 54.377 | 18.250 | -0.912 | 1.00 | 81.00 O |
| ANISOU | 1838 | OE2 | GLU | A | 256 | 10510 | 15301 | 9656 | 491 | 1274 | 1240 O |
| ATOM | 1839 | N | SER | A | 257 | 54.529 | 20.809 | 4.457 | 1.00 | 42.14 N |
| ANISOU | 1839 | N | SER | A | 257 | 5585 | 5012 | 5414 | 403 | 1207 | 1174 N |
| ATOM | 1840 | CA | SER | A | 257 | 54.105 | 22.205 | 4.552 | 1.00 | 45.40 C |
| ANISOU | 1840 | CA | SER | A | 257 | 6049 | 5338 | 5862 | 413 | 1215 | 1244 C |
| ATOM | 1841 | C | SER | A | 257 | 55.027 | 22.914 | 5.617 | 1.00 | 48.06 C |
| ANISOU | 1841 | C | SER | A | 257 | 6386 | 5583 | 6318 | 359 | 1251 | 1225 C |
| ATOM | 1842 | O | SER | A | 257 | 55.204 | 24.122 | 5.521 | 1.00 | 45.53 O |
| ANISOU | 1842 | O | SER | A | 257 | 6039 | 5180 | 6030 | 346 | 1290 | 1288 O |
| ATOM | 1843 | CB | SER | A | 257 | 52.655 | 22.332 | 5.112 | 1.00 | 48.56 C |
| ANISOU | 1843 | CB | SER | A | 257 | 6463 | 5733 | 6248 | 486 | 1135 | 1247 C |
| ATOM | 1844 | OG | SER | A | 257 | 51.815 | 21.518 | 4.339 | 1.00 | 45.74 O |
| ANISOU | 1844 | OG | SER | A | 257 | 6112 | 5476 | 5791 | 534 | 1091 | 1243 O |
| ATOM | 1845 | N | TYR | A | 258 | 55.615 | 22.170 | 6.554 | 1.00 | 45.34 N |
| ANISOU | 1845 | N | TYR | A | 258 | 5952 | 5244 | 6039 | 322 | 1234 | 1137 N |
| ATOM | 1846 | CA | TYR | A | 258 | 56.330 | 22.753 | 7.654 | 1.00 | 42.66 C |

TABLE 3-continued

| | | | | | | | | | | |
|---|---|---|---|---|---|---|---|---|---|---|
| ANISOU | 1846 | CA | TYR | A | 258 | 5584 4819 5804 | 279 | 1247 | 1103 | C |
| ATOM | 1847 | C | TYR | A | 258 | 57.645 22.004 7.785 | 1.00 | 42.78 | | C |
| ANISOU | 1847 | C | TYR | A | 258 | 5535 4863 5855 | 212 | 1253 | 1043 | C |
| ATOM | 1848 | O | TYR | A | 258 | 57.551 21.257 8.783 | 1.00 | 41.37 | | O |
| ANISOU | 1848 | O | TYR | A | 258 | 5300 4595 5725 | 199 | 1240 | 950 | O |
| ATOM | 1849 | CB | TYR | A | 258 | 55.475 22.689 8.946 | 1.00 | 42.57 | | C |
| ANISOU | 1849 | CB | TYR | A | 258 | 5556 4734 5835 | 303 | 1171 | 1053 | C |
| ATOM | 1850 | CG | TYR | A | 258 | 54.203 23.534 8.830 | 1.00 | 46.92 | | C |
| ANISOU | 1850 | CG | TYR | A | 258 | 6164 5207 6350 | 367 | 1139 | 1110 | C |
| ATOM | 1851 | CD1 | TYR | A | 258 | 54.259 24.910 8.894 | 1.00 | 44.73 | | C |
| ANISOU | 1851 | CD1 | TYR | A | 258 | 5042 4936 6195 | 363 | 1171 | 1157 | C |
| ATOM | 1852 | CD2 | TYR | A | 258 | 52.935 22.904 5.609 | 1.00 | 44.03 | | C |
| ANISOU | 1852 | CD2 | TYR | A | 258 | 5802 5010 5917 | 433 | 1073 | 1110 | C |
| ATOM | 1853 | CE1 | TYR | A | 258 | 53.131 25.679 8.762 | 1.00 | 51.11 | | C |
| ANISOU | 1853 | CE1 | TYR | A | 258 | 6797 5708 6913 | 429 | 1141 | 1220 | C |
| ATOM | 1854 | CE2 | TYR | A | 258 | 51.772 23.797 8.477 | 1.00 | 44.73 | | C |
| ANISOU | 1854 | CE2 | TYR | A | 258 | 5933 5075 5983 | 497 | 1049 | 1163 | C |
| ATOM | 1855 | CZ | TYR | A | 258 | 51.909 25.052 6.554 | 1.00 | 48.05 | | C |
| ANISOU | 1855 | CZ | TYR | A | 258 | 6407 5895 6453 | 497 | 1081 | 1217 | C |
| ATOM | 1855 | OH | TYR | A | 258 | 50.846 25.926 8.402 | 1.00 | 52.22 | | O |
| ANISOU | 1856 | OH | TYR | A | 258 | 5985 5892 5965 | 585 | 1054 | 1271 | O |
| ATOM | 1857 | N | PRO | A | 259 | 58.515 22.198 6.779 | 1.00 | 45.21 | | N |
| ANISOU | 1857 | N | PRO | A | 259 | 5351 5186 6140 | 178 | 1361 | 1334 | N |
| ATOM | 1858 | CA | PRO | A | 259 | 59.839 21.554 5.757 | 1.00 | 43.79 | | C |
| ANISOU | 1858 | CA | PRO | A | 259 | 5607 5038 5995 | 122 | 1405 | 1030 | C |
| ATOM | 1859 | C | PRO | A | 259 | 60.652 21.688 8.057 | 1.00 | 41.90 | | C |
| ANISOU | 1859 | C | PRO | A | 259 | 5308 4739 5873 | 71 | 1395 | 965 | C |
| ATOM | 1860 | O | PRO | A | 259 | 61.537 20.855 8.280 | 1.00 | 40.85 | | O |
| ANISOU | 1860 | O | PRO | A | 259 | 5108 4645 5767 | 42 | 1401 | 698 | O |
| ATOM | 1861 | CB | PRO | A | 259 | 60.572 22.171 5.533 | 1.00 | 47.54 | | C |
| ANISOU | 1861 | CB | PRO | A | 259 | 6110 5513 5436 | 58 | 1504 | 1105 | C |
| ATOM | 1862 | CG | PRO | A | 259 | 59.619 23.133 4.911 | 1.00 | 51.07 | | C |
| ANISOU | 1862 | CG | PRO | A | 259 | 6645 5530 5829 | 126 | 1506 | 1202 | C |
| ATOM | 1863 | OD | PRO | A | 259 | 58.267 22.989 5.545 | 1.00 | 47.90 | | C |
| ANISOU | 1863 | CD | PRO | A | 259 | 6264 5523 6413 | 193 | 1413 | 1186 | C |
| ATOM | 1864 | N | GLU | A | 260 | 60.245 22.655 5.928 | 1 00 | 43.76 | | N |
| ANISOU | 1864 | N | GLU | A | 260 | 5565 4885 4175 | 63 | 1373 | 975 | N |
| ATOM | 1865 | CA | GLU | A | 260 | 61.017 22.715 10.237 | 1.00 | 45.59 | | C |
| ANISOU | 1855 | CA | GLU | A | 260 | 5743 5057 8512 | 19 | 1350 | 905 | C |
| ATOM | 1866 | C | GLU | A | 260 | 60.790 21.423 11.108 | 1.00 | 44.94 | | C |

TABLE 3-continued

| | | | | | | | | | | |
|---|---|---|---|---|---|---|---|---|---|---|
| ANISOU | 1866 | C | GLU | A | 260 | 5509 5039 6429 44 1272 314 | | | | C |
| ATOM | 1867 | O | GLU | A | 260 | 61.601 | 21.125 | 12.326 | 1.00 42.78 | O |
| ANISOU | 1867 | O | GLU | A | 260 | 5276 4749 6228 5 1258 745 | | | | O |
| ATOM | 1868 | CB | GLU | A | 260 | 80.520 | 24.006 | 11.007 | 1.00 51.97 | C |
| ANISOU | 1868 | CB | GLU | A | 260 | 6593 5765 7384 14 1336 929 | | | | C |
| ATOM | 1869 | CG | GLU | A | 260 | 59.746 | 23.864 | 12.272 | 1.000 51.98 | C |
| ANISOU | 1869 | CG | GLU | A | 260 | 7353 7015 3675 52 1251 376 | | | | C |
| ATOM | 1870 | CD | GLU | A | 260 | 58.196 | 24.138 | 12.167 | 1.00 77.51 | C |
| ANISOU | 1870 | CD | GLU | A | 260 | 9886 6933 10582 129 1203 917 | | | | C |
| ATOM | 1871 | OE1 | GLU | A | 260 | 57.699 | 25.045 | 11.421 | 1.00 76.71 | O |
| ANISOU | 1871 | OE1 | GLU | A | 260 | 9849 8846 10452 154 1234 998 | | | | O |
| ATOM | 1872 | OE2 | GLU | A | 260 | 57.444 | 23.462 | 12.923 | 1.00 73.30 | O |
| ANISOU | 1872 | OE2 | GLU | A | 260 | 9333 8484 10032 167 1139 866 | | | | O |
| ATOM | 1873 | N | TYR | A | 261 | 59.696 | 20.592 | 13.847 | 1.00 37.51 | N |
| ANISOU | 1873 | N | TYR | A | 261 | 4689 4153 5406 105 1223 315 | | | | N |
| ATOM | 1874 | CA | TYR | A | 261 | 59.433 | 19.399 | 11.548 | 1.00 35.43 | C |
| ANISOU | 1874 | CA | TYR | A | 261 | 4508 4071 5231 123 1154 737 | | | | C |
| ATOM | 1875 | C | TYR | A | 261 | 60.573 | 18.379 | 11.306 | 1.00 35.34 | C |
| ANISOU | 1875 | C | TYR | A | 261 | 4312 3986 5131 97 1172 684 | | | | C |
| ATOM | 1876 | O | TYR | A | 261 | 60.627 | 17.531 | 12.131 | 1.00 34.64 | O |
| ANISOU | 1876 | O | TYR | A | 261 | 4173 39 1 5071 92 1123 514 | | | | O |
| ATOM | 1877 | CB | TYR | A | 261 | 58.141 | 15.730 | 11.175 | 1.00 36.44 | C |
| ANISOU | 1877 | CB | TYR | A | 261 | 4542 4130 5174 186 1102 751 | | | | C |
| ATOM | 1878 | CG | TYR | A | 261 | 55.951 | 19.533 | 11.776 | 1.00 35.73 | C |
| ANISOU | 1878 | CG | TYR | A | 261 | 4498 4004 5093 222 1061 778 | | | | C |
| ATOM | 1879 | CD1 | TYR | A | 261 | 56.873 | 19.786 | 13.159 | 1.00 34.45 | C |
| ANISOU | 1879 | CD1 | TYR | A | 261 | 4311 3785 4993 210 1022 733 | | | | C |
| ATOM | 1880 | CD2 | TYR | A | 261 | 55 892 | 19.885 | 10.989 | 1.00 33.64 | C |
| ANISOU | 1880 | CD2 | TYR | A | 261 | 4913 4386 5385 272 3357 840 | | | | C |
| ATOM | 1881 | CE1 | TYR | A | 261 | 55.772 | 20.431 | 13.711 | 1.00 35.36 | C |
| ANISOU | 1881 | CE1 | TYR | A | 261 | 4453 3869 5106 248 987 750 | | | | C |
| ATOM | 1882 | CE2 | TYR | A | 261 | 54.770 | 20.555 | 11.513 | 1.00 38.03 | C |
| ANISOU | 1882 | CE2 | TYR | A | 261 | 4364 4275 5310 313 1019 851 | | | | C |
| ATOM | 1883 | CZ | TYR | A | 261 | 54.728 | 23.821 | 12.863 | 1.00 38.70 | C |
| ANISOU | 1883 | CZ | TYR | A | 261 | 4920 4310 5465 300 937 515 | | | | C |
| ATOM | 1884 | OH | TYR | A | 261 | 53.584 | 21.461 | 13.335 | 1.00 39.14 | O |
| ANISOU | 1884 | OH | TYR | A | 261 | 5013 4341 5518 347 953 832 | | | | O |
| ATOM | 1885 | N | LYS | A | 262 | 61.274 | 18.098 | 10.193 | 1.00 38.53 | N |
| ANISOU | 1885 | N | LYS | A | 262 | 4723 4428 5522 78 1245 718 | | | | N |
| ATOM | 1886 | CA | LYS | A | 262 | 62.436 | 17.677 | 9.941 | 1.00 40.73 | C |

TABLE 3-continued

| | | | | |
|---|---|---|---|---|
| ANISOU | 1886 CA LYS A 262 | 4932 4743 5803 52 1274 656 | | C |
| ATOM | 1887 C LYS A 262 | 60.537 17.301 10.993 1.00 39.35 | | C |
| ANISOU | 1887 C LYS A 262 | 4692 4522 5736 0 1272 608 | | C |
| ATOM | 1888 O LYS A 262 | 64.254 16.844 11.187 1.00 35.30 | | O |
| ANISOU | 1888 O LYS A 262 | 4083 4011 5205 -4 1257 542 | | O |
| ATOM | 1889 CB LYS A 262 | 63.023 17.979 8.594 1.00 44.53 | | C |
| ANISOU | 1889 CB LYS A 262 | 5424 5255 5242 30 1365 717 | | C |
| ATOM | 1890 CG LYS A 262 | 62.243 17.469 7.405 1.00 44.15 | | C |
| ANISOU | 1890 CG LYS A 262 | 5423 5277 6075 87 1357 753 | | C |
| ATOM | 1891 CD LYS A 262 | 53.033 17.940 6.177 1.00 52.16 | | C |
| ANISOU | 1891 CD LYS A 262 | 5571 5443 7183 59 1470 305 | | C |
| ATOM | 1892 CE LYS A 262 | 52.435 17.331 4.845 1.00 57.87 | | C |
| ANISOU | 1892 CE LYS A 202 | 7213 7115 7655 104 1487 845 | | C |
| ATOM | 1893 NZ LYS A 262 | 63.402 17.683 3.767 1.00 63.92 | | N |
| ANISOU | 1893 NZ LYS A 262 | 7970 7922 8394 70 1591 370 | | N |
| ATOM | 1894 N ASP A 253 | 63.635 18.953 11.555 1.00 37.44 | | N |
| ANISOU | 1894 N ASP A 263 | 4459 4199 5535 -35 1282 527 | | N |
| ATOM | 1895 CA ASP A 263 | 64.614 19.003 12.798 1.00 40.79 | | C |
| ANISOU | 1895 CA ASP A 263 | 4135 4585 6002 -81 1252 568 | | C |
| ATOM | 1896 C ASP A 263 | 64.191 18.082 13.915 1.00 35.51 | | C |
| ANISOU | 1896 C ASP A 263 | 4135 3929 5430 -52 1163 494 | | C |
| ATOM | 1897 O ASP A 263 | 65.104 17.581 14.323 1.00 35.87 | | O |
| ANISOU | 1897 O ASP A 263 | 4116 3977 5536 -77 1145 427 | | O |
| ATOM | 1898 CB ASP A 263 | 64.775 20.400 19.421 1.00 41.55 | | C |
| ANISOU | 1898 CB ASP A 263 | 4937 4586 6264 -125 1278 488 | | C |
| ATOM | 1899 CG ASP A 263 | 65.132 21.460 12.362 1.00 50.17 | | C |
| ANISOU | 1899 CG ASP A 263 | 6060 5649 7353 -161 1371 669 | | C |
| ATOM | 1900 OD1 ASP A 263 | 65.644 21.092 11.310 1.00 50.37 | | O |
| ANISOU | 1900 OD1 ASP A 263 | 6068 5732 7337 -168 1431 689 | | O |
| ATOM | 1901 OD2 ASP A 263 | 64.836 22.634 12.574 1.00 52.98 | | O |
| ANISOU | 1901 OD2 ASP A 263 | 6457 5920 7735 -178 1384 713 | | O |
| ATOM | 1902 N SER A 264 | 62.859 17.959 14.208 1.00 37.21 | | N |
| ANISOU | 1902 N SER A 264 | 4401 4144 5393 -4 1112 509 | | N |
| ATOM | 1903 CA SER A 264 | 62.473 16.993 15.240 1.00 34.48 | | C |
| ANISOU | 1903 CA SER A 264 | 4037 3816 5248 19 1028 447 | | C |
| ATOM | 1904 C SER A 264 | 62.707 15.594 14.776 1.00 33.07 | | C |
| ANISOU | 1904 C SER A 264 | 3828 3710 5026 41 1010 409 | | C |
| ATOM | 1905 O SER A 264 | 63.055 14.791 15.591 1.00 32.65 | | O |
| ANISOU | 1905 O SER A 264 | 3764 3690 5028 39 957 348 | | O |
| ATOM | 1906 CB SER A 264 | 60.993 17.077 15.768 1.00 36.28 | | C |

TABLE 3-continued

| | | | | | | | | | | |
|---|---|---|---|---|---|---|---|---|---|---|
| ANISOU | 1906 | CB | SER | A | 264 | 4316 4037 5433 61 970 464 | | | | C |
| ATOM | 1907 | OG | SER | A | 264 | 60.846 | 18.369 | 16.414 | 1.00 36.41 | O |
| ANISOU | 1907 | OG | SER | A | 264 | 4357 3977 5501 44 979 484 | | | | O |
| ATOM | 1908 | N | VAL | A | 265 | 62.481 | 15.314 | 13.499 | 1.00 32.02 | N |
| ANISOU | 1908 | N | VAL | A | 265 | 3717 3628 4823 64 1049 445 | | | | N |
| ATOM | 1909 | CA | VAL | A | 265 | 62.696 | 13.920 | 12.995 | 1.00 34.47 | C |
| ANISOU | 1909 | CA | VAL | A | 265 | 4002 4006 5088 89 1030 403 | | | | C |
| ATOM | 1910 | C | VAL | A | 265 | 64.153 | 13.565 | 13.248 | 1.00 33.38 | C |
| ANISOU | 1910 | C | VAL | A | 265 | 3792 3870 5020 57 1050 346 | | | | C |
| ATOM | 1911 | O | VAL | A | 265 | 64.473 | 12.464 | 13.686 | 1.00 31.10 | O |
| ANISOU | 1911 | O | VAL | A | 265 | 3469 3604 4742 71 1000 32.29 | | | | O |
| ATOM | 1912 | CB | VAL | A | 265 | 62.372 | 13.779 | 11.498 | 1.00 32.29 | C |
| ANISOU | 1912 | CB | VAL | A | 265 | 3760 3785 4725 115 1079 448 | | | | C |
| ATOM | 1913 | CG1 | VAL | A | 265 | 62.976 | 12.454 | 10.909 | 1.00 33.70 | C |
| ANISOU | 1913 | CG1 | VAL | A | 265 | 3902 4028 4873 133 1078 393 | | | | C |
| ATOM | 1914 | CG2 | VAL | A | 265 | 60.843 | 13.997 | 11.207 | 1.00 33.58 | C |
| ANISOU | 1914 | CG2 | VAL | A | 265 | 3989 3959 4811 156 1045 497 | | | | C |
| ATOM | 1915 | N | GLN | A | 266 | 65.055 | 14.524 | 13.005 | 1.00 31.20 | N |
| ANISOU | 1915 | N | GLN | A | 266 | 3492 3567 4796 13 1121 367 | | | | N |
| ATOM | 1916 | CA | GLN | A | 266 | 66.472 | 14.242 | 13.154 | 1.00 31.47 | C |
| ANISOU | 1916 | CA | GLN | A | 266 | 3447 3611 4898 -19 1146 314 | | | | C |
| ATOM | 1917 | C | GLN | A | 266 | 66.815 | 14.083 | 14.636 | 1.00 33.70 | C |
| ANISOU | 1917 | C | GLN | A | 266 | 3692 3653 5259 -35 1074 254 | | | | C |
| ATOM | 1918 | O | GLN | A | 266 | 67.486 | 13 143 | 15.024 | 1.00 32.72 | O |
| ANISOU | 1918 | O | GLN | A | 266 | 3516 3753 5164 -27 1038 190 | | | | O |
| ATOM | 1919 | CB | GLN | A | 266 | 67.340 | 15.371 | 12.525 | 1.00 34.85 | C |
| ANISOU | 1919 | CB | GLN | A | 266 | 3856 4020 5364 -72 1244 356 | | | | C |
| ATOM | 1920 | CG | GLN | A | 266 | 68.834 | 15.137 | 12.794 | 1.00 36.53 | C |
| ANISOU | 1920 | CG | GLN | A | 266 | 3975 4245 5659 -110 1267 296 | | | | C |
| ATOM | 1921 | CD | GLN | A | 266 | 69.718 | 16.214 | 12.161 | 1.00 40.23 | C |
| ANISOU | 1921 | CD | GLN | A | 266 | 4417 4699 6168 -172 1369 337 | | | | C |
| ATOM | 1922 | OE1 | GLN | A | 266 | 69.404 | 16.740 | 11.111 | 1.00 39.64 | O |
| ANISOU | 1922 | OE1 | GLN | A | 266 | 4389 4637 6036 -175 1436 407 | | | | O |
| ATOM | 1923 | NE2 | GLN | A | 266 | 70.839 | 16.491 | 12.783 | 1.00 39.04 | N |
| ANISOU | 1923 | NE2 | GLN | A | 266 | 4191 4528 6115 -222 1378 295 | | | | N |
| ATOM | 1924 | N | GLU | A | 267 | 66.387 | 15.042 | 15.465 | 1.00 34.02 | N |
| ANISOU | 1924 | N | GLU | A | 267 | 3761 3830 5335 -57 1055 275 | | | | N |
| ATOM | 1925 | CA | GLU | A | 267 | 66.729 | 14.984 | 16.858 | 1.00 34.53 | C |
| ANISOU | 1925 | CA | GLU | A | 267 | 3794 3857 5468 -74 990 220 | | | | C |
| ATOM | 1926 | C | GLU | A | 267 | 66.139 | 13.749 | 17.601 | 1.00 33.60 | C |

TABLE 3-continued

| | | | | | | | | | | | |
|---|---|---|---|---|---|---|---|---|---|---|---|
| ANISOU | 1926 | C | GLU | A | 267 | 3685 | 3764 | 5319 | -32 | 897 | 175 | C |
| ATOM | 1927 | O | GLU | A | 267 | 66.832 | 13.167 | 18.443 | 1.00 | 31.77 | O |
| ANISOU | 1927 | O | GLU | A | 267 | 3406 | 3531 | 5135 | -38 | 848 | 114 | O |
| ATOM | 1928 | CB | GLU | A | 267 | 66.271 | 16.253 | 17.573 | 1.00 | 31.70 | C |
| ANISOU | 1928 | CB | GLU | A | 267 | 4234 | 438T | 5935 | -100 | 936 | 248 | C |
| ATOM | 1929 | CG | GLU | A | 267 | 66.593 | 16.110 | 190.084 | 1.00 | 31.41 | C |
| ANISOU | 1929 | CG | GLU | A | 267 | 4153 | 4315 | 5930 | -116 | 913 | 156 | C |
| ATOM | 1930 | CD | GLU | A | 267 | 66.789 | 17.543 | 19.686 | 1.00 | 48.73 | C |
| ANISOU | 1930 | CD | GLU | A | 267 | 5612 | 5475 | 1430 | -152 | 930 | 195 | C |
| ATOM | 1931 | OE1 | GLU | A | 267 | 66.074 | 18.495 | 19.269 | 1.00 | 45.70 | O |
| ANISOU | 1931 | OE1 | GLU | A | 267 | 5285 | 3055 | 7024 | -160 | 968 | 256 | O |
| ATOM | 1932 | OE2 | GLU | A | 267 | 67.653 | 11 653 | 20.565 | 1.00 | 59.54 | O |
| ANISOU | 1932 | OE2 | GLU | A | 267 | 6932 | 6320 | 8372 | -197 | 902 | 143 | O |
| ATOM | 1933 | N | THR | A | 268 | 64.877 | 13.405 | 17.324 | 1.00 | 27.89 | N |
| ANISOU | 1933 | N | THR | A | 268 | 3021 | 3050 | 4517 | 8 | 873 | 206 | N |
| ATOM | 1934 | CA | THR | A | 268 | 64.267 | 32.374 | 17.372 | 1.00 | 28.02 | C |
| ANISOU | 1934 | CA | THR | A | 268 | 3049 | 3102 | 4496 | 43 | 792 | 171 | C |
| ATOM | 1935 | C | THR | A | 268 | 55.055 | 17.557 | 17.438 | 1.00 | 29.90 | C |
| ANISOU | 1935 | C | THR | A | 268 | 3243 | 3387 | 4731 | 61 | 781 | 122 | C |
| ATOM | 1936 | O | THR | A | 268 | 55.175 | 9.967 | 18.243 | 1.00 | 32.56 | O |
| ANISOU | 1936 | O | THR | A | 268 | 3555 | 3724 | 5081 | 73 | 710 | 74 | O |
| ATOM | 1937 | CB | THR | A | 268 | 62.762 | 11.999 | 17.563 | 1.00 | 25.21 | C |
| ANISOU | 1937 | CB | THR | A | 268 | 2755 | 2755 | 4056 | 76 | 771 | 213 | C |
| ATOM | 1938 | OG1 | THR | A | 268 | 62.514 | 12.066 | 16.138 | 1.00 | 28.75 | O |
| ANISOU | 1938 | OG1 | THR | A | 268 | 3230 | 3255 | 5550 | 96 | 323 | 257 | O |
| ATOM | 1939 | CG2 | THR | A | 268 | 51.019 | 13.162 | 18.263 | 1.00 | 27.50 | C |
| ANISOU | 1939 | CG2 | THR | A | 268 | 3124 | 3046 | 4393 | 70 | 765 | 249 | C |
| ATOM | 1940 | N | ALA | A | 269 | 65.525 | 10.579 | 15.247 | 1.00 | 31.39 | N |
| ANISOU | 1940 | N | ALA | A | 269 | 3412 | 3530 | 4906 | 53 | 849 | 133 | N |
| ATOM | 1941 | CA | ALA | A | 269 | 56.475 | 9.787 | 15.733 | 1.00 | 54.59 | C |
| ANISOU | 1941 | CA | ALA | A | 269 | 3783 | 4072 | 3224 | 83 | 852 | 83 | C |
| ATOM | 1942 | C | ALA | A | 269 | 57.607 | 9.752 | 16.455 | 1.00 | 33.59 | C |
| ANISOU | 1942 | C | ALA | A | 269 | 3581 | 3930 | 5200 | 54 | 842 | 27 | C |
| ATOM | 1943 | O | ALA | A | 269 | 68.361 | 8.679 | 16.734 | 1.00 | 32.21 | O |
| ANISOU | 1943 | O | ALA | A | 269 | 3344 | 3747 | 5135 | 82 | 793 | -32 | O |
| ATOM | 1944 | CB | ALA | A | 269 | 56.742 | 9.994 | 14.212 | 1.00 | 34.24 | C |
| ANISOU | 1944 | CB | ALA | A | 269 | 3726 | 4060 | 5223 | 87 | 942 | 114 | C |
| ATOM | 1945 | N | GLU | A | 270 | 68.384 | 10.928 | 15.579 | 1.00 | 31.55 | N |
| ANISOU | 1945 | N | GLU | A | 270 | 3321 | 3563 | 5316 | 13 | 888 | 44 | N |
| ATOM | 1946 | CA | GLU | A | 270 | 69.538 | 11.031 | 17.407 | 1.00 | 32.33 | C |

TABLE 3-continued

| | | | |
|---|---|---|---|
| ANISOU | 1946 CA GLU A 270 | 3301 3705 5255 -19 377 -9 | C |
| ATOM | 1947 C GLU A 270 | 59.595 10.601 18.846 1.00 31.81 | C |
| ANISOU | 1947 C GLU A 270 | 3235 3612 5240 -14 773 -54 | C |
| ATOM | 1948 O GLU A 270 | 70.537 9.889 19.322 1.00 29.50 | O |
| ANISOU | 1948 O GLU A 270 | 2981 3332 4997 -5 735 -115 | O |
| ATOM | 1949 CB GLU A 270 | 70.223 12.499 17.327 1.00 33.91 | C |
| ANISOU | 1949 CB GLU A 270 | 3229 3623 5276 -81 949 22 | C |
| ATOM | 1950 CG GLU A 270 | 70.813 12.770 35.919 1.00 37.26 | C |
| ANISOU | 1950 CG GLU A 270 | 3880 4340 5939 -95 1055 51 | C |
| ATOM | 1951 CD GLU A 270 | 71.148 14.247 15.7.50 1.00 45.34 | C |
| ANISOU | 1951 CD GLU A 270 | 4900 5321 7007 -159 1193 99 | C |
| ATOM | 1952 OE1 GLU A 270 | 70.7139 14.995 16.640 1.00 46.57 | O |
| ANISOU | 1952 OE1 GLU A 270 | 5852 5581 7460 -181 1093 310 | O |
| ATOM | 1953 OE2 GLU A 270 | 71.684 14 587 14.718 1.00 45.33 | O |
| ANISOU | 1953 OE2 GLU A 270 | 5305 5470 7128 -185 1220 1131 | O |
| ATOM | 1954 N VAL A 271 | 68.516 10.892 19.552 1.00 29 03 | N |
| ANISOU | 1954 N VAL A 271 | 2945 3226 4858 -12 783 -28 | N |
| ATOM | 1955 CA VAL A 271 | 88.584 10.854 20.91 1.00 30.47 | C |
| ANISOU | 1955 CA VAL A 271 | 3122 3379 5077 -16 647 -73 | C |
| ATOM | 1956 C VAL A 271 | 58.356 9.163 21.370 1.00 29.52 | C |
| ANISOU | 1956 C VAL A 271 | 3011 3282 4924 29 566 -106 | C |
| ATOM | 1957 O VAL A 271 | 69.557 8.780 22.575 1.00 32.17 | O |
| ANISOU | 1957 O VAL A 271 | 3338 3597 5287 30 487 -144 | O |
| ATOM | 1958 CB VAL A 271 | 67.543 11.582 21 824 1.00 28.72 | C |
| ANISOU | 1958 CB VAL A 271 | 2957 3111 4845 -34 525 -39 | C |
| ATOM | 1959 CG1 VAL A 271 | 67.9799 13.093 21.634 1.00 30.67 | C |
| ANISOU | 1959 CG1 VAL A 271 | 3195 3318 5141 -81 695 -10 | C |
| ATOM | 1960 CG2 VAL A 271 | 86.146 11.244 21.574 1.00 28.94 | C |
| ANISOU | 1960 CG2 VAL A 271 | 3059 3152 4784 1 610 4 | C |
| ATOM | 1961 N VAL A 272 | 67.912 8.357 20.407 1.00 29.72 | N |
| ANISOU | 1961 N VAL A 272 | 3060 3345 4839 65 580 -94 | N |
| ATOM | 1962 CA VAL A 272 | 67.761 6.915 20.658 1.00 31.35 | C |
| ANISOU | 1962 CA VAL A 272 | 3276 3567 5370 105 506 -130 | C |
| ATOM | 1963 C VAL A 272 | 69.527 5.105 23.253 1.00 31.76 | C |
| ANISOU | 1964 C VAL A 272 | 3260 3545 5163 128 508 -186 | C |
| ATOM | 1964 O VAL A 272 | 69.132 4.891 20.530 1.00 32.93 | O |
| ANISOU | 1964 O VAL A 272 | 3410 3797 5305 163 442 -224 | O |
| ATOM | 1965 CB VAL A 272 | 66.500 5.321 20.048 1.00 30.43 | C |
| ANISOU | 1965 CB VAL A 272 | 3277 3521 4915 133 498 -95 | C |
| ATOM | 1966 CG1 VAL A 272 | 65.277 6.963 20.752 1.00 28.83 | C |

TABLE 3-continued

| | | | | | | | | | | | |
|---|---|---|---|---|---|---|---|---|---|---|---|
| ANISOU | 1966 | CG1 | VAL | A | 272 | 3082 | 3243 | 4529 | 116 | 478 | -52 C |
| ATOM | 1967 | CG2 | VAL | A | 272 | 65.544 | 6.459 | 18.501 | 1.00 | 28.45 | C |
| ANISOU | 1967 | CG2 | VAL | A | 272 | 2974 | 3250 | 4576 | 144 | 561 | -72 C |
| ATOM | 1968 | N | ILE | A | 273 | 70.905 | 6.770 | 19.638 | 1.00 | 31.66 | N |
| ANISOU | 1968 | N | ILE | A | 273 | 3186 | 3643 | 5195 | 157 | 583 | -192 N |
| ATOM | 1969 | CA | ILE | A | 273 | 71.301 | 6.108 | 19.291 | 1.00 | 30.55 | C |
| ANISOU | 1969 | CA | ILE | A | 273 | 2966 | 3538 | 5104 | 128 | 532 | -251 C |
| ATOM | 1970 | C | ILE | A | 273 | 71.929 | 5.427 | 20.498 | 1.00 | 32.51 | C |
| ANISOU | 1970 | C | ILE | A | 273 | 3192 | 3771 | 5421 | 142 | 491 | -308 C |
| ATOM | 1971 | O | ILE | A | 273 | 72.372 | 4.229 | 20.398 | 1.00 | 36.70 | O |
| ANISOU | 1971 | O | 1LE | A | 273 | 3588 | 4312 | 5943 | 193 | 454 | -356 O |
| ATOM | 1972 | CB | ILE | A | 273 | 72.302 | 7.054 | 16.538 | 1.00 | 29.95 | C |
| ANISOU | 1972 | CB | ILE | A | 273 | 2320 | 3484 | 5075 | 91 | 693 | -248 C |
| ATOM | 1973 | CG1 | ILL | A | 273 | 71.713 | 7.458 | 17.203 | 1.00 | 29.99 | C |
| ANISOU | 1973 | CG1 | ILE | A | 273 | 2565 | 3518 | 5011 | 89 | 782 | -192 C |
| ATOM | 1974 | CG2 | ILE | A | 273 | 73.711 | 6.401 | 18.378 | 1.00 | 32.11 | C |
| ANISOU | 1974 | CG2 | ILE | A | 273 | 2995 | 3792 | 5411 | 112 | 695 | -317 C |
| ATOM | 1975 | CD1 | ILE | A | 273 | 71.543 | 6.328 | 15.149 | 1.00 | 30.91 | C |
| ANISOU | 1975 | CD1 | ILE | A | 273 | 2997 | 3664 | 5063 | 144 | 793 | -210 C |
| ATOM | 1976 | N | PRO | A | 274 | 71.903 | 6.079 | 21.577 | 1.00 | 34.25 | N |
| ANISOU | 1976 | N | PRO | A | 274 | 3402 | 3945 | 5665 | 108 | 454 | -308 N |
| ATOM | 1977 | CA | PRO | A | 274 | 72.591 | 5.352 | 22.785 | 1.00 | 36.60 | C |
| ANISOU | 1977 | CA | PRO | A | 274 | 3665 | 4225 | 8312 | 127 | 359 | -362 C |
| ATOM | 1978 | C | PRO | A | 274 | 71.777 | 4.155 | 23.298 | 1.00 | 35.89 | C |
| ANISOU | 1978 | C | PRO | A | 274 | 3643 | 4124 | 5868 | 168 | 279 | -354 C |
| ATOM | 1979 | O | PRO | A | 274 | 72.252 | 3.441 | 24.202 | 1.00 | 35.7 | O |
| ANISOU | 1979 | O | PRO | A | 274 | 3604 | 4386 | 5875 | 190 | 184 | -404 O |
| ATOM | 1980 | CB | PRO | A | 274 | 72.649 | 6.383 | 23.930 | 1.00 | 33.69 | C |
| ANISOU | 1980 | CB | PRO | A | 274 | 3927 | 4455 | 6318 | 73 | 334 | -358 C |
| ATOM | 1981 | CG | PRO | A | 274 | 72.593 | 7.703 | 23.244 | 1.00 | 37.55 | C |
| ANISOU | 1981 | CG | PRO | A | 274 | 3719 | 4245 | 6114 | 32 | 432 | -314 C |
| ATOM | 1982 | CD | PRO | A | 274 | 71.572 | 7.479 | 22.068 | 1.00 | 36.93 | C |
| ANISOU | 1982 | CD | PRO | A | 274 | 3763 | 4254 | 6019 | 54 | 488 | -266 C |
| ATOM | 1983 | N | LEU | A | 275 | 70.524 | 3.387 | 22.688 | 1.00 | 33.93 | N |
| ANISOU | 1983 | N | LEU | A | 275 | 3466 | 3883 | 5542 | 180 | 288 | -321 N |
| ATOM | 1984 | CA | LEU | A | 275 | 59.792 | 2.729 | 23.110 | 1.00 | 30.54 | C |
| ANISOU | 1984 | CA | LEU | A | 275 | 3116 | 3452 | 5073 | 211 | 207 | -319 C |
| ATOM | 1985 | C | LEU | A | 275 | 59.978 | 1.552 | 22.319 | 1.00 | 32.57 | C |
| ANISOU | 1985 | C | LEU | A | 275 | 3357 | 3721 | 5296 | 250 | 210 | -340 C |
| ATOM | 1986 | O | LEU | A | 275 | 690.277 | 0.515 | 22.225 | 1.00 | 31.30 | O |

TABLE 3-continued

| | | | | |
|---|---|---|---|---|
| ANISOU | 1986 O LEU A 275 | 3254 3548 5090 285 151 -344 | | O |
| ATOM | 1987 CB LEU A 275 | 68.277 3.135 23.245 | 1.00 29.57 | C |
| ANISOU | 1987 CB LEU A 275 | 3003 3307 487 188 212 -258 | | C |
| ATOM | 1988 CG LEU A 275 | 67.950 4 512 23.856 | 1.00 29.65 | C |
| ANISOU | 1988 CG LEU A 275 | 3.082 3300 4889 143 238 -226 | | C |
| ATOM | 1989 CD1 LEU A 275 | 60.450 4.700 23.90 | 1.00 30.84 | C |
| ANISOU | 1989 CD1 LEU A 275 | 3305 3446 4965 105 239 -173 | | C |
| ATOM | 1990 CD2 LEU A 275 | 68.512 4.424 25.279 | 1.00 30.94 | C |
| ANISOU | 1990 CD2 LEU A 275 | 8225 3433 5097 134 150 -200 | | C |
| ATOM | 1991 N MET A 276 | 70. 953 1.595 21.210 | 1.00 31.88 | N |
| ANISOU | 1991 N MET A 276 | 3203 3007 5244 273 275 -875 | | |
| ATOM | 1992 CA MET A 276 | 71.193 0.633 20.196 | 1.00 35.63 | C |
| ANISOU | 1992 CA MET A 276 | 3678 4176 5704 324 255 -409 | | C |
| ATOM | 1993 C MET A 276 | 72.293 -0.249 20.725 | 1.00 36.41 | C |
| ANISOU | 1993 C MET A 276 | 3716 4258 5860 365 220 -475 | | C |
| ATOM | 1994 O MET A 276 | 73.027 0.186 21.569 | 1.00 37.20 | O |
| ANISOU | 1994 O MET A 276 | 3765 4346 6023 348 195 -494 | | O |
| ATOM | 1995 CB MET A 276 | 71.578 1.230 18.804 | 1.00 35.30 | C |
| ANISOU | 1995 CB MET A 276 | 3555 4152 5020 319 400 -402 | | C |
| ATOM | 1996 CG MET A 276 | 70.533 2.192 18.244 | 1.00 37.77 | C |
| ANISOU | 1996 CG MET A 276 | 3956 4498 5595 232 466 -332 | | C |
| ATOM | 1997 SD MET A 276 | 69.059 1 209 17.906 | 1.00 33.29 | S |
| ANISOU | 1997 SD MET A 276 | 4122 4560 5866 310 417 -308 | | S |
| ATOM | 1998 CE MET A 276 | 57.855 2.472 18.432 | 1.00 41.58 | C |
| ANISOU | 1998 CE MET A 276 | 4593 4955 5251 257 430 -230 | | C |
| ATOM | 1999 N ALA A 277 | 72.443 -1.484 20.216 | 1.00 34.03 | N |
| ANISOU | 1999 N ALA A 277 | 3423 3902 5545 422 190 -515 | | N |
| ATOM | 2000 CA ALA A 277 | 73.442 -2.397 20.751 | 1.00 40.65 | C |
| ANISOU | 2000 CA ALA A 277 | 4241 4811 6470 471 118 -579 | | C |
| ATOM | 2001 C ALA A 277 | 74.790 -1.891 20.303 | 1.00 47.10 | C |
| ANISOU | 2001 C ALA A 277 | 4920 5545 7320 475 153 -623 | | C |
| ATOM | 2002 O ALA A 277 | 75.503 2.111 20.076 | 1.00 50.59 | O |
| ANISOU | 2002 O ALA A 277 | 5297 6082 7644 497 135 -670 | | O |
| ATOM | 2003 CB ALA A 277 | 73.256 -3.809 20.238 | 1.00 41.34 | C |
| ANISOU | 2003 CB ALA A 277 | 4305 4825 6463 533 75 -613 | | C |
| ATOM | 2004 N ASN A 278 | 74.752 -1.153 19.205 | 1.00 44.86 | N |
| ANISOU | 2004 N ASN A 278 | 4517 5426 7020 452 293 -602 | | N |
| ATOM | 2005 CA ASN A 278 | 75.704 -1.328 18.134 | 1.00 57.59 | C |
| ANISOU | 2005 CA ASN A 278 | 74313 3353 9933 485 307 -649 | | C |
| ATOM | 2006 C ASN A 278 | 75.507 -2.649 17.340 | 1.00 69.65 | C |

TABLE 3-continued

| | | | | | | | | | | |
|---|---|---|---|---|---|---|---|---|---|---|
| ANISOU | 2006 | C | ASN | A | 278 | 7704 8613 10140 653 350 -695 | | | | C |
| ATOM | 2007 | O | ASN | A | 278 | 75.217 | -3.720 | 17.702 | 1.00 74.00 | O |
| ANISOU | 2007 | O | ASN | A | 278 | 3238 9142 10736 517 271 -756 | | | | O |
| ATOM | 2008 | CB | ASN | A | 278 | 77.033 | -0.852 | 18.509 | 1.00 50.20 | C |
| ANISOU | 2008 | CB | ASN | A | 278 | 7006 8053 9713 475 375 -689 | | | | C |
| ATOM | 2009 | CG | ASN | A | 278 | 75.995 | 8053 | 18.714 | 1.00 52.21 | C |
| ANISOU | 2009 | CG | ASN | A | 278 | 6607 7630 9349 390 444 -539 | | | | C |
| ATOM | 2010 | OD1 | ASN | A | 278 | 76.971 | 1.285 | 17.690 | 1.00 58.53 | O |
| ANISOU | 2010 | OD1 | ASN | A | 278 | 5130 7253 3856 370 549 -612 | | | | O |
| ATOM | 2011 | ND2 | ASN | A | 278 | 75.800 | 1.155 | 19.915 | 1.00 65.37 | N |
| ANISOU | 2011 | ND2 | ASN | A | 278 | 7024 8037 9778 357 384 -618 | | | | N |
| ATOM | 2012 | OXT | ASN | A | 278 | 75.073 | -2.576 | 10.261 | 1.00 71.58 | O |
| ANISOU | 2012 | OXT | ASN | A | 278 | 8002 8899 10333 556 417 -572 | | | | O |
| TER | 2013 | | ASN | A | 278 | | | | | |
| ATOM | 2014 | N | ASN | B | 6 | 50.962 | 15.155 | 4.943 | 1.00 73.54 | N |
| ANISOU | 2014 | N | ASN | B | 6 | 9137 8979 9824 -681 1694 -358 | | | | N |
| ATOM | 2015 | CA | ASN | B | 6 | 82.343 | 16.416 | 5.467 | 1.00 77.214 | C |
| ANISOU | 2015 | CA | ASN | B | 6 | 9559 9.515 10292 -859 1762 -495 | | | | C |
| ATOM | 2016 | C | ASN | B | 6 | 82.968 | 15.793 | 6.360 | 1.00 74.00 | C |
| ANISOU | 2016 | C | ASN | B | 6 | 8972 9252 9894 -872 1638 -624 | | | | C |
| ATOM | 2017 | O | ASN | B | 6 | 84.199 | 15.190 | 6.418 | 1.00 72.84 | O |
| ANISOU | 2017 | O | ASN | B | 6 | 8731 9226 9719 -986 1660 -728 | | | | O |
| ATOM | 2018 | CB | ASN | B | 6 | 82.445 | 17.841 | 6.084 | 1.00 72.41 | C |
| ANISOU | 2018 | CB | ASN | B | 6 | 9079 3732 9703 -989 19429 -499 | | | | C |
| ATOM | 2019 | CG | ASN | B | 6 | 83.503 | 17.951 | 7.174 | 1.00 72.65 | C |
| ANISOU | 2019 | CG | ASN | B | 6 | 9033 8831 9741 -1164 1954 -558 | | | | C |
| ATOM | 2020 | OD1 | ASN | B | 6 | 83.383 | 17.335 | 8.242 | 1.00 68.47 | O |
| ANISOU | 2020 | OD1 | ASN | B | 6 | 8410 8356 9240 -1142 1853 -722 | | | | O |
| ATOM | 2021 | ND2 | ASN | B | 6 | 84.533 | 18.762 | 6.924 | 1.00 73.29 | N |
| ANISOU | 2021 | ND2 | ASN | B | 6 | 9776 9548 13424 -1348 2092 -721 | | | | N |
| ATOM | 2022 | N | LEU | B | 7 | 82.130 | 14.462 | 7.332 | 1.50 62.57 | N |
| ANISOU | 2022 | N | LEU | B | 7 | 7431 7805 5489 -754 1514 -611 | | | | N |
| ATOM | 2023 | CA | LEU | B | 7 | 82.650 | 13.233 | 7.727 | 1.05 82.74 | C |
| ANISOU | 2023 | CA | LEU | B | 7 | 7349 7968 8021 -727 1383 -708 | | | | C |
| ATOM | 2024 | C | LEU | B | 7 | 83.409 | 12.244 | 6.755 | 1.00 63.86 | C |
| ANISOU | 2024 | C | LEU | B | 7 | 7380 8262 8623 -507 1332 -742 | | | | C |
| ATOM | 2025 | O | LEU | B | 7 | 84.339 | 11.521 | 7.175 | 1.00 53.00 | O |
| ANISOU | 2025 | O | LEU | B | 7 | 7139 8235 8511 -708 1280 -832 | | | | O |
| ATOM | 2026 | CB | LEU | B | 7 | 81.539 | 12.494 | 8.480 | 1.00 57.54 | C |
| ANISOU | 2026 | CB | LEU | B | 7 | 5685 7263 7913 -633 1280 -654 | | | | C |

TABLE 3-continued

```
ATOM   2027 CG  LEU B  7      81.809 11.000  8.002 1.00 57.28  C
ANISOU 2027 CG  LEU B  7      5525  7354  7886 -513 1143 -711  C
ATOM   2028 CD1 LEU B  7      82.320 10.741  9.607 1.00 57.57  C
ANISOU 2028 CD1 LEU B  7      7733  8782  5193 -590 1125 -812  C
ATOM   2029 CD2 LEU B  7      80.561 13.225  8.965 1.00 56.39  C
ANISOU 2029 CD2 LEU B  7      6489  7245  7882 -394 1057 -554  C
ATOM   2030 N   LEU B  8      82.939 12.222  5.503 1.00 60.17  N
ANISOU 2030 N   LEU B  8      5966  7775  8120 -523 1345 -670  N
ATOM   2031 CA  LEU B  8      39.575 11.521  4.419 1.00 58.45  C
ANISOU 2031 CA  LEU B  8      6677  7384  7849 -609 1322 -703  C
ATOM   2032 C   LEU B  8      85.048 12.153  4.198 1.00 51.00  C
ANISOU 2032 C   LEU B  8      6957  3385  3134 -755 1443 -781  C
ATOM   2033 O   LEU B  8      86.056 11.430  4.154 1.00 53.55  O
ANISOU 2033 O   LEU B  8      7146  3553  3448 -764 1417 -672  O
ATOM   2034 CB  LEU B  8      82.843 11.4B5  3.127 1.00 53.74  C
ANISOU 2034 CB  LEU B  8      6151  7356  7200 -528 1327 -513  C
ATOM   2035 CG  LEU B  8      81.579 10.592  2.121 1.00 61.25  C
ANISOU 2035 CG  LEU B  8      7114  7931  8132 -392 1201 -556  C
ATOM   2036 CD1 LEU B  8      83.957 10.285  1.825 1.00 51.99  C
ANISOU 2036 CD1 LEU B  8      7246  8108  8200 -324 1173 -535  C
ATOM   2037 CD2 LEU B  8      81.822  9.234  3.949 1.30 62.14  C
ANISOU 2037 CD2 LEU B  8      7112  8154  8343 -340 1099 -654  C
ATOM   2038 N   VAL B  9      85.060 13.492  4.377 1.30 56.85  N
ANISOU 2038 N   VAL B  9      6547  7450  7593 -854 1573 -733  N
ATOM   2039 CA  VAL B  9      36.273 14.286  3.875 1.00 51.59  C
ANISOU 2039 CA  VAL B  9      7144  8124  8173 -1333 1705 -803  C
ATOM   2040 C   VAL B  9      87.224 43.974  5.318 1 00 65.59  C
ANISOU 2040 C   VAL B  9      7487  8738  8695 -1115 1657 -932  C
ATOM   2041 O   VAL B  9      88.421 13.735  4.797 1.00 52.67  O
ANISOU 2041 O   VAL B  9      6987  8525  8299 -1193 1692 -1023 O
ATOM   2042 CB  VAL B  9      85.307 15.826  3.755 1.00 52.00  C
ANISOU 2042 CB  VAL B  9      7483  8118  8331 -1146 1863 -733  C
ATOM   2043 CG1 VAL B  9      37.281 15.589  3.288 1.00 50.15  C
ANISOU 2043 CG1 VAL B  9      7118  7312  7925 -1339 2019 -799  C
ATOM   2044 CG2 VAL B  9      34.638 15.089  2.741 1.00 53.57  C
ANISOU 2044 CG2 VAL B  9      7705  6077  8372 -1024 1377 -577  C
ATOM   2045 N   ARG B 10      35.632 13.933  6.238 1.00 63.22  N
ANISOU 2045 N   ARG B 10      7195  8380  3445 -1095 1602 -938  N
ATOM   2046 CA  ARG B 10      87.473 13.548  7.401 1.00 63.13  C
ANISOU 2046 CA  ARG B 10      7046  8507  8452 -1152 1540 -1047 C
```

TABLE 3-continued

| | | | | | | | | | | |
|---|---|---|---|---|---|---|---|---|---|---|
| ATOM | 2047 | C | ARG | B | 10 | 87.943 | 12.083 | 7.293 | 1.00 | 58.70 C |
| ANISOU | 2047 | C | ARG | B | 10 | 6311 3106 7888 | -1022 | 1413 | -1384 C | |
| ATOM | 2048 | O | ARG | B | 10 | 39.120 | 11.806 | 7.530 | 1.00 | 53 54 O |
| ANISOU | 2048 | O | ARG | B | 10 | 6304 6931 6521 | -1080 | 1405 | -1175 O | |
| ATOM | 2049 | CB | ARG | B | 10 | 86.762 | 13.880 | 8.724 | 1.00 | 65.65 C |
| ANISOU | 2049 | CB | ARG | B | 10 | 7550 8846 8927 | -1153 | 1510 | -1041 C | |
| ATOM | 2050 | CG | ARG | B | 10 | 67.715 | 14.1145 | 9.906 | 1.00 | 75.53 C |
| ANISOU | 2050 | CG | ARG | B | 10 | 8699 10213 10163 | -1313 | 1530 | -1162 C | |
| ATOM | 2051 | CD | ARG | B | 10 | 67.013 | 14.536 | 11.217 | 1.00 | 76.05 C |
| ANISOU | 2051 | CD | ARG | B | 10 | 8719 10058 11116 | -1330 | 1496 | -1166 C | |
| ATOM | 2052 | NE | ARG | B | 10 | 86.3615 | 13.394 | 11.882 | 1.00 | 74.71 N |
| ANISOU | 2052 | NE | ARG | B | 10 | 8500 9914 9973 | -1170 | 1345 | -1127 N | |
| ATOM | 2053 | CZ | ARG | B | 10 | 85.038 | 13.208 | 11.996 | 1.00 | 73.25 C |
| ANISOU | 2053 | CZ | ARG | B | 10 | 9056 13210 10455 | -1043 | 1315 | -1034 C | |
| ATOM | 2054 | NH1 | ARG | B | 10 | 84.587 | 12.126 | 12.625 | 1.00 | 68.61 N |
| ANISOU | 2054 | NH1 | ARG | B | 10 | 7732 9025 9252 | -912 | 1138 | -1010 N | |
| ATOM | 2055 | NH2 | ARG | B | 10 | 84.150 | 14.064 | 11.483 | 1.00 | 81.15 N |
| ANISOU | 2055 | NH2 | ARG | B | 10 | 9662 10466 10935 | -1042 | 1415 | -958 N | |
| ATOM | 2056 | N | LEU | B | 11 | 67.070 | 11.153 | 6.890 | 1.00 | 52.29 N |
| ANISOU | 2056 | N | LEU | B | 11 | 5527 7246 7096 | -850 | 1325 | -1317 N | |
| ATOM | 2057 | CA | LEU | B | 11 | 87.531 | 9.759 | 6.701 | 1.03 | 52.21 C |
| ANISOU | 2057 | CA | LEU | B | 11 | 5382 7361 7053 | -723 | 1229 | -1054 C | |
| ATOM | 2058 | C | LEU | B | 11 | 88.733 | 9.536 | 5.742 | 1.00 | 56.38 C |
| ANISOU | 2058 | C | LEU | B | 11 | 5765 7999 7544 | -761 | 1292 | -1120 C | |
| ATOM | 2059 | O | LEU | B | 11 | 89.617 | 8.830 | 6.035 | 1.00 | 59.87 O |
| ANISOU | 2059 | O | LEU | B | 11 | 6023 6555 7953 | -722 | 1248 | -1138 O | |
| ATOM | 2060 | CB | LEU | B | 11 | 36.304 | 8.913 | 6.152 | 1.00 | 55.81 C |
| ANISOU | 2060 | CB | LEU | B | 11 | 5913 7724 7573 | -565 | 1155 | -982 C | |
| ATOM | 2061 | CG | LEU | B | 11 | 66.306 | 7.379 | 6.086 | 1.30 | 53.17 C |
| ANISOU | 2061 | CG | LEU | B | 11 | 5495 7448 7260 | -436 | 1057 | -1006 C | |
| ATOM | 2062 | CD1 | LEU | B | 11 | 87.259 | 6.790 | 7.156 | 1.00 | 55.31 C |
| ANISOU | 2062 | CD1 | LEU | B | 11 | 5750 7964 7583 | -393 | 1301 | -1066 C | |
| ATOM | 2063 | CD2 | LEU | B | 11 | 84.949 | 6.331 | 6.200 | 1.00 | 57.55 C |
| ANISOU | 2063 | CD2 | LEU | B | 11 | 6142 7376 7333 | -309 | 980 | -936 C | |
| ATOM | 2064 | N | ARG | B | 12 | 88.893 | 10.277 | 4.605 | 1.30 | 55.00 N |
| ANISOU | 2064 | N | ARG | B | 12 | 5715 7820 7361 | -327 | 1398 | -1091 N | |
| ATOM | 2065 | CA | ARG | B | 12 | 89.741 | 10.165 | 3.572 | 1.00 | 56.45 C |
| ANISOU | 2065 | CA | ARG | B | 12 | 5316 8133 7499 | -366 | 1477 | -1147 C | |
| ATOM | 2066 | C | ARG | B | 12 | 91.021 | 10.712 | 4.143 | 1.00 | 62.35 C |
| ANISOU | 2066 | C | ARG | B | 12 | 6402 9018 8242 | -1020 | 1538 | -1240 C | |

TABLE 3-continued

| ATOM | 2067 | O | ARG | B | 12 | 92.094 | 10.035 | 4.043 | 1.00 | 65.52 | O |
|---|---|---|---|---|---|---|---|---|---|---|---|
| ANISOU | 2067 | O | ARG | B | 12 | 3670 | 9513 | 6553 | -1004 | 1533 | -1320 | O |
| ATOM | 2068 | CB | ARG | B | 12 | 89.412 | 11.012 | 2.312 | 1.00 | 53.58 | C |
| ANISOU | 2068 | CB | ARG | B | 12 | 5602 | 7535 | 7371 | -931 | 1593 | -1331 | C |
| ATOM | 2069 | CG | ARG | B | 12 | 86.342 | 10.455 | 1.407 | 1.00 | 53.86 | C |
| ANISOU | 2069 | CG | ARG | B | 12 | 5741 | 7645 | 7073 | -796 | 1542 | -1002 | C |
| ATOM | 2070 | CD | ARG | B | 12 | 68.424 | 10.661 | -0.064 | 1.00 | 53.09 | C |
| ANISOU | 2070 | CD | ARG | B | 12 | 5728 | 7556 | 6836 | -332 | 1643 | -962 | C |
| ATOM | 2071 | NE | ARG | B | 12 | 87.530 | 9.390 | -0.749 | 1.77 | 57.31 | N |
| ANISOU | 2071 | NE | ARG | B | 12 | 5302 | 8076 | 7396 | -685 | 1550 | -927 | N |
| ATOM | 2072 | CZ | ARG | B | 12 | 87.919 | 3.699 | -1.257 | 1.00 | 53.29 | C |
| ANISOU | 2072 | CZ | ARG | B | 12 | 6465 | 8430 | 7532 | -603 | 1511 | -1004 | C |
| ATOM | 2073 | NH1 | ARG | B | 12 | 39.240 | 8.394 | -1.247 | 1.90 | 94.11 | N |
| ANISOU | 2073 | NH1 | ARG | B | 12 | 55.54 | 7910 | 6985 | -5134 | 1564 | -1111 | N |
| ATOM | 2074 | NH2 | ARG | B | 12 | 86.980 | 7.834 | -1.797 | 1.00 | 54.51 | N |
| ANISOU | 2074 | NH2 | ARG | B | 12 | 5915 | 7794 | 7032 | -492 | 1428 | -979 | N |
| ATOM | 2075 | N | SER | B | 13 | 90.881 | 11.520 | 4.597 | 1.00 | 60.89 | N |
| ANISOU | 2075 | N | SER | B | 13 | 6335 | 8746 | 8055 | -1172 | 1808 | -1231 | N |
| ATOM | 2076 | CA | SER | B | 13 | 91.934 | 12.670 | 5.333 | 1.00 | 71.19 | C |
| ANISOU | 2076 | CA | SER | B | 13 | 7544 | 10157 | 9349 | -1380 | 1677 | -1324 | C |
| ATOM | 2077 | C | SER | B | 13 | 32.560 | 11.887 | 6.499 | 1.00 | 78.29 | C |
| ANISOU | 2077 | C | SER | B | 13 | 8245 | 11230 | 10271 | -1321 | 1554 | -1403 | C |
| ATOM | 2078 | O | SER | B | 13 | 93.787 | 11.333 | 3.506 | 1.00 | 95.60 | O |
| ANISOU | 2078 | O | SER | B | 13 | 10381 | 13751 | 12572 | -1404 | 1575 | -1493 | O |
| ATOM | 2079 | CB | SER | B | 13 | 91.354 | 13.979 | 5.843 | 1.00 | 39.23 | C |
| ANISOU | 2079 | CB | SER | B | 13 | 7457 | 9733 | 9104 | -1504 | 1751 | -1293 | C |
| ATOM | 2080 | OG | SER | B | 13 | 92.232 | 15.024 | 5.584 | 1.00 | 75.40 | O |
| ANISOU | 2080 | OG | SER | B | 13 | 8246 | 10547 | 9853 | -1723 | 1915 | -1355 | O |
| ATOM | 2081 | N | ASN | B | 14 | 91.7134 | 11.260 | 7.340 | 1.00 | 72.08 | N |
| ANISOU | 2081 | N | ASN | B | 14 | 7527 | 10415 | 9557 | -1187 | 1427 | -1354 | N |
| ATOM | 2082 | CA | ASN | B | 14 | 92.223 | 10.575 | 3.543 | 1.00 | 76.05 | C |
| ANISOU | 2082 | CA | ASN | B | 14 | 7830 | 11932 | 10032 | -1139 | 1807 | -1403 | C |
| ATOM | 2083 | C | ASN | B | 14 | 92.539 | 9.102 | 8.330 | 1.30 | 77.20 | C |
| ANISOU | 2083 | C | ASN | B | 14 | 7840 | 11291 | 10202 | -931 | 1208 | -1398 | C |
| ATOM | 2084 | O | ASN | B | 14 | 92.002 | 3.349 | 9.272 | 1.03 | 82.63 | O |
| ANISOU | 2084 | O | ASN | B | 14 | 8411 | 12034 | 10901 | -839 | 3057 | -1237 | O |
| ATOM | 2085 | CB | ASN | B | 14 | 91.222 | 10.749 | 9091 | 1.00 | 82.14 | C |
| ANISOU | 2085 | CB | ASN | B | 14 | 3744 | 11575 | 13321 | -1122 | 1239 | -1350 | C |
| ATOM | 2086 | CG | ASN | B | 14 | 91.240 | 12.151 | 10.271 | 1.00 | 84.08 | C |
| ANISOU | 2086 | CG | ASN | B | 14 | 9046 | 11858 | 11041 | -1342 | 1336 | -1403 | C |

TABLE 3-continued

| | | | | | | | | | | | | |
|---|---|---|---|---|---|---|---|---|---|---|---|---|
| ATOM | 2087 | OD1 | ASN | B | 14 | 93.938 | 12.339 | 11.440 | 1.00 | 53.17 | | O |
| ANISOU | 2987 | OD1 | ASN | B | 14 | 10853 | 13628 | 12820 | -1070 | 1237 | -1417 | O |
| ATOM | 2088 | ND2 | ASN | B | 14 | 91.603 | 13.138 | 5.455 | 1.09 | 87.38 | | N |
| ANISOU | 2088 | ND2 | ASN | B | 14 | 9525 | 12235 | 11441 | -1496 | 1483 | -1426 | N |
| ATOM | 2089 | N | MET | B | 15 | 9252 | 8.717 | 7.031 | 1.00 | 74.33 | | N |
| ANISOU | 2089 | N | MET | B | 15 | 7503 | 10903 | 9843 | -860 | 1258 | -1381 | N |
| ATOM | 2090 | CA | MET | B | 15 | 92 599 | 7.361 | 5.709 | 1.00 | 75.31 | | C |
| ANISOU | 2090 | CA | MET | B | 15 | 7502 | 11082 | 9990 | -453 | 1133 | -1370 | C |
| ATOM | 2091 | C | MET | B | 15 | 94.183 | 7.013 | 5.545 | 1.33 | 83.33 | | C |
| ANISOU | 2991 | C | MET | B | 15 | 7583 | 11999 | 10655 | -667 | 1219 | -1465 | C |
| ATOM | 2092 | O | MET | B | 15 | 94.588 | 5.326 | 6.499 | 1.00 | 71.59 | | O |
| ANISOU | 2092 | O | MET | B | 15 | 6763 | 10977 | 9578 | -450 | 1154 | -1474 | O |
| ATOM | 2093 | CB | MET | B | 15 | 92.142 | 1.304 | 5.205 | 1.00 | 75.51 | | C |
| ANISOU | 2093 | CB | MET | B | 15 | 7698 | 10594 | 9599 | -631 | 1258 | -1345 | C |
| ATOM | 2094 | CG | MET | B | 15 | 91.534 | 5.014 | 4.756 | 1.00 | 73.83 | | C |
| ANISOU | 2094 | CG | MET | B | 15 | 7522 | 10706 | 9812 | -434 | 1200 | -1314 | C |
| ATOM | 2095 | SD | MET | B | 15 | 90.666 | 6.340 | 3.182 | 3.00 | 65.70 | | S |
| ANISOU | 2095 | SD | MET | B | 15 | 7184 | 10359 | 9239 | -455 | 1280 | -1270 | S |
| ATOM | 2096 | CE | MET | B | 15 | 91.829 | 7.258 | 2.133 | 1.00 | 72.55 | | C |
| ANISOU | 2096 | CE | MET | B | 15 | 7506 | 10555 | 9541 | -615 | 1442 | -1325 | C |
| ATOM | 2097 | N | GLU | B | 16 | 94.983 | 8.077 | 6.487 | 1.00 | 83.34 | | N |
| ANISOU | 2097 | N | GLU | B | 16 | 8252 | 12445 | 10958 | -871 | 1312 | -1527 | N |
| ATOM | 2098 | CA | GLU | B | 16 | 90.442 | 5.001 | 7.539 | 1.00 | 93.59 | | C |
| ANISOU | 2098 | CA | GLU | B | 16 | 9314 | 14034 | 12241 | -923 | 1343 | -4619 | C |
| ATOM | 2099 | C | GLU | B | 16 | 97.033 | 3.379 | 7.439 | 1.09 | 52.96 | | C |
| ANISOU | 2099 | C | GLU | B | 16 | 9027 | 14103 | 12139 | -748 | 1208 | -1628 | C |
| ATOM | 2100 | O | GLU | B | 16 | 97.733 | 5.930 | 8.940 | 1.00 | 89.55 | | O |
| ANISOU | 2100 | O | GLU | B | 16 | 8457 | 13798 | 11786 | -605 | 1210 | -1651 | O |
| ATOM | 2101 | CB | GLU | B | 16 | 97.026 | 9.407 | 5.825 | 1.00 | 39.05 | | C |
| ANISOU | 2101 | CB | GLU | B | 16 | 9981 | 14767 | 12885 | -1204 | 1435 | -1557 | C |
| TOM | 2102 | CG | GLU | B | 16 | 98.417 | 9.661 | 5.266 | 1.00 | 104.39 | | C |
| ANISOU | 2102 | CG | GLU | B | 16 | 10454 | 15671 | 12539 | -1323 | 1541 | -1784 | C |
| ATOM | 2103 | CD | GLU | B | 16 | 99.459 | 8.722 | 7.853 | 1.00 | 106.33 | | C |
| ANISOU | 2103 | CD | GLU | B | 16 | 10410 | 16192 | 13300 | -1200 | 1445 | -1834 | C |
| ATOM | 2104 | OE1 | GLU | B | 16 | 99.703 | 3.794 | 8.079 | 1.00 | 110.29 | | O |
| ANISOU | 2104 | OE1 | GLU | B | 16 | 10803 | 15815 | 14286 | -1237 | 1344 | -3855 | O |
| ATOM | 2105 | OE2 | GLU | B | 16 | 100.011 | 7.901 | 7.092 | 1.00 | 101.66 | | O |
| ANISOU | 2105 | OE2 | GLU | B | 16 | 9701 | 15696 | 13228 | -1058 | 1471 | -1847 | O |
| ATOM | 2106 | N | PRO | B | 17 | 96.750 | 6.893 | 8.820 | 1.00 | 60.06 | | N |
| ANISOU | 2106 | N | PRO | B | 17 | 8523 | 19626 | 11691 | -748 | 1094 | -1600 | N |

TABLE 3-continued

```
ATOM    2107 CA  PRO B  17      37.354  5.868  9-737 1.00 87.03       C
ANISOU  2107 CA  PRO B  17      8373 13551 11453  -570  965 -1595     C
ATOM    2108 C   PRO B  17      96.738  4.436  3.865 1.00 68.46       C
ANISOU  2108 C   PRO B  17      8306 13631 11637  -291  870 -1507     C
ATOM    2109 O   PRO B  17      37.320  3.634 10.539 1.00 86.28       O
ANISOU  2109 O   PRO B  17      7862 19508 11413  -144  773 -1488     O
ATOM    2110 CB  PRO B  17      97.368  6.563 31.113 1.00 81.42       C
ANISOU  2110 CB  PRO B  17      7331 12922 10631  -710  891 -1512     C
ATOM    2111 CG  PRO B  17      97.098  8.017 30.833 1.00 86.45       C
ANISOU  2111 CG  PRO B  17      3303 13455 11259  -989 1010 -1662     C
ATOM    2112 CD  PRO B  17      36.231  3.0313 9.602 1.00 55.64       C
ANISOU  2112 CD  PRO B  17      8211 13106 11224  -943 1101 -1609     C
ATOM    2113 N   PHE B  18      95.610  4.104  9.185 1.00 84.80       N
ANISOU  2113 N   PHE B  18      8054 12917 11259  -234  835 -1453     N
ATOM    2114 CA  PHE B  18      94.928  2.759  9.317 1.00 33.29       C
ANISOU  2114 CA  PHE B  18      7934 12691 11121    28  818 -1876     C
ATOM    2115 C   PHE B  18      95.580  1.495  6.739 1.00 82.63       C
ANISOU  2115 C   PHE B  18      7744 12613 11108   244  823 -1300     C
ATOM    2116 O   PHE B  18      95.313  1.528  7.736 1.00 87.06       O
ANISOU  2116 O   PHE B  18      8328 13334 11757   228  927 -1452     O
ATOM    2117 CB  PHE B  18      93.435  2.743  8.722 1.00 76.40       C
ANISOU  2117 CB  PHE B  18      7333 11444 10271    93  340 -3326     C
ATOM    2118 CG  PHE B  18      92.541  3.794  9.282 3.00 77.63       C
ANISOU  2118 CG  PHE B  18      7619 11475 10402  -122  830 -1295     C
ATOM    2119 CD1 PHE B  18      92.662  4.274 10.536 1.00 79.88       C
ANISOU  2119 CD1 PHE B  18      7859 11835 10357  -107  763 -1290     C
ATOM    2120 CD2 PHE B  18      91.490  4.286  8.491 1.00 74.53       C
ANISOU  2120 CD2 PHE B  18      7423 10303 10015  -183  336 -1267     C
ATOM    2121 CE1 PHE B  18      91.776  5.278 11.070 1.00 78.16       C
ANISOU  2121 CE1 PHE B  18      7790 11486 10420  -333  776 -1268     C
ATOM    2122 CE2 PHE B  18      30.607  5.246  8.079 1.00 76.37       C
ANISOU  2122 CE2 PHE B  18      7786 11004 10223  -302  339 -1230     C
ATOM    2123 CZ  PHE B  18      93.754  5.729 10.259 1.00 75.98       C
ANISOU  2123 CZ  PHE B  18      7600 11012 10150  -973  843 -1235     C
ATOM    2124 N   SER B  19      95.572  0.302  9.545 1.30 79.21       N
ANISOU  2124 N   SER B  19      7203 12145 10690   449  737 -1825     N
ATOM    2125 CA  SER B  19      95.007 -0.977  9.180 1.00 73.03       C
ANISOU  2125 CA  SER B  19      6526 11482 10082   636  746 -1813     C
ATOM    2126 C   SER B  19      95.188 -1.500  7.999 1.00 74.48       C
ANISOU  2126 C   SER B  19      6784 11324 10190   743  824 -1328     C
```

TABLE 3-continued

| ATOM | 2127 | O | SER | B | 19 | 34.135 | -3.911 | 7.667 | 1.00 | 72.01 | O |
|---|---|---|---|---|---|---|---|---|---|---|---|
| ANISOU | 2127 | O | SER | B | 19 | 6602 | 10587 | 9805 | 611 | 838 | -1320 | O |
| ATOM | 2128 | CB | SER | B | 19 | 95.724 | -1.300 | 10.364 | 1.00 | 70.53 | C |
| ANISOU | 2128 | CB | SER | B | 19 | 6105 | 11016 | 9679 | 378 | 691 | -1214 | C |
| ATOM | 2129 | OG | SER | B | 19 | 94.298 | -2.037 | 13.557 | 1.30 | 60.33 | O |
| ANISOU | 2129 | OG | SER | B | 19 | 5051 | 9467 | 3403 | 850 | 602 | -1158 | O |
| ATOM | 2130 | N | LYS | B | 20 | 95.696 | -2.603 | 7.337 | 1.00 | 69.84 | N |
| ANISOU | 2130 | N | LYS | B | 20 | 6090 | 10665 | 9591 | 930 | 876 | -1350 | N |
| ATOM | 2131 | CA | LYS | B | 20 | 94.952 | -3.154 | 6.199 | 1.00 | 58.26 | C |
| ANISOU | 2131 | CA | LYS | B | 20 | 6120 | 10335 | 9477 | 964 | 953 | -1387 | C |
| ATOM | 2132 | C | LYS | B | 20 | 93.465 | -3.446 | 5.405 | 1.00 | 67.11 | C |
| ANISOU | 2132 | C | LYS | B | 20 | 6258 | 9991 | 9403 | 956 | 906 | -1331 | C |
| ATOM | 2133 | O | LYS | B | 20 | 92.654 | -6.056 | 5.570 | 1.00 | 62.77 | O |
| ANISOU | 2133 | O | LYS | B | 20 | 5804 | 9275 | 8771 | 842 | 946 | -1358 | O |
| ATOM | 2134 | CB | LYS | B | 20 | 95.574 | -4.384 | 5.641 | 1.00 | 67.73 | C |
| ANISOU | 2134 | CB | LYS | B | 20 | 5982 | 10282 | 9459 | 1180 | 1030 | -1426 | C |
| ATOM | 2135 | CG | LYS | B | 20 | 97.039 | -4.075 | 5.051 | 1.00 | 72.60 | C |
| ANISOU | 2135 | CG | LYS | B | 20 | 6384 | 11132 | 10067 | 1171 | 1118 | -1503 | C |
| ATOM | 2136 | CD | LYS | B | 20 | 97.525 | -5.200 | 4.142 | 1.00 | 75.92 | C |
| ANISOU | 2136 | CD | LYS | B | 20 | 6787 | 11517 | 10541 | 1358 | 1229 | -1564 | C |
| ATOM | 2137 | CE | LYS | B | 20 | 98.641 | -4.109 | 3.237 | 1.00 | 73.15 | C |
| ANISOU | 2137 | CE | LYS | B | 20 | 6902 | 12006 | 10790 | 1292 | 1347 | -1560 | C |
| ATOM | 2138 | NZ | LYS | B | 20 | 99.084 | -5.729 | 2.229 | 1 | 00 | 81.54 | N |
| ANISOU | 2138 | NZ | LYS | B | 20 | 7304 | 12665 | 11535 | 1455 | 1480 | -1737 | N |
| ATOM | 2139 | N | LYS | B | 21 | 93.112 | -4.130 | 7.498 | 1.00 | 67.70 | N |
| ANISOU | 2139 | N | LYS | B | 21 | 6309 | 9945 | 9567 | 1079 | 820 | -1250 | N |
| ATOM | 2140 | CA | LYS | B | 21 | 91.704 | -4.476 | 7.765 | 1.00 | 56.03 | C |
| ANISOU | 2140 | CA | LYS | B | 21 | 6304 | 9506 | 9216 | 1010 | 777 | -1195 | C |
| ATOM | 2141 | C | LYS | B | 21 | 90.839 | -3.280 | 7.074 | 1.00 | 54.71 | C |
| ANISOU | 2141 | C | LYS | B | 21 | 6225 | 9809 | 9058 | 863 | 740 | -1177 | C |
| ATOM | 2142 | O | LYS | B | 21 | 89.758 | -6.157 | 7.434 | 1.30 | 65.33 | O |
| ANISOU | 2142 | O | LYS | B | 21 | 6422 | 9192 | 9096 | 795 | 755 | -1181 | O |
| ATOM | 2143 | CB | LYS | B | 21 | 91.534 | -5.417 | 5.948 | 1.00 | 69.94 | C |
| ANISOU | 2143 | CB | LYS | B | 21 | 6815 | 9935 | 9824 | 1235 | 704 | -1106 | C |
| ATOM | 2144 | CG | LYS | B | 21 | 91.483 | -6.593 | 5.586 | 1.00 | 50.03 | C |
| ANISOU | 2144 | CG | LYS | B | 21 | 8163 | 11065 | 11179 | 1455 | 756 | -1102 | C |
| ATOM | 2145 | CD | LYS | B | 21 | 90.950 | -7.112 | 9.765 | 1.00 | 88.75 | C |
| ANISOU | 2145 | CD | LYS | B | 21 | 9346 | 12048 | 12327 | 1560 | 539 | -999 | C |
| ATOM | 2146 | CE | LYS | B | 21 | 91.836 | -7.565 | 11.010 | 1.00 | 89.16 | C |
| ANISOU | 2146 | CE | LYS | B | 21 | 9231 | 12293 | 12351 | 1549 | 533 | -914 | C |

TABLE 3-continued

| ATOM | 2147 | NZ | LYS | B | 21 | 91.107 | -6.026 | 12.224 | 1.00 | 92.50 | N |
|---|---|---|---|---|---|---|---|---|---|---|---|
| ANISOU | 2147 | NZ | LYS | B | 21 | 9758 | 12604 | 12784 | 1733 | 528 | -798 | N |
| ATOM | 2148 | N | LEU | B | 22 | 91.380 | -2.249 | 8.739 | 1.00 | 61.18 | N |
| ANISOU | 2148 | N | LEU | B | 22 | 5674 | 9007 | 8565 | 751 | 700 | -1162 | N |
| ATOM | 2149 | CA | LEU | B | 22 | 90.595 | -0.900 | 3.942 | 1.00 | 56.73 | C |
| ANISOU | 2149 | CA | LEU | B | 22 | 5196 | 8404 | 7955 | 556 | 568 | -1146 | C |
| ATOM | 2150 | C | LEU | B | 22 | 93.443 | -0.242 | 7.634 | 1.00 | 54.52 | C |
| ANISOU | 2150 | C | LEU | B | 22 | 4975 | 8101 | 7640 | 437 | 777 | -1203 | C |
| ATOM | 2151 | O | LEU | B | 22 | 89.408 | 6.343 | 7.275 | 1.00 | 52.07 | O |
| ANISOU | 2151 | O | LEU | B | 22 | 4804 | 7668 | 7213 | 341 | 782 | -1178 | O |
| ATOM | 2152 | CB | LEU | B | 22 | 91.291 | -0.091 | 9.989 | 1.00 | 60.57 | C |
| ANISOU | 2152 | CB | LEU | B | 22 | 5557 | 9062 | 8393 | 468 | 645 | -1144 | C |
| ATOM | 2153 | CG | LEU | B | 22 | 90.360 | -0.153 | 11.457 | 1.00 | 67.54 | C |
| ANISOU | 2153 | CG | LEU | B | 22 | 6501 | 9969 | 9308 | 490 | 545 | -1072 | C |
| ATOM | 2154 | CD1 | LEU | B | 22 | 90.867 | -1.691 | 11.964 | 1.00 | 68.31 | C |
| ANISOU | 2154 | CC1 | LEU | B | 22 | 6552 | 9987 | 9415 | 711 | 493 | -1010 | C |
| ATOM | 2155 | CD2 | LEU | B | 22 | 91.748 | 0.597 | 12.342 | 1 | 00 | 71.94 | C |
| ANISOU | 2155 | CD2 | LEU | B | 22 | 6874 | 10694 | 9762 | 330 | 514 | -1095 | C |
| ATOM | 2156 | N | ARG | B | 23 | 91.485 | -0.245 | 6.805 | 1.00 | 52.95 | N |
| ANISOU | 2156 | N | ARG | B | 23 | 4655 | 5032 | 7425 | 441 | 852 | -1271 | N |
| ATOM | 2157 | CA | ARG | B | 23 | 91.4153 | 0.492 | 5.545 | 1.00 | 53.40 | C |
| ANISOU | 2157 | CA | ARG | B | 23 | 4775 | 3382 | 7432 | 315 | 945 | -1317 | C |
| ATOM | 2158 | C | ARG | B | 23 | 90.458 | -0.210 | 4.574 | 1.00 | 51.02 | C |
| ANISOU | 2158 | C | ARG | B | 23 | 4530 | 7517 | 7137 | 372 | 954 | -1320 | C |
| ATOM | 2159 | O | ARG | B | 23 | 89.526 | 0.447 | 3.755 | 1.00 | 52.47 | O |
| ANISOU | 2159 | O | ARG | B | 23 | 4923 | 7742 | 7270 | 266 | 1002 | -1317 | O |
| ATOM | 2160 | CB | ARG | B | 23 | 92.874 | 0.683 | 4.930 | 1.00 | 57.54 | C |
| ANISOU | 2160 | CB | ARG | B | 23 | 5127 | 8804 | 7931 | 292 | 1034 | -1396 | C |
| ATOM | 2161 | CG | ARG | B | 23 | 92.987 | 1.455 | 3.601 | 1.00 | 60.85 | C |
| ANISOU | 2161 | CG | ARG | B | 23 | 5596 | 9238 | 8286 | 158 | 1148 | -1442 | C |
| ATOM | 2162 | CD | ARG | B | 23 | 92.496 | 2.931 | 3.625 | 1.00 | 61.20 | C |
| ANISOU | 2162 | CD | ARG | B | 23 | 5737 | 9241 | 8277 | -46 | 1172 | -1406 | C |
| ATOM | 2163 | NE | ARG | B | 23 | 92.393 | 3.528 | 2.257 | 1.00 | 62.96 | N |
| ANISOU | 2163 | NE | ARG | B | 23 | 6050 | 9441 | 8432 | -145 | 1280 | -1423 | N |
| ATOM | 2164 | CZ | ARG | B | 23 | 93.387 | 4.146 | 1.596 | 1.00 | 56.75 | C |
| ANISOU | 2164 | CZ | ARG | B | 23 | 6446 | 10051 | 8864 | -251 | 1392 | -1477 | C |
| ATOM | 2165 | NH1 | ARG | B | 23 | 94.579 | 4.287 | 2.161 | 1.00 | 66.11 | N |
| ANISOU | 2165 | NH1 | ARG | B | 23 | 6171 | 1.146 | 8801 | -284 | 1409 | -1530 | N |
| ATOM | 2166 | NH2 | ARG | B | 23 | 93.201 | 4.631 | 0.369 | 1.00 | 59.61 | N |
| ANISOU | 2166 | NH2 | ARG | B | 23 | 5846 | 9116 | 7888 | -330 | 1487 | -1477 | N |

TABLE 3-continued

| | | | | | | | | |
|---|---|---|---|---|---|---|---|---|
| ATOM | 2167 | N | VAL | B | 24 | 90.322 -1.528 4.661 1.00 48.90 | | N |
| ANISOU | 2167 | N | VAL | B | 24 | 4377 7276 5925 535 941 -1325 | | N |
| ATOM | 2168 | CA | VAL | B | 24 | 89.298 -2.219 3.857 1.00 50.40 | | C |
| ANISOU | 2168 | CA | VAL | B | 24 | 4722 7307 7119 565 952 -1340 | | C |
| ATOM | 2169 | C | VAL | B | 24 | 87.888 -1.651 4.196 1.00 46.68 | | C |
| ANISOU | 2169 | C | VAL | B | 24 | 4390 6711 6636 471 887 -1270 | | C |
| ATOM | 2170 | O | VAL | B | 24 | 87.091 -1.286 3.286 1.00 46.01 | | O |
| ANISOU | 2170 | O | VAL | B | 24 | 4410 6570 6501 389 907 -1274 | | O |
| ATOM | 2171 | CB | VAL | B | 24 | 89.334 -3.746 4.100 1.00 50.43 | | C |
| ANISOU | 2171 | CB | VAL | B | 24 | 4737 7225 7199 748 944 -1354 | | C |
| ATOM | 2172 | CG1 | VAL | B | 24 | 88.113 -4.423 3.474 1.00 51.21 | | C |
| ANISOU | 2172 | CG1 | VAL | B | 24 | 5007 7148 7303 745 944 -1373 | | C |
| ATOM | 2173 | CG2 | VAL | B | 24 | 90.638 -4.384 3.564 1.00 52.95 | | C |
| ANISOU | 2173 | CG2 | VAL | B | 24 | 4932 7651 7535 864 1029 -1428 | | C |
| ATOM | 2174 | N | VAL | B | 25 | 87.601 -1.551 5.490 1.00 48.29 | | N |
| ANISOU | 2174 | N | VAL | B | 25 | 4584 5886 5878 486 813 -1203 | | N |
| ATOM | 2175 | CA | VAL | B | 25 | 86.272 -1.020 5.917 1.00 48.89 | | C |
| ANISOU | 2175 | CA | VAL | B | 25 | 4778 6846 5953 408 760 -1136 | | C |
| ATOM | 2176 | C | VAL | B | 25 | 86.096 0.464 5.618 1.00 51.60 | | C |
| ANISOU | 2176 | C | VAL | B | 25 | 5145 7225 7235 256 790 -1115 | | C |
| ATOM | 2177 | O | VAL | B | 25 | 85.067 0.867 5.010 1.00 50.71 | | O |
| ANISOU | 2177 | O | VAL | B | 25 | 5140 7032 7095 198 792 -1086 | | O |
| ATOM | 2178 | CB | VAL | B | 25 | 85.745 -1.555 7.294 1.00 52.24 | | C |
| ANISOU | 2178 | CB | VAL | B | 25 | 5224 7190 7434 477 688 -1071 | | C |
| ATOM | 2179 | CG1 | VAL | B | 25 | 86.812 -1.879 8.279 1.00 49.75 | | C |
| ANISOU | 2179 | CG1 | VAL | B | 25 | 4786 6979 7139 562 657 -1061 | | C |
| ATOM | 2180 | CG2 | VAL | B | 25 | 84.576 -0.723 7.912 1.00 46.41 | | C |
| ANISOU | 2180 | CG2 | VAL | B | 25 | 4574 6371 6890 382 643 -1004 | | C |
| ATOM | 2181 | N | ALA | B | 26 | 87.137 1.246 5.922 1.00 45.34 | | N |
| ANISOU | 2181 | N | ALA | B | 26 | 4251 6460 6418 192 822 -1132 | | N |
| ATOM | 2182 | CA | ALA | B | 26 | 87.180 2.668 5.563 1.00 45.19 | | C |
| ANISOU | 2182 | CA | ALA | B | 26 | 4258 6589 6343 40 880 -1122 | | C |
| ATOM | 2183 | C | ALA | B | 26 | 86.920 2.859 4.056 1 00 45.79 | | C |
| ANISOU | 2183 | C | ALA | B | 26 | 4408 6628 6364 5 945 -1137 | | C |
| ATOM | 2184 | O | ALA | B | 26 | 86.073 3.639 3.671 1.00 44.41 | | O |
| ANISOU | 2184 | O | ALA | B | 26 | 4339 6379 6154 -65 958 -1084 | | O |
| ATOM | 2185 | CB | ALA | B | 26 | 86.552 3.276 5.947 1.00 45.27 | | C |
| ANISOU | 2185 | CB | ALA | B | 26 | 4127 6741 6333 -31 921 -1169 | | C |
| ATOM | 2186 | N | ASP | B | 27 | 87.705 2.200 3.200 1.00 44.99 | | N |
| ANISOU | 2186 | N | ASP | B | 27 | 4246 6604 6244 54 994 -1207 | | N |

TABLE 3-continued

| ATOM | 2187 | CA | ASP | B | 27 | 87.436 | 2.166 | 1.752 | 1.00 | 45.42 | C |
|---|---|---|---|---|---|---|---|---|---|---|---|
| ANISOU | 2187 | CA | ASP | B | 27 | 4376 | 6652 | 6231 | 33 | 1050 | -1230 C |
| ATOM | 2188 | C | ASP | B | 27 | 86.045 | 1.708 | 1.349 | 1.00 | 45.94 | C |
| ANISOU | 2188 | C | ASP | B | 27 | 4571 | 6597 | 6289 | 65 | 994 | -1195 C |
| ATOM | 2189 | O | ASP | B | 27 | 85.439 | 2.257 | 0.419 | 1.00 | 43.73 | O |
| ANISOU | 2189 | O | ASP | B | 27 | 4379 | 6304 | 5933 | 3 | 1016 | -1166 O |
| ATOM | 2190 | CB | ASP | B | 27 | 86.421 | 1.230 | 1.020 | 1.00 | 47.73 | C |
| ANISOU | 2190 | CB | ASP | B | 27 | 4586 | 7031 | 6517 | 109 | 1109 | -1325 C |
| ATOM | 2191 | CG | ASP | B | 27 | 89.801 | 1.854 | 0.827 | 1.00 | 52.63 | C |
| ANISOU | 2191 | CG | ASP | B | 27 | 5079 | 7807 | 7110 | 44 | 1199 | -1371 C |
| ATOM | 2192 | OD1 | ASP | B | 27 | 89.930 | 3.101 | 0.925 | 1.00 | 56.56 | O |
| ANISOU | 2192 | OD1 | ASP | B | 27 | 5585 | 6335 | 7572 | -90 | 1235 | -1336 O |
| ATOM | 2193 | OD2 | ASP | B | 27 | 90.749 | 1.077 | 0.601 | 1.00 | 51.71 | O |
| ANISOU | 2193 | OD2 | ASP | B | 27 | 4853 | 7779 | 7014 | 129 | 1241 | -1445 O |
| ATOM | 2194 | N | TYR | B | 28 | 85.558 | 0.686 | 2.007 | 1.00 | 45.07 | N |
| ANISOU | 2194 | N | TYR | B | 28 | 4468 | 6408 | 6249 | 160 | 925 | -1199 N |
| ATOM | 2195 | CA | TYR | B | 28 | 84.178 | 0.204 | 1.727 | 1.00 | 46.87 | C |
| ANISOU | 2195 | CA | TYR | B | 28 | 4805 | 6529 | 6475 | 172 | 868 | -1174 C |
| ATOM | 2196 | C | TYR | B | 28 | 83.111 | 1.284 | 1 999 | 1.00 | 45.62 | C |
| ANISOU | 2196 | C | TYR | B | 28 | 4716 | 6319 | 6299 | 98 | 832 | -1075 C |
| ATOM | 2197 | O | TYR | B | 28 | 82.213 | 1.490 | 1.202 | 1.00 | 42.86 | O |
| ANISOU | 2197 | O | TYR | B | 28 | 4440 | 5950 | 5893 | 86 | 818 | -1047 O |
| ATOM | 2198 | CB | TYR | B | 28 | 83.833 | 6897 | 6824 | 273 | 812 | -1187 C |
| ANISOU | 2198 | CB | TYR | B | 28 | 5067 | 6697 | 6824 | 273 | 812 | -1187 C |
| ATOM | 2199 | CG | TYR | B | 28 | 82.455 | -1.589 | 2.226 | 1.00 | 47.10 | C |
| ANISOU | 2199 | CG | TYR | B | 28 | 4936 | 6367 | 6593 | 265 | 764 | -1180 C |
| ATOM | 2200 | CD1 | TYR | B | 28 | 82.282 | -2.555 | 1.209 | 1 00 | 45.86 | C |
| ANISOU | 2200 | CD1 | TYR | B | 28 | 4826 | 6194 | 6406 | 282 | 787 | -1266 C |
| ATOM | 2201 | CD2 | TYR | B | 28 | 81.332 | -1.142 | 2.918 | 1.00 | 43.19 | C |
| ANISOU | 2201 | CD2 | TYR | B | 28 | 4484 | 5804 | 6123 | 231 | 702 | -1097 C |
| ATOM | 2202 | CE1 | TYR | B | 28 | 81.025 | -3.058 | 0.838 | 1.00 | 48.29 | C |
| ANISOU | 2202 | CE1 | TYR | B | 28 | 5212 | 6431 | 6705 | 251 | 742 | -1274 C |
| ATOM | 2203 | CE2 | TYR | B | 28 | 80.063 | -1.637 | 2.598 | 1.00 | 40.85 | C |
| ANISOU | 2203 | CE2 | TYR | B | 28 | 4257 | 5442 | 5825 | 213 | 657 | -1096 C |
| ATOM | 2204 | CZ | TYR | B | 28 | 79.905 | -2.583 | 1.601 | 1.00 | 44.29 | C |
| ANISOU | 2204 | CZ | TYR | B | 28 | 4729 | 5872 | 6227 | 216 | 672 | -1184 C |
| ATOM | 2205 | OH | TYR | B | 28 | 78.626 | -3.090 | 1.281 | 1.00 | 45.73 | O |
| ANISOU | 2205 | OH | TYR | B | 28 | 4969 | 6006 | 6401 | 176 | 624 | -1196 O |
| ATOM | 2206 | N | ILE | B | 29 | 83.239 | 1.968 | 3.140 | 1.00 | 44.02 | N |
| ANISOU | 2206 | N | ILE | B | 29 | 4484 | 6101 | 6140 | 75 | 818 | -1024 N |

TABLE 3-continued

| | | | | | | | | | |
|---|---|---|---|---|---|---|---|---|---|
| ATOM | 2207 | CA | ILE | B | 29 | 82.281 | 2.979 | 3.530 | 1.00 42.77 C |
| ANISOU | 2207 | CA | ILE | B | 29 | 4392 5878 5960 | 20 | 800 | -935 C |
| ATOM | 2208 | C | ILE | B | 29 | 82.361 | 4.140 | 2.539 | 1.00 44.51 C |
| ANISOU | 2208 | C | ILE | B | 29 | 4659 6135 6118 | -61 | 869 | -900 C |
| ATOM | 2209 | O | ILE | B | 29 | 81.319 | 4.595 | 2.094 | 1.00 41.92 O |
| ANISOU | 2209 | O | ILE | B | 29 | 4408 5763 5758 | -71 | 853 | -830 O |
| ATOM | 2210 | CB | ILE | B | 29 | 82.540 | 3.398 | 4.979 | 1.00 45.76 C |
| ANISOU | 2210 | CB | ILE | B | 29 | 4734 6238 6416 | F6 | 786 | -910 C |
| ATOM | 2211 | CG1 | ILE | B | 29 | 82.392 | 2.207 | 5.916 | 1.00 41.82 C |
| ANISOU | 2211 | CG1 | ILE | B | 29 | 4204 5699 5985 | 97 | 718 | -925 C |
| ATOM | 2212 | CG2 | ILE | B | 29 | 81.744 | 4.615 | 5.402 | 1.00 47.54 C |
| ANISOU | 2212 | CG2 | ILE | B | 29 | 5030 6394 6640 | -58 | 799 | -830 C |
| ATOM | 2213 | CD1 | ILE | B | 29 | 82.938 | 2.545 | 7.287 | 1.00 47.50 C |
| ANISOU | 2213 | CD1 | ILE | B | 29 | 4869 6444 6733 | 84 | 704 | -913 C |
| ATOM | 2214 | N | LEU | B | 30 | 83.580 | 4.571 | 2.129 | 1.00 41.39 N |
| ANISOU | 2214 | N | LEU | B | 30 | 4215 5830 5683 | -113 | 949 | -944 N |
| ATOM | 2215 | CA | LEU | B | 30 | 83.733 | 5.661 | 1.163 | 1.00 45.54 C |
| ANISOU | 2215 | CA | LEU | B | 30 | 4797 6383 6124 | -196 | 1032 | -906 C |
| ATOM | 2216 | C | LEU | B | 30 | 83.001 | 5.385 | -0.158 | 1.00 45.89 C |
| ANISOU | 2216 | C | LEU | B | 30 | 4914 6439 6085 | -172 | 1020 | -685 C |
| ATOM | 2217 | O | LEU | B | 30 | 82.340 | 6.281 | -0.668 | 1.00 45.60 O |
| ANISOU | 2217 | O | LEU | B | 30 | 4962 6374 5991 | -203 | 1039 | -793 O |
| ATOM | 2218 | CB | LEU | B | 30 | 85.201 | 6.017 | 0.860 | 1.00 40.30 C |
| ANISOU | 2218 | CB | LEU | B | 30 | 4438 6205 5808 | -265 | 1130 | -972 C |
| ATOM | 2219 | CG | LEU | B | 30 | 35.774 | 6.370 | 2.007 | 1.00 44.63 C |
| ANISOU | 2219 | CG | LEU | B | 30 | 4562 8371 8024 | -345 | 1160 | -970 C |
| ATOM | 2220 | CD1 | LEU | B | 30 | 87.303 | 68.30 | 2.022 | 1.00 45.29 C |
| ANISOU | 2220 | CD1 | LEU | B | 30 | 4512 6094 8102 | -304 | 1222 | -1062 C |
| ATOM | 2221 | CD2 | LEU | B | 30 | 85.287 | 8.317 | 1.960 | 1.00 45 45 C |
| ANISOU | 2221 | CD2 | LEU | B | 30 | 4781 5386 6101 | -439 | 1226 | -862 C |
| ATOM | 2222 | N | GLU | B | 31 | 63.142 | 4.160 | -0.584 | 1.00 45.41 N |
| ANISOU | 2222 | N | GLU | B | 31 | 4943 5547 5138 | -115 | 903 | -968 N |
| ATOM | 2223 | CA | GLU | B | 31 | 82.600 | 3.804 | -1.980 | 1.00 47.74 C |
| ANISOU | 2223 | CA | GLU | B | 31 | 5184 5760 5215 | -110 | 985 | -977 C |
| ATOM | 2224 | C | GLU | B | 31 | 81.159 | 3.403 | -1.375 | 1.00 44.12 C |
| ANISOU | 2224 | C | GLU | B | 31 | 4787 S235 8783 | -73 | 884 | -933 C |
| ATOM | 2225 | O | GLU | B | 31 | 80.485 | 3.280 | -2.856 | 1.00 41.60 O |
| ANISOU | 2225 | O | GLU | B | 31 | 4500 5957 5350 | -84 | 861 | -912 O |
| ATOM | 2226 | CB | GLU | B | 31 | 33.417 | 2.093 | -2.598 | 1.00 49.97 C |
| ANISOU | 2226 | CB | GLU | B | 31 | 5412 7101 6471 | -78 | 1019 | -1104 C |

TABLE 3-continued

```
ATOM    2227 CG  GLU B  31     84.799  3.286 -2.989 1.00 56.54     C
ANISOU  2227 CG  GLU B  31   5192  8026  7263  -129  1134 -1140    C
.ATOM   2228 CD  GLU B  31     85.913  2.231 -3.059 1.00 62.88     C
ANISOU  2228 CD  GLU B  31   8902  8890  8130   -74  1131 -1255    O
ATOM    2229 OE1 GLU B  31     35.621  1.012 -3.233 1.00 61 97     O
ANISOU  2229 OE1 GLU B  31   6795  8744  8307     1  3146 -1336    O
ATOM    2230 OE2 GLU B  31     87.092  2.672 -3.007 1.00 67.07     O
ANISOU  2230 OE2 GLU B  31   7349  9502  3633  -310  1254 -1294    O
ATOM    2231 N   ASN B  32     50.705  3.033 -0.679 1.00 42.67     N
ANISOU  2231 N   ASN B  32   4557  5968  5588   -34   823  -922    N
ATOM    2232 CA  ASN B  32     79.293  2.674 -0.529 1.30 42.38     C
ANISOU  2232 CA  ASN B  32   4554  5877  5670   -10   735  -830    C
ATOM    2233 C   ASN B  32     78.507  3.491  0.503 1.00 41.87     C
ANISOU  2233 C   ASN B  32   4502  5734  5072    -6   706  -774    C
ATOM    2234 O   ASN B  32     77.536  2.305  1.028 1.00 42.57     O
ANISOU  2234 O   ASN B  32   4539  5771  5815    22   639  -751    O
ATOM    2235 CB  ASN B  32     79.119  1.185 -0.207 1.00 39.37     C
ANISOU  2235 CB  ASN B  32   4152  5455  5352    34   889  -973    C
ATOM    2236 CB  ASN B  32     72.386  0.260 -1.155 1.00 44.49     C
ANISOU  2236 CG  ASN B  32   4796  5159  5949    41   733 -1091    C
ATOM    2237 CG  ASN B  32     81.029 -0.120 -0.361 1.00 40.90     O
ANISOU  2237 OD1 ASN B  32   5053  6471  6297    78   788  -154    O
ATOM    2238 OD1 ASN B  32     79.304  0.011 -2.011 1.00 40.21     N
ANISOU  2238 ND1 ASN B  32   4306  5873  5314     8   710 -1123    N
ATOM    2239 N   ALA B  33     79.893  4.768  0.730 1.30 43.80     N
ANISOU  2239 N   ALA B  33   4387  5587  5529   -41   769  -705    N
ATOM    2240 CA  ALA B  33     78.300  5.6134 1.792 3.30 39.74     C
ANISOU  2240 OA  ALA B  33   4273  5208  5401   -42   771  -021    C
ATOM    2241 C   ALA B  33     75.802  5.583  1.877 1.00 38.74     C
ANISOU  2241 C   ALA B  33   4169  5199  5353         700  -544    C
ATOM    2242 O   ALA B  33     76.210  5.415  2.972 1.00 39.50     O
ANISOU  2242 O   ALA B  33   4251  5224  5535    24   657  -529    O
ATOM    2243 CB  ALA B  33     78.347  7.077  1.597 1.00 38.04     C
ANISOU  2243 CB  ALA B  33   4173  5203  5270   -99   869  -557    C
ATOM    2244 N   HIS B  34     75.154  5.693  0.724 1.00 39.88     N
ANISOU  2244 N   HIS B  34   4333  5405  5409    11   674  -500    N
ATOM    2245 CA  HIS B  34     74.894  5.825  0.698 1.00 42.59     C
ANISOU  2245 CA  HIS B  34   4083  5742  5757    52   608  -414    C
ATOM    2246 C   HIS B  34     74.074  4.345  1.152 1.00 42.33     O
ANISOU  2246 C   HIS B  34   4568  5009 57115   62   529  -486    C
```

TABLE 3-continued

| | | | | |
|---|---|---|---|---|
| ATOM | 2247 | O HIS B 34 | 73.140 4.570 1.955 1.00 43.74 | O |
| ANISOU | 2247 | O HIS B 34 | 4750 5825 6036 87 496 -440 | O |
| ATOM | 2248 | CB HIS B 34 | 74.146 5.221 -0.689 1.00 46.83 | C |
| ANISOU | 2248 | CB HIS B 34 | 5243 6375 6163 64 585 -342 | C |
| ATOM | 2249 | CG HIS B 34 | 72.640 3.480 -0.691 1.00 48.79 | C |
| ANISOU | 2249 | CG HIS B 34 | 5473 6420 119 513 -238 | C |
| ATOM | 2250 | ND1 HIS B 34 | 71.732 5.490 -0.694 1.00 49.43 | N |
| ANISOU | 2250 | ND1 HIS B 34 | 5492 6776 5514 119 421 -284 | N |
| ATOM | 2251 | CD2 HIS B 34 | 71.910 7.872 -0.545 1.00 52.33 | C |
| ANISOU | 2251 | CD2 HIS B 34 | 5953 7073 6872 180 539 -85 | C |
| ATOM | 2252 | CE1 HIS B 34 | 73.483 6.305 -0.683 1.00 44.93 | C |
| ANISOU | 2252 | CE1 HIS B 34 | 4890 6234 5947 174 375 -170 | C |
| ATOM | 2253 | NE2 HIS 6 34 | 70.585 7.335 -0.846 1.00 49.63 | N |
| ANISOU | 2253 | NE2 HIS B 34 | 5543 6779 6537 223 447 -43 | N |
| ATOM | 2254 | N ASP B 35 | 74.591 3.406 0.698 1.00 44.46 | N |
| ANISOU | 2254 | N ASP B 35 | 4853 6010 6030 42 511 -602 | N |
| ATOM | 2255 | CA ASP B 35 | 74.019 2.121 1.355 1.00 40.24 | C |
| ANISOU | 2255 | CA ASP B 35 | 4377 5529 5648 43 452 -675 | C |
| ATOM | 2256 | C ASP B 35 | 74.257 1.754 2.524 1.00 40.97 | C |
| ANISOU | 2256 | C ASP B 35 | 4368 5424 5773 65 468 -695 | C |
| ATOM | 2257 | O ASP B 35 | 73.571 1.081 3.308 1.00 39.32 | O |
| ANISOU | 2257 | O ASP B 35 | 4147 5160 5534 70 425 -702 | O |
| ATOM | 2258 | CB ASP B 35 | 74.372 0.994 0.182 1.00 50.37 | C |
| ANISOU | 2258 | CB ASP B 35 | 5577 6780 5780 16 442 -797 | C |
| ATOM | 2259 | CG ASP B 35 | 73.463 -0.189 0.348 1.00 59.21 | C |
| ANISOU | 2259 | CG ASP B 35 | 6684 7871 7942 -5 384 -851 | C |
| ATOM | 2260 | OD1 ASP B 35 | 73.977 -1.312 0.496 1.00 61.43 | O |
| ANISOU | 2260 | OD1 ASP B 35 | 6979 8097 8254 -6 405 -968 | O |
| ATOM | 2261 | OD2 ASP B 35 | 72.220 0.013 0.404 1.00 65.29 | O |
| ANISOU | 2261 | OD2 ASP B 35 | 7429 8666 8714 -18 325 -502 | O |
| ATOM | 2262 | N VAL B 36 | 75.492 2.219 3.128 1.00 37.49 | N |
| ANISOU | 2262 | N VAL B 36 | 3928 4964 5351 71 526 -599 | N |
| ATOM | 2263 | CA VAL B 36 | 75.933 1 815 4.457 1.00 36.59 | C |
| ANISOU | 2263 | CA VAL B 36 | 3797 4778 5328 93 532 -720 | C |
| ATOM | 2264 | C VAL B 36 | 74.955 2.404 5.509 1.00 26.52 | C |
| ANISOU | 2264 | C VAL B 36 | 3070 4075 5253 97 519 -636 | C |
| ATOM | 2265 | O VAL B 36 | 74.850 1.332 6.598 1.00 35.98 | CO |
| ANISOU | 2265 | O VAL B 36 | 3722 4571 5379 115 505 -645 | O |
| ATOM | 2266 | CB VAL B 36 | 77.395 2.251 4.728 1.00 39.46 | C |
| ANISOU | 2266 | CB VAL B 36 | 4138 5173 5682 37 590 -747 | C |

TABLE 3-continued

| | | | | | | | | | | |
|---|---|---|---|---|---|---|---|---|---|---|
| ATOM | 2267 | CG1 | VAL | B | 36 | 77.362 | 2.413 | 6.221 | 1.00 | 37.15 C |
| ANISOU | 2267 | CG1 | VAL | B | 36 | 3829 4830 5458 | 97 | 593 | -728 | C |
| ATOM | 2268 | CG2 | VAL | B | 36 | 78.392 | 1.287 | 4.028 | 1.00 | 40.39 C |
| ANISOU | 2268 | CG2 | VAL | B | 36 | 4228 5343 5774 | 109 | 606 | -847 | C |
| ATOM | 2269 | N | GLN | B | 37 | 74.247 | 3.499 | 5.150 | 1.00 | 37.58 N |
| ANISOU | 2269 | N | GLN | B | 37 | 3950 4845 5482 | 89 | 530 | -550 | N |
| ATOM | 2270 | CA | GLN | B | 37 | 73.217 | 4.132 | 6.057 | 1.00 | 43.05 C |
| ANISOU | 2270 | CA | GLN | B | 37 | 4650 5473 6233 | 105 | 532 | -468 | C |
| ATOM | 2271 | C | GLN | B | 37 | 72.223 | 3.008 | 6.505 | 1.00 | 44.25 C |
| ANISOU | 2271 | C | GLN | B | 37 | 4774 5598 6441 | 115 | 474 | -486 | O |
| ATOM | 2272 | O | GLN | B | 37 | 71.683 | 3.135 | 7.615 | 1.00 | 40.05 O |
| ANISOU | 2772 | O | GLN | B | 37 | 4242 5000 5975 | 124 | 482 | -455 | C |
| ATOM | 2273 | CB | GLN | B | 37 | 72.322 | 5.112 | 5.287 | 1.00 | 40.78 C |
| ANISOU | 2273 | CB | GLN | B | 37 | 4375 5215 5933 | 124 | 533 | -370 | C |
| ATOM | 2274 | CG | GLN | B | 37 | 72.967 | 5.365 | 4.874 | 1.33 | 49.28 C |
| ANISOU | 2274 | CG | GLN | B | 37 | 5502 6290 5931 | 115 | 610 | -319 | C |
| ATOM | 2275 | CD | GLN | B | 37 | 71.955 | 7.137 | 4.140 | 1.00 | 44.63 C |
| ANISOU | 2275 | CD | GLN | B | 37 | 4926 5727 9304 | 160 | 905 | -208 | C |
| ATOM | 2276 | OE1 | GLN | B | 37 | 71.781 | 7.904 | 2.897 | 1.00 | 44.17 O |
| ANISOU | 2276 | OE1 | GLN | B | 37 | 4860 5765 6155 | 168 | 567 | -191 | O |
| ATOM | 2277 | NE2 | GLN | B | 37 | 71.180 | 7.852 | 4.395 | 1.00 | 46.82 N |
| ANISOU | 2277 | NE2 | GLN | B | 37 | 5215 5930 6643 | 199 | 637 | -129 | N |
| ATOM | 2278 | N | PHE | B | 38 | 71.955 | 2.121 | 5.601 | 1.00 | 38.24 N |
| ANISOU | 2278 | N | PHE | B | 38 | 3995 4839 5647 | 102 | 425 | -541 | N |
| ATOM | 2279 | CA | PHE | B | 38 | 70.925 | 1.118 | 5.817 | 1.00 | 39.79 C |
| ANISOU | 2279 | CA | PHE | B | 38 | 4166 6065 5387 | 88 | 377 | -568 | C |
| ATOM | 2280 | C | PHE | B | 38 | 71.446 | -0.234 | 6.281 | 1.00 | 40.72 C |
| ANISOU | 2280 | C | PHE | B | 38 | 4531 5119 6050 | 81 | 373 | -553 | C |
| ATOM | 2281 | O | PHE | B | 38 | 70.545 | -1.156 | 6.435 | 1.00 | 38.93 O |
| ANISOU | 2281 | O | PHE | B | 38 | 4068 4360 5353 | 54 | 353 | -690 | O |
| ATOM | 2282 | CB | PHE | B | 38 | 70.044 | 0.950 | 4.563 | 1.00 | 42.89 C |
| ANISOU | 2282 | CB | PHE | B | 38 | 4526 5550 6212 | 61 | 322 | -572 | C |
| ATOM | 2283 | CG | PHE | B | 38 | 69.506 | 2.237 | 4.055 | 1.00 | 42.03 C |
| ANISOU | 2283 | CG | PHE | B | 38 | 4521 5638 6173 | 92 | 319 | -453 | C |
| ATOM | 2284 | CD1 | PHE | B | 38 | 68.447 | 2.856 | 4.726 | 1.00 | 43.53 C |
| ANISOU | 2284 | CD1 | PHE | B | 38 | 4555 5636 5266 | 124 | 319 | -371 | C |
| ATOM | 2285 | CD2 | PHE | B | 38 | 70.136 | 2.895 | 8.028 | 1.00 | 44.39 C |
| ANISOU | 2285 | CD2 | PHE | B | 38 | 4802 8962 6331 | 59 | 334 | -442 | C |
| ATOM | 2286 | CE1 | PHE | B | 38 | 67.996 | 4.091 | 4.283 | 1.00 | 48.05 C |
| ANISOU | 2286 | CE1 | PHE | B | 38 | 5121 6303 6831 | 177 | 330 | -256 | C |

TABLE 3-continued

| | | | | | | | | | | | |
|---|---|---|---|---|---|---|---|---|---|---|---|
| ATOM | 2287 | CE2 | PHL | B | 38 | 69.687 | 4.127 | 2.582 | 1.00 | 50.65 | C |
| ANISOU | 2287 | CE2 | PHE | B | 38 | 5521 | 6723 | 7001 | 142 | 345 | -323 C |
| ATOM | 2288 | CZ | PHE | B | 38 | 68.605 | 4.730 | 3.205 | 1.00 | 47.65 | C |
| ANISOU | 2288 | CZ | PHE | B | 38 | 6110 | 6316 | 6682 | 159 | 342 | -226 C |
| ATOM | 2289 | N | GLN | B | 39 | 72.753 | -0.322 | 6.517 | 1.00 | 37.07 | N |
| ANISOU | 2289 | N | GLN | B | 39 | 3858 | 4540 | 5586 | 107 | 413 | -693 N |
| ATOM | 2290 | CA | GLN | B | 39 | 73.350 | -1.571 | 6.932 | 1.00 | 37.93 | C |
| ANISOU | 2290 | CA | GLN | B | 39 | 3986 | 4686 | 5740 | 132 | 422 | -751 C |
| ATOM | 2291 | C | GLN | B | 39 | 73.551 | -1.505 | 8.464 | 1.05 | 37.34 | C |
| ANISOU | 2291 | C | GLN | B | 39 | 3913 | 4543 | 5728 | 164 | 435 | -718 C |
| ATOM | 2292 | O | GLN | B | 39 | 73.817 | -0.581 | 9.134 | 1.09 | 40.94 | O |
| ANISOU | 2292 | O | GLN | B | 39 | 4366 | 5009 | 6130 | 157 | 452 | -553 O |
| ATOM | 2293 | CB | GLN | B | 39 | 74.735 | -1.835 | 5.312 | 1.00 | 35.26 | C |
| ANISOU | 2293 | CB | GLN | B | 39 | 3546 | 4391 | 5360 | 159 | 450 | -829 C |
| ATOM | 2294 | CG | GLN | B | 39 | 74.705 | -1.905 | 4.795 | 1.00 | 97.67 | C |
| ANISOU | 2294 | CG | GLN | B | 39 | 3954 | 4773 | 5584 | 125 | 447 | -885 C |
| ATOM | 2295 | CD | GLN | B | 33 | 76.092 | -2.223 | 4.175 | 1.00 | 40.26 | C |
| ANISOU | 2295 | CD | GLN | B | 39 | 4278 | 5143 | 5876 | 156 | 492 | -961 C |
| ATOM | 2296 | OE1 | GLN | B | 39 | 77.050 | -2.643 | 4.858 | 1.60 | 37.44 | O |
| ANISOU | 2296 | OE1 | GLN | B | 39 | 3906 | 4754 | 5565 | 214 | 520 | -979 O |
| ATOM | 2297 | NE2 | GLN | B | 39 | 75.185 | -2.056 | 2.878 | 1.00 | 42.55 | N |
| ANISOU | 2297 | NE2 | GLN | B | 39 | 4574 | 5515 | 6077 | 121 | 501 | -1001 N |
| ATOM | 2298 | N | THR | B | 40 | 73.478 | -2.809 | 8.963 | 1.00 | 37.93 | N |
| ANISOU | 2298 | N | THR | B | 40 | 4021 | 4535 | 5854 | 184 | 435 | -748 N |
| ATOM | 2299 | CA | THR | B | 40 | 79.706 | -3.047 | 10.375 | 1.30 | 38.13 | C |
| ANISOU | 2299 | CA | THR | B | 40 | 4061 | 4494 | 5923 | 224 | 445 | -705 C |
| ATOM | 2300 | C | THR | B | 40 | 75.207 | -3.266 | 10.555 | 1.00 | 38 | 92 C |
| ANISOU | 2300 | C | THR | B | 40 | 4149 | 4628 | 6010 | 292 | 453 | -728 C |
| ATOM | 2301 | O | THR | B | 40 | 75.972 | -3.402 | 9.547 | 1.00 | 37.01 | O |
| ANISOU | 2301 | O | THR | B | 40 | 9888 | 4439 | 5736 | 208 | 469 | -788 O |
| ATOM | 2302 | CB | THR | B | 40 | 72.933 | -4.920 | 10.606 | 1.00 | 98.14 | C |
| ANISOU | 2302 | CB | THR | B | 40 | 3859 | 4136 | 5735 | 221 | 450 | -716 C |
| ATOM | 2303 | OG1 | THR | B | 40 | 73.510 | -5.409 | 10.040 | 1.00 | 134.37 | O |
| ANISOU | 2303 | OG1 | THR | B | 40 | 2740 | 3955 | 5592 | 245 | 4355 | -795 O |
| ATOM | 2304 | CG2 | THR | B | 40 | 71.433 | -4.225 | 10.610 | 1.00 | 35.97 | C |
| ANISOU | 2304 | CG2 | THR | B | 40 | 3829 | 4103 | 5734 | 141 | 437 | -704 C |
| ATOM | 2305 | N | ILE | B | 41 | 75.557 | -3.321 | 11.810 | 1.00 | 37.54 | N |
| ANISOU | 2305 | N | ILE | B | 41 | 3988 | 4449 | 5864 | 336 | 457 | -582 N |
| ATOM | 2306 | CA | ILE | B | 41 | 77.099 | -3.521 | 12.048 | 1.00 | 38.34 | C |
| ANISOU | 2306 | CA | ILE | B | 41 | 4039 | 4591 | 5935 | 415 | 459 | -698 C |

TABLE 3-continued

| ATOM | 2307 | C | ILE | B | 41 | 77.425 | -4.998 | 11.484 | 1.00 | 40.96 | C |
|---|---|---|---|---|---|---|---|---|---|---|---|
| ANISOU | 2307 | C | ILE | B | 41 | 4490 | 4860 | 6303 | 466 | 477 | -749 | C |
| ATOM | 2308 | O | ILE | B | 41 | 78.503 | -5.159 | 10.926 | 1.00 | 37.11 | O |
| ANISOU | 2308 | O | ILE | B | 41 | 3859 | 4435 | 5796 | 539 | 492 | -794 | O |
| ATOM | 2309 | CB | ILE | B | 41 | 77.484 | -3.568 | 13.523 | 1.00 | 41.46 | C |
| ANISOU | 2309 | CB | ILE | B | 41 | 4428 | 4996 | 5328 | 455 | 443 | -635 | C |
| ATOM | 2310 | CG1 | ILE | B | 41 | 79.014 | -3.575 | 13.703 | 1.00 | 42.42 | C |
| ANISOU | 2310 | CG1 | ILE | B | 41 | 4475 | 5229 | 545 | 526 | 433 | -649 | C |
| ATOM | 2311 | CG2 | ILE | B | 41 | 75.768 | -4.656 | 14.363 | 1.00 | 42.03 | C |
| ANISOU | 2311 | CG2 | ILE | B | 41 | 4574 | 4945 | 8453 | 495 | 445 | -588 | C |
| ATOM | 2312 | CD1 | ILE | B | 41 | 79.267 | -3.472 | 15.138 | 1.00 | 43.15 | C |
| ANISOU | 2312 | CD1 | ILE | B | 41 | 4626 | 5422 | 5550 | 553 | 404 | -583 | C |
| ATOM | 2313 | N | THR | B | 42 | 76.487 | -5.944 | 11.590 | 1.00 | 45.42 | N |
| ANISOU | 2313 | N | THR | B | 42 | 4390 | 4654 | 5272 | 478 | 488 | -742 | N |
| ATOM | 2314 | CA | THR | B | 42 | 76.574 | -7.310 | 11.393 | 1.00 | 39.33 | C |
| ANISOU | 2314 | CA | THR | B | 42 | 4320 | 4433 | 8189 | 533 | 525 | -805 | C |
| ATOM | 2315 | C | THR | B | 42 | 76.633 | -7.252 | 9.583 | 1.00 | 41.78 | C |
| ANISOU | 2315 | C | THR | B | 42 | 4815 | 4795 | 6465 | 493 | 541 | -902 | C |
| ATOM | 2316 | O | THR | B | 42 | 77.753 | -7.900 | 9.035 | 1.00 | 39.07 | O |
| ANISOU | 2316 | O | THR | B | 42 | 4271 | 4448 | 4226 | 567 | 579 | -960 | O |
| ATOM | 2317 | CB | THR | B | 42 | 75.504 | -8.259 | 11.513 | 1.00 | 40.50 | C |
| ANISOU | 2317 | CB | THR | B | 42 | 4561 | 4428 | 6399 | 496 | 547 | -793 | C |
| ATOM | 2318 | OG1 | THR | B | 42 | 75.144 | -7.989 | 12.873 | 1.00 | 40.78 | O |
| ANISOU | 2318 | OG1 | THR | B | 42 | 4605 | 4443 | 5444 | 502 | 530 | -695 | O |
| ATOM | 2319 | CG2 | THR | B | 42 | 75.925 | -9.829 | 11.391 | 1.00 | 39.59 | C |
| ANISOU | 2319 | CG2 | THR | B | 42 | 4531 | 4159 | 8342 | 584 | 639 | -832 | C |
| ATOM | 2320 | N | ASP | B | 43 | 76.034 | -6.431 | 8.886 | 1 | 1.00 | 40.57 | N |
| ANISOU | 2320 | N | ASP | B | 43 | 4455 | 4714 | 5283 | 383 | 517 | -917 | N |
| ATOM | 2321 | CA | ASP | B | 43 | 76.229 | -6.287 | 7.418 | 1.00 | 45.51 | C |
| ANISOU | 2321 | CA | ASP | B | 43 | 5067 | 5412 | 6653 | 348 | 528 | -1.001 | C |
| ATOM | 2322 | C | ASP | B | 43 | 77.583 | -5.768 | 6.999 | 1.00 | 43.42 | C |
| ANISOU | 2322 | C | ASP | B | 43 | 4733 | 5241 | 4528 | 400 | 548 | -1020 | C |
| ATOM | 2323 | O | ASP | B | 43 | 76.164 | -5.252 | 5.035 | 1.00 | 43.52 | O |
| ANISOU | 2323 | O | ASP | B | 43 | 4747 | 5274 | 6516 | 421 | 567 | -1103 | O |
| ATOM | 2324 | CB | ASP | B | 43 | 75.270 | -5.322 | 6.780 | 1.00 | 45.07 | C |
| ANISOU | 2324 | CB | ASP | B | 43 | 4976 | 5422 | 6726 | 248 | 490 | -984 | C |
| ATOM | 2325 | CG | ASP | B | 43 | 73.932 | -5.649 | 5.570 | 1.00 | 50.29 | C |
| ANISOU | 2325 | CG | ASP | B | 43 | 5571 | 8030 | 7407 | 172 | 471 | -1006 | C |
| ATOM | 2326 | OD1 | ASP | B | 43 | 73.795 | -7.063 | 5.257 | 1.00 | 47.59 | O |
| ANISOU | 2326 | OD1 | ASP | 8 | 43 | 5295 | 5515 | 7005 | 160 | 5.00 | -1385 | O |

TABLE 3-continued

| | | | | | | | | | | |
|---|---|---|---|---|---|---|---|---|---|---|
| ATOM | 2327 | OD2 | ASP | B | 43 | 73.303 | -5.316 | 6.724 | 1.00 | 50.23 O |
| ANISOU | 2327 | OD2 | ASP | B | 43 | 5531 6067 7387 121 434 -944 | | | | O |
| ATOM | 2328 | N | LEU | B | 44 | 78.051 | -4.742 | 7.711 | 1.00 | 45.34 N |
| ANISOU | 2328 | N | LEU | B | 44 | 4917 5555 6755 407 530 -952 | | | | N |
| ATOM | 2329 | CA | LEU | B | 44 | 79.246 | -4 080 | 7.312 | 1.00 | 41.46 C |
| ANISOU | 2329 | CA | LEU | B | 44 | 4356 5130 6215 424 552 -971 | | | | C |
| ATOM | 2330 | C | LEU | B | 44 | 80.391 | -5.055 | 7.531 | 1.00 | 41.45 C |
| ANISOU | 2330 | C | LEU | B | 44 | 4328 5174 6249 540 582 -1006 | | | | C |
| ATOM | 2331 | O | LEU | B | 44 | 81.274 | -5.116 | 6.577 | 1.00 | 39.61 O |
| ANISOU | 2331 | O | LEU | B | 44 | 4062 5016 5993 565 823 -1070 | | | | O |
| ATOM | 2332 | CB | LEU | B | 44 | 79.455 | -2.810 | 8.114 | 1.00 | 25.64 C |
| ANISOU | 2332 | CB | LEU | B | 44 | 3701 4635 5584 367 534 -902 | | | | C |
| ATOM | 2333 | CG | LEU | B | 44 | 63.527 | -1.833 | 7.650 | 1.00 | 39.73 C |
| ANISOU | 2333 | CG | LEU | B | 44 | 4025 5153 5915 358 564 -921 | | | | C |
| ATOM | 2334 | CD1 | LEU | B | 44 | 80.549 | -1.587 | 6.174 | 1.00 | 40.53 C |
| ANISOU | 2334 | CD1 | LEU | B | 44 | 4144 5307 5966 313 599 -971 | | | | C |
| ATOM | 2335 | CD2 | LEU | B | 44 | 80.232 | -0.527 | 5.373 | 1.00 | 43.25 C |
| ANISOU | 2335 | CD2 | LEU | B | 44 | 4457 5622 6347 285 557 -858 | | | | C |
| ATOM | 2336 | N | ALA | B | 45 | 80.413 | -5.744 | 8.675 | 1.00 | 38.54 N |
| ANISOU | 2336 | N | ALA | B | 45 | 3975 4731 5938 613 556 -955 | | | | N |
| ATOM | 2337 | CA | ALA | B | 45 | 81.458 | -6.767 | 8.314 | 1.00 | 41.84 C |
| ANISOU | 2327 | CA | ALA | B | 45 | 4369 5135 6395 761 597 -570 | | | | C |
| ATOM | 2338 | C | ALA | B | 45 | 81.423 | -7.875 | 7.842 | 1.00 | 45.73 C |
| ANISOU | 2338 | C | ALA | B | 45 | 4925 5536 6913 796 560 -1064 | | | | C |
| ATOM | 2339 | O | ALA | B | 45 | 82.457 | -8.255 | 7.256 | 1.00 | 44.12 O |
| ANISOU | 2339 | O | ALA | B | 45 | 4676 5379 6757 878 711 -1121 | | | | O |
| ATOM | 3340 | CB | ALA | B | 45 | 81.335 | -7.325 | 10.323 | 1.00 | 39.83 C |
| ANISOU | 2340 | CB | ALA | B | 45 | 4140 4506 6186 841 568 -881 | | | | C |
| ATOM | 2341 | N | ARG | B | 46 | 80.248 | -3.400 | 7.551 | 1.05 | 43.39 N |
| ANISOU | 2341 | N | ARG | B | 46 | 4808 5193 6714 726 655 -1091 | | | | N |
| ATOM | 2342 | CA | ARG | B | 46 | 80.103 | -9.388 | 5.458 | 1.00 | 45.78 C |
| ANISOU | 2342 | CA | ARG | B | 46 | 5515 5542 7455 722 730 -1202 | | | | C |
| ATOM | 2343 | C | ARG | B | 46 | 80.103 | -8.871 | 6.458 | 1.00 | 51.03 C |
| ANISOU | 2343 | C | ARG | B | 46 | 5732 7121 7533 670 750 -1291 | | | | C |
| ATOM | 2344 | O | ARG | B | 46 | 81.284 | -9.579 | 4.343 | 1.00 | 45.48 O |
| ANISOU | 2344 | O | ARG | B | 46 | 6165 5530 5362 733 530 -1382 | | | | O |
| ATOM | 2345 | CB | ARG | B | 46 | 76.568 | -9.083 | 6.320 | 1.00 | 51.11 C |
| ANISOU | 2345 | CB | ARG | B | 46 | 5876 5885 7648 516 725 -1231 | | | | C |
| ATOM | 2346 | CG | ARG | B | 46 | 78.192 | -10.814 | 7.473 | 1.00 | 62.37 C |
| ANISOU | 2346 | CG | ARG | B | 46 | 7388 7149 9160 675 736 -1157 | | | | C |

TABLE 3-continued

| ATOM | 2347 | CD | ARG | B | 46 | 77.636 -12.121 5.905 1.00 65.37 C |
|---|---|---|---|---|---|---|
| ANISOU | 2347 | CD | ARG | B | 46 | 8360 7830 10054 630 609 -1257 C |
| ATOM | 2348 | NE | ARG | B | 46 | 77.020 -13.309 7.901 1.00 73.09 N |
| ANISOU | 2348 | NE | ARG | B | 46 | 5964 5160 10645 648 836 -1212 N |
| ATOM | 2349 | CZ | ARG | B | 46 | 75.363 -14.106 7.503 1.00 75.51 C |
| ANISOU | 2349 | CZ | ARG | B | 46 | 5520 3422 11123 530 908 -1290 C |
| ATOM | 2350 | NH1 | ARG | B | 46 | 75.229 -14.523 6.349 1.00 77.73 N |
| ANISOU | 2350 | NH1 | ARG | B | 46 | 9721 6574 11250 510 553 -1437 N |
| ATOM | 2251 | NH2 | ARG | B | 46 | 75.824 -14.871 8.572 1.00 76.76 N |
| ANISOU | 2351 | NH2 | ARG | B | 46 | 3642 8290 11233 601 541 -1226 N |
| ATOM | 2352 | N | ASN | B | 47 | 30.128 -7.562 4.758 1.00 43.48 N |
| ANISOU | 2352 | N | ASN | B | 47 | 4736 5275 5508 561 707 -1265 N |
| ATOM | 2353 | CA | ASN | B | 47 | 80.423 -7.133 3.440 1.00 40.50 C |
| ANISOU | 2353 | CA | ASN | B | 47 | 5597 5773 6500 500 733 -1335 C |
| ATOM | 2354 | C | ASN | B | 47 | 81.501 -6.774 3.314 1.00 47.12 C |
| ANISOU | 2354 | C | ASN | B | 47 | 5084 5955 5861 575 778 -1246 C |
| ATOM | 2355 | O | ASN | B | 47 | 82.407 -6.717 2.220 1.00 46.70 O |
| ANISOU | 2355 | O | ASN | B | 47 | 5023 5977 5747 557 331 -1423 O |
| ATOM | 2356 | CB | ASN | B | 47 | 75.546 -5.930 3.065 1.00 45.17 O |
| ANISOU | 2356 | CB | ASN | B | 47 | 4922 5563 5557 378 676 -1287 C |
| ATOM | 2357 | CG | ASN | B | 47 | 78.768 -6.301 8.007 1.00 50.54 C |
| ANISOU | 2357 | CG | ASN | B | 47 | 5658 6290 7245 300 632 -1288 C |
| ATOM | 2358 | OD1 | ASN | B | 47 | 77.752 -7.404 2.614 1.00 46.13 O |
| ANISOU | 2358 | OD1 | ASN | B | 47 | 5181 5665 6713 285 555 -1374 O |
| ATOM | 2359 | NH2 | ASN | B | 47 | 77.213 -5.356 3.445 1.00 42.75 N |
| ANISOU | 2359 | NH2 | ASN | B | 47 | 4564 5330 3250 243 573 -1199 N |
| ATOM | 2360 | N | THR | B | 48 | 32.587 -5.543 4.425 1.00 45.79 N |
| ANISOU | 2360 | N | THR | B | 48 | 4842 5817 5733 652 759 -1273 N |
| ATOM | 2361 | CA | THR | B | 48 | 34.001 -5.186 4.217 1.00 46.85 C |
| ANISOU | 2361 | CA | THR | B | 48 | 4565 6085 6555 710 726 -1259 C |
| ATOM | 2362 | C | THR | B | 48 | 54.008 -7.330 4.555 1.00 49.56 C |
| ANISOU | 2362 | C | THR | B | 48 | 5178 5387 7266 875 850 -1321 C |
| ATOM | 2363 | O | THR | B | 48 | 88.149 -7.273 4.424 1.06 47.49 O |
| ANISOU | 2363 | O | THR | B | 48 | 4804 6242 6997 546 891 -1343 O |
| ATOM | 2364 | CB | THR | B | 48 | 84.328 -5.021 5.236 1.00 47.70 C |
| ANISOU | 2364 | CB | THR | B | 48 | 4334 6292 6946 672 745 -1204 C |
| ATOM | 0 2365 | OG1 | THR | B | 48 | 84.144 -5.398 6.612 1.00 51.08 O |
| ANISOU | 2365 | OG1 | THR | B | 48 | 5311 6659 7435 741 695 -1127 O |
| ATOM | 2366 | CG2 | THR | B | 48 | 53.393 -3.811 4.901 1.90 46.15 C |
| ANISOU | 2366 | CG2 | THR | B | 48 | 4733 6113 6588 523 718 -1159 C |

TABLE 3-continued

| | | | | | | | | | |
|---|---|---|---|---|---|---|---|---|---|
| ATOM | 2367 | N | GLN | B | 49 | 54.259 | -8.510 | 4.357 | 1.00 49.56 N |
| ANISOU | 2367 | N | GLN | B | 49 | 5278 6219 7333 | 936 | 856 | -1320 N |
| ATOM | 2368 | CA | GLN | B | 49 | 84.982 | -9.718 | 5.349 | 1.00 54.89 C |
| ANISOU | 2368 | CA | OLN | B | 49 | 5954 6312 8039 | 1116 | 905 | -1319 C |
| ATOM | 2369 | C | GLN | B | 49 | 85.964 | -9.382 | 6 484 | 1.30 58.64 C |
| ANISOU | 2369 | C | GLN | B | 49 | 6235 7434 8582 | 1224 | 662 | -1224 C |
| ATOM | 2370 | O | GLN | B | 49 | 81.100 | -9.812 | 8.432 | 1.00 55.41 O |
| ANISOU | 2370 | O | GLN | B | 49 | 5795 7060 3155 | 1365 | 908 | -1237 O |
| ATOM | 2371 | CB | GLN | B | 49 | 86.704 | -19.413 | 4.173 | 1.00 54.40 C |
| ANISOU | 2371 | CB | GLN | B | 49 | 5403 7252 8533 | 1181 | 1015 | -1440 C |
| ATOM | 2372 | CG | GLN | B | 49 | 34.755 | -10.326 | 3.054 | 1.09 52.37 C |
| ANISOU | 2372 | CG | GLN | B | 49 | 7644 7552 9003 | 1564 | 1058 | -1550 C |
| ATOM | 2373 | CD | GLN | B | 49 | 85.386 | -11.781 | 2.023 | 1.00 72.57 C |
| ANISOU | 2373 | CD | GLN | B | 49 | 8370 8893 10304 | 1141 | 1185 | -1583 C |
| ATOM | 2374 | OE1 | GLN | B | 49 | 84.672 | -12.543 | 1.373 | 1.00 30.48 O |
| ANISOU | 2374 | OE1 | GLN | B | 49 | 9512 9752 11305 | 1082 | 1235 | -1778 O |
| ATOM | 2375 | NE2 | GLN | B | 49 | 86.717 | -11.751 | 1.389 | 1.03 13.02 N |
| ANISOU | 2375 | NE2 | GLN | B | 49 | 3315 9060 10370 | 1266 | 1245 | -1697 N |
| ATOM | 2376 | N | THR | B | 50 | 85.825 | -3.585 | 7.439 | 1.06 54.26 N |
| ANISOU | 2376 | N | THR | B | 50 | 5719 6391 8005 | 1154 | 774 | -1133 N |
| ATOM | 2377 | CA | THR | B | 50 | 80.350 | -6.283 | 3.813 | 1.00 55.78 C |
| ANISOU | 2377 | CA | THR | B | 50 | 5792 7204 5199 | 1237 | 720 | -1045 C |
| ATOM | 2378 | C | THR | B | 50 | 86.515 | -8.839 | 9.754 | 1.05 51.07 C |
| ANISOU | 2378 | C | THR | B | 50 | 6536 7310 8937 | 1275 | 674 | -950 C |
| ATOM | 2379 | O | THR | B | 50 | 84.859 | -9.807 | 9.554 | 1.00 71.07 O |
| ANISOU | 2379 | O | THR | B | 50 | 7953 8518 10231 | 1316 | 715 | -965 O |
| ATOM | 2380 | CB | THR | B | 50 | 86.645 | -6.780 | 8.732 | 1.00 54.60 C |
| ANISOU | 2380 | CB | THR | B | 50 | 5539 7234 7974 | 1101 | 675 | -1037 C |
| ATOM | 2381 | OG1 | THR | B | 50 | 85.402 | -6.012 | 8.790 | 1.00 54.53 O |
| ANISOU | 2381 | OG1 | THR | B | 50 | 5624 7150 7937 | 943 | 633 | -1610 O |
| ATOM | 2382 | CG2 | THR | B | 50 | 87.473 | -6.321 | 7.559 | 1.00 53.98 O |
| ANISOU | 2382 | CG2 | THR | B | 50 | 5376 7250 7355 | 1002 | 735 | -1125 C |
| ATOM | 2383 | N | SER | B | 51 | 85.495 | -8.203 | 10.512 | 1.00 58.95 N |
| ANISOU | 2383 | N | SER | B | 51 | 6244 7543 8612 | 1251 | 857 | -863 N |
| ATOM | 2384 | CA | SER | B | 51 | 84.615 | -8.626 | 12.007 | 1.00 54.55 C |
| ANISOU | 2384 | CA | SER | B | 51 | 5787 6359 8079 | 1265 | 559 | -771 C |
| ATOM | 2385 | C | SER | B | 51 | 83.835 | -7.393 | 12.587 | 1.00 53.82 C |
| ANISOU | 2385 | C | SER | B | 51 | 5597 5523 7932 | 1102 | 443 | -733 C |
| ATOM | 2386 | O | SER | B | 51 | 84.287 | -6.270 | 12.294 | 1.00 53.90 O |
| ANISOU | 2386 | O | SER | B | 51 | 5521 6972 7835 | 1057 | 435 | -774 O |

TABLE 3-continued

| | | | | | | | | | |
|---|---|---|---|---|---|---|---|---|---|
| ATOM | 2387 | CB | SER | B | 51 | 85.454 | -9.237 | 13.112 | 1.0 52.30 C |
| ANISOU | 2387 | CB | SER | B | 51 | 5519 6700 7879 1442 528 -674 | | | C |
| ATOM | 2388 | OG | SER | B | 51 | 88.342 | -8.250 | 13.531 | 1.00 49.27 O |
| ANISOU | 2388 | OG | SER | B | 51 | 4901 6471 7347 1410 466 -655 | | | O |
| ATOM | 2389 | N | GLU | B | 52 | 82.849 | -7.812 | 13.401 | 1.60 52.14 N |
| ANISOU | 2389 | N | GLU | B | 52 | 5536 6453 7737 1073 478 -572 | | | N |
| ATOM | 2390 | CA | GLU | B | 52 | 82.155 | -6.512 | 14.127 | 1.00 54.79 C |
| ANISOU | 2390 | CA | GLU | B | 52 | 5925 6354 8026 942 433 -634 | | | C |
| ATOM | 2391 | C | GLU | B | 52 | 83.134 | -5.722 | 15.029 | 1.00 53.65 C |
| ANISOU | 2391 | C | GLU | B | 52 | 5655 5907 7312 948 380 -598 | | | C |
| ATOM | 2392 | O | GLU | B | 52 | 83.062 | -4.509 | 15.139 | 1.00 49.16 O |
| ANISOU | 2392 | O | GLU | B | 52 | 5053 6423 7195 622 385 -618 | | | O |
| ATOM | 2393 | CB | GLU | B | 52 | 83.995 | -7.042 | 14.977 | 1.00 52.99 C |
| ANISOU | 2393 | CB | GLU | B | 52 | 5819 6484 7829 932 429 -564 | | | C |
| ATCOM | 2394 | CG | GLU | B | 52 | 73.843 | -7.674 | 14.206 | 1.00 52.53 C |
| ANISOU | 2394 | CG | GLU | B | 52 | 5883 6263 7345 879 478 -606 | | | C |
| ATOM | 2395 | CD | GLU | B | 52 | 78.035 | -7.953 | 15.083 | 1.00 63.01 C |
| ANISOU | 2395 | CD | GLU | B | 52 | 7295 7460 9164 533 477 -542 | | | C |
| ATOM | 2396 | OE1 | GLU | B | 52 | 78.597 | -7.648 | 16.300 | 1.30 56.29 O |
| ANISOU | 2396 | OE1 | GLU | B | 52 | 7705 7916 9558 646 445 -451 | | | O |
| ATOM | 2397 | OE2 | GLU | B | 52 | 77.609 | -8.479 | 14.570 | 1.00 70.17 O |
| ANISOU | 2397 | OE2 | GLU | B | 52 | 8283 8238 10140 771 513 -576 | | | O |
| ATOM | 2398 | N | ALA | B | 53 | 84.972 | -5.429 | 15.644 | 1.00 50.11 N |
| ANISOU | 2398 | N | ALA | B | 53 | 6422 7791 8625 1097 355 -549 | | | N |
| ATOM | 2399 | CA | ALA | B | 53 | 85.107 | -5.805 | 16.471 | 1.00 53.79 C |
| ANISOU | 2399 | CA | ALA | B | 53 | 5488 7205 7743 1108 296 -525 | | | C |
| ATOM | 2400 | C | ALA | B | 53 | 65.929 | -4.791 | 15.579 | 1.00 54.13 C |
| ANISOU | 2400 | C | ALA | B | 53 | 5406 7411 7758 1014 309 -515 | | | C |
| ATOM | 2401 | O | ALA | B | 53 | 86.311 | -5.748 | 16.202 | 1.00 55.84 O |
| ANISOU | 2401 | O | ALA | B | 53 | 5570 7898 5023 905 270 -829 | | | O |
| ATOM | 2402 | CB | ALA | B | 53 | 65.984 | -8.891 | 17.080 | 1.00 58.50 C |
| ANISOU | 2402 | CB | ALA | B | 53 | 5774 7595 5097 1315 269 -446 | | | C |
| ATOM | 2403 | N | THR | B | 54 | 36.21 5 | -5.097 | 14.412 | 1.33 54.66 N |
| ANISOU | 2403 | N | THR | B | 54 | 5461 7473 7891 1042 368 -585 | | | N |
| ATOM | 2404 | CA | THR | B | 54 | 35.969 | -4.197 | 13.539 | 1.00 55.27 C |
| ANISOU | 2404 | CA | THR | B | 54 | 5511 7757 7997 952 399 -772 | | | C |
| ATOM | 2405 | C | THR | B | 54 | 85.254 | -2.916 | 13.138 | 1.00 52.79 C |
| ANISOU | 2405 | C | THR | B | 54 | 5171 7324 7553 753 421 -810 | | | C |
| ATOM | 2406 | O | THR | B | 54 | 85.610 | -1.621 | 12.971 | 1.90 47.05 O |
| ANISOU | 2406 | O | THR | B | 54 | 4379 6732 6790 507 454 -854 | | | O |

TABLE 3-continued

| ATOM | 2407 | CB THR B 54 | 87.330 -4.918 12.225 1.00 58.49 C |
|---|---|---|---|
| ANISOU | 2407 | CB THR B 54 | 5328 8029 8355 1030 470 -337 C |
| ATOM | 2408 | OG1 THR B 54 | 83.041 -6.108 12.505 1.60 59.32 O |
| ANISOU | 2408 | OG1 THR B 54 | 5950 8203 8577 1234 471 -802 O |
| ATOM | 2409 | CG2 THR B 54 | 88.145 -4.014 11.271 1.00 52.36 C |
| ANISOU | 2409 | CG2 THR B 54 | 4944 7401 7548 933 516 -924 C |
| ATOM | 2410 | N VAL B 55 | 84.943 -3.098 12.678 1.00 52.25 N |
| ANISOU | 2410 | N VAL B 55 | 5245 7379 7530 718 435 -793 N |
| ATOM | 2411 | CA VAL B 55 | 34.054 -1.988 12.520 1.00 47.95 C |
| ANISOU | 2411 | CA VAL B 55 | 4769 6468 8565 564 455 -801 C |
| ATOM | 2412 | C VAL B 55 | 80.974 -1.056 15.598 1.00 43.22 C |
| ANISOU | 2412 | C VAL B 55 | 4159 5941 5320 431 424 -771 C |
| ATOM | 2413 | O VAL B 55 | 84.057 0.149 13.523 1.00 50.54 O |
| ANISOU | 2413 | O VAL B 55 | 5585 5933 7222 354 452 -500 O |
| ATOM | 2414 | CB VAL B 55 | 82.885 -2.458 12.397 1.00 48.78 C |
| ANISOU | 2414 | CB VAL B 55 | 5003 8417 7115 559 466 -791 C |
| ATOM | 2415 | CG1 VAL B 55 | 81.719 -1.304 11.994 1.00 43.71 C |
| ANISOU | 2415 | CG1 VAL B 55 | 4419 5738 8451 424 479 -781 C |
| ATOM | 2416 | CG2 VAL B 55 | 62.861 -3.237 10.810 1.00 47.49 C |
| ANISOU | 2416 | CG2 VAL B 55 | 4548 6221 5974 603 505 -853 C |
| ATOM | 2417 | N VAL B 56 | 83.374 -1.629 14.899 1.00 44.57 N |
| ANISOU | 2417 | N VAL B 56 | 4554 6115 6504 549 374 -710 N |
| ATOM | 2418 | CA VAL B 56 | 63.669 -0.795 16.081 1.05 45.22 C |
| ANISOU | 2418 | CA VAL B 56 | 4560 6355 6648 462 348 -682 C |
| ATOM | 2419 | C VAL B 56 | 84.974 -0.022 16.254 1.00 49.83 C |
| ANISOU | 2419 | C VAL B 56 | 4561 7018 7037 401 339 -733 C |
| ATOM | 2420 | O VAL B 56 | 84.937 1.219 15.335 1.00 48.30 O |
| ANISOU | 2420 | O VAL B 56 | 515 4752 6925 6865 252 370 -774 O |
| ATOM | 2421 | CB VAL B 56 | 83.458 -1.636 17.347 1.00 47.25 C |
| ANISOU | 2421 | CB VAL B 56 | 4721 6452 5770 557 295 -602 C |
| ATOM | 2422 | CG1 VAL B 56 | 83.569 -0.730 18.539 1.00 52.17 C |
| ANISOU | 2422 | CG1 VAL B 56 | 5327 7184 7315 461 268 -593 C |
| ATOM | 2423 | CG2 VAL B 56 | 82 148 -2.449 17.316 1.00 56.48 C |
| ANISOU | 2423 | CG2 VAL B 56 | 5264 6570 7246 500 314 -552 CN |
| ATOM | 2424 | N ARG B 57 | 85.095 -0.765 16.273 1.00 50.73 N |
| ANISOU | 2424 | N ARG B 57 | 4075 7257 7144 517 306 -754 N |
| ATOM | 2425 | CA ARG B 57 | 37.421 -3.123 15.415 1.00 51.13 C |
| ANISOU | 2425 | CA ARG B 57 | 4763 7534 7131 460 292 -739 C |
| ATOM | 2426 | C ARG B 57 | 87.628 1.061 15.443 1.00 51.50 C |
| ANISOU | 2426 | C ARG B 57 | 4796 7605 7167 297 358 -874 C |

TABLE 3-continued

| | | | | | | | | | | |
|---|---|---|---|---|---|---|---|---|---|---|
| ATOM | 2427 | O | ARG | B | 57 | 38.027 | 2.141 | 15.345 | 1.00 | 50.35 O |
| ANISOU | 2427 | O | ARG | B | 57 | 4607 7562 6962 | 148 | 380 | -920 | O |
| ATOM | 2428 | CB | ARG | B | 57 | 88.521 | -1.148 | 16.315 | 1.00 | 58.69 C |
| ANISOU | 2428 | CB | ARG | B | 57 | 5584 8616 8100 | 530 | 250 | -776 | C |
| ATOM | 2429 | CG | ARG | B | 57 | 89.793 | -0.641 | 16.941 | 1.00 | 50.75 C |
| ANISOU | 2429 | CG | ARG | B | 57 | 5557 9144 8230 | 583 | 213 | -807 | C |
| ATOM | 2430 | CD | ARG | B | 57 | 90.928 | -1.032 | 16.045 | 1.00 | 69.98 C |
| ANISOU | 2430 | CD | ARG | B | 57 | 5673 10441 9476 | 673 | 242 | -853 | C |
| ATOM | 2431 | NE | ARG | B | 57 | 91.314 | -2.418 | 16.216 | 1.00 | 74.27 N |
| ANISOU | 2431 | NE | ARG | B | 57 | 7153 10891 10060 | 915 | 205 | -782 | N |
| ATOM | 2432 | CZ | ARG | B | 57 | 92.408 | -2.931 | 15.664 | 1.00 | 82.84 C |
| ANISOU | 2432 | CZ | ARG | B | 57 | 6097 12210 11169 | 2037 | 223 | -606 | C |
| ATOM | 2433 | NH1 | ARG | B | 57 | 93.189 | -2.171 | 14.907 | 1.00 | 83.98 N |
| ANISOU | 2433 | NH1 | ARG | B | 57 | 8116 12496 11295 | 922 | 276 | -904 | N |
| ATOM | 2434 | NH2 | ARG | B | 57 | 92.718 | -4.201 | 15.950 | 1.00 | 83.20 N |
| ANISOU | 2434 | NH2 | ARG | B | 57 | 8114 12239 11259 | 1276 | 202 | -731 | N |
| ATOM | 2435 | N | LEU | B | 58 | 37.255 | 0.903 | 14.174 | 1.00 | 51.84 N |
| ANISOU | 2435 | N | LEU | B | 58 | 4897 7538 7261 | 311 | 428 | -895 | N |
| ATOM | 2436 | CA | LEU | B | 58 | 87.275 | 2.029 | 19.227 | 1.00 | 49.49 C |
| ANISOU | 2436 | CA | LEU | B | 58 | 4520 7236 5947 | 163 | 507 | -952 | C |
| ATOM | 2437 | C | LEU | B | 58 | 96.354 | 3.287 | 13.555 | 1.00 | 50.32 C |
| ANISOU | 2437 | C | LEU | B | 58 | 4845 7242 7082 | 8 | 543 | -942 | C |
| ATOM | 2438 | O | LEU | B | 58 | 85.732 | 4.491 | 13.443 | 1.00 | 48.03 O |
| ANISOU | 2438 | O | LEU | B | 58 | 4547 7013 6709 | -145 | 602 | -991 | O |
| ATOM | 2439 | CB | LEU | B | 58 | 85.867 | 1.552 | 11.834 | 1.00 | 45.00 C |
| ANISOU | 2439 | CB | LEU | B | 58 | 4301 6753 8612 | 222 | 552 | -960 | C |
| ATOM | 2440 | CG | LEU | B | 58 | 85.815 | 2.647 | 10.922 | 1.00 | 54.16 C |
| ANISOU | 2440 | CG | LEU | B | 58 | 5308 7714 7555 | 82 | 632 | -998 | C |
| ATOM | 2441 | CD1 | LEU | B | 58 | 38.205 | 0.251 | 11.019 | 1.00 | 55.44 C |
| ANISOU | 2441 | CD1 | LEU | B | 58 | 5451 8105 7799 | 0 | 651 | -1051 | C |
| ATOM | 2442 | CD2 | LEU | B | 58 | 86.475 | 2.144 | 9.512 | 1.00 | 51.92 C |
| ANISOU | 2442 | CD2 | LEU | B | 58 | 5579 7359 7291 | 133 | 673 | -1011 | C |
| ATOM | 2443 | N | CYS | B | 59 | 85.111 | 3.006 | 13.933 | 1.00 | 45.37 N |
| ANISOU | 2443 | N | CYS | B | 59 | 4352 8421 5401 | 48 | 522 | -961 | N |
| ATOM | 2444 | CA | CYS | B | 59 | 84.194 | 4 048 | 14.379 | 1.00 | 43.80 C |
| ANISOU | 2444 | CA | CYS | B | 59 | 4261 5175 5244 | -52 | 558 | -363 | C |
| ATOM | 2445 | C | CYS | B | 59 | 84.751 | 4.846 | 15.539 | 1.00 | 46.39 C |
| ANISOU | 2445 | C | CYS | B | 59 | 4533 6590 5498 | -171 | 554 | -895 | C |
| ATOM | 2446 | O | CYS | B | 59 | 34.599 | 6.099 | 15.531 | 1.00 | 51.43 O |
| ANISOU 8 | 2446 | O | CYS | B | 59 | 5230 7211 7119 | -314 | 626 | -930 | O |

TABLE 3-continued

| | | | | | | | | | | |
|---|---|---|---|---|---|---|---|---|---|---|
| ATOM | 2447 | CB | CYS | B | 59 | 82.845 | 3.394 | 14.724 | 1.00 | 43.94 C |
| ANISOU | 2447 | CB | CYS | B | 59 | 4372 5026 6298 18 527 -798 | | | | C |
| ATOM | 2448 | SG | CYS | B | 59 | 82.045 | 2.759 | 13.210 | 1.00 | 44.22 S |
| ANISOU | 2448 | SG | CYS | B | 59 | 4465 5947 6390 88 546 -777 | | | | S |
| ATOM | 2449 | N | ARG | B | 60 | 85.301 | 4.144 | 16.521 | 1.00 | 45.81 N |
| ANISOU | 2449 | N | ARG | B | 60 | 4511 5756 6520 -106 475 -955 | | | | N |
| ATOM | 2450 | CA | ARG | B | 60 | 88.023 | 4.764 | 17.667 | 1.00 | 50.04 C |
| ANISOU | 2450 | CA | ARG | B | 60 | 5270 7733 7254 -203 4513 -923 | | | | C |
| ATOM | 2451 | C | ARG | B | 60 | 87.240 | 5.680 | 37.173 | 1.50 | 55.93 C |
| ANISOU | 2451 | C | ARG | B | 60 | 5485 8218 7549 -348 500 -1022 | | | | C |
| ATOM | 2452 | O | ARG | B | 60 | 87.421 | 5.763 | 17.627 | 1.00 | 54.39 O |
| ANISOU | 2452 | O | ARG | B | 60 | 5309 8055 7311 -519 548 -1034 | | | | O |
| ATOM | 2453 | CB | ARG | B | 60 | 66.541 | 3.863 | 15.548 | 1.00 | 52.32 C |
| ANISOU | 2453 | CB | ARG | B | 60 | 5050 7730 7101 -79 349 -885 | | | | C |
| ATOM | 2454 | CG | ARG | B | 60 | 85.863 | 3.474 | 19.881 | 1.00 | 54.26 C |
| ANISOU | 2454 | CG | ARG | B | 60 | 5089 7943 71305 -84 302 -831 | | | | C |
| ATOM | 2455 | CD | ARG | B | 60 | 64.649 | 2.534 | 19.796 | 1.00 | 56.48 C |
| ANISOU | 2455 | CD | ARG | B | 60 | 5775 8024 7651 55 306 -746 | | | | C |
| ATOM | 2456 | NE | ARG | B | 60 | 84.710 | 1.561 | 20.782 | 1.00 | 50.91 N |
| ANISOU | 2456 | NE | ARG | B | 60 | 7083 9387 8953 185 228 -668 | | | | N |
| ATOM | 2457 | CZ | ARG | B | 60 | 83.664 | 0.868 | 21.263 | 1.00 | 72.54 C |
| ANISOU | 2457 | CZ | ARG | B | 60 | 7011 9053 3897 250 218 -585 | | | | C |
| ATOM | 2458 | NH1 | ARG | B | 60 | 82.407 | 1.131 | 20.887 | 1.00 | 72.15 N |
| ANISOU | 2458 | NH1 | ARG | B | 60 | 7985 9715 9714 221 280 -579 | | | | N |
| ATOM | 2459 | NH2 | ARG | B | 60 | 83.882 | -0.090 | 22.143 | 1.00 | 73.88 N |
| ANISOU | 2459 | NH2 | ARG | B | 60 | 8067 10174 9829 383 142 -510 | | | | N |
| ATOM | 2460 | N | ASP | B | 61 | 58.004 | 5.102 | 15.252 | 1.00 | 54.88 N |
| ANISOU | 2460 | N | ASP | B | 61 | 5241 8174 7438 -270 4618 -1040 | | | | C |
| ATOM | 2461 | CA | ASP | B | 61 | 89.145 | 5.885 | 15.700 | 1.00 | 56.50 C |
| ANISOU | 2461 | CA | ASP | B | 61 | 5360 8539 7230 -409 557 -1128 | | | | C |
| ATOM | 2462 | C | ASP | B | 61 | 88.677 | 7.352 | 14.969 | 1.00 | 5786 C |
| ANISOU | 2462 | C | ASP | B | 61 | 5635 8554 7793 -550 579 -1159 | | | | C |
| ATOM | 2463 | O | ASP | B | 61 | 89.378 | 8.137 | 15.011 | 1.00 | 63.39 O |
| ANISOU | 2463 | O | ASP | B | 61 | 5294 9842 8449 -741 741 -1236 | | | | O |
| ATOM | 2464 | CB | ASP | B | 61 | 90.005 | 3.010 | 14.787 | 1.00 | 69.44 C |
| ANISOU | 2464 | CB | ASP | B | 61 | 5578 3997 3011 -286 547 -1107 | | | | C |
| ATOM | 2465 | CG | ASP | B | 61 | 90.885 | 3.408 | 15.554 | 1.00 | 63.84 C |
| ANISOU | 2465 | CG | ASP | B | 61 | 5737 9459 8350 -124 408 -1105 | | | | C |
| ATOM | 2466 | OD1 | ASP | B | 61 | 90.512 | 3.850 | 16.801 | 1.00 | 63.50 O |
| ANISOU | 2466 | OD1 | ASP | B | 61 | 5938 9731 5459 -131 350 -1080 | | | | O |

TABLE 3-continued

| ATOM | 2467 | OD2 | ASP | B | 61 | 91.255 | 2.975 | 14.920 | 1.90 | 38.21 | O |
|---|---|---|---|---|---|---|---|---|---|---|---|
| ANISOU | 2467 | OD2 | ASP | B | 61 | 5176 | 9084 | 7878 | 19 | 429 | -1099 | O |
| ATOM | 2468 | N | MET | B | 62 | 87.500 | 7.146 | 14.328 | 1.00 | 58.23 | N |
| ANISOU | 2468 | N | MET | B | 62 | 5837 | 3694 | 7835 | -515 | 715 | -1007 | N |
| ATOM | 2469 | CA | MET | B | 62 | 85.951 | 8.358 | 13.738 | 1.00 | 54.05 | C |
| ANISOU | 2469 | CA | MET | B | 62 | 5443 | 7724 | 7373 | -541 | 833 | -1100 | C |
| ATOM | 2470 | C | MET | B | 62 | 86.341 | 9.383 | 14.7251 | 1.00 | 58.91 | C |
| ANISOU | 2470 | C | MET | B | 62 | 5167 | 8245 | 7989 | -761 | 373 | -1107 | C |
| ATOM | 2471 | O | MET | B | 62 | 85.848 | 13.457 | 14.339 | 1.00 | 57.96 | O |
| ANISOU | 2471 | O | MET | B | 62 | 5170 | 7990 | 1862 | -854 | 950 | -1101 | O |
| ATOM | 2472 | CB | MET | B | 62 | 85.303 | 5.015 | 12.657 | 1.00 | 55.82 | C |
| ANISOU | 2472 | CB | MET | B | 62 | 5772 | 7786 | 7651 | -583 | 846 | -1925 | C |
| ATOM | 2473 | CG | MET | B | 62 | 85.421 | 7.627 | 11.251 | 1.00 | 54.37 | C |
| ANISOU | 2473 | CG | MET | B | 62 | 5538 | 7551 | 7471 | -490 | 573 | -1037 | C |
| ATOM | 2474 | SD | MET | B | 62 | 67.785 | 8.740 | 13.704 | 3.00 | 7455 | S |
| ANISOU | 2474 | SD | MET | B | 62 | 8033 | 10344 | 9987 | -674 | 987 | -1123 | S |
| ATOM | 2475 | CE | MET | B | 62 | 86.925 | 10.2197 | 10.336 | 1.00 | 88.48 | C |
| ANISOU | 2475 | CE | MET | B | 62 | 7439 | 9364 | 9105 | -609 | 1115 | -1033 | C |
| ATOM | 2476 | N | GLY | B | 63 | 86.355 | 9.083 | 16.0213 | 1.00 | 32.13 | N |
| ANISOU | 2476 | N | GLY | B | 63 | 5271 | 7451 | 7073 | -755 | 800 | -1118 | N |
| ATOM | 2477 | CA | GLY | B | 63 | 85.745 | 9.974 | 17.010 | 1.30 | 54.53 | C |
| ANISOU | 2477 | CA | GLY | B | 63 | 5702 | 7677 | 7667 | -864 | 848 | -1134 | C |
| ATOM | 2478 | C | GLY | B | 63 | 84.388 | 9.570 | 17.598 | 1.00 | 54.73 | C |
| ANISOU | 2478 | C | GLY | B | 63 | 5832 | 7542 | 7421 | -755 | 318 | -1002 | C |
| ATOM | 2479 | O | GLY | B | 63 | 83.856 | 10.275 | 18.479 | 1.00 | 53.35 | O |
| ANISOU | 2479 | O | GLY | B | 63 | 5752 | 7293 | 7225 | -838 | 365 | -1069 | O |
| ATOM | 2480 | N | TYR | B | 64 | 33.845 | 8.423 | 17.178 | 1.00 | 50.03 | N |
| ANISOU | 2480 | N | TYR | B | 64 | 5234 | 5912 | 6884 | -584 | 747 | -974 | N |
| ATOM | 2481 | CA | TYR | B | 64 | 32.447 | 8.312 | 17.518 | 1.00 | 47.41 | C |
| ANISOU | 2481 | CA | TYR | B | 64 | 5008 | 5425 | 6602 | -487 | 733 | -893 | C |
| ATOM | 2482 | C | TYR | B | 64 | 82.418 | 7.017 | 18.6339 | 1.00 | 47.29 | C |
| ANISOU | 2482 | C | TYR | B | 64 | 4947 | 5463 | 6552 | -406 | 637 | -865 | C |
| ATOM | 2483 | O | TYR | B | 64 | 83.429 | 6.456 | 19.009 | 1.00 | 47.53 | O |
| ANISOU | 2483 | O | TYR | B | 64 | 4877 | 6575 | 6546 | -384 | 566 | -889 | O |
| ATOM | 2484 | CB | TYR | B | 64 | 61.681 | 7.511 | 16.256 | 1.00 | 43.31 | C |
| ANISOU | 2484 | CB | TYR | B | 64 | 4518 | 5790 | 6349 | -377 | 735 | -829 | C |
| ATOM | 2485 | CG | TYR | B | 64 | 81.583 | 3.535 | 15 230 | 1.00 | 46.41 | C |
| ANISOU | 2485 | CG | TYR | B | 64 | 4972 | 6109 | 6554 | -456 | 837 | -836 | C |
| ATOM | 2486 | CD1 | TYR | B | 64 | 80.655 | 9.663 | 15.403 | 1.00 | 46.12 | C |
| ANISOU | 2486 | CD1 | TYR | B | 64 | 5056 | 5928 | 6538 | -504 | 924 | -806 | C |

TABLE 3-continued

| | | | | | | | | | | |
|---|---|---|---|---|---|---|---|---|---|---|
| ATOM | 2487 | CD2 | TYR | B | 64 | 82.481 | 3.730 | 14.353 | 1.00 | 49.23 C |
| ANISOU | 2487 | CD2 | TYR | B | 64 | 5254 | 6533 | 6890 | -453 851 | -869 C |
| ATOM | 2488 | CE1 | TYR | B | 64 | 80.587 | 10.713 | 14.513 | 1.00 | 47.63 C |
| ANISOU | 2488 | CE1 | TYR | B | 64 | 5316 | 6343 | 6737 | -563 1026 | -706 C |
| ATOM | 2489 | CE2 | TYR | B | 64 | 82.415 | 9.797 | 13.265 | 1.00 | 46.64 C |
| ANISOU | 2489 | CE2 | TYR | B | 64 | 5011 | 6144 | 6567 | -559 964 | -863 C |
| ATOM | 2490 | CZ | TYR | B | 64 | 51.454 | 10.765 | 13.435 | 1.00 | 47.75 C |
| ANISOU | 2490 | CZ | TYR | B | 64 | 5281 | 6134 | 6731 | -592 1043 | -820 C |
| ATOM | 2491 | OH | TYR | B | 64 | 81.338 | 11.842 | 12.634 | 1.00 | 53.92 O |
| ANISOU | 2491 | OH | TYR | B | 64 | 6149 | 6825 | 7612 | -650 1154 | -794 O |
| ATOM | 2492 | N | LYS | B | 65 | 81.253 | 6.794 | 19.217 | 1.00 | 45.60 N |
| ANISOU | 2492 | N | LYS | B | 65 | 4952 | 6250 | 6492 | -358 538 | -809 N |
| ATOM | 2493 | CA | LYS | B | 65 | 81.173 | 5.876 | 20.341 | 1.00 | 47.73 C |
| ANISOU | 2493 | CA | LYS | B | 65 | 5077 | 6450 | 6593 | -287 550 | -772 C |
| ATOM | 2494 | C | LYS | B | 65 | 81.123 | 4.434 | 19.576 | 1.00 | 47.93 C |
| ANISOU | 2494 | C | LYS | B | 65 | 5064 | 5471 | 5576 | -127 487 | -709 C |
| ATOM | 2495 | O | LYS | B | 65 | 81.379 | 3.509 | 20.546 | 1.00 | 51.28 O |
| ANISOU | 2495 | O | LYS | B | 65 | 5456 | 6958 | 7069 | -46 417 | -671 O |
| ATOM | 2496 | CB | LYS | B | 65 | 79.924 | 6.167 | 21.131 | 1.00 | 53.02 C |
| ANISOU | 2496 | CB | LYS | B | 65 | 5869 | 6995 | 7282 | -303 505 | -736 C |
| ATOM | 2497 | CG | LYS | B | 65 | 50.224 | 5.784 | 22.532 | 1.30 | 55.55 C |
| ANISOU | 2497 | CG | LYS | B | 65 | 6213 | 7391 | 7537 | -411 515 | -735 C |
| ATOM | 2498 | CD | LYS | B | 65 | 80.195 | 8.238 | 22.458 | 1.00 | 61.44 C |
| ANISOU | 2498 | CD | LYS | B | 65 | 7020 | 8055 | 8239 | -564 730 | -811 C |
| ATOM | 2499 | CE | LYS | B | 65 | 79.898 | 8.358 | 23.844 | 1.00 | 51.35 C |
| ANISOU | 2499 | CE | LYS | B | 65 | 7085 | 3076 | 3150 | -663 772 | -902 C |
| ATOM | 2500 | NZ | LYS | B | 65 | 75.720 | 9.737 | 23.712 | 1.00 | 54.71 N |
| ANISOU | 2500 | NZ | LYS | B | 65 | 6374 | 7035 | 7373 | -634 899 | -892 N |
| ATOM | 2501 | N | GLY | B | 66 | 80.748 | 4.222 | 15.523 | 1.00 | 45.69 N |
| ANISOU | 2501 | N | GLY | B | 66 | 4792 | 5102 | 6464 | -31 510 | -597 N |
| ATOM | 2502 | CA | GLY | B | 66 | 80.475 | 2.853 | 18.153 | 1.00 | 40.00 C |
| ANISOU | 2502 | CA | GLY | B | 66 | 4067 | 5340 | 5802 | 55 462 | -650 C |
| ATOM | 2503 | C | GLY | B | 66 | 79.835 | 4.000 | 16.793 | 1.00 | 43.09 C |
| ANISOU | 2503 | C | GLY | B | 66 | 4422 | 5632 | 6251 | 57 503 | -651 C |
| ATOM | 2504 | O | GLY | B | 66 | 79.791 | 4.114 | 16.393 | 1.00 | 41.18 O |
| ANISOU | 2504 | O | GLY | B | 66 | 4257 | 5377 | 6003 | -28 553 | -577 O |
| ATOM | 2505 | N | TYR | B | 67 | 79.337 | 1 875 | 16.231 | 1.00 | 39.95 N |
| ANISOU | 2505 | N | TYR | B | 67 | 4311 | 5170 | 5910 | 152 476 | -522 N |
| ATOM | 2506 | CA | TYR | B | 67 | 78.821 | 1.6137 | 14.925 | 1.00 | 40.02 C |
| ANISOU | 2506 | CA | TYR | B | 67 | 4136 | 5116 | 5955 | 157 499 | -632 C |

TABLE 3-continued

| | | | | | |
|---|---|---|---|---|---|
| ATOM | 2507 | C TYR B 67 | 77.517 | 2.557 14.715 1.00 39.45 | C |
| ANISOU | 2507 | C TYR B 67 | 4135 4929 5908 103 541 -599 | | C |
| ATOM | 2508 | O TYR B 67 | 77.449 3.386 13.747 1.00 42.58 | | O |
| ANISOU | 2508 | O TYR B 67 | 4536 5345 6296 57 576 -607 | | O |
| ATOM | 2509 | CB TYR B 67 | 78.596 0.414 14.453 1.90 39.10 | | C |
| ANISOU | 2509 | CB TYR B 67 | 4024 4949 5882 2 52 487 -627 | | C |
| ATOM | 2510 | CG TYR B 67 | 77.992 0.334 19.065 1.00 35.81 | | C |
| ANISOU | 2510 | CG TYR B 67 | 3629 4499 5438 240 485 -647 | | C |
| ATOM | 2511 | CD1 TYR B 67 | 78.722 0.840 11.974 1.00 3468 | | C |
| ANISOU | 2511 | CD1 TYR B 67 | 3437 4408 5301 215 508 -591 | | C |
| ATOM | 2512 | CD2 TYR B 67 | 76.6159 -0.011 12.855 1.00 39.00 | | C |
| ANISOU | 2512 | CD2 TYR B 67 | 4086 4796 6934 239 481 -620 | | C |
| ATOM | 2513 | CE1 TYR B 67 | 78.155 0.853 10.690 1.30 35.59 | | C |
| ANISOU | 2513 | CE1 TYR B 67 | 3537 4513 5424 292 520 -705 | | C |
| ATOM | 2514 | CE2 TYR B 67 | 76.0133 0.019 11.573 1.09 35.90 | | C |
| ANISOU | 2514 | CE2 TYR B 67 | 3829 4024 5669 219 485 -639 | | C |
| ATOM | 2515 | CZ TYR B 67 | 76.876 0.426 10.476 1.00 35.72 | | C |
| ANISOU | 2515 | CZ TYR B 67 | 3660 4450 5479 205 502 -650 | | C |
| ATOM | 2516 | OH TYR B 67 | 79.335 0.492 9.200 1.08 61.81 | | O |
| ANISOU | 2516 | OH TYR B 67 | 3309 4599 5568 134 503 -694 | | O |
| ATOM | 2517 | N SER B 68 | 76.511 2.490 15.593 1.09 38.89 | | N |
| ANISOU | 2517 | N SER B 68 | 4112 4801 5864 110 541 -554 | | N |
| ATOM | 2518 | CA SER B 68 | 75.283 3.247 15.547 1.90 35.24 | | C |
| ANISOU | 2518 | CA SER B 68 | 3827 4385 5558 77 585 -517 | | C |
| ATOM | 2519 | C SER B 68 | 75.4351 4.164 15.511 1.00 34.10 | | C |
| ANISOU | 2519 | C SER B 68 | 3078 4121 5258 5 1552 -526 | | C |
| ATOM | 2520 | O SER B 68 | 74.839 5.465 14.743 1.00 35.95 | | O |
| ANISOU | 2520 | O SER B 68 | 3837 4312 5510 -2 590 -498 | | O |
| ATOM | 2521 | CB SER B 68 | 74.341 2.801 16.715 1.00 32.81 | | C |
| ANISOU | 2521 | CB SER B 68 | 3431 3834 5151 91 535 -476 | | C |
| ATOM | 2522 | OG SER B 68 | 73.948 1.443 15.442 1.00 36.41 | | O |
| ANISOU | 2522 | OG SER B 68 | 3831 4305 5647 147 543 -456 | | O |
| ATOM | 2523 | N ASP B 69 | 76.401 5.247 15.3137 1.09 39.63 | | N |
| ANISOU | 2523 | N ASP B 69 | 4273 4577 5909 -50 661 -563 | | N |
| ATOM | 2524 | CA ASP B 69 | 75.726 6.573 16.421 1.00 39.27 | | C |
| ANISOU | 2524 | CA ASP B 69 | 4261 4827 5823 -143 746 -589 | | C |
| ATOM | 2525 | C ASP B 69 | 77.335 7.159 15.091 1.00 43.08 | | C |
| ANISOU | 2525 | C ASP B 69 | 4723 5340 6304 -166 772 -607 | | C |
| ATOM | 2526 | O ASP B 69 | 76.854 8.146 14.483 1.00 97.99 | | O |
| ANISOU | 2526 | O ASP B 69 | 4105 4626 5672 -191 544 -573 | | O |

TABLE 3-continued

| | | | | | | | | | |
|---|---|---|---|---|---|---|---|---|---|
| ATOM | 2527 | CB | ASP B 69 | | 77.714 | 6.822 | 17.564 | 1.00 41.86 | C |
| ANISOU | 2527 | CB | ASP B 69 | | 4555 5243 6597 | -208 | 737 | -644 | C |
| ATOM | 2528 | CG | ASP B 69 | | 73.047 | 8.265 | 17.375 | 1.00 47.55 | C |
| ANISOU | 2528 | CB | ASP B 69 | | 5334 5950 6782 | -332 | 830 | -691 | C |
| ATOM | 2529 | OD1 | ASP B 69 | | 77.225 | 9.163 | 17.612 | 1.00 43.22 | O |
| ANISOU | 2529 | OD1 | ASP B 69 | | 4488 4904 5890 | -349 | 916 | -663 | O |
| ATOM | 2530 | OD2 | ASP B 69 | | 79.141 | 3.492 | 15.358 | 1.00 44.23 | O |
| ANISOU | 2530 | OD2 | ASP B 69 | | 4375 5646 6303 | -412 | 821 | -758 | O |
| ATOM | 2531 | N | PHE B 70 | | 78.398 | 5.469 | 14.647 | 1.00 31.87 | N |
| ANISOU | 2531 | N | PHE B 70 | | 3733 45132 5355 | -150 | 722 | -549 | N |
| ATOM | 2532 | CA | PHE B 70 | | 78.081 | 5.729 | 13.313 | 1.00 37.05 | C |
| ANISOU | 2532 | CA | PHE B 70 | | 3858 4722 5498 | -185 | 747 | -567 | C |
| ATOM | 2533 | C | PHE B 70 | | 77.905 | 6.732 | 12.185 | 1.09 35.51 | C |
| ANISOU | 2533 | C | PHE B 70 | | 3710 4452 5332 | -114 | 754 | -609 | C |
| ATOM | 2534 | O | PHE B 70 | | 71.894 | 7.651 | 11.351 | 1.00 39.73 | O |
| ANISOU | 2534 | O | PHE B 70 | | 4279 4962 5844 | -151 | 817 | -589 | O |
| ATOM | 2535 | CB | PHE B 70 | | 80.075 | 5.660 | 12.977 | 1.00 33.50 | C |
| ANISOU | 2535 | CB | PHE B 70 | | 3981 5059 5701 | -118 | 667 | -715 | C |
| ATOM | 2536 | CG | PHE B 70 | | 50.592 | 5.773 | 11.575 | 1.00 42.35 | C |
| ANISOU | 2536 | CG | PHE B 70 | | 4408 5553 6132 | -126 | 715 | -737 | C |
| ATOM | 2537 | CD1 | PHE B 70 | | 80.083 | 4.975 | 10.572 | 1.00 44.85 | C |
| ANISOU | 2537 | CD1 | PHE B 70 | | 4733 5845 6466 | -51 | 687 | -722 | C |
| ATOM | 2538 | CD2 | PHE B 70 | | 31.518 | 5.657 | 11.292 | 1.00 51.01 | C |
| ANISOU | 2588 | CD2 | PHE B 70 | | 5475 6722 7186 | -220 | 779 | -783 | C |
| ATOM | 2539 | CE1 | PHE B 70 | | 80.552 | 5.139 | 9.263 | 1.00 51.07 | C |
| ANISOU | 2539 | CE1 | PHE B 70 | | 5503 6480 7218 | -54 | 720 | -745 | C |
| ATOM | 2540 | CE2 | PHE B 70 | | 82.128 | 6.776 | 9.995 | 1.00 61.30 | C |
| ANISOU | 2540 | CE2 | PHE B 70 | | 6761 8070 8462 | -284 | 818 | -832 | C |
| ATOM | 2541 | CZ | PHE B 70 | | 81.580 | 5.999 | 8.954 | 1.00 55.55 | C |
| ANISOU | 2541 | CZ | PHE B 70 | | 6060 7330 7754 | -150 | 737 | -730 | C |
| ATOM | 2542 | N | ARG B 71 | | 77.045 | 5.704 | 12.129 | 1.00 34.14 | N |
| ANISOU | 2542 | N | ARG B 71 | | 3531 4245 5196 | -35 | 593 | -580 | N |
| ATOM | 2543 | CA | ARG B 71 | | 76.035 | 5.587 | 11.067 | 1.00 34.17 | C |
| ANISOU | 2543 | CA | ARG B 71 | | 3555 422 5214 | 6 | 582 | -534 | C |
| ATOM | 2544 | C | ARG B 71 | | 75.045 | 6.754 | 11.110 | 1.00 83.97 | C |
| ANISOU | 2544 | C | ARG B 71 | | 3590 4112 5235 | -5 | 740 | -434 | C |
| ATOM | 2545 | O | ARG B 71 | | 74.598 | 7.023 | 10.068 | 1.00 35.45 | O |
| ANISOU | 2545 | O | ARG B 71 | | 3799 4296 5376 | 10 | 760 | -416 | O |
| ATOM | 2546 | CB | ARG B 71 | | 75.222 | 4.271 | 11.206 | 1.00 32.54 | C |
| ANISOU | 2546 | CB | ARG B 71 | | 3711 4353 5430 | 67 | 613 | -529 | C |

TABLE 3-continued

| | | | | | |
|---|---|---|---|---|---|
| ATOM | 2547 CG ARG B 71 | 74.501 5.832 9.378 1.00 38.62 | | | C |
| ANISOU | 2547 CG ARG B 71 | 4093 4770 5810 91 582 −522 | | | C |
| ATOM | 2548 CD ARG B 71 | 73.902 2.037 10.071 1.00 37.33 | | | C |
| ANISOU | 2548 CD ARG B 71 | 3922 4581 5453 124 526 −538 | | | C |
| ATOM | 2549 NE ARG B 71 | 72.687 2.790 10.843 1.30 89.84 | | | N |
| ANISOU | 2549 NE ARG B 71 | 4250 4835 5354 124 534 −480 | | | N |
| ATOM | 2550 CZ ARG B 71 | 71.532 2.127 10.753 1.00 43.58 | | | C |
| ANISOU | 2550 CZ ARG B 71 | 4710 5285 6554 131 503 −466 | | | C |
| ATOM | 2551 NH1 ARG B 71 | 71.445 1.085 9.920 1.00 39.93 | | | N |
| ANISOU | 2551 NH1 ARG B 71 | 4231 4846 5093 128 441 −516 | | | N |
| ATOM | 2552 NH2 ARG B 71 | 70.448 2.523 11.475 1.30 38.37 | | | N |
| ANISOU | 2552 NH2 ARG B 71 | 4051 4582 5947 132 523 −410 | | | N |
| ATOM | 2553 N MET B 72 | 74.503 7.157 12.312 1.00 25.21 | | | N |
| ANISOU | 2553 N MET B 72 | 8784 4217 5895 −22 772 −432 | | | N |
| ATOM | 2554 CA MET B 72 | 73.824 8.851 12.527 1.00 37.45 | | | C |
| ANISOU | 2554 CA MET B 72 | 4123 4406 5609 −24 851 −390 | | | C |
| ATOM | 2555 C MET B 72 | 74.510 9.600 11.920 1.00 37.17 | | | C |
| ANISOU | 2555 C MET B 72 | 4143 4355 5625 −79 939 −387 | | | C |
| ATOM | 2556 O MET B 72 | 73.883 10.891 11.177 1.00 87.80 | | | O |
| ANISOU | 2556 O MET B 72 | 4267 4384 5710 −45 989 −312 | | | O |
| ATOM | 2557 CB MET B 72 | 73.608 8574 14.039 1.00 34.14 | | | C |
| ANISOU | 2557 CB MET B 72 | 3755 3922 5302 −52 888 −436 | | | C |
| ATOM | 2558 CG MET B 72 | 72.692 9.756 14.333 1.00 37.213 | | | C |
| ANISOU | 2558 CG MET B 72 | 4203 4219 5730 −43 987 −353 | | | C |
| ATOM | 2559 SD MET B 72 | 70.903 9.456 14.063 1.00 39.97 | | | S |
| ANISOU | 2559 SD MET B 72 | 4518 4526 6142 55 954 −254 | | | S |
| ATOM | 2560 CE MET B 72 | 70.608 10.439 12.573 1.00 41.53 | | | C |
| ANISOU | 2560 CE MET B 72 | 4749 4719 62130 117 1305 −170 | | | C |
| ATOM | 2561 N ALA B 73 | 75.798 9.775 12.205 1.00 37.23 | | | N |
| ANISOU | 2561 N ALA B 73 | 4147 4419 5613 −163 960 −452 | | | N |
| ATOM | 2562 CA ALA B 73 | 75.513 10.933 11.515 1.00 37.24 | | | C |
| ANISOU | 2562 CA ALA B 73 | 4192 4397 5560 −269 1057 −459 | | | C |
| ATOM | 2563 C ALA B 73 | 76.587 10.834 10.097 1.00 89.07 | | | C |
| ANISOU | 2563 C ALA B 73 | 4414 4671 5759 −202 1043 −429 | | | C |
| ATOM | 2564 O ALA B 73 | 16.437 11.864 9.399 1.00 41.64 | | | O |
| ANISOU | 2564 O ALA B 73 | 4615 4937 6070 −212 1128 −369 | | | O |
| ATOM | 2565 CB ALA B 73 | 77.905 11.0.99 12.247 1.00 33.57 | | | C |
| ANISOU | 2565 CB ALA B 73 | 4329 4638 5668 −354 1079 −570 | | | C |
| ATOM | 2566 N LEU B 74 | 76.759 9.505 9.601 1.30 37.40 | | | N |
| ANISOU | 2566 N LEU B 74 | 4123 4552 5535 −155 946 −455 | | | N |

TABLE 3-continued

| | | | | | |
|---|---|---|---|---|---|
| ATOM | 2567 | CA LEU B 74 | 76.394 9.381 3.188 | 1.00 39.66 | C |
| ANISOU | 2567 | CA LEU B 74 | 4397 4897 5775 -129 929 -438 | | C |
| ATOM | 2568 | C LEU B 74 | 75.555 9.793 7.552 | 1.00 39.33 | C |
| ANISOU | 2568 | C LEU B 74 | 4404 4802 5739 -57 929 -329 | | C |
| ATOM | 2569 | O LEU B 74 | 75.543 10.508 6.553 | 1.00 38.40 | O |
| ANISOU | 2569 | O LEU B 74 | 4333 4683 5574 -54 977 -270 | | C |
| ATOM | 2570 | CB LEU B 74 | 77.246 7.943 7.874 | 1.00 37.57 | C |
| ANISOU | 2570 | CB LEU B 74 | 4050 4723 5501 -91 836 -500 | | C |
| ATOM | 2571 | CG LEU B 74 | 77.169 7.6124 5.373 | 1.00 43.26 | C |
| ANISOU | 2571 | CG LEU B 74 | 4767 5505 6165 -63 316 -488 | | C |
| ATOM | 2572 | CD1 LEU B 74 | 78.235 3.417 5.573 | 1.00 45.21 | C |
| ANISOU | 2572 | CD1 LEU B 74 | 5034 5797 5347 -131 900 -802 | | C |
| ATOM | 2573 | CD2 LEU B 74 | 77.322 6.152 6.129 | 1.00 42.33 | C |
| ANISOU | 2573 | CD2 LEU B 74 | 4719 5581 5184 -21 725 -557 | | C |
| ATOM | 2574 | N ALA B 75 | 74.431 9.337 8.189 | 1.00 39.65 | N |
| ANISOU | 2574 | N ALA B 75 | 4429 4604 5384 4 380 -295 | | N |
| ATOM | 2575 | CA ALA B 75 | 73.125 9 773 7.585 | 1.00 39.16 | C |
| ANISOU | 2575 | CA ALA B 75 | 4384 4715 5779 81 374 -188 | | C |
| ATOM | 2576 | C ALA B 75 | 72.876 11.284 7.569 | 1.00 36.33 | C |
| ANISOU | 2576 | C ALA B 75 | 4371 4612 5580 92 988 -99 | | C |
| ATOM | 2577 | O ALA B 75 | 72.377 11.318 6.593 | 1.00 39.47 | C |
| ANISOU | 2577 | O ALA B 75 | 4544 4154 5789 148 1002 -3 | | C |
| ATOM | 2578 | CB ALA B 75 | 72.013 9.039 8.342 | 1.00 37.01 | C |
| ANISOU | 2578 | CB ALA B 75 | 4053 4428 5672 130 811 -180 | | C |
| ATOM | 2579 | N VAL B 76 | 73.245 11.981 8.639 | 1.00 37.71 | N |
| ANISOU | 2579 | N VAL B 76 | 4347 4340 5640 36 1076 -130 | | N |
| ATOM | 2580 | CA VAL B 76 | 72.988 13.425 8.742 | 1.00 41.28 | C |
| ANISOU | 2580 | CA VAL B 76 | 4908 4665 6112 42 1210 -56 | | C |
| ATOM | 2581 | C VAL B 76 | 73.873 14.073 7.576 | 1.00 46.17 | C |
| ANISOU | 2581 | C VAL B 76 | 5584 5276 6602 -8 1273 -39 | | C |
| ATOM | 2582 | O VAL B 76 | 73.443 14.951 6.904 | 1.00 44.98 | C |
| ANISOU | 2582 | O VAL B 76 | 5509 5088 6494 48 1341 75 | | C |
| ATOM | 2583 | CB VAL B 76 | 73.815 14.001 10.155 | 1.00 41.00 | C |
| ANISOU | 2583 | CB VAL B 76 | 4929 4530 6120 -38 1300 -125 | | C |
| ATOM | 2584 | CG1 VAL B 76 | 73.304 15.529 10.139 | 1.00 45.64 | C |
| ANISOU | 2584 | CG1 VAL B 76 | 5652 4967 6721 -58 1465 -71 | | C |
| ATOM | 2585 | CG VAL B 76 | 2 72.264 10.522 11.176 | 1.00 43.25 | C |
| ANISOU | 2585 | CG2 VAL B 76 | 5175 4788 6469 23 1252 -119 | | C |
| ATOM | 2586 | N ASP B 77 | 75.122 13.530 7.635 | 1.00 45.58 | N |
| ANISOU | 2586 | N ASP B 77 | 5593 5426 6673 -109 1257 -145 | | N |

TABLE 3-continued

| | | | | |
|---|---|---|---|---|
| ATOM | 2587 | CA ASP B 77 | 75.055 14.101 5.599 1.00 52.16 | C |
| ANISOU | 2587 | CA ASP B 77 | 6242 5166 7310 -172 1317 -143 | C |
| ATOM | 2588 | C ASP B 77 | 75.517 13.957 5.161 1.00 49.49 | C |
| ANISOU | 2588 | C ASP B 77 | 6006 5889 5908 -82 1274 -42 | C |
| ATOM | 2589 | O ASP B 77 | 75.467 14.941 4.444 1.00 52.20 | C |
| ANISOU | 2589 | O ASP B 77 | 5571 6301 7042 -72 1355 52 | C |
| ATOM | 2590 | CB ASP B 77 | 77.358 13.393 6.769 1.00 54.12 | C |
| ANISOU | 2590 | CB ASP B 77 | 5508 5525 7529 -270 1283 -275 | C |
| ATOM | 2591 | CG ASP B 77 | 78.501 14.299 6.641 1.00 65.00 | C |
| ANISOU | 2591 | CG ASP B 77 | 7939 7888 8871 -397 1404 -315 | C |
| ATOM | 2592 | OD1 ASP B 77 | 79.104 14.759 7.531 1.00 68.56 | O |
| ANISOU | 2592 | OD1 ASP B 77 | 8401 8302 9345 -504 1467 -392 | O |
| ATOM | 2593 | OD2 ASP B 77 | 78.745 14.559 5.356 1.00 63.95 | O |
| ANISOU | 2593 | OD2 ASP B 77 | 7839 7782 8677 -398 1442 -266 | O |
| ATOM | 2594 | N LEU B 78 | 75.038 12.755 4.740 1.01 48.18 | N |
| ANISOU | 2594 | N LEU B 78 | 5745 5808 5723 -21 1139 -59 | N |
| ATOM | 2595 | CA LEU B 78 | 74.517 12.610 3.396 1.00 46.92 | C |
| ANISOU | 2595 | CA LEU B 78 | 5584 5758 6487 53 1059 28 | C |
| ATOM | 2596 | C LEU B 78 | 78.177 13.346 3139 1.00 49.87 | C |
| ANISOU | 2596 | C LEU B 78 | 6000 6077 6570 170 1098 165 | C |
| ATOM | 2597 | O LEU B 78 | 72.354 13.358 2.308 1.00 52.20 | O |
| ANISOU | 2597 | O LEU B 78 | 6324 5425 7034 226 1091 280 | O |
| ATOM | 2598 | CB LEU B 78 | 74.358 11.132 3.040 1.00 47.82 | C |
| ANISOU | 2598 | CB LEU B 78 | 5592 6002 5577 72 952 -47 | C |
| ATOM | 2599 | CG LEU B 78 | 75.644 10.305 2.996 1.00 49.92 | C |
| ANISOU | 2599 | CG LEU B 78 | 5810 6345 6813 -6 936 -181 | C |
| ATOM | 2600 | CD1 LEU B 78 | 75.260 8.852 3.111 1.00 45.43 | C |
| ANISOU | 2600 | CD1 LEU B 78 | 5275 5950 6399 25 822 -258 | C |
| ATOM | 2601 | CD2 LEU B 78 | 76.244 10.500 1.515 1.00 51.59 | C |
| ANISOU | 2601 | CD2 LEU B 78 | 6039 5675 5950 -31 973 -157 | C |
| ATOM | 2602 | N SER B 79 | 72.381 13.612 4.105 1.00 48.45 | C |
| ANISOU | 2602 | N SER B 79 | 5834 5858 6847 218 1114 214 | N |
| ATOM | 2603 | CA SER B 79 | 71.127 14.333 3.920 1.00 53.19 | N |
| ANISOU | 2603 | CA SER B 79 | 6445 3361 7401 847 1132 869 | C |
| ATOM | 2604 | C SER B 79 | 71.412 15.813 3.723 1.06 60.06 | C |
| ANISOU | 2604 | C SER B 79 | 7500 7128 3301 356 1292 458 | C |
| ATOM | 2605 | O SER B 79 | 73.589 15.501 3.165 1.00 71.15 | O |
| ANISOU | 2605 | O SER B 79 | 8906 8476 9654 470 1315 522 | O |
| ATOM | 2606 | CB SER B 79 | 73.125 14.685 5.054 1.00 52.09 | C |
| ANISOU | 2606 | CB SER B 79 | 7139 1061 8251 402 3105 355 | C |

TABLE 3-continued

| | | | | | | | | | | |
|---|---|---|---|---|---|---|---|---|---|---|
| ATOM | 2607 | OG | SER | B | 79 | 70.478 | 14.809 | 6.236 | 1 00 | 59.27 O |
| ANISOU | 2607 | OG | SER | B | 79 | 7330 7018 8439 351 1227 324 | | | | O |
| ATOM | 2608 | N | GLN | B | 80 | 72.509 | 16.270 | 4.092 | 1.00 | 62.40 N |
| ANISOU | 2608 | N | GLN | B | 80 | 7841 7311 8555 225 1400 383 | | | | N |
| ATOM | 2609 | CA | GLN | B | 80 | 73.029 | 17.578 | 3.830 | 1.03 | 69.76 C |
| ANISOU | 2609 | CA | GLN | B | 80 | 8925 5093 9485 200 1574 461 | | | | C |
| ATOM | 2610 | C | GLN | B | 80 | 73.595 | 17.957 | 2.484 | 1.30 | 65.08 C |
| ANISOU | 2610 | C | GLN | B | 80 | 8510 7605 8906 171 1506 510 | | | | C |
| ATOM | 2611 | O | GLN | B | 80 | 73.776 | 17.093 | 1.605 | 1.00 | 72.54 O |
| ANISOU | 2611 | O | GLN | B | 80 | 9301 8721 9690 184 1489 504 | | | | O |
| ATOM | 2612 | CB | GLN | B | 80 | 73.902 | 18.199 | 4.978 | 1.00 | 74.50 C |
| ANISOU | 2612 | CB | GLN | B | 80 | 9504 0581 10160 55 1595 338 | | | | C |
| ATOM | 2613 | CG | GLN | B | 80 | 73.088 | 18.504 | 5.222 | 1.60 | 81.05 C |
| ANISOU | 2613 | CG | GLN | B | 80 | 10515 9353 11157 103 1734 336 | | | | C |
| ATOM | 2614 | CD | GLN | B | 80 | 73.942 | 18.829 | 7 423 | 1.00 | 92.72 C |
| ANISOU | 2614 | CD | GLN | B | 80 | 11961 10670 12599 −65 1625 190 | | | | C |
| ATOM | 2615 | OE1 | GLN | B | 80 | 73.739 | 19.858 | 8.078 | 1.00 | 104.45 O |
| ANISOU | 2615 | OE1 | GLN | B | 80 | 13566 11981 14143 −72 1973 204 | | | | O |
| ATOM | 2616 | NE2 | GLN | B | 80 | 74.907 | 17.904 | 7.720 | 1.00 | 86.87 N |
| ANISOU | 2616 | NE2 | GLN | B | 80 | 11503 10437 12206 −174 1743 48 | | | | N |
| ATOM | 2617 | N | ASP | B | 92 | 52.904 | 10.863 | −5.324 | 1.00 | 52.01 N |
| ANISOU | 2617 | N | ASP | B | 92 | 7323 6789 5651 912 1422 1097 | | | | N |
| ATOM | 2618 | CA | ASP | B | 92 | 51.921 | 14.227 | −5.313 | 1.00 | 63.42 C |
| ANISOU | 2618 | CA | ASP | B | 92 | 5763 9171 7102 925 1250 1007 | | | | C |
| ATOM | 2619 | C | ASP | B | 92 | 51.962 | 13.397 | −3980 | 1.00 | 66.46 C |
| ANISOU | 2619 | C | ASP | B | 92 | 9070 8517 7658 867 1283 980 | | | | C |
| ATOM | 2620 | O | ASP | B | 92 | 10.952 | 12.176 | −4.021 | 1.00 | 67.52 O |
| ANISOU | 2620 | O | ASP | B | 92 | 9153 8721 7767 860 1225 869 | | | | O |
| ATOM | 2621 | CB | ASP | B | 92 | 56.502 | 14.096 | −5.875 | 1.00 | 56.86 C |
| ANISOU | 2621 | CB | ASP | B | 92 | 8457 7926 6723 1014 1267 1120 | | | | C |
| ATOM | 2622 | CG | ASP | B | 92 | 49.439 | 14.423 | −4.813 | 1.00 | 65.27 C |
| ANISOU | 2622 | CG | ASP | B | 92 | 9013 8435 7355 1030 1193 1115 | | | | C |
| ATOM | 2623 | OD1 | ASP | B | 92 | 49.313 | 15.525 | −4.511 | 1.33 | 64.95 O |
| ANISOU | 2623 | OD1 | ASP | B | 92 | 90085 8308 7361 1043 1243 1198 | | | | O |
| ATOM | 2624 | OD2 | ASP | B | 92 | 48.760 | 13.540 | −4.237 | 1.00 | 67.56 O |
| ANISOU | 2624 | OD2 | ASP | B | 92 | 9249 8763 7657 1023 1099 1029 | | | | O |
| ATOM | 2625 | N | ILE | B | 93 | 51.918 | 14.067 | −2.819 | 1.05 | 61.50 N |
| ANISOU | 2625 | N | ILE | B | 93 | 8440 7782 7145 833 1282 987 | | | | N |
| ATOM | 2626 | CA | ILE | B | 93 | 52.083 | 13.395 | −3.521 | 3.00 | 61.50 C |
| ANISOU | 2626 | CA | ILE | B | 93 | 8375 7741 7249 775 1227 869 | | | | C |

TABLE 3-continued

| | | | | | | | | | | |
|---|---|---|---|---|---|---|---|---|---|---|
| ATOM | 2627 | C | ILE | B | 93 | 51.237 | 32.156 | -1.289 | 1.00 | 53.64 C |
| ANISOU | 2627 | C | ILE | B | 93 | 7339 6821 6220 794 1119 903 | | | | C |
| ATOM | 2628 | O | ILE | B | 93 | 51.306 | 11.143 | -0.923 | 1 00 | 51.92 O |
| ANISOU | 2628 | O | ILE | B | 93 | 7072 5517 5938 749 1097 717 | | | | O |
| ATM | 2629 | CB | ILE | B | 93 | 51.909 | 14.325 | -0.310 | 1.00 | 61.68 C |
| ANISOU | 2629 | CB | ILE | B | 93 | 8403 7853 7383 748 1229 908 | | | | C |
| ATOM | 2630 | CG1 | ILE | B | 93 | 53.013 | 15.374 | -0.306 | 1.00 | 65.63 C |
| ANISOU | 2630 | CG1 | ILE | B | 93 | 9056 8185 8075 700 1336 965 | | | | C |
| ATOM | 2631 | CG2 | ILE | B | 93 | 52.014 | 13.520 | 0.931 | 1.00 | 65.25 C |
| ANISOU | 2631 | CG2 | ILE | B | 93 | 8915 3206 8050 594 1167 816 | | | | C |
| ATOM | 2632 | CD1 | ILE | B | 93 | 53.510 | 15.718 | 1.083 | 1.00 | 7067 C |
| ANISOU | 2632 | CD1 | ILE | B | 93 | 9535 8894 8723 529 1339 922 | | | | C |
| ATOM | 2633 | N | CYS | B | 94 | 49.921 | 12.204 | -1.473 | 1.00 | 53.55 N |
| ANISOU | 2633 | N | CYS | B | 94 | 7344 6357 5145 857 1053 625 | | | | N |
| ATOM | 2634 | CA | CYS | B | 94 | 49.125 | 11.004 | -1.210 | 1.00 | 53.34 C |
| ANISOU | 2634 | CA | CYS | B | 94 | 7272 5399 6096 864 951 741 | | | | C |
| ATOM | 2635 | C | CYS | B | 94 | 49.850 | 9.355 | -2.031 | 1.00 | 54.96 C |
| ANISOU | 2635 | C | CYS | B | 94 | 7463 7190 6230 861 941 880 | | | | C |
| ATOM | 2636 | O | CYS | B | 94 | 49.525 | 8.897 | -1.615 | 1.00 | 47.33 O |
| ANISOU | 2636 | O | CYS | B | 94 | 6448 5243 5294 625 385 586 | | | | O |
| ATOM | 2637 | CB | CYS | B | 94 | 47.654 | 11.231 | -1.402 | 1.05 | 57.31 C |
| ANISOU | 2637 | CB | CYS | B | 94 | 7788 7452 6535 933 888 775 | | | | C |
| ATOM | 2638 | SG | CYS | B | 94 | 47.143 | 12.712 | -0.525 | 1.00 | 79.30 S |
| ANISOU | 2638 | SG | CYS | B | 94 | 10612 10146 91407 953 905 853 | | | | S |
| ATOM | 2639 | N | ASP | B | 95 | 40.317 | 10.173 | -3.349 | 1.00 | 50.78 N |
| ANISOU | 2639 | N | ASP | B | 95 | 5977 5714 5503 901 995 735 | | | | N |
| ATOM | 2640 | CA | ASP | B | 95 | 50.105 | 9.116 | -4.314 | 1.00 | 53.25 C |
| ANISOU | 2640 | CA | ASP | B | 95 | 7283 7123 5828 913 984 677 | | | | C |
| ATOM | 2641 | C | ASP | B | 95 | 51.492 | 8.530 | -4.125 | 1.00 | 49.40 C |
| ANISOU | 2641 | C | ASP | B | 95 | 5762 5604 5402 850 1038 616 | | | | C |
| ATOM | 2642 | O | ASP | B | 95 | 51.577 | 7.325 | -4.286 | 1.00 | 59.14 O |
| ANISOU | 2642 | O | ASP | B | 95 | 6824 8745 5481 338 998 523 | | | | O |
| ATOM | 2643 | CB | ASP | B | 95 | 49.931 | 9.616 | -5.742 | 1.00 | 62.50 C |
| ANISOU | 2643 | CB | ASP | B | 95 | 8512 8372 8863 976 1025 753 | | | | C |
| ATOM | 2644 | CG | ASP | B | 95 | 43.597 | 10.315 | -5.055 | 1.09 | 64.88 C |
| ANISOU | 2644 | CG | ASP | B | 95 | 8804 8651 7002 1045 976 827 | | | | C |
| ATOM | 2645 | OD1 | ASP | B | 95 | 48.676 | 13.493 | -5.359 | 1.00 | 72.78 O |
| ANISOU | 2645 | OD1 | ASP | B | 95 | 2599 9674 3081 1077 1041 936 | | | | O |
| ATOM | 2646 | OD2 | ASP | B | 95 | 47.508 | 9.705 | -5.736 | 1.00 | 81.14 O |
| ANISOU | 2646 | OD2 | ASP | B | 95 | 8344 8278 6609 1067 876 779 | | | | O |

TABLE 3-continued

| | | | | | | |
|---|---|---|---|---|---|---|
| ATOM | 2647 | N VAL B 96 | 52.452 | 9.295 | -3.821 | 1.00 45.09 N |
| ANISOU | 2647 | N VAL B 96 | 5224 5982 4928 | 813 | 1127 | 565 N |
| ATOM | 2648 | CA VAL B 96 | 53.362 | 8.947 | -3 576 | 1.00 46.20 C |
| ANISOU | 2648 | CA VAL B 96 | 6324 6953 5188 | 753 | 1163 | 512 C |
| ATOM | 2649 | C VAL B 96 | 53.911 | 8.089 | -2.294 | 1.00 41.20 C |
| ANISOU | 2649 | C VAL B 96 | 5630 5413 4611 | 704 | 1113 | 513 C |
| ATOM | 2650 | O VAL B 96 | 54.547 | 7.011 | -2.212 | 1.09 45.00 O |
| ANISOU | 2650 | O VAL B 96 | 5195 5040 5242 | 580 | 1098 | 433 O |
| ATOM | 2651 | CB VAL B 96 | 54.832 | 10.153 | -3.521 | 1.50 47.15 C |
| ANISOU | 2651 | CB VAL B 96 | 6463 6136 8315 | 718 | 1293 | 622 C |
| ATOM | 2652 | CG1 VAL B 96 | 55.208 | 9.764 | -3.925 | 1.50 47.30 C |
| ANISOU | 2652 | CG1 VAL B 96 | 5426 5119 5427 | 650 | 1340 | 634 C |
| ATOM | 2653 | CG2 VAL B 96 | 54.998 | 10.798 | -4.932 | 1.00 45.91 C |
| ANISOU | 2653 | CG2 VAL B 96 | 5744 6417 5424 | 761 | 1379 | 780 C |
| ATOM | 2654 | N SER B 97 | 63.182 | 6.535 | -1.296 | 1.30 37.85 N |
| ANISOU | 2654 | N SER B 97 | 5140 4869 4184 | 696 | 1066 | 534 N |
| ATOM | 2655 | CA SER B 97 | 53.139 | 7.755 | -0.002 | 1.30 93.28 C |
| ANISOU | 2655 | CA SER B 97 | 6202 4945 4396 | 550 | 996 | 453 C |
| ATOM | 2656 | C SER B 97 | 52.545 | 6.379 | -0.251 | 1.00 37.87 C |
| ANISOU | 2656 | C SER B 97 | 5130 4965 4292 | 670 | 913 | 374 C |
| ATOM | 2657 | O SER B 97 | 53.038 | 5.344 | 0.205 | 1.00 37.45 O |
| ANISOU | 2657 | O SER B 97 | 5099 4910 4296 | 535 | 882 | 293 O |
| ATOM | 2658 | CB SER B 97 | 52.225 | 8.467 | 0.952 | 1.00 35.18 C |
| ANISOU | 2658 | CB SER B 97 | 4316 4499 4050 | 651 | 967 | 437 C |
| ATOM | 2659 | OG SER B 97 | 52.714 | 5.769 | 1.204 | 1.00 46.10 O |
| ANISOU | 2659 | OG SER B 97 | 6225 5807 5483 | 634 | 1092 | 557 O |
| ATOM | 2660 | N ALA B 98 | 61.474 | 6.365 | -1.033 | 1.00 39.57 N |
| ANISOU | 2660 | N ALA B 98 | 5389 5265 4417 | 726 | 574 | 997 N |
| ATOM | 2661 | CA ALA B 98 | 50.787 | 5.199 | -1.370 | 1.00 41.74 C |
| ANISOU | 2661 | CA ALA B 98 | 5534 6596 4629 | 741 | 769 | 320 C |
| ATOM | 2662 | C ALA B 98 | 51.619 | 4.207 | -2.237 | 1.00 41.21 C |
| ANISOU | 2662 | C ALA B 98 | 5562 5578 4517 | 743 | 814 | 261 C |
| ATOM | 2663 | O ALA B 98 | 51.610 | 2.992 | -2.016 | 1.00 41.37 O |
| ANISOU | 2663 | O ALA B 98 | 5552 7609 4.557 | 725 | 757 | 171 O |
| ATOM | 2664 | CB ALA B 98 | 43.421 | 5.319 | -2.008 | 1.00 43.48 C |
| ANISOU | 2664 | CB ALA B 98 | 5861 5888 4750 | 799 | 706 | 355 C |
| ATOM | 2665 | N GLN B 99 | 52.316 | 4.778 | -3.232 | 1.00 44.06 N |
| ANISOU | 2665 | N GLN B 99 | 5956 5968 4817 | 765 | 900 | 307 N |
| ATOM | 2666 | CA GLN B 99 | 53.086 | 1.973 | -4.231 | 1.00 40.06 C |
| ANISOU | 2666 | CA GLN B 99 | 5448 5522 4254 | 777 | 939 | 251 C |

TABLE 3-continued

| ATOM | 2667 | C | GLN | B | 99 | 54.354 3.326 -3.491 1.33 42.57 | C |
| --- | --- | --- | --- | --- | --- | --- | --- |
| ANISOU | 2667 | C | GLN | B | 99 | 5715 5782 4677 725 958 184 | C |
| ATOM | 2668 | O | GLN | B | 99 | 64.647 2.166 -3.666 1.00 40.05 | O |
| ANISOU | 2668 | O | GLN | B | 99 | 5376 5491 4351 724 931 | O |
| ATOM | 2669 | CB | GLN | B | 99 | 53.573 4844 -5.398 1.00 44.39 | C |
| ANISOU | 2669 | CB | GLN | B | 99 | 6039 6113 4703 312 1031 329 | C |
| ATOM | 2670 | CG | GLN | B | 99 | 54.311 4.033 -6.445 1.00 45.63 | C |
| ANISOU | 2670 | CG | GLN | B | 99 | 6200 6349 4790 830 1068 269 | C |
| ATOM | 2671 | CD | GLN | B | 99 | 53.465 2.920 -7.023 1.93 51.40 | C |
| ANISOU | 2671 | CD | GLN | B | 99 | 6936 7159 5434 855 880 189 | C |
| ATOM | 2672 | OE1 | GLN | B | 99 | 52.420 3.192 -7.645 1.00 50.23 | O |
| ANISOU | 2672 | OE1 | GLN | B | 99 | 6824 7075 5185 910 939 225 | O |
| ATOM | 2673 | NE2 | GLN | B | 99 | 53.937 1.675 -6.889 1.00 52.16 | N |
| ANISOU | 2673 | NE2 | GLN | B | 99 | 6998 7256 5566 847 951 78 | N |
| ATOM | 2674 | N | SER | B | 100 | 54.937 4.112 -2.544 1.50 42.03 | N |
| ANISOU | 2674 | N | SER | B | 100 | 5630 5636 4706 684 1006 227 | N |
| ATOM | 2675 | CA | SER | B | 100 | 56.010 3.624 -1.369 1.00 45.37 | C |
| ANISOU | 2675 | CA | SER | B | 100 | 6063 6067 5297 635 1021 173 | C |
| ATOM | 2576 | C | SER | B | 100 | 56.560 2.412 -0.994 1.00 42.44 | C |
| ANISOU | 2676 | C | SER | B | 100 | 5594 5513 4919 619 919 66 | C |
| ATOM | 2677 | O | SER | B | 100 | 55.299 1.435 -0.871 1.00 39 10 | O |
| ANISOU | 2677 | O | SER | B | 100 | 5135 5135 4535 605 912 12 | O |
| ATOM | 2678 | CB | SER | B | 100 | 56.502 4.513 -1.097 1.00 51.13 | C |
| ANISOU | 2678 | CB | SER | B | 100 | 6721 6655 6051 594 1081 239 | C |
| ATOM | 2679 | OG | SER | B | 100 | 57.730 4.446 -0.406 1.00 60.02 | O |
| ANISOU | 2679 | OG | SER | B | 100 | 7792 7736 7275 543 1102 192 | O |
| ATOM | 2680 | N | ALA | B | 101 | 54.332 2.418 -0.474 1.00 43.43 | N |
| ANISOU | 2680 | N | ALA | B | 101 | 5725 5732 5041 629 841 95 | N |
| ATOM | 2681 | CA | ALA | B | 101 | 53.854 1.255 0.310 1.00 33.76 | C |
| ANISOU | 2681 | CA | ALA | B | 101 | 5106 5121 4501 6011 747 22 | C |
| ATOM | 2682 | C | ALA | B | 101 | 53.426 0.071 -0.530 1.00 38.90 | C |
| ANISOU | 2682 | C | ALA | B | 101 | 5133 5206 4442 631 896 -52 | C |
| ATOM | 2683 | O | ALA | B | 101 | 53.647 -1.090 -0.201 1.00 40.06 | O |
| ANISOU | 2683 | O | ALA | B | 101 | 5253 5336 4832 615 651 -131 | O |
| ATOM | 2684 | CB | ALA | B | 101 | 52.720 1.757 1.250 1.00 37.53 | C |
| ANISOU | 2684 | CB | ALA | B | 101 | 4952 4938 4370 590 689 59 | C |
| ATOM | 2685 | N | VAL | B | 102 | 52.853 0.352 -1.686 1.00 39.34 | N |
| ANISOU | 2685 | N | VAL | B | 102 | 5228 5337 4382 577 705 -28 | N |
| ATOM | 2686 | CA | VAL | B | 102 | 52.557 -0.702 -2.620 1.00 38.72 | C |
| ANISOU | 2686 | CA | VAL | B | 102 | 5161 5327 4224 705 666 -102 | C |

TABLE 3-continued

| | | | | | | | | | |
|---|---|---|---|---|---|---|---|---|---|
| ATOM | 2687 | C | VAL B 102 | | 53.860 | -1.405 | -3.032 | 1.00 42.14 | C |
| ANISOU | 2687 | C | VAL B 102 | 5579 | 5759 | 4674 | 705 | 718 -186 | C |
| ATOM | 2688 | O | VAL B 102 | | 53.923 | -2.644 | -3.057 | 1.00 42.72 | O |
| ANISOU | 2688 | O | VAL B 102 | 5638 | 5832 | 4751 | 702 | 670 -258 | O |
| ATOM | 2689 | CB | VAL B 102 | | 51.851 | -0.088 | -3.888 | 1.00 39.55 | C |
| ANISOU | 2689 | CB | VAL B 102 | 5314 | 5522 | 4195 | 753 | 078 -53 | C |
| ATOM | 2690 | CG1 | VAL B 102 | | 51.922 | -1.051 | -3.036 | 1.00 33.32 | C |
| ANISOU | 2690 | CG1 | VAL B 102 | 5174 | 5445 | 3941 | 791 | 667 -131 | C |
| ATOM | 2691 | CG2 | VAL B 102 | | 50.398 | 0.283 | -3.451 | 1.00 41.49 | C |
| ANISOU | 2691 | CG2 | VAL B 102 | 6582 | 5778 | 4422 | 764 | 607 -14 | C |
| ATOM | 2692 | N | ASP B 103 | | 54.910 | -0.532 | -0.320 | 1.00 38.49 | N |
| ANISOU | 2692 | N | ASP B 103 | 3117 | 3292 | 4216 | 707 | 817 -119 | N |
| ATOM | 2693 | CA | ASP B 103 | | 56.203 | -1.218 | -3.717 | 1.00 44.15 | C |
| ANISOU | 2693 | CA | ASP B 103 | 5811 | 5015 | 4949 | 711 | 877 -175 | C |
| ATOM | 2694 | C | ASP B 103 | | 55.791 | -2.140 | -2.674 | 1.00 41.55 | C |
| ANISOU | 2694 | C | ASP B 103 | 5431 | 5614 | 4741 | 675 | 839 -245 | C |
| ATOM | 2695 | O | ASP B 103 | | 37.268 | -3.265 | -2.985 | 1.00 38.72 | O |
| ANISOU | 2695 | O | ASP B 103 | 6058 | 5255 | 4386 | 591 | 828 -334 | O |
| ATOM | 2696 | CB | ASP B 103 | | 57.204 | -0.109 | -4.032 | 1.00 44.63 | C |
| ANISOU | 2696 | CB | ASP B 103 | 5874 | 6079 | 5006 | 708 | 993 -101 | C |
| ATOM | 2697 | CG | ASP B 103 | | 56.825 | 0.607 | -5.384 | 1.00 49.17 | C |
| ANISOU | 2697 | CG | ASP B 103 | 6504 | 6737 | 5443 | 753 | 1042 -40 | C |
| ATOM | 2698 | OD1 | ASP B 103 | | 54.555 | 0.104 | -5.147 | 1.00 45 36 | O |
| ANISOU | 2698 | OD1 | ASP B 103 | 6053 | 6323 | 4850 | 792 | 991 -72 | O |
| ATOM | 2699 | OD2 | ASP B 103 | | 57.364 | 1.677 | -5.661 | 1.00 51.38 | O |
| ANISOU | 2699 | OD2 | ASP B 103 | 5795 | 7015 | 5713 | 749 | 1132 42 | O |
| ATOM | 2700 | N | SER B 104 | | 55.752 | -1.691 | -1.428 | 1.00 40.53 | N |
| ANISOU | 2700 | N | SER B 104 | 5315 | 5451 | 4747 | 634 | 326 -267 | N |
| ATOM | 2701 | CA | SER B 104 | | 57.258 | -2.487 | -0.316 | 1.00 42.41 | C |
| ANISOU | 2701 | CA | SER B 104 | 5468 | 5583 | 5062 | 600 | 779 -253 | C |
| ATOM | 2702 | C | SER B 104 | | 56.428 | -3.733 | -0.103 | 1.00 44.05 | C |
| ANISOU | 2702 | C | SER B 104 | 5081 | 5785 | 5272 | 502 | 579 -331 | C |
| ATOM | 2703 | O | SER B 104 | | 57.000 | -4.755 | 0.223 | 1.00 42.74 | O |
| ANISOU | 2703 | O | SER B 104 | 6488 | 5586 | 5167 | 598 | 655 -398 | O |
| ATOM | 2704 | CB | SER B 104 | | 57.271 | -1.718 | 1.002 | 1.00 47.10 | C |
| ANISOU | 2704 | CB | SER B 104 | 6039 | 6108 | 5749 | 554 | 771 -204 | C |
| ATOM | 2705 | OG | SER B 104 | | 57.993 | -3.514 | 3.329 | 1.00 54.00 | O |
| ANISOU | 2705 | OG | SER B 104 | 5912 | 6979 | 6527 | 545 | 362 -137 | O |
| ATOM | 2706 | N | LEU B 105 | | 55.094 | -3.040 | -0.196 | 1.00 35.7 | N |
| ANISOU | 2706 | N | LEU B 105 | 5150 | 5260 | 4567 | 535 | 513 -313 | N |

TABLE 3-continued

| | | | | | | | | | | |
|---|---|---|---|---|---|---|---|---|---|---|
| ATOM | 2707 | CA | LEU | B | 105 | 54.294 | -4.368 | -0.161 | 1.30 | 27.08 C |
| ANISOU | 2707 | CA | LEU | B | 105 | 4907 5005 4405 504 527 -385 | | | | C |
| ATOM | 2708 | C | LEU | B | 105 | 54.085 | -5.850 | -1.248 | 1.00 | 40.18 C |
| ANISOU | 2708 | C | LEU | B | 105 | 5238 5363 4667 539 533 -472 | | | | C |
| ATOM | 2709 | O | LEU | B | 105 | 54.843 | -7.653 | -1.026 | 1.00 | 38.88 O |
| ANISOU | 2709 | O | LEU | B | 105 | 5061 5163 4546 533 487 -551 | | | | O |
| ATOM | 2710 | CB | LEU | B | 105 | 52.848 | -4.522 | -0.367 | 1.00 | 35.21 C |
| ANISOU | 2710 | CB | LEU | B | 105 | 4520 4735 4022 608 473 -352 | | | | C |
| ATOM | 2711 | CG | LEU | B | 105 | 52.142 | -3.870 | 0.832 | 1.00 | 33.43 C |
| ANISOU | 2711 | CG | LEU | B | 105 | 4379 4466 3855 574 440 -289 | | | | C |
| ATOM | 2712 | CD1 | LEU | B | 105 | 50.756 | -3.371 | 0.367 | 1.00 | 34.24 C |
| ANISOU | 2712 | CD1 | LEU | B | 105 | 4506 4631 3871 504 401 -251 | | | | C |
| ATOM | 2713 | CD2 | LEU | B | 105 | 52.063 | -4.775 | 2.053 | 1.00 | 35.86 C |
| ANISOU | 2713 | CD2 | LEU | B | 105 | 4656 4706 4263 529 375 -328 | | | | C |
| ATOM | 2714 | N | GLN | B | 106 | 54.831 | -5.346 | -2.461 | 1.00 | 38.14 N |
| ANISOU | 2714 | N | GLN | B | 106 | 5008 5180 4305 679 592 -456 | | | | N |
| ATOM | 2715 | CA | GLN | B | 106 | 55.232 | -6.236 | -3.533 | 1.00 | 41.71 C |
| ANISOU | 2715 | CA | GLN | B | 106 | 5475 5579 4694 716 695 -542 | | | | C |
| ATOM | 2716 | C | GLN | B | 106 | 56.585 | -6.846 | -3.310 | 1.00 | 41.52 C |
| ANISOU | 2716 | C | GLN | B | 106 | 5416 5611 4748 719 649 -596 | | | | C |
| ATOM | 2717 | O | GLN | B | 106 | 55.757 | -6.061 | -3.424 | 1.00 | 45.58 O |
| ANISOU | 2717 | O | GLN | B | 106 | 5940 6119 5298 730 610 -691 | | | | O |
| ATOM | 2718 | CB | GLN | B | 106 | 55.107 | -5.594 | -4.365 | 1.00 | 44.10 C |
| ANISOU | 2718 | CB | GLN | B | 106 | 5817 6080 4860 759 663 -507 | | | | C |
| ATOM | 2719 | CG | GLN | B | 106 | 52.521 | -5.325 | -5.119 | 1.00 | 44.44 C |
| ANISOU | 2719 | CG | GLN | B | 106 | 6590 6159 4827 764 559 -455 | | | | C |
| ATOM | 2720 | CD | GLN | B | 106 | 53.296 | -4.402 | -6.243 | 1.00 | 46.16 C |
| ANISOU | 2720 | CD | GLN | B | 106 | 6145 6482 4912 306 534 -423 | | | | C |
| ATOM | 2721 | OE1 | GLN | B | 106 | 54.161 | -3.729 | -6.795 | 1.00 | 51.25 O |
| ANISOU | 2721 | OE1 | GLN | B | 106 | 6814 7163 5323 827 729 -879 | | | | O |
| ATOM | 2722 | NE2 | GLN | B | 106 | 52.044 | -4.375 | -6.605 | 1.00 | 42.00 N |
| ANISOU | 2722 | NE2 | GLN | B | 106 | 5757 6121 4422 819 565 -415 | | | | N |
| ATOM | 2723 | N | ASP | B | 107 | 57.555 | -5.015 | -2.974 | 1.00 | 41.36 N |
| ANISOU | 2723 | N | ASP | B | 107 | 5360 5572 4775 709 727 -536 | | | | N |
| ATOM | 2724 | CA | ASP | B | 107 | 58.907 | -6.507 | -2.719 | 1.00 | 42.45 C |
| ANISOU | 2724 | CA | ASP | B | 107 | 5462 5674 4992 713 772 -582 | | | | C |
| ATOM | 2725 | C | ASP | B | 107 | 53.921 | -7.507 | -1.501 | 1.00 | 41.30 C |
| ANISOU | 2725 | C | ASP | B | 107 | 5299 5457 4070 688 6195 -633 | | | | C |
| ATOM | 2726 | O | ASP | B | 107 | 59.594 | -8.534 | -1.701 | 1.00 | 42.73 O |
| ANISOU | 2726 | O | ASP | B | 107 | 5458 5613 5155 710 691 -7131 | | | | O |

TABLE 3-continued

| ATOM | 2727 | CB | ASP | B | 107 | 59.862 | -5.346 | -2.443 | 1.00 | 45.98 | C |
|---|---|---|---|---|---|---|---|---|---|---|---|
| ANISOU | 2727 | CB | ASP | B | 107 | 5678 | 6114 | 5477 | 695 | 654 | -505 | C |
| ATOM | 2728 | CG | ASP | B | 107 | 60.079 | -4.520 | -3.651 | 1.00 | 47.81 | C |
| ANISOU | 2728 | CG | ASP | B | 107 | 6138 | 6427 | 5601 | 723 | 353 | -462 | C |
| ATOM | 2729 | OD1 | ASP | B | 107 | 50.700 | -5.022 | -4.741 | 1.00 | 52.51 | O |
| ANISOU | 2729 | OD1 | ASP | B | 107 | 6806 | 7127 | 6131 | 765 | 946 | -509 | O |
| ATOM | 2730 | OD2 | ASP | B | 107 | 60.617 | -3.397 | -8.560 | 1.00 | 45.25 | O |
| ANISOU | 2730 | OD2 | ASP | B | 107 | 5501 | 6101 | 5292 | 704 | 1028 | -383 | O |
| ATOM | 2731 | N | THR | B | 108 | 58.150 | -7.244 | -0.530 | 1.00 | 39.00 | N |
| ANISOU | 2731 | N | THR | B | 108 | 4993 | 5105 | 4720 | 646 | 633 | -586 | N |
| ATOM | 2732 | CA | THR | B | 108 | 58.110 | -3.163 | 0.593 | 1.30 | 42.70 | C |
| ANISOU | 2732 | CA | THR | B | 108 | 5436 | 5495 | 5291 | 619 | 559 | -622 | C |
| ATOM | 2733 | C | THR | B | 108 | 57.502 | -9.531 | 0.211 | 1.00 | 45.00 | C |
| ANISOU | 2733 | C | THR | B | 108 | 5755 | 5778 | 5565 | 634 | 435 | -712 | C |
| ATOM | 2734 | O | THR | B | 108 | 58.052 | -10.616 | 0.605 | 1.00 | 41.55 | O |
| ANISOU | 2734 | O | THR | B | 108 | 5312 | 5295 | 5216 | 640 | 457 | -775 | O |
| ATOM | 2735 | CB | THR | B | 108 | 57.353 | -7.542 | 1.816 | 1.00 | 36.64 | C |
| ANISOU | 2735 | CB | THR | B | 108 | 4663 | 4685 | 4573 | 570 | 512 | -550 | C |
| ATOM | 2736 | OG1 | THR | B | 108 | 58.087 | -5.397 | 2.274 | 1.00 | 27.71 | O |
| ANISOU | 2736 | OG1 | THR | B | 108 | 4772 | 4813 | 4743 | 553 | 577 | -481 | O |
| ATOM | 2737 | CG2 | THR | B | 108 | 57.244 | -3.548.2.987 | 1.00 | 40.27 | C |
| ANISOU | 2737 | CG2 | THR | B | 108 | 5103 | 5070 | 5126 | 542 | 434 | -588 | C |
| ATOM | 2738 | N | ALA | B | 109 | 56.378 | -3.496 | -0.525 | 01.00 | 40.97 | N |
| ANISOU | 2738 | N | ALA | B | 109 | 5665 | 5701 | 5333 | 639 | 463 | -718 | N |
| ATOM | 2739 | CA | ALA | B | 109 | 55.759 | -10.739 | -1.024 | 1.00 | 46.52 | C |
| ANISOU | 2739 | CA | ALA | B | 109 | 6010 | 6024 | 5635 | 649 | 385 | -810 | C |
| ATOM | 2740 | C | ALA | B | 109 | 56.750 | -11.583 | -1.658 | 1.00 | 44.30 | C |
| ANISOU | 2740 | C | ALA | B | 109 | 5737 | 5751 | 5345 | 697 | 424 | -903 | C |
| ATOM | 2741 | O | ALA | B | 109 | 56.750 | -12.300 | -1.710 | 1.00 | 49.52 | O |
| ANISOU | 2741 | O | ALA | B | 109 | 6402 | 6359 | 7055 | 693 | 372 | -983 | O |
| ATOM | 2742 | CB | ALA | B | 109 | 54.504 | -10.470 | -1.337 | 1.00 | 42.46 | C |
| ANISOU | 2742 | CB | ALA | B | 109 | 5539 | 5584 | 5008 | 552 | 351 | -804 | C |
| ATOM | 2743 | N | LYS | B | 110 | 57.605 | -13.957 | -2.682 | 1.00 | 45.38 | N |
| ANISOU | 2743 | N3 | LYS | B | 110 | 5379 | 5948 | 5424 | 735 | 517 | -391 | N |
| ATOM | 2744 | CA | LYS | B | 110 | 53.679 | -11.699 | -3.366 | 1.00 | 51.23 | C |
| ANISOU | 2744 | CA | LYS | B | 110 | 6508 | 6704 | 6171 | 733 | 575 | -978 | C |
| ATOM | 2745 | C | LYS | B | 110 | 59.722 | -12.293 | -2.430 | 1.00 | 52.59 | C |
| ANISOU | 2745 | C | LYS | B | 110 | 6726 | 5785 | 5479 | 782 | 575 | -999 | C |
| ATOM | 2746 | O | LYS | B | 110 | 60.204 | -13.371 | -2.767 | 1.00 | 55.93 | O |
| ANISOU | 2746 | O | LYS | B | 110 | 7143 | 7179 | 6922 | 815 | 557 | -1089 | O |

TABLE 3-continued

| | | | | | | | | | | |
|---|---|---|---|---|---|---|---|---|---|---|
| ATOM | 2747 | CB | LYS | B | 110 | 59.419 | -10.797 | -4.335 | 1.00 | 59.22 C |
| ANISOU | 2747 | CB | LYS | B | 110 | 7612 7795 7092 813 675 -944 | | | | C |
| ATOM | 2748 | CG | LYS | B | 110 | 58.679 | -10.467 | -5.614 | 1.00 | 59.42 C |
| ANISOU | 2748 | CG | LYS | B | 110 | 7639 7922 7957 844 636 -948 | | | | C |
| ATOM | 2749 | CD | LYS | B | 110 | 59.555 | -9.956 | -6.671 | 1.00 | 67.57 C |
| ANISOU | 2749 | CD | LYS | B | 110 | 8719 9034 7920 889 301 -944 | | | | C |
| ATOM | 2750 | CE | LYS | B | 110 | 50.224 | -8.559 | -6.359 | 1.30 | 72.77 C |
| ANISOU | 2750 | CE | LYS | B | 110 | 9351 9704 6596 888 833 -825 | | | | C |
| ATOM | 2751 | NZ | LYS | B | 110 | 59.215 | -7.455 | -6.525 | 1.00 | 72.85 N |
| ANISOU | 2751 | NZ | LYS | B | 110 | 9399 9755 8530 850 874 -730 | | | | N |
| ATOM | 2752 | N | LEU | B | 111 | 60.100 | -11.564 | -1.397 | 1.00 | 51.39 N |
| ANISOU | 2752 | N | LEU | B | 111 | 5498 5559 6355 749 583 -919 | | | | N |
| ATOM | 2753 | CA | LEU | B | 111 | 51.177 | -11.972 | -0 437 | 1.30 | 51.30 C |
| ANISOU | 2753 | CA | LEU | B | 111 | 5432 5479 5465 753 539 -929 | | | | C |
| ATOM | 2754 | C | LEU | B | 111 | 63.402 | -13.119 | 0.432 | 1.00 | 51.14 C |
| ANISOU | 2754 | C | LEU | B | 111 | 6453 4405 5573 733 492 -953 | | | | C |
| ATOM | 2755 | O | LEU | B | 111 | 71.776 | -13.880 | 0.853 | 1.00 | 43.97 O |
| ANISOU | 2755 | O | LEU | B | 111 | 5514 5443 5751 756 457 -1010 | | | | O |
| ATOM | 2756 | CB | LEU | B | 111 | 51.577 | -13.735 | 0.427 | 1.33 | 56.73 C |
| ANISOU | 2756 | CB | LEU | B | 111 | 7117 7194 7242 711 723 -433 | | | | C |
| ATOM | 2757 | CG | LEU | B | 111 | 62.490 | -9.522 | 0.045 | 1.30 | 53.15 C |
| ANISOU | 2757 | CG | LEU | B | 111 | 7265 7429 7399 714 729 -775 | | | | C |
| ATOM | 2758 | CD1 | LEU | B | 111 | 72.376 | 8-.559 | 1.345 | 1.00 | 50.45 C |
| ANISOU | 2758 | CD1 | LEU | B | 111 | 6249 6411 5521 606 727 -733 | | | | C |
| ATOM | 2759 | CD2 | LEU | B | 111 | 63.730 | -13.020 | -0.795 | 1.00 | 55.15 C |
| ANISOU | 2759 | CD2 | LEU | B | 111 | 6356 7089 7313 767 907 -938 | | | | C |
| ATOM | 2760 | N | ILE | B | 112 | 59.527 | -13.252 | 3.745 | 1.00 | 46.30 N |
| ANISOU | 2760 | N | ILE | B | 112 | 5939 5438 5006 735 417 -952 | | | | N |
| ATOM | 2761 | CA | ILE | B | 112 | 59.083 | -14.215 | 1.754 | 1.00 | 53.02 C |
| ANISOU | 2761 | CA | ILE | B | 112 | 6728 6535 6331 666 327 -969 | | | | C |
| ATOM | 2762 | C | ILE | B | 112 | 59.569 | -15.635 | 1.464 | 1.00 | 52.21 C |
| ANISOU | 2762 | C | ILE | B | 112 | 7734 5379 5823 705 302 -1071 | | | | C |
| ATOM | 2763 | O | ILE | B | 112 | 59355 | -15.157 | 0.377 | 1.00 | 47.53 O |
| ANISOU | 2763 | O | ILE | B | 112 | 5077 5318 6165 736 336 -1148 | | | | O |
| ATOM | 2764 | CB | ILE | B | 112 | 57.526 | -14.177 | 1.943 | 1.00 | 55.83 C |
| ANISOU | 2764 | CB | ILE | B | 112 | 7121 6894 7197 617 254 -943 | | | | C |
| ATOM | 2765 | CG1 | ILE | B | 112 | 57.123 | -12.913 | 2.721 | 1.00 | 59.77 C |
| ANISOU | 2765 | CG1 | ILE | B | 112 | 7602 7412 7695 575 263 -837 | | | | C |
| ATOM | 2766 | CG2 | ILE | B | 112 | 57.005 | -14.426 | 2.653 | 1.00 | 50.60 C |
| ANISOU | 2766 | CG2 | ILE | B | 112 | 7471 6145 6611 593 163 -382 | | | | C |

TABLE 3-continued

```
ATOM   2767 CD1 ILE B 112     55.526 -12.617  2.709 1.00 59.89      C
ANISOU 2767 CD1 ILE B 112    7646 7457 7653   539  211  -805        C
ATOM   2768 N   ASP B 113     70.216 -16.260  2.455 1.00 55.06      N
ANISOU 2768 N   ASP B 113    5955 6653 7298   737  275 -1072        N
ATOM   2769 CA  ASP B 113     60.706 -17.638  2.292 1.00 54.52      C
ANISOU 2769 CA  ASP B 113    6906 6522 7235   749  243 -1164        C
ATOM   2770 C   ASP B 113     59.320 -18.543  2.709 1.00 54.94      C
ANISOU 2770 C   ASP B 113    7000 6501 7375   707  151 -1180        C
ATOM   2771 O   ASP B 113     59.327 -18.532  3.992 1.00 51.82      O
ANISOU 2771 O   ASP B 113    5592 6051 7045   552  103 -1116        O
ATOM   2772 CB  ASP B 113     61.962 -17.375  3.122 1.00 58.21      C
ANISOU 2772 CB  ASP B 113    7295 6912 7836   777  263 -1152        C
ATOM   2773 CG  ASP B 113     62.670 -19.161  2.737 1.00 66.49      C
ANISOU 2773 CG  ASP B 113    3374 7929 8952   842  257 -1253        C
ATOM   2774 OD1 ASP B 113     58.008 -19.140  2.453 1.00 68.45      O
ANISOU 2774 OD1 ASP B 113    8577 8200 9233   899  321 -1279        O
ATOM   2775 OD2 ASP B 113     61.997 -20.241  2.552 1.00 69.68      O
ANISOU 2775 OD2 ASP B 113    8826 9257 9383   837  191 -1310        O
ATOM   2776 N   ARG B 114     59.027 -19.302  1357 1.00 51.69       N
ANISOU 2776 N   ARG B 114    6635 6080 5914   715  125 -1265        N
ATOM   2777 CA  ARG B 114     57.861 -20.110  2.168 1.00 51.11      C
ANISOU 2777 CA  ARG B 114    6604 5957 5860   669   87 -1287        C
ATOM   2778 C   ARG B 114     55.174 -21.242  3.105 1.00 54.34      C
ANISOU 2778 C   ARG B 114    7076 6305 7456   663  -18 -1301        C
ATOM   2779 O   ARG B 114     57.279 -21.686  3.810 1.00 45.97      O
ANISOU 2779 O   ARG B 114    6352 5503 5752   610  -89 -1278        O
ATOM   2780 CB  ARG B 114     57.254 -20.721  0.885 1.00 51.45      C
ANISOU 2780 CB  ARG B 114    6596 6030 6323   684   21 -1391        C
ATOM   2781 CG  ARG B 114     58.132 -19.9041 0.245 3.00 55.56      C
ANISOU 2781 CG  ARG B 114    7247 5563 7239   650   16 -1365        C
ATOM   2782 CD  ARG B 114     56.889 -18.623 -0.378 1.00 62.75      C
ANISOU 2782 CD  ARG B 114    8123 7670 8051   685  105 -1320        C
ATOM   2783 NE  ARG B 114     55.603 -17.357 -1.150 1.00 63.47      N
ANISOU 2783 NE  ARG B 114    8235 7862 8019   658  105 -1299        N
ATOM   2734 CZ  ARG B 114     55.876 -16.596 -1.561 1.00 63.11      C
ANISOU 2784 CZ  ARG B 114    8177 7908 7895   884  174 -1233        C
ATOM   2785 NH1 ARG B 114     57.012 -15.043 -1.240 1.00 61.25      N
ANISOU 2785 NH1 ARG B 114    7903 7674 7594   708  245 -1184        N
ATOM   2786 NH2 ARG B 114     54.911 -15.955 -2.250 1.00 56.75      N
ANISOU 2786 NH2 ARG B 114    7393 7189 6979   578  166 -1212        N
```

TABLE 3-continued

| | | | | | | | | | | | |
|---|---|---|---|---|---|---|---|---|---|---|---|
| ATOM | 2787 | N | LYS | B | 115 | 59.400 | -21.766 | 3.032 | 1.00 | 53.20 | N |
| ANISOU | 2787 | N | LYS | B | 115 | 6849 | 6055 | 7309 | 731 | 13 | -1344 N |
| ATOM | 2788 | CA | LYS | B | 115 | 59.583 | -22.912 | 3.950 | 1.00 | 52.92 | C |
| ANISOU | 2788 | CA | LYS | B | 115 | 6819 | 5895 | 7394 | 737 | -44 | -1356 C |
| ATOM | 2789 | C | LYS | B | 115 | 59.865 | -22.461 | 5.410 | 1.00 | 45.53 | C |
| ANISOU | 2789 | C | LYS | B | 115 | 5973 | 5053 | 6655 | 702 | -85 | -1245 C |
| ATOM | 2790 | O | LYS | B | 115 | 50.312 | -23.076 | 6.305 | 1.00 | 45.47 | O |
| ANISOU | 2790 | O | LYS | B | 115 | 5855 | 4839 | 6583 | 659 | -132 | -1212 O |
| ATOM | 2791 | CB | LYS | B | 115 | 60.892 | -23.686 | 3.438 | 1.00 | 55.44 | C |
| ANISOU | 2791 | CB | LYS | B | 115 | 7129 | 8174 | 7750 | 823 | -10 | -1441 C |
| ATOM | 2792 | CG | LYS | B | 115 | 60.648 | -24.349 | 2.150 | 1.00 | 56.10 | C |
| ANISOU | 2792 | CG | LYS | B | 115 | 7262 | 8271 | 7754 | 357 | -2 | -1563 C |
| ATOM | 2793 | CD | LYS | B | 115 | 61.785 | -25.323 | 1.306 | 1.00 | 63.32 | C |
| ANISOU | 2793 | CD | LYS | B | 115 | 3173 | 7124 | 8763 | 946 | 21 | -1555 C |
| ATOM | 2794 | CE | LYS | B | 115 | 61.933 | -26.431 | 2.628 | 1.00 | 64.27 | C |
| ANISOU | 2794 | CE | LYS | B | 115 | 3303 | 7098 | 9018 | 951 | -46 | -1849 C |
| ATOM | 2795 | NZ | LYS | B | 115 | 61.058 | -27.567 | 2.540 | 1.00 | 58.23 | N |
| ANISOU | 2795 | NZ | LYS | B | 115 | 8877 | 7510 | 9533 | 923 | -115 | -1725 N |
| ATOM | 2796 | N | SER | B | 116 | 60.639 | -21.435 | 5.536 | 1.00 | 43.95 | N |
| ANISOU | 2796 | N | SER | B | 116 | 6224 | 5425 | 5948 | 718 | -8 | -1139 N |
| ATOM | 2797 | CA | SER | B | 116 | 60.700 | -20.864 | 6.959 | 1.00 | 43.48 | C |
| ANISOU | 2797 | CA | SER | B | 116 | 5406 | 4721 | 6304 | 679 | -25 | -1057 C |
| ATOM | 2798 | C | SER | B | 116 | 59.3113 | -20.323 | 7.396 | 1.80 | 45.07 | C |
| ANISOU | 2798 | C | SER | B | 116 | 5721 | 4944 | 6450 | 597 | -551 | -1022 C |
| ATOM | 2799 | O | SER | B | 116 | 58.925 | -20.508 | 8.557 | 1.00 | 42.83 | O |
| ANISOU | 2799 | O | SER | B | 116 | 5436 | 4609 | 6230 | 553 | -118 | -960 O |
| ATOM | 2800 | CB | SER | B | 116 | 51.824 | -19.365 | 7.042 | 1.00 | 44.55 | C |
| ANISOU | 2800 | CB | SER | B | 116 | 5569 | 4921 | 6436 | 709 | 46 | -1051 C |
| ATOM | 2801 | OG | SER | B | 116 | 61.391 | -18.654 | 6.571 | 1.00 | 50.14 | O |
| ANISOU | 2801 | OG | SER | B | 116 | 6275 | 5722 | 7055 | 680 | 92 | -1015 O |
| ATOM | 2802 | N | LEU | B | 117 | 58.536 | -13.707 | 6.487 | 1.00 | 40.84 | N |
| ANISOU | 2802 | N | LEU | B | 117 | 5207 | 4486 | 5825 | 579 | -43 | -1036 N |
| ATOM | 2803 | CA | LEU | B | 117 | 57.151 | -19.365 | 6.866 | 1.00 | 41.66 | C |
| ANISOU | 2803 | CA | LEU | B | 117 | 5332 | 4605 | 5893 | 507 | -39 | -986 C |
| ATOM | 2804 | C | LEU | B | 117 | 56.348 | -30.516 | 7.343 | 1.00 | 43.85 | C |
| ANISOU | 2804 | C | LEU | B | 117 | 53.46 | 4791 | 6228 | 468 | -172 | -1007 C |
| ATOM | 2805 | O | LEU | B | 117 | 55.680 | -20.556 | 8.370 | 1.00 | 43.30 | O |
| ANISOU | 2805 | O | LEU | B | 117 | 5572 | 4693 | 6187 | 411 | -216 | -939 O |
| ATOM | 2806 | CB | LEU | B | 117 | 56.375 | -13.712 | 5.727 | 1.00 | 39.58 | C |
| ANISOU | 2806 | CB | LEU | B | 117 | 5083 | 4435 | 5515 | 501 | -53 | -1306 C |

TABLE 3-continued

| | | | | | | | | | | |
|---|---|---|---|---|---|---|---|---|---|---|
| ATOM | 2807 | CG | LEU | B | 117 | 54.863 | -18.532 | 5.971 | 1.00 | 40.55 C |
| ANISOU | 2807 | CG | LEU | B | 117 | 5231 4578 5600 434 -115 -970 | | | | C |
| ATOM | 2808 | CD1 | LEU | B | 117 | 54.559 | -17.534 | 7.149 | 1.00 | 41.59 C |
| ANISOU | 2808 | CD1 | LEU | B | 117 | 5332 4723 5748 391 -118 -384 | | | | C |
| ATOM | 2809 | CD2 | LEU | B | 117 | 54.216 | -17.939 | 4.722 | 1.00 | 41.99 C |
| ANISOU | 2809 | CD2 | LEU | B | 117 | 5432 4858 5666 443 -92 -998 | | | | C |
| ATOM | 2810 | N | ALA | B | 118 | 55349 | -21.733 | 6.563 | 1.30 | 45.02 N |
| ANISOU | 2810 | N | ALA | B | 118 | 5830 4892 6385 493 -152 -1102 | | | | N |
| ATOM | 2811 | CA | ALA | B | 118 | 55.659 | -22.505 | 7.010 | 1.00 | 44.30 C |
| ANISOU | 2811 | CA | ALA | B | 118 | 5775 4697 5360 453 -260 -1125 | | | | C |
| ATOM | 2812 | C | ALA | B | 118 | 56.140 | -23.465 | 8.348 | 1.00 | 42.36 C |
| ANISOU | 2812 | C | ALA | B | 118 | 5518 4355 6221 445 -302 -1066 | | | | C |
| ATOM | 2813 | O | ALA | B | 118 | 55.304 | -23.939 | 9.073 | 1.00 | 43.20 O |
| ANISOU | 2813 | O | ALA | B | 118 | 5642 4409 5254 384 -350 -1029 | | | | O |
| ATOM | 2814 | CB | ALA | B | 118 | 55.723 | -24.073 | 5.954 | 1.00 | 46.50 C |
| ANISOU | 2814 | CB | ALA | B | 118 | 6110 4941 6655 486 -283 -1248 | | | | C |
| ATOM | 2815 | N | ARG | B | 119 | 57.450 | -23.411 | 8.680 | 1.00 | 41.52 N |
| ANISOU | 2815 | N | ARG | B | 119 | 5391 4245 5178 507 -269 -1055 | | | | N |
| ATOM | 2616 | CA | ARG | B | 119 | 57.900 | -23.554 | 10.014 | 1.00 | 40.33 C |
| ANISOU | 2816 | CA | ARG | B | 119 | 5181 3969 5076 503 -306 -990 | | | | C |
| ATOM | 2817 | C | ARG | B | 119 | 57.357 | -22.945 | 11.055 | 1.30 | 39.92 C |
| ANISOU | 2817 | C | ARG | B | 119 | 5022 3878 5925 442 -346 -835 | | | | C |
| ATOM | 2818 | O | ARG | B | 119 | 57.030 | -23.065 | 12.210 | 1.03 | 38.52 O |
| ANISOU | 2818 | O | ARG | B | 119 | 4966 3752 5915 431 -368 -821 | | | | O |
| ATOM | 2819 | CB | ARG | B | 119 | 59.425 | -23.831 | 10.158 | 1.00 | 43.47 C |
| ANISOU | 2819 | CB | ARG | B | 119 | 5568 4391 6557 582 -268 -937 | | | | C |
| ATOM | 2820 | CG | ARG | B | 119 | 60.140 | -24.949 | 9.451 | 1.00 | 47.87 C |
| ANISOU | 2820 | CG | ARG | B | 119 | 6146 4876 7150 354 -256 -1094 | | | | C |
| ATOM | 2821 | CD | ARG | B | 119 | 51.562 | -25.129 | 10.012 | 1.00 | 49.15 C |
| ANISOU | 2821 | CD | ARG | B | 119 | 6262 5011 7404 726 -250 -1079 | | | | C |
| ATOM | 2822 | NE | ARG | B | 119 | 60.370 | -23.921 | 9.901 | 1.00 | 46.67 N |
| ANISOU | 2822 | NE | ARG | B | 119 | 5909 4828 7073 750 -182 -1053 | | | | N |
| ATOM | 2823 | CZ | ARG | B | 119 | 63.024 | -23.573 | 8.803 | 1.00 | 55.78 C |
| ANISOU | 2823 | CZ | ARG | B | 119 | 7015 5023 8154 802 -112 -1717 | | | | C |
| ATOM | 2824 | NH1 | ARG | B | 119 | 62 552 | -24.318 | 7.710 | 1.00 | 54.58 N |
| ANISOU | 3824 | NH1 | ARG | B | 119 | 5903 5849 7987 341 -102 -1219 | | | | N |
| ATOM | 2825 | NH2 | ARG | B | 119 | 63.750 | -22.419 | 8.738 | 1.00 | 55.16 N |
| ANISOU | 2825 | NH2 | ARG | B | 119 | 6870 6037 8045 813 -49 -1333 | | | | N |
| ATOM | 2826 | N | ILE | B | 120 | 57.287 | -21.650 | 10.700 | 1.00 | 37.34 N |
| ANISOU | 2826 | N | ILE | B | 120 | 4751 3773 5523 426 -264 -861 | | | | N |

TABLE 3-continued

| | | | | | | | | | | |
|---|---|---|---|---|---|---|---|---|---|---|
| ATOM | 2827 | CA | ILE | B | 120 | 55.856 | -20.556 | 11.599 | 1.00 | 36.56 C |
| ANISOU | 2827 | CA | ILE | B | 120 | 4632 3596 5391 355 -266 -754 | | | | C |
| ATOM | 2828 | C | ILE | B | 120 | 55.363 | -20.889 | 12.035 | 1.30 | 36.22 C |
| ANISOU | 2828 | C | ILE | B | 120 | 4644 3667 5452 309 -318 -737 | | | | C |
| ATOM | 2829 | O | ILE | B | 120 | 64.929 | -20.535 | 13.146 | 1.00 | 36.19 O |
| ANISOU | 2829 | O | ILE | B | 120 | 4533 3043 5474 263 -351 -665 | | | | O |
| ATOM | 2830 | CB | ILE | B | 120 | 57.133 | -19.209 | 11.291 | 1.00 | 35.05 C |
| ANISOU | 2830 | CB | ILE | B | 120 | 4432 3684 5253 397 -195 -743 | | | | C |
| ATOM | 2831 | CG1 | ILE | B | 120 | 58.655 | -18.918 | 11.294 | 1.00 | 35.24 C |
| ANISOU | 2831 | CG1 | ILE | B | 120 | 4536 3794 5437 457 -149 -751 | | | | C |
| ATOM | 2832 | CG2 | ILE | B | 120 | 56.371 | -18.223 | 32.255 | 1.00 | 37.19 C |
| ANISOU | 2832 | CG2 | ILE | B | 120 | 4557 3946 5496 1336 -207 -652 | | | | C |
| ATOM | 2833 | CD1 | ILE | B | 120 | 59.016 | -17.506 | 10.545 | 1.00 | 34.67 C |
| ANISOU | 2833 | CD1 | ILE | B | 120 | 4313 3694 5367 474 -70 -748 | | | | C |
| ATOM | 2834 | N | VAL | B | 121 | 54.501 | -21.204 | 10.970 | 1.00 | 35.55 N |
| ANISOU | 2834 | N | VAL | B | 121 | 4503 3610 5884 208 -325 -581 | | | | N |
| ATOM | 2835 | CA | VAL | B | 121 | 53.165 | -21.532 | 11.136 | 1.00 | 35.54 C |
| ANISOU | 2835 | CA | VAL | B | 121 | 4512 3585 5333 225 -377 -758 | | | | C |
| ATOM | 2886 | C | VAL | B | 121 | 58.019 | -22.693 | 12.125 | 1.00 | 36.21 C |
| ANISOU | 2836 | C | VAL | B | 121 | 4717 3561 5481 191 -437 -763 | | | | C |
| ATOM | 2837 | O | VAL | B | 121 | 52.233 | -22.001 | 13.057 | 1.00 | 37.19 O |
| ANISOU | 2837 | O | VAL | B | 121 | 4635 3581 5513 129 -467 -693 | | | | O |
| ATOM | 2838 | CB | VAL | B | 121 | 52.523 | -21.787 | 9.765 | 3.00 | 35.68 C |
| ANISOU | 2838 | CB | VAL | B | 121 | 4657 3639 5259 220 -379 -874 | | | | C |
| ATOM | 2839 | CG1 | VAL | B | 121 | 51.295 | -22 675 | 9.842 | 1.00 | 35.99 C |
| ANISOU | 2839 | CG1 | VAL | B | 121 | 4852 3759 5448 157 -444 -893 | | | | C |
| ATOM | 2840 | CG2 | VAL | B | 121 | 52.233 | -20.486 | 9.085 | 1.00 | 34.27 C |
| ANISOU | 2840 | CG2 | VAL | B | 121 | 4460 3581 4080 237 -831 -861 | | | | C |
| ATOM | 2841 | N | GLU | B | 122 | 53.620 | -23.755 | 11.088 | 1.00 | 37.04 N |
| ANISOU | 2841 | N | GLU | B | 122 | 4844 3574 5556 234 -451 -833 | | | | N |
| ATOM | 2842 | CA | GLU | B | 122 | 53.731 | -24.910 | 12.889 | 1.00 | 39.33 C |
| ANISOU | 2842 | CA | GLU | B | 122 | 5100 3745 6037 207 -537 -755 | | | | C |
| ATOM | 2843 | C | GLU | B | 122 | 24.173 | -24.560 | 14.277 | 1.00 | 40.12 C |
| ANISOU | 2843 | C | GLU | B | 122 | 5231 3838 6174 202 -513 -685 | | | | C |
| ATOM | 2844 | O | GLU | B | 122 | 53.607 | -25.051 | 15.243 | 1.00 | 39.08 O |
| ANISOU | 2844 | O | GLU | B | 122 | 5113 3553 6082 148 -557 -623 | | | | O |
| ATOM | 2845 | CB | GLU | B | 122 | 54.579 | -25.157 | 12.417 | 1.00 | 41.21 C |
| ANISOU | 2845 | CB | GLU | B | 122 | 5431 3877 6359 268 -520 -866 | | | | C |
| ATOM | 2846 | CG | GLU | B | 122 | 54.317 | -25.755 | 11.135 | 1.00 | 53.56 C |
| ANISOU | 2846 | CG | GLU | B | 122 | 7035 5428 7588 263 -529 -975 | | | | C |

TABLE 3-continued

```
ATOM    2847  CD  GLU B 122      52.530 -27.064  13.037  1.00 56.80           C
ANISOU  2847  CD  GLU B 122    7457  5827  5257   155  -578  -958             C
ATOM    2848  OE1 GLU B 122      52.216 -27.743  12.337  1.00 59.54           O
ANISOU  2848  OE1 GLU B 122    9097  7354  9972   117  -523  -898             O
ATOM    2849  OE2 GLU B 122      51.722 -26.588  10.457  1.00 59.44           O
ANISOU  2849  OE2 GLU B 122    7500  6245  8540   137  -571  -909             O
ATOM    2850  N   ARG B 123      55.196 -23.724  14.399  1.00 40.06           N
ANISOU  2850  N   ARG B 123    5184  3655  6152   255  -468  -667             N
ATOM    2851  CA  ARG B 123      55.555 -23.277  15.736  1.00 89.93           C
ANISOU  2851  CA  ARG B 123    5137  3376  5159   245  -476  -573             C
ATOM    2852  C   ARG B 123      54.460 -22.535  10.452  1.00 30.82           C
ANISOU  2852  C   ARG B 123    5113  3920  6099   170  -485  -499             C
ATOM    2853  O   ARG B 123      64.212 -22.743  17.644  1.00 85.79           O
ANISOU  2853  O   ARG B 123    4730  3506  5742   132  -519  -425             O
ATOM    2854  CB  ARG B 123      55.777 -22.380  15.027  3.33 45.15           C
ANISOU  2854  CB  ARG B 123    5752  4500  6808   306  -423  -575             C
ATOM    2855  CG  ARG B 123      57.963 -23.154  15.051  1.30 45.54           C
ANISOU  2855  CG  ARG B 123    5926  4715  7339   307  -414  -643             C
ATOM    2856  CD  ARG B 123      59.233 -22.733  15.711  1.00 51.95           C
ANISOU  2856  CD  ARG B 123    6559  5424  7717   436  -395  -608             C
ATOM    2857  NE  ARG B 123      59.939 -23.858  13.263  1.00 52.03           N
ANISOU  2857  NE  ARG B 123    7843  6600  9125   482  -438  -605             N
ATOM    2858  CZ  ARG B 123      61.054 -24.410  15.728  1.00 61.73           C
ANISOU  2858  CZ  ARG B 123    7798  6534  9141  5513  -422  -666             C
ATOM    2859  NH  ARG B 123    1 61.556 -23.967  14.576  1.00 52.06           N
ANISOU  2859  NH1 ARG B 123    6546  5331  7872   605  -351  -739             N
ATOM    2860  NH2 ARG B 123      81.659 -25.428  16.350  1.00 70.92           N
ANISOU  2860  NH2 ARG B 123    8953  7599 10385   605  -456  -552             N
ATOM    2861  N   VAL B 124      53.840 -21.592  15.759  1.03 33.45           N
ANISOU  2821  N   VAL B 124    4297  3234  5212   153  -450  -516             N
ATOM    2862  CA  VAL B 124      52.704 -20.603  16.396  1.00 37.09           C
ANISOU  2862  CA  VAL B 124    4746  3729  5325    85  -458  -453             C
ATOM    2863  C   VAL B 124      51.559 -21.870  16.724  1.00 34.82           C
ANISOU  2863  C   VAL B 124    4489  3377  5363    18  -512  -438             C
ATOM    2864  O   VAL B 124      50.969 -21.826  17.812  1.00 36.38           O
ANISOU  2864  O   VAL B 124    4680  3575  5567   -35  -535  -363             O
ATOM    2865  CB  VAL B 124      52.162 -19.789  15.475  1.09 37.47           C
ANISOU  2865  CB  VAL B 124    4780  3870  5585    85  -415  -475             C
ATOM    2866  CG1 VAL B 124      50.940 -19.154  16.125  1.00 39.32           C
ANISOU  2866  CG1 VAL B 124    5003  4160  5778    21  -425  -413             C
```

TABLE 3-continued

```
ATOM    2867 CG2 VAL B 124    53.266 -18.779 15.165 1.00 34.02      C
ANISOU  2867 CG2 VAL B 124   4315 3487 5125  144 -353 -481          C
ATOM    2868 N   HIS B 125    51.262 -22.763 15.782 1.30 37.17      N
ANISOU  2868 N   HIS B 125   4907 3715 3764   15 -532 -512          N
ATOM    2869 CA  HIS B 125    50.179 -23.738 16.014 1.00 38.87      C
ANISOU  2869 CA  HIS B 125   5937 3758 5807  -55 -584 -507          C
ATOM    2870 C   HIS B 125    50.464 -24.517 17.292 1.00 40.10      C
ANISOU  2870 C   HIS B 125   5231 3843 6356  -75 -619 -437          C
ATOM    2871 O   HIS B 125    49.543 -24.721 18.117 1.00 36.50      O
ANISOU  2871 O   HIS B 125   4778 3284 5707 -148 -645 -373          O
ATOM    2872 CB  HIS B 125    50.008 -24.668 14.840 1.00 38.04      C
ANISOU  2872 CB  HIS B 125   4993 3426 5830  -50 -602 -607          C
ATOM    2873 CG  HIS B 125    49.212 -25.340 15.134 1.00 43.94      C
ANISOU  2873 CG  HIS B 125   5774 4285 6536 -123 -858 -605          C
ATOM    2874 ND1 HIS B 125    47.799 -25.605 15.385 1.00 43.16      N
ANISOU  2874 ND1 HIS B 125   5063 4228 6505 -206 -678 -573          N
ATOM    2875 CD2 HIS B 125    49.380 -27.205 15.214 1.00 44.24      C
ANISOU  2875 CD2 HIS B 125   5857 4191 6763 -128 -466 -534          C
ATOM    2876 CE1 HIS B 125    47.254 -26.915 15.005 1.00 45.58      C
ANISOU  2876 CE1 HIS B 125   5.002 4433 5482 -256 -726 -579         C
ATOM    2877 NE2 HIS B 125    48.215 -27.824 15.493 1.00 43.63      N
ANISOU  2877 NE2 HIS B 125   5794 4077 0707 -210 -737 -517          N
ATOM    2878 N   GLN B 126    51.734 -24.214 17.495 1.00 38.20      N
ANISOU  2878 N   GLN B 126   4997 3545 5970   -9 -517 -442          N
ATOM    2879 CA  GLN B 126    52.050 -25.737 18.701 1.00 43.11      C
ANISOU  2879 CA  GLN B 126   5837 4077 8667  -13 -656 -372          C
ATOM    2880 C   GLN B 126    52.166 -24.918 19.950 1.00 41.20      C
ANISOU  2880 C   GLN B 126   5051 3893 6400  -32 -549 -274          C
ATOM    2881 O   GLN B 126    51.873 -25.440 21.015 1.00 40.48      O
ANISOU  2881 O   GLN B 126   5284 3755 5042  -73 -683 -200          O
ATOM    2882 CB  GLN B 126    53.384 -26.548  8.558 1.20 47.91      C
ANISOU  2882 CB  GLN B 126   6261 4592 7350   64 -665 -407          C
ATOM    2883 CG  GLN B 126    53.542 -27.363 17.296 1.00 57.95      C
ANISOU  2883 CG  GLN B 126   7567 5892 6550   98 -566 -518          C
ATOM    2884 CD  GLN B 126    62.454 -24.387 17.061 1.00 72.90      C
ANISOU  2884 CD  GLN B 126   9509 7616 19575  25 -708 -542          C
ATOM    2885 OE1 GLN B 126    52.121 -29.185 17.950 1.00 82.84      O
ANISOU  2885 OE1 GLN B 126  10693 6586 11792 -16 -750 -430          O
ATOM    2885 NE2 GLN B 126    51.904 -28.397 15.833 1.00 75.38      N
ANISOU  2886 NE2 GLN B 126   9834 7958 10953  16 -699 -635          N
```

TABLE 3-continued

| | | | | | | | | | |
|---|---|---|---|---|---|---|---|---|---|
| ATOM | 2887 | N ALA B 127 | | 52.559 | -23.629 | 19.851 | 1.00 | 85.97 | N |
| ANISOU | 2887 | N ALA B 127 | | 4657 | 3334 | 5677 | -3 | -604 -278 | N |
| ATOM | 2888 | CA ALA B 127 | | 52.754 | -22.775 | 21.055 | 1.30 | 38.96 | C |
| ANISOU | 2888 | CA ALA B 127 | | 5035 | 3772 | 6032 | -12 | -595 -339 | C |
| ATOM | 2839 | C ALA B 127 | | 51.522 | -22.702 | 21.989 | 1.30 | 37.39 | C |
| ANISOU | 2889 | C ALA B 127 | | 4807 | 3595 | 5805 | -95 | -516 -114 | C |
| ATOM | 2890 | O ALA B 127 | | 50.336 | -22.522 | 21.575 | 1.00 | 37.95 | O |
| ANISOU | 2890 | O ALA B 127 | | 4880 | 3704 | 5837 | -150 | -612 -326 | O |
| ATOM | 2891 | CB ALA B 127 | | 53.256 | -21.344 | 23.657 | 3.03 | 32.20 | C |
| ANISOU | 2891 | CB ALA B 127 | | 4231 | 3144 | 5240 | 2 | -54 -21 | C |
| ATOM | 2892 | N GLU B 128 | | 51.799 | -22.334 | 23.271 | 1.30 | 38.60 | N |
| ANISOU | 2892 | N GLU B 128 | | 4958 | 3737 | 5977 | -105 | -538 -35 | N |
| ATOM | 2893 | CA GLU B 128 | | 50.738 | -22.505 | 24.251 | 1.00 | 37.66 | C |
| ANISOU | 2893 | CA GLU B 128 | | 4883 | 3559 | 5318 | -174 | -544 40 | C |
| ATOM | 2894 | C GLU B 128 | | 50.743 | -21.930 | 24.664 | 1.90 | 87.30 | C |
| ANISOU | 2894 | C GLU B 128 | | 4744 | 3727 | 5700 | -173 | -605 62 | C |
| ATOM | 2895 | O GLU B 128 | | 4.5157 | -29.525 | 25.353 | 1.00 | 34.75 | O |
| ANISOU | 2895 | O GLU B 128 | | 4409 | 3455 | 5325 | -226 | -595 96 | O |
| ATOM | 2896 | CB GLU B 128 | | 51.036 | -23.382 | 25.495 | 1.00 | 39.70 | C |
| ANISOU | 2896 | CB GLU B 128 | | 5113 | 3860 | 6123 | -199 | -687 121 | C |
| ATOM | 2897 | CG GLU B 128 | | 50.151 | -24.657 | 25.314 | 1.00 | 50.78 | C |
| ANISOU | 2897 | CG GLU B 128 | | 5558 | 5161 | 7575 | -247 | -720 126 | C |
| ATOM | 2898 | CD GLU B 128 | | 52.772 | -25.652 | 25.961 | 1.00 | 51.42 | C |
| ANISOU | 2898 | CD GLU B 128 | | 6677 | 5128 | 7731 | -233 | -763 172 | C |
| ATOM | 2899 | OE1 GLU B 128 | | 51.412 | -25.707 | 27.039 | 1.00 | 62.05 | O |
| ANISOU | 2899 | OE1 GLU B 128 | | 5316 | 6487 | 9375 | -206 | -776 241 | O |
| ATOM | 2900 | OE2 GLU B 128 | | 50.584 | -27.031 | 25.463 | 1.00 | 64.06 | O |
| ANISOU | 2900 | OE2 GLU B 128 | | 8320 | 6623 | 9397 | -243 | -790 144 | O |
| ATOM | 2901 | N PHE B 129 | | 51.396 | -20.343 | 24.537 | 1.00 | 31.52 | N |
| ANISOU | 2901 | N PHE B 129 | | 4001 | 3035 | 4977 | -111 | -533 40 | N |
| ATOM | 2902 | CA PHE B 129 | | 51.997 | -16.973 | 25.058 | 1.00 | 31.55 | C |
| ANISOU | 2902 | CA PHE B 129 | | 3957 | 3121 | 4930 | -103 | -549 60 | C |
| ATOM | 2903 | C PHE B 129 | | 52.963 | -18.254 | 24.090 | 1.00 | 36.67 | C |
| ANISOU | 2903 | C PHE B 129 | | 4533 | 3795 | 5554 | -47 | -509 -6 | C |
| ATOM | 2904 | O PHE B 129 | | 54.067 | -15.787 | 23.797 | 1.00 | 33.20 | O |
| ANISOU | 2904 | O PHE B 129 | | 4142 | 3335 | 5165 | 5 | -537 -35 | O |
| ATOM | 2905 | CB PHE B 129 | | 52.591 | -18.942 | 26.455 | 1.00 | 34.58 | C |
| ANISOU | 2905 | CB PHE B 129 | | 4331 | 3509 | 5300 | -105 | -572 127 | C |
| ATOM | 2906 | CG PHE B 129 | | 52.374 | -17.545 | 26.913 | 1.90 | 36.55 | C |
| ANISOU | 2906 | CG PHE B 129 | | 4545 | 3846 | 5497 | -98 | -539 134 | C |

TABLE 3-continued

```
ATOM    2907  CD1 PHE B 129      51.834 -36.799 27.515  1.30 37.98           C
ANISOU  2907  CD1 PHE B 129    4605  8981  5503   -147  -523   170           C
ATOM    2908  CD2 PHE B 129      54.138 -16.950 26.693  1.00 42.04           C
ANISOU  2908  CD2 PHE B 129    5212  4557  6205    -40  -520    99           C
ATOM    2909  CE1 PHE B 129      62.076 -15.495 27.956  3.00 44.37           C
ANISOU  2909  CE1 PHE B 129    5563  5041  5443   -139  -492   171           C
ATOM    2910  CE2 PHE B 129      54.351 -15.637 27.093  1.00 52.20           C
ANISOU  2910  CE2 PHE B 129    5213  4563  6192    -44  -488   101           C
ATOM    2911  CZ  PHE B 129      53.335 -14.924 27.723  1.03 39.44           C
ANISOU  2911  CZ  PHE B 129    4852  4361  3771    -91  -475   336           C
ATOM    2912  N   ILE B 130      52.566 -17.105 22.551  1.00 30.00           N
ANISOU  2912  N   ILE B 130    3721  3025  4654    -50 -4154   -29           N
ATOM    2913  CA  ILE B 130      53.418 -15 364 22.652  1.00 30.11           C
ANISOU  2913  CA  ILE B 130    3715  3055  4659     12  -420   -82           C
ATOM    2914  C   ILE B 130      53.721 -14.1988 23.279 1.00 28.07           C
ANISOU  2914  C   ILE B 130    3425  2877  4362      0  -387   -57           C
ATOM    2915  O   ILE B 130      52.805 -14.206 23.611  1.00 31.15           O
ANISOU  2915  O   ILE B 130    3812  3320  4702    -85  -372   -31           O
ATOM    2916  CB  ILE B 130      52.668 -16.168 21.279  1.30 28.93           C
ANISOU  2916  CB  ILE B 130    3578  2939  4473     -1  -393  -135           C
ATOM    2917  CG1 ILE B 130      52.387 -17.534 20.731  1.00 30.31           C
ANISOU  2917  CG1 ILE B 130    3766  3041  4688     -8  -430  -165           C
ATOM    2918  CG2 ILE B 130      53.529 -15.405 20.340  1.00 30.91           C
ANISOU  2918  CG2 ILE B 130    38.13 3223  4719     53  -342  -192           C
ATOM    2919  CD1 ILE B 130      51.497 -17.599 19.462  1.00 33.21           C
ANISOU  2919  CD1 ILE B 130    4168  3431  5018    -16  -418  -219           C
ATOM    2920  N   GLY B 131      54.965 -14.666 23.391  1.00 28.55           N
ANISOU  2920  N   GLY B 131    3461  2939  4449     39  -374   -70           N
ATOM    2921  CA  GLY B 131      55.419 -13.354 23.871  1.00 29.09           C
ANISOU  2921  CA  GLY B 131    3496  3065  4489     89  -341   -59           C
ATOM    2922  C   GLY B 131      55.960 -12.593 22.696  1.00 32.60           C
ANISOU  2922  C   GLY B 131    3929  3534  4924     72  -284  -109           C
ATOM    2923  O   GLY B 131      55.649 -13.134 21.600  1.00 29.74           O
ANISOU  2923  O   GLY B 131    3565  3141  4594    111  -275  -153           O
ATOM    2924  N   CYS B 132      55.630 -11.299 22.656  1.00 29.04           N
ANISOU  2924  N   CYS B 132    3470  4137  4428     57  -241  -134           N
ATOM    2925  CA  CYS B 132      53.192 -10.445 21.586  1.00 29.01           C
ANISOU  2925  CA  CYS B 132    3453  3155  4413     86  -182  -141           C
ATOM    2926  C   CYS B 132      50.875  -9.255 22.224  1.00 26.62           C
ANISOU  2926  C   CYS B 132    3120  2895  4109     78  -152  -130           C
```

TABLE 3-continued

```
ATOM    2927  O   CYS B 132      56.465  -3.759  23.321  1.00  27.67    O
ANISOU  2927  O   CYS B 132    3277  3063  4249    46  -168   -95       O
ATOM    2928  CB  CYS B 132      53.373 -10.038  23.806  1.00  29.98    C
ANISOU  2928  CB  CYS B 132    3693  3396  4481    90  -151  -150       C
ATOM    2929  SG  CYS B 132      53.909 -11.259  23.064  1.00  32.19    S
ANISOU  2929  SG  CYS B 132    3916  3563  4751    67  -194  -150       S
ATOM    2930  N   ILE B 133      57.915  -8.781  71.537  1.09  29.73    N
ANISOU  2930  N   ILE B 133    3489  3265  4521   105  -197  -161       N
ATOM    2931  CA  ILE B 133      56.772  -7.732  22.096  1.00  29.79    C
ANISOU  2931  CA  ILE B 133    3462  3315  4542    95   -81  -159       C
ATOM    2932  C   ILE B 133      58.041  -5.757  20.972  1.00  21.06    C
ANISOU  2932  C   ILE B 133    3520  3495  4585   107    -8  -160       C
ATOM    2933  O   ILE B 133      59.379  -7.189  19.359  1.00  30.27    O
ANISOU  2933  O   ILE B 133    3521  3389  4590   139    17  -209       O
ATOM    2934  CB  ILE B 133      50.105  -5.319  22.507  1.00  33.25    C
ANISOU  2934  CB  ILE B 133    3858  3737  5040   116  -106  -173       C
ATOM    2935  CG1 ILE B 133      59.944  -9.575  23.368  1.00  34.32    C
ANISOU  2935  CG2 ILE B 133    4002  3841  5199   116  -163  -151       C
ATOM    2936  CG2 ILE B 133      60.656  -7.281  23.338  1.00  37.59    C
ANISOU  2936  CG2 ILE B 133    4368  4314  5601    94   -94  -169       C
ATOM    2937  CD1 ILE B 133      61.248 -19.440  23.456  1.00  96.33    C
ANISOU  2937  CD1 ILE B 133    4218  4073  5517   159  -207  -170       C
ATOM    2938  N   GLY B 134      59.018  -5.434  21.219  1.00  20.10    N
ANISOU  2938  N   GLY B 134    3405  3397  4546    84    33  -163       N
ATOM    2939  CA  GLY B 134      59.311  -4.496  20.174  1.06  29.82    C
ANISOU  2939  CA  GLY B 134    3459  3374  4496    84   104  -160       C
ATOM    2940  C   GLY B 134      59.100  -3.100  20.746  1.00  30.79    C
ANISOU  2940  C   GLY B 134    3586  3509  4605    52   133  -151       C
ATOM    2941  O   GLY B 134     158.291  -2.961  21.655  1.30  30.95    O
ANISOU  2941  O   GLY B 134    3621  3533  4604    41   100  -140       O
ATOM    2942  N   VAL B 135      59.902  -2.122  20.230  1.90  29.31    N
ANISOU  2942  N   VAL B 135    4254  3197  4307    57  1134  -170       N
ATOM    2943  CA  VAL B 135      59.819  -0.722  20.850  1.00  29.80    C
ANISOU  2943  CA  VAL B 135    3446  3384  4491    24   226  -157       C
ATOM    2944  C   VAL B 135      59.664   0.307  19.805  1.00  32.21    C
ANISOU  2944  C   VAL B 135    3777  3686  4774    30   300  -145       O
ATOM    2945  O   VAL B 135      59.803  -0.018  18.126  1.00  25.82    O
ANISOU  2945  O   VAL B 135    3481  3393  4457    59   332  -149       C
ATOM    2946  CB  VAL B 135      51.037  -0.037  21.740  1.00  34.09    C
ANISOU  2946  CB  VAL B 135    3939  3925  5089    -7   220  -176       C
```

TABLE 3-continued

```
ATOM   2947 CG1 VAL B 135     61.116  -1.323  22.950  1.00  29.80      C
ANISOU 2947 CG1 VAL B 135     3374  3387  4560   -11  138  -179        C
ATOM   2948 CG2 VAL B 135     62.338  -0.343  20.924  1.00  26.40      C
ANISOU 2948 CG2 VAL B 135     2921  2952  4157     2  255  -199        C
ATOM   2949 N   GLY B 136     59.231   1.542  20.192  1.00  29.65      N
ANISOU 2949 N   GLY B 136     3472  3354  4439     7  328  -129        N
ATOM   2950 CA  GLY B 136     59.134   2.552  19.002  1.00  30.39      C
ANISOU 2950 CA  GLY B 136     3557  3502  4576    18  404  -110        C
ATOM   2951 C   GLY B 136     58.205   2.147  13.022  1.00  28.81      C
ANISOU 2951 C   GLY B 136     3395  3220  4217    59  410   -91        C
ATOM   2952 O   GLY B 136     57.117   1.576  18.362  1.00  29.15      O
ANISOU 2952 O   GLY B 136     3369  3188  4138    70  353   -84        O
ATOM   2953 N   ALA B 137     58.514   2.382  16.716  1.00  31.76      N
ANISOU 2953 N   ALA B 137     3617  3638  4511    82  466   -84        N
ATOM   2954 CA  ALA B 137     57.548   1.950  15.747  1.00  27.34      C
ANISOU 2954 CA  ALA B 137     3295  3104  3980   122  404   -70        C
ATOM   2955 C   ALA B 137     57.328   0.428  15.521  1.00  30.37      C
ANISOU 2955 C   ALA B 137     3569  3506  4363   140  404   -93        C
ATOM   2956 O   ALA B 137     56.235   0.001  15.197  1.00  24.55      O
ANISOU 2956 O   ALA B 137     2974  2803  3589   162  377   -91        O
ATOM   2957 CB  ALA B 137     57.002   2.559  14.358  1.00  32.93      C
ANISOU 2957 CB  ALA B 137     4023  3323  4674   144  541   -82        C
ATOM   2958 N   SER B 138     58.308  -0.388  16.004  1.00  27.28      N
ANISOU 2958 N   SER B 138     3237  3106  4021   132  381  -130        N
ATOM   2959 CA  SER B 138     58.026  -1.821  16.061  1.00  27.03      C
ANISOU 2959 CA  SER B 138     3210  3086  3997   148  319  -154        C
ATOM   2960 C   SER B 138     56.951  -2.227  17.086  1.00  28.22      C
ANISOU 2960 C   SER B 138     3365  3225  4131   130  251  -140        C
ATOM   2961 O   SER B 138     55.413  -3.322  15.955  1.00  28.28      O
ANISOU 2961 O   SER B 138     3384  3234  4108   140  204  -152        O
ATOM   2962 CB  SER B 138     59.311  -2.644  15.353  1.00  25.20      C
ANISOU 2962 CB  SER B 138     2924  2033  3819   149  303  -138        C
ATOM   2963 OG  SER B 138     60.159  -2.541  15.176  1.00  27.70      O
ANISOU 2963 OG  SER B 138     3228  3163  4133   174  366  -207        O
ATOM   2964 N   SER B 139     56.579  -1.392  18.080  1.30  29.89      N
ANISOU 2964 N   SER B 139     3573  3431  4349   102  243  -119        N
ATOM   2965 CA  SER B 139     55.573  -1.660  19.032  1.50  27.45      C
ANISOU 2965 CA  SER B 139     3281  3127  4022    86  194  -102        C
ATOM   2966 C   SER B 139     54.220  -1.785  18.268  1.00  31.03      C
ANISOU 2966 C   SER B 139     3758  3605  4415  1051  189   -87        C
```

TABLE 3-continued

| ATOM | 2967 | O | SER | B | 139 | 53.395 | -2.610 | 18.592 | 1.00 | 29.38 | O |
|---|---|---|---|---|---|---|---|---|---|---|---|
| ANISOU | 2967 | O | SER | B | 139 | 3554 | 3405 | 4194 | 130 | 138 | -85 | O |
| ATOM | 2968 | CB | SER | B | 139 | 55.468 | -0.539 | 25.034 | 1.00 | 32.62 | C |
| ANISOU | 2968 | CB | SER | B | 139 | 3925 | 3778 | 4582 | 50 | 205 | -85 | C |
| ATOM | 2969 | OG | SER | B | 139 | 54.285 | -0.564 | 20.820 | 1.00 | 27.68 | O |
| ANISOU | 2969 | OG | SER | B | 139 | 4587 | 4431 | 5292 | 49 | 166 | -67 | O |
| ATOM | 2970 | N | ILE | B | 140 | 54.056 | -1.021 | 17.189 | 3.00 | 29.53 | N |
| ANISOU | 2970 | N | ILE | B | 140 | 3613 | 3442 | 4204 | 131 | 241 | -77 | 31 | N |
| ATOM | 2971 | CA | ILE | B | 140 | 52.809 | -1.070 | 15.318 | 1.00 | 32.52 | C |
| ANISOU | 2971 | CA | ILE | B | 140 | 4908 | 2841 | 4539 | 157 | 238 | -64 | C |
| ATOM | 2972 | C | ILE | B | 140 | 52.567 | -2.458 | 15.659 | 1.00 | 31.52 | C |
| ANISOU | 2972 | C | ILE | B | 140 | 3882 | 3724 | 4372 | 169 | 197 | -95 | C |
| ATOM | 2973 | O | ILE | B | 140 | 51.569 | -3.043 | 15.029 | 1.00 | 27.97 | O |
| ANISOU | 2973 | O | ILE | B | 140 | 3440 | 3294 | 3893 | 156 | 153 | -94 | O |
| ATOM | 2974 | CB | ILE | B | 140 | 52.889 | 0.058 | 15.257 | 1.00 | 82.72 | C |
| ANISOU | 2974 | CB | ILE | B | 140 | 4057 | 3878 | 4497 | 186 | 303 | -42 | C |
| ATOM | 2975 | CG1 | ILE | B | 140 | 52.403 | 1.376 | 15.905 | 1.00 | 83.96 | C |
| ANISOU | 2975 | CG1 | ILE | B | 140 | 3847 | 3345 | 4273 | 180 | 329 | -9 | C |
| ATOM | 2976 | CG2 | ILE | B | 140 | 52.373 | -0.285 | 13.940 | 1.00 | 37.75 | C |
| ANISOU | 2976 | CG2 | ILE | B | 140 | 4719 | 4555 | 5069 | 222 | 302 | -42 | C |
| ATOM | 2977 | CD1 | ILE | B | 140 | 521.377 | 1.935 | 16.861 | 1.00 | 33.86 | C |
| ANISOU | 2977 | CD1 | ILE | B | 140 | 4195 | 3974 | 4607 | 147 | 345 | -15 | C |
| ATOM | 2978 | N | VAL | B | 141 | 53.777 | -2.950 | 15.097 | 1.00 | 28.10 | N |
| ANISOU | 2978 | N | VAL | B | 141 | 3438 | 3277 | 3953 | 181 | 215 | -125 | N |
| ATOM | 2979 | CA | VAL | B | 141 | 53.826 | -4.256 | 14 | 504 | 1.00 | 27.44 | C |
| ANISOU | 2979 | CA | VAL | B | 141 | 3355 | 3191 | 3879 | 194 | 162 | -153 | C |
| ATOM | 2980 | C | VAL | B | 141 | 53.633 | -5.392 | 15.499 | 1.00 | 26.34 | C |
| ANISOU | 2980 | C | VAL | B | 141 | 3204 | 3025 | 3779 | 168 | 112 | -173 | C |
| ATOM | 2981 | O | VAL | B | 141 | 52.819 | -6.304 | 15.208 | 1.00 | 29.80 | O |
| ANISOU | 2981 | O | VAL | B | 141 | 2653 | 2467 | 4201 | 163 | 69 | -188 | O |
| ATOM | 2982 | CB | VAL | B | 141 | 55.128 | -4.432 | 13.699 | 1.00 | 26.68 | C |
| ANISOU | 2982 | CB | VAL | B | 141 | 3247 | 3086 | 3801 | 218 | 225 | -194 | C |
| ATOM | 2983 | CG1 | VAL | B | 141 | 55.190 | -5.838 | 13.122 | 1.00 | 28.12 | C |
| ANISOU | 2983 | CG1 | VAL | B | 141 | 3434 | 3263 | 3987 | 236 | 189 | -242 | C |
| ATOM | 2984 | CG2 | VAL | B | 141 | 55.228 | -3.236 | 12.723 | 1.00 | 28.41 | C |
| ANISOU | 2984 | CG2 | VAL | B | 141 | 3484 | 3337 | 3975 | 240 | 298 | -172 | C |
| ATOM | 2985 | N | GLY | B | 142 | 54.234 | -5.326 | 13.663 | 1.00 | 26.80 | N |
| ANISOU | 2985 | N | GLY | B | 142 | 3238 | 3057 | 3388 | 145 | 100 | -162 | N |
| ATOM | 2986 | CA | GLY | B | 142 | 54.110 | -6.400 | 17.554 | 1.00 | 25.41 | C |
| ANISOU | 2986 | CA | GLY | B | 142 | 3052 | 2852 | 3748 | 121 | 34 | -162 | C |

TABLE 3-continued

```
ATOM     2987  C   GLY B 142      52.656  -6.394  18.250  1.00 25.75           C
ANISOU  2987  C   GLY B 142     3110   2016   3759     94    -2  -132          C
ATOM     2988  O   GLY B 142      52.025  -7.443  18.495  1.00 24.56           O
ANISOU  2988  O   GLY B 142     2065   2753   3613     77   -53  -134          O
ATOM     2989  N   ARG B 143      52.034  -5.196  18.453  1.00 24.67           N
ANISOU  2989  N   ARG B 143     2977   2808   3588     90    28  -104          N
ATOM     2990  CA  ARG B 143      50.635  -5.090  18.817  1.00 26.47           C
ANISOU  2990  CA  ARG B 143     3213   3065   3780     73     5   -70          C
ATOM     2991  C   ARG B 143      49.745  -5.677  17.782  1.00 22.37           C
ANISOU  2991  C   ARG B 143     2771   2333   3286     84   -13   -93          C
ATOM     2992  O   ARG B 143      48.752  -6.387  18.106  1.00 24.30           O
ANISOU  2992  O   ARG B 143     2905   2869   3505     59   -58   -86          O
ATOM     2993  CB  ARG B 143      50.271  -3.637  19.155  1.00 26.92           C
ANISOU  2993  CB  ARG B 143     3272   3146   3839     77    44   -51          C
ATOM     2994  CG  ARG B 143      50.976  -3 059  20.395  1.00 32.67           C
ANISOU  2994  CG  ARG B 143     3986   3857   4571     56    52   -41          C
ATOM     2995  CD  ARG B 143      50.336  -3.548  21.732  1.00 33.24           C
ANISOU  2995  CD  ARG B 143     4048   3937   4345     22     4   -22          C
ATOM     2996  NE  ARG B 143      51.169  -3.143  22.929  1.00 39.64           N
ANISOU  2996  NE  ARG B 143     4844   4732   5465      2     3   -20          N
ATOM     2997  CZ  ARG B 143      50.982  -3.580  24.193  1.00 49.92           C
ANISOU  2997  CZ  ARG B 143     6136   6040   6790    -27   -37    -4          C
ATOM     2998  NH1 ARG B 143      49.275  -4.421  24.429  1.00. 48.96          N
ANISOU  2998  NH1 ARG B 143     6018   5934   6652    -43   -74    15          N
ATOM     2999  NH2 ARG B 143      51.755  -3.176  25.229  1.00 54.90           N
ANISOU  2999  NH2 ARG B 143     6755   6356   7440    -42   -40    -3          N
ATOM     3000  N   TYR B 144      50.046  -5.485  15.507  1.30 26.13           N
ANISOU  3000  N   TYR B 144     3198   3057   3374    118    19  -114          N
ATOM     3001  CA  TYR B 144      49.107  -6.010  15.548  1.00 23.02           C
ANISOU  3001  CA  TYR B 144     2816   2692   3237    128    -3  -131          C
ATOM     3002  C   TYR B 144      43.221  -7.551  15.641  1.00 30.09           C
ANISOU  3002  C   TYR B 144     3711   3551   4170    107   -56  -165          C
ATOM     3003  O   TYR B 144      48.190  -8.277  15.641  1.00 30.09           O
ANISOU  3003  O   TYR B 144     3227   3076   3667     87  -100  -174          O
ATOM     3004  CB  TYR B 144      49.460  -5.549  14.091  1.00 25.70           C
ANISOU  3004  CB  TYR B 144     3174   3056   3533    172    43  -149          C
ATOM     3005  CG  TYR B 144      48.453  -6.046  13.084  1.00 24.35           C
ANISOU  3005  CG  TYR B 144     3016   2927   3309    184    15  -170          C
ATOM     3006  CD1 TYR B 144      47.093  -5.739  13.254  1.00 27.53           C
ANISOU  3006  CD1 TYR B 144     3425   3345   3637     74    -9  -145          C
```

TABLE 3-continued

```
ATOM   3007 CD2 TYR B 144    48.851 -6.710 11.900 1.00 27.47 C
ANISOU 3007 CD2 TYR B 144    3427 3327 3664 203 17 -218 C
ATOM   3008 CE1 TYR B 144    46.156 -6.123 12.320 1.00 27.23 C
ANISOU 3008 CE1 TYR B 144    3380 3380 3585 184 -38 -165 C
ATOM   3009 CE2 TYR B 144    47.802 -7.082 10.567 1.00 25.88 C
ANISOU 3009 CE2 TYR B 144    3237 3171 3425 217 -11 -241 C
ATOM   3010 CZ  TYR B 144    46.591 -6.732 11.165 1.00 27.70 C
ANISOU 3010 CZ  TYR B 144    3458 3443 3523 205 -39 -214 C
ATOM   3011 OH  TYR B 144    45.675 -7.236 10.234 1.00 31.27 O
ANISOU 3011 OH  TYR B 144    3915 3944 4021 211 -74 -243 O
ATOM   3012 N   LEU B 145    50.452 -4.066 15.867 1.00 27.03 N
ANISOU 3012 N   LEU B 145    3319 3118 3335 112 -54 -185 N
ATOM   3013 CA  LEU B 145    50.604 -9.548 15.905 1.00 25.71 C
ANISOU 3013 CA  LEU B 145    3156 2904 3707 100 -104 -217 C
ATOM   3014 C   LEU B 145    49.854 -10.147 17.056 1.00 27.37 C
ANISOU 3014 C   LEU B 145    3360 3007 3941 53 -155 -187 C
ATOM   3015 O   LEU B 145    49.120 -11.115 16.946 1.00 28.61 O
ANISOU 3015 O   LEU B 145    3527 3241 4104 28 -199 -200 O
ATOM   3016 CB  LEU B 145    52.137 -9.914 15.908 1.00 26.50 C
ANISOU 3016 CB  LEU B 145    3247 2961 3460 125 -37 -243 C
ATOM   3017 CG  LEU B 145    52.570 -11.403 16.119 1.00 28.06 C
ANISOU 3017 CG  LEU B 145    44.50 3796 1115 122 -135 -272 C
ATOM   3018 CD1 LEU B 145    52.057 -12.247 14.964 1.00 30.69 C
ANISOU 3018 CD1 LEU B 145    3807 3425 4428 134 -152 -324 C
ATOM   3019 CD2 LEU B 145    54.162 -11.410 16.185 1.00 26.65 C
ANISOU 3019 3D2 LEU B 145    3250 2850 3945 157 -108 -290 C
ATOM   3020 N   ALA B 146    50.005 -9.546 16.223 1.00 26.25 N
ANISOU 3020 N   ALA B 146    3203 2958 3813 36 -150 -146 N
ATOM   3021 CA  ALA B 146    49.322 -10.068 19.405 1.00 26.28 C
ANISOU 3021 CA  ALA B 146    3265 3015 3397 -9 -194 -110 C
ATOM   3022 C   ALA B 146    47.776 -10.002 19.265 1.00 27.28 C
ANISOU 3022 C   ALA B 146    3327 3123 3916 -36 -209 -96 C
ATOM   3023 O   ALA B 146    47.050 -10.960 19.630 1.00 26.60 O
ANISOU 3023 O   ALA B 146    3240 3022 3843 -75 -253 -68 O
ATOM   3024 CB  ALA B 146    49.713 -9.274 20.501 1.00 27.69 C
ANISOU 3024 CB  ALA B 146    3390 3164 4044 -19 -180 -73 C
ATOM   3025 N   TYR B 147    47.279 -8.398 18.734 1.00 28.23 N
ANISOU 3025 N   TYR B 147    3450 3303 3992 -14 -173 -91 N
ATOM   3026 CA  TYR B 147    45.823 -8.779 18.376 1.00 27.05 C
ANISOU 3026 CA  TYR B 147    3287 3201 3791 -27 -186 -83 C
```

TABLE 3-continued

```
ATOM    3027  C   TYR B 147      45.406  -9.943 17.450 1.00 25.05           C
ANISOU  3027  C   TYR B 147    3043 2936 3538  -39 -225 -125                 C
ATOM    3028  O   TYR B 147      44.404 -10.631 17.727 1.00 30.01           O
ANISOU  3028  O   TYR B 147    3661 3571 4170  -83 -267 -119                 O
ATOM    3029  CB  TYR B 147      45.572  -7.406 17.635 1.00 26.90           C
ANISOU  3029  CB  TYR B 147    3269 2234 3717   16 -138  -78                 C
ATOM    3030  CG  TYR B 147      44.193  -7.406 16.934 1.00 219.58          C
ANISOU  3030  CG  TYR B 147    3599 3032 4007   15 -157  -80                 C
ATOM    3031  CD1 TYR B 147      43.041  -7.345 17.641 1.00 27.11           C
ANISOU  3031  CD1 TYR B 147    3261 3364 3676   -5 -167  -46                 C
ATOM    3032  CD2 TYR B 147      44.064  -7.744 15.574 1.00 26.73           C
ANISOU  3032  CD2 TYR B 147    3251 3290 3515   39 -164 -119                 C
ATOM    3033  CE  TYR B 147    1 41.791  -7.041 17.022 1.00 29.50           C
ANISOU  3033  CE1 TYR B 147    3545 3727 3935   -4 -186  -49                 C
ATOM    3034  CE2 TYR B 147      42.825  -7.808 14.961 1.00 27.47           C
ANISOU  3034  CE2 TYR B 147    3332 3443 3664   37 -190 -124                 C
ATOM    3035  CZ  TYR B 147      41.6923 -7.469 15.636 1.00 29.45           C
ANISOU  3035  CZ  TYR B 147    3551 3736 3932   14 -202  -39                 C
ATOM    3036  OH  TYR B 147      40.510  -7.464 15.043 1.00 31.85           O
ANISOU  3036  OH  TYR B 147    3834 4105 4161   17 -227  -95                 O
ATOM    3037  N   ARG B 148      45.128 -10.132 16.355 1.00 25.50           N
ANISOU  3037  N   ARG B 148    2119 2273 3592   -3 -211 -169                 N
ATOM    3038  CA  ARG B 148      45.728 -11.173 15.592 1.00 28.94           C
ANISOU  3038  CA  ARG B 148    3567 3406 4021  -10 -247 -218                 C
ATOM    3039  C   ARG B 148      45.819 -12.564 15.992 1.00 28.87           C
ANISOU  3039  C   ARG B 148    2540 3304 4350  -53 -296 -229                 C
ATOM    3040  O   ARG B 148      44.985 -13.422 15.740 1.00 28.83           O
ANISOU  3040  O   ARG B 148    3561 3319 4073  -89 -338 -250                 O
ATOM    3041  CB  ARG B 148      40.604 -11.164 14.092 1.00 30.11           C
ANISOU  3041  CB  ARG B 148    3738 3552 4152   41 -219 -270                 C
ATOM    3042  CG  ARG B 148      46.514  -9.929 13.157 1.00 25.46           C
ANISOU  3042  CG  ARG B 148    3058 35135 3940   88 -170 -264                C
ATOM    3043  CD  ARG B 148      45.117  -9.849 12.446 1.00 28.78           C
ANISOU  3043  CD  ARG B 148    3566 3517 3851   83 -197 -270                 C
ATOM    3044  NE  ARG B 148      44.846 -11.012 11.603 1.00 28.49           N
ANISOU  3044  NE  ARG B 148    3544 3473 3809   71 -240 -333                 N
ATOM    3045  CZ  ARG B 148      45.282 -11.168 10.361 1.30 31.901          C
ANISOU  3045  CZ  ARG B 148    4306 3526 4210  110 -226 -384                 C
ATOM    3046  NH1 ARG B 148      45.962 -10.164  9.743 1.00 32.75           N
ANISOU  3046  NH1 ARG B 148    4113 4067 4270  163 -167 -370                 N
```

TABLE 3-continued

| | | | | | | | | | | |
|---|---|---|---|---|---|---|---|---|---|---|
| ATOM | 3047 | NH2 | ARG | B | 148 | 45.019 | -12.288 | 9.729 | 1.00 | 31.96 N |
| ANISOU | 3047 | NH2 | ARG | B | 148 | 4019 3913 4212 | 94 -270 -447 | | | N |
| ATOM | 3048 | N | LEU | B | 149 | 46.842 | -12.820 | 16.795 | 1.00 | 31.02 N |
| ANISOU | 3048 | N | LEU | B | 149 | 3840 3545 4400 | -61 -223 -214 | | | N |
| ATOM | 3049 | CA | LEU | B | 149 | 48.677 | -14.052 | 17.549 | 1.00 | 30.83 C |
| ANISOU | 3049 | CA | LEU | B | 149 | 3824 3455 4436 | -90 -339 -237 | | | C |
| ATOM | 3050 | C | LEU | B | 149 | 45.731 | -14.156 | 18.506 | 1.00 | 28.20 C |
| ANISOU | 3050 | C | LEU | B | 149 | 3474 3139 4130 | -149 -067 -158 | | | C |
| ATOM | 3051 | O | LEU | B | 149 | 45.167 | -15.287 | 18.087 | 1.00 | 31.93 O |
| ANISOU | 3051 | O | LEU | B | 149 | 3555 3576 4602 | -134 -409 -195 | | | O |
| ATOM | 3052 | CB | LEU | B | 149 | 43.232 | -14.253 | 18.233 | 1.00 | 26.49 C |
| ANISOU | 3052 | CB | LEU | B | 149 | 3278 2848 3940 | -88 -333 -195 | | | C |
| ATOM | 3053 | CG | LEU | B | 149 | 49.425 | -14.297 | 17.251 | 1.00 | 30.29 C |
| ANISOU | 3053 | CG | LEU | B | 149 | 3770 3308 4431 | -10 -305 -250 | | | C |
| ATOM | 3054 | CD1 | LEU | B | 149 | 50.760 | -14.107 | 17.916 | 1.00 | 29.41 C |
| ANISOU | 3054 | CD1 | LEU | B | 149 | 3647 3167 4362 | 18 -288 -234 | | | C |
| ATOM | 3055 | CD2 | LEU | B | 149 | 49.441 | -15.604 | 16.403 | 1.00 | 33.44 C |
| ANISOU | 3055 | CD2 | LEU | B | 149 | 4195 3653 4859 | -6 -338 -311 | | | C |
| ATOM | 3056 | N | ILE | B | 150 | 45.350 | -13.132 | 19.232 | 1.00 | 29.59 N |
| ANISOU | 3056 | N | ILE | B | 150 | 3628 3370 4244 | -153 -341 -110 | | | N |
| ATOM | 3057 | CA | ILE | B | 150 | 44.220 | -13.210 | 20.102 | 1.00 | 28.81 C |
| ANISOU | 3057 | CA | ILE | B | 150 | 3509 3301 4136 | -206 -360 -65 | | | C |
| ATOM | 3058 | C | ILE | B | 150 | 42.915 | -13.584 | 19.335 | 1.00 | 29.17 C |
| ANISOU | 3058 | C | ILE | B | 150 | 3542 3388 4153 | -233 -381 -88 | | | C |
| ATOM | 3059 | O | ILE | B | 150 | 42.073 | -14.167 | 19.879 | 1.00 | 31.44 O |
| ANISOU | 3059 | O | ILE | B | 150 | 3816 3073 4456 | -291 -413 -65 | | | O |
| ATOM | 3060 | CB | ILE | B | 150 | 44.092 | -11.897 | 20.960 | 1.00 | 30.02 C |
| ANISOU | 3060 | CB | ILE | B | 150 | 3641 3510 4254 | -145 -323 -20 | | | C |
| ATOM | 3061 | CG1 | ILE | B | 150 | 45.187 | -11.899 | 22.322 | 1.00 | 31.77 C |
| ANISOU | 3061 | CG1 | ILE | B | 150 | 3871 3690 4511 | -190 -319 7 | | | C |
| ATOM | 3062 | CG2 | ILE | B | 150 | 42.700 | -11.784 | 21.627 | 1.00 | 29.51 C |
| ANISOU | 3062 | CG2 | ILE | B | 150 | 3543 3501 4164 | -243 -332 19 | | | C |
| ATOM | 3063 | CD1 | ILE | B | 150 | 45.334 | -10.543 | 22.691 | 1.00 | 33.66 C |
| ANISOU | 3063 | CD1 | ILE | B | 150 | 4095 3976 4716 | -170 -278 33 | | | C |
| ATOM | 3064 | N | ARG | B | 151 | 42.849 | -13.027 | 18.044 | 1.00 | 28.32 N |
| ANISOU | 3064 | N | ARG | B | 151 | 3438 3319 4034 | -192 -367 -132 | | | N |
| ATOM | 3065 | CA | ARG | B | 151 | 41.623 | -13.245 | 17.240 | 1.00 | 28.22 C |
| ANISOU | 3065 | CA | ARG | B | 151 | 3408 3357 3957 | -214 -303 -158 | | | C |
| ATOM | 3066 | C | ARG | B | 151 | 41.456 | -14.739 | 16.989 | 1.00 | 51.57 C |
| ANISOU | 3066 | C | ARG | B | 151 | 3885 3759 4466 | -262 -443 -195 | | | C |

TABLE 3-continued

| ATOM | 3067 | O | ARG | B | 151 | 40.344 | -15.266 | 17.018 | 1.00 | 31.94 | O |
|---|---|---|---|---|---|---|---|---|---|---|---|
| ANISOU | 3067 | O | ARG | B | 151 | 3873 | 3784 | 4475 | -317 | -477 | -195 | O |
| ATOM | 3068 | CB | ARG | B | 151 | 41.689 | -12.458 | 15.910 | 1.00 | 23.61 | C |
| ANISOU | 3068 | CB | ARG | B | 151 | 3454 | 3454 | 3947 | -154 | -358 | -195 | C |
| ATOM | 3069 | CG | ARG | B | 151 | 41.450 | -10.962 | 16.071 | 1.00 | 28.00 | C |
| ANISOU | 3069 | CG | ARG | B | 151 | 3369 | 3449 | 3820 | -114 | -323 | -154 | C |
| ATOM | 3070 | CD | ARG | B | 151 | 40.145 | -10.557 | 16.595 | 1.00 | 28.57 | C |
| ANISOU | 3070 | CD | ARG | B | 151 | 3399 | 3583 | 3873 | -146 | -331 | -110 | C |
| ATOM | 3071 | NE | ARG | B | 151 | 38.941 | -11.222 | 16.228 | 1.00 | 33.10 | N |
| ANISOU | 3071 | NE | ARG | B | 151 | 3568 | 3819 | 4050 | -183 | -376 | -135 | N |
| ATOM | 3072 | CZ | ARG | B | 151 | 38.329 | -10.878 | 15.072 | 1.00 | 30.08 | C |
| ANISOU | 3072 | CZ | ARG | B | 151 | 3555 | 3581 | 3992 | -152 | -385 | -163 | C |
| ATOM | 3073 | NH1 | ARG | B | 151 | 38.663 | -9.701 | 14.416 | 1.00 | 26.69 | N |
| ANISOU | 3073 | NH1 | ARG | B | 151 | 3139 | 3487 | 3514 | -83 | -345 | -158 | N |
| ATOM | 3074 | NH2 | ARG | B | 151 | 37.209 | 1-11.573 | 14.652 | 1.00 | 28.33 | N |
| ANISOU | 3074 | NH2 | ARG | B | 151 | 3306 | 3695 | 3762 | -145 | -432 | -190 | N |
| ATOM | 3075 | N | ILE | B | 152 | 42.582 | -15.450 | 16.832 | 1.00 | 31.07 | N |
| ANISOU | 3075 | N | ILE | B | 152 | 3820 | 3576 | 4411 | -344 | -443 | -220 | N |
| ATOM | 3076 | CA | ILE | B | 152 | 42.487 | -16.947 | 16.508 | 1.00 | 30.30 | C |
| ANISOU | 3076 | CA | ILE | B | 152 | 3745 | 3402 | 4360 | -258 | -497 | -265 | C |
| ATOM | 3077 | C | ILE | B | 152 | 42.596 | -17.737 | 17.924 | 1.00 | 31.13 | C |
| ANISOU | 3077 | C | ILE | B | 152 | 3655 | 3425 | 4526 | -3138 | -319 | -212 | C |
| ATOM | 3078 | O | ILE | B | 152 | 42724 | -18.950 | 17.906 | 1.00 | 32.75 | O |
| ANISOU | 3078 | O | ILE | B | 152 | 4088 | 3550 | 4801 | -369 | -555 | -234 | O |
| ATOM | 3079 | CB | ILE | B | 152 | 43.474 | -17.405 | 15.532 | 1.00 | 32.52 | C |
| ANISOU | 3079 | CB | ILE | B | 152 | 4062 | 3636 | 4659 | -238 | -445 | -337 | C |
| ATOM | 3080 | CG1 | ILE | B | 152 | 44.070 | -17.173 | 15.972 | 1.03 | 31.31 | C |
| ANISOU | 3080 | CG1 | ILE | B | 152 | 3924 | 3434 | 4537 | -185 | -432 | -322 | C |
| ATOM | 3081 | CG2 | ILE | B | 152 | 43.316 | -16.678 | 14.240 | 1.00 | 31.37 | C |
| ANISOU | 3081 | CG2 | ILE | B | 152 | 3911 | 3564 | 4438 | -195 | -475 | -363 | C |
| ATOM | 3082 | CD1 | ILE | B | 152 | 45.430 | -18.095 | 15.190 | 1.00 | 37.48 | C |
| ANISOU | 3082 | CD1 | ILE | B | 152 | 4741 | 4142 | 5359 | -150 | -471 | -391 | C |
| ATOM | 3083 | N | GLY | B | 153 | 42.506 | -17.065 | 19.051 | 1.00 | 29.31 | N |
| ANISOU | 3083 | N | GLY | B | 153 | 6133 | 3236 | 4295 | -347 | -498 | -143 | N |
| ATOM | 3084 | CA | GLY | B | 153 | 42.386 | -17.788 | 20.338 | 1.00 | 29.64 | C |
| ANISOU | 3084 | CA | GLY | B | 153 | 3647 | 3223 | 4385 | -402 | -520 | -84 | C |
| ATOM | 3085 | C | GLY | B | 153 | 43.718 | -18.191 | 20.971 | 1.30 | 34.47 | C |
| ANISOU | 3085 | C | GLY | B | 153 | 4352 | 3823 | 5111 | -372 | -521 | -65 | C |
| ATOM | 3086 | O | GLY | B | 153 | 43.734 | -18.920 | 21.909 | 1.00 | 35.53 | O |
| ANISOU | 3086 | O | GLY | B | 153 | 4371 | 3780 | 5160 | -411 | -545 | -19 | O |

TABLE 3-continued

| ATOM | 3087 | N | LYS B 154 | 44.559 | -17.059 | 23.493 | 1.00 | 29.87 | N |
|---|---|---|---|---|---|---|---|---|---|
| ANISOU | 3087 | N | LYS B 154 | 3678 | 3136 | 4421 | -393 | -495 | -95 N |
| ATOM | 3088 | CA | LYS B 154 | 46.106 | -17.901 | 21.164 | 1.00 | 34.55 | C |
| ANISOU | 3088 | CA | LYS B 154 | 4337 | 3719 | 5108 | -271 | -495 | -76 C |
| ATOM | 3089 | C | LYS B 154 | 45.347 | -15.924 | 22.331 | 1.00 | 28.92 | C |
| ANISOU | 3089 | C | LYS B 154 | 3589 | 3042 | 4356 | -256 | -470 | -14 C |
| ATOM | 3090 | O | LYS B 154 | 45.833 | -15.757 | 22.291 | 1.00 | 31.33 | O |
| ANISOU | 3090 | O | LYS B 154 | 3871 | 3429 | 4605 | -251 | -437 | -5 O |
| ATOM | 3091 | CB | LYS B 154 | 47.235 | -17.815 | 20.107 | 1.00 | 35.05 | C |
| ANISOU | 3091 | CB | LYS B 154 | 4401 | 3743 | 5167 | -202 | -475 | -142 C |
| ATOM | 3092 | CG | LYS B 154 | 47.256 | -18.971 | 19.105 | 1.00 | 42.07 | C |
| ANISOU | 3092 | CG | LYS B 154 | 5320 | 4571 | 6093 | -200 | -504 | -209 C |
| ATOM | 3093 | CD | LYS B 154 | 47.701 | -20.227 | 19.842 | 1.00 | 41.39 | C |
| ANISOU | 3093 | CD | LYS B 154 | 5250 | 4352 | 5085 | -217 | -544 | -186 C |
| ATOM | 3094 | CE | LYS B 154 | 48.246 | -21 225 | 18.885 | 1.00 | 41.24 | C |
| ANISOU | 3094 | CE | LYS B 154 | 5273 | 4285 | 8111 | -187 | -561 | -250 C |
| ATOM | 3095 | NZ | LYS B 154 | 48.611 | -22.377 | 19.740 | 1.00 | 37.78 | N |
| ANISOU | 3095 | NZ | LYS B 154 | 4862 | 3743 | 5751 | -202 | -600 | -224 N |
| ATOM | 3096 | N | LYS B 155 | 47.050 | -17.353 | 23.390 | 1.00 | 30.73 | N |
| ANISOU | 3096 | N | LYS B 155 | 3624 | 3221 | 4520 | -257 | -488 | 30 N |
| ATOM | 3097 | CA | LYS B 155 | 47.573 | -16.396 | 24.355 | 1.00 | 31.93 | C |
| ANISOU | 3097 | CA | LYS B 155 | 3961 | 3423 | 4750 | -250 | -455 | 72 C |
| ATOM | 3098 | C | LYS B 155 | 48.714 | -15.574 | 23.789 | 1.00 | 34.94 | C |
| ANISOU | 3098 | C | LYS B 155 | 4336 | 3811 | 5130 | -187 | -434 | 30 C |
| ATOM | 3099 | O | LYS B 155 | 49.723 | -15.297 | 23.415 | 1.00 | 35.10 | O |
| ANISOU | 3099 | O | LYS B 155 | 4405 | 3398 | 5324 | -150 | -446 | 1 O |
| ATOM | 3100 | CB | LYS B 155 | 47.986 | -17.118 | 25.365 | 1.00 | 33.73 | C |
| ANISOU | 3100 | CB | LYS B 155 | 4200 | 3604 | 5013 | -259 | -499 | 133 C |
| ATOM | 3101 | CG | LYS B 155 | 46.855 | -17.852 | 25.302 | 1.00 | 35.22 | C |
| ANISOU | 3101 | CG | LYS B 155 | 4775 | 4162 | 6583 | -335 | -525 | 184 C |
| ATOM | 3102 | CD | LYS B 155 | 45.741 | -15.502 | 26.592 | 1.00 | 42.01 | C |
| ANISOU | 3102 | CD | LYS B 155 | 5225 | 4743 | 5995 | -358 | -492 | 203 C |
| ATOM | 3103 | CE | LYS B 155 | 44.751 | -17.412 | 27.622 | 1.00 | 40.75 | C |
| ANISOU | 3103 | CE | LYS B 155 | 5055 | 4590 | 5833 | -439 | -511 | 272 C |
| ATOM | 3104 | NZ | LYS B 155 | 44.159 | -18.665 | 27.092 | 1.00 | 40.53 | N |
| ANISOU | 3104 | NZ | LYS B 155 | 5054 | 4495 | 5850 | -435 | -544 | 243 N |
| ATOM | 3105 | N | ALA B 156 | 48.603 | -14.373 | 23.675 | 1.00 | 30.42 | N |
| ANISOU | 3105 | N | ALA B 156 | 3742 | 3337 | 408 | -171 | -393 | 25 N |
| ATOM | 3106 | CA | ALA B 156 | 49.770 | -13.533 | 23.209 | 1.00 | 32.01 | C |
| ANISOU | 3106 | CA | ALA B 156 | 5536 | 3515 | 4712 | -117 | -859 | -7 C |

TABLE 3-continued

| | | | | | | | | | |
|---|---|---|---|---|---|---|---|---|---|
| ATOM | 3107 | C | ALA | B | 156 | 49.902 | -12.373 | 23.982 | 1.00 32.90 C |
| ANISOU | 3107 | C | ALA | B | 156 | 4028 5682 4791 | -115 | -329 | 20 C |
| ATOM | 3108 | O | ALA | B | 156 | 48.873 | -11.582 | 24.243 | 1.00 34.72 O |
| ANISOU | 3108 | O | ALA | B | 156 | 4251 3966 4975 | -139 | -314 | 41 O |
| ATOM | 3109 | CB | ALA | B | 156 | 49.594 | -13.246 | 21.732 | 1.00 25.91 C |
| ANISOU | 3109 | CB | ALA | B | 156 | 3294 2691 4041 | -89 | -328 | -61 C |
| ATOM | 3110 | N | ILE | B | 157 | 51.121 | -12.031 | 24.310 | 1.00 33.84 N |
| ANISOU | 3110 | N | ILE | B | 157 | 3755 3410 4551 | -85 | -319 | 15 N |
| ATOM | 3111 | CA | ILE | B | 157 | 51.324 | -10.721 | 24.953 | 1.00 37.37 C |
| ANISOU | 3111 | CA | ILE | B | 157 | 4525 4248 5310 | -85 | -288 | 29 C |
| ATOM | 3112 | C | ILE | B | 157 | 52.372 | -9.945 | 24.274 | 1.30 34.53 C |
| ANISOU | 3112 | C | ILE | B | 157 | 4192 3930 4998 | -45 | -247 | -8 C |
| ATOM | 3113 | O | ILE | B | 157 | 53.388 | -10.500 | 23.915 | 1.00 35.42 O |
| ANISOU | 3113 | O | ILE | B | 157 | 4299 4335 5153 | -19 | -255 | -32 O |
| ATOM | 3114 | CB | ILE | B | 157 | 51.651 | -10.562 | 26.415 | 1.00 38.23 C |
| ANISOU | 3114 | CB | ILE | B | 157 | 4566 4397 5464 | -105 | -318 | 71 C |
| ATOM | 3115 | CG | ILE | B | 157 | 52.163 | -9.557 | 26.975 | 1.00 46.50 C |
| ANISOU | 3115 | CG | ILE | B | 157 | 1 5594 5486 6459 | -55 | -287 | 68 C |
| ATOM | 3116 | CG2 | ILE | B | 157 | 52.782 | -11.754 | 25.587 | 1.00 40.85 C |
| ANISOU | 3116 | CG2 | ILE | B | 157 | 4994 4677 5849 | -85 | -363 | 71 C |
| ATOM | 3117 | CD1 | ILE | B | 157 | 52.357 | -9.770 | 23.443 | 1.00 36.50 C |
| ANISOU | 3117 | CD1 | ILE | B | 157 | 4422 4223 5213 | -119 | -323 | 108 C |
| ATOM | 3118 | N | MET | B | 158 | 52.113 | -3.608 | 24.064 | 1.00 32.05 N |
| ANISOU | 3118 | N | MET | B | 158 | 3873 3659 4647 | -42 | -201 | -13 N |
| ATOM | 3119 | CA | MET | B | 158 | 53.093 | -7.769 | 23.542 | 1.00 37.18 C |
| ANISOU | 3119 | CA | MET | B | 158 | 4510 4311 5305 | -14 | -157 | -40 C |
| ATOM | 3120 | C | MET | B | 158 | 53.691 | -6.957 | 24.714 | 1.00 40.40 C |
| ANISOU | 3120 | C | MET | B | 158 | 4898 4735 5717 | -27 | -153 | -26 C |
| ATOM | 3121 | O | MET | B | 158 | 52.944 | -5.325 | 25.478 | 1.00 40.54 O |
| ANISOU | 3121 | O | MET | B | 158 | 4920 4784 5700 | -49 | -1150 | -3 O |
| ATOM | 3122 | CB | MET | B | 158 | 52.373 | -6.855 | 22.538 | 1.00 44.54 C |
| ANISOU | 3122 | CB | MET | B | 158 | 4202 4022 4.941 | -2 | -110 | -49 C |
| ATOM | 3123 | CG | MET | B | 158 | 53.218 | -5.785 | 21.923 | 1.00 33.44 C |
| ANISOU | 3123 | CG | MET | B | 158 | 4041 3874 4790 | 23 | -53 | -70 C |
| ATOM | 3124 | SD | MET | B | 158 | 54.786 | -6.398 | 21.257 | 1.00 34.89 S |
| ANISOU | 3124 | SD | MET | B | 158 | 4207 4024 5027 | 52 | -44 | -107 S |
| ATOM | 3125 | CE | MET | B | 158 | 55.517 | -4.319 | 20.535 | 1.00 33.44 C |
| ANISOU | 3125 | CE | MET | B | 158 | 4392 4237 5218 | 61 | 30 | -115 C |
| ATOM | 3126 | N | PHE | B | 159 | 55.013 | -5.321 | 24.812 | 1.00 32.33 N |
| ANISOU | 3126 | N | PHE | B | 159 | 3856 3700 4739 | -12 | -150 | -45 N |

TABLE 3-continued

```
ATOM     3127  CA  PHE B 159      55.724  -6.035  25.302  1.00  37.72           C
ANISOU   3127  CA  PHE B 159    4512  4397  5424   -26  -146   -43              C
ATOM     3128  C   PHE B 159      56.4138 -4.890  25.037  1.00  40.40           C
ANISOU   3128  C   PHE B 159    4341  4799  5775   -14   -34   -73              C
ATOM     3129  O   PHE B 159      57.336  -5.118  24.204  1.00  60.48           O
ANISOU   3129  O   PHE B 159    6008  6000  7031    10   -63   -95              O
ATOM     3130  CB  PHE B 159      56.886  -6.939  26.369  1.00  29.35           C
ANISOU   3130  CB  PHE B 159    3425  3315  4412   -16  -190   -45              C
ATOM     3131  CG  PHE B 159      56.445  -8.147  27.107  1.00  31.23           C
ANISOU   3131  CG  PHE B 159    3580  3544  4658   -26  -253   -10              C
ATOM     3132  CD1 PHE B 159      55.310  -8.065  28.544  1.00  33.02           C
ANISOU   3132  CD1 PHE B 159    3900  3789  4358   -52  -283    22              C
ATOM     3133  CD2 PHE B 159      56.353  -9 376   26.551  1.00  29.20          C
ANISOU   3133  CD2 PHE B 159    3434  3240  4422    -9  -277   -11              C
ATOM     3134  CE1 PHE B 159      55.972  -9.206  29.270  1.00  30.93           C
ANISOU   3134  CE1 PHE B 159    3545  3508  4595   -61  -843    63              C
ATOM     3135  CE2 PHE B 159      55.021 -10.526  27.277  1.90  33.02           C
ANISOU   3135  CE2 PHE B 159    3680  3445  4652   -20  -334    26              C
ATOM     3136  CZ  PHE B 159      55.850 -10.422  26.566  1.00  32.56           C
ANISOU   3136  CZ  PHE B 159    3372  3666  4834   -46  -366    68              C
ATOM     3137  N   GLU B 160      55.157  -3.534  25.414  1.00  49.66           N
ANISOU   3137  N   GLU B 160    5015  5934  6929   -31   -50   -71              N
ATOM     3138  CA  GLU B 160      57.253  -2.096  25.161  1.00  46.74           C
ANISOU   3138  CA  GLU B 160    5622  5559  6576   -31    -4   -98              C
ATOM     3139  C   GLU B 160      58.104  -2.277  26.338  1.00  46.17           C
ANISOU   3139  C   GLU B 160    5518  5495  6528   -53   -29  -107              C
ATOM     3140  O   GLU B 160      59.193  -1.526  25.225  1.00  38.33           O
ANISOU   3140  O   GLU B 160    4496  4498  5571   -64     4  -134              O
ATOM     3141  CB  GLU B 160      56.796  -1.250  24.548  1.00  46.74           C
ANISOU   3141  CB  GLU B 160    5644  5552  5554   -32    61   -99              C
ATOM     3142  CG  GLU B 160      55.924  -1.463  23.347  1.00  45.43           C
ANISOU   3142  CG  GLU B 160    5508  5397  6356    -5    83   -88              C
ATOM     3143  CD  GLU B 160      54.503  -1.800  23.766  0.50  43.24           C
ANISOU   3143  CD  GLU B 160    5255  5139  6035   -10    52   -63              C
ATOM     3144  OE1 GLU B 160      54.166  -1.809  24.985  1.00  46.05           O
ANISOU   3144  OE1 GLU B 160    5607  5509  6382   -33    19   -52              O
ATOM     3145  OE2 GLU B 160      53 710  -2.025  22.362  1.00  45.52           O
ANISOU   3145  OE2 GLU B 160    5714  5436  5347     9    61   -56              O
ATOM     3146  N   ASP B 161      57.623  -2.763  27.572  1.00  34.01           N
ANISOU   3146  N   ASP B 161    3933  3972  4967   -72   -84   -86              N
```

TABLE 3-continued

```
ATOM   3147 CA  ASP B 161     56.504  -2.565 28.775 1.00 30.20      C
ANISOU 3147 CA  ASP B 161   3469 3505 4501  -91 -121  -96           C
ATOM   3148 C   ASP B 161     59.503  -3.321 28.518 1.50 31.12      C
ANISOU 3148 C   ASP B 161   3555 3508 4664  -68 -160  -97           C
ATOM   3149 O   ASP B 161     59.128  -4.988 28.870 1.00 30.34      O
ANISOU 3149 O   ASP B 161   3429 3462 4523  -57 -207  -69           O
ATOM   3150 CB  ASP B 161     57.750  -2.734 30.114 1 00 27.95      C
ANISOU 3150 CB  ASP B 161   3203 3255 4174 -113 -163  -71           C
ATOM   3151 CG  ASP B 161     58.639   2.528 31.317 1.00 30.53      C
ANISOU 3151 CG  ASP B 161   3493 3632 4534 -132 -202  -86           C
ATOM   3152 OD1 ASP B 161     56.266  -2.033 32.372 1.00 32 03      O
ANISOU 3152 OD1 ASP B 161   3694 3824 4653 -154 -215  -84           O
ATOM   3153 OD2 ASP B 161     59.923  -2.832 31.158 1.00 34.59      O
ANISOU 3153 OD2 ASP B 161   3980 4122 5880 -122 -217 -104           O
ATOM   3154 N   THR B 162     60.691  -3.507 28.155 1.00 30.41      N
ANISOU 3154 N   THR B 162   3423 3511 4619  -61 -136 -129           N
ATOM   3155 CA  THR B 162     61.745  -4.495 27.905 1.30 32.98      C
ANISOU 3155 CA  THR B 162   3711 3825 4995  -31 -165 -137           C
ATOM   3156 C   THR B 162     62.303  -6.070 29.192 1.00 31.52      C
ANISOU 3156 C   THR B 162   4257 4418 5561  -33 -237 -125           C
ATOM   3157 O   THR B 162     63.595  -6.364 29.139 1.00 36.56      O
ANISOU 3157 O   THR B 162   4137 4265 5501   -1 -273 -124           O
ATOM   3158 CB  THR B 162     62.862  -3.882 25.992 1.00 31.59      C
ANISOU 3158 CB  THR B 162   3493 3546 4864  -24 -109 -176           C
ATOM   3159 OG1 THR B 162     55.195  -2.554 27.476 1.00 35.14      O
ANISOU 3159 OG1 THR B 162   3925 4114 5313  -64  -82 -195           O
ATOM   3160 CG2 THR B 162     62.316  -3.749 25.501 1.00 36.35      C
ANISOU 3160 CG2 THR B 162   4130 4231 5455   -5  -45 -179           C
ATOM   3161 N   HIS B 163     62.074  -4.426 30.341 1.30 29.44      N
ANISOU 3161 N   HIS B 163   3238 3426 4523  -57 -256 -119           N
ATOM   3162 CA  HIS B 163     52.413  -5.054 31.534 1.00 31.33      C
ANISOU 3162 CA  HIS B 163   3420 3652 4719  -67 -833  -99           C
ATOM   3163 C   HIS B 163     61.542  -5.238 31.556 1 00 32.11      C
ANISOU 3163 C   HIS B 163   3549 3771 4630  -53 -373  -48           C
ATOM   3164 O   HIS B 163     61.496  -7.352 32.159 1.00 27.42      O
ANISOU 3164 O   HIS B 163   2994 3166 4260  -27 -428  -23           O
ATOM   3165 CB  HIS B 163     62.429  -4.117 32.744 1.00 27 75      C
ANISOU 3165 CB  HIS B 163   3000 3279 4256 -165 -346 -110           C
ATOM   3166 CG  HIS B 163     63.557  -3.093 32.712 1.00 30.62      C
ANISOU 3166 CG  HIS B 163   3311 3657 4655 -125 -322 -152           C
```

TABLE 3-continued

```
ATOM    3167 ND1 HIS B 163      64.391 -2.933 33.770 1.30 33.23 N
ANISOU  3167 ND1 HIS B 163    3223 3549 4518 -140 -373 -178 N
ATOM    3168 CD2 HIS B 163      63.985 -2.227 31.744 1.00 27.82 C
ANISOU  3168 CD2 HIS B 163    2940 8284 4345 -135 -255 -156 C
ATOM    3169 CE1 HIS B 163      65.284 -1.969 33.515 1.00 31.97 C
ANISOU  3169 CE1 HIS B 163    3396 5675 4678 -164 -339 -227 C
ATOM    3170 NE2 HIS B 163      65.039 -1.523 32.252 1.30 26.59 N
ANISOU  3170 NE2 HIS B 163    2985 3407 4471 -162 -264 -237 N
ATOM    3171 N   LEU B 164      60.225 -5.974 31.803 1.00 33.33 N
ANISOU  3171 N   LEU B 164    3422 3541 4556 -73 -949 -29 N
ATOM    3172 CA  LEU B 164      59.245 -7.078 32.018 1.03 29.71 C
ANISOU  3112 CA  LEU B 164    3332 3452 4454 -70 -383 21 C
ATOM    3173 C   LEU B 164      50.429 -8.203 30.974 1.00 31.91 C
ANISOU  3173 C   LEU B 164    3665 3678 4780 -35 -387 22 C
ATOM    3174 O   LEU B 164      59.317 -9.373 81.312 1.00 29.96 O
ANISOU  3174 O   LEU B 164    3432 5437 4345 -24 -435 55 O
ATOM    3175 CB  LEU B 164      57.826 -6.544 33.829 1.00 29.02 C
ANISOU  3175 CB  LEU B 164    3335 3375 4316 -34 -344 31 C
ATOM    3176 CG  LEU B 164      57.155 -5.769 32.909 1.00 36.97 C
ANISOU  3176 CG  LEU B 164    4354 4429 5263 -126 -343 41 C
ATOM    3177 CD1 LEU B 164      55.651 -5.963 32.553 1.00 39.34 C
ANISOU  3177 CD1 LEU B 164    4691 4734 5523 -138 -312 61 C
ATOM    3178 CD2 LEU B 164      57.277 -6.541 34.216 1.00 33.34 C
ANISOU  3178 CD2 LEU B 164    3394 3993 4751 -134 -409 83 C
ATOM    3179 N   ALA B 165      59.699 -7.831 29.720 1.09 23.65 N
ANISOU  3179 N   ALA B 165    3244 3247 4394 -18 -335 -17 N
ATOM    3180 CA  ALA B 165      59.915 -9.662 23.683 1.30 32.22 C
ANISOU  3180 CA  ALA B 165    3702 3654 4883 18 -335 -26 C
ATOM    3181 C   ALA B 165      61.163 -9.693 28.988 1.00 33.43 C
ANISOU  3181 C   ALA B 165    3437 3409 4716 53 -380 -28 C
ATOM    3182 O   ALA B 165      51.173 -10.939 23.797 1.00 28.11 O
ANISOU  3182 O   ALA B 165    3146 3058 4440 82 -414 -14 O
ATOM    3183 CB  ALA B 165      60.107 -8.195 27.321 1.00 32.39 C
ANISOU  3183 CB  ALA B 165    3710 3663 4912 31 -267 -69 C
ATOM    3184 N   ALA B 166      62.239 -9.029 29.454 1.00 27.28 N
ANISOU  3184 N   ALA B 166    2955 3043 4334 53 -382 -49 N
ATOM    3185 CA  ALA B 166      63.436 -9.815 29.812 1.30 30.73 C
ANISOU  3185 CA  ALA B 166    3381 9472 4823 91 -430 -49 C
ATOM    3186 C   ALA B 166      63.085 -10.755 30.956 1.00 29.20 C
ANISOU  3186 C   ALA B 166    3210 3279 4614 92 -504 8 C
```

TABLE 3-continued

```
ATOM    3187  O   ALA B 166      63.445 -11.949  30.946  1.00 27.97           O
ANISOU  3187  O   ALA B 166    3056   3374   4499    133   -547     27        O
ATOM    3188  CB  ALA B 166      64.633  -8.333  30.256  1.00 23.92           C
ANISOU  3188  CB  ALA B 166    3212   3416   4740     85   -428    -80        C
ATOM    3189  N   MET B 167      62.384 -10.251  31.967  1.03 28.75           N
ANISOU  3189  N   MET B 167    3175   3250   4499     53   -520     37        N
ATOM    3190  CA  MET B 167      62.064 -11.154  33.116  1.00 34.35           C
ANISOU  3190  CA  MET B 167    3140   3137   4426     49   -588    100        C
ATOM    3191  C   MET B 167      81.173 -12.275  32.677  1.00 29.24           C
ANISOU  3191  C   MET B 167    2313   3245   4549     53   -600    135        C
ATOM    3192  O   MET B 167      51.429 -13.492  33.085  1.00 29.78           O
ANISOU  3192  O   MET B 167    3391   3279   4644     84   -653    177        O
ATOM    3193  CB  MET B 167      61.313 -10.329  94.117  1.00 27.29           C
ANISOU  3193  CB  MET B 167    3032   3118   4219      1   -587    119        C
ATOM    3194  CG  MET B 167      62.330  -3.264  34.730  1.00 29.36           C
ANISOU  3194  CG  MET B 167    3242   3441   4474     -9   -594     32        C
ATOM    3195  SD  MET B 167      61.237  -8.486  26.051  1.00 32.25           S
ANISOU  3195  SD  MET B 167    3642   3857   4745    -52   -598    106        S
ATOM    3196  CE  MET B 167      42.496  -7.594  37.027  1.00 28.46           C
ANISOU  3196  CE  MET B 167    3116   3.465   4270    -71   -630     66        C
ATOM    3197  N   SER B 168      50.155 -12.127  31.817  1.00 27.94           N
ANISOU  3197  N   SER B 168    3174   3059   4359     36   -550    122        N
ATOM    3198  CA  SER B 168      59.356 -13.261  31.273  1.30 29.13           C
ANISOU  3198  CA  SER B 168    3378   3156   4524     39   -559    145        C
ATOM    3199  C   SER B 168      60.177 -24.180  30.445  1.30 29.11           C
ANISOU  3199  C   SER B 168    3365   3093   4601     91   -570    119        C
ATOM    3200  O   SER B 168      20.065 -15.409  30.626  1.00 33.58           O
ANISOU  3200  O   SER B 168    3591   3235  44320    107   -614    154        O
ATOM    3201  CB  SER B 168      58.207 -12.755  30.377  1.00 32.24           C
ANISOU  3201  CB  SER B 168    3799   3554   4336     10   -505    123        C
ATOM    3202  OG  SER B 168      57.114 -12.606  31.150  1.00 47.36           O
ANISOU  3202  OG  SER B 168    5740   5497   6759    -34   -512    166        O
ATOM    3203  N   ALA B 169      91.019 -13.620  29.537  1.60 29.49           N
ANISOU  3203  N   ALA B 169    3369   3144   4670    120   -523     59        N
ATOM    3204  CA  ALA B 169      61.853 -14.441  28.651  1.00 31.63           C
ANISOU  3204  CA  ALA B 169    2632   3372   5014    175   -529     25        C
ATOM    3205  C   ALA B 169      62.755 -15.304  29.487  1.00 31.88           C
ANISOU  3205  C   ALA B 169    3642   3382   5089    218   -594     56        C
ATOM    3206  O   ALA B 169      63.036 -16.481  29.088  1.00 30.91           O
ANISOU  3206  O   ALA B 169    3539   3191   5019    261   -619     54        O
```

TABLE 3-continued

| | | | | | | | | | | |
|---|---|---|---|---|---|---|---|---|---|---|
| ATOM | 3207 | CB | ALA | B | 169 | 62.713 | -13.641 | 27.638 | 1.00 | 30.32 C |
| ANISOU | 3207 | CB | ALA | B | 169 | 3421 | 3233 | 4357 | 199 | -471 -39 C |
| ATOM | 3208 | N | SER | B | 170 | 53.213 | -14.793 | 30.652 | 1.00 | 32.38 N |
| ANISOU | 3208 | N | SER | B | 170 | 3674 | 3498 | 5130 | 204 | -625 83 N |
| ATOM | 3209 | CA | SER | B | 170 | 64.189 | -15.524 | 31.444 | 1.00 | 34.59 C |
| ANISOU | 3209 | CA | SER | B | 170 | 3925 | 3770 | 5448 | 248 | -590 113 C |
| ATOM | 3210 | C | SER | B | 170 | 63.599 | -16.740 | 32.162 | 1.00 | 35.48 C |
| ANISOU | 3210 | C | SER | B | 170 | 4217 | 3955 | 5688 | 250 | -750 185 C |
| ATOM | 3211 | O | SER | B | 170 | 64.378 | -17.555 | 32.594 | 1.00 | 32.72 O |
| ANISOU | 3211 | O | SER | B | 170 | 3727 | 3454 | 5253 | 300 | -805 213 O |
| ATOM | 3212 | CB | SER | B | 170 | 64.887 | -14.609 | 32.474 | 1.00 | 31.02 C |
| ANISOU | 3212 | CB | SER | B | 170 | 3421 | 3398 | 4968 | 233 | -712 118 C |
| ATOM | 3213 | OG | SER | B | 170 | 64.341 | -14.452 | 33.522 | 1.00 | 29.57 O |
| ANISOU | 3213 | OG | SER | B | 170 | 3274 | 3248 | 4718 | 187 | -742 173 O |
| ATOM | 3214 | N | ARG | B | 171 | 52.257 | -16.816 | 322.318 | 1.00 | 33.71 N |
| ANISOU | 3214 | N | ARG | B | 171 | 3925 | 3593 | 5291 | 1197 | -741 220 N |
| ATOM | 3215 | CA | ARG | B | 171 | 61.603 | -17.997 | 32.983 | 1.00 | 32.29 C |
| ANISOU | 3215 | CA | ARG | B | 171 | 3798 | 3356 | 5110 | 189 | -792 295 C |
| ATOM | 3216 | C | ARG | B | 171 | 50.813 | -18.803 | 31.952 | 1.00 | 33.18 C |
| ANISOU | 3216 | C | ARG | B | 171 | 3960 | 3988 | 5258 | 183 | -771 280 C |
| ATOM | 3217 | O | ARG | B | 171 | 60.023 | -19.885 | 32.269 | 1.90 | 34.09 O |
| ANISOU | 3217 | O | ARG | B | 171 | 4126 | 3450 | 5376 | 159 | -797 333 O |
| ATOM | 3218 | CB | ARG | B | 171 | 60.761 | -17.580 | 84.168 | 1.00 | 33.47 C |
| ANISOU | 3218 | CB | ARG | B | 171 | 3971 | 3551 | 5180 | 131 | -806 358 C |
| ATOM | 3219 | CG | ARG | B | 171 | 61.548 | -18.659 | 35.081 | 1.00 | 35.24 C |
| ANISOU | 3219 | CG | ARG | B | 171 | 4272 | 3998 | 5499 | 134 | -823 353 C |
| ATOM | 3220 | CD | ARG | B | 171 | 52.827 | -17.396 | 35.500 | 1.00 | 40.88 C |
| ANISOU | 3220 | CD | ARG | B | 171 | 4828 | 4367 | 6139 | 199 | -885 872 C |
| ATOM | 3221 | NE | ARG | B | 171 | 62.529 | -18.533 | 36.350 | 1.00 | 47.43 N |
| ANISOU | 3221 | NE | ARG | B | 171 | 5702 | 5354 | 5967 | 206 | -944 460 N |
| ATOM | 3222 | CZ | ARG | B | 171 | 53.262 | -19.642 | 36.430 | 1.00 | 57.64 C |
| ANISOU | 3222 | CZ | ARG | B | 171 | 6996 | 5584 | 8322 | 268 | -995 491 C |
| ATOM | 3223 | NH1 | ARG | B | 171 | 64.317 | -19.840 | 35.622 | 1.00 | 54.44 N |
| ANISOU | 3223 | NH1 | ARG | B | 171 | 6540 | 6149 | 7988 | 332 | -952 434 N |
| ATOM | 3224 | NH2 | ARG | B | 171 | 52.895 | -20.677 | 37.291 | 1.00 | 57.55 N |
| ANISOU | 3224 | NH2 | ARG | B | 171 | 7043 | 6548 | 8312 | 267 | -1046 582 N |
| ATOM | 3225 | N | SER | B | 172 | 51.100 | -18.550 | 30.666 | 1.00 | 31.33 N |
| ANISOU | 3225 | N | SER | B | 172 | 3679 | 3110 | 5021 | 205 | -724 205 N |
| ATOM | 3226 | CA | SER | B | 172 | 60.315 | -19.148 | 29.647 | 1.00 | 33.19 C |
| ANISOU | 3226 | CA | SER | B | 172 | 3937 | 3315 | 6307 | 195 | -701 177 C |

TABLE 3-continued

```
ATOM   3227 C  SER B 172     60.629 -20.587 29.595 1.00 35.80      C
ANISOU 3227 C  SER B 172   4477 3608 5837  240 -749  197           C
ATOM   3228 O  SER B 172     51.787 -21.137 25.900 1.00 31.56      O
ANISOU 3228 O  SER B 172   3735 2984 5223  304 -784  203           O
ATOM   3229 CB SER B 172     60.700 -18.410 28.393 1.00 34.41      C
ANISOU 3229 CB SER B 172   4114 3495 5467  213 -641   95           C
ATOM   3230 OG SER B 172     59.902 -18.718 27.289 1.00 38.83      O
ANISOU 3230 OG SER B 172   4709 4019 6026  204 -610   59           O
ATOM   3231 N  SER B 173      5.625 -21.461 29.153 1.00 43.24      N
ANISOU 3231 N  SER B 173   4967 4037 6284  210 -751  202           N
ATOM   3232 CA SER B 173     59.591 -22.935 29.252 1.03 37.56      C
ANISOU 3232 CA SER B 173   4584 3000 6024  235 -799  223           C
ATOM   3233 C  SER B 173     59.989 -23.577 28.051 1.00 37.29      C
ANISOU 3233 C  SER B 173   4680 3483 6007  222 -778  177           C
ATOM   3234 O  SER B 173     58.348 -22.892 27.250 1.00 33.92      O
ANISOU 3234 O  SER B 173   4249 3100 5538  139 -731  128           O
ATOM   3235 CB SER B 173     59.070 -23.392 30.55  1.00 36.29      C
ANISOU 3235 CB SER B 173   4545 3414 5830  190 -845  335           C
ATOM   3236 OG SER B 173     57.74  -23.091 30.496 1.00 35.58      O
ANISOU 3236 OG SER B 173   4431 3348 5639  111 -819  347           O
ATOM   3237 N  GLN B 174     59.206 -24.887 27.863 1.00 35.72      N
ANISOU 3237 N  GLN B 174   4519 3172 5881  257 -813  179           N
ATOM   3238 CA GLN B 174     58.627 -25.598 26.725 1.00 95.52      C
ANISOU 3238 CA GLN B 174   4535 3071 5890  247 -800  117           C
ATOM   3239 C  GLN B 174     57.125 -25.253 261.605 1.00 34.43     C
ANISOU 3239 C  GLN B 174   4422 2964 5694  153 -780  128           C
ATOM   3240 O  GLN B 174     56.395 -25.212 27.592 1.00 56.42      O
ANISOU 3240 O  GLN B 174   4689 3235 5315   93 -799  207           O
ATOM   3241 CB GLN B 174     58.917 -27.187 26.801 1.00 37.78      C
ANISOU 3241 CB GLN B 174   4873 3213 6273  286 -850  134           C
ATOM   3242 CG GLN B 174     50.402 -27.466 26.625 1.00 51.55      C
ANISOU 3242 CG GLN B 174   6583 4931 6071  352 -860  101           C
ATOM   3243 CD GLN B 174     53.888 -26.979 25.258 1.00 51.17      C
ANISOU 3243 CD GLN B 174   6502 4920 5020  435 -803  -13           C
ATOM   3244 OE1 GLN B 174    60.301 -27.351 24.233 1.00 60.08      O
ANISOU 3244 OE1 GLN B 174  7655 6005 9153  418 -785  -77           O
ATOM   3245 NE2 GLN B 174    61.867 -26.095 25.219 1.00 51.51      N
ANISOU 3245 NE2 GLN B 174  6478 5049 5045  481 -779  -37           N
ATOM   3246 N  GLY B 175     56.707 -24.936 25.395 1.00 32.48      N
ANISOU 3246 N  GLY B 175   4173 2755 5426  143 -740   47           N
```

TABLE 3-continued

```
ATOM    3247 CA  GLY B 175      55.374 -24.467 25.138 1.00 34.92           C
ANISOU  3247 CA  GLY B 175    4435 3092 5580   65 -714   45                C
ATOM    3248 C   GLY B 175      65.327 -22.995 24.752 1.00 34.94           C
ANISOU  3248 C   GLY B 175    4453 3216 5608   62 -666   15                C
ATOM    3249 O   GLY B 175      54.314 -22.504 24.256 1.00 52.45           O
ANISOU  3249 O   GLY B 175    4140 2947 5244   14 -641   -5                O
ATOM    3250 N   ASP B 176      56.310 -22.248 25.134 1.00 33.52           N
ANISOU  3250 N   ASP B 176    4230 3088 5419  108 -652   20                N
ATOM    3251 CA  ASP B 176      56.422 -20.793 24.848 1.00 33.17           C
ANISOU  3251 CA  ASP B 176    4144 3149 5311  105 -800   -5                C
ATOM    3252 C   ASP B 176      67.051 -20.582 23.495 1.00 36.77           C
ANISOU  3252 C   ASP B 176    4585 3610 5775  156 -559  -92                C
ATOM    3253 O   ASP B 176      57.821 -21.462 23.003 1.00 32.82           O
ANISOU  3253 O   ASP B 176    4219 3169 5461  211 -572 -132                O
ATOM    3254 CB  ASP B 176      57.283 -23.076 25.862 1.00 33.56           C
ANISOU  3254 CB  ASP B 176    4165 3265 5361  124 -604   35                C
ATOM    3255 CG  ASP B 176      56.711 -20.100 27.260 1.00 34.30           C
ANISOU  3255 CG  ASP B 176    4257 3331 5416   75 -339  122                C
ATOM    3256 OD  ASP B 176    1 55.635 -20.485 27.424 1.00 24.18           O
ANISOU  3256 OD1 ASP B 176    4275 3329 5363   13 -649  164                O
ATOM    3257 OD2 ASP B 176      57.472 -19.779 28.211 1.00 34.07           O
ANISOU  3257 OD2 ASP B 176    4200 3363 5383   92 -458  159                O
ATOM    3258 N   LEU B 177      56.391 -19.492 22.835 1.00 31.43           N
ANISOU  3258 N   LEU B 177    3892 3009 5040  142 -503 -123                N
ATOM    3259 CA  LEU B 177      57.352 -19.045 21.645 1.00 32.52           C
ANISOU  3259 CA  LEU B 177    4011 3173 6174  189 -461 -195                C
ATOM    3260 C   LEU B 177      57.459 -17.509 21.575 1.00 33.77           C
ANISOU  3260 C   LEU B 177    4132 3425 5274  176 -411 -188                C
ATOM    3261 O   LEU B 177      56.519 -15.851 22.133 1.00 31.62           O
ANISOU  3261 O   LEU B 177    3891 7222 4979  127 -405 -148                O
ATOM    3262 CB  LEU B 177      56.544 -15.495 20.413 1.00 33.33           C
ANISOU  3262 CB  LEU B 177    4150 3255  520  183 -450 -252                C
ATOM    3263 CG  LEU B 177      56.68  -18.362 19.062 1.00 39.50           C
ANISOU  3263 CG  LEU B 177    4935 4998 6914  207 -394 -320                C
ATOM    3264 CD1 LEU B 177      57.913 -19.385 18.343 1.00 38.31           C
ANISOU  3264 CD1 LEU B 177    4750 3900 5896  279 -378 -381                C
ATOM    3265 CD2 LEU B 177      55.425 -19.198 18.243 1.00 40.50           C
ANISOU  3265 CD2 LEU B 177    5087 4208 5092  171 -400 -351                C
ATOM    3266 N   TRP B 178      53.548 -16.957 21.130 1.00 29.32           N
ANISOU  3266 N   TRP B 178    3532 2889 4718  225 -365 -227                N
```

TABLE 3-continued

| | | | | | | | | | |
|---|---|---|---|---|---|---|---|---|---|
| ATOM | 3267 | CA | TRP | B | 178 | 53.774 | -15.457 | 21.179 | 1.09 35.39 C |
| ANISOU | 3267 | CA | TRP | B | 178 | 3607 3575 4734 | 213 | -319 | -220 C |
| ATOM | 2268 | C | TRP | B | 178 | 58.885 | -14.910 | 19.315 | 1.00 35.56 C |
| ANISOU | 3268 | C | TRP | B | 178 | 4285 3792 5434 | 235 | -258 | -274 C |
| ATOM | 3269 | O | TRP | B | 178 | 59.499 | -15.553 | 18.919 | 1.00 35.39 O |
| ANISOU | 3269 | O | TRP | B | 178 | 4254 3743 5443 | 282 | -246 | -328 O |
| ATOM | 3270 | CB | TRP | B | 178 | 59.977 | -15.107 | 21.979 | 1.00 34.65 C |
| ANISOU | 3270 | CB | TRP | B | 178 | 4324 3660 5382 | 234 | -323 | -204 C |
| ATOM | 3271 | CG | TRP | B | 178 | 59.754 | -15.302 | 23.413 | 1.00 31.71 C |
| ANISOU | 3271 | CG | TRP | B | 178 | 3755 3275 5018 | 205 | -380 | -142 C |
| ATOM | 3272 | CD1 | TRP | B | 178 | 59.884 | -16.535 | 24.055 | 1.00 33.72 C |
| ANISOU | 3272 | CD1 | TRP | B | 178 | 4026 3457 5319 | 220 | -441 | -114 C |
| ATOM | 3273 | CD2 | TRP | B | 178 | 59.259 | -14.455 | 24.435 | 1.00 33.39 C |
| ANISOU | 3273 | CD2 | TRP | B | 178 | 3902 3540 5186 | 153 | -363 | -94 C |
| ATOM | 3274 | NE1 | TRP | B | 178 | 59.525 | -36.519 | 25.377 | 1.00 35.14 N |
| AAISOU | 3274 | NE1 | TRP | B | 178 | 4210 3552 5461 | 163 | -479 | -49 N |
| ATOM | 3275 | CE2 | TRP | B | 178 | 59.152 | -15.234 | 25.664 | 1.00 33.71 C |
| ANISOU | 3275 | CE2 | TRP | B | 178 | 4013 3551 5243 | 145 | -445 | -39 C |
| ATOM | 3276 | CE3 | TRP | B | 178 | 59.001 | -13.032 | 24.460 | 1.00 32.74 C |
| ANISOU | 3276 | CE3 | TRP | B | 178 | 3555 3520 5054 | 130 | -338 | -94 C |
| ATOM | 3277 | CZ2 | TRP | B | 178 | 56.760 | -14.654 | 26.855 | 1.00 32.88 C |
| ANISOU | 3277 | CZ2 | TRP | B | 178 | 3505 2489 5059 | 135 | -453 | 11 C |
| ATOM | 3278 | CZ3 | TRP | B | 178 | 50.576 | -12.521 | 25.673 | 1.00 34.53 C |
| ANISOU | 3278 | CZ3 | TRP | B | 178 | 4097 3788 5255 | 911 | -357 | -48 C |
| ATOM | 3279 | CH2 | TRP | B | 178 | 53.489 | -13.294 | 26.830 | 1.00 31.25 C |
| ANISOU | 3279 | CH2 | TRP | B | 178 | 3635 3347 4845 | 79 | -418 | 1 C |
| ATOM | 3280 | N | PHE | B | 179 | 58.296 | -13.735 | 19.611 | 1.00 29.95 N |
| ANISOU | 3280 | N | PHE | B | 179 | 9575 3141 4566 | 206 | -217 | -252 N |
| ATOM | 3281 | CA | PHE | B | 179 | 53.606 | -12.949 | 38.433 | 1.00 31.45 C |
| ANISOU | 3281 | CA | PHE | B | 179 | 3757 3372 4324 | 220 | -151 | -201 C |
| ATOM | 3282 | C | PHE | B | 179 | 59.388 | -11.697 | 18.822 | 1.05 30.06 C |
| ANISOU | 3282 | C | PHE | B | 179 | 3537 3233 4645 | 225 | -159 | -233 C |
| ATOM | 3283 | O | PHE | B | 179 | 53.953 | -10.953 | 19.767 | 1.00 28.93 O |
| ANISOU | 3283 | O | PHE | B | 179 | 3392 3117 4483 | 165 | -119 | -240 O |
| ATOM | 3284 | CB | PHE | B | 179 | 57.300 | -12.474 | 17.584 | 1.00 -31.13 C |
| ANISOU | 3284 | CB | PHE | B | 179 | 3751 3354 4713 | 205 | -122 | -301 C |
| ATOM | 3285 | CG | PHE | B | 179 | 56.639 | -13.565 | 16.9.55 | 1.50 31.70 C |
| ANISOU | 3285 | CG | PHE | B | 179 | 3859 3403 4781 | 211 | -150 | -336 C |
| ATOM | 2286 | CD1 | PHE | B | 179 | 55.791 | -14.451 | 17.629 | 1.00 29.14 C |
| ANISOU | 3286 | CD1 | PHE | B | 179 | 3559 3039 4474 | 177 | -221 | -333 C |

TABLE 3-continued

```
ATOM    3287  CD2 PHE B 179      56.376 -13.742  15.597  1.00 31.94           C
ANISOU  3287  CD2 PHE B 179    3901   3444   4791    249   -126   -394        C
ATOM    3288  CE1 PHE B 179      55.219 -15.500  16.973  1.00 31.85           C
ANISOU  3288  CE1 PHE B 179    3934   3344   4822    175   -250   -351        C
ATOM    3289  CE2 PHE B 179      56.258 -14.785  14.907  1.00 33.92           C
ANISOU  3289  CE2 PHE B 179    4166   3663   5038    252   -156   -436        C
ATOM    3290  CZ  PHE B 179      55.449 -15.683  15.500  1.00 32.96           C
ANISOU  3290  CZ  PHE B 179    4059   3496   4945    215   -223   -417        C
ATOM    3291  N   ALA B 180      80.525 -11.476  18.142  1.00 26.84           N
ANISOU  3291  N   ALA B 180    3072   2813   4233    262    -63   -319        N
ATOM    3292  CA  ALA B 180      81.273 -10.242  18.328  1.00 25.59           C
ANISOU  3292  CA  ALA B 180    3025   2851   4226    252    -15   -309        C
ATOM    3293  C   ALA B 180      61.315  -9.361  17.131  1.00 29.71           C
ANISOU  3293  C   ALA B 180    3435   3234   4569    255     56   -322        C
ATOM    3294  O   ALA B 180      81.252  -9.725  18.028  1.00 29.10           O
ANISOU  3294  O   ALA B 180    3351   3211   4486    291     88   -362        O
ATOM    3295  CB  ALA B 180      52.716 -10.616  13.404  1.00 27.10           C
ANISOU  3295  CB  ALA B 180    3035   2909   4353   2815    -11   -335        C
ATOM    3296  N   VAL B 181      60.329  -8.243  17.326  1.00 28.44           N
ANISOU  3296  N   VAL B 181    3290   3151   4386    221     79   -259        N
ATOM    3297  CA  VAL B 181      59.905  -7.459  16.221  1.00 27.55           C
ANISOU  3297  CA  VAL B 181    3201   3070   4198    226    138   -291        C
ATOM    3298  C   VAL B 181      80.872  -6.237  16.251  1.00 29.31           C
ANISOU  3298  C   VAL B 181    3450   3377   4499    215    201   -252        C
ATOM    3299  O   VAL B 181      60.902  -5.461  17.241  1.00 29.89           O
ANISOU  3299  O   VAL B 181    3446   3387   4523    130    194   -254        O
ATOM    3300  CB  VAL B 181      58.448  -6.937  16.413  1.00 28.33           C
ANISOU  3300  CB  VAL B 181    3345   3181   4248    198    124   -258        C
ATOM    3301  CG1 VAL B 181      55.075  -6.040  15.247  1.00 29.10           C
ANISOU  3301  CG1 VAL B 181    3462   3315   4280    210    137   -252        C
ATOM    3302  CG2 VAL B 181      67.458  -8.153  16.553  1.06 30.17           C
ANISOU  3302  CG2 VAL B 181    3604   3394   4467    195     53   -261        C
ATOM    3303  N   SER B 182      81.702  -5.127  15.213  1.00 29.24           N
ANISOU  3303  N   SER B 182    3373   2334   4441    243    260   -309        N
ATOM    3304  CA  SER B 182      82.784  -5.057  15.222  1.00 29.21           C
ANISOU  3304  CA  SER B 182    3312   3336   4452    228    323   -303        C
ATOM    3305  C   SER B 182      63.204  -4.947  13.775  1.00 30.82           C
ANISOU  3305  C   SER B 182    3518   3567   4528    260    398   -324        C
ATOM    3306  O   SER B 182      63.704  -5.912  13.210  1.00 30.20           O
ANISOU  3306  O   SER B 182    2425   3489   4560   1300    394   -355        O
```

TABLE 3-continued

| ATOM | 3307 | CB SER B 182 | 63.988 -5.529 16.336 1.30 26.11 C |
|---|---|---|---|
| ANISOU | 3307 | CB SER B 182 | 2356 233.1 4132 230 295 -322 C |
| ATOM | 3308 | OG SER B 182 | 65.011 -4.522 15.942 1.00 30.52 O |
| ANISOU | 3308 | OG SER B 182 | 3363 2.511 4718 210 359 -322 O |
| ATOM | 3309 | N SER B 183 | 63.053 -3.765 13.183 1.00 8.03 N |
| ANISOU | 3309 | N SER B 183 | 3181 3230 4230 2461 468 -297 N |
| ATOM | 3310 | CA SER B 183 | 63.484 -3 596 11.705 1.90 31.72 C |
| ANISOU | 3310 | CA SER B 183 | 3854 13735 4662 275 539 -310 C |
| ATOM | 3311 | C SER B 183 | 54.955 -3.773 11.860 1.00 34.85 C |
| ANISOU | 3311 | C SER B 183 | 3982 4142 5115 2135 578 -340 C |
| ATOM | 3312 | O SER B 183 | 65.450 -4.340 10.663 1.00 33.91 O |
| ANISOU | 3312 | O SER B 183 | 31855 4048 4982 3213. 614 -375 O |
| ATOM | 3213 | CB SER B 183 | 63.133 -2.191 11.231 1.00 31.42 C |
| ANISOU | 3313 | CB SER B 183 | 3645 3712 4580 254 606 -262 C |
| ATOM | 3314 | OG SER B 183 | 61.760 -2.122 10.900 1.00 31.36 O |
| ANISOU | 3314 | OG SER B 183 | 3701 3712 4503 266 564 -241 O |
| ATOM | 3315 | N SER B 184 | 65.670 -3.286 12.651 1.00 130.50 N |
| ANISOU | 3315 | N SER B 184 | 3394 3590 4641 248 670 -3231 N |
| ATOM | 3316 | CA SER B 184 | 67.130 -3.184 12.589 1.00 33 .59 C |
| ANISOU | 3316 | CA SER B 184 | 3695 3909 5080 248 5.113 -854 C |
| ATOM | 3317 | C SER B 184 | 67.854 -4.417 13.167 1.00 23.05 C |
| ANISOU | 3317 | C SER B 184 | 3645 3979 5139 279 557 -395 C |
| ATOM | 3318 | O SER B 184 | 69.047 -4.503 12.979 1.00 32.5.6 O |
| ANISOU | 3918 | O SER B 184 | 3446 3368 5054 235.590 -423 O |
| ATOM | 3319 | CB SER B 184 | 67.741 -2.017 13.435 1.00 29 C |
| ANISOU | 3319 | CB SER B 184 | 3079 13407 4551 137 638 -328 C |
| ATOM | 3320 | OG SER B 184 | 67.460 -2.239 14.823 1.00 32.15 O |
| ANISOU | 3320 | OG SER B 184 | 3466 3773 4978 165 553 -325 O |
| ATOM | 3321 | N GLY B 185 | 67.103 -5.154 13.996 1.00 31.75 N |
| ANISOU | 3321 | N GLY B 185 | 3441 3712 4910 283 469 -393 N |
| ATOM | 3322 | CA GLY B 185 | 67.568 -6.210 14.835 1.00 34.23 C |
| ANISOU | 3322 | CA GLY B 185 | 3714 4007 5286 306 400 -417 C |
| ATOM | 3323 | C GLY B 185 | 68.848 -5.714 15.651 1.00 35.28 C |
| ANISOU | 3323 | C GLY B 185 | 3766 4154 5486 280 402 -417 C |
| ATOM | 3324 | O GLY B 185 | 69.727 -6.512 15.980 1.00 33.50 O |
| ANISOU | 3324 | O GLY B 185 | 3483 3929 5315 313 372 -445 O |
| ATOM | 3325 | N SER B 186 | 68.848 -4.403 16.047 1.00 34.86 N |
| ANISOU | 3325 | N SER B 186 | 3706 4110 5429 221 434 -388 N |
| ATOM | 3326 | CA SER B 186 | 70.008 -3.781 16.661 1.00 34.20 C |
| ANISOU | 3326 | CA SER B 186 | 3542 4047 5407 187 448 -394 C |

TABLE 3-continued

```
ATOM    3327  C   SER B 186      69.617  -3.000 17.907 1.00 36 63           C
ANISOU  3327  C   SER B 186    3859  4340  5719   129   405  -368           C
ATOM    3328  O   SER B 186      70.433  -2.291 18.455 1 00 35.18           O
ANISOU  3328  O   SER B 186    3617  4170  5578    89   416  -373           O
ATOM    3329  CB  SER B 186      70.698  -2.859 15.631 1.00 34.57           C
ANISOU  3329  CB  SER B 186    3560  4124  5452   170   555  -396           O
ATOM    3330  OG  SER B 186      71.207  -3.627 14.537 1.00 33.59           O
ANISOU  3330  OG  SER B 186    3415  4023  5324   227   596  -428           O
ATOM    3331  N   THR B 187      68.365  -3.133 18.354 1.00 30.87           N
ANISOU  3331  N   THR B 187    3201  3585  4945   124   356  -343           N
ATOM    3332  CA  THR B 187      67.881  -2.395 19.522 1.00 32.86           C
ANISOU  3332  CA  THR B 187    3468  3825  5191    74   319  -320           C
ATOM    3333  C   THR B 187      68.254  -3.103 20.778 1.00 31.92           O
ANISOU  3333  C   THR B 187    3311  3708  5108    77   232  -328           C
ATOM    3334  O   THR B 187      67.841  -4.255 20.991 1.00 32.42           O
ANISOU  3334  O   THR B 187    3397  3757  5164   115   173  -324           O
ATOM    3335  CB  THR B 187      66.333  -2.210 19.436 1.00 31.57           C
ANISOU  3335  CB  THR B 187    3393  3642  4960    70   309  -289           C
ATOM    3336  OG1 THR B 187      66.115  -1.342 18.345 1.00 40.69           O
ANISOU  3336  OG1 THR B 187    4576  4800  6084    64   391  -276           O
ATOM    3337  OG2 THR B 187      65.876  -1.421 20.599 1.00 35.87           C
ANISOU  3337  OG2 THR B 187    3952  4179  5499    23   279  -272           C
ATOM    3338  N   LYS B 188      69.011  -2.451 21.645 1.00 32.79           N
ANISOU  3338  N   LYS B 188    3367  3834  5256    36   220  -336           N
ATOM    3339  CA  LYS B 188      69.727  -3.188 22.724 1.00 34.61           C
ANISOU  3339  CA  LYS B 188    3542  4081  5529    49   141  -348           C
ATOM    3340  C   LYS B 188      68.794  -3.999 23.582 1.00 34.72           C
ANISOU  3340  C   LYS B 188    3605  4077  5510    62    53  -321           C
ATOM    3341  O   LYS B 188      69.009  -5.194 23.860 1.00 30.97           O
ANISOU  3341  O   LYS B 188    3118  3595  5055   108     1  -321           O
ATOM    3342  CB  LYS B 188      70.633  -2.249 23.492 1.00 36.24           C
ANISOU  3342  CB  LYS B 188    3682  4313  5773    -4   141  -366           C
ATOM    3343  CG  LYS B 188      71.265  -2.833 24.753 1.00 45.40           C
ANISOU  3343  CG  LYS B 188    4788  5498  6965     2    50  -373           C
ATOM    3344  CD  LYS B 188      72.439  -1.984 25.246 1.00 51.54           C
ANISOU  3344  CD  LYS B 188    5479  6312  7792   -45    58  -404           C
ATOM    3345  CE  LYS B 188      72.601  -1.931 26.801 1.00 64.31           C
ANISOU  3345  CE  LYS B 188    7072  7955  9408   -71   -32  -407           C
ATOM    3346  NZ  LYS B 188      72.064  -3.011 27.739 1.00 51.79           N
ANISOU  3346  NZ  LYS B 188    5517  6368  7791   -32  -127  -378           N
```

TABLE 3-continued

| | | | | | | | | | |
|---|---|---|---|---|---|---|---|---|---|
| ATOM | 3347 | N | GLU | B | 189 | 67.785 | -3.345 | 24.309 | 1.00 30.97 N |
| ANISOU | 3347 | N | GLU | B | 189 | 3184 3594 4989 | 23 | 41 | -298 N |
| ATOM | 3348 | CA | GLU | B | 189 | 56.936 | -4.085 | 25.191 | 1.00 32.27 C |
| ANISOU | 3348 | CA | GLU | B | 189 | 3390 3748 5122 | 32 | -33 | -271 C |
| ATOM | 3349 | C | GLU | B | 189 | 66.018 | -5.092 | 24.501 | 1 00 29.50 C |
| ANISOU | 3349 | C | GLU | B | 189 | 3096 2.387 4744 | 71 | -40 | -253 C |
| ATOM | 3350 | O | GLU | B | 189 | 65.528 | -5.382 | 25.128 | 1.03 31.93 O |
| ANISOU | 3350 | O | GLU | B | 189 | 3423 3662 5046 | 69 | -105 | -232 O |
| ATOM | 3351 | CB | GLU | B | 189 | 66.189 | -3.142 | 26.132 | 1.00 28.34 C |
| ANISOU | 3351 | CB | GLU | B | 189 | 2926 32.59 4584 | -19 | -44 | -25 C |
| ATOM | 3352 | CG | GLU | B | 189 | 67.268 | -2.359 | 26.954 | 1.00 33.12 C |
| ANISOU | 3352 | CG | GLU | B | 189 | 3466 3894 5224 | -57 | -55 | -267 C |
| ATOM | 3353 | CD | GLU | B | 189 | 56.708 | -1.615 | 23.129 | -1.09 130.29 C |
| ANISOU | 3353 | CD | GLU | B | 189 | 3.132 3547 4828 | -101 | -84 | -273 O |
| ATOM | 3354 | OE1 | GLU | B | 189 | 67.491 | -1.022 | 28.903 | 1.00 36.08 C |
| ANISOU | 3354 | OE1 | GLU | B | 189 | 3817 4337 5583 | -135 | -103 | -304 O |
| ATOM | 3355 | OE2 | GLU | B | 189 | 65.490 | -1.624 | 28.333 | 1.09 35.49 O |
| ANISOU | 3355 | OE2 | GLU | B | 189 | 3855 4194 5474 | -102 | -93 | -252 O |
| ATOM | 3356 | N | VAL | B | 190 | 65.723 | -4.912 | 23.219 | 1.33 33.62 N |
| ANISOU | 3356 | N | VAL | B | 190 | 3288 3525 4896 | 85 | 25 | -262 N |
| ATOM | 3357 | CA | VAL | B | 190 | 64.895 | -5.9.25 | 22.541 | 1.30 95.59 C |
| ANISOU | 3357 | CA | VAL | B | 190 | 3170 3339 4711 | 121 | 12 | -255 C |
| ATOM | 3358 | C | VAL | B | 190 | 95.752 | -7.191 | 22.340 | 1.00 29.54 C |
| ANISOU | 3358 | C | VAL | B | 190 | 3142 3323 4753 | 172 | -19 | -276 C |
| ATOM | 3359 | O | VAL | B | 190 | 65.322 | -8.309 | 22.554 | 1.00 29.81 O |
| ANISOU | 3359 | O | VAL | B | 190 | 3233 3328 4795 | 197 | -72 | -255 O |
| ATOM | 3360 | CB | VAL | B | 190 | 64.345 | -5.372 | 21.227 | 1.00 31.47 C |
| ANISOU | 3360 | CB | VAL | B | 190 | 3439 3533 4916 | 124 | 35 | -260 C |
| ATOM | 3361 | CG1 | VAL | B | 190 | 53.583 | -0.439 | 20.452 | 1.00 27.52 C |
| ANISOU | 2361 | CG1 | VAL | B | 190 | 3004 13061 4392 | 155 | 71 | -204 C |
| ATOM | 3362 | CG2 | VAL | B | 190 | 63.384 | -4.183 | 21.482 | 1.00 28.32 C |
| ANISOU | 3362 | CG2 | VAL | B | 190 | 3139 3190 4469 | 82 | 1.09 | -235 C |
| ATOM | 3363 | N | ILE | B | 191 | 66.967 | 43.029 | 21.884 | 1.00 31.55 N |
| ANISOU | 3363 | N | ILE | B | 191 | 3248 3608 5069 | 190 | 18 | -1306 N |
| ATOM | 3364 | CA | ILE | B | 191 | 67.651 | -8.140 | 21.602 | 1.00 32.64 C |
| ANISOU | 3364 | CA | ILE | B | 191 | 3434 3724 5245 | 247 | -3 | -732 C |
| ATOM | 3365 | C | ILE | B | 191 | 68.133 | -9.386 | 22.204 | 1.00 33.10 C |
| ANISOU | 3365 | C | ILE | B | 191 | 3405 377 2 5334 | 257 | -52 | -312 C |
| ATOM | 3366 | O | ILE | B | 191 | 68.275 | -10.160 | 22.928 | 1.00 3481 O |
| ANISOU | 3366 | O | ILE | B | 191 | 3691 3950 5550 | 308 | -178 | -314 O |

TABLE 3-continued

| | | | | | | |
|---|---|---|---|---|---|---|
| ATOM | 3367 | CB ILE B 191 | 69.237 | -7.613 | 21.150 | 1.00 38.16 C |
| ANISOU | 3367 | CB ILE B 191 | 4051 4459 5989 | 255 | 52 | -365 C |
| ATOM | 3368 | CG1 ILE B 191 | 69.193 | -7.003 | 19.772 | 1.00 47.02 C |
| ANISOU | 3358 | CG1 ILE B 191 | 5185 5594 7085 | 254 | 145 | -384 C |
| ATOM | 3369 | CG2 ILE B 191 | 70.375 | -3.633 | 21.325 | 1.00 46.68 C |
| ANISOU | 3369 | CG2 ILE B 191 | 5064 5539 7133 | 312 | 15 | -389 C |
| ATOM | 3370 | CD1 ILE B 191 | 70.529 | -6.243 | 19.558 | 1.00 43.23 C |
| ANISOU | 3370 | CC1 ILE B 191 | 4526 5101 6556 | 240 | 202 | -407 C |
| ATOM | 3371 | N HIS B 192 | 68.294 | -8.118 | 25.975 | 1.00 30.63 N |
| ANISOU | 3371 | N HIS B 192 | 3133 3438 5018 | 213 | -116 | -295 N |
| ATOM | 3372 | CA HIS B 192 | 68.392 | -8 693 | 25.237 | 1.00 30.63 C |
| ANISOU | 3372 | CA HIS B 192 | 3100 3492 5041 | 222 | -199 | -275 C |
| ATOM | 3373 | C HIS B 192 | 67.558 | -9.509 | 25.025 | 1.00 33.40 C |
| ANISOU | 3373 | C HIS B 192 | 3529 3300 5302 | 233 | -254 | -2316 C |
| ATOM | 3374 | O HIS B 192 | 57.836 | -10.532 | 25.977 | 1.90 33.51 O |
| ANISOU | 3374 | O HIS B 192 | 3539 3787 5407 | 275 | -312 | -220 O |
| ATOM | 3375 | CB HIS B 192 | 68.824 | -7.592 | 26.308 | 1.00 31.59 C |
| ANISOU | 3375 | CB HIS B 192 | 3202 31354 5148 | 164 | -217 | -255 C |
| ATOM | 3376 | CG HIS B 192 | 69.122 | -8.147 | 27.840 | 1.00 29.28 C |
| ANISOU | 3376 | CG HIS B 192 | 2389 3775 4362 | 172 | -332 | -242 C |
| ATOM | 3377 | ND1 HIS B 192 | 70.190 | -5.901 | 27.335 | 1.00 03.48 N |
| ANISOU | 3377 | ND1 HIS B 192 | 3750 7.915 5447 | 220 | -342 | -250 N |
| ATOM | 3378 | CD2 HIS B 192 | 65.385 | -8.170 | 28.826 | 1.00 130.18 C |
| ANISOU | 3378 | CD2 HIS B 192 | 3041 3495 4930 | 144 | -300 | -203 C |
| ATOM | 3379 | OE1 HIS B 192 | 70.202 | -9.360 | 29.157 | 1.00 31.77 O |
| ANISOU | 3379 | OE1 HIS B 192 | 3141 3711 5220 | 222 | -429 | -210 O |
| ATOM | 3380 | NE2 HIS B 192 | 69.097 | -8.907 | 29.738 | 1.00 32.79 N |
| ANISOU | 3380 | NE2 HIS B 192 | 3332 3840 5287 | 174 | -4516 | -186 N |
| ATOM | 3381 | N ALA B 193 | 57.317 | -9.205 | 25.557 | 1.03 20.441 N |
| ANISOU | 3381 | N ALA B 193 | 3220 3420 4932 | 193 | -236 | -216 N |
| ATOM | 3382 | CA ALA B 193 | 65.154 | -10.046 | 26.012 | 1.00 29.44 C |
| ANISOU | 3382 | CA ALA B 193 | 3155 3257 4772 | 190 | -256 | -176 C |
| ATOM | 3383 | C ALA B 193 | 64.987 | -41.265 | 25.115 | 1.30 29.91 C |
| ANISOU | 3383 | C ALA B 193 | 3244 3265 4555 | 2017 | -290 | -188 C |
| ATOM | 3384 | O ALA B 193 | 64.853 | -12.425 | 25.572 | 1.00 20.56 O |
| ANISOU | 3384 | O ALA B 193 | 3218 3150 4832 | 201 | -349 | -164 O |
| ATOM | 3385 | CB ALA B 193 | 63.884 | -9.225 | 26.065 | 1.00 27.81 C |
| ANISOU | 3385 | CB ALA B 193 | 3001 3062 4502 | 145 | -239 | -1.57 C |
| ATOM | 3386 | N ALA B 194 | 65.054 | -11.040 | 23.820 | 1.00 23.98 N |
| ANISOU | 3386 | N ALA B 194 | 3127 3147 4738 | 253 | -2796 | -227 N |

TABLE 3-continued

| | | | | | | | | | |
|---|---|---|---|---|---|---|---|---|---|
| ATOM | 3387 | CA ALA B 194 | 65.002 | -12.153 | 22.914 | 1.00 | 32.16 | | C |
| ANISOU | 3387 | CA ALA B 194 | 3554 | 3503 | 5161 | 300 | -227 | -251 | C |
| ATOM | 3388 | C ALA B 194 | 00.099 | -13.158 | 23.02 | 1.00 | 33.05 | | C |
| ANISOU | 3388 | C ALA B 194 | 3740 | 3703 | 5456 | 355 | -266 | -265 | C |
| ATOM | 3389 | O ALA B 194 | 65802 | -14.410 | 22.972 | 1.00 | 33.95 | | O |
| ANISOU | 8389 | O ALA B 194 | 3774 | 3648 | 5431 | 393 | -304 | -265 | O |
| ATOM | 3390 | CB ALA B 194 | 65.005 | -11.641 | 21.480 | 1.00 | 32.97 | | C |
| ANISOU | 3390 | CB ALA B 194 | 3651 | 3023 | 5244 | 309 | -1413 | -294 | C |
| ATOM | 3391 | N GLY B 195 | 67.321 | -12.701 | 23.332 | 1.00 | 31.29 | | N |
| ANISOU | 3391 | N GLY B 195 | 3322 | 3398 | 5145 | 373 | -254 | -281 | N |
| ATOM | 3392 | CA GLY B 195 | 65.442 | -13.52 | 23.573 | 1.00 | 31.60 | | C |
| ANISOU | 3392 | CA GLY B 195 | 3324 | 3430 | 5246 | 434 | -.292 | -293 | C |
| ATOM | 3393 | C GLY B 195 | 68.202 | -14.457 | 24.517 | 1.00 | 35.22 | | C |
| ANISOU | 3393 | C GLY B 195 | 3794 | 3854 | 5733 | 443 | -383 | -242 | C |
| ATOM | 3394 | O GLY B 195 | 56.745 | -15.005 | 24.573 | 1.00 | 34.74 | | O |
| ANISOU | 3394 | O GLY B 195 | 3728 | 3749 | 5724 | 503 | -425 | -242 | O |
| ATOM | 3395 | N LEU B 196 | 67.591 | -13.959 | 25.831 | 1.00 | 33.44 | | N |
| AMISOU | 3395 | N LEU B 196 | 3002 | 3049 | 5463 | 387 | -414 | -195 | N |
| ATOM | 3396 | CA LEU B 196 | 57.351 | -14.803 | 27.025 | 1.00 | 33.40 | | C |
| ANISOU | 3396 | CA LEU B 196 | 3615 | 3623 | 5470 | 393 | -498 | -138 | C |
| ATOM | 3397 | C LEU B 196 | 65.452 | -16.051 | 25.729 | 1.00 | 34.14 | | C |
| ANISOU | 3397 | C LEU B 196 | 3778 | 3029 | 5555 | 411 | -524 | -1113 | C |
| ATOM | 3398 | O LEU B 196 | 60.747 | -17.101 | 27.246 | 1.00 | 32.70 | | O |
| ANISOU | 3398 | O LEU B 196 | 31505 | 3398 | 5423 | 451 | -585 | -88 | O |
| ATOM | 3399 | CB LEU B 196 | 66.680 | -13.969 | 28.143 | 1.00 | 31.43 | | C |
| ANISOU | 3399 | CB LEU B 196 | 3378 | 3412 | 5155 | 324 | -519 | -93 | C |
| ATOM | 3400 | OG LEU B 196 | 67.029 | -12.800 | 28.792 | 1.00 | 31.82 | | O |
| ANISOU | 3400 | OG LEU B 196 | 3339 | 3537 | 5190 | 301 | -513 | -107 | O |
| ATOM | 3401 | CD1 LEU B 196 | 60 577 | -11.342 | 29.542 | 1.00 | 29.84 | | C |
| ANISOU | 3401 | CD1 LEU B 196 | 3142 | 3322 | 4874 | 231 | -510 | -81 | C |
| ATOM | 3402 | CD2 LEU B 196 | 68.799 | -13.299 | 29.602 | 1.00 | 34.84 | | C |
| ANISOU | 3402 | CD2 LEU B 196 | 3674 | 3939 | 5626 | 348 | -578 | -98 | C |
| ATOM | 3403 | N ALA B 197 | 55.458 | -15.865 | 25.901 | 1.00 | 31.75 | | N |
| ANISOU | 3403 | N ALA B 197 | 3525 | a.311 | 5225 | 379 | -480 | -13.5 | N |
| ATOM | 3404 | CA ALA B 197 | 64.625 | -15.995 | 26.403 | 1.00 | 32.72 | | C |
| AMISOU | 3404 | CA ALA B 197 | 3716 | 3358 | 5359 | 389 | -497 | -133 | C |
| ATOM | 3405 | C ALA B 197 | 65.430 | -17.950 | 24.512 | 1.00 | 31.01 | | C |
| ANISOU | 4405 | C ALA B 197 | 3487 | 3090 | 5207 | 454 | -492 | -132 | C |
| ATOM | 3406 | O ALA B 197 | 65.397 | -19.196 | 24.673 | 1.00 | 31.92 | | O |
| ANISOU | 3406 | O ALA B 197 | 3634 | 3128 | 5300 | 498 | -540 | -168 | O |

TABLE 3-continued

```
ATOM     3407  CB  ALA B 197      63.390 -16.441  24.559  1.00 30.29           C
ANISOU   3407  CB  ALA B 197      3453  3062  4992    338  -450  -147          C
ATOM     3408  N   TYR B 198      66.112 -17.394  23.540  3.00 39.47           N
ANISOU   3408  N   TYR B 198      3376  3957  5144    489  -430  -242          N
ATOM     3409  CA  TYR B 198      67.005 -18.155  22.582  1.00 34.35           C
ANISOU   3409  CA  TYR B 198      3344  3515  5592   1-365  -415  -293         C
ATOM     3410  C   TYR B 198      67.960 -39.049  23.458  1.00 86.58           C
ANISOU   3410  C   TYR B 198      4090  3760 50141    626  -477  -277          C
ATOM     3411  O   TYR B 198      55.078 -20.252  23.129  1.00 35.44           O
ANISOU   3411  O   TYR B 198      3975  3541  5949    681  -502  -295          O
ATOM     3412  CB  TYR B 198      67.761 -17.212  21.747  1.00 33.03           C
ANISOU   3412  CB  TYR B 198      3725  3519  5621     57 -3445  -354          C
ATOM     3413  CG  TYR B 198      68.6195  7.930  20.772  1.00 39.44           C
ANISOU   3413  CG  TYR B 198      4402  4253  6380    557  -308  -418          C
ATOM     3414  CD1 TYR B 198      68.214 -18.350  19.514  1.00 39.130          C
ANISOU   3414  CD1 TYR B 198      4495  4219  6436    575  -267  -472          C
ATOM     3415  CD2 TYR B 198      70.042 -130385  21.104  1.00 39.29           C
ANISOU   3415  CD2 TYR B 198      4307  4198  6425    717  -322  -429          C
ATOM     3416  CE1 TYR B 198      69.047 -15.964  18.589  1.00 43.17           C
ANISOU   3416  CE1 TYR B 198      4896  4630  6875    750  -235  -538          C
ATOM     3417  CE2 TYR B 198      70.873 -13.652  20.138  1.00 44.26           C
ANISOU   3417  CE2 TYR B 198      4906  4810  7102    797  -292  -493          C
ATOM     3418  CZ  TYR B 198      70.331 -19.245  18.940  1.00 40.95           C
ANISOU   3418  CZ  TYR B 198      4541  4358  0659    811  -247  -547          C
ATOM     3419  OH  TYR B 198      71.114 -19.821   1.5014 1.00 46.84           O
ANISOU   3419  OH  TYR B 198      5514  5347  7597    588  -211  -615          O
ATOM     3420  N   LYS B 199      58.588 -18.  517  24.510  1.00 35.36         N
ANISOU   3420  N   LYS B 199      38813  3659  5892    611  -507 -2139         N
ATOM     3421  CA  LYS B 199      69.623 -19.275  25.227  1   00 39.91         C
ANISOU   3421  CA  LYS B 199      4414  4218  0533    684  -557  -220          C
ATOM     3422  C   LYS B 199      69.003 -20.371  26.050  1.00 43.57           C
ANISOU   3422  C   LYS B 199      4942  4505  7005    588  -643  -156          C
ATOM     3423  O   LYS B 199      69.085 -21.260  25.504  1.50 44.13           O
ANISOU   3423  O   LYS B 199      4998  46.33  7138    753  -696  -138         O
ATOM     3424  CB  LYS B 199      19.410 -13.387  25.130  1.00 41.15           C
ANISOU   3424  CB  LYS B 199      4495  4458  5681    606  -585  -197          C
ATOM     3425  CB  LYS B 199      71.353 -17.444  25.435  1.00 43.13           C
ANISOU   3425  CB  LYS B 199      4064  4760  6943    673  -516  -258          C
ATOM     3426  CD  LYS B 199      71.595 -16.348  26.350  1.00 50.45           C
ANISOU   3426  CD  LYS B 199      5525  5792  7851    630  -528  -249          C
```

TABLE 3-continued

| | | | | | |
|---|---|---|---|---|---|
| ATOM | 3427 CE LYS B 199 | 72.657 -15.315 25.509 1.00 57.34 | | | C |
| ANISOU | 3427 CE LYS B 199 | 8301 6703 8705 618 -446 -390 | | | C |
| ATOM | 3428 NZ LYS B 199 | 73.926 -14.846 25.133 140 44.58 | | | N |
| ANISOU | 3428 NZ LYS B 199 | 7133 7715 9664 579 -466 -308 | | | N |
| ATOM | 3429 N ARG B 200 | 67.691 -201.282 25.246 1.00 38.18 | | | N |
| ANISOU | 3429 N ARG B 200 | 4331 2501 6273 6119 -546 -121 | | | N |
| ATOM | 3430 CA ARG B 200 | 66.972 -21.325 25.958 1.00 38.04 | | | C |
| ANISOU | 3430 CA ARG B 200 | 4332 13807 5255 611 -710 -57 | | | C |
| ATOM | 3431 C ARG B 200 | 65.303-22.326 26.084 1.00 37.24 | | | C |
| ANISOU | 3431 C ARG B 200 | 4346 3510 6193 523 -702 -65 | | | C |
| ATOM | 3432 O ARG B 200 | 65.454 -23.568 25.577 1.00 40.75 | | | O |
| ANISOU | 3432 O ARG B 200 | 4858 3992 6638 594 -744 -33 | | | O |
| ATOM | 3433 CB ARG B 200 | 05.931 -20.734 27.900 1.00 37.92 | | | C |
| ANISOU | 3433 CB ARG B 200 | 4400 3629 6179 527 -726 7 | | | C |
| ATOM | 3434 CG ARG B 200 | 66.520. -20.110 29.133 1 00 33.72 | | | C |
| ANISOU | 3434 CG ARG B 200 | 5085 4637 6891 519 -763 513 | | | C |
| ATOM | 3435 CD ARG B 200 | 65.432 -19.282 29.843 1.00 41.95 | | | C |
| ANISOU | 3435 CD ARG B 200 | 4891 4454 6585 431 -757 96 | | | C |
| ATOM | 3436 NE ARG B 200 | 64.304 -20.034 30.463 1.00 43.84 | | | N |
| ANISOU | 3436 NE ARG B 200 | 4824 4263 6-1426 396 -797 166 | | | N |
| ATOM | 3437 CZ ARG B 200 | 64.414 -23.710 31.148 1.00 45.47 | | | C |
| ANISOU | 3437 CZ ARG B 200 | 5425 4839 7012 404 -8.64 244 | | | C |
| ATOM | 3438 NH1 ARG B 200 | 65.522 -20.641 132.a68 1.00 44.36 | | | N |
| ANISOU | 3438 NH1 ARG B 200 | 5234 4800 6950 450 -306 259 | | | N |
| ATOM | 3439 NH2 ARG B 200 | 63.3934 -21.422 32.167 1.03 41.48 | | | N |
| ANISOU | 3439 NH2 ARG B 200 | 4937 4234 6493 366 -92 310 | | | N |
| ATOM | 3440 N ASP B 201 | 66.615 -22.355 24.787 1.00 35.72 | | | N |
| ANISOU | 3440 N ASP B 201 | 44 3410 6019 6t.0 -648 -168 | | | N |
| ATOM | 3441 CA ASP B 201 | 66.078 -23.351 23.846 1.00 37.86 | | | C |
| ANISOU | 3441 CA ASP B 201 | 4477 3533 631 577 -641 -211 | | | C |
| ATOM | 3442 C ASP B 201 | 64.532 -23.107 23.606 1.00 33.51 | | | C |
| ANISOU | 3442 C ASP B 201 | 4750 3796 6466 590 -526 -201 | | | C |
| ATOM | 3443 O ASP B 201 | 63.829 -24.043 23.404 1.00 37.54 | | | O |
| ANISOU | 3443 O ASP B 201 | 4564 3462 6206 577 -650 -200 | | | O |
| ATOM | 3444 CB ASP B 201 | 66.344 -24813 24.316 1.00 40.69 | | | C |
| ANISOU | 3444 CB ASP B 201 | 4870 3835 6754 733 -708 -181 | | | C |
| ATOM | 3445 CG ASP B 201 | 65003 -25.916 23.132 1.33 45.82 | | | C |
| ANISOU | 3445 CG ASP B 201 | 5706 4507 7575 765 -697 -240 | | | C |
| ATOM | 3446 OD1 ASP B 201 | 65.992 -25.637 21.343 1.00 44.27 | | | O |
| ANISOU | 3446 OD1 ASP B 201 | 5379 4206 7234 774 -637 -334 | | | O |

TABLE 3-continued

| | | | | | | | | | | |
|---|---|---|---|---|---|---|---|---|---|---|
| ATOM | 3447 | OD2 | ASP B 201 | 65.701 | -27.038 | 23.564 | 1.30 | 47.52 | | O |
| ANISOU | 3447 | OD2 | ASP B 201 | 5853 | 4487 | 77153 | 773 | -750 | -215 | O |
| ATOM | 3448 | N | ILE B 202 | 64.162 | -21.840 | 23.565 | 1.00 | 36.68 | | N |
| ANISOU | 3448 | N | ILE B 202 | 4397 | 3555 | 6062 | 531 | -534 | -1313 | N |
| ATOM | 3449 | CA | ILE B 202 | 62.772 | -21.461 | 23.367 | 1.30 | 35.51 | | C |
| ANISOU | 3449 | CA | ILE B 202 | 4271 | 3394 | 5825 | 455 | -558 | -18 | C |
| ATOM | 3450 | C | ILE B 202 | 62.927 | -20.912 | 21.940 | 1.00 | 37.17 | | C |
| ANISOU | 3450 | C | ILE B 202 | 4471 | 3642 | 6010 | 468 | -428 | -269 | C |
| ATOM | 3451 | O | ILE B 202 | 63.755 | -20.753 | 21.532 | 1.00 | 37.24 | | O |
| ANISOU | 3451 | O | ILE B 202 | 4423 | 3739 | 6316 | 5.040 | -455 | -302 | O |
| ATOM | 3452 | CB | ILE B 202 | 52.243 | -23.434 | 24.390 | 1.00 | 35.32 | | C |
| ANISOU | 3452 | CB | ILE B 202 | 4311 | 3520 | 5818 | 389 | -572 | -123 | C |
| ATOM | 3453 | CG1 | ILE B 202 | 62.396 | -21022 | 25.833 | 1.00 | 30.15 | | C |
| ANISOU | 3453 | CG1 | ILE B 202 | 3366 | 3143 | 5490 | 2851 | -642 | -42 | C |
| ATOM | 3454 | CG2 | ILE B 202 | 60.807 | -13.933 | 24.326 | 1.00 | 34.84 | | C |
| ANISOU | 3454 | CG2 | ILE B 202 | 4216 | 3404 | 5617 | 315 | -548 | -121 | C |
| ATOM | 3455 | CD1 | ILE B 202 | 51.525 | -2230 | 26.043 | 1.00 | 40.86 | | C |
| ANISOU | 3455 | CD1 | ILE B 202 | 5008 | 4019 | 6437 | 373 | -683 | -6 | C |
| ATOM | 3456 | N | PRO B 203 | 63.836 | -21.311 | 21.097 | 1.00 | 26.92 | | N |
| ANISOU | 3456 | N | PRO B 203 | 4490 | 3577 | 5960 | 446 | -434 | -304 | N |
| ATOM | 3457 | CA | PRO B 203 | 61.961 | -20.762 | 19750 | 1.30 | 33.26 | | C |
| ANISOU | 3457 | CA | PRO B 203 | 4017 | 3153 | 5461 | 462 | -422 | -374 | C |
| ATOM | 3458 | C | PRO B 203 | 61.770 | -19.211 | 19.752 | 1.00 | 34 15 | | C |
| ANISOU | 3458 | C | PRO B 203 | 4099 | 3374 | 5533 | 420 | -372 | -361 | C |
| ATOM | 3459 | O | PRO B 203 | 60.319 | -10.713 | 20.475 | 1.30 | 32.93 | | O |
| ANISOU | 3459 | O | PRO B 203 | 3964 | 3250 | 5316 | 263 | -338 | -307 | O |
| ATOM | 3460 | CB | PRO B 203 | 60.851 | -21.431 | 9.315 | 1.00 | 37.47 | | C |
| ANISOU | 3460 | CB | PRO B 203 | 4665 | 3695 | 6029 | 434 | -431 | -410 | C |
| ATOM | 3461 | CG | PRO B 203 | 63.120 | -22.309 | 23.326 | 1.00 | 301.74 | | C |
| ANISOU | 3461 | CG | PRO B 203 | 4343 | 3863 | 5297 | 7.93 | -499 | -343 | C |
| ATOM | 3462 | CD | PRO B 203 | 60.775 | -22.250 | 21.313 | 1.013 | 43.28 | | C |
| ANISOU | 3462 | CD | PRO B 203 | 4932 | 3928 | 7396 | 434 | -534 | -279 | C |
| ATOM | 3463 | N | VAL B 204 | 52.566 | -13.482 | 18.050 | 1.00 | 34.10 | | N |
| ANISOU | 3463 | N | VAL B 204 | 4051 | 3422 | 5483 | 453 | -313 | -436 | N |
| ATOM | 3464 | CA | VAL B 204 | 62.480 | -17.052 | 18.852 | 1.00 | 32.36 | | C |
| ANISOU | 3464 | CA | VAL B 204 | 3883 | 3362 | 5282 | 419 | -259 | -393 | C |
| ATOM | 3465 | C | VAL B 204 | 52.402 | -16.796 | 17.369 | 1.33 | 32.79 | | C |
| ANISOU | 3465 | C | VAL B 204 | 3869 | 3368 | 5222 | 439 | -197 | -456 | C |
| ATOM | 3466 | O | VAL B 204 | 62.337 | -17.165 | 15.605 | 1.00 | 03.31 | | O |
| ANISOU | 3466 | O | VAL B 204 | 3912 | 3428 | 5316 | 498 | -167 | -511 | O |

TABLE 3-continued

| ATOM | 3467 | CB | VAL | B | 204 | 63.738 | -15.38 | 19.446 | 1.00 | 31.23 | C |
|---|---|---|---|---|---|---|---|---|---|---|---|
| ANISOU | 3467 | CB | VAL | B | 204 | 3590 3155 5091 438 -243 -380 | | | | | C |
| ATOM | 3468 | CG1 | VAL | B | 204 | 63.567 | -14.880 | 19.375 | 1.00 | 33.15 | C |
| ANISOU | 3468 | CG1 | VAL | B | 204 | 3434 3122 4899 395 -190 -365 | | | | | C |
| ATOM | 3469 | CG2 | VAL | B | 204 | 53.940 | -16.726 | 20.919 | 1.00 | 27.58 | C |
| ANISOU | 3469 | CG2 | VAL | B | 204 | 3115 2599 4564 429 -311 -321 | | | | | C |
| ATOM | 3470 | N | VAL | B | 205 | 61.327 | -16.140 | 16.986 | 1.00 | 39.29 | N |
| ANISOU | 3470 | N | VAL | B | 205 | 3572 3075 4826 394 -176 -446 | | | | | N |
| ATOM | 3471 | CA | VAL | B | 205 | 61.302 | -15.788 | 15.595 | 1.00 | 30.77 | C |
| ANISOU | 3471 | CA | VAL | B | 205 | 3651 3185 4840 408 -1.20 -496 | | | | | C |
| ATOM | 3472 | C | VAL | B | 205 | 51.325 | -14.264 | 15.500 | 1.00 | 131.87 | C |
| ANISOU | 3472 | C | VAL | B | 205 | 3769 3400 4941 389 -56 -471 | | | | | C |
| ATOM | 3473 | O | VAL | B | 205 | 60 760 | -13.457 | 16.256 | 3.00 | 34.93 | O |
| ANISOU | 3473 | O | VAL | B | 205 | 4156 3810 5304 342 -66 -418 | | | | | O |
| ATOM | 3474 | CB | VAL | B | 205 | 59.677 | -15 134 | 1.5.124 | 1.00 | 34.10 | C |
| ANISOU | 3474 | CB | VAL | B | 205 | 4141 3595 5220 375 -142 -503 | | | | | C |
| ATOM | 3475 | CG1 | VAL | B | 205 | 59.511 | -15.710 | 12.66.5 | 1.00 | 34.14 | C |
| ANISOU | 3475 | CG1 | VAL | B | 205 | 4159 3650 5161 3915 -86 -554 | | | | | C |
| ATOM | 3476 | CG2 | VAL | B | 205 | 69.349 | -17.527 | 15.350 | 1.00 | 32.90 | C |
| ANISOU | 3476 | CG2 | VAL | B | 205 | 4024 3358 5118 379 -209 -521 | | | | | C |
| ATOM | 3477 | N | SER | B | 206 | 52.209 | -13.854 | 14.607 | 1.00 | 34.14 | N |
| ANISOU | 3477 | N | SER | B | 206 | 4026 2721 5220 426 6 -508 | | | | | N |
| ATOM | 3478 | CA | SER | B | 206 | 62.429 | -12.412 | 14.425 | 1.09 | 33.93 | C |
| ANISOU | 3478 | CA | SER | B | 206 | 3976 3759 5156 404 70 -4614 | | | | | C |
| ATOM | 3479 | C | SER | B | 206 | 61.664 | 1.879 | 12.243 | 1.00 | 39.67 | C |
| ANISOU | 3479 | C | SER | B | 206 | 3601 3387 4664 401 117 -496 | | | | | C |
| ATOM | 3480 | O | SER | B | 206 | 61.737 | -12.485 | 12.151 | 1.00 | 35.23 | O |
| ANISOU | 3480 | O | SER | B | 206 | 4497 2956 5221 443 135 -550 | | | | | O |
| ATOM | 3481 | CB | SER | B | 206 | 53.933 | -12.100 | 14.270 | 1.00 | 39.12 | C |
| ANISOU | 3481 | CB | SER | B | 206 | 4569 4436 5857 440 117 -506 | | | | | C |
| ATOM | 3482 | OG | SER | B | 206 | 54.453 | -12.340 | 15.603 | 1.00 | 43.35 | O |
| ANISOU | 3482 | OG | SER | B | 206 | 5068 4949 6455 429 67 -475 | | | | | O |
| ATOM | 3483 | N | LEU | B | 207 | 61.037 | -10.703 | 13.394 | 1.00 | 30.04 | N |
| ANISOU | 3483 | N | LEU | B | 207 | 2531 13344 4537 352 140 -451 | | | | | N |
| ATOM | 3484 | CA | LEU | B | 207 | 50.406 | -10.034 | 121199 | 1.00 | 30.81 | C |
| ANISOU | 3484 | CA | LEU | B | 207 | 3653 3489 4555 366 392 -455 | | | | | C |
| ATOM | 3485 | C | LEU | B | 207 | 61.141 | -8.742 | 11.905 | 1.00 | 31.29 | C |
| ANISOU | 3485 | C | LEU | B | 207 | 3693 3591 4632 362 269 -433 | | | | | C |
| ATOM | 3486 | O | LEU | B | 207 | 60.993 | -7.850 | 13.717 | 1.00 | 32.74 | O |
| ANISOU | 3486 | O | LEU | B | 207 | 3868 3778 4793 325 270 -387 | | | | | O |

TABLE 3-continued

| | | | | | | | | | | |
|---|---|---|---|---|---|---|---|---|---|---|
| ATOM | 3487 | CB | LEU B 207 | 58.918 | -9.594 | 12.497 | 1.00 | 23.26 | | C |
| ANISOU | 3487 | CB | LEU B 207 | 4027 | 3520 | 4530 | 227 | 157 | -417 | C |
| ATOM | 3488 | CG | LEU B 207 | 57.927 | -10.344 | 12.811 | 1.00 | 33.86 | | C |
| ANISOU | 3488 | CG | LEU B 207 | 4121 | 3546 | 4599 | 313 | 80 | -429 | C |
| ATOM | 3489 | CD1 | LEU B 207 | 56.458 | -10.423 | 12.854 | 1.00 | 35.46 | | C |
| ANISOU | 3489 | CD1 | LEU B 207 | 4355 | 4074 | 5044 | 280 | 58 | -395 | C |
| ATOM | 3490 | CD2 | LEU B 207 | 58.032 | -12.106 | 11.968 | 1.00 | 37.58 | | C |
| ANISOU | 3490 | CC2 | LEU B 207 | 4612 | 4291 | 5377 | 346 | 61 | -404 | C |
| ATOM | 3491 | N | THR B 208 | 61.900 | -8.618 | 10.810 | 1.00 | 36.47 | | N |
| ANISOU | 3491 | N | THR B 208 | 338 | 4279 | 5243 | 397 | 236 | -455 | N |
| ATOM | 3492 | CA | THR B 208 | 52.918 | -7.567 | 10 630 | 1.00 | 33.75 | | C |
| ANISOU | 3492 | CA | THR B 208 | 3952 | 3967 | 4906 | 393 | 413 | -447 | C |
| ATOM | 3493 | C | THR B 208 | 62.758 | -7.046 | 9.239 | 1.00 | 32.20 | | C |
| ANISOU | 3493 | C | THR B 208 | 2784 | 13819 | 4633 | 413 | 434 | -452 | C |
| ATOM | 3494 | O | THR B 208 | 61.922 | -7.544 | 3.436 | 1.00 | 38.97 | | O |
| ANISOU | 3494 | O | THR B 208 | 3676 | 3677 | 441 | 5 | 435 | 469 | -474 O |
| ATOM | 3495 | CB | THR B 208 | 64.370 | -8.160 | 10.759 | 1.00 | 37.79 | | C |
| ANISOU | 3495 | CB | THR B 208 | 4389 | 4469 | 54610 | 422 | 427 | -467 | C |
| ATOM | 3496 | OG1 | THR B 208 | 64.605 | -9.097 | 9.662 | 1.00 | 06.26 | | O |
| ANISOU | 3496 | OG1 | THR B 208 | 4473 | 4541 | 558.2 | 477 | 444 | -543 | O |
| ATOM | 3497 | OG2 | THR B 208 | 64.456 | -9.012 | 1.931 | 1.00 | 36.13 | | O |
| ANISOU | 3497 | OG2 | THR B 208 | 4171 | 4209 | 5348 | 47 | 344 | -490 | O |
| ATOM | 3498 | N | ASN B 209 | 83.552 | -6.045 | 8 931 | 1.30 | 31.22 | | N |
| ANISOU | 3498 | N | ASN B 209 | 3630 | 3723 | 4503 | 405 | 562 | -429 | N |
| ATOM | 3499 | CA | ASN B 209 | 83.647 | -5.6019 | 7.554 | 1.00 | 32.39 | | C |
| ANISOU | 3499 | CA | ASN B 209 | 3303 | 3966 | 4649 | 409 | 640 | -432 | C |
| ATOM | 3500 | C | ASN B 209 | 613.063 | -5.720 | 7.093 | 1.00 | 35.06 | | C |
| ANISOU | 3500 | C | ASN B 209 | 4330 | 4284 | 4953 | 453 | 706 | -464 | C |
| ATOM | 3501 | O | ASN B 209 | 65.508 | -4.904 | 6.191 | 1.00 | 04.98 | | O |
| ANISOU | 3501 | O | ASN B 209 | 4067 | 4316 | 4906 | 458 | 792 | -449 | O |
| ATOM | 3502 | CB | ASN B 209 | 63.197 | -4.126 | 7.436 | 1.00 | 31.33 | | C |
| ANISOU | 3502 | CB | ASN B 209 | 3753 | 3847 | 4472 | 396 | 589 | -363 | C |
| ATOM | 3503 | CG | ASN B 209 | 61.716 | -8.938 | 7.774 | 1.00 | 34.03 | | C |
| ANISOU | 3503 | CG | ASN B 209 | 4087 | 4136 | 4706 | 381 | 631 | -330 | C |
| ATOM | 3504 | OD1 | ASN B 209 | 60.910 | -3.576 | 6.923 | 1.00 | 136.65 | | O |
| ANISOU | 3504 | OD1 | ASN B 209 | 4467 | 4500 | 4960 | 396 | 643 | -311 | O |
| ATOM | 3505 | ND2 | ASN B 209 | 61.379 | -4.120 | 9.004 | 1.00 | 30.66 | | N |
| ANISOU | 3505 | ND2 | ASN B 209 | 3658 | 3667 | 4331 | 352 | 565 | -321 | N |
| ATOM | 3506 | N | ILE B 210 | 65.833 | -5.611 | 7.702 | 1.00 | 34.73 | | N |
| ANISOU | 3506 | N | ILE B 210 | 13995 | 4221 | 4998 | 459 | 569 | -505 | N |

TABLE 3-continued

| | | | | | | | | | | |
|---|---|---|---|---|---|---|---|---|---|---|
| ATOM | 3507 | CA | ILE | B | 210 | 67.227 | -9.753 | 7.272 | 1.00 | 35.05 C |
| ANISOU | 3507 | CA | ILE | B | 210 | 4392 4410 5196 496 733 -540 C | | | | |
| ATOM | 3508 | C | ILE | B | 210 | 67.632 | -8.221 | 7.514 | 1.00 | 36.23 C |
| ANISOU | 3508 | C | ILE | B | 210 | 4345 4655 5526 545 676 -685 C | | | | |
| ATOM | 3509 | O | ILE | B | 210 | 67.224 | -5.304 | 4.521 | 1.00 | 3459 O |
| ANISOU | 3509 | O | ILE | B | 210 | 3691 4143 5100 535 590 -602 O | | | | |
| ATOM | 3510 | CB | ILE | B | 210 | 68.151 | -5.754 | 8.040 | 1.00 | 36.14 C |
| ANISOU | 3510 | CB | ILE | B | 210 | 4039 4422 5272 449 768 -501 C | | | | |
| ATOM | 3511 | CG1 | ILE | B | 210 | 69.568 | -5.758 | 7.459 | 1.00 | 4149 C |
| ANISOU | 3511 | CG1 | ILE | B | 210 | 4691 5193 6831 473 846 -532 C | | | | |
| ATOM | 3512 | CG2 | ILE | B | 210 | 68.184 | -6.087 | 9.521 | 1.00 | 38.13 C |
| ANISOU | 3512 | CG2 | ILE | B | 210 | 4007 4372 5347 42.6 682 -496 C | | | | |
| ATOM | 3513 | CD1 | ILE | B | 210 | 69.631 | -5.909 | 6.145 | 1.00 | 42.07 C |
| ANISOU | 3513 | CD1 | ILE | B | 210 | 47135 5271 5977 476 951 -1315 C | | | | |
| ATOM | 3514 | N | ASN | B | 211 | 68.438 | -3.826 | 6.641 | 1.30 | 37.22 N |
| ANISOU | 3514 | N | ASN | B | 211 | 4191 4555 5396 599 723 -662 N | | | | |
| ATOM | 3515 | CA | ASN | B | 211 | 63.767 | -13.262 | 6.837 | 1.00 | 42.30 C |
| ANISOU | 3515 | CA | ASN | B | 211 | 4819 5160 6092 653 667 -727 C | | | | |
| ATOM | 3516 | C | ASN | B | 211 | 89.763 | -10.527 | 7.962 | 1 00 | 44.21 C |
| ANISOU | 3516 | C | ASN | B | 211 | 4934 5374 8440 654 633 -726 C | | | | |
| ATOM | 3517 | O | ASN | B | 211 | 69.606 | -11.496 | 6.679 | 1.00 | 42.79 O |
| ANISOU | 3517 | O | ASN | B | 211 | 4810 5138 6310 673 552 -743 O | | | | |
| ATOM | 3518 | CB | ASN | B | 211 | 69.249 | -18.919 | 5.519 | 1.00 | 49.36 C |
| ANISOU | 3518 | CB | ASN | B | 211 | 5776 6156 7012 723 724 -789 C | | | | |
| ATOM | 3519 | CG | ASN | B | 211 | 63.100 | -11.074 | 4.537 | 1.00 | 56.09 C |
| ANISOU | 3519 | CG | ASN | B | 211 | 66.54 6961 7697 729 723 -817 C | | | | |
| ATOM | 3520 | OD1 | ASN | B | 211 | 87.911 | -12.002 | 4.63 2133 | 1.00 | 60.74 O |
| ANISOU | 3520 | OD1 | ASN | B | 211 | 7292 7504 3284 742 649 -849 O | | | | |
| ATOM | 3521 | ND2 | ASN | B | 211 | 67.981 | -10.156 | 3.539 | 1.00 | 54.42 N |
| ANISOU | 3521 | ND2 | ASN | B | 211 | 6462 91817 7400 720 803 -793 N | | | | |
| ATOM | 3522 | N | HIS | B | 212 | 791.7819 | -9.540 | 8.425 | 1.00 | 40.35 N |
| ANISOU | 3522 | N | HIS | B | 212 | 4426 4929 5988 631 594 -702 N | | | | |
| ATOM | 3523 | CA | HIS | B | 212 | 71.821 | -9.8610 | 0.125 | 1.00 | 39.54 C |
| ANISOU | 3523 | CA | HIS | B | 212 | 4234 430 5980 536 564 -706 C | | | | |
| ATOM | 3524 | C | HIS | B | 212 | 71.922 | -3.729 | 10.039 | 1.00 | 21771 C |
| ANISOU | 3524 | C | HIS | B | 212 | 3972 458.3 5773 564 1562 -647 C | | | | |
| ATOM | 3525 | O | HIS | B | 212 | 72.379 | -7-558 | 9.599 | 1.00 | 37.72 O |
| ANISOU | 3525 | O | HIS | B | 212 | 3954 4524 5743 522 739 -9116 O | | | | |
| ATOM | 3526 | CB | HIS | B | 212 | 73.162 | -9.9781 | 8.447 | 1.00 | 41.13 C |
| ANISOU | 3526 | CB | HIS | B | 212 | 4354 5366. 32-111 1 680 741 -760 C | | | | |

TABLE 3-continued

| | | | | | | | | | | | |
|---|---|---|---|---|---|---|---|---|---|---|---|
| ATOM | 3527 | CG | HIS | B | 212 | 73.223 | -10931 | 7.392 | 1.00 | 43.90 | C |
| ANISOU | 3527 | CG | HIS | B | 212 | 4732 | 1423 | 6524 | 754 | 770 | -817 C |
| ATOM | 3528 | ND1 | HIS | B | 212 | 73.223 | -12.2518 | 7.479 | 1.00 | 50.73 | N |
| ANISOU | 3528 | ND1 | HIS | B | 212 | 5511 | 5246 | 7437 | 817 | 704 | -670 N |
| ATOM | 3529 | CD2 | HIS | B | 212 | 73.108 | -10.714 | 5.9132 | 1.00 | 45.88 | C |
| ANISOU | 3529 | CD2 | HIS | B | 212 | 5011 | 5727 | 6694 | 775 | 855 | -841 C |
| ATOM | 3530 | CE1 | HIS | B | 212 | 73.222 | -12.881 | 6.278 | 1.00 | 46.31 | C |
| ANISOU | 3530 | CE1 | HIS | B | 212 | 5074 | 5700 | 6823 | 876 | 751 | -930 C |
| ATOM | 3531 | NE2 | HIS | B | 212 | 78.142 | -11.946 | 5.338 | 1.05 | 49.86 | N |
| ANISOU | 3531 | NE2 | HIS | B | 212 | 55136 | 5216 | 7193 | 851 | 841 | -916 N |
| ATOM | 3532 | N | SER | B | 213 | 71.910 | -9.0158 | 11.310 | 1.09 | 35.75 | N |
| ANISOU | 3532 | N | SER | B | 213 | 3700 | 4294 | 5582 | 551 | 576 | -531 N |
| ATOM | 3533 | CA | SER | B | 213 | 71.899 | -8.052 | 12.387 | 1.00 | 35.09 | C |
| ANISOU | 3533 | CA | SER | B | 213 | 3600 | 42021 | 5522 | 481 | 556 | -580 C |
| ATOM | 3534 | C | SER | B | 213 | 72.253 | -8.077 | 13.647 | 1.00 | 32.30 | C |
| ANISOU | 3534 | C | SER | B | 213 | 3283 | 3897 | 5316 | 498 | 4611 | -565 C |
| ATOM | 3535 | O | SER | B | 213 | 72.303 | -10.100 | 10.577 | 1.90 | 3480 | O |
| ANISOU | 3535 | O | SER | B | 213 | 3580 | 4110 | 5580 | 559 | 417 | -518 O |
| ATOM | 3536 | CB | SER | B | 213 | 70.441 | -7534 | 12.534 | 1.00 | 35.54 | C |
| ANISOU | 3536 | CB | SER | B | 213 | 8750 | 4241 | 5513 | 435 | 531 | -536 C |
| ATOM | 3537 | OG | SER | B | 213 | 69.431 | -8.637 | 13.025 | 1.04 | 35.38 | O |
| ANISOU | 3537 | OG | SER | B | 213 | 3779 | 4171 | 5493 | 451 | 441 | -543 O |
| ATOM | 3538 | N | PRO | B | 214 | 72.549 | -8.228 | 14.791 | 1.00 | 33.80 | N |
| ANISOU | 3538 | N | PRO | B | 214 | 33.58 | 4016 | 5450 | 448 | 427 | -553 N |
| ATOM | 3539 | CA | PRO | B | 214 | 72.781 | -8.926 | 16.081 | 1.00 | 37.95 | C |
| ANISOU | 3539 | CA | PRO | B | 214 | 38137 | 4516 | 6050 | 451 | 332 | -547 C |
| ATOM | 3540 | C | PRO | B | 214 | 71.657 | -3.848 | 16.432 | 1.00 | 37.64 | C |
| ANISOU | 3540 | C | PRO | B | 214 | 3697 | 4418 | 5986 | 478 | 253 | -533 C |
| ATOM | 3541 | O | PRO | B | 214 | 71.900 | -10.332 | 17.066 | 1.00 | 35.65 | O |
| ANISOU | 3541 | O | PRO | B | 214 | 3759 | 4261 | .5905 | 519 | 182 | -539 O |
| ATOM | 3542 | CB | PRO | B | 214 | 72.862 | -7.782 | 174342 | 1.00 | 86.22 | C |
| ANISOU | 3542 | CB | PRO | B | 214 | 8608 | 4314 | 5640 | 386 | 320 | -511 C |
| ATOM | 3543 | CG | PRO | B | 214 | 73.661 | -6.783 | 15.233 | 1.00 | 35.43 | C |
| ANISOU | 3543 | CG | PRO | B | 214 | 3582 | 4855 | 5870 | 861 | 421 | -523 C |
| ATOM | 3544 | CD | PRO | B | 214 | 72.855 | -6.730 | 14.952 | 1.00 | 34.84 | C |
| ANISOU | 3544 | CD | PRO | B | 214 | 3714 | 4437 | 5855 | 378 | 481 | -525 C |
| ATOM | 3545 | N | LEU | B | 215 | 70.430 | -9.449 | 16.150 | 1.09 | 33.89 | N |
| ANISOU | 3545 | N | LEU | B | 215 | 3504 | 3929 | 5424 | 440 | 262 | -.509 N |
| ATOM | 3546 | CA | LEU | B | 215 | 69.299 | -10.299 | 16.524 | 1.00 | 05.481 | C |
| ANISOU | 3646 | CA | LEU | B | 215 | 3779 | 4078 | 5524 | 450 | 139 | -404 C |

TABLE 3-continued

| ATOM | 3547 | C | LEU | B | 215 | 392317 -11.517 15.725 1.00 86.16 C |
|------|------|---|-----|---|-----|------|
| ANISOU | 3547 | C | LEU | B | 215 | 3892 4181 5717 518 179 -539 C |
| ATOM | 3548 | O | LEU | B | 215 | 68.737 -12.558 16.205 1.00 34.29 O |
| ANISOU | 3548 | O | LEU | B | 215 | 3590 3839 5496 539 106 -537 O |
| ATOM | 3549 | CB | LEU | B | 215 | 67.984 -9.430 16.319 1.00 31.19 C |
| ANISOU | 3549 | CB | LEU | B | 215 | 3309 3537 .5004 393 207 -461 C |
| ATOM | 3550 | CG | LEU | B | 215 | 66.6167 -10.220 10.500 1.00 33.41 C |
| ANISOU | 3550 | CG | LEU | B | 215 | 3665 8774 5254 395 144 -445 C |
| ATOM | 3551 | CD1 | LEU | B | 215 | 65.534 -10.539 18.015 1.00 33.42 C |
| ANISOU | 3551 | CD1 | LEU | B | 215 | 3552 3746 5290 377 50 5011 C |
| ATOM | 3552 | CD2 | LEU | B | 215 | 65.537 -9.253 13.136 1.30 32.161 C |
| ANISOU | 3552 | CD2 | LEU | B | 215 | 3553. 3635 5022 352 179 -418 C |
| ATOM | 3553 | N | LEU | B | 215 | 69.759 -11.611 14.507 1.00 59.04 N |
| ANISOU | 3553 | N | SER | B | 216 | 4239 4525 15070 5.54 252 -5.84 N |
| ATOM | 3554 | CA | SER | B | 216 | 69.730 -12.870 13.789 3.30 41.54 C |
| ANISOU | 3554 | CA | SER | B | 216 | 4.584 4505 6592 519 243 -535 C |
| ATOM | 3555 | C | SER | B | 216 | 70.510 -14.040 14.439 1.00 43.26 C |
| ANISOU | 3555 | C | SER | B | 216 | 4762 4931 51592 577 178 -555 C |
| ATOM | 3556 | O | SER | B | 216 | 70.053 -35.185 14.344 1400 43.51 O |
| ANISOU | 3556 | O | SER | B | 216 | 4341 4254 6737 714 131 -677 O |
| ATOM | 3557 | CB | SER | B | 216 | 59.893 -12.729 12.279 1.00 46.49 C |
| ANISOU | 3557 | CB | SER | B | 216 | 5220 5473 5971 549 327 -682 C |
| ATOM | 3558 | CG | SER | B | 216 | 11.077 -12.142 13.898 1.00 44.461 C |
| ANISOU | 3558 | OG | SER | B | 216 | 6 4855 5271 57155 6512 4010 -6197 C |
| ATOM | 3559 | N | SER | B | 217 | 71.550 -13 7515 15.204 1.00 38.07 N |
| ANISOU | 3559 | N | SER | B | 217 | 4023 4349 5092 673 159 -541 N |
| ATOM | 3560 | CA | SER | B | 217 | 72.286 -14.804 15.912 1.00 411.96 C |
| ANISOU | 3560 | CA | SER | B | 217 | 4475 4805 6663 737 104 -650 C |
| ATOM | 3561 | C | SER | B | 217 | 71.513 -15.3135 17.087 1.00 41.25 C |
| ANISOU | 3561 | C | SER | B | 217 | 4424 46519 9552 714 9 -503 C |
| ATOM | 3562 | O | SER | B | 217 | 71.970 -16.355 17.332 1.510 35.97 O |
| ANISOU | 3562 | O | SER | B | 217 | 3863 4372 6092 755 -57 -591 O |
| ATOM | 3563 | CB | SER | B | 217 | 73.556 -14.165 36.544 1.00 43.28 C |
| ANISOU | 3563 | CB | SER | B | 217 | 4534 5030 5582 733 115 -641 C |
| ATOM | 3564 | OG | SER | B | 217 | 74.502 -14.071 15.552 1.00 55.36 O |
| ANISOU | 3564 | OG | SER | B | 217 | 6004 6605 6427 775 194 -692 O |
| ATOM | 3565 | N | LEU | B | 218 | 70.375 -14.558 17.394 3.330 375.25 N |
| ANISOU | 3565 | N | LEU | B | 218 | 3951 4153 6015 644 3 -553 N |
| ATOM | 3566 | CA | LEU | B | 218 | 59.503 -14.995 18.590 1.00 36.55 C |
| ANISOU | 3566 | CA | LEU | B | 218 | 3940 4020 5927 510 -56 -502 C |

TABLE 3-continued

| | | | | | | | | | | |
|---|---|---|---|---|---|---|---|---|---|---|
| ATOM | 3567 | C | LEU | B | 218 | 63.151 | -15.365 | 13.136 | 1.00 | 37.55 C |
| ANISOU | 3567 | C | LEU | B | 218 | 4163 | 4104 | 6002 | 584 -99 | -495 C |
| ATOM | 3568 | O | LEU | B | 218 | 57.229 | -16.254 | 18.951 | 1.00 | 34.56 O |
| ANISOU | 3568 | O | LEU | B | 218 | 3326 | 3103 | 5528 | 535 -144 | -447 O |
| ATOM | 3569 | CB | LEU | B | 218 | 69.554 | -13.759 | 19.528 | 1.00 | 35.00 C |
| ANISOU | 3569 | CB | LEU | B | 218 | 3717 | 3575 | 5709 | 541 -551 | -455 C |
| ATOM | 3570 | CG | LEU | B | 218 | 70.572 | -13.347 | 20.200 | 1.00 | 38.56 C |
| ANISOU | 3570 | CG | LEU | B | 218 | 4071 | 4359 | 5211 | 550 -94 | -454 C |
| ATOM | 3571 | CD1 | LEU | B | 218 | 70.712 | -12.024 | 23.956 | 1.00 | 36.92 C |
| ANISOU | 3571 | CD1 | LEU | B | 218 | 3843 | 4209 | 5975 | 476 -87 | -421 C |
| ATOM | 3572 | CD2 | LEU | B | 218 | 71.411 | 4.425 | 21.329 | 1.00 | 40.31 C |
| ANISOU | 3572 | CD2 | LEU | B | 218 | 4257 | 4556 | 5402 | 600 -178 | -439 C |
| ATOM | 3573 | N | SER | B | 219 | 57.992 | -15.793 | 16.940 | 1.00 | 35.30 N |
| ANISOU | 3573 | N | SER | B | 219 | 3907 | 3807 | 5700 | 618 -57 | -553 N |
| ATOM | 3574 | CA | SER | B | 219 | 56.686 | -16.136 | 15.425 | 1.30 | 34.49 C |
| ANISOU | 3574 | CA | SER | B | 219 | 3837 | 3572 | 5547 | 594 -57 | -554 C |
| ATOM | 3575 | C | SER | B | 219 | 56.787 | -17.565 | 15.9.58 | 1.00 | 33.05 C |
| ANISOU | 3575 | C | SER | B | 219 | 4355 | 4053 | 603.9 | 555 -95 | -1403 C |
| ATOM | 3576 | O | SER | B | 219 | 67.779 | -13.038 | 15.383 | 1.00 | 35.95 O |
| ANISOU | 3576 | O | SER | B | 219 | 45163 | 13785 | 5813 | 721 -70 | -655 O |
| ATOM | 3577 | CB | SER | B | 219 | 66.393 | -15.510 | 15.223 | 1.00 | 37.71 C |
| ANISOU | 3577 | CB | SER | B | 219 | 4307 | 4133 | 5587 | 581 11 | -583 C |
| ATOM | 3578 | OG | SER | B | 219 | 66.451 | -13.985 | 15.534 | 1.00 | 37.01 O |
| ANISOU | 3578 | OG | SER | B | 219 | 4190 | 4101 | 5772 | 531 42 | -541 O |
| ATOM | 3579 | N | THR | B | 220 | 55.727 | -18.269 | 15.194 | 1.00 | 34.80 N |
| ANISOU | 3579 | N | THR | B | 220 | 4020 | 3582 | 5520 | 530 -150 | -583 N |
| ATOM | 3580 | CA | THR | B | 220 | 65.650 | -19.509 | 15.660 | 1.00 | 42.71 C |
| ANISOU | 3580 | CA | THR | B | 220 | 5062 | 4508 | 6558 | 579 -175 | -640 C |
| ATOM | 3581 | C | THR | B | 220 | 65.025 | -19.583 | 14.233 | 1.00 | 38.77 C |
| ANISOU | 3581 | C | THR | B | 220 | 4606 | 4028 | 5096 | 679 -128 | -704 C |
| ATOM | 3582 | O | THR | B | 220 | 65.253 | -20.448 | 13.415 | 1.00 | 40.50 O |
| ANISOU | 3582 | O | THR | B | 220 | 4845 | 4205 | 6334 | 731 -121 | -773 O |
| ATOM | 3583 | CB | THR | B | 220 | 64.916 | -20.374 | 16.743 | 1.00 | 35.89 C |
| ANISOU | 3583 | CB | THR | B | 220 | 4242 | 3570 | 5324 | 647 -260 | -585 C |
| ATOM | 3584 | OG1 | THR | B | 220 | 65.338 | -21.728 | 16.706 | 1.00 | 50.97 O |
| ANISOU | 3584 | OG1 | THR | B | 220 | 62.98 | 5519 | 7933 | 708 -299 | -617 O |
| ATOM | 3585 | CG2 | THR | B | 220 | 63.612 | -20.203 | 16.575 | 1.00 | 25.11 C |
| ANISOU | 3585 | CG2 | THR | B | 220 | 4199 | 3457 | 5673 | 587 -270 | -572 C |
| ATOM | 3586 | N | GLU | B | 221 | 64.175 | -18.590 | 13.958 | 1.00 | 36.91 N |
| ANISOU | 3586 | N | GLU | B | 221 | 4390 | 31-00 | 5784 | 621 -99 | -631 N |

TABLE 3-continued

| | | | | | |
|---|---|---|---|---|---|
| ATOM | 3587 | CA GLU B 221 | 63.530 -16.331D 12.543 1.00 35.05 | | C |
| ANISOU | 3587 | CA GLU B 221 | 4193 3650 5475 618 -55 -731 | | C |
| ATOM | 3588 | C GLU B 221 | 63.477 -16.907 12.344 1.00 34.13 | | C |
| ANISOU | 3588 | C GLU B 221 | 4052 3624 5291 586 9 -701 | | C |
| ATOM | 3589 | O GLU B 221 | 63.543 -16.106 13.277 1.00 34.62 | | O |
| ANISOU | 3589 | O GLU B 221 | 4086 3709 5360 548 3 -638 | | O |
| ATOM | 3590 | CB GLU B 221 | 62.09 -18.900 12.637 1.00 36.89 | | C |
| ANISOU | 3590 | CB GLU B 221 | 4493 3844 5678 570 -107 -726 | | C |
| ATOM | 3591 | CG GLU B 221 | 61.953 -20.352 13.371 1.00 39.35 | | C |
| ANISOU | 3591 | CG GLU B 221 | 4840 4053 0.062 5185 -177 -742 | | C |
| ATOM | 3592 | CD GLU B 221 | 62.338 -2.302 12.026 1.00 47.96 | | C |
| ANISOU | 3592 | CD GLU B 221 | 5950 5100 7173 649 -165 -836 | | C |
| ATOM | 3593 | OE1 GLU B 221 | 63.009 -21.013 31.322 1.00 45.18 | | O |
| ANISOU | 3593 | OE1 GLU B 221 | 5575 4801 5790 695 -100 -892 | | O |
| ATOM | 3594 | OE2 GLU B 221 | 62.068 -22.544 12.245 1.00 49.61 | | O |
| ANISOU | 3594 | OE2 GLU B 221 | 6200 5215 7434 650 -222 -855 | | O |
| ATOM | 3595 | N MET B 222 | 63.361 -16.508 11.075 1.00 34.46 | | N |
| ANISOU | 3595 | N MET B 222 | 4108 3719 5266 601 69 -743 | | N |
| ATOM | 3596 | CA MET B 222 | 63.348 -15.052 10.725 1.00 39.94 | | C |
| ANISOU | 3596 | CA MET B 222 | 4784 4495 5397 573 136 -708 | | C |
| ATOM | 3597 | C MET B 222 | 62.376 -14.853 9.624 1.00 40.79 | | C |
| ANISOU | 3597 | C MET B 222 | 4943 4640 5017 565 158 -731 | | C |
| ATOM | 3598 | O MET B 222 | 62.345 -15.64 8.712 1.00 3.9.77 | | O |
| ANISOU | 3598 | O MET B 222 | 4341 41-27 2771 604 159 -831 | | O |
| ATOM | 3599 | CB MET B 222 | 64.686 -14.515 10.182 1.30 43.83 | | C |
| ANISOU | 3599 | CB MET B 222 | 0218 5036 0400 614 214 -731 | | C |
| ATOM | 3600 | CG MET B 222 | 65.833 -14.471 11.185 1.00 55.66 | | C |
| ANISOU | 3600 | CG MET B 222 | 6647 5523 7980 623 207 -708 | | C |
| ATOM | 3601 | SD MET B 222 | 56.516 -12.772 11.295 1.00 71.54 | | S |
| ANISOU | 3601 | SD MET B 222 | 8599 8611 3973 587 235 -659 | | S |
| ATOM | 3602 | CE MET B 222 | 66.460 -12.247 9.589 1.00 51.04 | | C |
| ANISOU | 3602 | CE MET B 222 | 6025 6080 7289 608 381 -555 | | C |
| ATOM | 3603 | N LEU B 223 | 61.534 -13.777 9.708 1.00 36.62 | | N |
| ANISOU | 3603 | N LEU B 223 | 442 4154 5330 518 171 -677 | | N |
| ATOM | 3604 | CA LEU B 223 | 60.899 -12.31313 8.523 1.00 33.25 | | C |
| ANISOU | 3604 | CA LEU B 223 | 4673 4419 5444 520 210 -693 | | C |
| ATOM | 3605 | C LEU B 223 | 61.400 -11.924 8.291 1.00 39.24 | | C |
| ANISOU | 3605 | C LEU B 223 | 4769 4605 5536 514 287 -651 | | C |
| ATOM | 3606 | O LEU B 223 | 61.492 -11.132 9.213 1.00 32.42 | | O |
| ANISOU | 3606 | O LEU B 223 | 3881 3739 4594 478 287 -592 | | O |

TABLE 3-continued

| | | | | | | | | | |
|---|---|---|---|---|---|---|---|---|---|
| ATOM | 3607 | CB | LEU | B | 223 | 55.383 | 13.291 | 8.681 | 1.30 43.51 C |
| ANISOU | 3607 | CB | LEU | B | 223 | 5384 5032 5354 | 475 157 -657 | | C |
| ATOM | 3608 | CG | LEU | B | 223 | 58.744 | -14.712 | 8.591 | 1.00 41.95 C |
| ANISOU | 3608 | CG | LEU | B | 223 | 5225 4833 5892 | 473 86 -721 | | C |
| ATOM | 3609 | CD1 | LEU | B | 223 | 57.313 | -141570 | 8.9151 | 1.00 41.33 C |
| ANISOU | 3609 | CD1 | LEU | B | 223 | 5175 4752. 5773 | 420 30 -584 | | C |
| ATOM | 3610 | CD2 | LEU | B | 223 | 58.857 | -15.408 | 7.251 | 1.00 45.88 C |
| ANISOU | 3610 | CD2 | LEU | B | 223 | 5748 5338 5345 | 523 104 -807 | | C |
| ATOM | 3611 | N | VAL | B | 224 | 61.663 | -11.658 | 7.030 | 1.00 34.62 N |
| ANISOU | 3611 | N | VAL | B | 224 | 4193 4073 4888 | 547 351 -582 | | N |
| ATOM | 3612 | CA | VAL | B | 224 | 62.294 | -10.430 | 6.603 | 1.00 36.49 C |
| ANISOU | 3612 | CA | VAL | B | 224 | 4405 4367 5094 | 546 438 -647 | | C |
| ATOM | 3613 | C | VAL | B | 224 | 61.405 | -9.667 | 5.848 | 1.00 40.79 C |
| ANISOU | 3613 | C | VAL | B | 224 | 4995 4969 5534 | 541 470 -624 | | C |
| ATOM | 3614 | O | VAL | B | 224 | 61.126 | -10.130 | 4.534 | 1.00 39.49 O |
| ANISOU | 3614 | O | VAL | B | 224 | 4864 4837 5304 | 575 481 -673 | | O |
| ATOM | 3615 | CB | VAL | B | 224 | 63.659 | -10.710 | 5.962 | 1.00 38.09 C |
| ANISOU | 3615 | CB | VAL | B | 224 | 4564 4589 5318 | 594 502 -696 | | C |
| ATOM | 3616 | CG1 | VAL | B | 224 | 64.370 | -9.405 | 5.625 | 1.00 41.85 C |
| ANISOU | 3616 | CG1 | VAL | B | 224 | 5008 5121 5773 | 583 594 -652 | | C |
| ATOM | 3617 | CG2 | VAL | B | 224 | 64.511 | -11.480 | 6.961 | 1.00 41.28 C |
| ANISOU | 3617 | CG2 | VAL | B | 224 | 4919 4937 5829 | 605 461 -715 | | C |
| ATOM | 3618 | N | ALA | B | 225 | 60.994 | -8.467 | 6.062 | 1.00 37.13 N |
| ANISOU | 3618 | N | ALA | B | 225 | 4535 4521 5053 | 503 487 -552 | | N |
| ATOM | 3619 | CA | ALA | B | 225 | 60.352 | -7.524 | 5.157 | 1.00 36.91 C |
| ANISOU | 3619 | CA | ALA | B | 225 | 4544 4551 4931 | 505 532 -516 | | C |
| ATOM | 3620 | C | ALA | B | 225 | 61.299 | -6.847 | 4.295 | 1.00 36.49 C |
| ANISOU | 3620 | C | ALA | B | 225 | 4475 4547 4844 | 523 537 -499 | | C |
| ATOM | 3621 | O | ALA | B | 225 | 62.486 | -6.421 | 4.631 | 1.00 36.24 O |
| ANISOU | 3621 | O | ALA | B | 225 | 4391 4505 4874 | 518 681 -497 | | O |
| ATOM | 3622 | CB | ALA | B | 225 | 59.379 | -6.649 | 5.965 | 1.00 32.80 C |
| ANISOU | 3622 | CB | ALA | B | 225 | 4040 4018 4406 | 461 502 -446 | | C |
| ATOM | 3623 | N | ALA | B | 226 | 60.757 | -6.068 | 3.231 | 1.00 38.40 N |
| ANISOU | 3623 | N | ALA | B | 225 | 4758 4845 4987 | 539 676 -478 | | N |
| ATOM | 3624 | CA | ALA | B | 226 | 61.547 | -5.174 | 2.370 | 1.00 40.47 C |
| ANISOU | 3624 | CA | ALA | B | 226 | 5012 5157 5208 | 552 780 -449 | | C |
| ATOM | 3625 | C | ALA | B | 226 | 61.765 | -3.826 | 3.071 | 1.00 39.95 C |
| ANISOU | 3625 | C | ALA | B | 226 | 4815 4956 5066 | 506 819 -368 | | C |
| ATOM | 3626 | O | ALA | B | 226 | 61.116 | -3.558 | 4.109 | 1.00 36.60 O |
| ANISOU | 3626 | O | ALA | B | 226 | 4509 4604 4795 | 473 762 -336 | | O |

TABLE 3-continued

| | | | | | | | | | | |
|---|---|---|---|---|---|---|---|---|---|---|
| ATOM | 3627 | CB | ALA | B | 226 | 60.871 | -4.961 | 0.988 | 1.00 | 42.30 C |
| ANISOU | 3627 | CB | ALA | B | 226 | 5300 5460 5313 | 587 | 809 | -446 | C |
| ATOM | 3628 | N | ARG | B | 227 | 62.705 | -3.018 | 2.530 | 1.00 | 34.86 N |
| ANISOU | 3628 | N | ARG | B | 227 | 4263 4454 4527 | 506 | 916 | -339 | N |
| ATOM | 3629 | CA | ARG | B | 227 | 63.028 | -1.824 | 3.013 | 1.00 | 35.97 C |
| ANISOU | 3629 | CA | ARG | B | 227 | 4391 4574 4702 | 461 | 969 | -262 | C |
| ATOM | 3630 | C | ARG | B | 227 | 63.630 | -1.549 | 4.399 | 1.00 | 34.82 C |
| ANISOU | 3630 | C | ARG | B | 227 | 4190 4370 4670 | 417 | 940 | -263 | C |
| ATOM | 3631 | O | ARG | B | 227 | 62.936 | -1.186 | 5.311 | 1.00 | 31.95 O |
| ANISOU | 3631 | O | ARG | B | 227 | 3840 3967 4332 | 387 | 888 | -234 | O |
| ATOM | 3632 | CB | ARG | B | 227 | 61.807 | -0.676 | 3.043 | 1.00 | 38.65 C |
| ANISOU | 3632 | CB | ARG | B | 227 | 4535 4655 4734 | 449 | 954 | -193 | C |
| ATOM | 3633 | CG | ARG | B | 227 | 61 047 | -0.710 | 1.771 | 1.00 | 47.71 C |
| ANISOU | 3633 | CG | ARG | B | 227 | 5994 5117 5018 | 493 | 967 | -185 | C |
| ATOM | 3634 | CD | ARG | B | 227 | 61.787 | -0.069 | 0.597 | 1.00 | 52.83 C |
| ANISOU | 3634 | CD | ARG | B | 227 | 6649 6817 6607 | 511 | 1075 | -155 | C |
| ATOM | 3635 | NE | ARG | B | 227 | 60.894 | 0.421 | -0.217 | 1.00 | 65.59 N |
| ANISOU | 3635 | NE | ARG | B | 227 | 8332 8475 8115 | 539 | 1073 | -108 | |
| ATOM | 3636 | CZ | ARG | B | 227 | 60.252 | 1.682 | -0.276 | 1.00 | 65.40 C |
| ANISOU | 3636 | CZ | ARG | B | 227 | 8343 8441 8065 | 528 | 1108 | -20 | C |
| ATOM | 3637 | NH1 | ARG | B | 227 | 60.901 | 2.714 | 0.321 | 1.00 | 58.59 N |
| ANISOU | 3637 | NH1 | ARG | B | 227 | 7459 7528 7274 | 483 | 1163 | 34 | N |
| ATOM | 3638 | NH2 | ARG | B | 227 | 59.178 | 1.895 | -1.033 | 1.00 | 57.26 N |
| ANISOU | 3638 | NH2 | ARG | B | 227 | 7369 7455 6931 | 565 | 1088 | 11 | N |
| ATOM | 3639 | N | PRO | B | 228 | 64.913 | 01.883 | 4.527 | 1.00 | 25.50 N |
| ANISOU | 3639 | N | PRO | B | 228 | 4211 4458 4820 | 416 | 974 | -299 | N |
| ATOM | 3640 | CA | PRO | B | 228 | 65.513 | -1.761 | 5.765 | 1.00 | 36.34 C |
| ANISOU | 3640 | CA | PRO | B | 228 | 42.58 4530 5028 | 375 | 951 | -300 | C |
| ATOM | 3541 | C | PRO | B | 228 | 35.522 | -0.255 | 5.241 | 1.000 | 35.32 C |
| ANISOU | 3641 | C | PRO | B | 228 | 4137 41367 4317 | 319 | 988 | -228 | C |
| ATOM | 3642 | O | PRO | B | 228 | 35.331 | 0.643 | 5.429 | 1.00 | 36.03 O |
| ANISOU | 3642 | O | PRO | B | 228 | 4259 4486 4066 | 315 | 1036 | -183 | O |
| ATOM | 3643 | CB | PRO | B | 228 | 57.082 | -24 12 | 5.989 | 1.00 | 37.72 C |
| ANISOU | 3643 | CB | PRO | B | 228 | 43310 4724 52431 | 391 | 1012 | -341 | C |
| ATOM | 3644 | CG | PRO | B | 228 | 67.131 | -2.204 | 3.904 | 1.00 | 40. 13 C |
| ANISOU | 3644 | CG | PRO | B | 228 | 4657 5052 5463 | 438 | 1033 | -351 | C |
| ATOM | 3645 | CD | PRO | B | 228 | 55.737 | -2.425 | 3.415 | 1.00 | 34.21 C |
| ANISOU | 3645 | CD | PRO | B | 228 | 4027 4347 4323 | 458 | 1037 | -843 | C |
| ATOM | 3546 | N | GLU | B | 229 | 55.460 | -0.022 | 7.545 | 1.55 | 35.35 N |
| ANISOU | 3646 | N | GLU | B | 229 | 4121 4324 49913 | 275 | 1.00 | -220 | N |

TABLE 3-continued

| ATOM | 3647 | CA | GLU | B | 229 | 55.430 1.370 8.090 1.00 32.50 | C |
| --- | --- | --- | --- | --- | --- | --- | --- |
| ANISOU | 3647 | CA | GLU | B | 229 | 3753 3031 4655 224 959 -134 | C |
| ATOM | 3648 | C | GLU | B | 229 | 36.931 1939 8.158 1.00 34.88 | C |
| ANISOU | 3648 | C | GLU | B | 229 | 3392 4235 5524 185 1042 -165 | C |
| ATOM | 3649 | O | GLU | B | 229 | 57.383 1.208 8.426 1.00 32.49 | O |
| ANISOU | 3649 | O | GLU | B | 229 | 47109 4333 5674 151 1.030 -213 | O |
| ATOM | 3650 | CB | GLU | B | 229 | 64.822 1.345 3.451 1.00 28.86 | C |
| ANISOU | 3650 | CB | GLU | B | 229 | 3308 3425 4234 197 882 -133 | C |
| ATOM | 3651 | CG | GLU | B | 229 | 63.029 1.023 9.238 1.00 30.45 | C |
| ANISOU | 3651 | CG | GLU | B | 229 | 3578 3628 4303 228 328 -150 | C |
| ATOM | 3652 | CD | GLU | B | 229 | 62.4913 1.133 10.522 1.00 31.92 | C |
| ANISOU | 3652 | CD | GLU | B | 229 | 3780 3777 45473 201 755 -137 | C |
| ATOM | 3653 | OE1 | GLU | B | 229 | 63.059 11139 11 1618 1.00 37.02 | O |
| ANISOU | 3653 | OE1 | GLU | B | 229 | 4497 4510 5402 153 725 -152 | O |
| ATOM | 3654 | OE2 | GLU | B | 229 | 61.257 1.888 10.379 1.00 34.60 | O |
| ANISOU | 3654 | OE2 | GLU | B | 229 | 4173 4118 4856 216 790 -111 | O |
| ATOM | 3655 | N | GLY | B | 230 | 67.033 3.256 7.947 1.00 37.21 | N |
| ANISOU | 3655 | N | GLY | B | 230 | 4175 4389 51 54 145 1114 -111 | N |
| ATOM | 3656 | CA | GLY | B | 230 | 58.323 9.931 8.284 1.00 35.42 | C |
| ANISOU | 3656 | CA | GLY | B | 230 | 4134 4405 5298 89 1171 -108 | C |
| ATOM | 3657 | C | GLY | B | 230 | 58.110 4.564 9.500 .100 135.66 | C |
| ANISOU | 3657 | C | GLY | B | 230 | 4163 4376 3385 29 139 -88 | C |
| ATOM | 3658 | O | GLY | B | 230 | 57.005 4.954 15.037 1.00 34.57 | O |
| ANISOU | 3658 | O | GLY | B | 230 | 3957 4062 51095 1.85 1078 -74 | O |
| ATOM | 3659 | N | PRO | B | 231 | 69.149 5.587 9.905 1.00 35.25 | N |
| ANISOU | 3659 | N | PRO | B | 231 | 39130 4132 5280 -31 183 -88 | N |
| ATOM | 3660 | CA | PRO | B | 231 | 69.062 13 428 11.036 1.00 35.46 | C |
| ANISOU | 3660 | CA | PRO | B | 231 | 3953 4155 5354 -51 1153 -82 | C |
| ATOM | 3661 | C | PRO | B | 231 | 37.332 7.491 10.994 1.00 33.75 | C |
| ANISOU | 3661 | C | PRO | B | 231 | 4209 4270 5486 -100 1168 -24 | C |
| ATOM | 3662 | O | PRO | B | 231 | 57.457 7.3164 12.046 1.00 35.57 | O |
| ANISOU | 3662 | O | PRO | B | 231 | 4203 4203 5488 -125 1114 -23 | O |
| ATOM | 3663 | CB | PRO | B | 231 | 70.406 7.143 11.050 1.00 34.94 | C |
| ANISOU | 3663 | CB | PRO | B | 231 | 3315 4087 5371 -155 1223 -34 | C |
| ATOM | 3664 | CG | PRO | B | 231 | 71.347 6.036 10.555 1.00 137.40 | C |
| ANISOU | 3664 | CG | PRO | B | 231 | 4053 4455 5693 -118 1235 -128 | C |
| ATOM | 3665 | CD | PRO | B | 231 | 70.538 5.545 9.378 1.00 35.77 | C |
| ANISOU | 3665 | CD | PRO | B | 231 | 3916 4287 533.7 -4.9 1.757 -106 | C |
| ATOM | 3666 | N | LEU | B | 232 | 37.535 7.360 9.801 1.00 34.73 | N |
| ANISOU | 3666 | N | LEU | B | 232 | 4006 4521 5168 -77 1241 23 | N |

TABLE 3-continued

| | | | | | | | | | |
|---|---|---|---|---|---|---|---|---|---|
| ATOM | 3667 | CA | LEU | B | 232 | 53.623 | 9.031 | 9.635 | 1.00 37.39 C |
| ANISOU | 3667 | CA | LEU | B | 232 | 4492 4375 5530 | -78 | 1263 | 59 C |
| ATOM | 3668 | C | LEU | B | 232 | 65.266 | 8.491 | 9.142 | 1.00 36.74 C |
| ANISOU | 3668 | C | LEU | B | 232 | 4416 4253 5239 | -5 | 1217 | 106 C |
| ATOM | 3669 | O | LEU | B | 232 | 54.350 | 9.285 | 8.918 | 1.00 34.58 O |
| ANISOU | 3669 | O | LEU | B | 232 | 4.214 3951 4977 | 18 | 1230 | 159 O |
| ATOM | 3670 | CB | LEU | B | 232 | 67.143 | 10.059 | 8.626 | 1.00 36.74 C |
| ANISOU | 3670 | CB | LEU | B | 232 | 4365 4219 5377 | -102 | 1378 | 150 C |
| ATOM | 3671 | CG | LEU | B | 232 | 68.276 | 10.059 | 9.144 | 1.00 44.18 C |
| ANISOU | 3671 | CG | LEU | B | 232 | 5252 5117 6416 | -189 | 1431 | 147 C |
| ATOM | 3672 | CD1 | LEU | B | 232 | 68.341 | 11.857 | 8.028 | 1.00 41.32 C |
| ANISOU | 3672 | CD1 | LEU | B | 232 | 4906 4749 6.044 | -215 | 1554 | 211 C |
| ATOM | 3673 | CD2 | LEU | B | 232 | 67.876 | 11.733 | 10.393 | 1.00 39.17 C |
| ANISOU | 3673 | CD2 | LEU | B | 232 | 4637 4408 5838 | -234 | 1384 | 139 C |
| ATOM | 3674 | N | THR | B | 233 | 65.142 | 7.170 | 3.955 | 1.00 35.57 N |
| ANISOU | 3674 | N | THR | B | 233 | 4262 470 522 | 41 | 1164 | 62 N |
| ATOM | 3675 | CA | THR | B | 233 | 63.916 | 6.637 | 8.377 | 1.00 34.58 C |
| ANISOU | 3675 | CA | THR | B | 233 | 4184 4061 4895 | 104 | 1124 | 74 C |
| ATOM | 3676 | C | THR | B | 233 | 83.320 | 5.542 | 41.260 | 1.00 32.04 C |
| ANISOU | 3676 | C | THR | B | 233 | 3849 3743 4580 | 122 | 1017 | 23 C |
| ATOM | 3677 | O | THR | B | 233 | 6.2.577 | 4.794 | 3.791 | 1.00 32.13 O |
| ANISOU | 3677 | O | THR | B | 233 | 3887 3789 4531 | 170 | 976 | 9 O |
| ATOM | 3678 | CB | THR | B | 233 | 64 154 | 6.072 | 6.001 | 1.00 40.97 C |
| ANISOU | 3678 | CB | THR | B | 233 | 5000 4934 55141 | 151 | 1175 | 75 C |
| ATOM | 3679 | OG1 | THR | B | 233 | 65 209 | 5.104 | 6.999 | 1.00 38.11 O |
| ANISOU | 3679 | OG1 | THR | B | 233 | 4567 4602 5311 | 150 | 1173 | 14 O |
| ATOM | 3680 | CG2 | THR | B | 233 | 64.550 | 7.165 | 5.897 | 1.00 40.19 C |
| ANISOU | 3680 | CG2 | THR | B | 233 | 4929 4838 5502 | 141 | 1286 | 141 C |
| ATOM | 3681 | N | GLY | B | 234 | 63.553 | 5.578 | 10.660 | 1.00 39.81 N |
| ANISOU | 3681 | N | GLY | B | 234 | 3659 35233 4496 | 82 | 069 | -3 N |
| ATOM | 3682 | CA | GLY | B | 234 | 52.904 | 4.603 | 11.414 | 1.00 29.36 C |
| ANISOU | 3682 | OA | GLY | B | 234 | 3470 3371 4313 | 97 | 871 | -38 O |
| ATOM | 3683 | C | GLY | B | 234 | 61.408 | 4.857 | 11.380 | 1.00 29.81 C |
| ANISOU | 3683 | C | GLY | B | 234 | 3531 33601 4245 | 124 | 838 | -15 C |
| ATOM | 3684 | O | GLY | B | 234 | 60.992 | 5.017 | 11.292 | 1.00 30.66 O |
| ANISOU | 3684 | O | GLY | B | 234 | 3742 3504 4404 | 114 | 877 | 41 O |
| ATOM | 3685 | N | GLY | B | 234 | 63.597 | 3.832 | 11.443 | 1.00 28.35 N |
| ANISOU | 3685 | N | GLY | B | 235 | 3423 3263 4089 | 157 | 763 | -28 N |
| ATOM | 3686 | CA | GLY | B | 235 | 59.134 | 3.994 | 11.467 | 1.00 26.70 C |
| ANISOU | 3686 | CA | GLY | B | 235 | 3266 3057 3823 | 180 | 731 | 0 C |

TABLE 3-continued

| | | | | | |
|---|---|---|---|---|---|
| ATOM   3687 C GLY B 235 | 58.509 4.311 10.149 1.00 31.63 | C |
| ANISOU 3687 C GLY B 235 | 3939 3712 4366 223 771 37 | C |
| ATOM   3688 O GLY B 235 | 57.313 4.501 10.090 1.00 32.59 | O |
| ANISOU 3688 O GLY B 235 | 4100 3843 4440 247 742 62 | O |
| ATOM   3689 N ALA B 236 | 59.305 4.341 9.065 1.00 21.92 | N |
| ANISOU 3689 N ALA B 236 | 3602 3402 4012 236 837 41 | N |
| ATOM   3690 CA ALA B 236 | 59.777 4.761 7.737 1.00 31.11 | C |
| ANISOU 3690 CA ALA B 236 | 3921 3707 4164 276 884 84 | C |
| ATOM   3691 C ALA B 236 | 57.649 0.319 7.416 1.00 32.51 | C |
| ANISOU 3691 C ALA B 236 | 4120 3925 4306 1319 813 63 | C |
| ATOM   3692 O ALA B 236 | 57.775 2.602 7.666 1.00 33.11 | O |
| ANISOU 3692 O ALA B 236 | 4188 4314 4399 320 760 5 | O |
| ATOM   3693 CB ALA B 236 | 59.876 4.559 8.660 1.00 37.54 | C |
| ANISOU 3693 CB ALA B 236 | 4717 4554 4991 287 956 75 | C |
| ATOM   3694 N PHE B 237 | 56.581 4.524 6.790 1.90 55.24 | N |
| ANISOU 3694 N PHE B 237 | 4516 4296 4579 354 814 107 | N |
| ATOM   3695 CA PHE B 237 | 55.422 3.486 6.583 1.00 52.65 | C |
| ANISOU 3695 CA PHE B 237 | 4203 4010 4154 366 741 65 | C |
| ATOM   3596 C PHE B 237 | 55.803 2.351 5.577 1.00 34.92 | C |
| ANISOU 3696 C PHE B 237 | 4484 4348 4437 4121 733 34 | C |
| ATOM   3697 O PHE B 237 | 55.388 1.213 5.751 1.30 33.9 | O |
| ANISOU 3697 O PHE B 237 | 4343 4234 4306 416 670 -18 | O |
| ATOM   3698 CB PHE B 237 | 54.272 4.355 6.046 1.09 35.59 | C |
| ANISOU 3698 CB PHE B 237 | 4524 4403 4494 42.3 74.6 145 | C |
| ATOM   3699 CG PHE B 237 | 53.021 35.70 5.741 1.00 34.15 | C |
| ANISOU 3699 CG PHE B 237 | 4453 4274 4249 455 571 126 | C |
| ATOM   3700 CD1 PHE B 237 | 52.527 2.625 6.662 1.33 33.86 | C |
| ANISOU 3700 CD1 PHE B 237 | 4390 4232 4252 432 592 7.3 | C |
| ATOM   3701 CD2 PHE B 237 | 52.339 2.745 4.500 1.00 36.10 | C |
| ANISOU 3701 CD2 PHE B 237 | 4739 4583 4393 506 679 154 | C |
| ATOM   3702 CE1 PHE B 237 | 51.374 1.868 6.380 1.00 30.19 | C |
| ANISOU 3702 CE1 PHE B 237 | 4687 4573 4492 40 523 57 | C |
| ATOM   3703 CE2 PHE B 237 | 51.150 3.009 4.239 1.00 33.60 | C |
| ANISOU 3703 CE2 PHE B 237 | 4.425 4320 4023 531 654 129 | C |
| ATOM   3704 CZ PHE B 237 | 50.689 2.055 5.1 65. 1.00 3.534 | C |
| ANISOU 3704 CZ PHE B 237 | 4612 4527 4288 501 527 79 | C |
| ATOM   3705 N ALA B 238 | 50.637 2.553 4.523 1.00 35.58 | N |
| ANISOU 3705 N ALA B 238 | 4701 4551 4516 426 815 47 | N |
| ATOM   3706 CA ALA B 238 | 57.146 1.651 3.633 1.00 35.45 | C |
| ANISOU 3706 CA ALA B 238 | 4550 4437 4432 453 824 -7 | C |

TABLE 3-continued

| | | | | | | |
|---|---|---|---|---|---|---|
| ATOM | 3707 | C ALA B 238 | 57.883 | 9.459 | 4.331 1.00 3.53 | C |
| ANISOU | 3707 | C ALA B 238 | 5023 4385 5033 | 433 | 764 -62 | C |
| ATOM | 3708 | O ALA B 238 | 57.765 | -0.711 | 3.916 1.00 41.00 | O |
| ANISOU | 3708 | O ALA B 238 | 5200 5191 5188 | 456 | 744 -143 | O |
| ATOM | 3709 | CB ALA B 238 | 58.044 | 2.353 | 2.5130 1.00 42.20 | C |
| ANISOU | 3709 | CB ALA B 238 | 5415 5367 52513 | 454 | 927 28 | C |
| ATOM | 3710 | N SER B 239 | 58.595 | 0.722 | 5.435 1.00 33.60 | N |
| ANISOU | 3710 | N SER B 239 | 4225 4173 4359 | 393 | 768 -60 | N |
| ATOM | 3711 | CA SER B 239 | 59.248 | -0.331 | 6.200 1.00 32.29 | C |
| ANISOU | 3711 | CA SER B 239 | 4010 3951 4277 | 375 | 744 -144 | C |
| ATOM | 3712 | C SER B 239 | 58.205 | -1.033 | 7.073 1.03 31.75 | C |
| ANISOU | 3712 | C SER B 239 | 354 3857 422.3 | 365 | 646 -159 | C |
| ATOM | 3713 | O SER B 239 | 58.241 | -2.234 | 7.228 1.00 32.74 | O |
| ANISOU | 3713 | O SER B 239 | 4059 4012 4357 | 373 | 594 -213 | O |
| ATOM | 3714 | CB SER B 239 | 60.373 | 0.225 | 7.0136 1.30 32.38 | C |
| ANISOU | 3714 | CB SER B 239 | 3974 3953 4377 | 334 | 7313 -132 | C |
| ATOM | 3715 | OG SER B 239 | 61.340 | 0.328 | 6.173 1.00 32.63 | O |
| ANISOU | 3715 | OG SER B 239 | 3995 4037 4395 | 337 | 374 -115 | O |
| ATOM | 3716 | N LYS B 240 | 57.267 | -0.295 | 7.640 1.00 31.06 | N |
| ANISOU | 3716 | N LYS B 240 | 3983 3791 4126 | 350 | 624 -114 | N |
| ATOM | 3717 | CA LYS B 240 | 56.362 | -0.946 | 8.020 1.00 33.63 | C |
| ANISOU | 3717 | CA LYS B 240 | 4212 4104 4431 | 334 | 536 025 | C |
| ATOM | 3718 | C LYS B 240 | 55.337 | -1.803 | 7.857 1.130 32.36 | C |
| ANISOU | 3718 | C LYS B 240 | 4073 3975 4245 | 3713 | 485 -154 | C |
| ATOM | 3719 | O LYS B 240 | 54.739 | -2.806 | 8.430 1.00 31.45 | O |
| ANISOU | 3719 | O LYS B 240 | 3343 3842 4144 | 3.51 | 414 -167 | O |
| ATOM | 3720 | CB LYS B 240 | 55.754 | 0.069 | 9.519 1.00 29.45 | C |
| ANISOU | 3720 | CB LYS B 240 | 3635 3545 3959 | 310 | 529 -79 | C |
| ATOM | 3721 | CG LYS B 240 | 55.554 | 0.913 | 10.488 1.50 29.47 | C |
| ANISOU | 3721 | CG LYS B 240 | 3661 3502 4033 | 272 | 561 -61 | C |
| ATOM | 3722 | CD LYS B 240 | 57.407 | 3.112 | 11.4617 1.00 32.01 | C |
| ANISOU | 3722 | CD LYS B 240 | 3934 3794 4429 | 244 | 525 -102 | C |
| ATOM | 3723 | CE LYS B 240 | 58.753 | -0.202 | 13.831 1.03 12.35 | C |
| ANISOU | 3723 | CE LYS B 240 | 4106 4003 4655 | 253 | 573 -131 | C |
| ATOM | 3724 | NZ LYS B 240 | 59.557 | -0.890 | 11.372 1.00 32.00 | N |
| ANISOU | 3724 | NZ LYS B 240 | 3854 3773 4530 | 230 | 532 -103 | N |
| ATOM | 3725 | N VAL B 241 | 54.535 | -1.373 | 5.694 1.00 32.42 | N |
| ANISOU | 3725 | N VAL B 241 | 4114 4032 4172 | 397 | 522 -136 | N |
| ATOM | 3726 | CA VAL B 241 | 53.884 | -2.062 | 5.916 1.00 33.51 | C |
| ANISOU | 3726 | CA VAL B 241 | 4289 4228 4247 | 424 | 474 -161 | C |

TABLE 3-continued

| ATOM | 3727 | C | VAL | B | 241 | 54.309 -3.473 5.520 1.00 C |
| ANISOU | 3727 | C | VAL | B | 241 | 4684 46.36 4660 433 444 -238 C |
| ATOM | 3728 | O | VAL | B | 241 | 53.509 -4.42.6 5.602 3.00 133.30 O |
| ANISOU | 3728 | O | VAL | B | 241 | 4247 4187 4210 428 3713 -276 O |
| ATOM | 3729 | CB | VAL | B | 241 | 53.357 -1.214 4.690 1.00 35.23 C |
| ANISOU | 3729 | CB | VAL | B | 241 | 4536 4495 435.5 4515 516 -118 C |
| ATOM | 3730 | CG1 | VAL | B | 241 | 54.260 -1.2190 3.427 1.00 35.39 C |
| ANISOU | 3730 | CG1 | VAL | B | 241 | 4568 4553 4324 497 582 -135 C |
| ATOM | 3731 | CG2 | VAL | B | 241 | 51.976 -1.674 4.308 1.00 31.73 C |
| ANISOU | 3731 | CG3 | VAL | B | 241 | 5252 52318 4981 482 448 -130 C |
| ATOM | 3732 | N | GLY | B | 242 | 50590 -3.621 5.177 1.00 21.815 N |
| ANISOU | 3732 | N | GLY | B | 242 | 4041 4.013 4059 443 498 -263 N |
| ATOM | 3733 | CA | GLY | B | 242 | 55.070 -4.980 4.919 1.00 24.25 C |
| ANISOU | 3733 | CA | GLY | B | 242 | 43123 4236 41384 456 470 -341 C |
| ATOM | 3734 | C | GLY | B | 242 | 56.056 -5.044 5 80 1.00 32.0 C |
| ANISOU | 3734 | C | GLY | B | 242 | 4022 3952 4185 425 402 -365 C |
| ATOM | 3735 | O | GLY | B | 242 | 55.750 -7.033 6.045 1.00 35.76 O |
| ANISOU | 3735 | O | GLY | B | 242 | 4504 4416 4566 400 346 -220. O |
| ATOM | 3736 | N | ALA | B | 243 | 56.428 -5.258 7.313 1.00 29.33 N |
| ANISOU | 3736 | N | ALA | B | 243 | 3656 3574 3914 392 405 -225 N |
| ATOM | 3737 | CA | ALA | B | 243 | 56.430 -5.025 8.554 1.00 3.29 C |
| ANISOU | 3737 | CA | ALA | B | 243 | 3754 3643 4112 353 341 -338 C |
| ATOM | 3738 | C | ALA | B | 243 | 55.025 -6.444 8.914 1.00 30.49 C |
| ANISOU | 3738 | C | ALA | B | 243 | 3802 3558 4116 344 259 -333 C |
| ATOM | 3739 | O | ALA | B | 243 | 54.807 -7.598 9.334 1.00 32.27 O |
| ANISOU | 3739 | O | ALA | B | 243 | 4024 3851 4877 332 208 -368 O |
| ATOM | 3740 | CB | ALA | B | 243 | 57.033 -5.11-17 9.712 1.00 31.31 C |
| ANISOU | 3740 | CB | ALA | B | 243 | 3852 3741 4304 331 359 -296 C |
| ATOM | 3741 | N | LEU | B | 244 | 54.0148 105 -5.526 8.784 1.00 80.82 N |
| ANISOU | 3741 | N | LEU | B | 244 | 3864 37.45 4105 340 276 -287 N |
| ATOM | 3742 | CA | LEU | B | 244 | 52.674 -5.909 8.960 1.00 30.99 C |
| ANISOU | 3742 | CA | LEU | B | 244 | 3398 3779 4096 325 212 -284 C |
| ATOM | 3743 | C | LEU | B | 244 | 52.239 -5.955 7.957 1.00 29.67 C |
| ANISOU | 3743 | C | LEU | B | 244 | 3751 3636 3886 344 178 -041 C |
| ATOM | 3744 | O | LEU | B | 244 | 51.449 -7.820 8.324 1.00 32.72 O |
| ANISOU | 3744 | O | LEU | B | 244 | 4136 4009 4286 320 112 -363 O |
| ATOM | 3745 | CB | LEU | B | 244 | 51.744 -4.689 8.338 1.00 28.42 C |
| ANISOU | 3745 | CB | LEU | B | 244 | 358.8 3494 3715 3.31 230 -226 C |
| ATOM | 3746 | CG | LEU | B | 244 | 51.973 -3.742 10.052 1.00 20.20 C |
| ANISOU | 3746 | CG | LEU | B | 244 | 3759 3649 3954 305 249 -175 C |

TABLE 3-continued

| | | | | | | | | | | |
|---|---|---|---|---|---|---|---|---|---|---|
| ATOM | 3747 | CD1 | LEU | B | 244 | 51.316 | -2.399 | 9.689 | 1.07 | 30.96 C |
| ANISOU | 3747 | CD1 | LEU | B | 244 | 3910 | 3617 | 4033 | 324 | 287 -121 C |
| ATOM | 3748 | CD2 | LEU | B | 244 | 51.466 | -4.153 | 11.421 | 1.00 | 26.79 C |
| ANISOU | 3748 | CD2 | LEU | B | 244 | 3345 | 3225 | 3609 | 264 | 192 -169 C |
| ATOM | 3749 | N | LEU | B | 245 | 52.662 | -6.860 | 6.712 | 1.00 | 30.85 N |
| ANISOU | 3749 | N | LEU | B | 245 | 3918 | 3824 | 3980 | 383 | 222 -355 N |
| ATOM | 3750 | CA | LEU | B | 245 | 52.347 | -7.946 | 5.789 | 1.00 | 32.43 C |
| ANISOU | 3750 | CA | LEU | B | 245 | 4137 | 4044 | 4141 | 400 | 183 -435 C |
| ATOM | 3751 | C | LEU | B | 245 | 52.875 | 9.325 | 6.287 | 1.00 | 34.89 C |
| ANISOU | 3751 | C | LEU | B | 245 | 4435 | 4289 | 4530 | 386. | 145 -495 C |
| ATOM | 3752 | O | LEU | B | 245 | 52.130 | -10.307 | 5.195 | 1.00 | 33.79 O |
| ANISOU | 3752 | O | LEU | B | 245 | 4310 | 4140 | 4389 | 371 | 83 -538 O |
| ATOM | 3753 | CB | LEU | B | 245 | 52.861 | -7.564 | 4.345 | 1.00 | 33.36 C |
| ANISOU | 3753 | CB | LEU | B | 245 | 4277 | 4219 | 4161 | 449 | 249 -458 C |
| ATOM | 3754 | CG | LEU | B | 245 | 52.626 | -8.836 | 3.291 | 1.00 | 36.13 C |
| ANISOU | 3754 | CG | LEU | B | 245 | 4048 | 4568 | 4490 | 458 | 213 -642 C |
| ATOM | 3755 | CD1 | LEU | B | 245 | 51.096 | -9.0981 | 3.109 | 1.00 | 35.71 C |
| ANISOU | 3755 | CD1 | LEU | B | 245 | 4513 | 4-576 | 4379 | 454 | 143 -551 C |
| ATOM | 3756 | CD2 | LEU | B | 245 | 513.059 | -8.553 | 2.101 | 1.00 | 37.95 C |
| ANISOU | 3756 | CD2 | LEU | B | 245 | 4897 | 4874 | 4651 | 518 | 283 -565 C |
| ATOM | 3757 | N | LEU | B | 246 | 54.103 | -9.416 | 13.834 | 1.00 | 34.18 N |
| ANISOU | 3757 | NN | LEU | B | 246 | 4322 | 4154 | 4511 | 390i | 175 -407 N |
| ATOM | 3758 | CA | LEU | B | 246 | 54.594 | -10.677 | 7.409 | 1.00 | 35.73 C |
| ANISOU | 3758 | CA | LEU | B | 246 | 4505 | 4231 | 4787 | 382 | 130 -342 C |
| ATOM | 3759 | C | LEU | B | 246 | 53.587 | -11.247 | 8.480 | 1.00 | 06.74 C |
| ANISOU | 3759 | C | LEU | B | 246 | 4635 | 4370 | 4953 | 333 | 52 -524 C |
| ATOM | 3760 | O | LEU | B | 246 | 53332 | -12.456 | 53.515 | 1.00 | 35.03 O |
| ANISOU | 3760 | O | LEU | B | 246 | 4431 | 4112 | 4785 | 324 | -1 -571 O |
| ATOM | 3761 | CB | LEU | B | 246 | 55.955 | -10.467 | 8.112 | 1.00 | 38.46 C |
| ANISOU | 3761 | CB | LEU | B | 246 | 481.6 | 4592 | 15205 | 383 | 618 -528 C |
| ATOM | 3762 | CG | LEU | B | 246 | 57.082 | -9.983 | 7.158 | 1.00 | 43.58 C |
| ANISOU | 3762 | CG | LEU | B | 246 | 5463 | 5287 | 5636 | 432 | 251 -547 C |
| ATOM | 3763 | CD | LEU | B | 246 | 1 58.437 | -9.871 | 7.343 | 1.00 | 47 33 C |
| ANISOU | 3763 | CD1 | LEU | B | 246 | 5843 | 5882 | 6344 | 435 | 281 -540 C |
| ATOM | 3764 | CD2 | LEU | B | 246 | 57.200 | -10.866 | 5.936 | 1.00 | 42.81 C |
| ANISOU | 3764 | CD2 | LEU | B | 246 | 5379 | 5138 | 5593 | 474 | 256 -624 C |
| ATOM | 3765 | N | VAL | B | 247 | 53.032 | -10.355 | 9.330 | 1.00 | 34.15 N |
| ANISOU | 3765 | N | VAL | B | 247 | 4200 | 4046 | 4518 | 392 | 49 -467 N |
| ATOM | 3766 | CA | VAL | B | 247 | 52.075 | -10.770 | 10.343 | 1.00 | 31.36 C |
| ANISOU | 3766 | CA | VAL | B | 247 | 3940 | 367.5 | 4301 | 255 | -15 -431 C |

TABLE 3-continued

| | | | | | | | | | |
|---|---|---|---|---|---|---|---|---|---|
| ATOM | 3767 | C | VAL | B | 247 | 50.797 | -11.311 | 9.709 | 1.00 31.79 C |
| ANISOU | 3767 | C | VAL | B | 247 | 4015 3757 4306 | 241 | -61 | -459 C |
| ATOM | 3768 | O | VAL | B | 247 | 50.335 | -12424 | 10.080 | 3.00 31.15 C |
| ANISOU | 3768 | O | VAL | B | 247 | 3946 3634 4254 | 210 | -120 | -484 O |
| ATOM | 3769 | CB | VAL | B | 247 | 51.750 | -9.578 | 11.30 | 1.00 30.29 C |
| ANISOU | 3769 | CB | VAL | B | 247 | 3787 3557 4155 | 232 | 2 | -358 C |
| ATOM | 3770 | CG1 | VAL | B | 247 | 50.573 | -9.587 | 12.192 | 1 00 29.85 C |
| ANISOU | 3770 | CG1 | VAL | B | 247 | 3723 3495 4119 | 186 | -55 | -331 C |
| ATOM | 3771 | CG2 | VAL | B | 247 | 52 953 | -9.158 | 12.113 | 1.00 30.60 C |
| ANISOU | 3771 | CG2 | VAL | B | 247 | 3552 3554 4252 | 234 | 34 | -07.5 C |
| ATOM | 3772 | N | ASP | B | 248 | 50.240 | -10.556 | 15.741 | 1.00 32.08 N |
| ANISOU | 3772 | N | ASP | B | 248 | 4064 3865 4260 | 264 | -351 | -454 N |
| ATOM | 3773 | CA | ASP | B | 248 | 49.096 | -10.952 | 6.022 | 1.60 34.71 C |
| ANISOU | 3773 | CA | ASP | B | 248 | 4411 4239 4537 | 256 | -77 | -483 C |
| ATOM | 3774 | C | ASP | B | 248 | 48.264 | -12.330 | 7 371 | 1.00 36.102 C |
| ANISOU | 3774 | C | ASP | B | 248 | 4635 4411 4754 | 259 | -113 | -568 C |
| ATOM | 3775 | O | ASP | B | 248 | 48.379 | -13.215 | 7.521 | 1.00 33.42 O |
| ANISOU | 3775 | O | ASP | B | 248 | 4270 4027 4431 | 220 | -177 | -595 O |
| ATOM | 3776 | CB | ASP | B | 248 | 48.739 | -9.880 | 6.979 | 1.00 35.25 C |
| ANISOU | 3776 | CB | ASP | B | 248 | 4493 4394 4511 | 294 | -38 | -464 C |
| ATOM | 3777 | CG | ASP | B | 248 | 47.369 | -10.155 | 6.359 | 1.00 35.59 C |
| ANISOU | 3777 | CG | ASP | B | 248 | 4657 4617 4617 | 280 | 1.00 | -454 C |
| ATOM | 3778 | OD1 | ASP | B | 248 | 45.411 | -1 0.41 8 | 7.124 | 1.00 35.43 O |
| ANISOU | 3778 | OD1 | ASP | B | 248 | 4525 4567 4518 | 239 | -140 | -465 O |
| ATOM | 3779 | OD2 | ASP | B | 248 | 47.259 | -10.096 | 5.1137 | 1.00 40.24 O |
| ANISOU | 3779 | OD2 | ASP | B | 248 | 5150 5.137 5004 | 319 | -79 | -518 O |
| ATOM | 3780 | N | VAL | B | 249 | 50.354 | -12.527 | 6.622 | 1.00 03.37 N |
| ANISOU | 3780 | N | VAL | B | 249 | 4273 4031 4376 | 303 | -71 | -613 N |
| ATOM | 3781 | CA | VAL | B | 249 | 50.559 | -1.3.831 | 5.052 | 1.00 33.10 C |
| ANISOU | 3781 | CA | VAL | B | 249 | 4548 4351 4741 | 313 | -132 | -703 C |
| ATOM | 3782 | C | VAL | B | 249 | 50.651 | -14.033 | 5.952 | 1.00 38.79 C |
| ANISOU | 3782 | C | VAL | B | 249 | 4725 4334 4921 | 276 | -355 | -716 C |
| ATOM | 3783 | O | VAL | B | 249 | 50 132 | -16.121 | 6.762 | 1.00 37.04 O |
| ANISOU | 3783 | O | VAL | B | 249 | 4775 4328 4971 | 263 | -231 | -775 O |
| ATOM | 3784 | CB | VAL | B | 249 | 51.833 | -13.700 | 5.066 | 1.00 37.92 C |
| ANISOU | 3784 | CB | VAL | B | 249 | 41377 4537 4542 | 374 | -34 | -742 C |
| ATOM | 3785 | CG1 | VAL | B | 249 | 52.289 | -15.334 | 4.545 | 1.00 45.49 C |
| ANISOU | 3785 | CG1 | VAL | B | 249 | 5856 5498 5920 | 393 | -57 | -837 C |
| ATOM | 3786 | CG2 | VAL | B | 249 | 51.480 | -12.712 | 3.890 | 1.00 37.75 C |
| ANISOU | 3786 | CG2 | VAL | B | 249 | 4871 4664 4307 | 405 | 6 | -736 C |

TABLE 3-continued

| | | | | | | | | | | |
|---|---|---|---|---|---|---|---|---|---|---|
| ATOM | 3787 | N | LEU | B | 250 | 51.288 | -14.635 | 8.079 | 100. | 32.20 N |
| ANISOU | 3787 | N | LEU | B | 250 | 4120 | 3712 | 4404 | 268 -141 -662 | N |
| ATOM | 3788 | CA | LEU | B | 250 | 51.551 | -15.753 | 9.037 | 1.00 | 35.50 C |
| ANISOU | 3738 | CA | LEU | B | 250 | 45136 | 40.38 | 4913 | 243 -185 -169 | C |
| ATOM | 3789 | C | LEU | B | 250 | 50.198 | 6.177 | 9.503 | 1.00 | 35.32 C |
| ANISOU | 3789 | C | LEU | B | 250 | 4518 | 4007 | 4894 | 161 -249 -651 | C |
| ATOM | 3790 | O | LEU | B | 250 | 49.911 | -17.334 | 9.532 | 1.00 | 34.44 O |
| ANISOU | 3790 | O | LEU | B | 250 | 4424 | 3837 | 4823 | 1.57 -298 -692 | O |
| ATOM | 3791 | CB | LEU | B | 250 | 52.422 | -15.281 | 13.162 | 3.00 | 34.53 C |
| ANISOU | 3791 | CB | LEU | B | 250 | 4398 | 3898 | 4832 | 244 -162 -608 | C |
| ATOM | 3792 | CG | LEU | B | 250 | 52.445 | -13.1198 | 11.409 | 1.00 | 35.16 C |
| ANISOU | 3792 | CG | LEU | B | 250 | 4462 | 3884 | 5015 | 210 -216 -584 | C |
| ATOM | 3793 | CD1 | LEU | B | 250 | 53.006 | -17.581 | 11.155 | 1.00 | 33.41 C |
| ANISOU | 3793 | CD1 | LEU | B | 250 | 426.1 | 3580 | 4855 | 230 -245 -550 | C |
| ATOM | 3794 | CD2 | LEU | B | 250 | 53.231 | -15.473 | 12.525 | 1.00 | 34.79 C |
| ANISOU | 3794 | CD2 | LEU | B | 250 | 4382 | 3829 | 5006 | 211 -193 -520 | C |
| ATOM | 3795 | N | VAL | B | 251 | 49.353 | -15.238 | 9.906 | 1.000 | 0033.71 N |
| ANISOU | 3795 | N | VAL | B | 251 | 4297 | 3861 | 4652 | 154 -245 -589 | N |
| ATOM | 3796 | CA | VAL | B | 251 | 48.130 | -15.655 | 10.595 | 1.00 | 34.72 C |
| ANISOU | 3796 | CA | VAL | B | 251 | 4419 | 3979 | 4795 | 90 -303 -553 | C |
| ATOM | 3797 | C | VAL | B | 251 | 47.117 | -16.223 | 9.544 | 1.00 | 35.45 C |
| ANISOU | 3797 | C | VAL | B | 251 | 4527 | 4104 | 4339 | 74 -342 -525 | C |
| ATOM | 3798 | O | VAL | B | 251 | 46.390 | -17.179 | 9.809 | 1.00 | 37.83 O |
| ANISOU | 3798 | O | VAL | B | 251 | 4839 | 4372 | 5182 | 22 -398 -544 | O |
| ATOM | 3799 | CB | VAL | B | 251 | 47.570 | -14.486 | 11.496 | 1.00 | 33.03 C |
| ANISOU | 3799 | CB | VAL | B | 251 | 4175 | 13814 | 4551 | 69 -287 -477 | C |
| ATOM | 3800 | CG1 | VAL | B | 251 | 46.165 | -14.827 | 12.035 | 1.00 | 28.03 C |
| ANISOU | 3800 | CG1 | VAL | B | 251 | 3529 | 3193 | 3928 | 6 -3.39 -454 | C |
| ATOM | 3801 | CG2 | VAL | B | 251 | 48.641 | -14.129 | 12.512 | 1.00 | 32.54 C |
| ANISOU | 3801 | CG2 | VAL | B | 251 | 4101 | 3711 | 4551 | 81 -258 -433 | C |
| ATOM | 3802 | N | ASN | B | 252 | 47.061 | -15.633 | 0.340 | 1.00 | 28.19 N |
| ANISOU | 3802 | N | ASN | B | 252 | 4832 | 4526 | 5104 | 116 -3.14 -656 | N |
| ATOM | 3803 | CA | ASN | B | 252 | 46.256 | -16.231 | 7.272 | 1.00 | 37.04 C |
| ANISOU | 3803 | CA | ASN | B | 252 | 475.2 | 4413 | 4900 | 107 -353 -727 | C |
| ATOM | 3804 | C | ASN | B | 252 | 46.755 | -17 | 621 | 6.885 1.00 | 38.88 C |
| ANISOU | 3804 | C | ASN | B | 252 | 5016 | 4567 | 5191 | 105 -332 -314 | C |
| ATOM | 3805 | O | ASN | B | 252 | 45.930 | -18.434 | 6.542 | 1.00 | 37.12 O |
| ANISOU | 3805 | O | ASN | B | 252 | 4803 | 4332 | 4969 | 65 -438 -857 | O |
| ATOM | 3806 | CB | ASN | B | 252 | 415.254 | -15.3.70 | 6.019 | 1.00 | 38.03 C |
| ANISOU | 3806 | CB | ASN | B | 252 | 4085 | 4635 | 4933 | 1150 -315 -744 | C |

TABLE 3-continued

| | | | | | | | | | | | |
|---|---|---|---|---|---|---|---|---|---|---|---|
| ATOM | 3807 | CG | ASN | B | 252 | 45.683 | -13.962 | 6.283 | 1.00 | 39.82 | C |
| ANISOU | 3807 | CG | ASN | B | 252 | 5057 | 49361 | 5105 | 158 | -287 | -659 | C |
| ATOM | 3808 | OD1 | ASN | B | 252 | 45.053 | -13.730 | 7.322 | 1.00 | 35.44 | O |
| ANISOU | 3808 | OOD | ASN | B | 252 | 46133 | 4502 | 4711 | 126 | -307 | -502 | O |
| ATOM | 3809 | ND2 | ASN | B | 252 | 46.030 | -1 3.08 | 5.4133 | 1.00 | 34.41 | N |
| ANISOU | 3809 | ND2 | ASN | B | 252 | 46.37 | 4572 | 4597 | 223 | -235 | -548 | N |
| ATOM | 3810 | N | SER | B | 253 | 48.073 | -17.854 | 6.902 | 1.00 | 41.14 | N |
| ANISOU | 3810 | N | SER | B | 253 | 5314 | 4799 | 5513 | 151 | -345 | -333 | N |
| ATOM | 3811 | CA | SER | B | 253 | 48.543 | -19 281 | 5.675 | 1.00 | 44.01 | C |
| ANISOU | 3811 | CA | SER | B | 253 | 57081 | 5052 | 504.5 | 152 | -376 | -916 | C |
| ATOM | 3812 | C | SER | B | 253 | 48.138 | -20.212 | 7.797 | 1.00 | 41.84 | C |
| ANISOU | 3812 | C | SER | B | 253 | 5434 | 4733 | 5764 | 44 | -432 | -892 | C |
| ATOM | 3813 | O | SER | B | 253 | 47.760 | -21.1428 | 7.524 | 1.00 | 42.34 | O |
| ANISOU | 3813 | O | SER | B | 253 | 5522 | 4706 | 58.59 | 61 | -480 | -955 | O |
| ATOM | 3814 | CB | SER | B | 253 | 50.336 | -19.406 | 6.432 | 1.00 | 40.42 | C |
| ANISOU | 3814 | CB | SER | B | 253 | 5262 | 4578 | 55.19 | 220 | -326 | -946 | C |
| ATOM | 3815 | OG | SER | B | 253 | 50.4213 | -18.469 | 5.457 | 1.30 | 46.63 | O |
| ANISOU | 3815 | OG | SER | B | 253 | 5645 | 54.54 | 5217 | 273 | -206 | -956 | O |
| ATOM | 3816 | N | LEU | B | 254 | 48.189 | -19.746 | 9.049 | 1.00 | 39422 | N |
| ANISOU | 3816 | N | LEU | B | 254 | 5076 | 4353 | 5472 | 66 | -426 | -809 | N |
| ATOM | 3817 | CA | LEU | B | 254 | 47.536 | -20.533 | 10.168 | 1.00 | 67.62 | C |
| ANISOU | 3817 | CA | LEU | B | 254 | 4873 | 4075 | 5345 | -1 | -473 | -752 | C |
| ATOM | 3818 | C | LEU | B | 254 | 46.175 | -20.833 | 9.027 | 1.00 | 38197 | C |
| ANISOU | 3818 | C | LEU | B | 254 | 5041 | 4277 | 5483 | -68 | -527 | -777 | C |
| ATOM | 3819 | O | LEU | B | 254 | 45.736 | -22.014 | 10.067 | 1.140 | 38.013 | O |
| ANISOU | 3819 | O | LEU | B | 254 | 42 | 4382 | 5.25 | -119 | -579 | -310 | O |
| ATOM | 3820 | CB | LEU | B | 254 | 47.745 | -19.786 | 11.484 | 1.00 | 35.92 | C |
| ANISOU | 3820 | CB | LEU | B | 254 | 4628 | 3868 | 5151 | -16 | -461 | -659 | C |
| ATOM | 3821 | CG | LEU | B | 254 | 49.094 | -191935 | 12.204 | 100 | 36.45 | C |
| ANISOU | 3821 | CG | LEU | B | 254 | 4695 | 3677 | 5282 | 24 | -438 | -633 | C |
| ATOM | 3822 | CD1 | LEU | B | 254 | 49.298 | -16.742 | 13.107 | 1.99 | 39.13 | C |
| ANISOU | 3822 | CD1 | LEU | B | 254 | 5600 | 4257 | 5509 | 23 | -405 | -545 | C |
| ATOM | 3823 | CD2 | LEU | B | 254 | 49.177 | -2112913 | 12.378 | 1.00 | 36.80 | C |
| ANISOU | 3823 | CD2 | LEU | B | 254 | 4764 | 3799 | 5420 | -7 | -480 | -837 | C |
| ATOM | 3824 | N | LEU | B | 255 | 451408 | -19.702 | 9.558 | 1.00 | 35.65 | N |
| ANISOU | 3824 | N | LEU | B | 255 | 4974 | 4347 | 5355 | -6.0 | -512 | -753 | N |
| ATOM | 3825 | CA | LEU | B | 255 | 44.975 | -20.010 | 9.251 | 1.06 | 41.30 | C |
| ANISOU | 3825 | CA | LEU | B | 255 | 5296 | 4729 | 5668 | -122 | -561 | -770 | C |
| ATOM | 3826 | C | LEU | B | 255 | 43.734 | -21.028 | 8.003 | 1.00 | 44.33 | C |
| ANISOU | 3826 | C | LEU | B | 255 | 5774 | 5105 | 51135 | -137 | -601 | -882 | C |

TABLE 3-continued

| | | | | | | | | | | | |
|---|---|---|---|---|---|---|---|---|---|---|---|
| ATOM | 3827 | O | LEU | B | 255 | 42.789 | -21.635 | 8.108 | 1.00 | 42.25 | O |
| ANISOU | 3827 | O | LEU | B | 255 | 5442 | 4806 | 5804 | -2211 | -557 -911 | O |
| ATOM | 3828 | CB | LEU | B | 255 | 43.204 | -18.673 | 3.984 | 1.00 | 39.52 | C |
| ANISOU | 3828 | CB | LEU | B | 255 | 5036 | 4528 | 5351 | -114 | -537 -726 | C |
| ATOM | 3829 | CG | LEU | B | 255 | 42.958 | -17.805 | 10.223 | 1.90 | 42.01 | C |
| ANISOU | 3829 | CG | LEU | B | 255 | 5316 | 4063 | 5678 | -134 | -518 -623 | C |
| ATOM | 3830 | CD1 | LEU | B | 255 | 42.744 | -11.334 | 94514 | 1.00 | 43.432 | C |
| ANISOU | 3830 | CD1 | LEU | B | 255 | 5524 | 5306 | 5821 | -86 | -475 -566 | C |
| ATOM | 3831 | CD2 | LEU | B | 255 | 41.745 | -18.372 | 16.930 | 1.00 | 30.18 | C |
| ANISOU | 3831 | CD2 | LEU | B | 255 | 4931 | 4501 | 5355 | -220 | -553 -595 | C |
| ATOM | 3332 | N | GLU | B | 256 | 44.593 | -254991 | 7.083 | 1.00 | 45.23 | N |
| ANISOU | 3832 | N | GLU | B | 256 | 5352 | 5216 | 6118 | -58 | -570 -947 | N |
| ATOM | 3833 | CA | GLU | B | 256 | 44.479 | -21.926 | 5.968 | 1.06 | 47.83 | C |
| ANISOU | 3833 | CA | GLU | B | 256 | 6214 | 5527 | 0432 | -57 | -6135 -1001 | C |
| ATOM | 3834 | C | GLU | B | 256 | 44.841 | -23.360 | 5.361 | 1.00 | 47.22 | C |
| ANISOU | 3834 | C | GLU | B | 256 | 6171 | 5339 | 5462 | -97 | -630 -1107 | C |
| ATOM | 3835 | O | GLU | B | 256 | 44.123 | -24.284 | 6.030 | 1.00 | 51.41 | O |
| ANISOU | 3835 | O | GLU | B | 256 | 6717 | 5803 | 7013 | -120 | -694 -1172 | O |
| ATOM | 3836 | CB | GLU | B | 256 | 45.318 | -21.435 | 4.790 | 1 00 | 48.10 | C |
| ANISOU | 3836 | CB | GLU | B | 256 | 6268 | 5610 | 6390 | 10 | -554 -1114 | C |
| ATOM | 3837 | CG | GLU | B | 256 | 45.167 | -22.219 | 3.508 | 1.00 | 61.20 | C |
| ANISOU | 3837 | CG | GLU | B | 256 | 7950 | 7287 | 8035 | 23 | -5313 -1238 | C |
| ATOM | 3838 | CD | GLU | B | 256 | 46.023 | -21.556 | 2.412 | 1.00 | 613.02 | C |
| ANISOU | 3838 | CD | GLU | B | 256 | 8958 | 8344 | 8913 | 117 | -524 -1279 | C |
| ATOM | 3839 | OE1 | GLU | B | 256 | 47.209 | -224355 | 2.328 | 1.00 | 77.05 | O |
| ANISOU | 3839 | OE1 | GLU | B | 256 | 0007 | 9298 | 9971 | 508 | -487 -1315 | O |
| ATOM | 3840 | OE2 | GLU | B | 256 | 45.563 | -20.759 | 1.563 | 1.00 | 75.93 | O |
| ANISOU | 3840 | OE2 | GLU | B | 256 | 9054 | 94744 | 9813 | 139 | -509 -1270 | O |
| ATOM | 3841 | N | SER | B | 257 | 45.044 | -23.560 | 7.059 | 1.00 | 45.90 | N |
| ANISOU | 3841 | N | SER | B | 257 | 6015 | 5059 | 6306 | -53 | -611 -1075 5 | N |
| ATOM | 3842 | CA | SER | B | 257 | 46.300 | -24.912 | 7.487 | 1.00 | 48.42 | C |
| ANISOU | 3842 | CA | SER | B | 257 | 6369 | 5237 | 6790 | -84 | -646 -1110 | C |
| ATOM | 3843 | C | SER | B | 257 | 45.432 | -25.477 | 8.509 | 1.00 | 49.77 | C |
| ANISOU | 3843 | C | SER | B | 257 | 6532 | 5345 | 7034 | -177 | -694 -1048 | C |
| ATOM | 3844 | O | SER | B | 257 | 45.288 | -26.680 | 8.707 | 1.00 | 47.14 | O |
| ANISOU | 3844 | O | SER | B | 257 | 6231 | 4904 | 6775 | -217 | -737 -1090 | O |
| ATOM | 3845 | CB | SER | B | 257 | 47.764 | -25.004 | 7.913 | 1.00 | 47.28 | C |
| ANISOU | 3845 | CB | SER | B | 257 | 6235 | 5026 | 6703 | -14 | -606 -1092 | C |
| ATOM | 3846 | OG | SER | B | 257 | 48.622 | -24.230 | 7.093 | 1.00 | 44.81 | O |
| ANISOU | 3846 | OG | SER | B | 257 | 5916 | 4786 | 6232 | 68 | -546 -1121 | O |

TABLE 3-continued

| ATOM   | 3847 | N   | TYR | B | 258 | 44.874 | -24.615 | 9.456  | 1.00 | 44.35 | N |
|--------|------|-----|-----|---|-----|--------|---------|--------|------|-------|---|
| ANISOU | 3847 | N   | TYR | B | 258 | 5803   | 4722    | 6325   | -210 | -685  | -948 N |
| ATOM   | 3848 | CA  | TYR | B | 258 | 44.055 | -25.037 | 10.587 | 1.00 | 42.12 | C |
| ANISOU | 3848 | CA  | TYR | B | 258 | 5507   | 4395    | 6102   | -297 | -721  | -878 C |
| ATOM   | 3849 | C   | TYR | B | 258 | 42.753 | -24.292 | 10.674 | 1.00 | 46.14 | C |
| ANISOU | 3849 | C   | TYR | B | 258 | 5969   | 5014    | 6549   | -352 | -732  | -837 C |
| ATOM   | 3850 | O   | TYR | B | 258 | 42.578 | -23.379 | 11.539 | 1.00 | 43.90 | O |
| ANISOU | 3850 | O   | TYR | B | 258 | 5648   | 4786    | 6245   | -355 | -705  | -743 O |
| ATOM   | 3851 | CB  | TYR | B | 258 | 44.820 | -24.899 | 11.877 | 1.00 | 42.85 | C |
| ANISOU | 3851 | CB  | TYR | B | 258 | 5596   | 4433    | 6252   | -282 | -699  | -784 C |
| ATOM   | 3852 | CG  | TYR | B | 258 | 46.081 | -25.680 | 11.875 | 1.00 | 45.24 | C |
| ANISOU | 3852 | CG  | TYR | B | 258 | 5939   | 4527    | 6625   | -226 | -694  | -818 C |
| ATOM   | 3853 | CD1 | TYR | B | 258 | 46.044 | -27.069 | 12.139 | 1.00 | 49.80 | C |
| ANISOU | 3853 | CD1 | TYR | B | 258 | 6557   | 5071    | 7295   | -265 | -739  | -843 C |
| ATOM   | 3854 | CD2 | TYR | B | 258 | 47.310 | -25.082 | 11.593 | 1.00 | 43.27 | C |
| ANISOU | 3854 | CD2 | TYR | B | 258 | 5886   | 4400    | 6353   | -135 | -644  | -828 C |
| ATOM   | 3855 | CE1 | TYR | B | 258 | 47.211 | -27.834 | 12.124 | 1.00 | 47.89 | C |
| ANISOU | 3855 | CE1 | TYR | B | 258 | 8352   | 4721    | 7122   | -205 | -738  | -877 C |
| ATOM   | 3856 | CE2 | TYR | B | 258 | 48.488 | -25.837 | 11.585 | 1.00 | 48.97 | C |
| ANISOU | 3856 | CE2 | TYR | B | 258 | 6439   | 5025    | 7143   | -78  | -640  | -863 C |
| ATOM   | 3857 | CZ  | TYR | B | 258 | 48.401 | -27.216 | 11.824 | 1.00 | 49.72 | C |
| ANISOU | 3857 | CZ  | TYR | B | 258 | 6575   | 4989    | 7328   | -111 | -687  | -890 C |
| ATOM   | 3858 | OH  | TYR | B | 258 | 49.499 | -27.985 | 11.819 | 1.00 | 53.37 | O |
| ANISOU | 3858 | OH  | TYR | B | 258 | 7067   | 5351    | 7861   | -50  | -686  | -924 O |
| ATOM   | 3859 | N   | PRO | B | 259 | 41.807 | -24.681 | 9.792  | 1.00 | 45.61 | N |
| ANISOU | 3859 | N   | PRO | B | 259 | 5899   | 4981    | 6450   | -394 | -772  | -910 N |
| ATOM   | 3860 | CA  | PRO | B | 259 | 40.567 | -23.968 | 9.670  | 1.00 | 46.11 | C |
| ANISOU | 3860 | CA  | PRO | B | 259 | 5911   | 5161    | 6446   | -435 | -785  | -884 C |
| ATOM   | 3861 | C   | PRO | B | 259 | 39.792 | -23.826 | 10.991 | 1.00 | 44.68 | C |
| ANISOU | 3861 | C   | PRO | B | 259 | 5691   | 4984    | 6302   | -507 | -792  | -782 C |
| ATOM   | 3862 | O   | PRO | B | 259 | 39.013 | -22.895 | 11.113 | 1.00 | 43.30 | O |
| ANISOU | 3862 | O   | PRO | B | 259 | 5457   | 4917    | 6067   | -515 | -782  | -737 O |
| ATOM   | 3863 | CB  | PRO | B | 259 | 39.791 | -24.801 | 8.621  | 1.00 | 47.63 | C |
| ANISOU | 3863 | CB  | PRO | B | 259 | 6115   | 5356    | 5627   | -481 | -840  | -991 C |
| ATOM   | 3864 | CG  | PRO | B | 259 | 40.832 | -25.414 | 7.784  | 1.00 | 48.18 | C |
| ANISOU | 3864 | CG  | PRO | B | 259 | 6242   | 5358    | 6708   | -421 | -834  | -1084 C |
| ATOM   | 3865 | CD  | PRO | B | 259 | 41.934 | -25.742 | 8.768  | 1.00 | 49.33 | C |
| ANISOU | 3865 | CD  | PRO | B | 259 | 6414   | 5390    | 6940   | -394 | -806  | -1029 C |
| ATOM   | 3866 | N   | GLU | B | 260 | 40.012 | -24.735 | 11.957 | 1.00 | 45.60 | N |
| ANISOU | 3866 | N   | GLU | B | 260 | 5829   | 4934    | 6513   | -554 | -807  | -746 N |

TABLE 3-continued

| | | | | | | | | | |
|---|---|---|---|---|---|---|---|---|---|
| ATOM | 3867 | CA | GLU | B | 260 | 39.382 | -24.650 | 13.282 | 1.00 45.05 C |
| ANISOU | 3867 | CA | GLU | B | 260 | 5726 4914 6476 | -621 | -608 | -543 C |
| ATOM | 3868 | C | GLU | B | 260 | 39.635 | -23.302 | 13.922 | 1.00 43.78 C |
| ANISOU | 3868 | C | GLU | B | 260 | 5533 4639 6263 | -570 | -757 | -560 C |
| ATOM | 3869 | O | GLU | B | 260 | 38.857 | -22.876 | 14.791 | 1.00 45.12 O |
| ANISOU | 3869 | O | GLU | B | 260 | 5560 5060 6424 | -617 | -751 | -485 O |
| ATOM | 3870 | CB | GLU | B | 260 | 39.874 | -25.745 | 14.232 | 1.00 46.43 C |
| ANISOU | 3870 | CB | GLU | B | 260 | 5940 4946 6755 | -657 | -822 | -605 C |
| ATOM | 3871 | CG | GLU | B | 260 | 41.393 | -25.355 | 14.338 | 1.00 60.00 C |
| ANISOU | 3871 | CG | GLU | B | 260 | 7704 6586 8506 | -572 | -796 | -610 C |
| ATOM | 3872 | CD | GLU | B | 260 | 42.059 | -26.909 | 33.413 | 1.00 62.93 C |
| ANISOU | 3372 | CD | GLU | B | 260 | 8132 6856 8924 | -543 | -81 | -714 C |
| ATOM | 3873 | OE1 | GLU | B | 260 | 41.756 | -25.995 | 12.178 | 1.00 58.05 O |
| ANISOU | 3873 | OE1 | GLU | B | 260 | 7557 6313 8301 | -535 | -334 | -312 O |
| ATOM | 3374 | OE2 | GLU | B | 260 | 42.960 | -27.625 | 13.923 | 1.00 66.44 O |
| ANISOU | 3874 | OE2 | GLU | B | 260 | 8606 7184 9443 | -520 | -821 | -699 O |
| ATOM | 3875 | N | TYR | B | 261 | 40.738 | -22.523 | 13.560 | 1.00 41.38 N |
| ANISOU | 3875 | N | TYR | B | 261 | 5247 4550 5927 | -478 | -71 | -571 N |
| ATOM | 3376 | CA | TYR | B | 261 | 40.925 | -21.251 | 14.108 | 1.00 381.45 C |
| ANISOU | 3876 | CA | TYR | B | 261 | 4843 4261 5504 | -435 | -6167 | -439 C |
| ATOM | 3877 | C | TYR | B | 261 | 39.791 | -20.295 | 13.723 | 1.00 38.27 C |
| ANISOU | 3877 | C | TYR | B | 261 | 4772 4309 5401 | -443 | -063 | -489 C |
| ATOM | 3878 | O | TYR | B | 261 | 39.623 | -19.259 | 14.347 | 1.00 34.93 O |
| ANISOU | 3878 | O | TYR | B | 261 | 4313 4010 4944 | -427 | -630 | -422 O |
| ATOM | 3879 | CB | TYR | B | 261 | 42.261 | -23.666 | 13.729 | 1.00 37.23 C |
| ANISOU | 3879 | CB | TYR | B | 261 | 4713 4104 4930 | -342 | -623 | -514 C |
| ATOM | 3880 | CG | TYR | B | 261 | 43.439 | -21.293 | 14.415 | 1.00 37.28 C |
| ANISOU | 3880 | CG | TYR | B | 261 | 48139 4091 5500 | -322 | -618 | -407 C |
| ATOM | 3881 | CD1 | TYR | B | 261 | 4.3.485 | -21.428 | 15.785 | 1.00 30.90 C |
| ANISOU | 3881 | CD1 | TYR | B | 261 | 4695 3915 .5410 | -3561 | -621 | -414 C |
| ATOM | 3882 | CD2 | TYR | B | 261 | 44.541 | -21.720 | 13.666 | 1.00 39.21 C |
| ANISOU | 3882 | CD2 | TYR | B | 261 | 5031 4192 5674 | -261 | -502 | -563 C |
| ATOM | 3883 | CE1 | TYR | B | 261 | 44.597 | -21.945 | 10.443 | 1.00 37.99 C |
| ANISOU | 3883 | CE1 | TYR | B | 261 | 4861 3963 5612 | -329 | -019 | -392 C |
| ATOM | 3884 | CE2 | TYR | B | 261 | 45.6.58 | -22.244 | 14.283 | 1.00 38.54 C |
| ANISOU | 3884 | CE2 | TYR | B | 261 | 4970 4015 5659 | -232 | -604 | -547 C |
| ATOM | 3885 | CZ | TYR | B | 261 | 45.695 | -22.308 | 15.0.50 | 1.00 41 31 C |
| ANISOU | 3885 | CZ | TYR | B | 261 | 53111. 4328 6055 | -265 | -612 | -461 C |
| ATOM | 3386 | OH | TYR | B | 261 | 40.822 | -22.949 | 16.212 | 1.00 41.52 O |
| ANISOU | 3886 | OH | TYR | B | 261 | 5362 4264 16150 | -243 | -014 | -447 O |

TABLE 3-continued

```
ATOM    3887  N   LYS B 262      03.293 -20.645  12.711  1.00 39.64      N
ANISOU  3887  N   LYS B 262     4938  4580  5545  -467  -699  -547       N
ATOM    3888  CA  LYS B 262     137.905 -19.797  12.295  1.00 40.89      C
ANISOU  3888  CA  LYS B 262     7040  4804  5628  -471  -702  -550       C
ATOM    3889  C   LYS B 262      36.305  -1 0.719  13.318  1.00 42.26    C
ANISOU  3889  C   LYS B 262     5167  5072  6613  -540  -713  -481       C
ATOM    3890  O   LYS B 262      35.108 -18.701  13.399  1.00 4069       O
ANISOU  3890  O   LYS B 262     4922  4978  5562  -527  -690  -443       O
ATOM    3891  CB  LYS B 262     137.3130 -20.246  10. 966  1.00 46.22    C
ANISOU  3891  CB  LYS B 262     5722  5576  0264  -480  -744  -643       C
ATOM    3892  SG  LYS B 262      38.201 -19.894   9.752  1.00 47.84      C
ANISOU  3892  CG  LYS B 262     5965  5800  6412  -394  -722  -735       C
ATOM    3893  CG  LYS B 262      37.418 -20.379   8.548  1.00 57.68      C
ANISOU  3893  CD  LYS B 262     7207  7097  7513  -415  -773  -737       C
ATOM    3894  CD  LYS B 262      38.334 -20.719   7.397  1.00 62.90      C
ANISOU  3894  CE  LYS B 262     7921  7730  8247  -356  -707  -880       C
ATOM    3895  CE  LYS B 262      37.704 -21.747   6.505  1.00 75.75      C
ANISOU  3895  NZ  LYS B 262     9559  9352  9873  -404  -830  -990       N
ATOM    3896  NZ  ASP B 263     361.641 -20.754  14.119  1.00 41.28      N
ANISOU  3896  N   ASP B 263      .5051  4862  5772  -619  -738  -462     N
ATOM    3897  N   ASP B 263      35.741 -20.725  15.287  1.00 43.12      N
ANISOU  3897  CA  ASP B 263     3238  5.121  6026  -489  -738  -383      C
ATOM    3898  CA  ASP B 263      36.124 -19.643  16.280  1.00 33.37      C
ANISOU  3398  C   ASP B 263     4698  4532  5476  -645  -686  -299       C
ATOM    3899  C   ASP B 263      35.245 -19.002  10.904  1.00 38.09      C
ANISOU  3899  C   ASP B 263     4533  46102  5337  -663  -672  -244      C
ATOM    3900  CB  ASP B 263      35.7E1 -22.0138  16.053  1.00 44.25     C
ANISOU  3900  CB  ASP B 263     5407  5146  62.65  -774  -767  -366      C
ATOM    3901  CG  ASP B 263      35.232 -22.229  15.181  1.00 43.65      C
ANISOU  3901  CG  ASP B 263     5978  5655  5357 -83148 10  -822  -450   C
ATOM    3902  OD1 ASP B 263      94.596 -22.972  14.137  1.30 48.14      O
ANISOU  3902  OD1 ASP B 263     5832  5672  0738  -831  -848  -510       O
ATOM    3903  OD2 ASP B 263     -24.36.6  15.442  1.90 50.51             O
ANISOU  3903  OD2 ASP B 263     5255  5767  7109  -874  -844  -461       O
ATOM    3904  N   SER B 264     137.433 -19.433  16.511  1.30 35.53      N
ANISOU  3904  N   SER B 264     4707  4538  5456  -585  -5.57  -239      N
ATOM    3905  CA  SER B 264      37.918 -13 425  17.350  1.00 35.02      C
ANISOU  3905  CA  SER B 264      423  4102  4959  -539  -539  -222       C
ATOM    3906  C   SER B 264      37.717 -17.949  16.775  1.00 30.07      C
ANISOU  3906  C   SER B 264     3709  3707 41390  -474  -576  -225       C
```

TABLE 3-continued

```
ATOM    3907 O   SER B 264      37.401 -16.1 56 17.510 1.00 34.30  O
ANISOU  3907 O   SER B 264      4088 4174 4772 -465 -545 -169     O
ATOM    3908 CB  SER B 264      39.11L9 -18.557 17.391 1.00 39.18 C
ANISOU  3908 CB  SER B 264      4431 4162 5 53 -493 -589 -216     C
ATOM    3909 OG  SER B 264      39.555 -19.599 18.737 1.00 44 77  O
ANISOU  3909 OG  SER B 264      5535 5163 6307 -544 -609 -174     O
ATOM    3910 N   VAL B 265      37948 -16901 15.482 1.00 32.99    N
ANISOU  3910 N   VAL B 265      39.56 3969 4594 -427 -583 -290    N
ATOM    3911 CA  VAL B 265      37.701 -15.514 14.809 1.00 32.41  C
ANISOU  3911 CA  VAL B 265      3874 3997 4444 -3.64 -5.51 -291   C
ATOM    3912 C   VAL B 265      36.233 -15.222 15.003 1.00 32.52  C
ANISOU  3912 C   VAL B 265      13827 4106 4424 -400 -565 -263    C
ATOM    3913 O   VAL B 265      35.879 -14.096 15.432 1.00 32.52  O
ANISOU  3913 O   VAL B 265      3796 4174 4365 -363 -532 -214     O
ATOM    3914 CB  VAL B 265      38.065 -15.751 13.331 1.00 34.55  C
ANISOU  3914 CB  VAL B 265      4174 4276 4678 -319 -561 -368     C
ATOM    3915 CG1 VAL B 265      37.602 -14.523 12.533 1.00 38.90  C
ANISOU  3915 CG1 VAL B 265      4703 4935 5142 -260 -540 -365     C
ATOM    3916 CG2 VAL B 265      39.504 -15.383 13.132 1.00 30.28  C
ANISOU  3916 CG2 VAL B 265      3685 3645 4164 -269 -532 -388     C
ATOM    3917 N   GLN B 266      35.350 -16.155 14.752 1.30 32.13  N
ANISOU  3917 N   GLN B 266      3882 4182 4523 -470 -615 -295     N
ATOM    3918 CA  GLN B 266      33.922 -15.958 -5.05 1.00 313.3.9 C
ANISOU  3918 CA  GLN B 266      3871 4332 4553 -515 -533 -271     C
ATOM    3919 C   GLN B 266      39.552 -15.504 16.455 1.00 25.95  C
ANISOU  3919 C   GLN B 266      3251 3759 3901 -545 -604 -189     C
ATOM    3920 O   GLN B 266      32.81313 -14.550 16.597 1.00 30.26 O
ANISOU  3920 O   GLN B 266      3368 4016 4113 -523 -583 -154     O
ATOM    3921 CB  GLN B 266      33.078 -17.176 14.5813 1.00 33.02 C
ANISOU  3921 CB  GLN B 266      37119 4250 4517 -6100 -694 -321   C
ATOM    3922 CG  GLN B 266      611.573 -16.829 14.602 1.00 35.33 C
ANISOU  3922 CG  GLN B 266      40513 4722 4840 -536 -713 -306    C
ATOM    3923 CD  GLN B 266      30.721 -17.964 14.025 1.00 38.13  C
ANISOU  3923 CD  GLN B 266      4319 5013 5157 -722 -777 -366     C
ATOM    3924 OE1 GLN B 266      41136 -13.491 12.938 1.05 43.91   O
ANISOU  3924 OE1 GLN B 266      5095 5715 5382 -7113 -810 -442    O
ATOM    3925 NE2 GLN B 266      29.690 -13.356 14.734 1.00 33.76  N
ANISOU  3925 NE2 GLN B 266      4333 5120 5268 -307 -793 -834     N
ATOM    3926 N   GLU B 267      34.021 -15.392 17.407 1.53 30.37  N
ANISOU  3926 N   GLU B 267      3455 3461 4234 -1595 -604 -151    N
```

TABLE 3-continued

```
ATOM    3927 CA  GLU B 267      33.510 -151.182  16.616  1.00 30.19      C
ANISOU  3927 OA  GLU B 267      3432  31345  4225  -15.33  -580   -32    C
ATOM    3928 C   GLU B 267      34.203  -14.859  19.356  1.00 30.70     C
ANISOU  3928 C   GLU B 267      3473  3941  4231  -557  -5215   -40     C
ATOM    3929 O   GLU B 267      93.537  -14.150  20.163  1.00 32.75     O
ANISOU  3929 O   GLU B 267      3689  4270  4485  -559  -495           O
ATOM    3930 CB  GLU B 267      34.1817 -17.333  19.537  1.33 35.10     C
ANISOU  3930 CB  GLU B 267      4072  48169  4960  -693  -592  -518    C
ATOM    3931 CG  GLU B 267      1148  10148  1021  313  1.00 37.37     C
ANISOU  3931 CG  GLU B 267      4315  45.171  5211  -737  -557   27    C
ATOM    3932 CD  GLU B 267      3.615-485  21.895  1.00 52.51          C
ANISOU  3932 CD  GLU B 267      521  -1502  71  4327  -592  711.1      C
ATOM    3933 OE1 GLU B 267      34.474 -19.388  21.584  1.00 5174      O
ANISOU  3933 OE1 GLU B 267      6211  62.95  7152  -831  -518   30     O
ATOM    3934 OE2 GLU B 267      32.786 -18.030  22.835  1.00 73.14     O
ANISOU  3934 OE2 GLU B 267      161535  5955  7323  -892  -5313  117   O
ATOM    3935 N   THR B 268      135.42 -14.795  19.042  1.30 26.291    N
ANISOU  3935 N   THR B 268      8021  3581  3047  -495  -507   -58     N
ATOM    3936 CA  THR B 268      35.034 -13.2.5  19.511  1.00 29.481    C
ANISOU  3936 CA  THR B 268      3371  3753  4058  -427  -455   -24     C
ATOM    3937 C   THR B 268      35.2611 -12.099  13.901  1.00 30.05    C
ANISOU  3937 C   THR B 268      8470  3993  4134  -375  -435   -27     C
ATOM    3998 O   THR B 268      136.106  11.061  1 9.555  1.00 2057    O
ANISOU  3938 O   THR B 268      3460  4045  4111  -344  -396   13      O
ATOM    3939 CB  THR B 268      37.537-13.117  19.251  1.00 27.08      C
ANISOU  3939 CB  THR B 268      31.130  3385  3774  -370  -434  -43    C
ATOM    3940 OG1 THR B 268      37.869 -13.3135  17.844  1.00 25.24    O
ANISOU  3940 OG1 THR B 268      2920  3143  3527  -337  -449  -106     O
ATOM    3941 OG2 THR B 268      138.962 -14.131  20.027  1.00 25.15    O
ANISOU  3941 OG2 THR B 268      9044  3171  13719  -467  -470  -28     O
ATOM    3942 N   ALA B 269      34.781 -12.240  17.573  1.00.3055      N
ANISOU  3942 N   ALA B 269      34015  3972  4044  -354  -463   -75    N
ATOM    3943 CA  ALA B 269      33.526 -11.193  17.072  1.00 30.17     C
ANISOU  3943 CA  ALA B 269      3378  4090  13995  -315  -4.73  -73    C
ATOM    3944 C   ALA B 269      32.572 -11.072  17.783  1.00 31.29     C
ANISOU  3944 C   ALA B 269      3441  4302  4122  -655  -458   -37     C
ATOM    3945 O   ALA B 269      32.022  -9.924  17.945  1.00 32.45     O
ANISOU  3945 O   ALA B 269      3553  4532  4236  -306  -428   -8      O
ATOM    3946 CB  ALA B 269      33.730-11476  15.590  1.00 29.56       C
ANISOU  3946 CB  ALA B 269      3319  4051  3899  -295  -438  -133     C
```

TABLE 3-continued

| | | | | | | | | | | |
|---|---|---|---|---|---|---|---|---|---|---|
| ATOM | 3947 | N GLU B 270 | | 32.021 | -12.161 | 15.249 | 1.00 | 33.60 | | N |
| ANISOU | 3947 | N GLU B 270 | 3717 | 4085 | 4465 | -445 | -492 | -36 | | N |
| ATOM | 3948 | CA GLU B 270 | | 30.630 | -12.152 | 15.680 | 1.00 | 31.261 | | C |
| ANISOU | 3948 | CA GLU B 270 | 3024 | 4389 | 4184 | -495 | -497 | -4 | | C |
| ATOM | 3949 | C GLU B 270 | | 133.725 | -11.567 | 20.217 | 1.00 | 30.90 | | C |
| ANISOU | 3949 | C GLU B 270 | 12.23 | 8 273 | 3235 | 4633 | 4119 | -459 | -440 | 75 | C |
| ATOM | 3950 | O GLU B 270 | | 25.798 | -10.6138 | 20.573 | 1.00 | 27.91 | | O |
| ANISOU | 3950 | O GLU B 270 | 2851 | 4044 | 3709 | -74 | -429 | 32 | | O |
| ATOM | 3951 | CB GLU B 270 | | 30.068 | -13.518 | 36.969 | 1.00 | 3175 | | C |
| ANISOU | 3951 | CB GLU B 270 | 3352 | 4404 | 4276 | -603 | -545 | -19 | | C |
| ATOM | 3952 | CG GLU B 270 | | 29.720 | -14.1133 | 17.508 | 1.05 | 313 | 90 | C |
| ANISOU | 3952 | CG GLU B 270 | 4283 | 5325 | 5173 | -614 | -799 | -90 | | C |
| ATOM | 3953 | CD GLU B 270 | | 20.241 | -15.549 | 17.5.17 | 1.00 | 42.89 | | C |
| ANISOU | 3953 | CD GLU B 270 | 4765 | 8777 | 5729 | -724 | -645 | -115 | | C |
| ATOM | 3954 | OE1 GLU B 270 | | 29.662 | -15.421 | 18.4761 | 1.00 | 50.55 | | O |
| ANISOU | 3954 | OE1 GLU B 270 | 5774 | 6668 | 5763 | -731 | -644 | -86 | | O |
| ATOM | 3955 | OE2 GLU B 270 | | 26.487 | -15.039 | 15.753 | 1.00 | 46.06 | | O |
| ANISOU | 3955 | OE2 GLU B 270 | 5217 | 6307 | 6203 | -754 | -694 | -155 | | O |
| ATOM | 3956 | N VAL B 271 | | 33.751 | -11.832 | 21.010 | 1.00 | 28.53 | | N |
| ANISOU | 3956 | N VAL B 271 | 31041 | 3046 | 13852 | -499 | -433 | 79 | | N |
| ATOM | 3957 | CA VAL B 271 | | 21.742 | -11.364 | 22.362 | 1.30 | 26.43 | | C |
| ANISOU | 3957 | CA VAL B 271 | 3016 | 3952 | 3536 | -504 | -390 | 334 | | C |
| ATOM | 3958 | C VAL B 271 | | 31.9.35 | -9.343 | 22.540 | 1.00 | 28.37 | | C |
| ANISOU | 3958 | C VAL B 271 | 2974 | 3946 | 3744 | -41 | 5 -341 | 147 | | C |
| ATOM | 3959 | O VAL B 271 | | 31.882 | -9.335 | 23.671 | 1.00 | 32.50 | | O |
| ANISOU | 3959 | O VAL B 271 | 3523 | 4531 | 4296 | -4 | 4 -305 | 186 | | O |
| ATOM | 3960 | CB VAL B 271 | | 32.721 | -12 143 | 23.267 | 1.00 | 28.17 | | C |
| ANISOU | 3960 | CB VAL B 271 | 30134 | 3820 | 13849 | -545 | -391 | 150 | | C |
| ATOM | 3961 | CG1 VAL B 271 | | 32.373 | -13.613 | 23.217 | 1.00 | 31.50 | | C |
| ANISOU | 3961 | CG1 VAL B 271 | 3455 | 4208 | 41333 | -636 | -436 | 156 | | C |
| ATOM | 3962 | CG2 VAL B 271 | | 34.174 | -11.906 | 22.773 | 1.00 | 20.93 | | C |
| ANISOU | 3962 | CG2 VAL B 271 | 2945 | 3580 | 3703 | -484 | -385 | 132 | | C |
| ATOM | 3963 | N VAL B 272 | | 32.451 | -9.147 | 21.524 | 1.00 | 26.36 | | N |
| ANISOU | 3963 | N VAL B 272 | 2746 | 3689 | 3463 | -343 | -335 | 115 | | N |
| ATOM | 3964 | CA VAL B 272 | | 32079 | -7.711 | 21.644 | 1.00 | 29.19 | | C |
| ANISOU | 3964 | CA VAL B 272 | 3145 | 4120 | 3824 | -26.3 | -288 | 129 | | C |
| ATOM | 3965 | C VAL B 272 | | 31.355 | -6.952 | 21.055 | 1.00 | 29.92 | | C |
| ANISOU | 3965 | C VAL B 272 | 3181 | 4315 | 3873 | -221 | -287 | 127 | | C |
| ATOM | 3966 | O VAL B 272 | | 31 285 | -5.707 | 2 104 | 1.00 | 30.40 | | O |
| ANISOU | 3966 | O VAL B 272 | 3243 | 44001 | 0902 | -149 | -248 | 140 | | O |

TABLE 3-continued

| | | | | | | | | | | |
|---|---|---|---|---|---|---|---|---|---|---|
| ATOM | 3967 | CB | VAL | B | 272 | 33.896 | -7.224 | 20.992 | 1.00 | 29.75 C |
| ANISOU | 3967 | CB | VAL | B | 272 | 3282 | 412.5 | 389.5 | -204 | -271 107 C |
| ATOM | 3968 | CG1 | VAL | B | 272 | 35.342 | -7.847 | 21.739 | 1.30 | 31.37 C |
| ANISOU | 3968 | CG1 | VAL | B | 272 | 3532 | 4243 | 4144 | -239 | -270 115 C |
| ATOM | 3969 | CG2 | VAL | B | 272 | 33.903 | -7.519 | 19.527 | 1.00 | 32.01 C |
| ANISOU | 3969 | CG2 | VAL | B | 272 | 3555 | 4497 | 4245 | -188 | -305 54 C |
| ATOM | 3970 | N | ILE | B | 273 | 30.365 | -7.558 | 20.542 | 1.00 | 29.31 N |
| ANISOU | 3970 | N | ILE | B | 273 | 3053 | 4288 | 3795 | -288 | -330 112 N |
| ATOM | 3971 | CA | ILE | B | 273 | 29.055 | -7 074 | 20.106 | 1.00 | 29.53 C |
| ANISOU | 3971 | CA | ILE | B | 273 | 3010 | 4428 | 13783 | -232 | -335 114 C |
| ATOM | 3972 | C | ILE | B | 273 | 28.437 | -6.214 | 21.234 | 1.00 | 30.42 C |
| ANISOU | 3972 | C | ILE | B | 273 | 3459 | 4977 | 4231 | -211 | -288 154 C |
| ATOM | 3973 | O | ILE | B | 273 | 27.987 | -5.076 | 23.977 | 1.00 | 35.43 O |
| ANISOU | 3973 | O | ILE | B | 273 | 3599 | 5297 | 4480 | -131 | -255 181 O |
| ATOM | 3974 | CB | ILE | B | 273 | 28.032 | -8.076 | 19.610 | 1.30 | 32.26 C |
| ANISOU | 3974 | CB | ILE | B | 273 | 3294 | 4827 | 4137 | -301 | -350 92 C |
| ATOM | 3975 | CG1 | ILE | B | 273 | 28.457 | -3.719 | 18.300 | 1 30 | 33.46 C |
| ANISOU | 3975 | CG1 | ILE | B | 273 | 3484 | 4941 | 4288 | -333 | -437 40 C |
| ATOM | 3976 | CG2 | ILE | B | 273 | 28.679 | -7.355 | 19.255 | 1.00 | 38.02 C |
| ANISOU | 3976 | CG2 | ILE | B | 273 | 3941 | 5679 | 4824 | -259 | -394 97 C |
| ATOM | 3977 | CD1 | ILE | B | 273 | 26.30 | -7.743 | 17.227 | 1.00 | 85.44 C |
| ANISOU | 3977 | CD1 | ILE | B | 273 | 17771 | 5233 | 4490 | -203 | -4261 25 C |
| ATOM | 3978 | N | PRO | B | 274 | 28.428 | -6.729 | 22.470 | 1.00 | 33.29 N |
| ANISOU | 3978 | N | PRO | B | 274 | 3433 | 4944 | 4270 | -276 | -274 19 N |
| ATOM | 3979 | CA | PRO | B | 274 | 27.844 | -5.927 | 23.513 | 1311 | 35.89 C |
| ANISOU | 3979 | CA | PRO | B | 274 | 3723 | 5335 | 4580 | -253 | -228 213 C |
| ATOM | 3980 | C | PRO | B | 274 | 28.644 | -4.634 | 23.779 | 1.00 | 38.47 C |
| ANISOU | 3980 | C | PRO | B | 274 | 4101 | 5828 | 4886 | -165 | -177 217 C |
| ATOM | 3981 | O | PRO | B | 274 | 28.210 | -3.774 | 24.306 | 1.00 | 34.70 O |
| ANISOU | 3981 | O | PRO | B | 274 | 3598 | 5197 | 4388 | -131 | -135 236 O |
| ATOM | 3982 | CB | PRO | B | 274 | 27.934 | -8.844 | 24.716 | 1.00 | 34.49 C |
| ANISOU | 3982 | CB | PRO | B | 274 | 3544 | 5131 | 4431 | -344 | -223 242 C |
| ATOM | 3983 | CG | PRO | B | 274 | 27.878 | -3.234 | 24.152 | 1.00 | 36.37 C |
| ANISOU | 3983 | CG | PRO | B | 274 | 3750 | 5332 | 4700 | -423 | -278 227 C |
| ATOM | 3934 | CD | PRO | B | 274 | 28.8013 | -8.071 | 22.997 | 1.00 | 35.74 C |
| ANISOU | 3984 | CD | PRO | B | 274 | 3763 | 5191 | 4827 | -373 | -293 1821 C |
| ATOM | 3985 | N | LEU | B | 275 | 29.810 | -4.452 | 23.148 | 1.30 | 32.71 N |
| ANISOU | 3985 | N | LEU | B | 275 | 2.444 | 48121 | 4165 | -133 | -180 199 N |
| ATOM | 3986 | CA | LEU | B | 275 | 30.076 | -3.256 | 23.372 | 1.00 | 35.50 C |
| ANISOU | 3986 | CA | LEU | B | 275 | 3871 | 5149 | 4528 | -61 | -134 230 C |

TABLE 3-continued

| | | | | | | | | | | |
|---|---|---|---|---|---|---|---|---|---|---|
| ATOM | 3987 | C | LEU | B | 275 | 30.477 | -2.184 | 22.280 | 1.00 | 35.47 13 C |
| ANISOU | 3987 | C | LEU | B | 275 | 3973 | 5278 | 4531 | 131 | -123 131 C |
| ATOM | 3988 | O | LEU | B | 275 | 31.124 | -1.099 | 22.1315 | 1.00 | 35.49 O |
| ANISOU | 3988 | O | LEU | B | 275 | 3899 | 5115 | 44709.5 | -83 | 1148 103 O |
| ATOM | 3989 | CB | LEU | B | 275 | 32.183 | -3.645 | 23.502 | 1.00 | 29.25 C |
| ANISOU | 3989 | CB | LEU | B | 275 | 3145 | 4245 | 3763 | -82 | -135 191 C |
| ATOM | 3990 | OG | LEU | B | 275 | 32.506 | -4.354 | 24.411 | 1.00 | 34.71 O |
| ANISOU | 3990 | OG | LEU | B | 275 | .3821 | 4887 | 4471 | -1 39 | -155 204 O |
| ATOM | 3991 | CD1 | LEU | B | 275 | 34.005 | -5.142 | 24.536 | 1.06 | 28.38 C |
| ANISOU | 3991 | CD1 | LEU | B | 275 | 3095 | 3988 | 3730 | -177 | -1.57 19.5 C |
| ATOM | 3992 | CD2 | LEU | B | 275 | 31.858 | -4.586 | 25.772 | 1.00 | 28.73 C |
| ANISOU | 3993 | CD2 | MET | B | 276 | 3034 | 4181 | 3732 | -195 | -129 234 C |
| ATOM | 3993 | N | MET | B | 276 | 29.571 | -2.489 | 21.353 | 1.00 | 35.93 N |
| ANISOU | 3993 | N | MET | B | 276 | 3834 | 5273 | 4515 | 30 | -150 5C N |
| ATOM | 3994 | CA | MET | B | 276 | 29.158 | -1.591 | 23.28.5 | 1.30 | 37.45 C |
| ANISOU | 3994 | CA | MET | B | 276 | 4051 | 5507 | 4671 | 121 | -159 181 C |
| ATOM | 3995 | C | MET | B | 276 | 28.081 | -0.345 | 20.735 | 1.00 | 43 91 C |
| ANISOU | 3995 | C | MET | B | 276 | 4432 | 6027 | 5.336 | 177 | -132 202 C |
| ATOM | 3996 | O | MET | B | 276 | 27.291 | -0.962 | 21.638 | 1 00 | 35.36 O |
| ANISOU | 3996 | O | MET | B | 276 | 3659 | 6.378 | 4390 | 135 | -128 21 O |
| ATOM | 3997 | CB | MET | B | 276 | 28.587 | -2.413 | 191387 | 1.00 | 34.08 C |
| ANISOU | 3997 | CB | MET | B | 276 | 3574 | 5195 | 4306 | 99 | -219 158 C |
| ATOM | 3998 | CG | MET | B | 276 | 29.801 | -3.220 | 18.450 | 1.00 | 34.54 C |
| ANISOU | 3998 | CG | MET | B | 276 | 3720 | 5097 | 4357 | 65 | -242 130 C |
| ATOM | 3999 | SD | MET | B | 276 | 31.405 | -2.358 | 18.159 | 1.00 | 36.59 S |
| ANISOU | 3999 | SD | MET | B | 276 | 4127 | 5308 | 4519 | 126 | -195 532 S |
| ATOM | 4000 | CE | MET | B | 276 | 32.513 | -19754 | 18.405 | 1.00 | 44.55 C |
| ANISOU | 4000 | CE | MET | B | 276 | 5127 | 6176 | 5325 | 40 | -218 1135 C |
| ATOM | 4001 | N | ALA | B | 277 | 2-.988 | 0.698 | 20.094 | 1.00 | 38.41 N |
| ANISOU | 4001 | N | ALA | B | 277 | 4139 | 5729 | 4750 | 275 | -111 211 N |
| ATOM | 4002 | CA | ALA | B | 277 | 26.927 | 1.549 | 20.535 | 1.50 | 39.22 C |
| ANISOU | 4002 | CA | ALA | B | 277 | 4179 | 5899 | 41025 | 344 | -82 230 C |
| ATOM | 4003 | C | ALA | B | 277 | 25.479 | 0.994 | 20.372 | 1 00 | 40.89 C |
| ANISOU | 4003 | C | ALA | B | 277 | 4286 | 6229 | 5022 | 321 | -121 230 C |
| ATOM | 4004 | O | ALA | B | 277 | 25.326 | 3.196 | 19.422 | 1.00 | 38.58 O |
| ANISOU | 4004 | O | ALA | B | 277 | 3960 | 5958 | 4722 | 288 | -175 215 O |
| ATOM | 4005 | CB | ALA | B | 277 | 27.073 | 2.189 | 19.545 | 1.00 | 34.94 C |
| ANISOU | 4005 | CB | ALA | B | 277 | 3.575 | 5343 | 4258 | 4.53 | -61 243 C |
| TEF | 4306 | | ALA | B | 277 | | | | | |
| HETATM | 4007 | C1 | BMX | A | 1000 | 35.951 | -4.950 | 18.275 | 0.40 | 12.00 C |

TABLE 3-continued

| | | | | | | | | |
|---|---|---|---|---|---|---|---|---|
| HETATM | 4008 | C2 BMX A1000 | 36.393 | -5.915 | 17.210 | 0.40 | 12.88 | C |
| HETATM | 4009 | C3 BMX A1000 | 37.834 | -5.506 | 16.1356 | 0.40 | 12.35 | C |
| HETATM | 4010 | C4 BMX A1000 | 37.896 | -4.121 | 16.436 | 0.40 | 12.97 | C |
| HETATM | 4011 | C5 BMX A1000 | 37.430 | -3.163 | 17.578 | 0.40 | 12.35 | C |
| HETATM | 4012 | C6 BMX A1000 | 37.3E2 | -1.356 | 17.242 | 0.40 | 1 1.98 | C |
| HETATM | 4013 | C7 BMX A1000 | 30.212 | -0.507 | 15.280 | 0.40 | 13.34 | C |
| HETATM | 4014 | C8 BMX A1000 | 34.190 | -5.327 | 14.150 | 0.40 | 15.65 | C |
| HETATM | 4015 | N2 BMX A1000 | 35.427 | -5.693 | 151078 | 3.40 | 12.59 | N |
| HETATM | 4016 | O1 BMX A1000 | 35.677 | -5.278 | 19.503 | 0.40 | 12.10 | O |
| HETATM | 4017 | O3 BMX A1000 | 38.276 | -3.497 | 15.843 | 3.43 | 12.50 | O |
| HETATM | 4018 | O4 BMX A1000 | 39.211 | -3.784 | 16.0313 | 0.40 | 12.01 | O |
| HETATM | 4019 | O5 BMX A1000 | 96.124 | -3.574 | 17.984 | 0.40 | 13.50 | O |
| HETATM | 4020 | O6 BMX A1000 | .35.576 | -1.4841 | 15.032 | 0.40 | 12.52 | O |
| HETATM | 4021 | O7 BMX A1000 | 35.7.82 | -7.664 | 15.426 | 0.40 | 14.76 | O |
| HETATM | 4022 | P BMX A1000 | 36.529 | -3.381 | 15.428 | 0.40 | 12.70 | P |
| HETATM | 4023 | O19 BMX A1000 | 35.473 | -0.222 | 14.347 | 0.40 | 12.53 | O |
| HETATM | 4024 | O17 BMX A1000 | 36 329 | 0.13.1 8 | 16.500 | 0.40 | 13.63 | O |
| HETATM | 4025 | O18 BMX A1000 | 37.856 | 0.035 | 14.833 | 0.40 | 13.15 | O |
| HETTAM | 4026 | C1 BMX B1010 | 64.385 | 3.763 | 17.8.49 | 0.40 | 13.55 | C |
| HETATM | 4027 | C2 BMX B1000 | 63.911 | 4.6213 | 16.704 | 0.40 | 113.45 | C |
| HETATM | 4028 | C3 BMX B1000 | 132.489 | 4.221 | 10.321 | 0.40 | 12.62 | C |
| HETATM | 4029 | C4 BMX B1000 | 62.371 | 2.849 | 151073 | 0.40 | 12.57 | C |
| HETATM | 4030 | C5 BMX B1000 | 62. 780 | 2.025 | 17.191 | 0.40 | 11.53 | C |
| HETATM | 4031 | C6 BMX B1000 | 52.780 | 0.467 | 17.35 | 0.40 | 12.40 | C |
| HETATM | 4032 | C7 BMX B1000 | 05.096 | 5.076 | 14.609 | 0.40 | 14.20 | C |
| HETATM | 4033 | C8 BMX B1000 | 66.104 | 4.645 | 133.590 | 0.40 | 14. 11 | C |
| HETATM | 4034 | N2 BMX B1000 | 64.951 | 4.326 | 15.60.6 | 0.40 | 13.41 | N |
| HETATM | 4035 | O1 8MX 81000 | 53.605 | 4.171 | 39.029 | O. | 12.52 | O |
| HETATM | 4036 | O3 BMX B1000 | 82. I1 515 | 4.968 | 15.140 | 0.40 | 11.00 | 0 |
| HETATM | 4037 | O4 BMX B1000 | 61.090 | 2002 | 15.532 | 040 | 12.142 | O |
| HETATM | 4038 | O5 BMX B1000 | 94. I 39 | 2.397 | 17.4619 | 0.40 | 14.10 | O |
| HETATM | 4039 | O6 BMX B1000 | 63.755 | 0.045 | 16.220 | 0.40 | 14.36 | O |
| HETATM | 4040 | O7 BMX B1000 | 64.440 | 6.104 | 14.426 | 0.46 | 14.53 | O |
| HETATM | 4041 | P BMX B1000 | 53.612 | -1.431 | 15.592 | 0.40 | 13.06 | P |
| HETATM | 4042 | O19 BMX 81000 | 54.055 | -2.214 | 16.804 | 0.40 | 12.42 | O |
| HETATM | 4043 | O17 BMX B1000 | 02.520 | -1.596 | 14.878 | 0.40 | 13.41 | O |
| HETATM | 4044 | O18 BMX B1000 | 614.846 | -1367 | 14.515 | 0.40 | 14.95 | O |
| HETATM | 4045 | O HOH A1101 | 30.465 | -0.098 | 29.486 | 1.00 | 28.80 | O |
| HETATM | 4046 | O HOH A1102 | 39.030 | -2.218 | 13.942 | 1.00 | 05.02 | O |
| HETATM | 4047 | O HOH A1103 | 38.435 | 1.950 | 18. 1 39 | 1.00 | 27.90 | O |

TABLE 3-continued

| | | | | | | | | | |
|---|---|---|---|---|---|---|---|---|---|
| HETATM | 4048 | O | HOH | A1104 | 41.206 | 15.194 | 32.047 | 1.00 | 29.52 O |
| HETATM | 4049 | O | HOH | A1105 | 24.122 | -3187 | 45.575 | 1.00 | 32.50 O |
| HETATM | 4050 | O | HOH | A1106 | 28.552 | 5.104 | 4.7813 | 1.00 | 44.36 O |
| HETATM | 4051 | O | HOH | A1107 | 39 011 | 0.578 | 28.874 | 1.00 | 30.12 O |
| HETATM | 4052 | O | HOH | A1108 | 34.971 | -2.503 | 12.953 | 1.00 | 133.62 O |
| HETATM | 4053 | O | HOH | A1109 | 35.717 | -9.56.5 | 13.356 | 1.00 | 31.00 O |
| HETATM | 4054 | O | HOH | A1110 | 41.621 | -0.576 | 12.205 | 1.00 | 30.37 O |
| HETATM | 4055 | O | HOH | A1111 | 31.410 | -0.020 | 0.502 | 1.00 | 35.17 O |
| HETATM | 4059 | O | HOH | A1112 | 58.166 | 8.145 | 8.5.38 | 1.00 | 34.35 O |
| HETATM | 4057 | O | HOH | AA113 | 56.635 | 7.216 | 6.355 | 1.00 | 30.85 O |
| HETATM | 4058 | O | HOH | AA114 | 67 208 | -0.418 | 23.775 | 1.00 | 30.20 O |
| HETATM | 4059 | O | HOH | A1115 | 23.474 | -1.938 | 13.231 | 1.00 | 39.56 O |
| HETATM | 4060 | O | HOH | A4116 | 41.617 | 1.441 | 12.532 | 1.00 | 29.73 O |
| HETATM | 4061 | O | HOH | A1117 | 43.151 | -8.191 | 4.13 | 1.00 | 37.99 O |
| HETATM | 4062 | O | HOH | A1118 | 34.754 | 6.476 | 27.195 | 1.00 | 35.64 O |
| HETATM | 4063 | O | HOH | A1119 | 66.715 | 7.574 | 3.049 | 1.00 | 41.41 O |
| HETATM | 4064 | O | HOH | A1120 | 30.255 | 1.006 | 28.320 | 1.00 | 33.01 O |
| HETATM | 4065 | O | HOH | A1121 | 32.403 | -8.000 | 12.153 | 1.00 | 34.17 O |
| HETATM | 4066 | O | HOH | A1122 | 57.669 | 20.047 | 16.073 | 1.00 | 36.58 O |
| HETATM | 4067 | O | HOH | A1123 | 56.846 | 14.757 | 21.072 | 1.00 | 32.45 O |
| HETATM | 4068 | O | HOH | A1124 | 53.117 | 4.579 | 19.863 | 1.00 | 32.03 O |
| HETATM | 4069 | O | HOH | A1125 | 52.710 | 19.584 | 20.978 | 1.00 | 33.28 O |
| HETATM | 4070 | O | HOH | A1126 | 45.251 | 4.092 | -6.444 | 1.00 | 45.84 O |
| HETATM | 4071 | O | HOH | A1127 | 24.099 | 0.043 | 8719 | 1.00 | 32.03 O |
| HETATM | 4072 | O | HOH | A1128 | 31.887 | 17.106 | 27.223 | 1.00 | 37.16 O |
| HETATM | 4073 | O | HOH | A1129 | 27 750 | -5.905 | 34.060 | 1.00 | 34.00 O |
| HETATM | 4074 | O | HOH | A1130 | 41.985 | 23.528 | 20.633 | 1.00 | 37.00 O |
| HETATM | 4075 | O | HOH | A1131 | 35.617 | 2.935 | 2071.00 | 40.86 | O |
| HETATM | 4076 | O | HOH | 01132 | 43.640 | 22.266 | 16266 | 1.00 | 46.36 O |
| HETATM | 4077 | O | HOH | A1133 | 59.071 | 14.463 | 20.497 | 1.30 | 32.43 O |
| HETATM | 4078 | O | HOH | A1134 | 23.153 | -4.551 | 19.068 | 1.00 | 39.58 O |
| HETATM | 4079 | O | HOH | A1135 | 35.5231 | -6.086 | 5.61731 | 1.00 | 36.75 O |
| HETATM | 4080 | O | HOH | A1136 | 310 142 | -0.007 | 0.105 | 1.00 | 43.31 O |
| HETATM | 4081 | O | HOH | A1137 | 43.2134 | 3.553 | 10.847 | 1.00 | 32.43 O |
| HETATM | 4082 | O | HOH | A1138 | 74.313 | 12.8137 | 1499.5 | 1.00 | 51.72 O |
| HETATM | 4083 | O | HOH | A1139 | 55.508 | 11.245 | 11.765 | 1.00 | 33.81 O |
| HETATM | 4084 | O | HOH | A1140 | 30.370 | -1.050 | 11.032 | 1.00 | 38.06 O |
| HETATM | 4085 | O | HOH | A1141 | 42.445 | 2.13.92 | 9.635 | 1.00 | 44.35 O |
| HETATM | 4086 | O | HOH | A1142 | 38.461 | 110.587 | 3.2141 | 1.00 | 40.74 O |
| HETATM | 4087 | O | HOH | A1143 | 20.9115 | 13.4154 | 1.00 | 34.21 O | |

TABLE 3-continued

| | | | | | | | | | | |
|---|---|---|---|---|---|---|---|---|---|---|
| HETATM | 4088 | O | HOH | A1144 | 53.546 | 21.573 | 19.214 | 1.06 | 44.07 | O |
| HETATM | 4089 | O | HOH | A1145 | 1134.057 | 20.084 | 1 84502 | 1.190 | 38.13 | O |
| HETATM | 4090 | O | HOH | A1146 | 34.928 | 20.835 | 6.690 | 1.00 | 43.83 | O |
| HETATM | 4091 | O | HOH | A1147 | 47.275 | 22.301 | 5.1 23 | 1.00 | 38.67 | O |
| HETATM | 4092 | O | HOH | A1148 | 38.435 | -1.1.335 | 11 .2915 | 1.00 | 40.65 | O |
| HETATM | 4093 | O | HOH | A1149 | 65.101 | 14.753 | 9.176 | 1.00 | 44.42 | O |
| HETATM | 4094 | O | HOH | A4150 | 55.167 | 5.379 | 2.528 | LOC | 48.95 | O |
| HETATM | 4095 | O | HOH | A1151 | Si 967 | 118.590 | 5.654 | 1.00 | 58.83 | |
| HETATM | 4096 | O | HOH | A1152 | 58.137 | 13.747 | 8.963 | 1.00 | 38.1 | O |
| HETATM | 4097 | O | HOH | A1153 | 57.028 | 14.677 | 3.327 | 101 | 44.19 | O |
| HETATM | 4098 | O | HOH | A1154 | 39.073 | 25.399 | 26.3.55 | 1.00 | 51.90 | O |
| HETATM | 4099 | O | HOH | 41155 | 21.205 | -0.650 | 17.748 | 1.00 | 37.56 | O |
| HETATM | 4100 | O | HOH | A1156 | 53.905 | 22.451 | 15.518 | 1.00 | 46.38 | O |
| HETATM | 4101 | O | HOH | A1157 | 60.311 | 20.554 | 14.377 | 1.00 | 54.87 | O |
| HETATM | 4102 | O | HOH | A1158 | 45 175 | 22.841 | 25.078 | 1.00 | 48.02 | O |
| HETATM | 4103 | O | HOH | A1159 | 35.1351 | -13.551 | 8.451 | 1.00 | 50.40 | O |
| HETATM | 4104 | O | HOH | A1160 | 30.036 | -5.172 | 4.501 | 1.00 | 34.43 | O |
| HETATM | 4105 | O | HOH | A1161 | 28.780 | 5.316 | 28.446 | 1.00 | 40.01 | O |
| HETATM | 4106 | O | HOH | A1162 | 5.05E | 11002 | 5.327 | 1.00 | 47.15 | O |
| HETATM | 4107 | O | HOH | A1163 | 13.551 | 1.784 | 18.231 | 1.00 | 53.17 | O |
| HETATM | 4108 | O | HOH | A1164 | 36.586 | 16.314 | E.E22. | 1.00 | 44.73 | O |
| HETATM | 4109 | O | HOH | A1165 | 58 632 | 24.913 | 8.912 | 1.00 | 51.32 | O |
| HETATM | 4110 | O | HOH | A1166 | 32.254 | -9.40.6 | 4.077 | 1.00 | 43.27 | O |
| HETATM | 4111 | O | HOH | A1167 | 13.130 | -1.308 | 0.926 | 1.00 | 52.06 | O |
| HETATM | 4112 | O | HOH | A1168 | 39.255 | -10.485 | 6.207 | 1.00 | 41.34 | O |
| HETATM | 4113 | O | HOH | A1169 | 42.040 | 0.213 | 3.713 | 1.00 | 42.51 | O |
| HETATM | 4114 | O | HOH | A1170 | 20.276 | 4.602 | 17.070 | 1.00 | 52.01 | O |
| HETATM | 4115 | O | HOH | A1171 | 24.227 | -7.525 | -3.4 79 | 1.00 | 58.07 | O |
| HETATM | 4116 | O | HOH | A1172 | 68 290 | 6.836 | 14.687 | 1.00 | 36.25 | O |
| HETATM | 4117 | O | HOH | A1173 | 28.488 | -3.131 | 14.77.5 | 1.00 | 47.26 | O |
| HETATM | 4118 | O | HOH | A1174 | 77.346 | 3.633 | 18.650 | 1.00 | 47.51 | O |
| HETATM | 4119 | O | HOH | A1175 | 54.010 | 12.709 | 23.603 | 1.00 | 42.75 | O |
| HETATM | 4120 | O | HOH | A1176 | 25.791 | -7.495 | -3.071 | 1.00 | 62.43 | O |
| HETATM | 4121 | O | HOH | A1177 | 26.392 | 13.046 | 17.978 | 1.00 | 50.24 | O |
| HETATM | 4122 | O | HOH | A1178 | 40.114 | 15.398 | -2.954 | 1.00 | 52.69 | O |
| HETATM | 4123 | O | HOH | A1179 | 22.281 | 2.038 | 17.799 | 1.00 | 57.68 | O |
| HETATM | 4124 | O | HOH | A1180 | 39.580 | -10.265 | 0.165 | 1.00 | 40.17 | O |
| HETATM | 4125 | O | HOH | 41181 | 78.174 | -2.251 | 22.270 | 1.00 | 63.98 | O |
| HETATM | 4126 | O | HOH | 41182 | 55.579 | 21.061 | 17.087 | 1.00 | 54.36 | O |
| HETATM | 4127 | O | HOH | A1188 | 49.560 | 2.32.6 | -6.677 | 1.50 | 54.33 | O |

TABLE 3-continued

| | | | | | | | | | |
|---|---|---|---|---|---|---|---|---|---|
| HETATM | 4128 | O | HOH | A1134 | 10.605 | 6.963 | 6.381 | 1.00 | 58.45 | O |
| HETATM | 4129 | O | HOH | A1185 | 27.486 | -0.031 | 1.856 | 1.00 | 58.54 | O |
| HETATM | 4130 | O | HOH | A1186 | 17.432 | 4.022 | 18.027 | 1.00 | 53.25 | O |
| HETATM | 4131 | O | HOH | A1187 | 28 145 | -1.454 | 12.645 | 1.00 | 47.59 | O |
| HETATM | 4132 | O | HOH | A1388 | 15.826 | 3.344 | 155.3 | 1.00 | 54.47 | O |
| HETATM | 4133 | O | HOH | A1189 | 76.534 | 5.024 | 29.679 | 1.00 | 52.40 | O |
| HETATM | 4134 | O | HOH | A1190 | 29.670 | -0.501 | 3.280 | 1.00 | 54.57 | O |
| HETATM | 4135 | O | HOH | A1191 | 34.828 | -4.100 | 2.643 | 1.00 | 54.50 | O |
| HETATM | 4136 | O | HOH | A1192 | 17.875 | 8.877 | 11.913 | 1.00 | 57.82 | O |
| HETATM | 4137 | O | HOH | A1193 | 30.703 | 4.390 | 13.614 | 1.00 | 50.75 | O |
| HETATM | 4138 | O | HOH | A1194 | 150.71 | -12.775 | 21.159 | 1.00 | 56.73 | O |
| HETATM | 4139 | O | HOH | A1195 | 15.747 | -4.073 | 23.77.5 | 1.00 | 57.54 | O |
| HETATM | 4140 | O | HOH | A1196 | 23.5.52 | 6.396 | 10.25.5 | 1.00 | 50.77 | O |
| HETATM | 4141 | O | HOH | A1197 | 72.578 | 14.721 | 11.504 | 1.00 | 53.18 | O |
| HETATM | 4142 | O | HOH | A1198 | 50.930 | -10.094 | -4.530 | 1.08 | 61.96 | O |
| HETATM | 4143 | O | HOH | A1199 | 31.293 | -3.475 | 14.65.8 | 3 | .00 43.66 | O |
| HETATM | 4144 | O | HOH | A1200 | 74.7 | 1123.574 | 20.512 | 1.00 | 52.16 | O |
| HETATM | 4145 | O | HCH | A1201 | 28 322 | 8.300 | 24.68 | 1.00 | 53.68 | O |
| HETATM | 4146 | O | HOH | A1202 | 6.272 | 14228 | 1 2.21 | 71.30 | 60.57 | O |
| HETATM | 4147 | O | HOH | A1203 | 15.763 | 7.723 | 15.403 | 1.00 | 53.24 | O |
| HETATM | 4148 | O | HOH | A1204 | 45.842 | 20.652 | 27.74.5 | 1.00 | 48.24 | O |
| HETATM | 4149 | O | HOH | A1205 | 1034 | 7.319 | 17 .647 | 1.00 | 49.01 | O |
| HETATM | 4150 | O | HOH | A1206 | 70.204 | -0.047 | 133.040 | 1.00 | 53.02 | O |
| HETATM | 4151 | O | HOH | A1207 | 26.170 | 10.770 | 8.655 | 1.00 | 53.05 | O |
| HETATM | 4152 | O | HOH | A1208 | 29.139 | -5.559 | -0.384 | 1.00 | 57.78 | O |
| HETATM | 4153 | O | HOH | A1209 | 31 24-7 | 3.811 | -4073 | 1.00 | 58.20 | O |
| HETATM | 4154 | O | HOH | A1210 | 1.208E-i | 8.783 | 35.359 | 1.60 | 51.55 | O |
| HETATM | 4155 | O | HOH | A1211 | 73.371 | 16.646 | 15.914 | 1.00 | 63.09 | O |
| HETATM | 4156 | O | HOH | A1212 | 37 392 | 2000 | 14.789 | 1.00 | 52.80 | O |
| HETATM | 4157 | O | HOH | A1213 | 132.554 | -3.592 | 1.350 | 1.00 | 57.00 | O |
| HETATM | 4158 | O | HOH | B1101 | 43.445 | -12.933 | 13.130 | 1.00 | 30.77 | O |
| HETATM | 4159 | O | HOH | B1102 | 61.957 | -3.228 | 18.426 | 1.00 | 27.72 | O |
| HETATM | 4160 | O | HOH | B1103 | 56.644 | 7.580 | 11.066 | 1.00 | 2055 | O |
| HETATM | 4161 | O | HOH | B1104 | 64.584 | 7.679 | 12.162 | 1.00 | 26.43 | O |
| HETATM | 4162 | O | HOH | B1105 | 68.294 | 7.048 | 7.1 18 | 1.00 | 39.24 | O |
| HETATM | 4163 | O | HOH | B1106 | 38.148 | 0.065 | 23.727 | 1.00 | 28.31 | O |
| HETATM | 4164 | O | HOH | B1107 | 88.593 | 0.080 | -4.686 | 1.00 | 40.19 | O |
| HETATM | 4165 | O | HOH | B1108 | 54.350 | -20.633 | 30.086 | 1.00 | 42.25 | O |
| HETATM | 4166 | O | HOH | B1109 | 58024 | -16.951 | 33.625 | 1.00 | 38.70 | O |
| HETATM | 4167 | O | HOH | B1110 | 48.893 | -9.716 | 7.282 | 1.00 | 31.70 | O |

TABLE 3-continued

| | | | | | | | | |
|---|---|---|---|---|---|---|---|---|
| HETATM | 4168 | O | HOH | B1111 | 73.605 | -2.672 | 11 3.724 | 1.00 35.48 O |
| HETATM | 4169 | O | HOH | B1112 | 47.346 | -5.509 | 20.446 | 1.00 30.24 O |
| HETATM | 4170 | O | HOH | B1113 | 65.410 | 01710 | 12.765 | 1.00 29.59 O |
| HETATM | 4171 | O | HOH | B1114 | 42.218 | -15.442 | 8.515 | 1.00 40.01 O |
| HETATM | 4172 | O | HOH | B1115 | 59.595 | 10.150 | 11.257 | 1.00 31.84 O |
| HETATM | 4173 | O | HOH | B1116 | 61.405 | 6.525 | 13.733 | 1.00 29.38 O |
| HETATM | 4174 | O | HOH | B1117 | 61.288 | -0.564 | 28.141 | 1.00 32.31 O |
| HETATM | 4175 | O | HOH | B1118 | 73.783 | 10284 | 4 508 | 1.50 29.90 O |
| HETATM | 4176 | O | HOH | B1119 | 66.299 | 1.756 | 15.268 | 1.00 30.10 O |
| HETATM | 4177 | O | HOH | B1120 | 68.906 | -1329 | 3.525 | 1.00 39.52 O |
| HETATM | 4178 | O | HOH | B1121 | 58.023 | -3.308 | 12.958 | 1.00 35.26 0 O |
| HETATM | 4179 | O | HOH | B1122 | 63.854 | -0.357 | 25.535 | 1.00 27.81 O |
| HETATM | 4180 | O | HOH | B1123 | 69.335 | 1.910 | 14.691 | 1.00 37.18 O |
| HETATM | 4181 | O | HOH | B1124 | 39.732 | -22.286 | 17.526 | 1.00 51.75 O |
| HETATM | 4182 | O | HOH | B1125 | 66.367 | -2.401 | 8.678 | 1.00 31.75 O |
| HETATM | 4183 | O | HOH | B1126 | 72.632 | 4.309 | 13.519 | 1.50 36.19 O |
| HETATM | 4134 | O | HOH | B1127 | 63.846 | -18.881 | 9.336 | 1.00 44.52 O |
| HETATM | 4185 | O | HOH | B1128 | 45.644 | -0.269 | 3.608 | 1.00 42.45 O |
| HETATM | 4186 | O | HOH | B1129 | 71.416 | -8.351 | 5.550 | 1.00 44.26 O |
| HETATM | 4187 | O | HOH | B1130 | 40.923 | -12.250 | 12.628 | 1.00 30.58 O |
| HETATM | 4188 | O | HOH | B1131 | 69.872 | 4.518 | 13.787 | 1.00 34.81 O |
| HETATM | 4189 | O | HOH | B1132 | 50.304 | -5.522 | 25.727 | 1.00 59.39 O |
| HETATM | 4190 | O | HOH | B1133 | 69.135 | -24.163 | 25.129 | 1.00 36.44 O |
| HETATM | 4191 | O | HOH | B1134 | 65.221 | -21.288 | 23.182 | 1.00 39.91 O |
| HETATM | 4192 | O | HOH | B1135 | 42.215 | -13.132 | 10.462 | 1.00 39.94 |
| HETATM | 4193 | O | HOH | B1136 | 86.594 | -2.855 | 16712 | 1.00 56.19 O |
| HETATM | 4194 | O | HOH | B1137 | 43.508 | -15.265 | 23.787 | 1.00 33.71 O |
| HETATM | 4195 | O | HOH | B1138 | 46.883 | -22.512 | 21.907 | 1.00 46.45 O |
| HETATM | 4196 | O | HOH | B1139 | 71.612 | -6.230 | 23.991 | 1.00 40.05 O |
| HETATM | 4197 | O | HOH | B1140 | 85.465 | -1.039 | -1 331 | 1.00 50.57 O |
| HETATM | 4198 | O | HOH | B1141 | 64.878 | 3.401 | 4.887 | 1.00 41.08 O |
| HETATM | 4199 | O | HOH | 91142 | 72.251 | -9.109 | 25.995 | 1.00 48.37 O |
| HETATM | 4200 | O | HOH | B1143 | 61.795 | 9.075 | 10.217 | 1.00 41.33 O |
| HETATM | 4201 | O | HOH | B1144 | 47.5 | -20.177 | 23.304 | 1.00 35.78 O |
| HETATM | 4202 | O | HOH | B1145 | 72.25 | -5.453 | 26.533 | 1.00 47.83 O |
| HETATM | 4203 | O | HOH | B1146 | 84.575 | -21.473 | 3.479 | 1.00 48.79 O |
| HETATM | 4204 | O | HOH | B1147 | 509.95 | -26.151 | 09.529 | 1.00 54.01 O |
| HETATM | 4205 | O | HOH | B1148 | 42.278 | -17.325 | 25.240 | 1.00 37.14 O |
| HETATM | 4206 | O | HOH | B1149 | 64.141 | 11.1195 | 6.974 | 1.40 41.72 O |
| HETATM | 4207 | O | HOH | B1150 | 32.737 | -19.072 | 17.314 | 1.00 44.42 O |

TABLE 3-continued

| | | | | | | | | |
|---|---|---|---|---|---|---|---|---|
| HETATM | 4208 | O | HOH | B1151 | 73.40 -12. 59 26.324 | 1.00 | 45.95 | O |
| HETATM | 4209 | O | HOH | B1152 | 64.118 -3.623 0.383 | 1.011 | 48.28 | O |
| HETATM | 4210 | O | HOH | B1153 | 64.332 -5.449 11.375 | 1.00 | 34.16 | O |
| HETATM | 4211 | O | HOH | B1154 | 65.586 -5.1858 28.028 | 1.00 | 33.16 | O |
| HETATM | 4212 | O | HOH | B1155 | 25.136 -7.023 11.315 | 1.00 | 45.59 | O |
| HETATM | 4213 | O | HOH | B1156 | 65.065 4.530 2.331 | 1.00 | 56.64 | O |
| HETATM | 4214 | O | HOH | B1157 | 55.473 0.531 19.553 | 1.00 | 37.85 | O |
| HETATM | 4215 | O | HOH | B1158 | 55.433 -9.285 -5.505 | 1.00 | 45.37 | O |
| HETATM | 4216 | O | HOH | B1159 | 64.8515 -8.140 3090 | 1.03 | 42.78 | O |
| HETATM | 4217 | O | HOH | B1160 | 42.493 -237 19.229 | 1.00 | 39.45 | O |
| HETATM | 4218 | O | HOH | B1161 | 40.534-17.709 5.155 | 1.00 | 48.87 | O |
| HETATM | 4219 | O | HOH | B1162 | 52.315 -10.548 14.290 | 1.00 | 61.77 | O |
| HETATM | 4220 | O | HOH | B1163 | 69.579 -1.052 11.195 | 1.00 | 39.94 | O |
| HETATM | 4221 | O | HOH | B1164 | 65058 -25.022 27.155 | 1.00 | 58.23 | O |
| HETATM | 4222 | O | HOH | B1165 | 27.364 -20.364 13.978 | 1.00 | 58.12 | O |
| HETATM | 4223 | O | HOH | B1166 | 56.743 -3.350 -7.001 | 1.00 | 55.60 | O |
| HETATM | 4224 | O | HOH | B1167 | 57.455 5.089 3.767 | 1.00 | 42.61 | O |
| HETATM | 4225 | O | HOH | B1168 | 74.410 -11158 14.258 | 1.00 | 45.27 | O |
| HETATM | 4226 | O | HOH | B1169 | 75.149 3.405 -1.880 | 1.00 | 47.09 | O |
| HETATM | 4227 | O | HOH | B1170 | 73.933 -11.056 15.525 | 1.00 | 49.39 | O |
| HETATM | 4228 | O | HOH | B1171 | 60.095 -19.355 -1.096 | 1.00 | 60.45 | O |
| HETATM | 4229 | O | HOH | B1172 | 76.550 10.871 15.710 | 1.00 | 50.97 | O |
| HETATM | 4230 | O | HOH | B1173 | 65.515 1.051 2.667 | 1.00 | 44.41 | O |
| HETATM | 4231 | O | HOH | B1174 | 48.765 -3.773 27.310 | 1.00 | 52.46 | O |
| HETATM | 4232 | O | HOH | B1175 | 55.035 1.172 11.890 | 1.03 | 35.08 | O |
| HETATM | 4233 | O | HOH | B1175 | 55.580 -2.225 30.146 | 1.00 | 38.49 | O |
| HETATM | 4234 | O | HOH | B1177 | 60.982 -22.825 20.125 | 1.00 | 60.83 | O |
| HETATM | 4235 | O | HOH | B1178 | 70.874 4.773 1.547 | 1.00 | 59.50 | O |
| HETATM | 4236 | O | HOH | B1179 | 33.353 -2.624 2.943 | 1.00 | 60.79 | O |
| HETATM | 4237 | O | HOH | B1180 | 45.955 -24.132 18.709 | 1.00 | 56.26 | O |
| HETATM | 4238 | O | HOH | B1181 | 74.945 1 .752 -0.840 | 1.00 | 56.16 | O |
| HETATM | 4239 | O | HOH | B1182 | 74.922 -13.8003 20.013 | 1.00 | 46.41 | O |
| HETATM | 4240 | O | HOH | B1183 | 67.533 0.340 1.045 | 1.00 | 54.61 | O |
| HETATM | 4241 | O | HOH | B1184 | 62.224 -24.765 21.501 | 1.00 | 53.17 | O |
| HETATM | 4242 | O | HOH | B1185 | 72.114 -0.599 12.716 | 1.00 | 45.35 | O |
| HETATM | 4243 | O | HOH | B1185 | 58.409 -17.060 29.630 | 1.00 | 36.20 | O |
| HETATM | 4244 | O | HOH | B1187 | 58.269 -24.629 23.224 | 1.00 | 46.73 | O |
| HETATM | 4245 | O | HOH | B1188 | 25110 -14575 16.100 | 1.00 | 49.70 | O |
| HETATM | 4246 | O | HOH | B1189 | 43.338 -25.893 16.745 | 1.00 | 70.93 | O |
| HETATM | 4247 | O | HOH | B1190 | 69.241 -7.602 4.510 | 1.00 | 54.36 | O |

TABLE 3-continued

```
HETATM 4248  O   HOH B1191      90.426  -4.832 10.952 1.00 57.23      O
HETATM 4249  O   HOH B1192      60.6.40 -1.837 -1.553 1.00 55.15      O
HETATM 4250  O   HOH B1193      30.525 -18.750 13.084 1.00 45.99      O
HETATM 4251  O   HOH B1194      65.805 -23.265 13.381 1.00 53.74      O
HETATM 4252  O   HOH B1135      61.269 -12.59.5  4.931 1.00 54.63     O
HETATM 4253  O   HOH B1196      74.321  -5.E.05  2.777 1.00 49.84     O
HETATM 4254  O   HOH B1197      76.1.33 15.725  1.187 1.00 60.42      O
HETATM 4255  O   HOH B1198      56.275 -23.442 14.182 1.00 43.55      O
HETATM 4256  O   HOH B1199      55.157 -24.527 21.55.7 1.00 56.56     O
HETATM 4257  O   HOH B1200      73.165  -0.542 23.441 1.00 40.52      O
HETATM 4258  O   HOH B1201      58.271  -4.513  3.739 1.00 45.72      O
HETATM 4259  O   HOH B1202      98.042  -0.400  0.918 1.00 54.85      O
HETATM 4260  O   HDH B1203      76.096 -11.404  4.579 1.00 58.79      O
HETATM 4261  O   HOH B1204      70.970 -14.429 11.398 1.00 50.39      O
HETATM 4262  O   HOH B1205      97.205 -17.263 31.503 1.00 48.05      O
HETATM 4263  O   HOH B1206      58.029 -75.055  5.295 1.00 50.57      O
HETATM 4264  O   HOH B1207      53.174 -25.139  8.451 1.00 50.23      O
HETATM 4265  O   HOH B1208      77.029 14.1343 13.644 1.00 48.90      O
CONECT 4007 4008 4016 4019
CONECT 4008 4007 4009 4015
CONECT 4009 4008 4010 4017
CONECT 4010 4009 4011 4018
CONECT 4011 4010 4012 4019
CONECT 4012 4011 4020
CONECT 4013 4014 4015 4021
CONECT 4014 4013
CONECT 4015 4008 4013
CONECT 4016 4007
CONECT 4017 4009
CONECT 4018 4010
CONECT 4019 4007 4011
CONECT 4020 4012 4022
CONECT 4021 4013
CONECT 4022 4020 4023 4024 4025
CONECT 4023 4022
CONECT 4024 4022
CONECT 4025 4022
CONECT 4026 4027 4035 4038
CONECT 4027 4025 4028 4034
CONECT 4028 4027 4029 4036
```

TABLE 3-continued

```
CONECT 4029 4028 4030 4037
CONECT 4030 4029 4031 4038
CONECT 4031 4030 4039
CONECT 4032 4033 4034 4040
CONECT 4033 4032
CONECT 4034 4077 4032
CONECT 4035 4025
CONECT 4036 4028
CONECT 4037 4029
CONECT 4038 4025 4030
CONECT 4039 4031 4041
CONECT 4040 4032
CONECT 4041 4039 4042 4043 4044
CONECT 4042 4041
CONECT 4043 4041
CONECT 4044 4041
MASTER 478 0 2 28 10 0 10 6 4263 2 38 44
END
```

Example 9

Electron Microscopy and Single Particle Analysis

Purified NanR protein, the NanR/ligand complex, and the NanR/DNA complex were diluted to a final concentration of 300 nM with 300 mM NaCl and 50 mM Tris-HCl (pH 7.0). 5 µl of each sample solution were applied to a carbon-coated grid that had been glow-discharged for 3 minutes in air, and the grid was immediately negatively stained using 1% uranyl acetate. Grids were examined in a Technai G2 Spirit Twin transmission electron microscope (FEI, Hillsboro, Oreg., USA), and images were recorded on a 4K×4K Ultrascan 895 CCD (Gatan, Pleasanton, Calif., USA) at a magnification of 0.36 nm/pixel. For single particle analysis, images of individual particles were selected interactively, windowed out, and imported into the SPIDER program (Health Research, Rensselaer, N.Y., USA). A total of 894 NanR particles, 1131 NanR/ligand particles, and 1039 NanR/DNA particles were used in the processing and class averages were produced by the known reference free method. To compare similar views of the three samples, the datasets were combined and then co-aligned and classified. Averages in which the NanR region was similarly observed were selected for further analysis. The UCSF Chimera program was used for visualization and comparative analyses of atomic models and averages.

Example 10

Isothermal Titration Calorimetry

NanR-binding duplex DNA (5'-gtttgaaaaaaatcttcgtt atg-gattattatggcgatggagattattttcaaac-3', SEQ ID NO:15) was chemically synthesized. NanR was dialyzed extensively against Tris buffer (50 mM Tris-HCl, pH 7.0; 300 mM NaCl) and the DNA was diluted to 0.03 mM in the same buffer. Protein and DNA samples were degassed by vacuum aspiration for 20 minutes prior to loading and titration was carried out at 25° C. The NanR dimer in the syringe (0.48 mM) was titrated against the 0.03 mM DNA sample in the reaction cell. Analysis of the interaction between the NanR/ManNAc-6P complex and the DNA sample was performed using 0.48 mM of complex and 0.03 mM of DNA. The calorimetric assays were performed using a VP-ITC (Micro-Cal Inc., Northampton, Mass.). The stirring speed was 300 rpm and the thermal power was recorded every 10 seconds. Data were processed and plotted using the Origin program (version 7) supplied with the instrument.

Example 11

Sequence Comparison of NanR Protein

Figure 13:
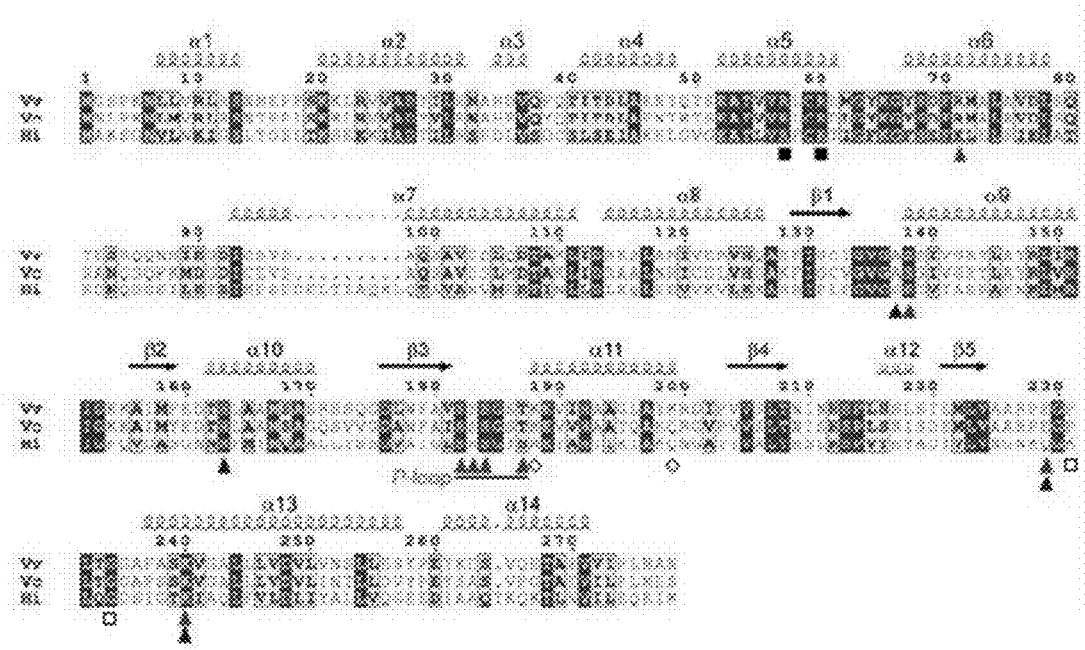
FIG. 13 shows conservation of V. vulnificus, V. cholerae, and H. influenzae-derived NanR sequences. Black squares (■) indicate residues essential for DNA-binding, gray triangles indicate residues involved in binding to the phosphate group of ManNAc-6P, empty squares (□) indicate residues involved in binding to the N-acetyl group of ligand, and diamonds (◇) indicate additional DNA-binding residues. Vv represents V. vulnificus UJ016 (gi37676858) (SEQ ID NO:1); Vc represents V. cholerae O1 biovarE1 Tor str. N16961 (gi:15641775) (SEQ ID NO:16); and Hi represents H. influenzae Rd KW20 (gi:16272110) (SEQ ID NO:17).

Conservation of *V. vulnificus*, *V. cholerae*, and *H. influenza*-derived NanR sequences was examined. NanR amino acid sequences of *V. vulnificus* UJ016 (gi37676858), *V. cholerae* O1 biovarE1 Tor str. N16961 (gi:15641775), and *H. influenzae* Rd KW20 (gi:16272110) were compared to each other. For sequence comparison, T-COFFEE software was used and for visualization, ESPript software was used. These two softwares are available in ExPASy portal (http://au.>>---<<expasy.org/) (FIG. 13). High conservation was observed, and in particular, amino acids critical for ligand-binding and DNA-binding are conserved well.

Experimental Example 1

Structure of NanR/ManNAc-6P Complex

Unlike the typical structure of other transcriptional regulators, the NanR/ManNAc-6P complex analyzed by the above method contains two molecules in an asymmetric unit (A of FIG. 1). The symmetry mate in the dimer was analyzed, and a functional dimeric form of NanR was confirmed by electron microscopy (B of FIG. 1). The two NanR molecules at the dimer face each other and tilt approximately 45° in opposite directions (FIG. 2a). NanR adopts a two domain architecture that includes an N-terminal DNA-binding domain (DBD) and a large C-terminal ligand-binding domain (LBD) (FIG. 2b). The DBD comprises six helices while the LBD forms α/β structure characterized by a five-stranded parallel β-sheet flanked by α helices (FIG. 2b). The residues between α6 and α7 were not included in the final model because they were invisible in the electron density map; these regions are presumably very flexible. A DALI search revealed that no structures similar to that of NanR have been published. However, the structure of the LDB resembles the isomerase domain of glucosamine-6-phosphate synthase (GlmS), a bienzyme complex that catalyzes the first step in hexosamine metabolism. The fructose 6-phosphate binding site in the N-terminal isomerase subdomain of GlmS is located in the same position as that of the ManNAc-6P binding site in the NanR LBD, suggesting that NanR has evolutionarily adapted the isomerase domain to sense the nan regulatory molecule, whose structure is similar to that of fructose 6-phosphate. The structure of the NanR DBD is similar to the N-terminal domain of the *Bacillus subtilis* putative transcriptional regulator ybbH(PDB accession ID 2O3F). ManNAc-6P is located at the C-terminal edge of the β sheet in the LBD domain (FIG. 2b).

Experimental Example 2

Characterization of Interaction Between ManNAc-6P and NanR

An electron density difference map demonstrated that ManNAc-6P binds to NanR in the site formed by loops L9, L13, and L17 of the LBD domain (FIG. 3a). L13, which corresponds to the P-loop in the GlmS isomerase subdomain, crosses over and embraces the phosphate group of ManNAc-6P (FIGS. 3a and 3b); the phosphate oxygen atoms form hydrogen bonds with the side chains of S182, S184, and T187, and with the backbone amide of S183 in the P-loop (FIG. 3b, upper panel). This binding structure is very similar to that of the GlmS isomerase (FIG. 3b, lower panel). The side chain hydroxyl group of S138 in loop L9 is also hydrogen-bonded to a ManNAc-6P phosphate oxygen atom (FIGS. 3a and 3b). The hydroxyl group at position of the sugar ring forms a hydrogen bond with the A137 backbone amide. A hand-in-hand interaction between the two NanR monomers is formed by hydrogen bonds between the hydroxyl group at position O1 of the sugar ring in each NanR monomer and the nitrogen atom in the imidazole ring of each H163 (FIGS. 3a and 3c). This structure is critical for the conformational change of the NanR dimer and delivery of the signal to the nan operon genes when ligand-binding occurs. Furthermore, the phosphoryl group of the ligand forms a water-mediated hydrogen bond with the side chain amino group of R71 on α6 in the DBD (FIGS. 3a and 3c). These interactions may enable ligand-mediated relocation of the NanR dimer and influence its interaction with the nan operator. P231 and G234 form water-mediated hydrogen bonds with the carbonyl oxygen atom of the N-acetyl group (FIG. 3a). In addition, E229 and K240 form water-mediated hydrogen bonds with the sugar and phosphate oxygen atoms of ManNAc-6P (FIG. 3a).

Figure 3D:
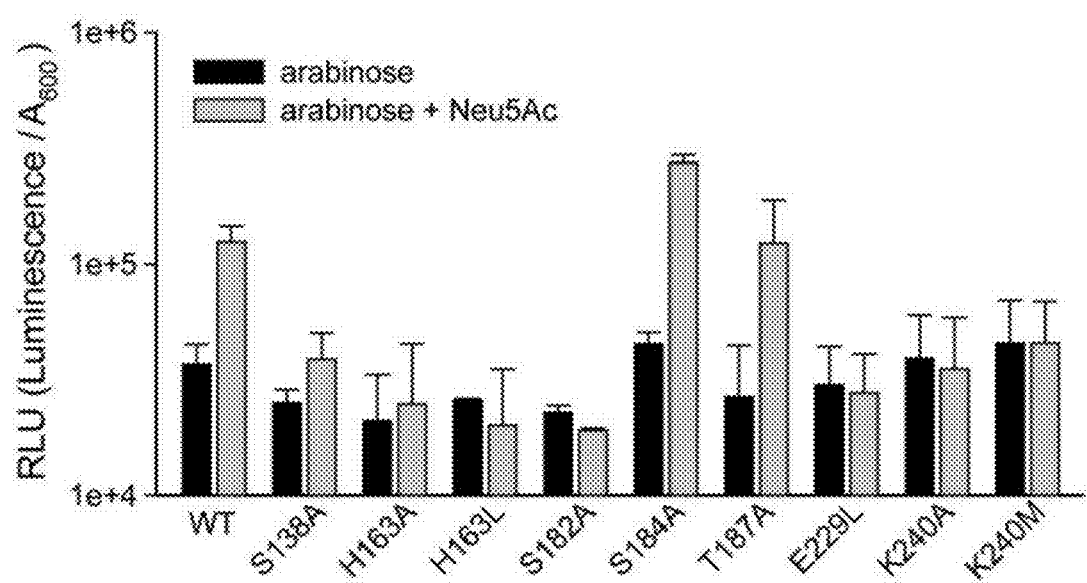

To assess the importance of the interaction between ManNAc-6P and NanR to regulation of the nan genes, the residues involved in ligand-binding were mutated and the impact on NanR function was investigated using an *E. coli* dual plasmid system. Cells were cotransformed with plasmids containing a luciferase reporter gene fused to the NanR-binding nanT(PSL)AR promoter (PnanTp), and wild-type or mutant NanR, and then incubated in the presence of arabinose and the presence or absence of Neu5Ac. Luciferase activity in cells expressing the wild-type NanR was increased following addition of Neu5Ac; however, Neu5Ac was unable to activate PnanTp in cells expressing the mutant NanR (S138A, H163A, H163L, S182A, E229L, K240A or K240M), except the S184A and T187A mutants (FIG. 3d). These results suggest that precise binding of ManNAc-6P, the metabolic intermediate of Neu5Ac to NanR is critical for regulation of the nan genes.

Experimental Example 3

Characterization of DBD of NanR

Figure 4A:
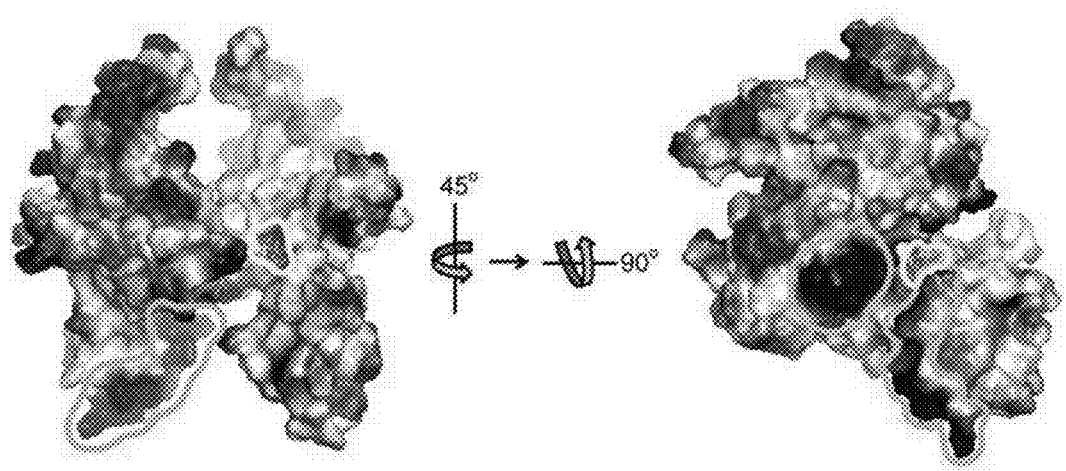
Figure 4B:
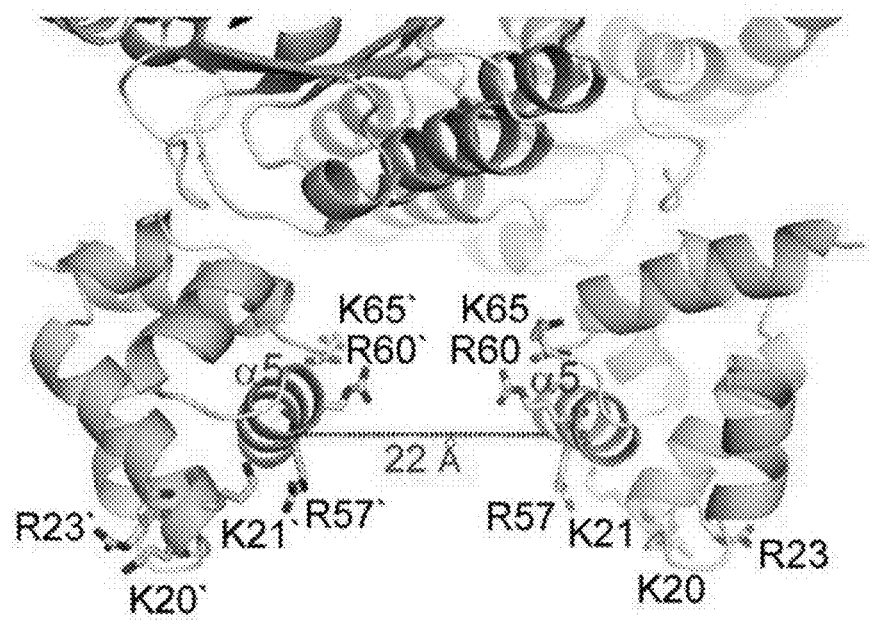
Figure 4C:
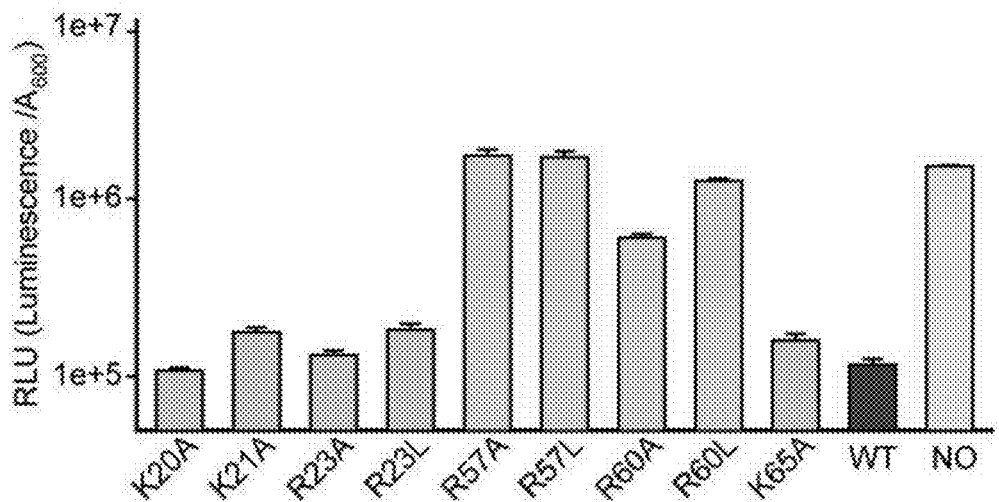
Figure 5:
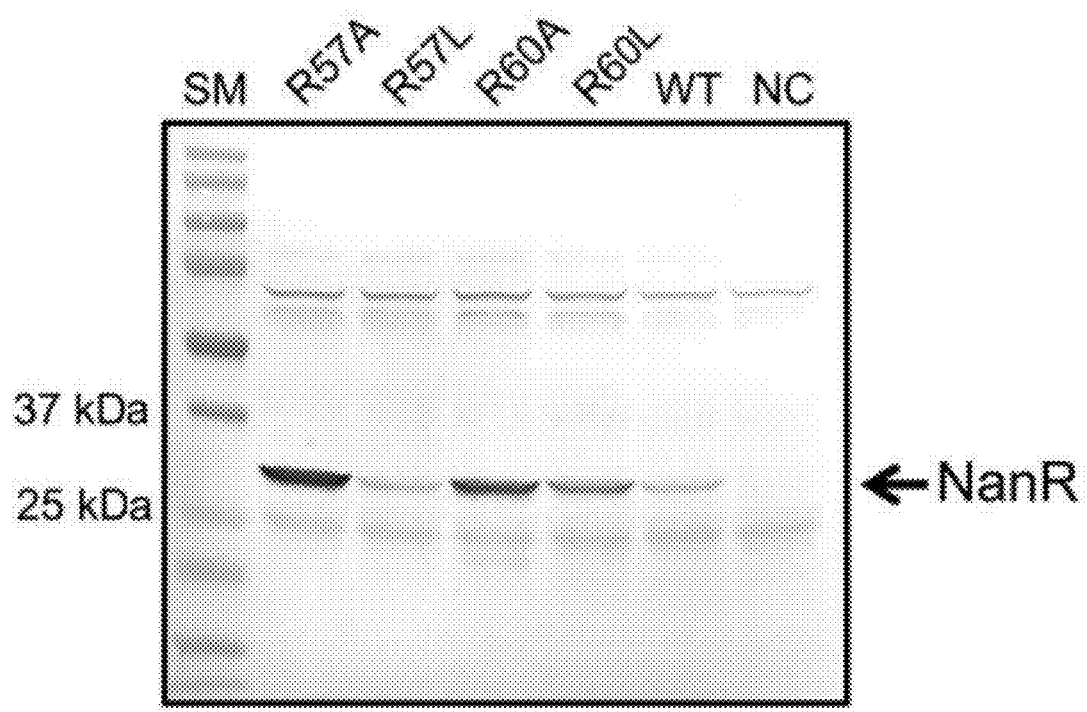
FIG. 5 shows the result of immunoblot analysis for wild-type and mutant NanR expressions using an E. coli dual plasmid system, in which SM represents a size marker, and NC represents a negative control.

The simplest helix-turn-helix (HTH)-containing DBD includes three core helices; the HTH domains can form tetra-helical bundle, winged helix, and ribbon-helix-helix type configurations. The DBD of NanR is composed of a six-helix bundle, which is not the archetypal conformation of HTH-containing domains; therefore, the recognition helix required for DNA-binding could not been determined. Nevertheless, analysis of the surface electrostatic potential of NanR revealed a number of positively charged residues in the DBD domain (K20, K21, R23, R57, R60, and K65) that may be responsible for binding to the phosphate backbone of DNA (FIGS. 4a and 4b). The importance of these residues to DNA-binding was examined using an *E. coli* dual plasmid system described in Example 2. The repressive effect of wild-type NanR on activity of PnanTp was abolished by the R57A, R57L, R60A, and R60L point mutations (FIG. 4c). Immunoblot analyses using anti-NanR antiserum revealed that these results were attributable to functional defects of the mutants and not to reduced cellular expression (FIG. 5).

Figure 4D:
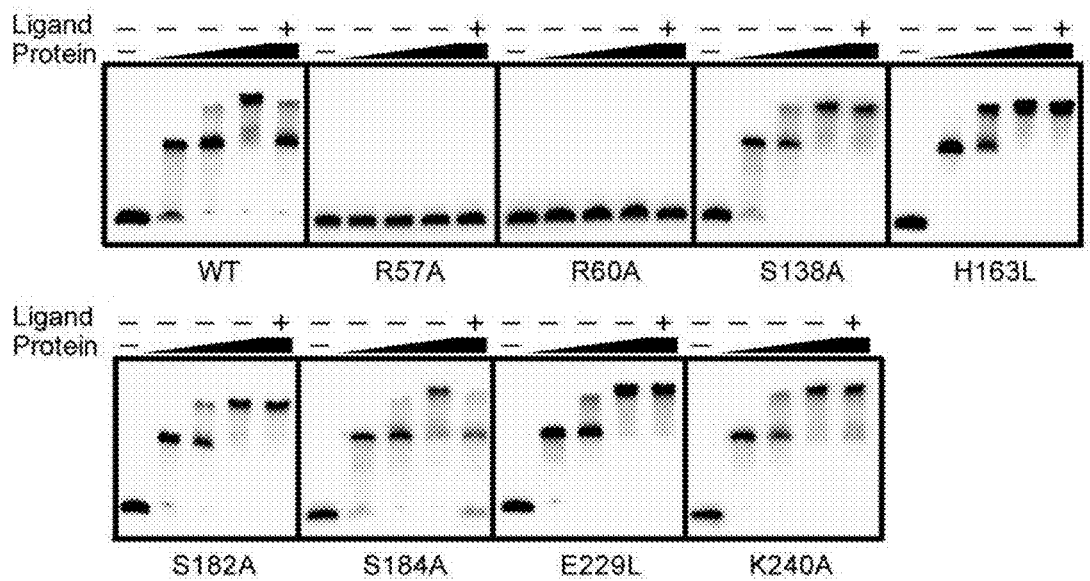

NanR represses both nan T(PSL)AR and nanEK nagA operons by binding to an operator within the nanTp-nanE intergenic region. To examine the role of R57 and R60 residues in DNA binding, EMSA (electrophoretic gel mobility shift assays), in which the nanTp-nanE intergenic region was incubated with wild-type or mutant NanR in the absence or presence of ManNAc-6P, were performed. In the experiment using the wild-type NanR, addition of ManNAc-6P resulted the retardation of DNA migration, suggesting that ManNAc-6P alters the ability of NanR to bind to the nan operator. No DNA migration was detected in the experiment using the mutant NanR(R57A or R60A) (FIG. 4d). With the exception of the S184A mutant, which was as active as wild-type NanR in the *E. coli* dual plasmid system experiments, the DNA migration by the ligand-binding defective mutants of NanR was not affected by addition of ManNAc-6P (FIG. 4d).

Figure 4E:
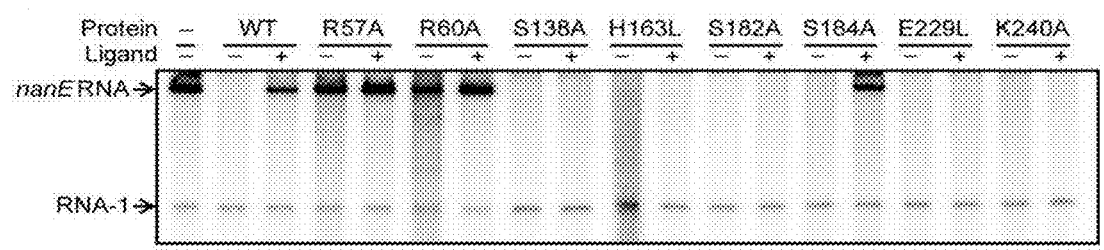

In addition, an in vitro transcription assay revealed that the R57A and R60A mutants did not repress PnanE even in the absence of ManNAc-6P, unlike the wild-type and S184A mutant (FIG. 4e). Consistent with the results of EMSA and the *E. coli* dual plasmid system assay, the other ligand-binding defective mutants of NanR did not enable transcription of nanE in either the presence or absence of ManNAc-6P (FIG. 4e). These results indicate that R57 and R60 in α5 are indispensable for binding of NanR to the nan operator and that the DNA-binding HTH motif in each NanR monomer includes α4 and α5. The distance between the two α5 helices in the NanR dimer is approximately 22 Å (FIG. 4b), suggesting that the method of DNA-binding employed by NanR differs from that of other HTH motif containing transcriptional regulators.

Experimental Example 4

Figure 6:
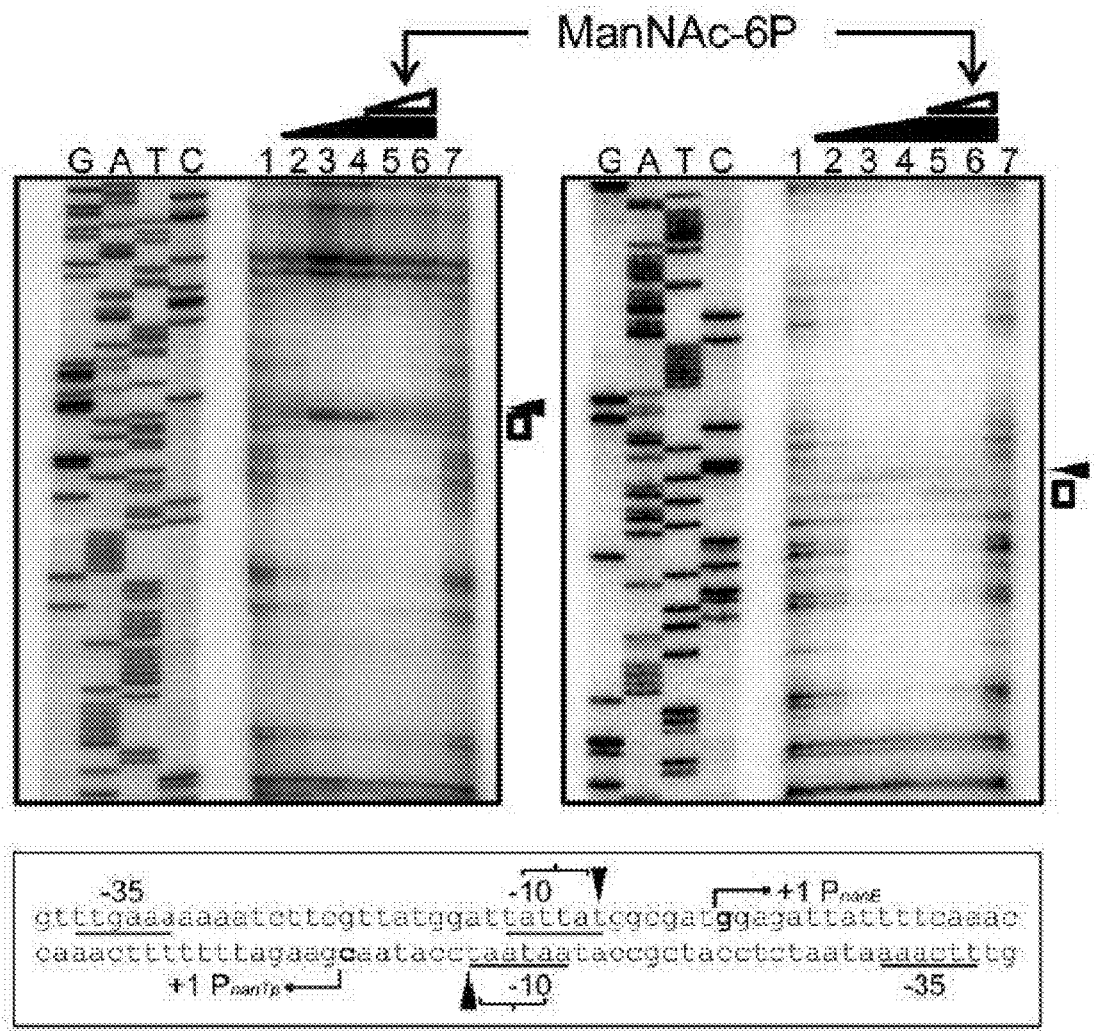
FIG. 6 shows the effect of ManNAc-6P ligand on binding of NanR to DNA (SEQ ID NO:15), in which DNaseI footprinting assay was performed by using NanR protein and 32P-labeled transcriptional control region of nan operon (299 bp) in the presence or absence of ManNAc-6P. After the addition of ManNAc-6P, the hypersensitive cleavage bands (black triangle, ▼) at the PnanE and PnanTp disappeared, and the neighboring regions were deprotected (white box and parentheses). Lanes 1 and 7 represent no addition of NanR; Lanes 2 and 3 represent 100 nM or 200 nM NanR treatment, respectively; Lanes 4 to 6 represent 400 nM NanR treatment; and Lanes 5 and 6 represent 0.1 mM or 1 mM ManNAc-6P treatment, respectively.

ManNAc-6P Alleviates the Interaction Between NanR and Transcriptional Control Region of Nan Operon The EMSA and in vitro transcription experiments demonstrated that S138, H163, S182, E229, and K240 residues are critical for ligand-sensing and regulation of the nan genes by NanR. Therefore, the present inventors hypothesized that binding of ManNAc-6P may alter the conformation of NanR and alleviate its interaction with the transcriptional control region of nan operon. In detail, a DNaseI footprinting assay using NanR protein and $^{32}$P-labeled transcriptional control region of nan operon was performed. Upon addition of ManNAc-6P, cleavage bands at the center of the NanR-binding site disappeared and neighboring regions were de-protected by the protein (FIG. 6). Isothermal titration calorimetry analyses revealed a robust interaction between the NanR dimer and the target DNA, with a 1:1 binding stoichiometry and a dissociation constant (Kd) of 1.40 μM. However, the interaction affinity of NanR complexed with ManNAc-6P was reduced by 130-fold (Kd=185.87 μM). Taken together, these results support the hypothesis that ManNAc-6P alters the conformation of NanR via relocation of ligand-binding residues, thereby reducing nan-binding activity of NanR which is a transcriptional repressor of the nan genes.

Experimental Example 5

Electron Microscopic Analysis of the Interaction Between NanR and Nan Genes

Figure 7A:
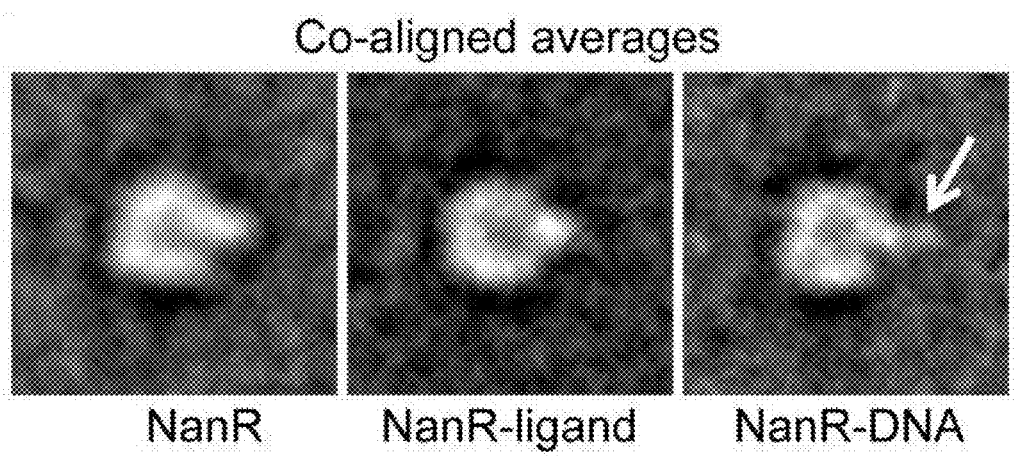
FIGS. 7a to 7c show the results of electron microscopy of NanR.
Figure 9:
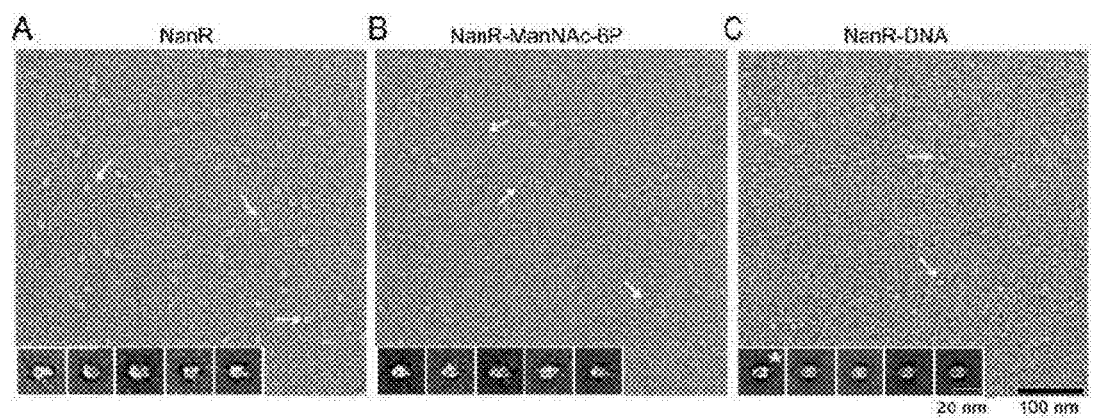
FIG. 9 shows electron microscopic images for negative staining of apo-NanR (A), NanR/ManNAc-6P complex (B) and apo-NanR/DNA complex (C), in which the white arrows indicate averaged images.

Electron microscopy using negative staining followed by single particle analysis showed that apo-NanR and the NanR/ManNAc-6P complex share similar structural features when analyzed at the molecular level of approximately 2 nm resolution (FIG. 7a; A and B of FIG. 9). Additional electron microscopy densities were observed for the DNA-bound NanR dimer (FIGS. 7a and 7b, indicated by white arrows; FIG. S5C). The DNA binding pattern revealed that it passes between the DBD domains in the NanR dimer.

Figure 7B:
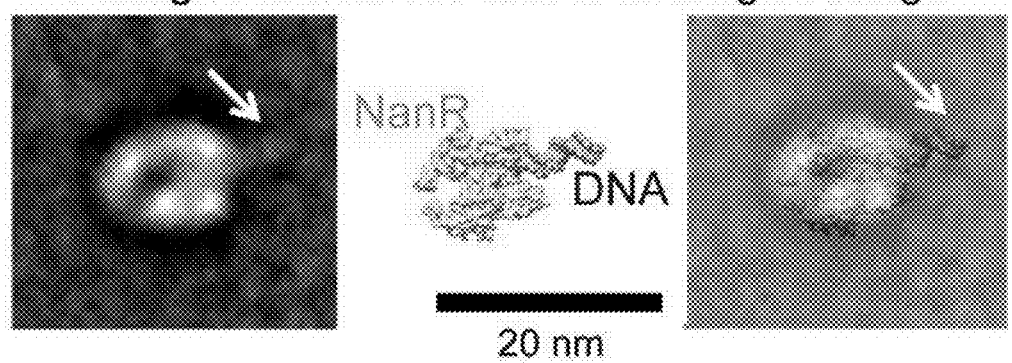

It was confirmed that α5 of each NanR molecule is essential for DNA-binding. The distance between the α5 helices that project towards the interior of the DBD domains is approximately 22 Å (FIG. 4b), which is close to the width of the DNA double helix (20 Å). Two-dimensional fitting demonstrated that the atomic models assembled from the crystal structures of NanR and DNA (FIG. 7b, middle panel) fit onto the averaged image of the NanR/DNA complex well (FIG. 7b, right panel). However, the entire length of DNA associated with NanR does not match perfectly due to its flexibility.

Figure 7C:
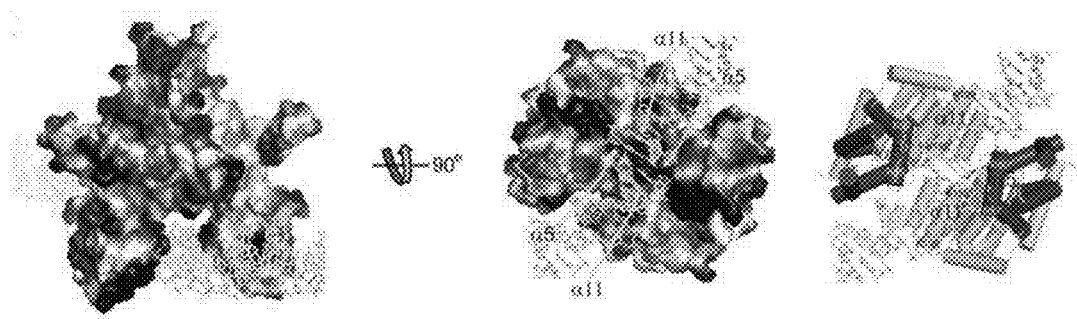
Figure 8:
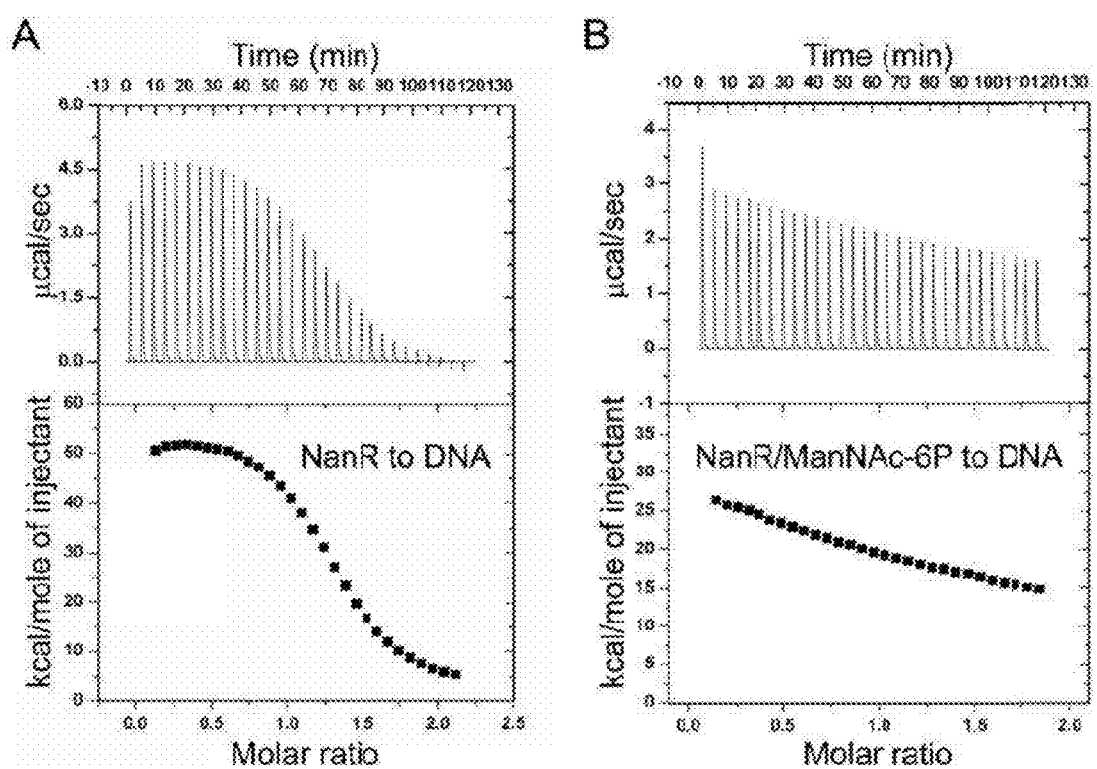
FIG. 8 shows the results of isothermal titration calorimetry for interaction between DNA and NanR protein. (A) shows the result for interaction between DNA and apo-NanR protein, and (B) shows the result for interaction between DNA and NanR/ManNAc-6P complex, and the upper panel shows the raw data and the lower panel shows the result of analysis.
Figure 10:
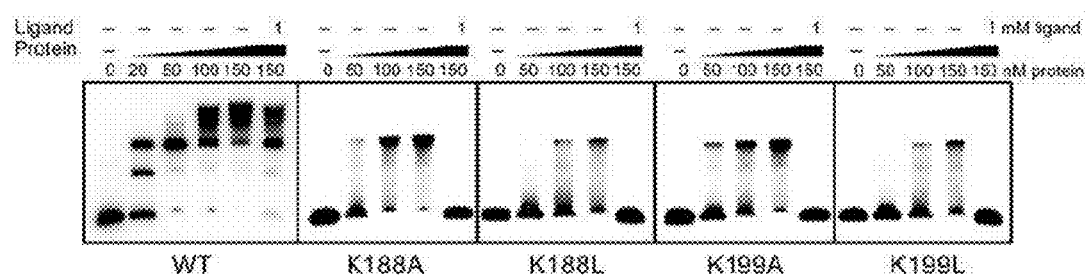
FIG. 10 shows the result of EMSA for examining the effect of K188 and K199 residues in all on binding of NanR to the transcriptional control region of nan operon, in which EMSA was carried out with increasing amount of each wild-type or mutant NanR protein, and 1 mM ManNAc-6P was further added to carry out the experiment.

Meanwhile, inspection of the surface electrostatic potential of all in the LBD of NanR revealed the existence of positively charged residues that may also be responsible for DNA-binding (FIG. 7C). The importance of K188 and K199 residues on all to binding of NanR to DNA was assessed by EMSA. Although the K188A, K188L, K199A, and K199L NanR mutants were able to bind to DNA, the binding activity of the mutants was not as conspicuous as that of wild-type NanR (FIG. 10). Furthermore, the mutants were much more susceptible to ManNAc-6P than wild-type NanR (FIG. 10). Taken together, these results demonstrate that the NanR dimer forms an arched tunnel-like DNA-binding space that is formed mainly by α5 and α11 in each monomer. The transcriptional control region of nan operon interacts with the dimer via the positively charged residues in this space (FIGS. 7b and 7c).

Experimental Example 6

Figure 11A:
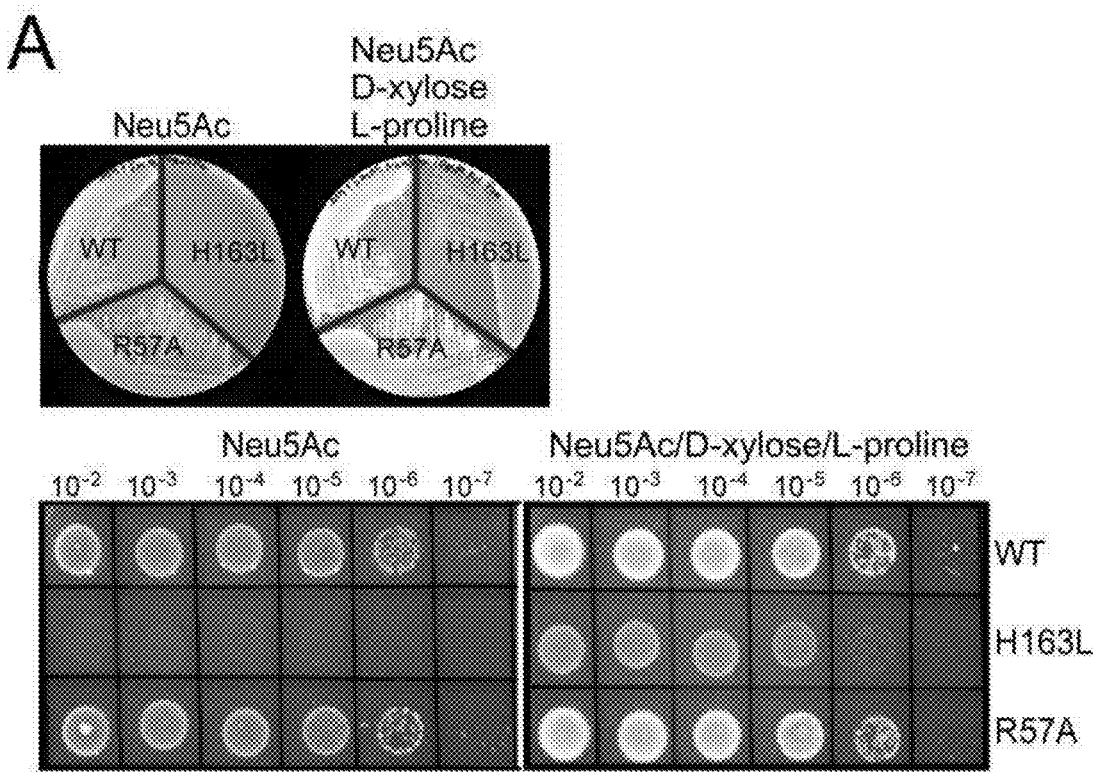
FIGS. 11a to 11d show the effect of the ManNAc-6P-mediated regulation of NanR on bacterial pathogenesis.
Figure 11B:
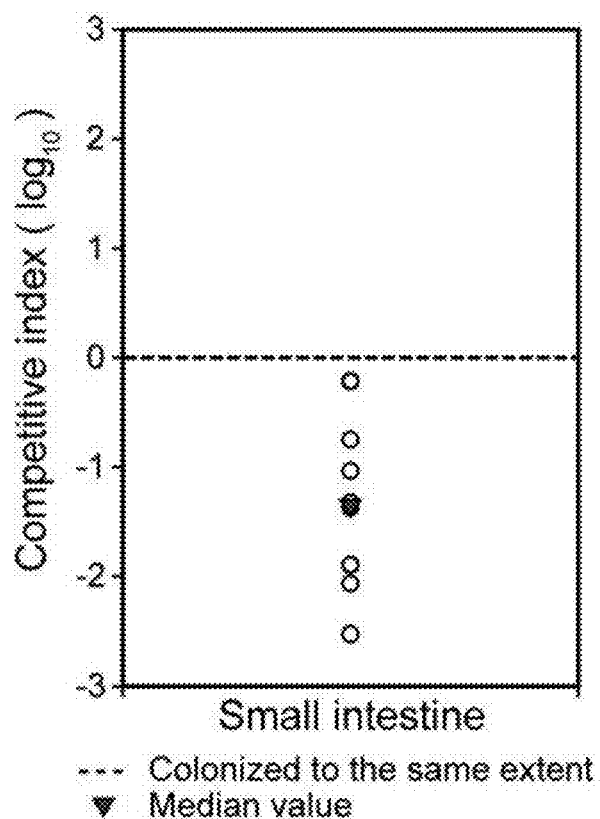
Figure 12:
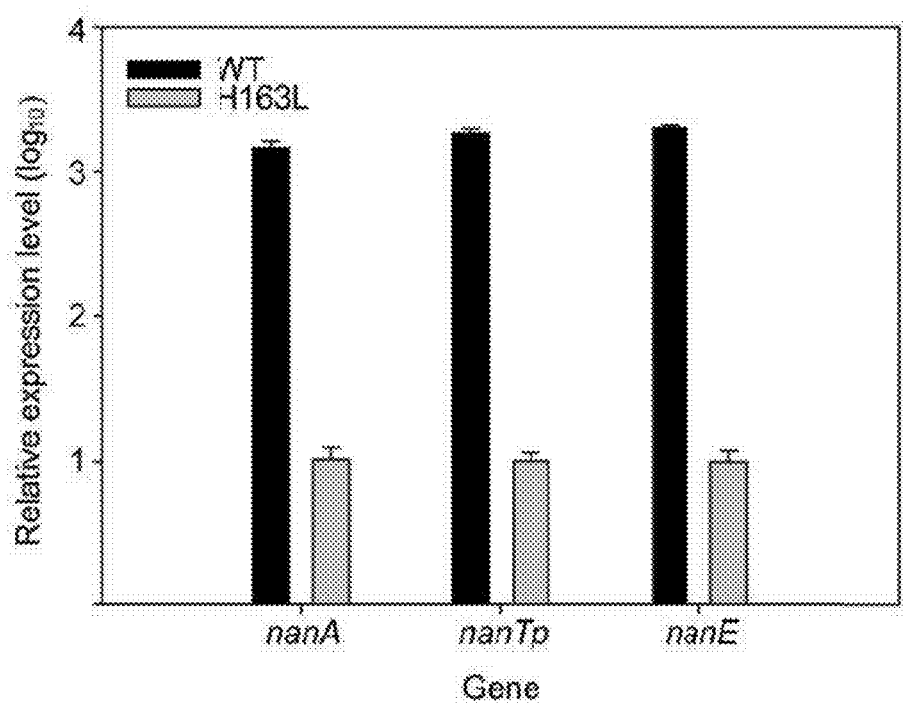
FIG. 12 shows the result of analyzing the effect of H163L mutation of NanR protein on expression of nan genes in V. vulnificus, in which the wild-type or H163L NanR-expressing strain was cultured in the presence of Neu5Ac, total RNA was extracted, and the amount of the transcript was analyzed by qRT-PCR (normalization to 16S rRNA), and quantity of the transcript of H163L mutant was considered as 1 to calculate $\log_{10}$. The data represent the mean±SD from at least three experiments.

Effect of Interaction Between ManNAc-6P and NanR on Growth and Survival During Infection Robust control of the genes encoding catabolic enzymes and the putative transporter for Neu5Ac is crucial for growth and survival of pathogenic bacteria in the host. To investigate the biological relevance of ligand-sensing by NanR, the present inventors examined the effects of mutation of R57 and H163, which are critical for DNA-binding and ligand-binding, respectively, on growth of the pathogenic bacteria *V. vulnificus*. The R57A or H163L mutation was introduced into *V. vulnificus* chromosomal DNA and the in vitro growth of each mutant strain was examined. Growth of the R57A strain was similar to that of the wild-type strain; however, growth of the H163L strain was impaired in minimal M9 medium supplemented with Neu5Ac as a sole carbon source (FIG. 11a). Addition of D-xylose and L-proline restored the growth of the H163L strain (which had an altered colony morphotype with reduced opacity), as observed previously for the nanA mutant strain. In the supplemented medium with D-xylose, L-proline and Neu5Ac, the expression levels of nan genes in the H163L nanR mutant were at least 142-fold lower than those in wild-type nanR (FIG. 12). These results suggest that the H163L mutant is indeed defective for ManNAc-6P sensing and nan gene regulation, thus affecting the growth of *V. vulnificus* when Neu5Ac is available. To examine the importance of the residue for ligand-binding, a mouse intestine colonization competition assay was performed. In eight of the 10 mice studied, colonization of the H163L mutant strain was 22.4-fold lower than that of the wild-type strain, resulting in a median competitive index of 0.045 (FIG. 11b).

Figure 11C:
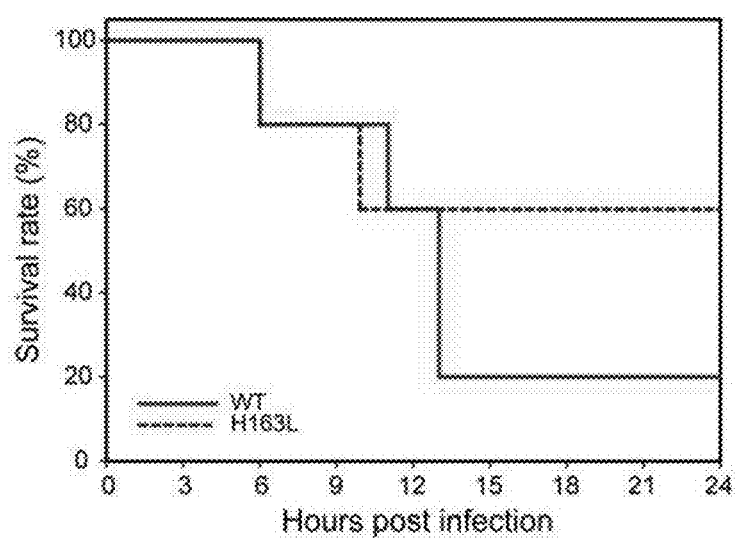
Figure 11D:
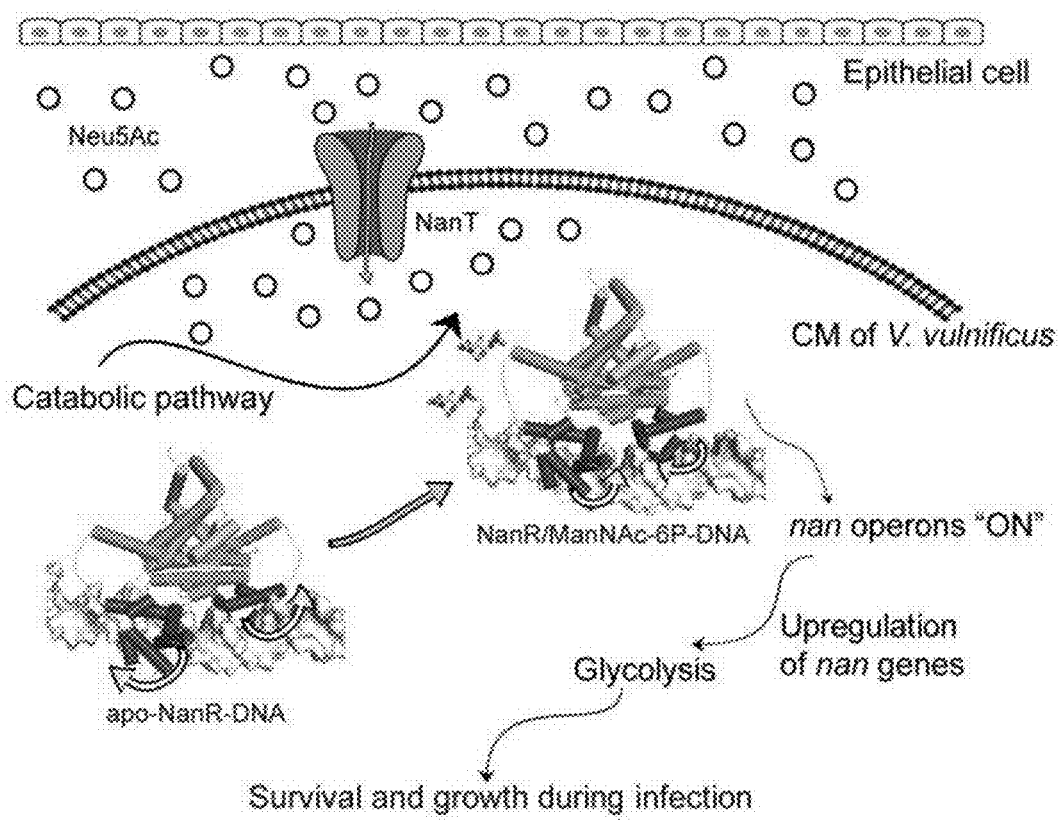

Finally, mice were challenged with a lethal dose of *V. vulnificus*. At 24 hours after infection, the percentages of surviving mice challenged with *V. vulnificus* expressing the H163L mutant or wild-type strain were 60% and 20%, respectively (FIG. 11c). These results indicate that regulation of NanR by ManNAc-6P is required not only for growth and survival, but also for the pathogenesis of *V. vulnificus*.

Taken together, the NanR protein is an important protein that affects growth, survival, and pathogenesis of a variety of bacteria having nan genes, since it binds to nan operator to suppress nan operon expression. It was confirmed that the functions of NanR are regulated by binding of its regulatory ligand, ManNAc-6P. Therefore, substances or new drugs against symptoms caused by a variety of bacteria having nan genes can be developed by regulation of nan gene expression using the three-dimensional structure of the NanR/ManNAc-6P complex of the present invention.

Based on the above description, it will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

EFFECT OF THE INVENTION

The NanR protein is an important protein that affects growth, survival, and pathogenesis of a variety of bacteria having nan genes, since it binds to nan operator to suppress nan operon expression. Therefore, new drugs for the prevention or treatment of diseases associated with a variety of bacteria having nan genes can be developed using a crystal of NanR and its regulatory ligand ManNAc-6P complex, a crystallization method, and a three-dimensional structure thereof.

What is claimed is:

1. A method for screening a substance regulating the interaction between NanR and the transcriptional control region of a nan operon, comprising
   (a) designing and displaying a tertiary structure of a complex of NanR protein and ManNAc-6P using the atomic coordinates of the complex shown in Table 3, wherein the complex comprises binding site amino acid residues R71, A137, S138, H163, S182, S183, S184, T187, E229, P231, G234 and K240;
   (b) preparing candidate substances binding to NanR by employing the identified binding site amino acids from (a) to design and fit said substances; and
   (c) examining binding affinity of the candidate substances for NanR and its regulation of the interaction between NanR and the transcriptional control region of nan operon,
   wherein step (a) is carried out using a computer, and
   wherein the atomic coordinates of the complex shown in Table 3 are stored on non-transitory electronic media that is used by the computer.

2. The method according to claim 1, further comprising determining the candidate as a bacterial growth inhibitor, when the candidate binding to NanR has the NanR binding affinity similar to or higher than that of ManNAc-6P and maintains or increases interaction between NanR and the transcriptional control region of nan operon, compared to a control group treated without the corresponding candidate.

3. The method according to claim 1, further comprising determining the candidate as a bacterial growth stimulant, when the candidate binding to NanR has the NanR binding affinity similar to or higher than that of ManNAc-6P and decreases interaction between NanR and the transcriptional control region of nan operon, compared to a control group treated without the corresponding candidate.

4. A method for screening a substance regulating the interaction between NanR and ManNAc-6P, comprising
   (a) designing and displaying a tertiary structure of a complex of NanR protein and ManNAc-6P using the atomic coordinates of the complex shown in Table 3, wherein the complex comprises binding site amino acid residues R71, A137, S138, H163, S182, S183, S184, T187, E229, P231, G234 and K240;
   (b) preparing candidate substances binding to NanR by employing the identified binding site amino acids from (a) to design and fit said substances; and
   (c) examining whether the candidate regulates the interaction between NanR protein and ManNAc-6P,
   wherein step (a) is carried out using a computer, and
   wherein the atomic coordinates of the complex shown in Table 3 are stored on non-transitory electronic media that is used by the computer.

5. The method according to claim 4, further comprising determining the candidate as a nan operon expression enhancer or as a bacterial growth stimulant, when the candidate increases interaction between NanR and ManNAc-6P, compared to a control group treated without the corresponding candidate.

6. The method according to claim 4, further comprising determining the candidate as a nan operon expression suppressor or as a bacterial growth inhibitor, when the candidate decreases interaction between NanR and ManNAc-6P, compared to a control group treated without the corresponding candidate.

* * * * *

SEQUENCE LISTING

```
<160> NUMBER OF SEQ ID NOS: 17

<210> SEQ ID NO 1
<211> LENGTH: 278
<212> TYPE: PRT
<213> ORGANISM: Vibrio vulnificus

<400> SEQUENCE: 1

Met Gly Ser Pro Lys Asn Leu Leu Val Arg Leu Arg Ser Asn Met Glu
1               5                   10                  15

Pro Phe Ser Lys Lys Leu Arg Val Val Ala Asp Tyr Ile Leu Glu Asn
            20                  25                  30

Ala His Asp Val Gln Phe Gln Thr Ile Thr Asp Leu Ala Arg Asn Thr
        35                  40                  45

Gln Thr Ser Glu Ala Thr Val Val Arg Leu Cys Arg Asp Met Gly Tyr
    50                  55                  60

Lys Gly Tyr Ser Asp Phe Arg Met Ala Leu Ala Val Asp Leu Ser Gln
65                  70                  75                  80

Thr Glu Ser Arg Gln Gln Asn His Ile Glu Gly Asp Ile Cys Asp Val
                85                  90                  95

Ser Ala Gln Ser Ala Val Asp Ser Leu Gln Asp Thr Ala Lys Leu Ile
            100                 105                 110

Asp Arg Lys Ser Leu Ala Arg Ile Val Glu Arg Val His Gln Ala Glu
        115                 120                 125

Phe Ile Gly Cys Ile Gly Val Gly Ala Ser Ser Ile Val Gly Arg Tyr
    130                 135                 140

Leu Ala Tyr Arg Leu Ile Arg Ile Gly Lys Lys Ala Ile Met Phe Glu
145                 150                 155                 160

Asp Thr His Leu Ala Ala Met Ser Ala Ser Arg Ser Ser Gln Gly Asp
                165                 170                 175

Leu Trp Phe Ala Val Ser Ser Ser Gly Ser Thr Lys Glu Val Ile His
            180                 185                 190

Ala Ala Gly Leu Ala Tyr Lys Arg Asp Ile Pro Val Val Ser Leu Thr
        195                 200                 205

Asn Ile Asn His Ser Pro Leu Ser Ser Leu Ser Thr Glu Met Leu Val
    210                 215                 220

Ala Ala Arg Pro Glu Gly Pro Leu Thr Gly Gly Ala Phe Ala Ser Lys
225                 230                 235                 240

Val Gly Ala Leu Leu Leu Val Asp Val Leu Val Asn Ser Leu Leu Glu
                245                 250                 255

Ser Tyr Pro Glu Tyr Lys Asp Ser Val Gln Glu Thr Ala Glu Val Val
            260                 265                 270

Ile Pro Leu Met Ala Asn
        275

<210> SEQ ID NO 2
<211> LENGTH: 837
<212> TYPE: DNA
<213> ORGANISM: Vibrio vulnificus
```

-continued

<400> SEQUENCE: 2

```
gtgggttcgc cgaaaaattt attagtccga cttcgttcca acatggaacc atttagtaag      60
aaactgcgtg ttgtggcgga ctacatattg gaaaatgcgc atgatgtgca gtttcaaacc     120
atcacggatc ttgctcgcaa cacacaaacc agtgaagcga cagtcgtacg cttatgtcgc     180
gacatgggct ataagggcta ttccgatttt cgtatggcgc ttgccgttga tttgagccaa     240
accgaaagtc gtcagcaaaa tcatatcgaa ggtgacattt gcgatgtgtc tgcgcaaagc     300
gcggtagaca gcctgcaaga caccgcaaaa cttatcgatc gtaaatcatt ggcccgcatt     360
gttgagcggg ttcatcaagc cgagtttatt gggtgcattg gtgttggagc gtcgagcatt     420
gttggccgtt acctcgccta cgccttata cgtatcggta agaaagcgat catgtttgaa      480
gatacccatt tagccgcaat gagtgcaagc cgctcaagtc aaggtgatct gtggtttgct     540
gtttccagtt caggttcgac gaaagaagtc attcatgccg ctgggcttgc gtataagcgt     600
gatattcccg tcgtttctct gacaaacatc aatcacagcc cgctctcttc tctctcaact     660
gaaatgctgg tggctgcaag accagaaggg ccactaacag gtggtgcttt tgcctcgaaa     720
gtcggcgcgc tgctcttagt ggacgtgttg gtcaactctt tattagagag ctacccggaa     780
tacaaagact cggtgcaaga aacagcagaa gtagtcattc ctttaatggc aaattaa      837
```

<210> SEQ ID NO 3
<211> LENGTH: 299
<212> TYPE: PRT
<213> ORGANISM: Vibrio vulnificus

<400> SEQUENCE: 3

```
Met Met Asn Lys Leu Lys Gly Leu Ile Ala Ala Pro His Thr Pro Phe
  1               5                  10                  15

Asp Ser Asn Asn Gln Val Asn Tyr Ala Val Ile Asp Gln Ile Ala Ala
             20                  25                  30

Leu Leu Ile Glu Gln Gly Val Thr Gly Ala Tyr Val Cys Gly Thr Thr
         35                  40                  45

Gly Glu Gly Ile His Cys Ser Val Glu Arg Lys Ala Ile Ala Glu
     50                  55                  60

Arg Trp Val Lys Ala Ala Asp Gly Lys Leu Asp Ile Ile Leu His Thr
 65                  70                  75                  80

Gly Ala Leu Ser Ile Val Asp Thr Leu Glu Leu Thr Arg His Ala Glu
                 85                  90                  95

Thr Leu Asp Ile Leu Ala Thr Ser Ala Ile Gly Pro Cys Phe Phe Lys
            100                 105                 110

Pro Ser Ser Val Ala Asp Leu Val Asn Tyr Cys Ala Gln Ile Ala Glu
        115                 120                 125

Ala Ala Pro Ser Lys Gly Phe Tyr Tyr His Ser Gly Met Ser Gly
    130                 135                 140

Val Asn Leu Asp Leu Glu Gln Phe Leu Ile Gln Gly Glu Gln Arg Ile
145                 150                 155                 160

Pro Asn Leu Ser Gly Ala Lys Phe Asn Asn Val Asp Leu Tyr Glu Tyr
                165                 170                 175

Gln Arg Ala Leu Arg Val Ala Asn Gly Lys Phe Asp Ile Pro Phe Gly
            180                 185                 190

Val Asp Glu Phe Leu Pro Ala Gly Leu Ala Val Gly Ala Ile Gly Ala
        195                 200                 205

Val Gly Ser Thr Tyr Asn Tyr Ala Ala Pro Leu Tyr Leu Lys Ile Ile
```

```
                    210                 215                 220
Glu Ala Phe Asn Gln Gly Lys His Ser Glu Val Gln Ala Leu Met Asp
225                 230                 235                 240

Lys Val Ile Ala Leu Ile Arg Val Leu Val Glu Tyr Gly Gly Val Ala
                245                 250                 255

Ala Gly Lys Ala Ala Met Gln Leu His Gly Ile Asp Ala Gly Asp Pro
                260                 265                 270

Arg Leu Pro Ile Arg Ala Leu Thr Ala Gln Gln Lys Ala Asp Val Val
                275                 280                 285

Ala Lys Met Arg Asp Ala Asp Phe Leu Asn Leu
                290                 295

<210> SEQ ID NO 4
<211> LENGTH: 427
<212> TYPE: PRT
<213> ORGANISM: Vibrio vulnificus

<400> SEQUENCE: 4

Met Ala Gly Ser Ile Phe Gly Trp Leu Gly Leu Leu Phe Ala Gly Met
1               5                   10                  15

Pro Val Gly Phe Ser Leu Ile Phe Val Ala Leu Val Phe Leu Ile Val
                20                  25                  30

Thr Asn Ser Thr Gly Ile Asn Phe Ala Ala Gln Gln Met Leu Gly Gly
            35                  40                  45

Ile Asp Asn Phe Thr Leu Leu Ala Val Pro Phe Phe Val Leu Thr Gly
50                  55                  60

His Leu Met Asn Ser Ala Gly Ile Thr Glu Arg Ile Phe Asn Phe Ala
65                  70                  75                  80

Lys Ser Met Val Gly His Ile Thr Gly Ser Leu Gly His Val Asn Ile
                85                  90                  95

Met Ala Ser Leu Leu Phe Ser Gly Met Ser Gly Ser Ala Leu Ala Asp
                100                 105                 110

Ala Gly Gly Leu Gly Gln Leu Glu Ile Lys Ser Met Arg Asp Ala Lys
            115                 120                 125

Tyr Asp Asp Phe Ala Gly Gly Leu Thr Ala Ser Cys Ile Ile
130                 135                 140

Gly Pro Leu Val Pro Pro Ser Val Pro Leu Val Ile Tyr Gly Val Val
145                 150                 155                 160

Ser Asn Thr Ser Ile Gly Ala Leu Phe Leu Ala Gly Ala Ile Pro Gly
                165                 170                 175

Ile Leu Cys Cys Val Ala Leu Met Val Met Ser Tyr Phe Ile Cys Lys
                180                 185                 190

Lys Arg Gly Tyr Met Thr Leu Pro Lys Ala Ser Arg Lys Glu Gln Phe
            195                 200                 205

Thr Ser Phe Lys Glu Ala Phe Leu Ser Leu Met Thr Pro Val Ile Ile
    210                 215                 220

Ile Gly Gly Ile Phe Ser Gly Lys Phe Thr Pro Thr Glu Ala Ala Val
225                 230                 235                 240

Val Ser Ser Leu Tyr Ala Leu Phe Leu Gly Thr Val Val Tyr Lys Gln
                245                 250                 255

Leu Thr Leu Thr Gly Phe Val Glu Ile Leu Arg Glu Thr Val Asn Thr
                260                 265                 270

Thr Ala Val Val Ala Leu Met Val Met Gly Val Thr Val Phe Gly Trp
            275                 280                 285
```

```
Ile Val Ala Arg Glu Gln Leu Pro Gln Met Leu Ala Asp Tyr Phe Leu
    290                 295                 300
Ser Ile Ser Glu Asn Pro Leu Val Leu Leu Leu Ile Asn Leu Leu
305                 310                 315                 320
Leu Leu Phe Leu Gly Thr Phe Ile Glu Ser Leu Ala Leu Leu Leu Leu
                325                 330                 335
Leu Val Pro Phe Leu Val Pro Val Ala Ser Val Gly Ile Asp Pro
            340                 345                 350
Val His Phe Gly Val Met Ala Ile Leu Asn Leu Met Ile Gly Ile Leu
                355                 360                 365
Thr Pro Pro Met Gly Met Ala Leu Tyr Val Val Ser Arg Val Gly Asp
370                 375                 380
Ile Pro Phe His Thr Leu Thr Arg Gly Val Leu Pro Leu Leu Val Pro
385                 390                 395                 400
Leu Phe Ile Val Leu Ala Val Ala Val Phe Pro Gln Ile Thr Leu
            405                 410                 415
Leu Leu Pro Glu Leu Leu Leu Gly Tyr Gly Gln
            420                 425
```

<210> SEQ ID NO 5
<211> LENGTH: 168
<212> TYPE: PRT
<213> ORGANISM: Vibrio vulnificus

<400> SEQUENCE: 5

```
Met Leu Arg Lys Ile Phe Asp Asn Leu Glu Glu Ile Ile Thr Val Pro
1               5                   10                  15
Leu Met Ala Ser Leu Leu Val Val Leu Thr Trp Gln Ile Ala Thr Arg
                20                  25                  30
Trp Leu Leu Asn Asp Pro Ser Leu Trp Ser Glu Leu Ala Arg Val
            35                  40                  45
Leu Phe Met Tyr Met Ser Leu Ile Gly Cys Ala Ile Ala Ile Lys Arg
    50                  55                  60
Gly Thr His Val Asn Ile Thr Phe Phe Ser Asp Lys Leu Pro Glu Lys
65                  70                  75                  80
Ile Arg Leu Leu Leu Val Leu Ser Leu Glu Ala Ala Val Leu Val Ser
                85                  90                  95
Ile Phe Ala Ile Ile Tyr Leu Gly Tyr Gln His Val Glu Arg Thr Ala
                100                 105                 110
Phe Phe Glu Leu Ile Thr Leu Gly Val Ser Ser Lys Trp Met Asn Tyr
            115                 120                 125
Ser Leu Pro Leu Gly Gly Leu Phe Met Val Ile Arg Gln Leu Gln Lys
130                 135                 140
Met Val Gly Ile Val Thr Glu Phe Arg Gln Gln Cys Gly Val Val Thr
145                 150                 155                 160
Ala Ser Asn His Ala Glu Gln Arg
            165
```

<210> SEQ ID NO 6
<211> LENGTH: 321
<212> TYPE: PRT
<213> ORGANISM: Vibrio vulnificus

<400> SEQUENCE: 6

```
Met Lys Thr Met Asn Arg Ile Thr Leu Ala Met Leu Thr Val Gly Leu
1               5                   10                  15
```

```
Ser Leu Ser Ser Asn Ala Ala Thr Thr Leu Lys Met Gly Met Gln Ala
            20                  25                  30

Ser Val Gly Ser Val Glu Tyr Thr Ser Ala Lys Leu Leu Ala Asp Thr
        35                  40                  45

Val Glu Glu Met Ser Lys Gly Glu Leu Lys Leu Ala Leu Tyr Pro Ser
 50                  55                  60

Ala Gln Leu Gly Asp Asp Arg Ala Met Leu Gln Gln Leu Ser Met Gly
 65                  70                  75                  80

Asp Leu Asp Ile Thr Tyr Ala Glu Phe Gly Arg Met Gly Leu Trp Ile
                85                  90                  95

Pro Arg Ala Glu Ala Val Thr Leu Pro Tyr Val Ala Arg Asp Tyr Asp
            100                 105                 110

His Leu Arg Arg Met Phe Asp Ser Glu Phe Gly Gln Gly Ile Arg Gln
        115                 120                 125

Glu Met Leu Thr Lys Phe Asn Trp Arg Ala Leu Asp Thr Trp Tyr Asn
130                 135                 140

Gly Thr Arg Glu Thr Thr Ser Asn Arg Pro Leu Lys Ser Ile Ser Asp
145                 150                 155                 160

Phe Lys Gly Leu Lys Leu Arg Val Pro Asn Ala Lys Pro Asn Leu Asn
                165                 170                 175

Tyr Ala Lys Leu Ser Gly Ala Ser Pro Thr Pro Met Ala Phe Ser Glu
            180                 185                 190

Val Tyr Leu Ala Leu Gln Thr Asn Ala Val Asp Gly Gln Glu Asn Pro
        195                 200                 205

Leu Pro Thr Ile Lys Thr Met Lys Phe Tyr Glu Val Gln Ser Asn Leu
210                 215                 220

Ala Ile Thr Asn His Ile Val Asn Asp Gln Met Val Leu Ile Ser Glu
225                 230                 235                 240

Ser Thr Trp Gln Lys Leu Ser Glu Gln Glu Arg Glu Ile Val Ala Asn
                245                 250                 255

Ala Val Lys Gln Thr Gly Glu Ala His Thr Ala Ser Val Lys Lys Gln
            260                 265                 270

Glu Ala Glu Leu Ile Ser Phe Phe Glu Ala Gln Gly Val Asn Val Thr
        275                 280                 285

Tyr Pro Glu Leu Ala Pro Phe Arg Glu Ala Met Gln Pro Leu Tyr Ser
290                 295                 300

Glu Phe Glu Lys Lys Ile Gly Gln Pro Ile Val Ser Lys Leu Ala Ala
305                 310                 315                 320

Met

<210> SEQ ID NO 7
<211> LENGTH: 225
<212> TYPE: PRT
<213> ORGANISM: Vibrio vulnificus

<400> SEQUENCE: 7

Met Leu Ser Gly Gln Thr Val Val Ser Ile Gln Pro Val Val Gly Ser
1               5                   10                  15

Pro Leu Asp Lys Thr Glu Phe Ile Val Ala Met Ala Val Ala Ala Glu
            20                  25                  30

Gln Ala Gly Ala Lys Ala Leu Arg Ile Glu Gly Val Glu Asn Val Arg
        35                  40                  45

His Val Ser Gln Ala Thr Asn Val Pro Ile Ile Gly Ile Val Lys Arg
 50                  55                  60
```

```
Asp Leu Gln Asp Ser Pro Val Arg Ile Thr Pro Phe Val Cys Asp Val
 65                  70                  75                  80

Asp Ala Leu Ala Thr Ala Gly Ala Thr Ile Ile Ala Phe Asp Ala Thr
                 85                  90                  95

Asp Arg Gln Arg Pro Glu Ser Arg Glu Thr Ile Ala Asn Ala Ile Lys
            100                 105                 110

Asn Ser Gly Cys Phe Ala Met Ala Asp Cys Ser Cys Phe Ala Asp Gly
        115                 120                 125

Gln Trp Ala Ala Gln Ile Gly Val Asp Ile Ile Gly Ser Thr Leu Ser
130                 135                 140

Gly Tyr Val Gly Glu Ile Glu Pro Thr Glu Pro Asp Leu Glu Leu Val
145                 150                 155                 160

Lys Gln Phe Ser Ser Ala Gly Phe Phe Thr Met Ala Glu Gly Arg Tyr
                165                 170                 175

Asn Thr Pro Gln Leu Ala Ala Lys Ala Ile Glu Asn Gly Ala Val Ala
            180                 185                 190

Val Thr Val Gly Ser Ala Ile Thr Arg Met Glu Val Val Thr His Trp
        195                 200                 205

Phe Asn Ser Ala Thr Gln Ala Val Arg Gln Asn Asn Glu Ser Ile Ser
    210                 215                 220

Tyr
225

<210> SEQ ID NO 8
<211> LENGTH: 293
<212> TYPE: PRT
<213> ORGANISM: Vibrio vulnificus

<400> SEQUENCE: 8

Met Lys Val Leu Ala Ile Asp Ile Gly Gly Thr Lys Ile Ala Leu Gly
  1               5                  10                  15

Asn Val Val Asp Gly His Leu Gln His Arg Lys Gln Phe Pro Thr Pro
             20                  25                  30

Val Val Asn Asp Ala Thr Thr Leu Ala Lys Glu Ile Leu Ala His Cys
         35                  40                  45

Gln Ala Trp Leu Ser Asp Val Asp Ala Ile Gly Ile Ser Thr Thr Gly
     50                  55                  60

Leu Val Ser Glu Gln Gly Ile Ser Ala Ile Asn Pro Gly Thr Leu Ser
 65                  70                  75                  80

Phe Pro Thr Pro Phe Pro Leu His Ser Glu Leu His Arg Leu Ser Gly
                 85                  90                  95

Lys Pro Val Lys Met Leu Asn Asp Ala Gln Ala Ala Trp Tyr Glu
            100                 105                 110

Phe Leu Gln Leu Ser Pro Glu Leu Asp Val Arg Asn Met Ala Tyr Ile
        115                 120                 125

Thr Val Ser Thr Gly Val Gly Gly Leu Val Ile Asn Gln Gln Leu
130                 135                 140

His Lys Gly Lys Ser Asn Phe Ala Gly His Ile Gly His Thr Val Leu
145                 150                 155                 160

Asp Pro Asn Gly Pro Leu Cys Cys Gln Gln Arg Gly Cys Val Glu
                165                 170                 175

Ala Ile Ala Ser Gly Asn Ala Ile Asn Ala Gly Ala Gln Ala Leu Phe
            180                 185                 190

Gly Gln Ala Ile Ser Asn Ile Glu Leu Phe Gln Leu Ala Gln His Asn
        195                 200                 205
```

```
Glu Gln Ala Ser Ala Leu Ile Gln Gln Ser Ala Glu Ala Ile Ala Gln
    210                 215                 220

Leu Cys Leu Asn Leu Lys Ala Thr Leu Asp Leu Asp Leu Val Val Ile
225                 230                 235                 240

Gly Gly Gly Val Gly Leu Ala His Gly Tyr Leu Ala Arg Val Gln Ala
                245                 250                 255

Phe Ile Asp Lys Gln Pro Leu Val Phe Gln Val Lys Val Arg Ala Ala
            260                 265                 270

Val Gly Asp Tyr Asp Ala Cys Leu Leu Gly Ala Ala Phe Gln Phe Glu
        275                 280                 285

Glu Ser Asn Leu Ser
    290

<210> SEQ ID NO 9
<211> LENGTH: 900
<212> TYPE: DNA
<213> ORGANISM: Vibrio vulnificus

<400> SEQUENCE: 9
atgatgaaca aattaaaagg gctgatcgcc gctcctcata caccgtttga tagcaataat     60
caggtgaact atgcggtgat cgatcaaatt gctgcattac tcattgaaca aggtgttaca    120
ggggcttacg tatgtggcac caccggagaa ggcatacatt gttcagttga agagcgaaaa    180
gcgattgccg agcgttgggt gaaagccgca gatggtaagt tagacattat tcttcatacg    240
ggggctctga gtatcgttga tacccttgag cttacacgac acgctgaaac actggatatt    300
cttgccactt ccgcgatcgg gccttgcttt ttcaaaccga gcagcgtcgc tgatcttgtc    360
aattactgcg cgcagattgc ggaagcggca ccgtcaaaag gcttctatta ctaccactca    420
ggaatgtctg gcgtgaatct cgatctggaa cagttcctca tccaaggaga gcagcgtatt    480
ccgaacttat ctggcgccaa gtttaataac gtggatcttt atgagtacca acgcgcgctg    540
agagtagcca atgcaagtt tgatattcca ttcggcgttg atgaattttt gccagcaggg    600
cttgccgtag ggctattgg ggcggttggc agcacttata attacgccgc accactgtat    660
ctgaagatca ttgaggcgtt caaccaaggg aaacatagta agttcaggc gttgatggat    720 aaagtgatcg cattgatccg tgtcttggtt gaatacggtg gcgttgcggc agggaaagca    780
gcgatgcaat acacggcat tgatgccggt gatccgcgtt tgccaattcg agcgctcact    840
gcgcaacaaa aagccgatgt cgtggcgaaa atgcgcgatg cggattttct taatctgtag    900

<210> SEQ ID NO 10
<211> LENGTH: 1284
<212> TYPE: DNA
<213> ORGANISM: Vibrio vulnificus

<400> SEQUENCE: 10
atggctggtt caattttttgg ttggctaggc ttgctttttg ctggcatgcc agttggcttt     60
tctctgattt ttgtggcgtt ggttttttctt attgttacca acagcacagg tattaacttc    120
gcagcgcagc agatgctggg cggcatcgat aattttacgt tattggccgt accattcttc    180
gtcctaacgg gccatttgat gaacagtgcc ggtattacga gcgaattttt aactttgcc    240 aaatccatgg ttggccatat cacgggcagt ctagggcatg taaacatcat ggcgagttta    300
ctcttttctg gtatgtctgg ctctgcgctt gccgatgccg gaggcttggg gcagcttgaa    360
atcaaatcaa tgcgtgacgc gaaatacgat gatgattttg ctggtggtct cacggcggcc    420
```

```
tcgtgcatca ttggtccgct tgttccgcct tctgtgccat tggtgattta tggtgtggtg      480
tccaacacat cgattggtgc gttgttttta gccggtgcaa taccaggcat attgtgctgc      540
gtggctttga tggtgatgag ctatttcatc tgtaagaaac gtggctacat gaccttgcca      600
aaagcgtcga gaaggagca gttcacatcg ttcaaagagg catttctttc tctaatgact       660
ccggtcatca tcattggcgg gatcttttcg ggtaagttca ccccgacgga agcagcagtg      720
gtttcctctc tttacgcttt gttccttggt accgtggtgt acaaacagct gaccttgacg      780
gggtttgtgg aaattctgcg cgaaaccgtg aataccaccg ctgttgttgc cttgatggtg      840 atggggtaa cggtgtttgg ctggatcgtg gcgcgtgagc aattaccaca gatgcttgcg       900
gattatttct tgtcgatcag tgaaaaccca ttggtactac tgctactcat caacttgctc      960
ttgctgtttt tgggaacctt cattgaatca ctcgcgctat tgctattgct ggttccattt      1020
ttagtcccag tggcatcagc ggtcgggatt gaccctgtgc actttggtgt tatggccatt      1080
ttgaacttga tgatcggcat tctcacgcca ccaatgggca tggctttata tgtggtgtca      1140
cgtgtcggag acattccatt tcatacctta actcgaggcg tacttcctct tctggtgcca      1200
ttgtttattg tgctggcgct ggtggcggta ttccctcaaa tcaccttgct attgcctgag      1260
ctgcttttgg gttacggaca ataa                                             1284

<210> SEQ ID NO 11
<211> LENGTH: 507
<212> TYPE: DNA
<213> ORGANISM: Vibrio vulnificus

<400> SEQUENCE: 11
atgttacgca agatcttcga taatttagaa gagatcatca cagtgccact tatggcctct      60
cttcttgttg tgctgacatg gcaaattgcg acgcgctggt tacttaacga tccttcacta      120
tggagtgaag agttagcgcg agtgctgttt atgtatatgt cgctcattgg ctgtgccatc      180
gctatcaaac gtggaactca cgtcaatatc acgttttttct cagataagtt gccagaaaaa      240
atacgccttt tgttggtgtt gtccttggaa gctgcggtat tggtttcgat attcgccatc      300
atttatttgg gctatcaaca cgtggaaaga accgcctttt ttgaattgat taccttaggt      360
gtgtccagca aatggatgaa ctacagttta ccccttggcg ggcttttcat ggtgattcgt      420
caattgcaaa aaatggtcgg tattgtgacg gaatttcgtc agcagtgcgg tgtcgttacc      480
gcgtcgaatc atgcagagca aaggtaa                                          507

<210> SEQ ID NO 12
<211> LENGTH: 966
<212> TYPE: DNA
<213> ORGANISM: Vibrio vulnificus

<400> SEQUENCE: 12
atgaaaacca tgaaccgaat tacacttgct atgctgactg tgggattgag cctttcttcg      60
aatgctgcaa cgacgttgaa aatgggaatg caagcgtcgg ttggctcagt ggaatacacc      120
tctgccaagc tgcttgccga cacggttgaa gagatgagta aggtgagtt gaagctagcg       180 ttatatccaa gtcgcaaact gggcgacgac cgtgccatgt acagcagct ctctatgggt       240 gacttagaca tcacttacgc ggaatttggc cgtatgggac tttggatccc aagagcagaa      300
gcggtgacct taccttacgt tgctcgtgat tatgaccatt tacgccgcat gtttgattcc      360
gagtttggcc aaggcattcg tcaggaaatg ctaaccaagt taattggcg tgcgctagat      420 acttggtaca acggaacacg tgaaaccacc tctaaccgtc cattgaagtc aatttcagat      480
```

```
tttaaaggtc tgaaattgcg cgtgccgaat gcgaaaccaa atctgaatta cgccaagttg    540 tctgggcat caccaacacc gatggcattt tctgaagttt acctcgcgct acaaaccaat    600
gcagttgacg ggcaagagaa cccattgcca accattaaga caatgaagtt ctacgaggtg    660
caaagcaact tggcgatcac caatcacatc gtgaacgacc agatggtgct gatttcagaa    720
agcacgtggc aaaagctctc tgagcaggaa cgtgaaattg tcgctaacgc ggtgaaacaa    780
acaggggaag cgcataccgc atcggtgaaa agcaagaag cggagctgat ctcttctt      840 gaggcgcagg gtgtgaatgt cacctaccca gaacttgccc cgttccgtga agccatgcag    900
ccgctttact cagagtttga aagaaaatt ggtcagccga tcgtgtctaa gttggcggca    960
atgtag                                                              966

<210> SEQ ID NO 13
<211> LENGTH: 678
<212> TYPE: DNA
<213> ORGANISM: Vibrio vulnificus

<400> SEQUENCE: 13
atgctttccg ccagactgt tgtttcaatt cagcctgttg tcggtagccc tcttgataaa     60
accgagttca tcgttgctat ggcagttgct gcagaacaag ccggagctaa ggcactgcgt    120
attgaaggcg ttgaaaacgt acgccatgtt tctcaagcga ccaatgtacc aataattgga    180
attgtgaaac gtgatttaca ggacagtcct gtgcgcatca cacctttcgt ctgtgacgtg    240
gatgctctag cgactgctgg cgcaaccatc atcgcctttg atgcgaccga tcgtcagcga    300
ccagagagcc gagaaacgat agccaacgca atcaaaaaca gtggttgttt cgcgatggca    360
gattgctctt gcttcgcgga tgggcaatgg gcggcgcaaa ttggggtcga tattattggc    420
tcaaccttgt ctggctacgt gggcgaaatt gaaccaactg aacccgattt ggaactggtg    480 aaacagttt cttcggcggg attttttacc atggcggaag gtcgctacaa cacgcctcaa    540
ctcgccgcca aagcgattga aaatggcgct gtcgcggtga cggtgggctc ggccatcaca    600
cgaatggaag tggttactca ctggtttaat tctgcaacac aagcggtaag acagaataat    660
gaaagtatta gctattga                                                 678

<210> SEQ ID NO 14
<211> LENGTH: 882
<212> TYPE: DNA
<213> ORGANISM: Vibrio vulnificus

<400> SEQUENCE: 14
atgaaagtat tagctattga tattggcggt acaaaaatcg ccttaggcaa cgtggtcgat     60
gggcatttgc agcatcgcaa acagtttccg accctgttg tcaacgatgc aacaaccta    120 gcgaaagaga ttcttgccca ctgccaagca tggctaagcg acgttgatgc catcggtatt    180
tcgactaccg ggcttgtcag cgaacaaggg ataagtgcca ttaatccagg cacattgagc    240
ttccctacgc cttttcctct gcatagcgaa ctacacagat aagtggcaa gccagttaaa    300 atgctcaatg atgctcaagc ggctgcctgg tatgagtttt tgcaacttc acctgaactg    360 gatgttcgca atatggccta tattactgtc tcgacaggtg tgggaggcgg tttggtgatt    420
aaccaacaac tgcataaggg taagtcaaat tttgccggac atattggcca tacggtgctt    480
gatccaaatg ccccactttg tggctgccaa cagcgaggtt gtgttgaggc catcgcctct    540
ggaaatgcaa ttaacgcagg cgctcaagcc ctttttggcc aagcgatttc taatatcgaa    600
```

```
                                                         -continued ctgtttcagc ttgctcaaca caatgaacaa gcctccgcac tcattcaaca aagcgccgaa      660
gccatcgccc agctctgcct aaatttaaaa gccacgctgg atctcgattt ggtggtcatc      720
ggcggcggtg tgggccttgc tcacggctac ctcgctcgtg tacaagcgtt tatcgacaaa      780
cagcctctcg tgtttcaggt taaggtgaga gcggcagttg gcgattacga cgcatgctta      840
cttggcgcag cctttcaatt tgaggagagt aatctttcat ga                          882

<210> SEQ ID NO 15
<211> LENGTH: 110
<212> TYPE: DNA
<213> ORGANISM: Artificial Sequence
<220> FEATURE:
<223> OTHER INFORMATION: Synthetic NanR-binding duplex DNA

<400> SEQUENCE: 15
gtttgaaaaa atcttcgtt atggattatt atggcgatgg agattatttt caaaccaaac       60 ttttttaga agcaatacct aataataccg ctacctctaa taaaactttg                   110

<210> SEQ ID NO 16
<211> LENGTH: 278
<212> TYPE: PRT
<213> ORGANISM: Vibrio cholerae

<400> SEQUENCE: 16
```

Met Asn Leu Pro Lys Asn Leu Met Val Arg Leu Arg Ser Asn Thr Arg
1               5                   10                  15

Pro Ile Ser Lys Lys Leu Arg Val Val Ala Asp Tyr Val Leu Phe Asn
            20                  25                  30

Ala His Arg Val Gln Tyr Gln Thr Ile Thr Asp Leu Ala Pro Asn Thr
        35                  40                  45

Lys Thr Ser Arg Ala Thr Val Val Arg Leu Cys Arg Asp Leu Gly Tyr
    50                  55                  60

Lys Gly Tyr Ser Asp Phe Arg Met Ala Leu Ala Val Asp Leu Ser Gln
65                  70                  75                  80

Ser Ala Asn Gln Ser Gln Pro Lys Met Asp Gly Asp Ile Cys Glu Val
                85                  90                  95

Ser Ala Gln Ser Ala Val Asp Ser Leu Met Asp Thr Ala Lys Leu Ile
            100                 105                 110

Asp Arg Ala Ala Leu Asn Arg Ile Cys Glu Leu Val His Gly Ala Lys
        115                 120                 125

Phe Ile Gly Cys Val Gly Val Gly Ala Ser Ile Val Gly Arg Tyr
    130                 135                 140

Leu Ala Tyr Arg Leu Val Arg Ile Gly Lys Lys Ala Ile Met Tyr Glu
145                 150                 155                 160

Asp Thr His Leu Ala Ala Met Ser Ala Gly Gln Ser Val Val Gly Asp
                165                 170                 175

Ala Trp Phe Ala Ile Ser Ser Ser Gly Ser Thr Lys Glu Val Val His
            180                 185                 190

Ala Ala Thr Gln Ala His Gln Arg Gly Val Pro Val Val Ser Leu Thr
        195                 200                 205

Asn Ile Ser His Ser Pro Leu Ser Ser Ile Ser Asp Glu Met Leu Val
    210                 215                 220

Ala Ala Arg Pro Glu Gly Pro Leu Thr Gly Gly Ala Phe Ser Ser Lys
225                 230                 235                 240

Val Gly Ala Leu Leu Leu Val Asp Val Leu Ile Asn Thr Leu Leu Asp
                245                 250                 255

```
Val Tyr Pro Glu Tyr Ser Ala Ser Val Phe Gly Thr Ala Glu Val Ile
            260                 265                 270

Leu Pro Leu Met Asp Ser
        275

<210> SEQ ID NO 17
<211> LENGTH: 288
<212> TYPE: PRT
<213> ORGANISM: Haemophilus influenzae

<400> SEQUENCE: 17

Met Ala Lys Ser Gly Asn Val Leu Asn Lys Ile Gly Ser Leu Tyr Gln
1               5                   10                  15

Ser Leu Thr Lys Ser Glu Lys Lys Ile Ala Asp Thr Ile Leu Arg Ser
            20                  25                  30

Pro Asp Leu Val Ser Gln Cys Ser Leu Ser Glu Ile Ala Lys His Leu
        35                  40                  45

Gln Val Gly Glu Ala Thr Leu Val Arg Phe Cys Arg Thr Ile Gly Phe
    50                  55                  60

Lys Gly Phe Ser Glu Phe Lys Leu Glu Leu Ser Ile Glu Leu Ala Thr
65                  70                  75                  80

Lys Asp Asn Gln Asp Glu Glu Ile Leu Glu Thr Glx Ile Met Pro Glu
                85                  90                  95

Asp Asp Glu Leu Thr Ile Ala Gln Lys Leu Gln Thr Ala Val Ala Asn
            100                 105                 110

Val Met Glu Glu Thr Ile Asn Leu Leu Asp Leu Lys Gln Leu Glu Glu
        115                 120                 125

Val Val Lys Val Leu Lys Lys Ala Arg Arg Ile Pro Leu Phe Cys Val
    130                 135                 140

Cys Glu Glu Cys Val Thr Ala Glu Asp Ala Lys Asn Lys Leu Met Arg
145                 150                 155                 160

Ile Gly Pro Gln Val Val Ala Ser Gly Asn Asn His Pro Met Ala Met
                165                 170                 175

Gln Ala Ala Leu Leu Thr Ser Ser Asp Val Ala Thr Gly Leu Ser Arg
            180                 185                 190

Ser Gly Pro Ser Ala Glu Ile Ala His Ile Ile Lys Ile Ala Met Val
        195                 200                 205

Asn Gly Ala Thr Thr Val Ala Leu Tyr His Ser Leu Met Ser Pro Val
    210                 215                 220

Thr Glu Thr Ala Val Tyr Val Leu Val Asn Gly Asn Lys Val Gly Lys
225                 230                 235                 240

Leu Gln Gly Asp Ser Ile Gly Thr Lys Ile Ala Gln Leu Phe Val Leu
                245                 250                 255

Asp Leu Ile Tyr Ala Leu Leu Val Gln Gly Glu Glu Asp Ile Ala Ala
            260                 265                 270

Gln Thr Lys Gln Lys Thr Leu Asn Val Ile Leu Glu Gln Arg Ile Lys
        275                 280                 285
```